US012082496B2

(12) United States Patent
Kim et al.

(10) Patent No.: US 12,082,496 B2
(45) Date of Patent: Sep. 3, 2024

(54) COMPOSITION MATERIAL FOR ORGANIC ELECTROLUMINESCENT DEVICE, PLURALITY OF HOST MATERIALS, AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Bitnari Kim, Gyeonggi-do (KR); Sang-Hee Cho, Gyeonggi-do (KR); Hyo-Jung Lee, Gyeonggi-do (KR); Ye-Jin Jeon, Gyeonggi-do (KR); Hyun-Ju Kang, Gyeonggi-do (KR); Su-Hyun Lee, Gyeonggi-do (KR); Jeong-Eun Yang, Gyeonggi-do (KR)

(73) Assignee: Rohm and Haas Electronic Materials Korea Ltd. (KR)

( * ) Notice: Subject to any disclaimer, the term of this patent is extended or adjusted under 35 U.S.C. 154(b) by 801 days.

(21) Appl. No.: 17/042,652

(22) PCT Filed: Mar. 26, 2019

(86) PCT No.: PCT/KR2019/003473
§ 371 (c)(1),
(2) Date: Sep. 28, 2020

(87) PCT Pub. No.: WO2019/190149
PCT Pub. Date: Oct. 3, 2019

(65) Prior Publication Data

US 2021/0028369 A1 Jan. 28, 2021

(30) Foreign Application Priority Data

Mar. 27, 2018 (KR) ........................ 10-2018-0035261
Mar. 15, 2019 (KR) ........................ 10-2019-0030023

(51) Int. Cl.

| | |
|---|---|
| ***C09K 11/06*** | (2006.01) |
| ***C07D 209/86*** | (2006.01) |
| ***C07D 209/88*** | (2006.01) |
| ***C07D 403/04*** | (2006.01) |
| ***C07D 403/10*** | (2006.01) |
| ***C07D 487/16*** | (2006.01) |
| ***C07F 15/00*** | (2006.01) |
| ***C09K 11/02*** | (2006.01) |
| ***H10K 85/30*** | (2023.01) |
| ***H10K 85/60*** | (2023.01) |
| *H10K 50/11* | (2023.01) |
| *H10K 101/00* | (2023.01) |

(52) U.S. Cl.

CPC ......... *H10K 85/636* (2023.02); *C07D 209/86* (2013.01); *C07D 209/88* (2013.01); *C07D 403/04* (2013.01); *C07D 403/10* (2013.01); *C07D 487/16* (2013.01); *C07F 15/0033* (2013.01); *C09K 11/02* (2013.01); *C09K 11/06* (2013.01); *H10K 85/342* (2023.02); *H10K 85/633* (2023.02); *H10K 85/654* (2023.02); *H10K 85/6572* (2023.02); *C09K 2211/1007* (2013.01); *C09K 2211/1029* (2013.01); *C09K 2211/185* (2013.01); *H10K 50/11* (2023.02); *H10K 85/615* (2023.02); *H10K 85/626* (2023.02); *H10K 2101/90* (2023.02)

(58) Field of Classification Search

CPC .. H10K 85/636; H10K 85/342; H10K 85/633; H10K 85/654; H10K 85/6572; H10K 50/11; H10K 85/615; H10K 85/626; H10K 2101/90; H10K 50/00; C07D 209/86; C07D 209/88; C07D 403/04; C07D 403/10; C07D 487/16; C07F 15/0033; C09K 11/02; C09K 11/06; C09K 2211/1007; C09K 2211/1029; C09K 2211/185; C09K 2211/1037; C09K 2211/1044; C09K 2211/1051; C09K 2211/1059; C09K 2211/1066

See application file for complete search history.

(56) References Cited

U.S. PATENT DOCUMENTS

| | | | |
|---|---|---|---|
| 6,902,831 | B2 | 6/2005 | Chen |
| 2017/0207396 | A1 | 7/2017 | Park et al. |

FOREIGN PATENT DOCUMENTS

| | | | |
|---|---|---|---|
| KR | 20130106255 | A | 9/2013 |
| KR | 20140097044 | A | 8/2014 |
| KR | 20150121337 | A | 10/2015 |
| WO | 2012026780 | A1 | 3/2012 |
| WO | 2016013867 | A1 | 1/2016 |

(Continued)

OTHER PUBLICATIONS

Szlachcic, P. et al., "Organic light emitting diodes (OLED) based on helical structures containing 7-membered fused rings", Dyes and Pigments, 2015, vol. 114, pp. 184-195.

(Continued)

*Primary Examiner* — Mark Kopec
*Assistant Examiner* — Jaison P Thomas
(74) *Attorney, Agent, or Firm* — G. Creston Campbell

(57) ABSTRACT

The present disclosure relates to a composition material for an organic electroluminescent device, a plurality of host materials, and an organic electroluminescent device comprising the same. By comprising the composition material for an organic electroluminescent device of the present disclosure, it is possible to provide an organic electroluminescent device having high luminous efficiency and/or long lifespan characteristics.

9 Claims, No Drawings

(56) References Cited

FOREIGN PATENT DOCUMENTS

| | | | | | |
|---|---|---|---|---|---|
| WO | 2016080791 | A1 | | 5/2016 | |
| WO | 2016204394 | A1 | | 12/2016 | |
| WO | WO-2018056645 | A1 | * | 3/2018 | ............... H01B 1/12 |
| WO | 2018160022 | A1 | | 9/2018 | |
| WO | WO-2018159970 | A1 | * | 9/2018 | ........... C07D 209/94 |
| WO | 2019066258 | A1 | | 4/2019 | |

OTHER PUBLICATIONS

Search Report from China National Intellectual Property Administration for China Patent application No. 201980016650.6; Application Date: Mar. 26, 2019.

* cited by examiner

COMPOSITION MATERIAL FOR ORGANIC ELECTROLUMINESCENT DEVICE, PLURALITY OF HOST MATERIALS, AND ORGANIC ELECTROLUMINESCENT DEVICE COMPRISING THE SAME

TECHNICAL FIELD

The present disclosure relates to a composition material for an organic electroluminescent device, a plurality of host materials, and an organic electroluminescent device comprising the same.

BACKGROUND ART

In 1987, Tang et al. of Eastman Kodak first developed a small molecule green organic electroluminescent device (OLED) of TPD/Alq3 bilayer consisting of a light-emitting layer and a charge transport layer. Since then, the research on an OLED has been rapidly carried out, and it has been commercialized. An OLED changes electric energy into light by applying electricity to an organic light-emitting material, and commonly comprises an anode, a cathode, and an organic layer formed between the two electrodes. The organic layer of the OLED may comprise a hole injection layer, a hole transport layer, a hole auxiliary layer, a light-emitting auxiliary layer, an electron blocking layer, a light-emitting layer (containing host and dopant materials), an electron buffer layer, a hole blocking layer, an electron transport layer, an electron injection layer, etc. The materials used in the organic layer can be classified into a hole injection material, a hole transport material, a hole auxiliary material, a light-emitting auxiliary material, an electron blocking material, a light-emitting material, an electron buffer material, a hole blocking material, an electron transport material, an electron injection material, etc., depending on functions.

The most important factor determining luminous efficiency in an OLED is light-emitting materials. The light-emitting materials are required to have high quantum efficiency, high movement degree of an electron and a hole, and uniformity and stability of the formed light-emitting material layer. The light-emitting material is classified into blue, green, and red light-emitting materials according to the light-emitting color, and further includes yellow or orange light-emitting materials. Furthermore, the light-emitting material is classified into a host material and a dopant material in a functional aspect. Recently, an urgent task is the development of an OLED having high efficiency and long lifespan. In particular, the development of highly excellent light-emitting material over conventional materials is urgently required, considering the EL properties necessary for medium- and large-sized OLED panels. For this, preferably, as a solvent in a solid state and an energy transmitter, a host material should have high purity and a suitable molecular weight in order to be deposited under vacuum. Furthermore, a host material is required to have high glass transition temperature and pyrolysis temperature to achieve thermal stability, high electrochemical stability to achieve a long lifespan, easy formability of an amorphous thin film, good adhesion with adjacent layers, and no movement between layers.

U.S. Pat. No. 6,902,831 discloses an azulene derivative as an organic electroluminescent compound. However, said reference does not specifically disclose an organic electroluminescent compound of a fused azulene derivative, and a composition material for an organic electroluminescent device comprising a compound comprising a carbazole and an arylamino and a fused azulene derivative.

DISCLOSURE OF THE INVENTION

Problems to be Solved

The objective of the present disclosure is to provide a composition material for an organic electroluminescent device having high luminous efficiency and/or long lifespan characteristics. Another objective of the present disclosure is to provide an organic electroluminescent device having high luminous efficiency and/or long lifespan characteristics by comprising such composition material.

Solution to Problems

As a result of intensive studies to solve the technical problem above, the present inventors found that the above objective can be achieved by a composition material for an organic electroluminescent device comprising a compound represented by the following formula 1 and a compound represented b the following formula 2:

(1)

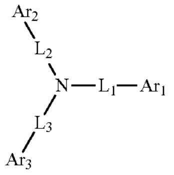

wherein $Ar_1$ to $Ar_3$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsiyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino;

$L_1$ to $L_3$ each independently represent a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

excluding when $L_1$ to $L_3$ are all single bonds and $Ar_1$ to $Ar_3$ are all hydrogen;

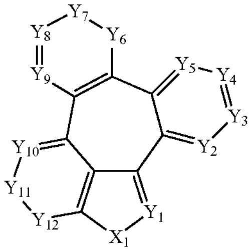
(2)

wherein $X_1$ represents N-L-$(Ar)_a$, S, or O;

L represents a single bond, a substituted or unsubstituted (C6-C30)arylene, or a substituted or unsubstituted (3- to 30-membered)heteroarylene;

Ar represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

$Y_1$ to $Y_{12}$ each independently represent N or $CR_{10}$;

$R_{10}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or may be linked to an adjacent substituent to form a substituted or unsubstituted ring; and a represents an integer of 1 to 4, where if a is an integer of 2 or more, each of Ar may be the same or different.

Effects of the Invention

By comprising the composition material for an organic electroluminescent device of the present disclosure, an organic electroluminescent device having high luminous efficiency and/or long lifespan characteristics is provided, and a display device or a lighting device using the organic electroluminescent device can be manufactured.

EMBODIMENTS OF THE INVENTION

Hereinafter, the present disclosure will be described in detail. However, the following description is intended to explain the disclosure, and is not meant in any way to restrict the scope of the disclosure.

The term "composition material for an organic electroluminescent device" in the present disclosure means two or more materials, which can be used in an organic electroluminescent device, existing together or being ready to exist together. Herein, "existing together" does not only mean a state in which two or more materials are mixed but also includes a state in which the materials are separated. In addition, the composition material for an organic electroluminescent device is a concept including not only a material before being comprised in an organic electroluminescent device, e.g., before evaporation, but also a material being comprised in an organic electroluminescent device, e.g., after evaporation. For example, the composition material for an organic electroluminescent device may comprise two or more of a hole injection material, a hole transport material, a hole auxiliary material, a light-emitting auxiliary material, an electron blocking material, a light-emitting material (host material and dopant material), an electron buffer material, a hole blocking material, an electron transport material, and an electron injection material, or may comprise two or more hole injection materials, two or more hole transport materials, two or more hole auxiliary materials, two or more light-emitting auxiliary materials, two or more electron blocking materials, two or more light-emitting materials (host material and dopant material), two or more electron buffer materials, two or more hole blocking materials, two or more electron transport materials, and two or more electron injection materials. The composition material for an organic electroluminescent device may be comprised in any layer constituting an organic electroluminescent device. The two or more materials comprised in the composition material may be comprised together in one layer, or may be each comprised in separate layers. When the two or more materials are comprised in one layer, a layer may be formed by a mixture-evaporation process wherein the materials are mixed, or a layer may be formed by a co-evaporation process wherein the materials are separately and simultaneously evaporated.

The term "a plurality of host materials" in the present disclosure means a host material as a combination of at least two compounds, which may be comprised in any light-emitting layer constituting an organic electroluminescent device. It may mean both a material before being comprised in an organic electroluminescent device (for example, before vapor deposition) and a material after being comprised in an organic electroluminescent device (for example, after vapor deposition). The plurality of host materials of the present disclosure may be a combination of at least two host materials, and may optionally comprise a conventional material used in organic electroluminescent materials. At least two compounds comprised in the plurality of host materials may be comprised together in one light-emitting layer by a method known in the field, or may respectively be comprised in different light-emitting layers. For example, the at least two compounds may be mixture-evaporated, co-evaporated, or separately evaporated.

According to one embodiment of the present disclosure, among the materials comprised in the composition material for an organic electroluminescent device, the compound represented by formula 1 is a first host material, and the compound represented by formula 2 is a second host material. That is, in accordance with one embodiment of the present disclosure, a plurality of host materials which comprises the first host material comprising the compound represented by formula 1 and the second host material comprising the compound represented by formula 2 is provided. Herein, the first and second host materials may be comprised in one light-emitting layer, or each may be comprised in different light-emitting layers among plural light-emitting layers. In the composition material for an organic electroluminescent device of the present disclosure, the compound represented by formula 1 and the compound represented by formula 2 may be comprised in a ratio of 1:99 to 99:1, preferably 10:90 to 90:10, and more preferably 30:70 to 70:30. In addition, the compound represented by formula 1 and the compound represented by formula 2 may be combined in a desired ratio by mixing them after putting into a shaker, collecting them by melting them with heat after putting into a glass tube, etc.

Hereinafter, the compounds represented by formulas 1 and 2 will be described in detail.

Herein, the term "(C1-C30)alkyl(ene)" is meant to be a linear or branched alkyl having 1 to 30 carbon atoms constituting the chain, in which the number of carbon atoms is preferably 1 to 10, and more preferably 1 to 6. The above alkyl may include methyl, ethyl, n-propyl, iso-propyl, n-butyl, iso-butyl, tert-butyl, etc. The term "(C3-C30)cycloalkyl(ene)" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered)heterocycloalkyl" is meant to be a cycloalkyl having 3 to 7 ring backbone atoms, and including at least one heteroatom selected from the group consisting of B, N, O, S, Si, P, and Ge and preferably the group consisting of O, S, and N. The above heterocycloalkyl may include tetrahydrofuran, pyrrolidine, thiolan, tetrahydropyran, etc. The term "(C6-C30)aryl(ene)" is meant to be a monocyclic or fused ring radical derived from an aromatic hydrocarbon having 6 to 30 ring backbone carbon atoms, in which the number of the ring backbone carbon atoms is preferably 6 to 20, more preferably 6 to 15. The above aryl(ene) may be partially saturated. The above aryl may include phenyl, biphenyl, terphenyl, quaterphenyl, naphthyl, binaphthyl, phenylnaphthyl, naphthylphenyl, fluorenyl, phenylfluorenyl, dimethylfluorenyl, diphenylfluorenyl, benzofluorenyl, diphenylbenzofluorenyl, dibenzofluorenyl, phenanthrenyl, benzophenanthrenyl, phenylphenanthrenyl, anthracenyl, benzanthracenyl, indenyl, triphenylenyl, pyrenyl, tetracenyl, perylenyl, chrysenyl, benzochrysenyl, naphthacenyl, fluoranthenyl, benzofluoranthenyl, tolyl, xylyl, mesityl, cumenyl, spiro[fluorene-fluorene]yl, spiro[fluorene-benzofluorene]yl, azulenyl, etc. More specifically, the above aryl may include o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4'-methylbiphenyl, 4"-t-butyl-p-terphenyl-4-yl, o-biphenyl, m-biphenyl, p-biphenyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 1-naphthyl, 2-naphthyl, 1-fluorenyl, 2-fluorenyl, 3-fluorenyl, 4-fluorenyl, 9-fluorenyl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 1-anthryl, 2-anthryl, 9-anthryl, 1-phenanthryl, 2-phenanthryl, 3-phenanthryl, 4-phenanthryl, 9-phenanthryl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 3-fluoranthenyl, 4-fluoranthenyl, 8-fluoranthenyl, 9-fluoranthenyl, benzofluoranthenyl, etc. The term "(3- to 30-membered)heteroaryl(ene)" is an aryl having 3 to 30 ring backbone atoms, in which the number of the ring backbone atoms is preferably 3 to 20, more preferably 5 to 15, and including at least one, preferably 1 to 4 heteroatoms selected from the group consisting of B, N, O, S, Si, P, and Ge. The above heteroaryl(ene) may be a monocyclic ring, or a fused ring condensed with at least one benzene ring; may be partially saturated; and may be one formed by linking at least one heteroaryl or aryl group to a heteroaryl group via a single bond(s). The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridinyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, benzimidazolyl, benzothiazolyl, benzoisothiazolyl, benzoisoxazoyl, benzoxazolyl, imidazopyridinyl, isoindolyl, indolyl, benzoindolyl, indazolyl, benzothiadiazolyl, quinolyl, isoquinolyl, cinnolinyl, quinazolinyl, quinoxalinyl, carbazolyl, azacarbazolylyl, benzocarbazolyl, dibenzocarbazolyl, phenoxazinyl, phenanthridinyl, benzodioxolyl, indolizidinyl, acridinyl, silafluorenyl, germafluorenyl, etc. More specifically, the above heteroaryl may include 1-pyrroyl, 2-pyrroyl, 3-pyrrolyl, 2-pyridinyl, 3-pyrdinyl, 4-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolizidinyl, 2-indolizidinyl, 3-indolizidinyl, 5-indolizidinyl, 6-indolizidinyl, 7-indolizidinyl, 8-indolizidinyl, 2-imidazopyrdinyl, 3-imidazopyridinyl, 5-imidazopyrdinyl, 6-imidazopyridinyl, 7-imidazopyridinyl, 8-imidazopyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazoyl, 2-carbazoyl, 3-carbazolyl, 4-carbazoyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, etc. Furthermore, "halogen" includes F, Cl, Br, and I.

In addition, "ortho (o)," "meta (m)," and "para (p)" signify substitution positions of two substituents. The ortho position represents a just neighboring position, and, for example, in the case of benzene, represents 1,2 positions. The meta position represents the position next to the just neighboring position, and, for example, in the case of benzene, represents 1,3 positions. The para position represents the position next to the meta position, and, for example, in the case of benzene, represents 1,4 positions.

Herein, “substituted” in the expression “substituted or unsubstituted” means that a hydrogen atom in a certain functional group is replaced with another atom or functional group, i.e., a substituent. The substituents of the substituted (C1-C30)alkyl(ene), the substituted (C6-C30)aryl(ene), the substituted (3- to 30-membered)heteroaryl(ene), the substituted (C3-C30)cycloalkyl(ene), the substituted (C1-C30) alkoxy, the substituted tri(C1-C30)alkylsilyl, the substituted di(C1-C30)alkyl(C6-C30)arylsilyl, the substituted (C1-C30) alkyldi(C6-C30)arylsilyl, the substituted tri(C6-C30)arylsilyl, the substituted mono- or di-(C1-C30)alkylamino, the substituted mono- or di-(C6-C30)arylamino, and the substituted (C1-C30)alkyl(C6-C30)arylamino in $Ar_1$ to $Ar_3$, $L_1$ to $L_3$, L, Ar, and $R_{10}$ each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered)heteroaryl unsubstituted or substituted with a (C6-C30)aryl; a (C6-C30)aryl unsubstituted or substituted with a (5- to 30-membered)heteroaryl; a tri(C1-C30)alkylsilyl; a tri(C6-C30)arylsilyl; a di(C1-C30)alkyl(C6-C30)arylsiyl; a (C1-C30)alkyldi(C6-C30)arylsilyl; an amino; a mono- or di-(C1-C30)alkylamino; a mono- or di-(C6-C30) arylamino unsubstituted or substituted with a (C1-C30) alkyl; a (C1-C30)alkyl(C6-C30)arylamino; a (C1-C30)alkylcarbonyl; a (C1-C30)alkoxycarbonyl; a (C6-C30) arylcarbonyl; a di(C6-C30)arylboronyl; a di(C1-C30) alkylboronyl; a (C1-C30)alkyl(C6-C30)arylboronyl; a (C6-C30)aryl(C1-C30)alkyl; and a (C1-C30)alkyl(C6-C30)aryl. Preferably, the substituents each independently are at least one selected from the group consisting of a (C1-C6)alkyl and a (C6-C20)aryl. Specifically, the substituents may be methyl, phenyl, naphthyl, biphenyl, phenanthrenyl, naphthylphenyl, triazinyl substituted with phenyl and/or naphthyl, quinazolinyl substituted with phenyl, carbazolyl, diphenylamino, dimethylfluorenylphenylamino, etc.

Formula 1 may be represented by at least one of the following formulas 3 to 6.

(3)

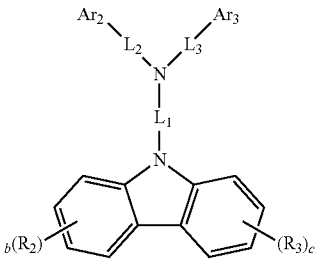

(4)

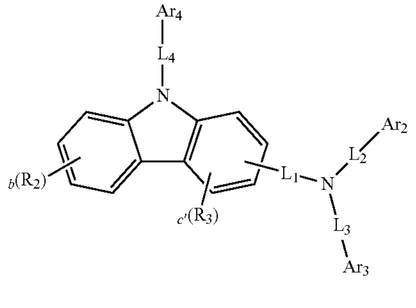

-continued (5)

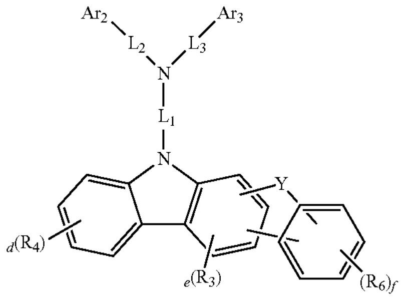

(6)

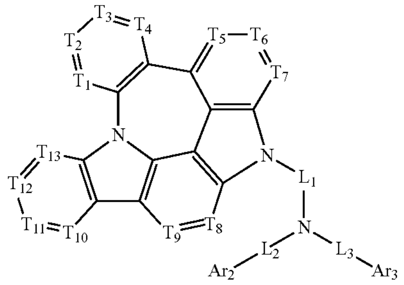

wherein

Y represents $CR_7R_8$, $NR_9$, O, or S;

$T_1$ to $T_{13}$ each independently represent N or $CV_1$;

$V_1$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or two adjacent $V_1$'s may be linked to each other to form a ring;

$R_2$ to $R_9$ each independently represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or may be linked to an adjacent substituent to form a ring;

$L_4$ represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

$Ar_4$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl;

b, c, d, and f each independently represent an integer of 1 to 4, e represents an integer of 1 or 2, c' represents an integer of 1 to 3, where if b to f and c' each independently are an integer of 2 or more, each of $R_2$ to $R_6$ may be the same or different; and $Ar_2$, $Ar_3$, and $L_1$ to $L_3$ are as defined in formula 1.

In formula 1, $Ar_1$ to $Ar_3$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsiyl, a substituted or unsubstituted mono- or di-(C1-C30)alkylamino, a substituted or unsubstituted mono- or di-(C6-C30) arylamino, or a substituted or unsubstituted (C1-C30)alkyl (C6-C30)arylamino. According to one embodiment of the present disclosure, $Ar_1$ to $Ar_3$ each independently represent a substituted or unsubstituted (C6-C20)aryl, or a substituted or unsubstituted (5- to 30-membered)heteroaryl. According to another embodiment of the present disclosure, $Ar_1$ to $Ar_3$ each independently represent a (C6-C20)aryl unsubstituted or substituted with a (C1-C6)alkyl, or a (5- to 30-membered) heteroaryl unsubstituted or substituted with a (C1-C6)alkyl or a (C6-C20)aryl. Specifically, $Ar_1$ to $Ar_3$ may each independently represent a phenyl, a biphenyl, a naphthylphenyl, a phenanthrenylphenyl, a dimethylfluorenyl, a dimethylbenzofluorenyl, a dibenzofuranyl, a dibenzothiophenyl, a carbazolyl, a biphenylcarbazolyl, a carbazoyl substituted with a naphthylphenyl, a benzocarbazolyl, a dibenzocarbazolyl, a dimethylindenocarbazoyl, a benzofuranocarbazolyl, a benzofuranobenzocarbazoyl, a benzothiophenocarbazolyl, a benzothiophenobenzocarbazolyl, a dimethylbenzothiophenoindenocarbazolyl, a phenylindolobenzocarbazolyl, a (13- to 27-membered)heteroaryl containing one or more of nitrogen, oxygen, sulfur, etc.

In formula 1, $L_1$ to $L_3$ each independently represent a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene. According to one embodiment of the present disclosure, $L_1$ to $L_3$ each independently represent a single bond, or a substituted or unsubstituted (C6-C20)arylene. According to another embodiment of the present disclosure, $L_1$ to $L_3$ each independently represent a single bond, or a (C6-C20)arylene unsubstituted or substituted with a (C1-C6)alkyl. Specifically, $L_1$ to $L_3$ may each independently represent a single bond, a phenylene, a naphthylene, a biphenylene, a naphthylphenylene, a phenylnaphthylene, or a dimethylfluorenylene, etc.

Formula 2 may be represented by formula 2-1.

(2-1)

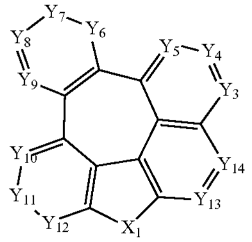

wherein $X_1$ and $Y_1$ to $Y_{12}$ are as defined in formula 2, and $Y_{13}$ and $Y_{14}$ are each independently identical to the definition of $Y_1$.

In formula 2, $X_1$ represents N-L-$(Ar)_a$, S, or O.

In formula 2, L represents a single bond, a substituted or unsubstituted (C6-C30)arylene, or a substituted or unsubstituted (3- to 30-membered)heteroarylene; preferably a single bond, a substituted or unsubstituted (C6-C25)arylene, or a substituted or unsubstituted (5- to 25-membered)heteroarylene; and more preferably a single bond, an unsubstituted (C6-C18)arylene, or an unsubstituted (5- to 18-membered)heteroarylene. The heteroarylene may contain one or more of nitrogen, oxygen, and sulfur.

According to one embodiment of the present disclosure, in formula 2, L may represent a single bond, a substituted or unsubstituted phenylene, a substituted or unsubstituted naphthylene, a substituted or unsubstituted biphenylene, a substituted or unsubstituted pyridylene, a substituted or unsubstituted pyrimidinylene, a substituted or unsubstituted triazinylene, a substituted or unsubstituted quinazolinylene, a substituted or unsubstituted quinoxalinylene, a substituted or unsubstituted naphthyridinylene, a substituted or unsubstituted benzoquinazolinylene, a substituted or unsubstituted benzothienopyrimidinylene, a substituted or unsubstituted acenaphthopyrimidinylene, a substituted or unsubstituted (13- to 16-membered)heteroarylene containing one or more of nitrogen, oxygen, sulfur, etc.

In formula 2, Ar represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; preferably a substituted or unsubstituted (C6-C25) aryl, a substituted or unsubstituted (5- to 30-membered) heteroaryl, or a substituted or unsubstituted di(C6-C25) arylamino; and more preferably a substituted or unsubstituted (C6-C18)aryl, a substituted or unsubstituted (5- to 25-membered)heteroaryl, or a substituted or unsubstituted di(C6-C18)arylamino.

According to one embodiment of the present disclosure, in formula 2, Ar may represent a substituted or unsubstituted phenyl, a substituted or unsubstituted naphthyl, a substituted or unsubstituted biphenyl, a substituted or unsubstituted terphenyl, a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted carbazoyl, a substituted or unsubstituted dibenzothiophenyl, a substituted or unsubstituted benzothiophenyl, a substituted or unsubstituted dibenzofuranyl, a substituted or unsubstituted benzofuranyl, a substituted or unsubstituted naphthyridinyl, a substituted or unsubstituted benzothienopyrimidinyl, a substituted or unsubstituted benzothienoquinoyl, a substituted or unsubstituted benzofuroquinoyl, a substituted or unsubstituted triaindenyl, a substituted or unsubstituted phenanthroimidazoyl, a substituted or unsubstituted (9- to 25-membered)heteroaryl containing at least one of nitrogen, oxygen, and sulfur, a substituted or unsubstituted diphenylamino, a substituted or unsubstituted phenylbiphenylamino, a substituted or unsubstituted fluorenylphenylamino, or a substituted or unsubstituted fluorenylbiphenylamino, etc.

In formula 2, a represents an integer of 1 to 4, preferably 1 or 2, and where if a is an integer of 2 or more, each of Ar may be the same or different.

In formula 2, $Y_1$ to $Y_{12}$ each independently represent N or $CR_{10}$. According to one embodiment of the present disclosure, $Y_1$ to $Y_{12}$ may all represent $CR_{10}$. According to another embodiment of the present disclosure, at least one of $Y_1$ to $Y_{12}$ may represent N. When there are plural $R_{10}$'s, each of $R_{10}$ may be the same or different.

$R_{10}$ each independently represent hydrogen, deuterium, a halogen, a cyano, a substituted or unsubstituted (C1-C30) alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsiyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent to form a substituted or unsubstituted ring; preferably each independently represent hydrogen, a substituted or unsubstituted (C1-C20)alkyl, a substituted or unsubstituted (C6-C25)aryl, a substituted or unsubstituted (5- to 25-membered)heteroaryl, or a substituted or unsubstituted di(C6-C25)arylamino; or may be linked to an adjacent substituent to form a substituted or unsubstituted, mono- or polycyclic, (3- to 25-membered) aromatic ring, in which at least one carbon atom of the formed aromatic ring may be replaced with at least one heteroatom selected from nitrogen, oxygen, and sulfur, and more preferably each independently represent hydrogen, a substituted or unsubstituted (C1-C10)alkyl, a substituted or unsubstituted (C6-C18)aryl, a substituted or unsubstituted (5- to 18-membered)heteroaryl, or a substituted or unsubstituted di(C6-C18)arylamino; or may be linked to an adjacent substituent to form a substituted or unsubstituted, mono- or polycyclic, (5- to 18-membered) aromatic ring, in which at least one carbon atom of the formed aromatic ring may be replaced with at least one heteroatom selected from nitrogen, oxygen, and sulfur.

According to one embodiment of the present disclosure, $R_{10}$ each independently represent hydrogen, a substituted or unsubstituted methyl, a substituted or unsubstituted phenyl, a substituted or unsubstituted naphthyl, a substituted or unsubstituted biphenyl, a substituted or unsubstituted pyridyl, a substituted or unsubstituted pyrimidinyl, a substituted or unsubstituted triazinyl, a substituted or unsubstituted quinazolinyl, a substituted or unsubstituted quinoxalinyl, a substituted or unsubstituted phenylbiphenylamino, etc.

According to one embodiment of the present disclosure, in formula 2, at least one adjacent pair among $Y_1$ to $Y_{12}$ is $CR_{10}$, and $R_{10}$'s of the adjacent two $CR_{10}$'s are fused to each other to independently form a ring represented by any one of the following formulas 7 to 11, but are not limited thereto. Herein, $Y_1$ and $Y_2$, $R_5$ and $Y_6$, and $Y_9$ and $Y_{10}$ are also regarded as being adjacent to each other. For example, the formed ring may be a substituted or unsubstituted benzene ring, a naphthalene ring, a furan ring, a thiophene ring, a substituted or unsubstituted pyrrole ring, a pyridine ring, a benzofuran ring, a benzothiophene ring, a substituted or unsubstituted indole ring, a dibenzofuran ring, a dibenzothiophene ring, a substituted or unsubstituted carbazole ring, or a phenanthrene ring, including the rings represented by formulas 7 to 11.

(7)

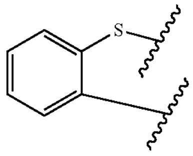

(8)

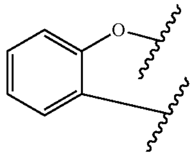

(9)

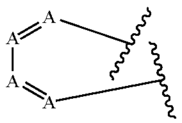

(10)

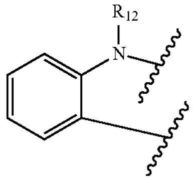

(11)

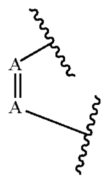

In formulas 7 to 11,  represents a fusing site at the adjacent $CR_{10}$'s of formula 2.

In formulas 9 to 11, A each independently represent N or $CR_{11}$. According to an embodiment of the present disclosure, all A may be $CR_{11}$. According to another embodiment of the present disclosure, at least one A may be N. When there are plural $R_{11}$'s, each of $R_{11}$ may be the same or different.

$R_{11}$ each independently represents hydrogen, deuterium, a halogen, a cyano, a substituted or unsubstituted (C1-C30) alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsiyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; preferably a substituted or unsubstituted (C6-C25) aryl, or a substituted or unsubstituted (5- to 25-membered) heteroaryl; and more preferably a substituted or unsubstituted (C6-C18)aryl, or a substituted or unsubstituted (5- to 18-membered)heteroaryl.

In formula 10, $R_{12}$ represents hydrogen, deuterium, a halogen, a cyano, a substituted or unsubstituted (C1-C30) alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; preferably a substituted or unsubstituted (C6-C25) aryl, or a substituted or unsubstituted (5- to 25-membered) heteroaryl; and more preferably an unsubstituted (C6-C18) aryl, or an unsubstituted (5- to 18-membered)heteroaryl; for example, phenyl.

In the present disclosure, in the expression "is linked to an adjacent substituent to form a ring," two or more adjacent substituents are linked to or fused with each other to form a substituted or unsubstituted (3- to 30-membered) ring, the ring may be a mono- or polycyclic, alicyclic or aromatic ring, or the combination thereof, and preferably a substituted or unsubstituted (3- to 26-membered) ring of mono- or polycyclic, and alicyclic or aromatic, or the combination thereof. The formed ring may contain at least one heteroatom selected from B, N, O, S, Si, P, and Ge, and preferably selected from N, O, and S. According to one embodiment of the present disclosure, the number of the ring backbone atoms is preferably 5 to 20, and in another embodiment, 5 to 15.

In the formulas of the present disclosure, the heteroaryl (ene) may each independently contain at least one heteroatom selected from B, N, O, S, Si, P, and Ge. In addition, the heteroatom may be combined with at least one substituent selected from the group consisting of hydrogen, deuterium, a halogen, a cyano, a substituted or unsubstituted (C1-C30) alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

The compound represented by formula 1 includes the following compounds, but is not limited thereto.

C-1-1

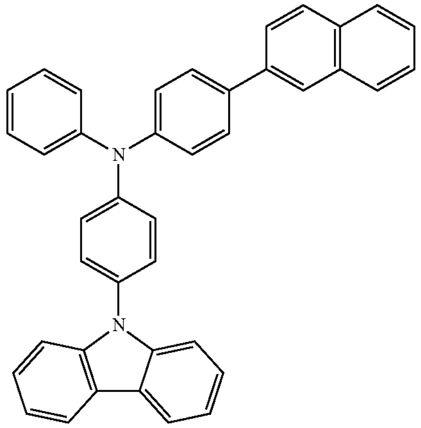

C-1-2

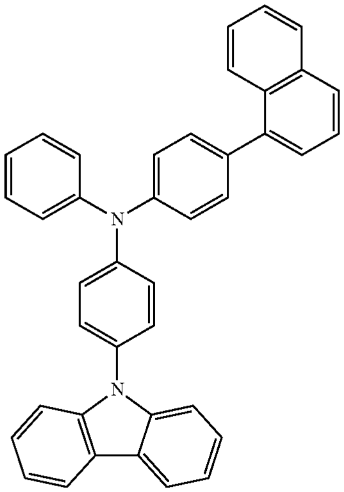

C-1-3

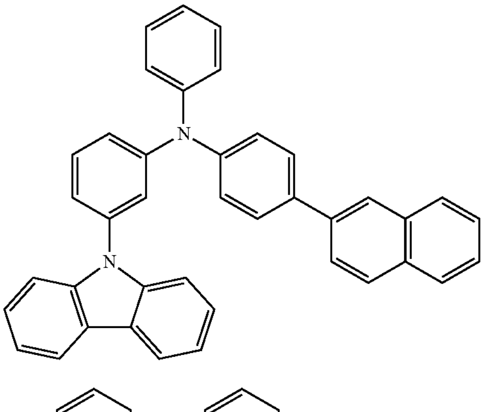

C-1-4

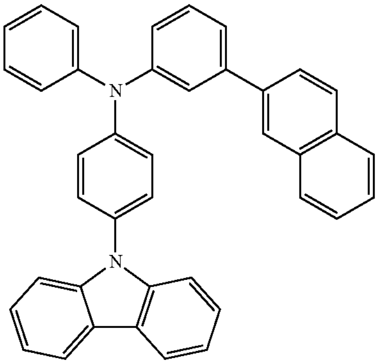

-continued
C-1-5
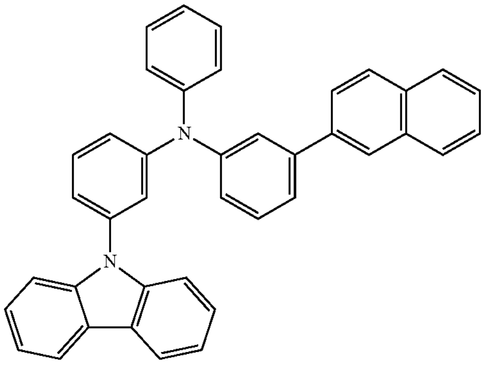
C-1-6
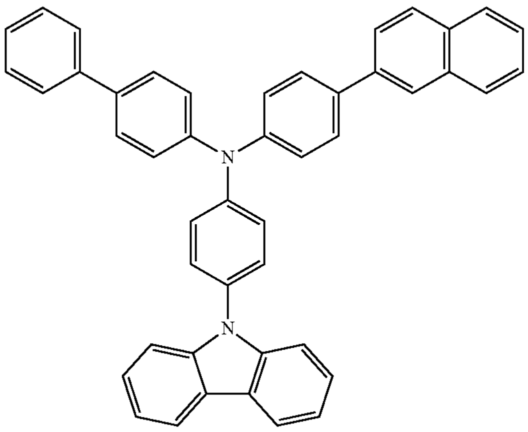
C-1-7
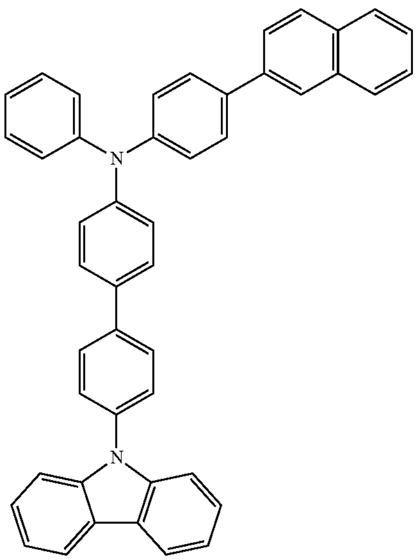
-continued
C-1-8
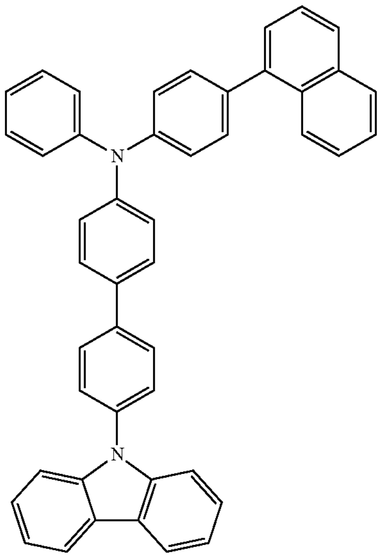
C-1-9
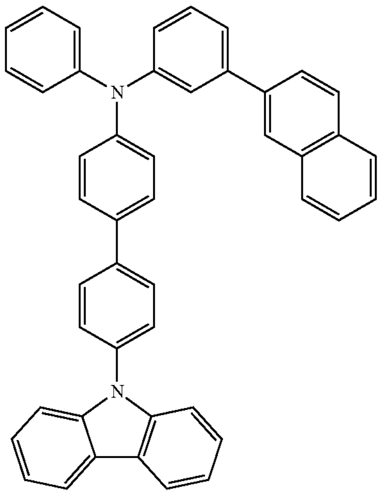
C-1-10
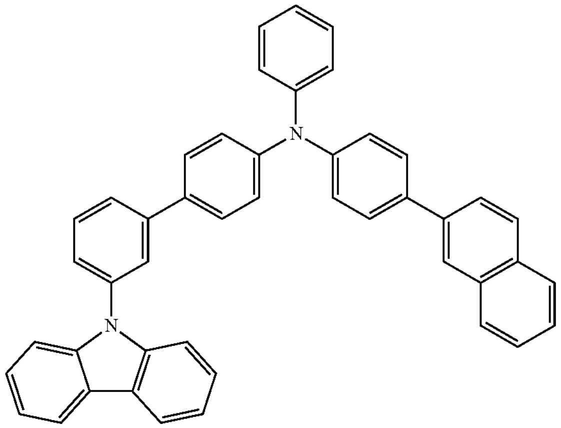

-continued
C-1-11
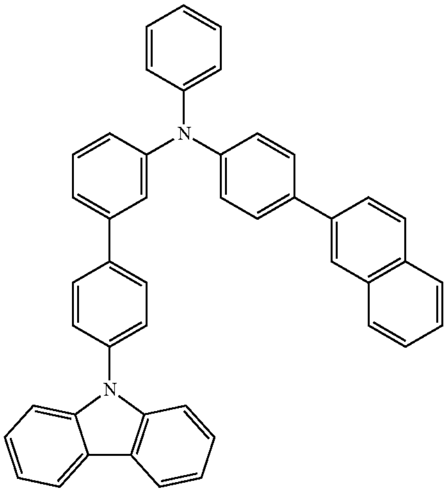
C-1-12
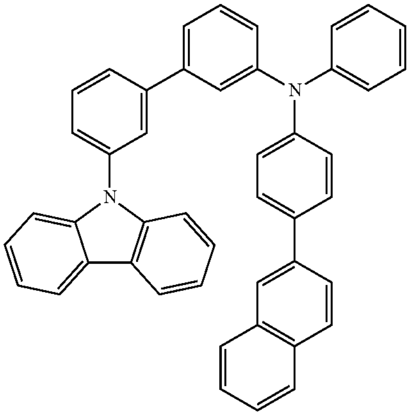
C-1-13
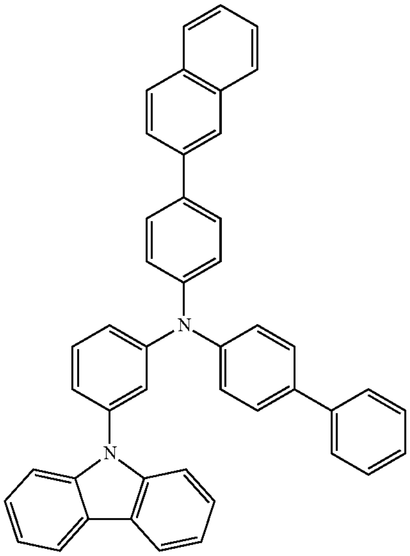
-continued
C-1-14
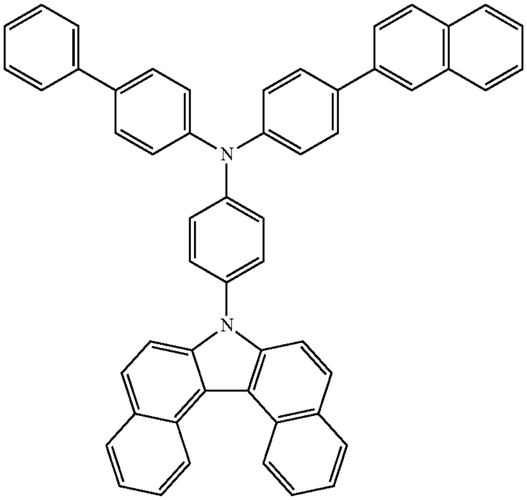
C-1-15
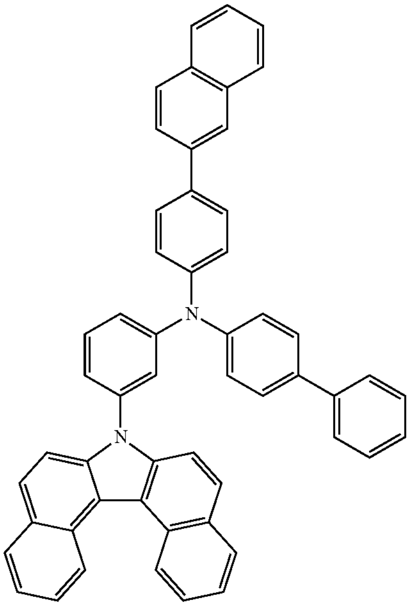
C-1-16
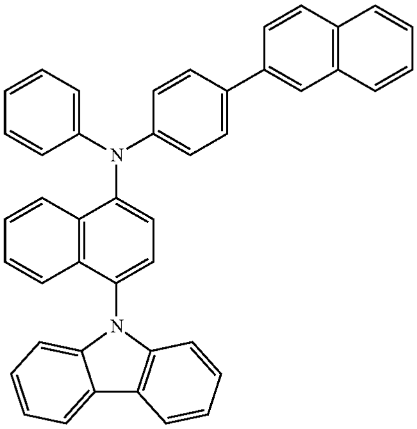

-continued
C-1-17
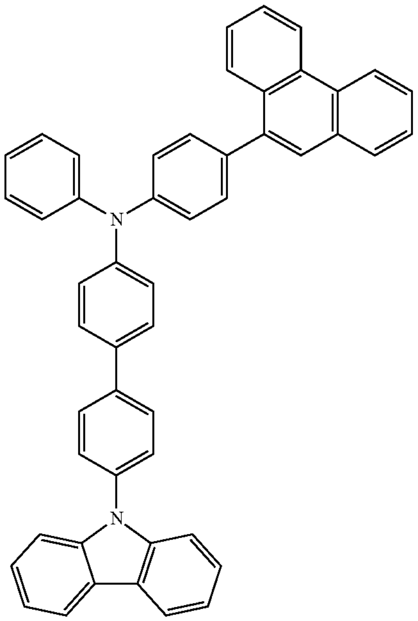
C-1-18
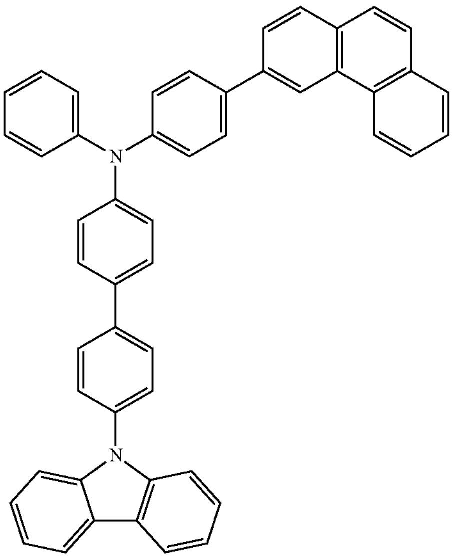
-continued
C-1-19
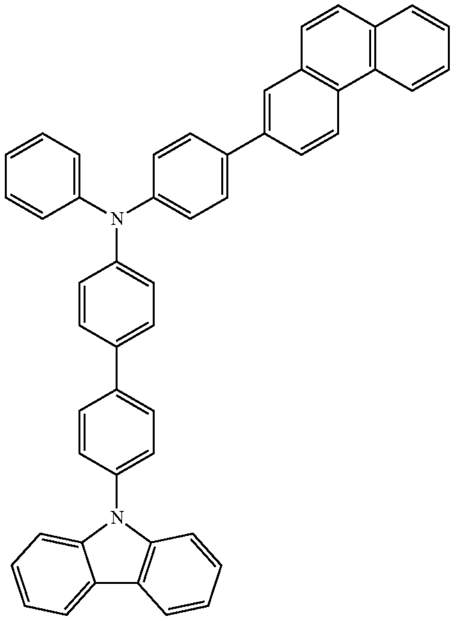
C-1-20
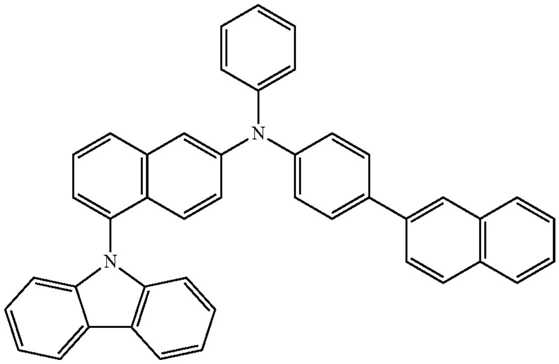
C-1-21
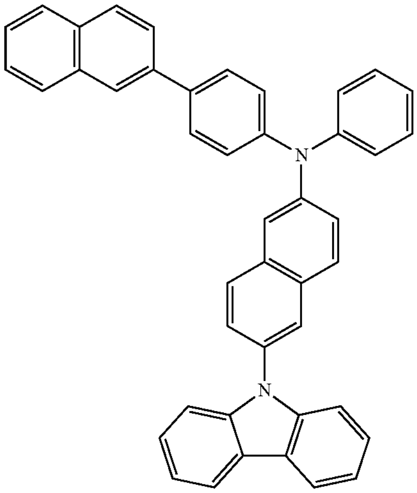

-continued
C-1-22
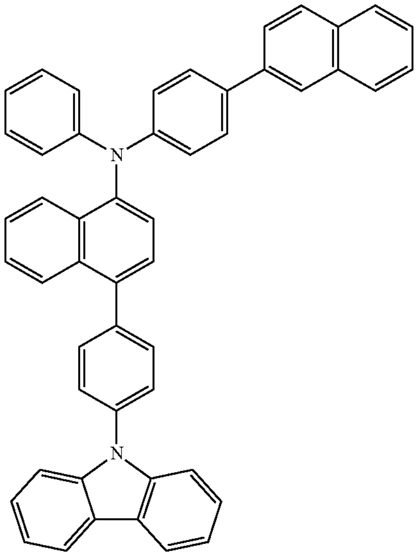
C-1-23
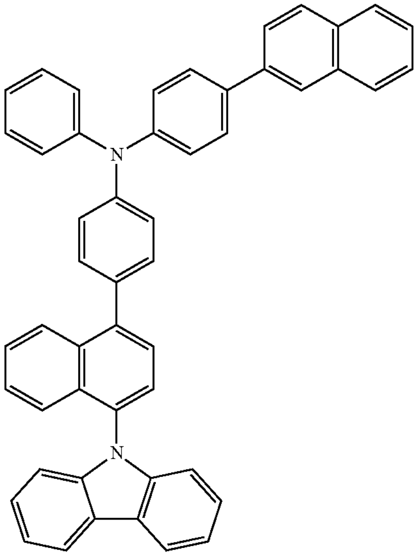
-continued
C-1-24
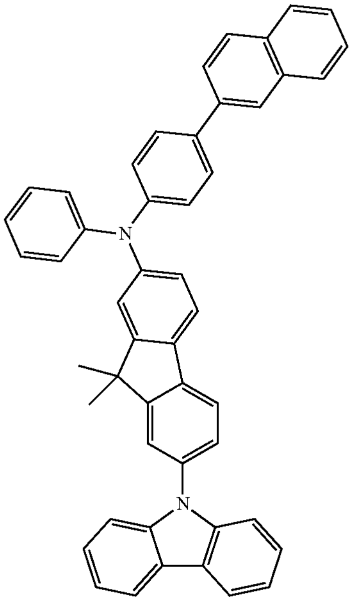
C-1-25
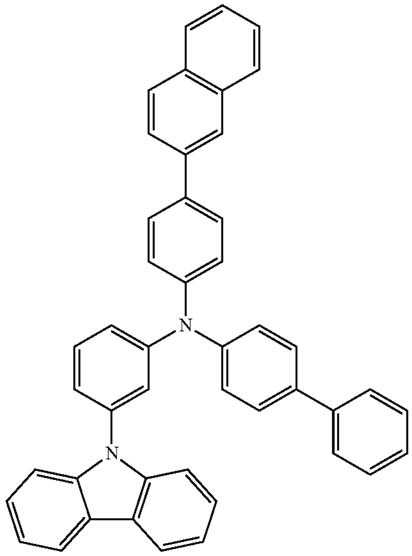

-continued
C-1-26
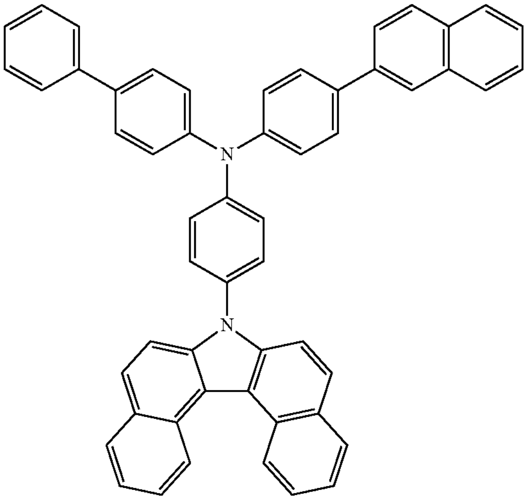
C-1-27
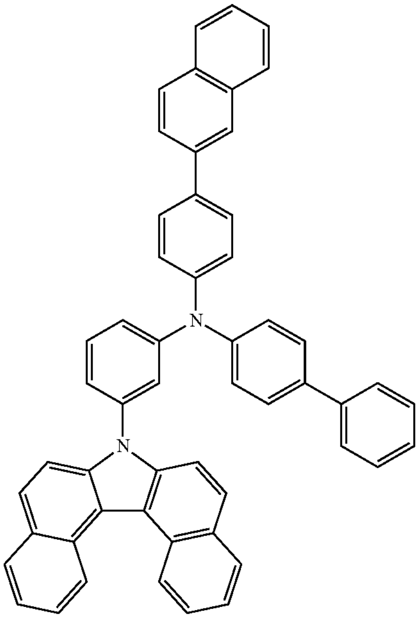
-continued
C-1-28
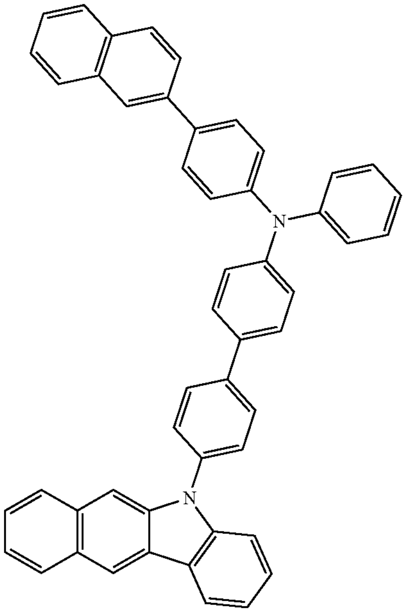
C-1-29
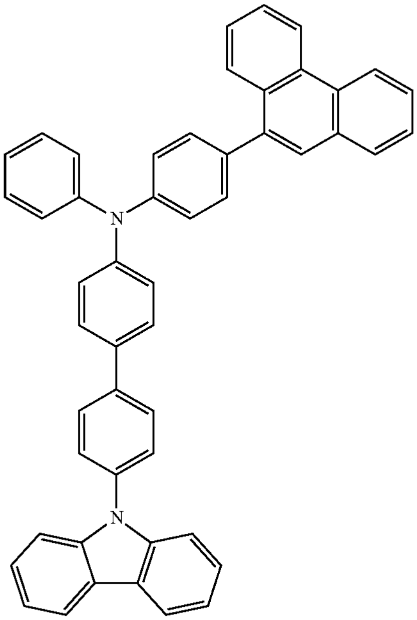

C-1-30
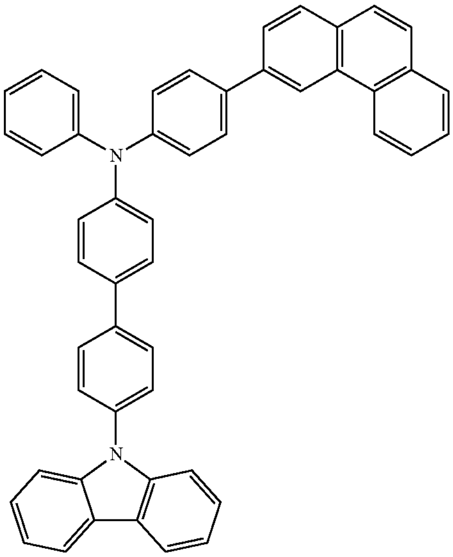
C-1-31
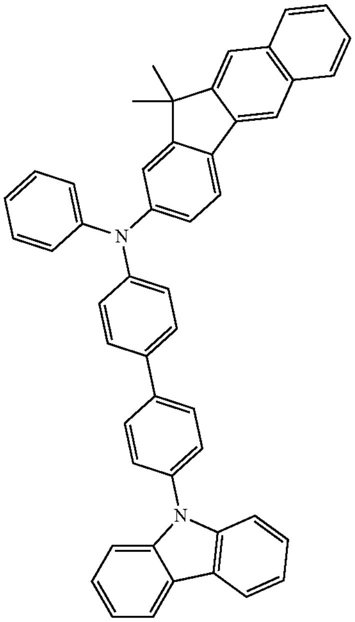
C-1-32
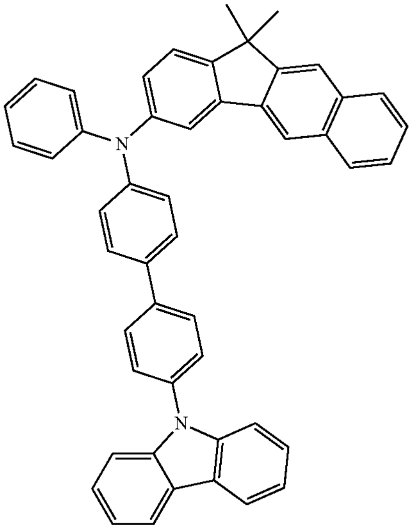
C-1-33
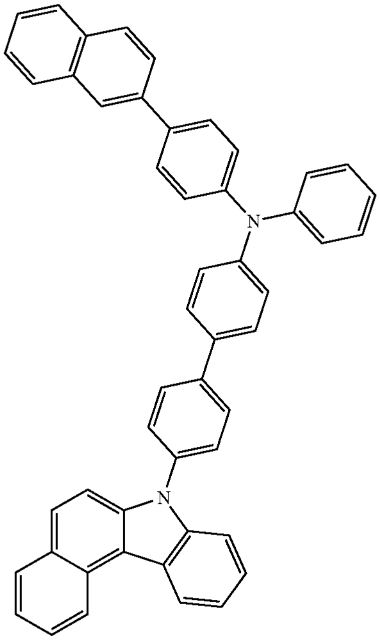

-continued
C-1-34
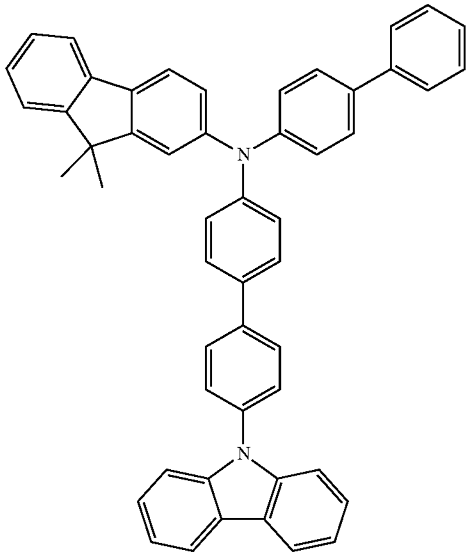
C-1-35
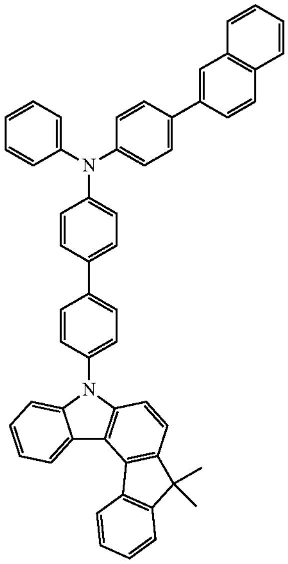
-continued
C-1-36
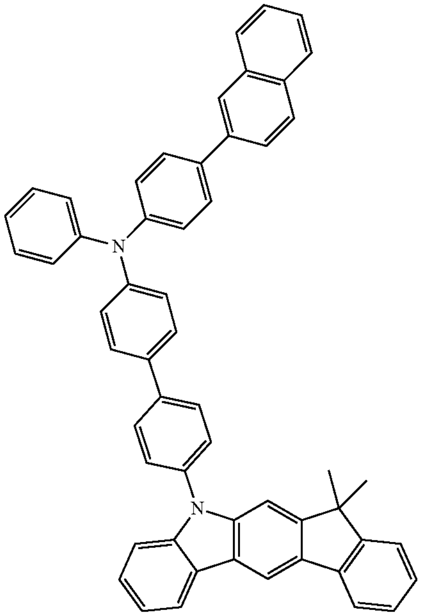
C-1-37
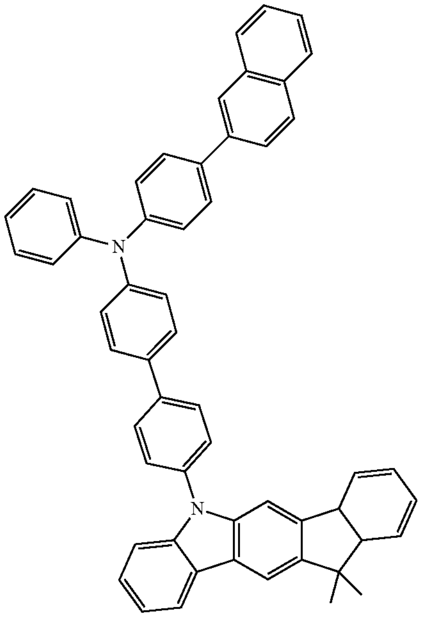
C-1-38
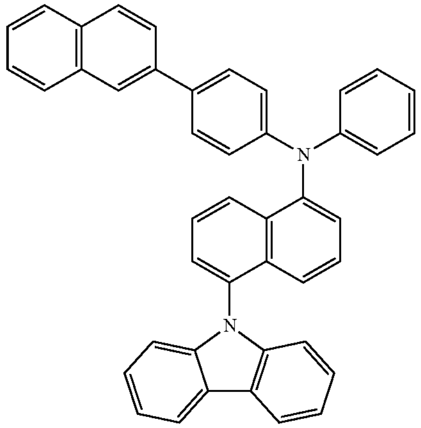

-continued
C-1-39
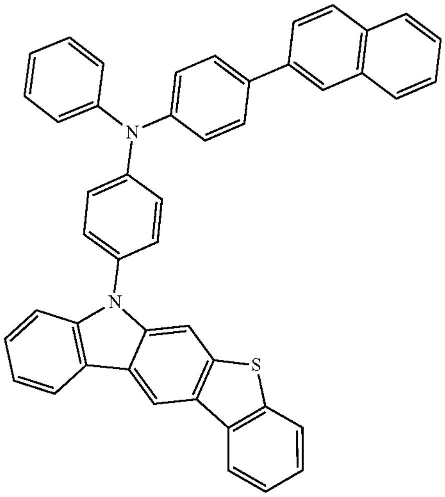
C-1-40
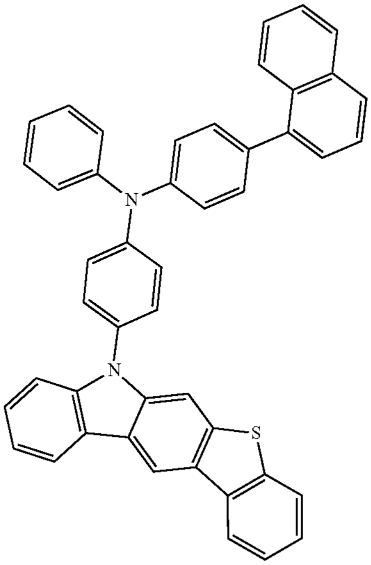
C-1-41
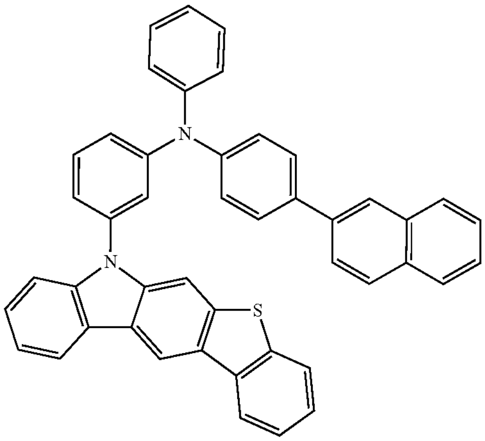
-continued
C-1-42
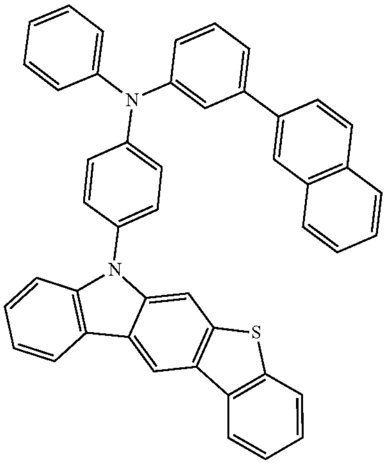
C-1-43
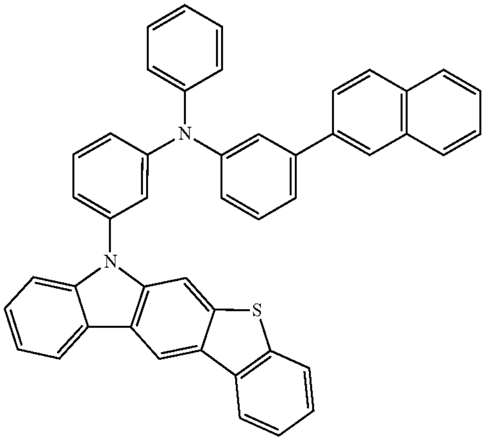
C-1-44
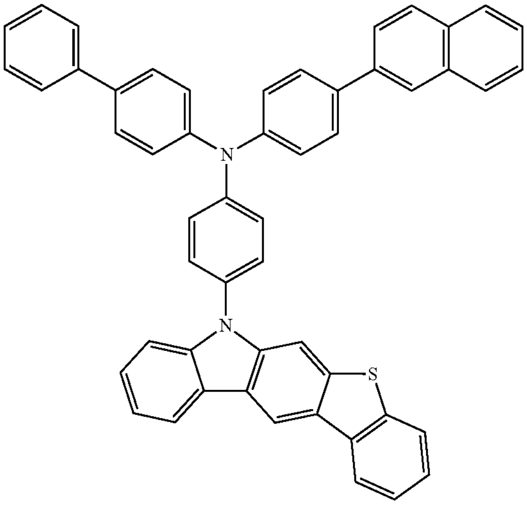

-continued
C-1-45
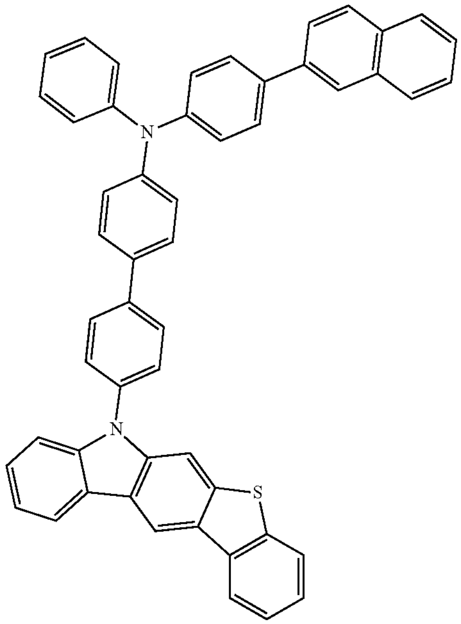
C-1-46
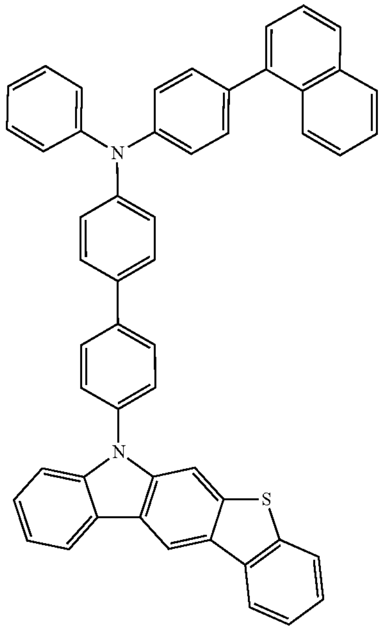
-continued
C-1-47
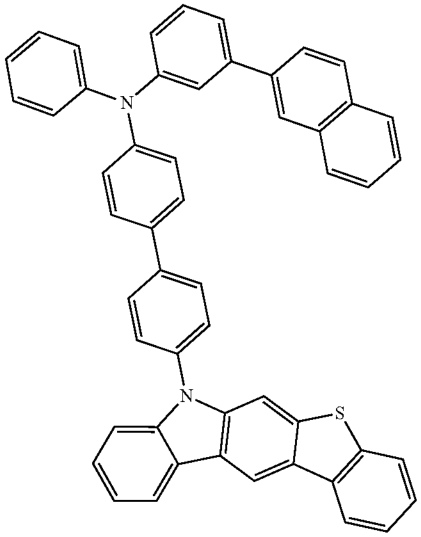
C-1-48
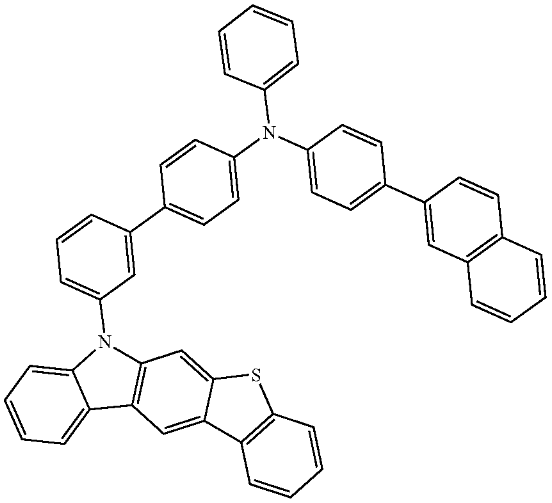
C-1-49
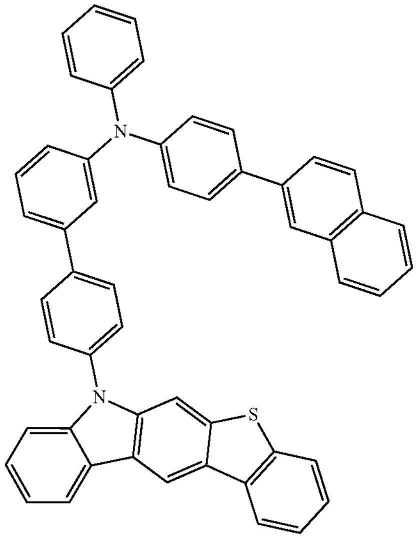

-continued
C-1-50
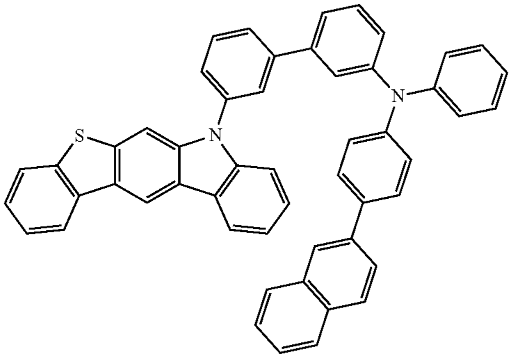
C-1-51
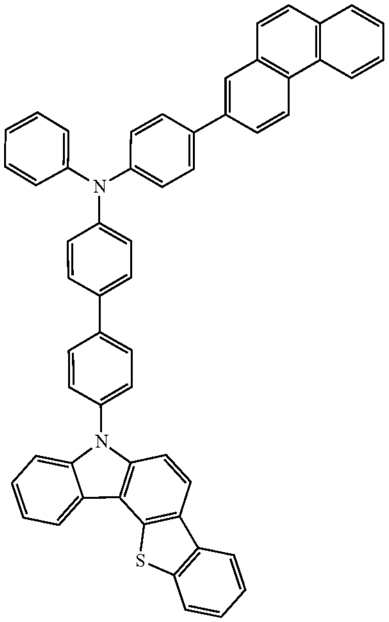
C-1-52
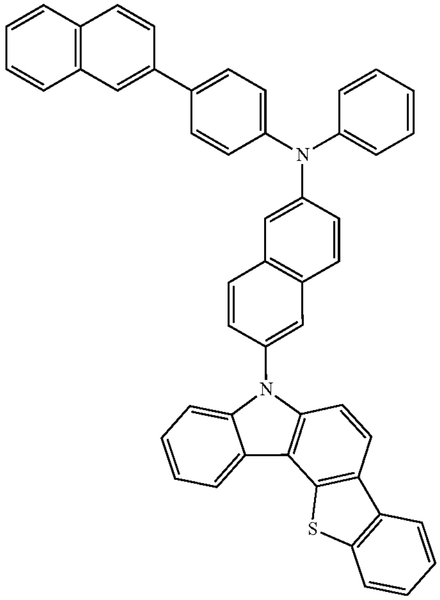
-continued
C-1-53
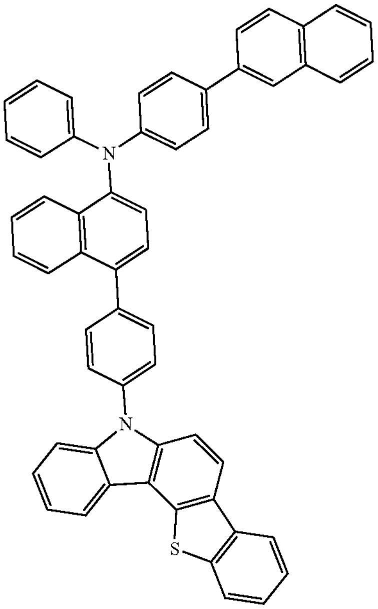
C-1-54
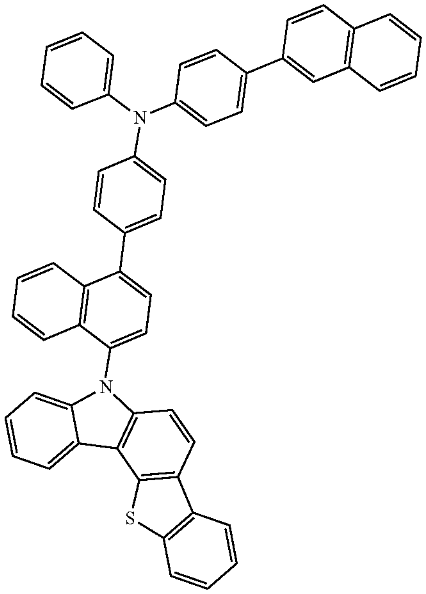

-continued
C-1-55
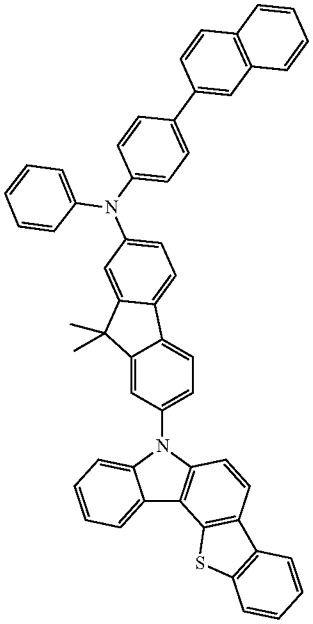
C-1-56
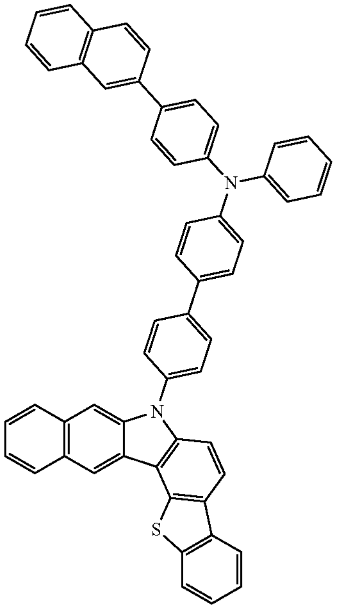
-continued
C-1-57
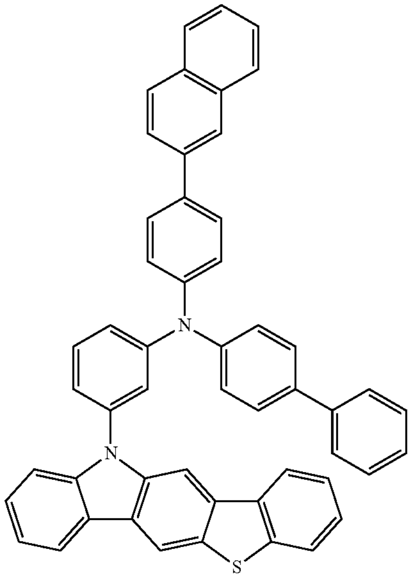
C-1-58
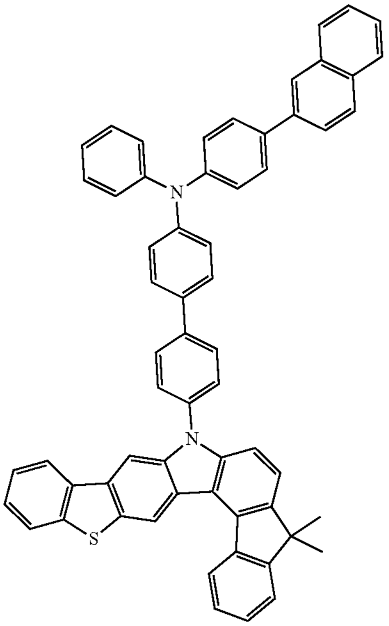

-continued
C-1-59
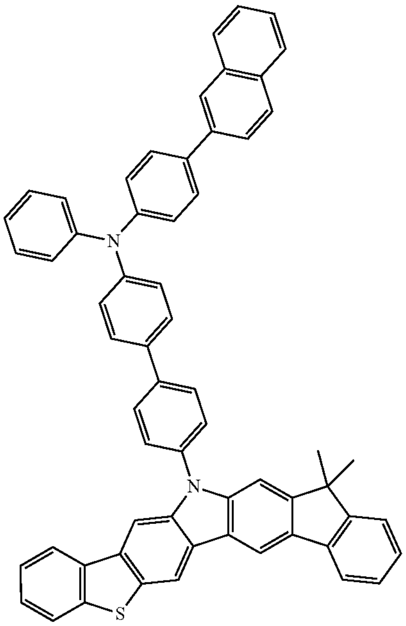
C-1-60
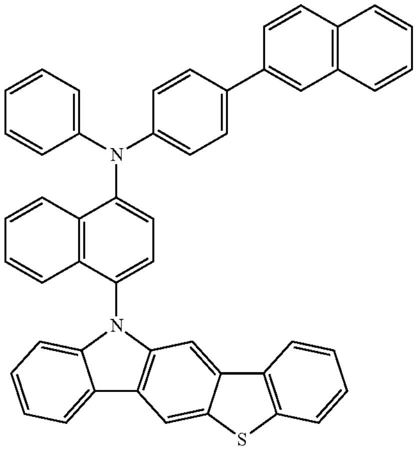
-continued
C-1-61
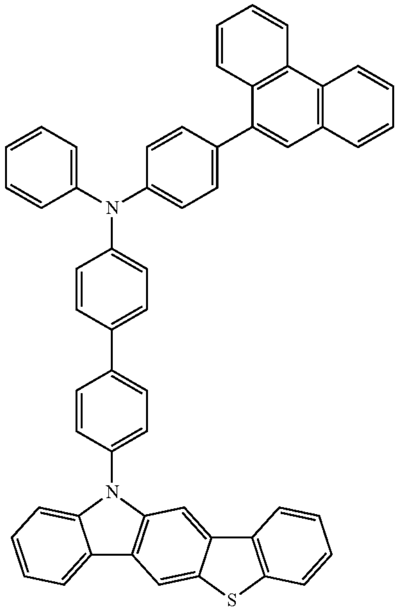
C-1-62
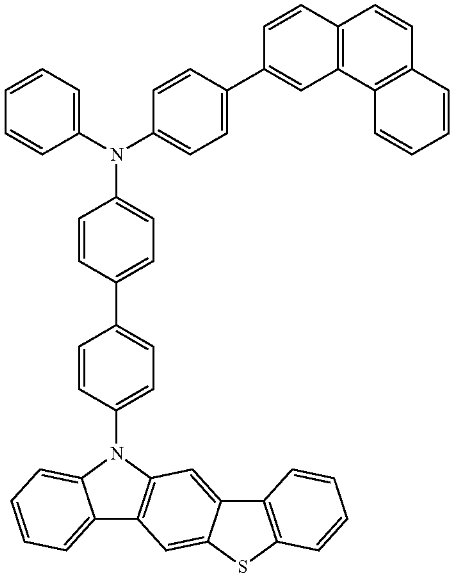
C-1-63
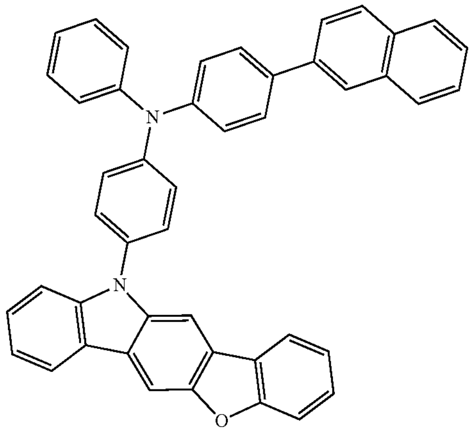

-continued
C-1-64
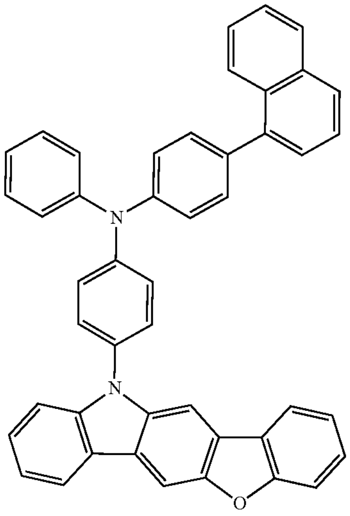
C-1-65
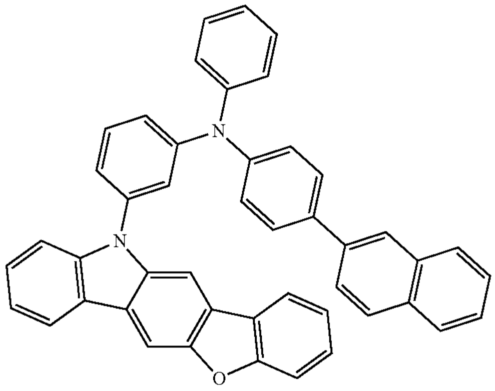
C-1-66
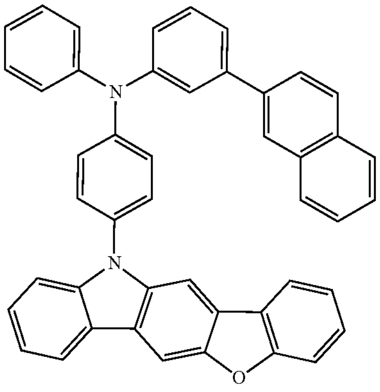
-continued
C-1-67
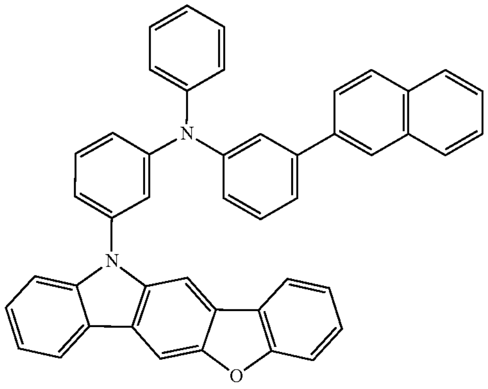
C-1-68
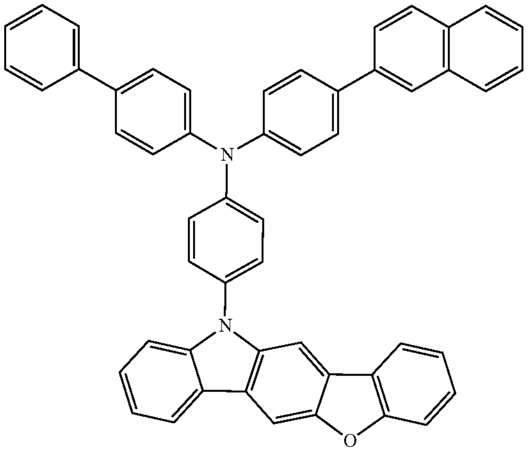
C-1-69
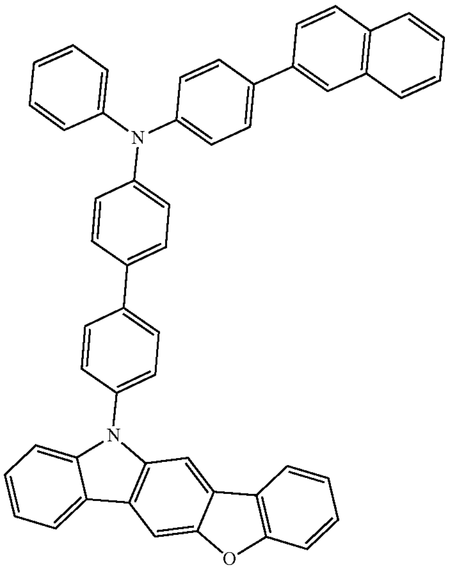

-continued
C-1-70
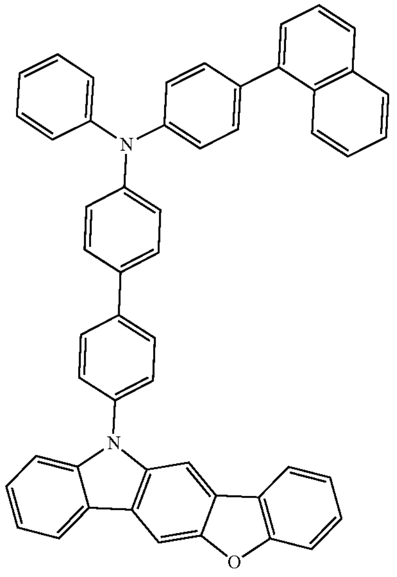
C-1-71
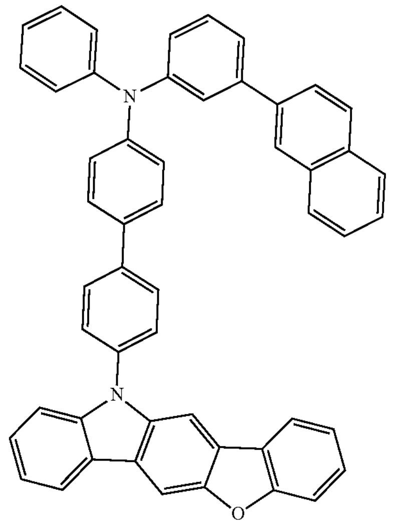
C-1-72
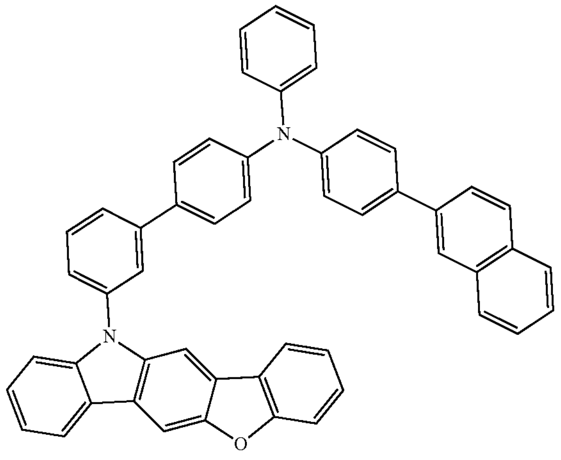
-continued
C-1-73
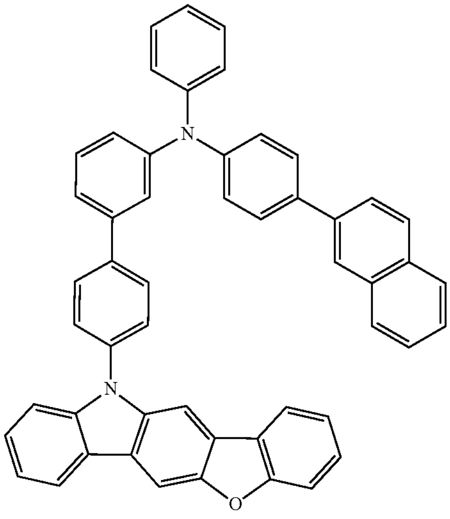
C-1-74
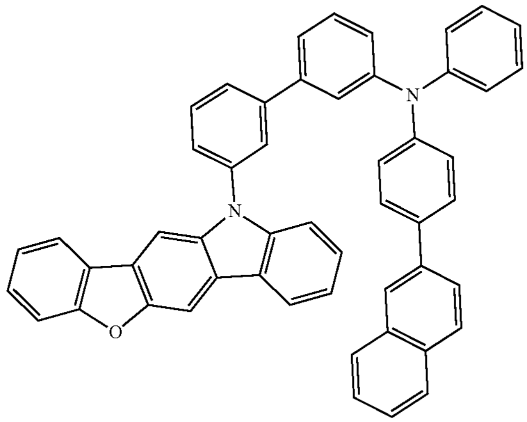
C-1-75
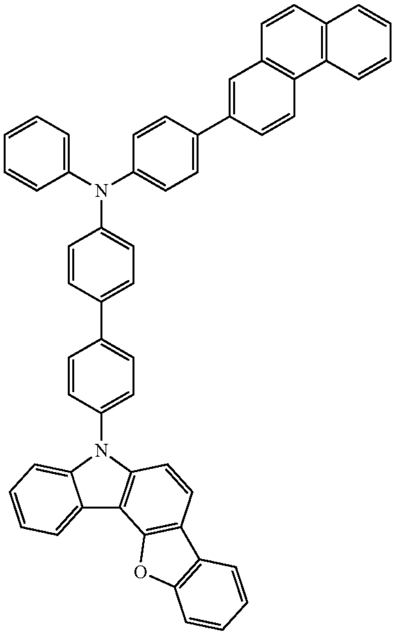

-continued
C-1-76
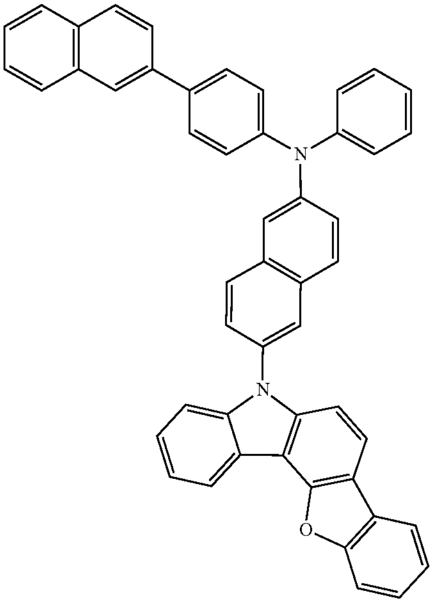
C-1-77
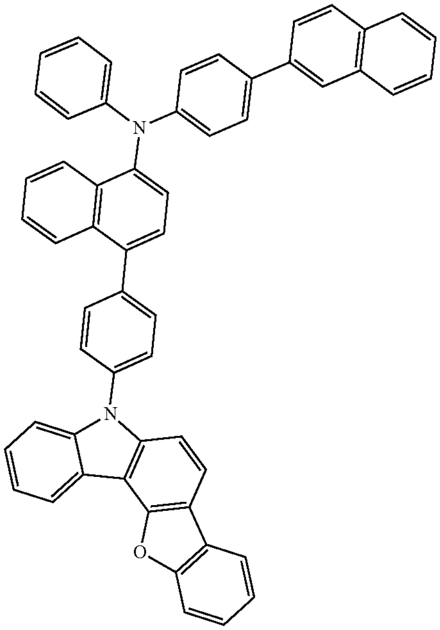
-continued
C-1-78
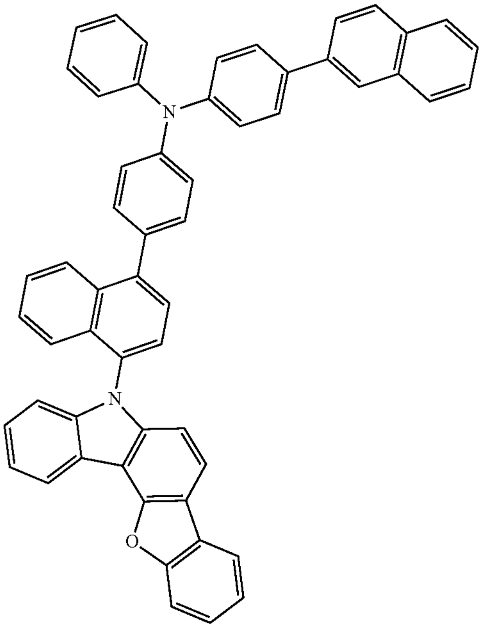
C-1-79
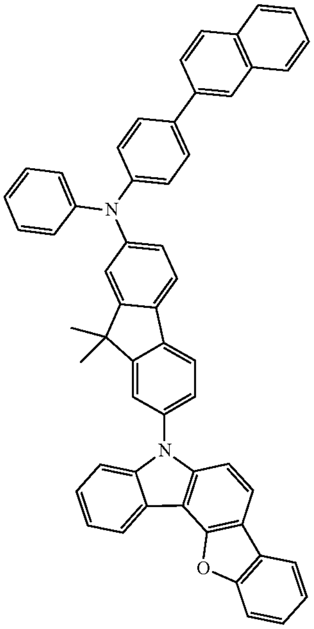

-continued
C-1-80
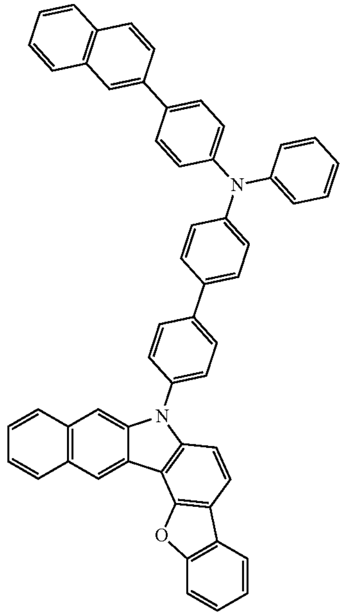
C-1-81
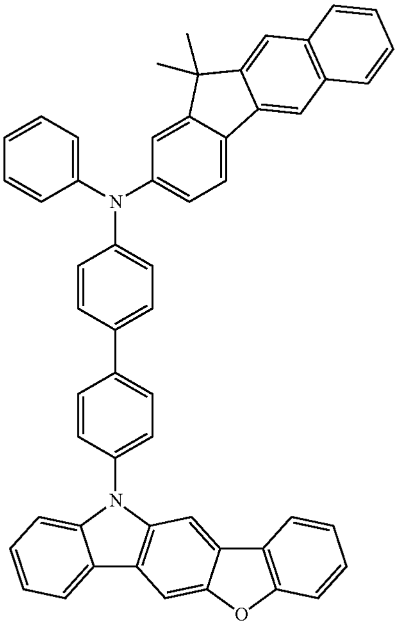
-continued
C-1-82
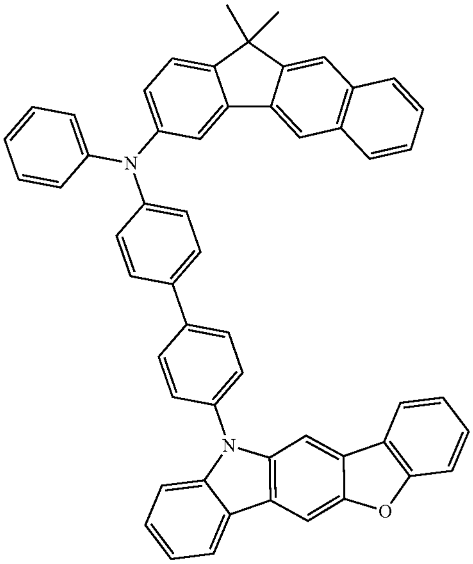
C-1-83
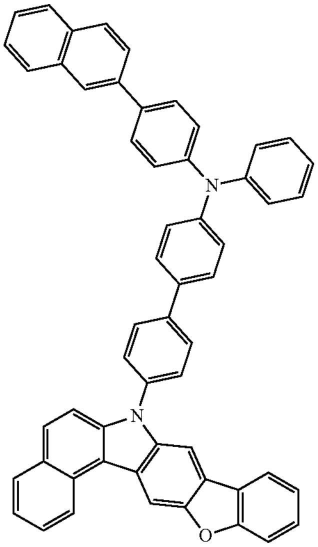

-continued
C-1-84
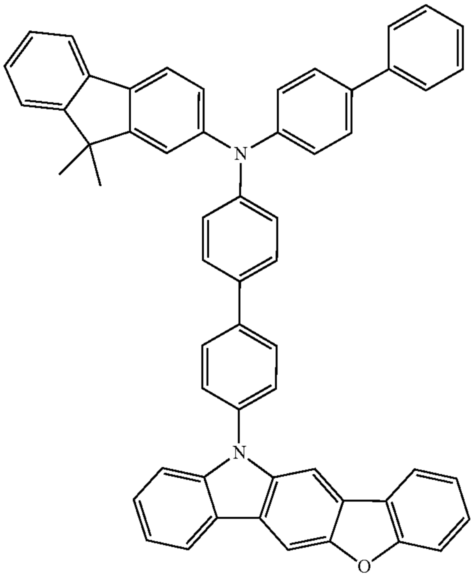
C-1-85
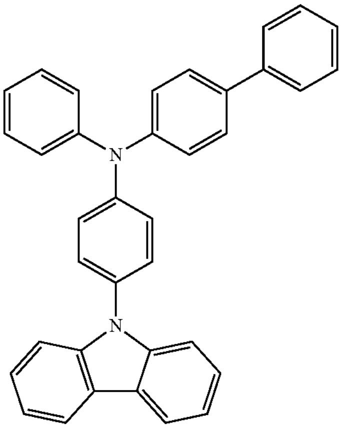
C-1-86
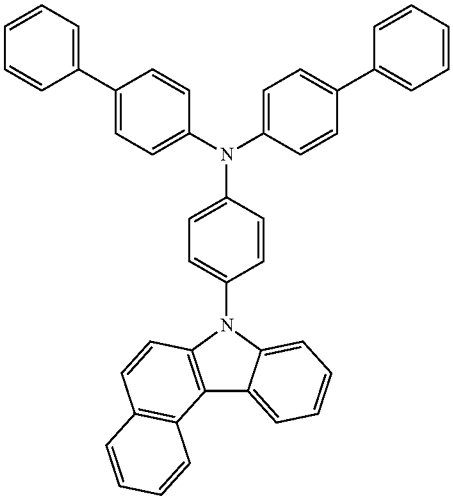
-continued
C-1-87
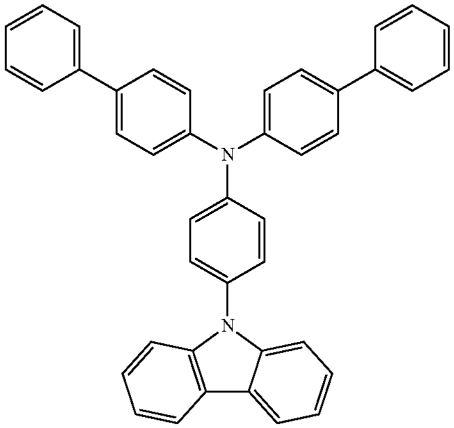
C-1-88
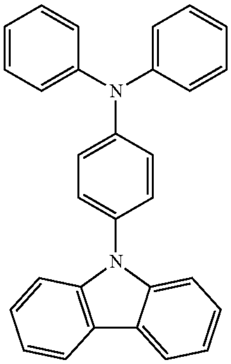
C-1-89
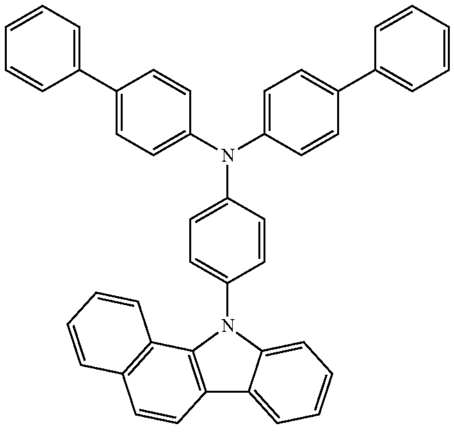

-continued
C-1-90
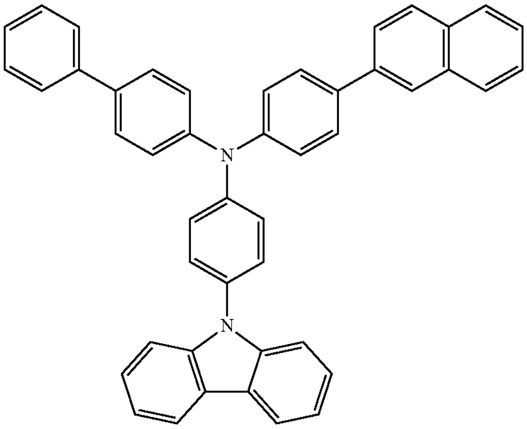
C-1-91
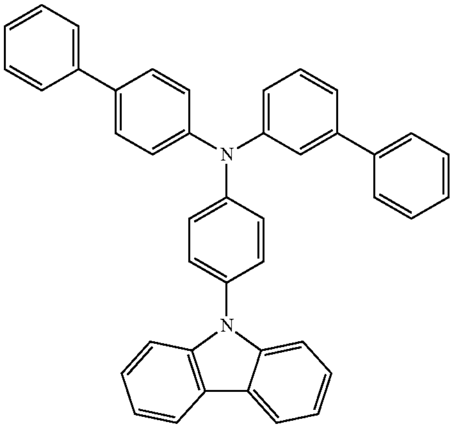
C-1-92
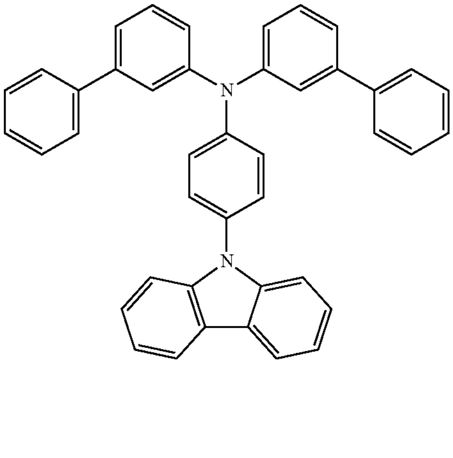
-continued
C-1-93
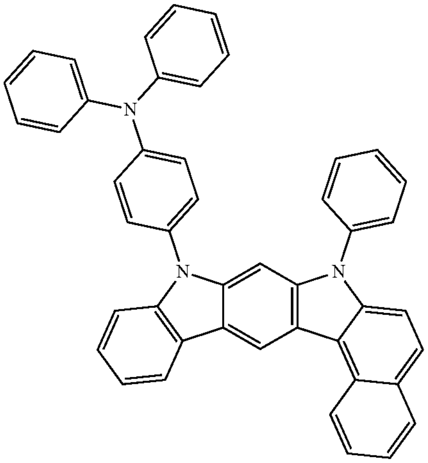
C-1-94
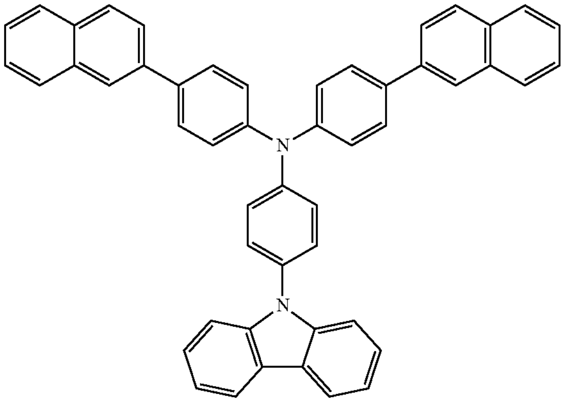
C-1-95
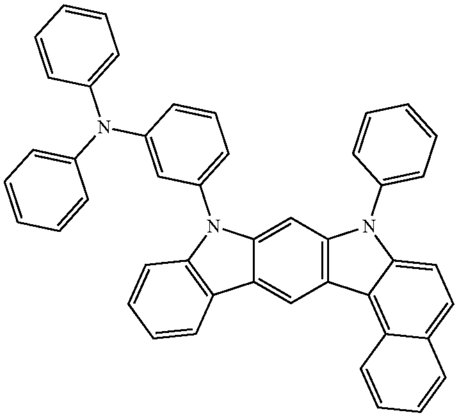

-continued
C-1-96
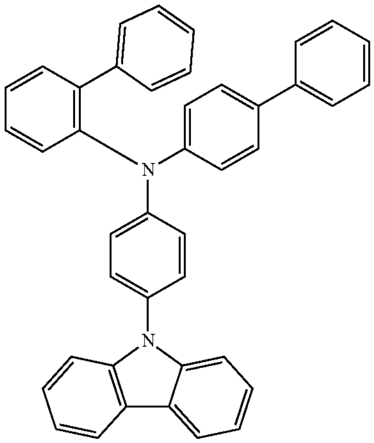
C-1-97
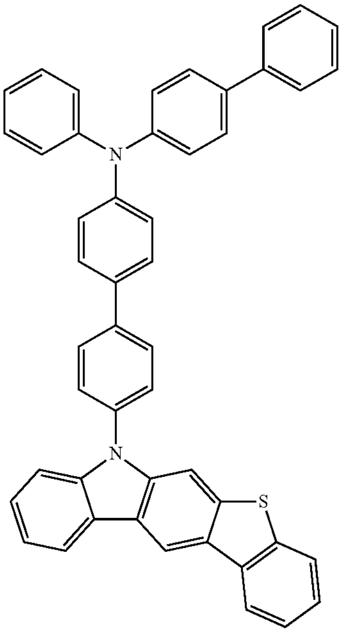
C-1-98
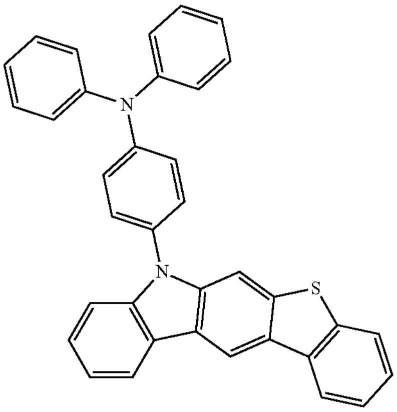
-continued
C-1-99
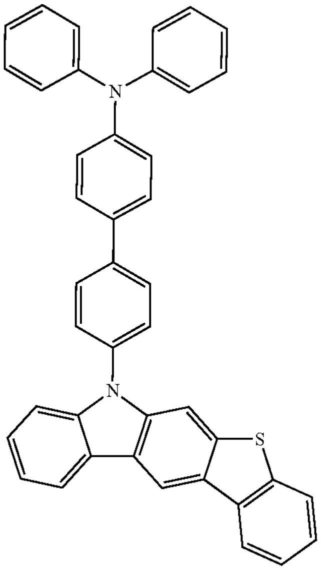
C-1-100
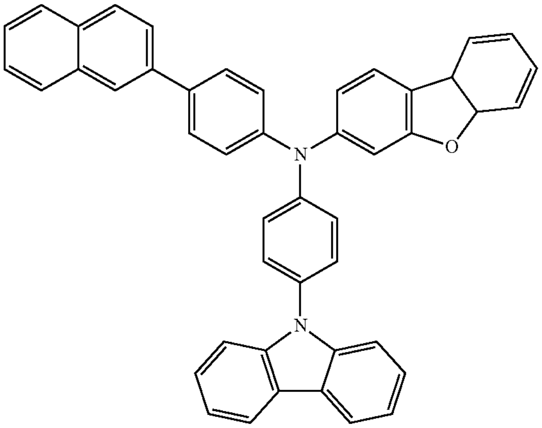
C-1-101
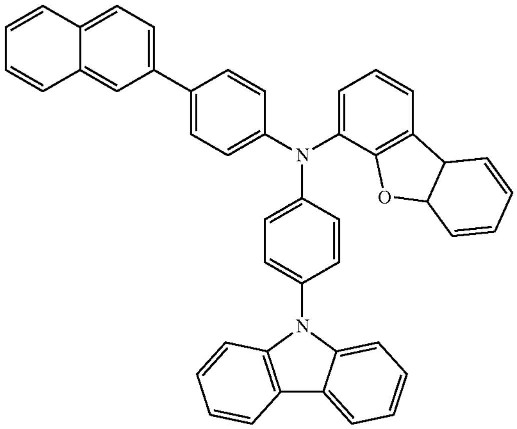

-continued
C-1-102
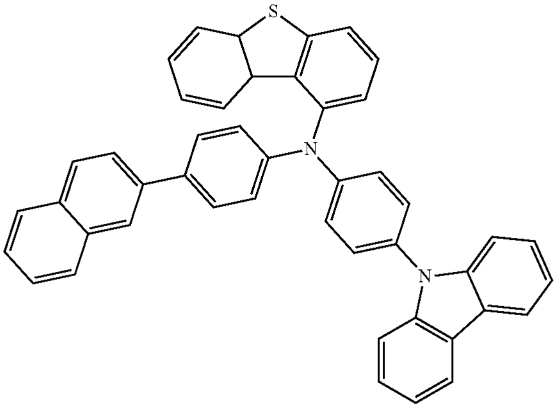
C-1-103
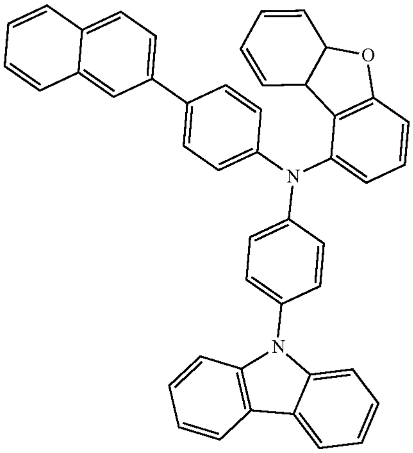
C-1-104
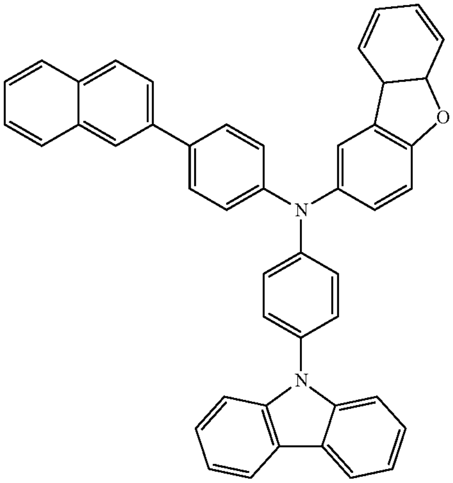
-continued
C-1-105
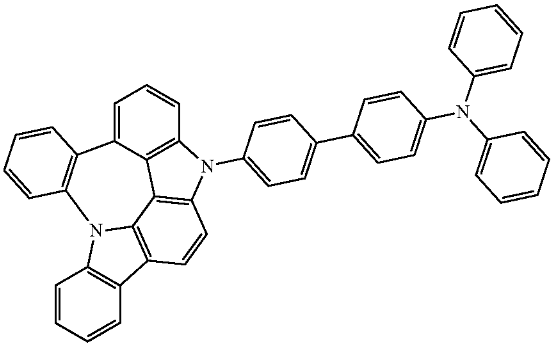
C-1-106
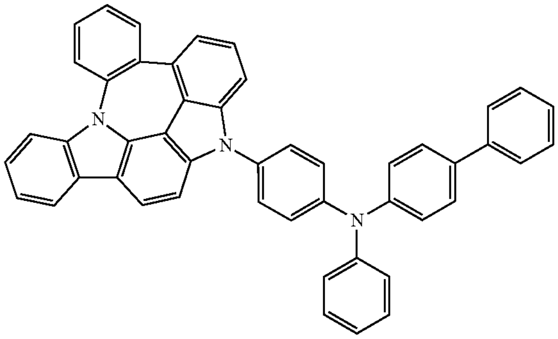
C-1-107
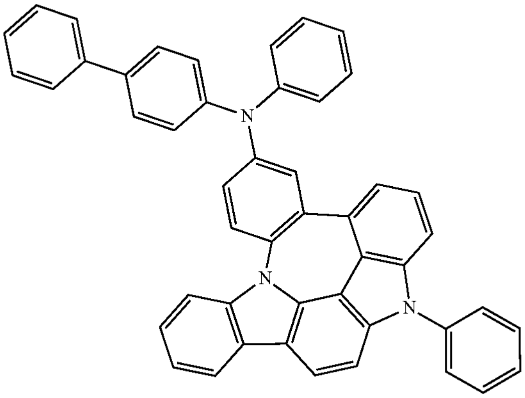
C-1-108
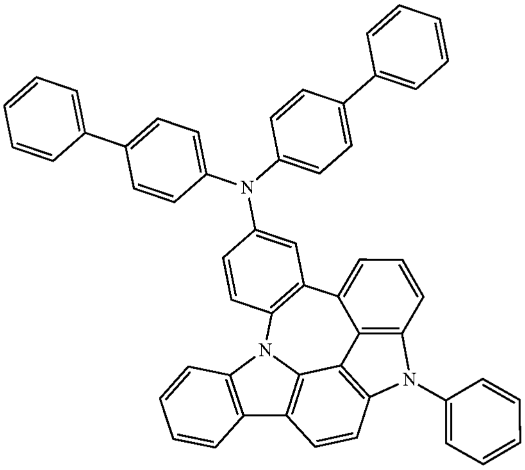

-continued
C-1-109
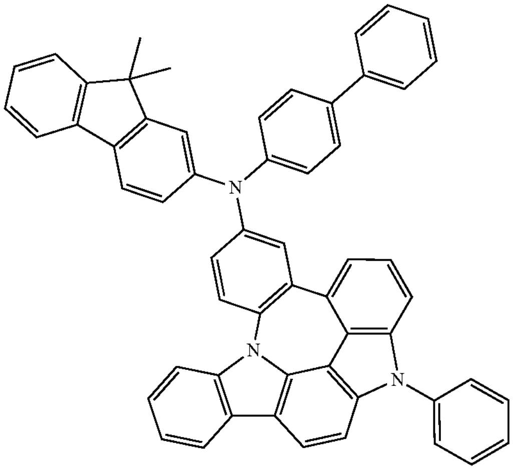
C-1-110
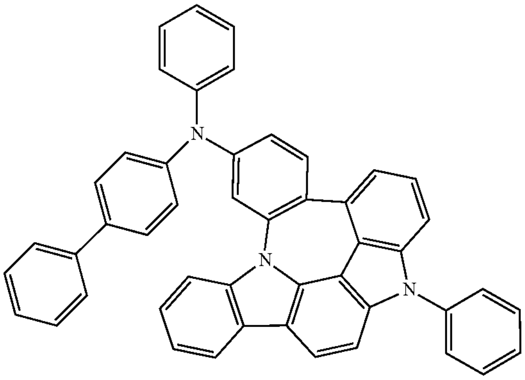
C-1-111
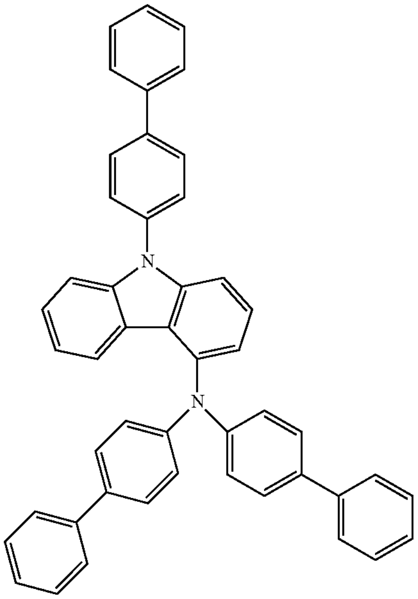
-continued
C-1-112
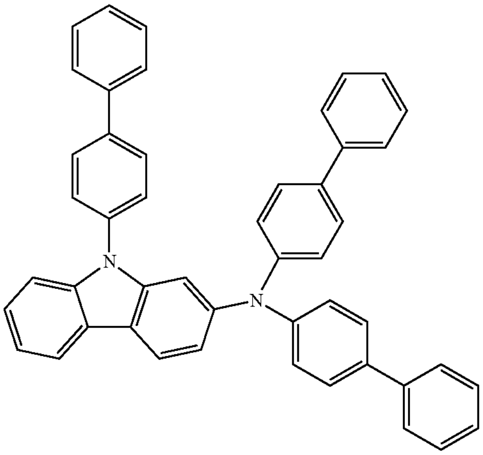
C-1-113
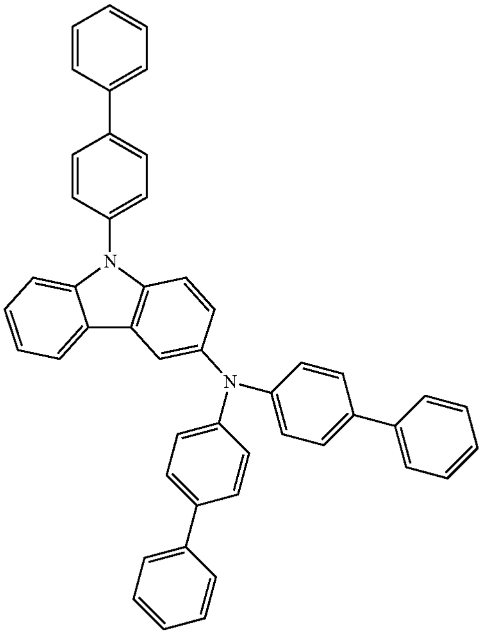

-continued
C-1-114
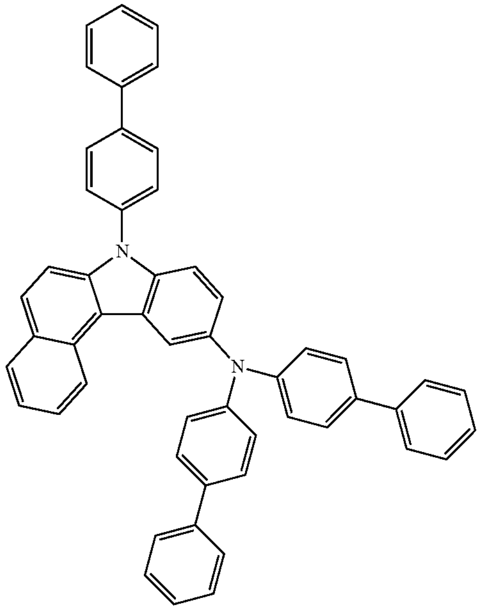
C-1-115
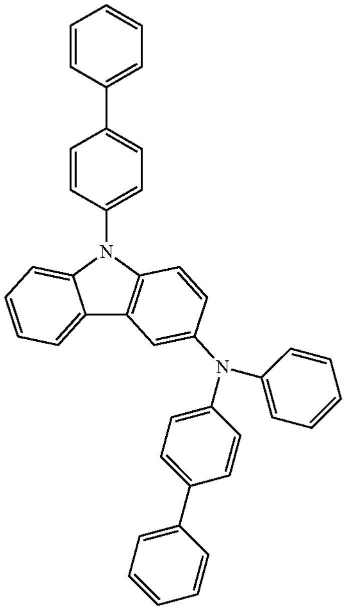
-continued
C-1-116
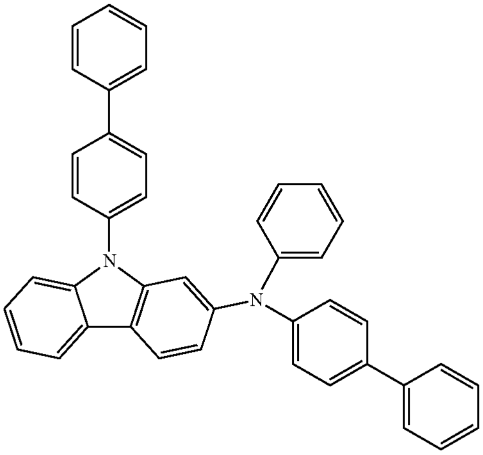
C-1-117
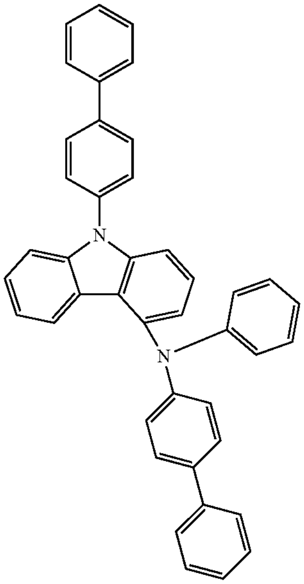
C-1-118
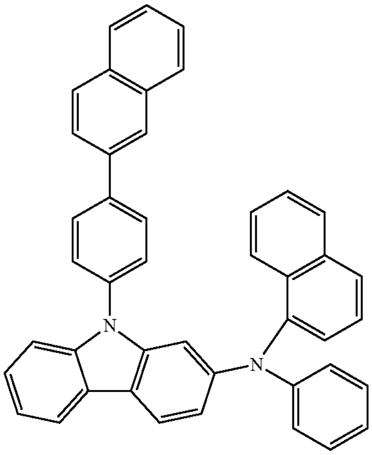

-continued
C-1-119
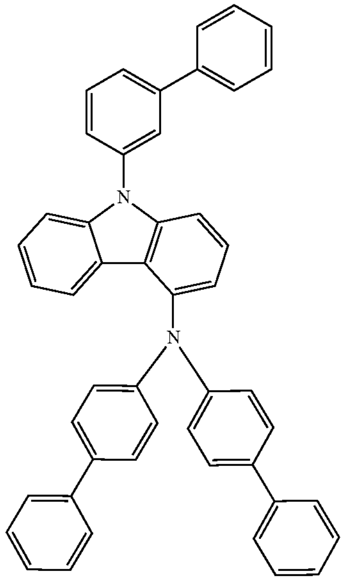
C-1-120
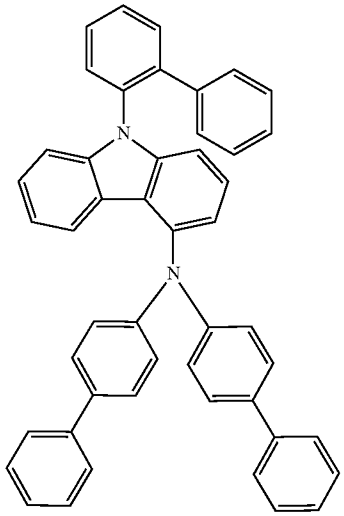
-continued
C-1-121
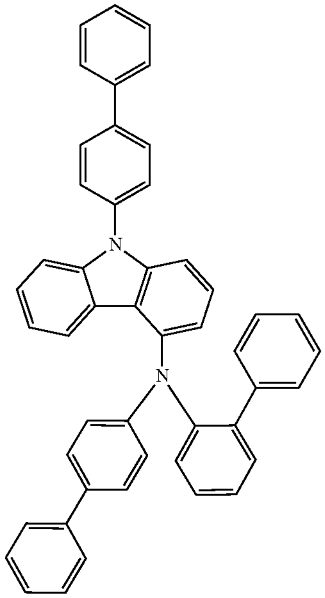
C-1-122
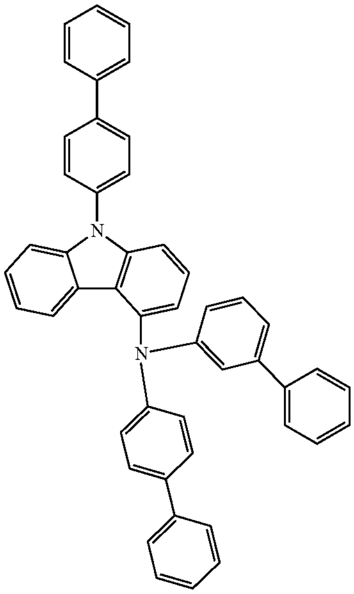

-continued
C-1-123
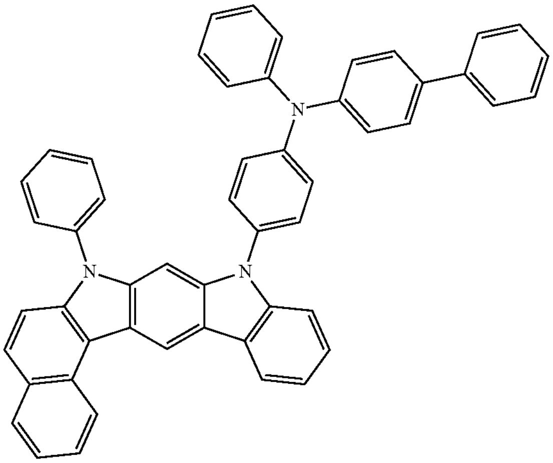
C-1-124
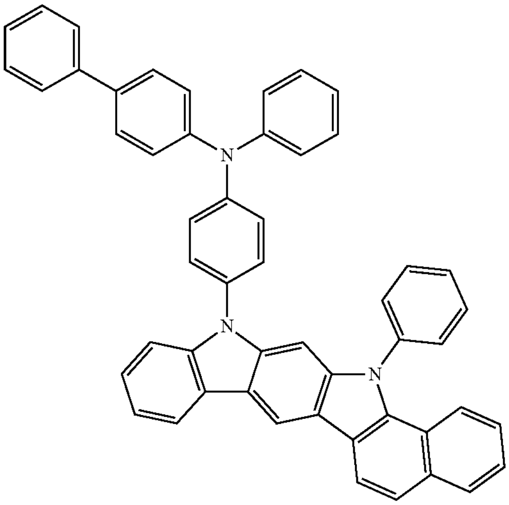
C-1-125
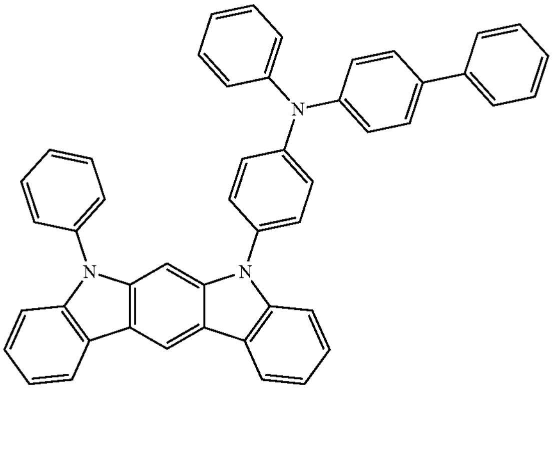
-continued
C-1-126
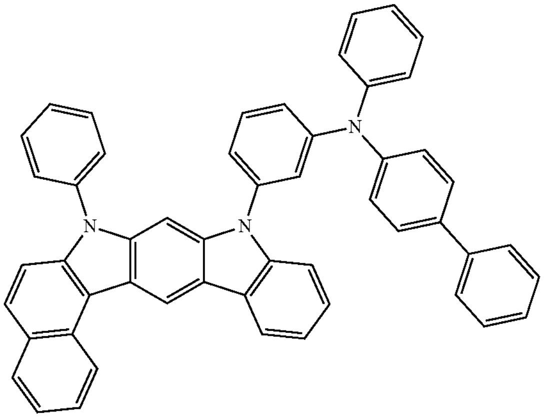
C-1-127
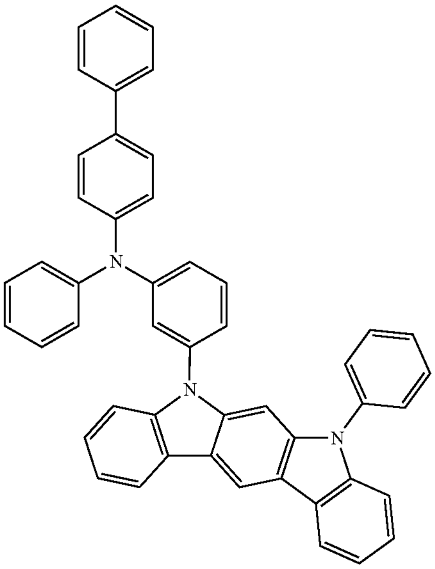
The compound represented by formula 2 includes the following compounds, but is not limited thereto.
C-1
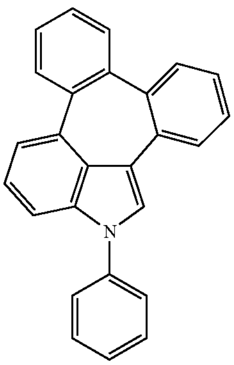

-continued
C-2
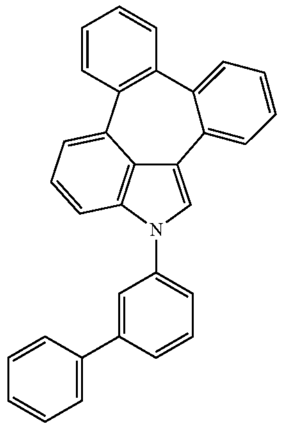
C-3
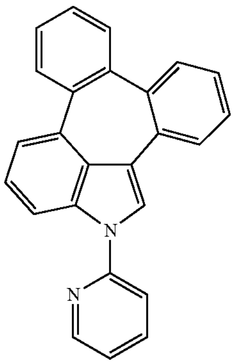
C-4
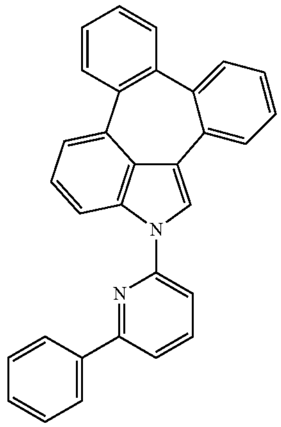
C-5
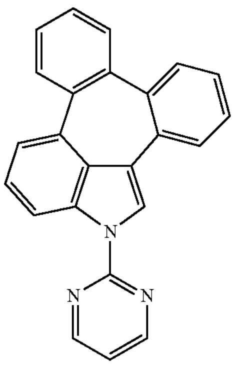
-continued
C-6
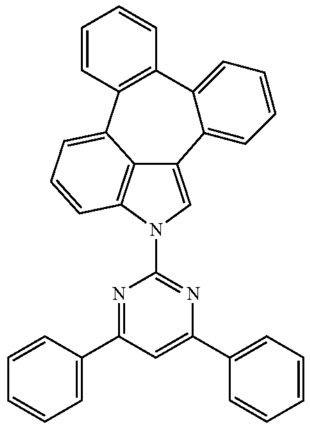
C-7
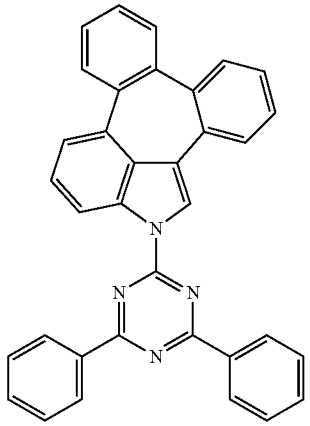
C-8
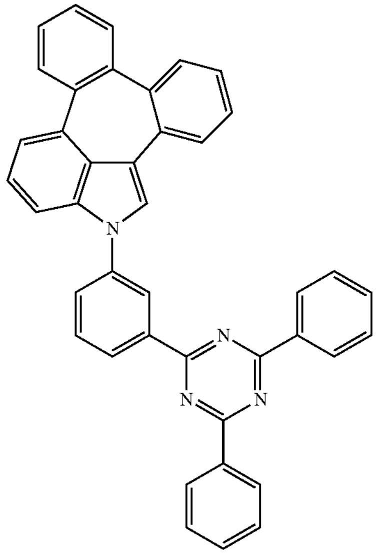

-continued
C-9
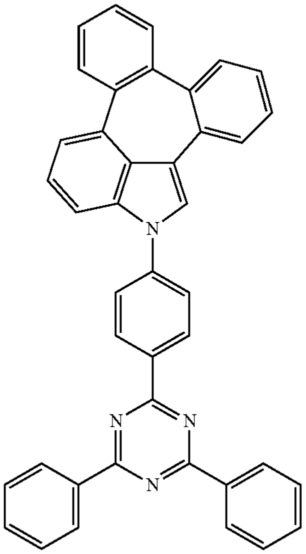
C-10
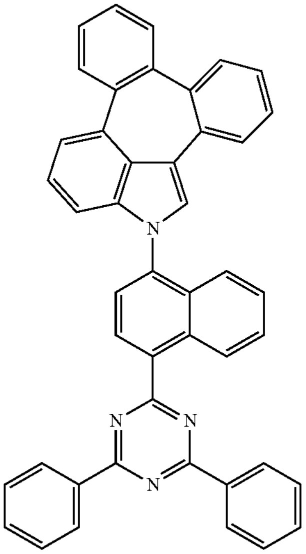
C-11
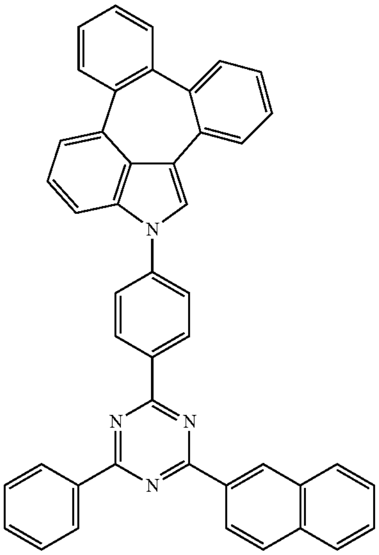
-continued
C-12
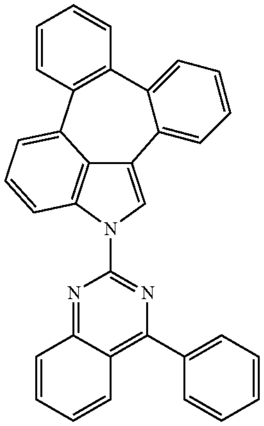
C-13
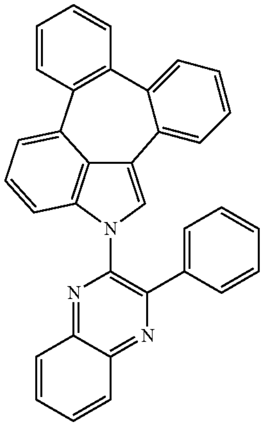
C-14
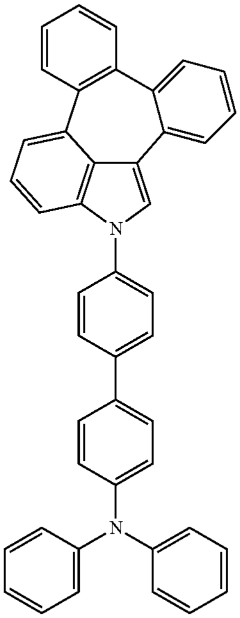

-continued
C-15
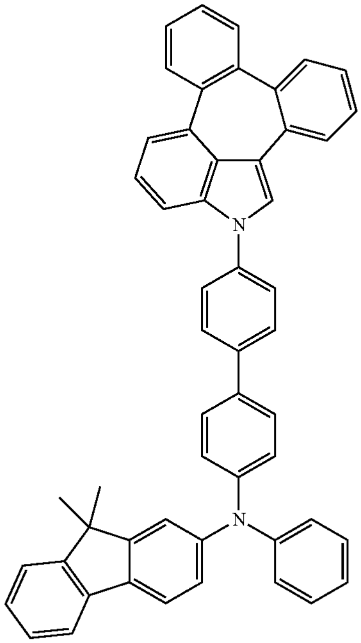
C-16
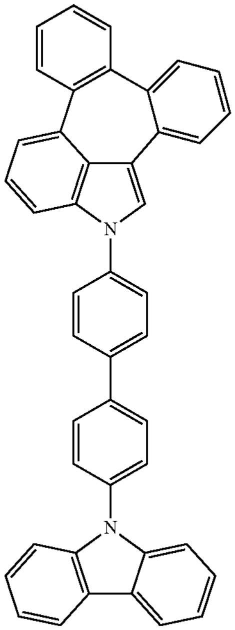
C-17
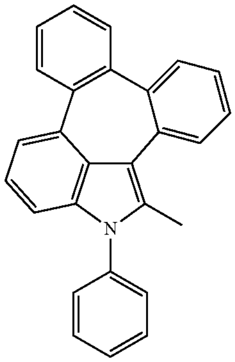
-continued
C-18
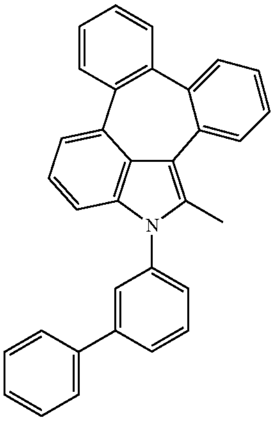
C-19
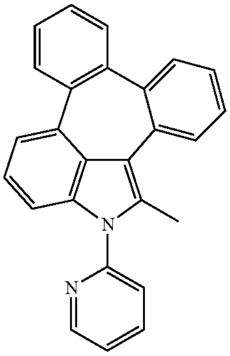
C-20
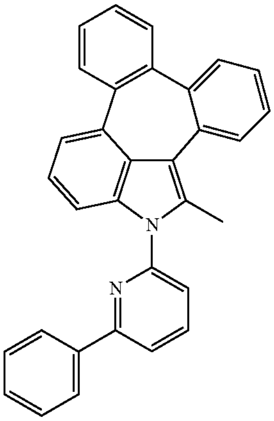
C-21
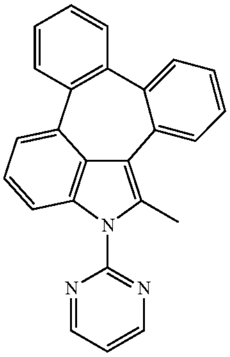

C-22
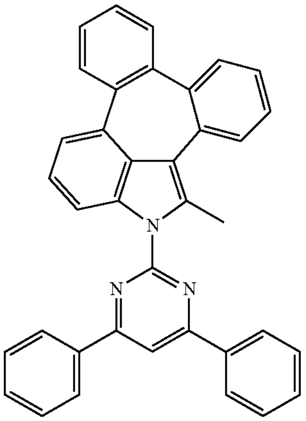
C-23
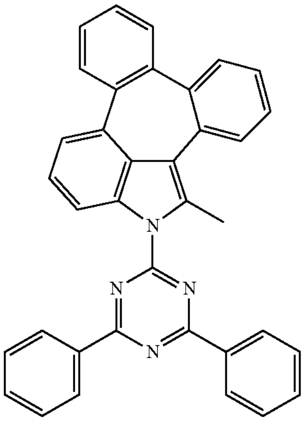
C-24
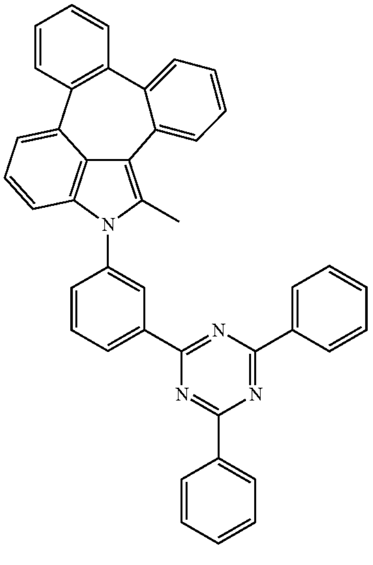
C-25
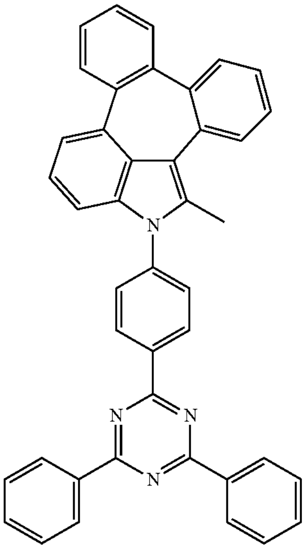
C-26
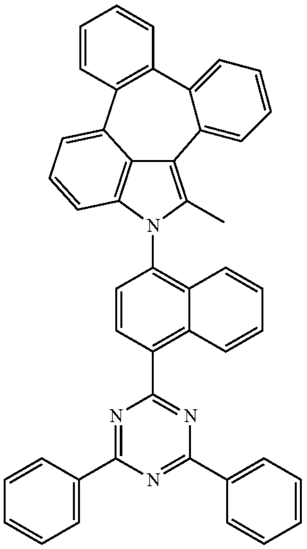
C-27
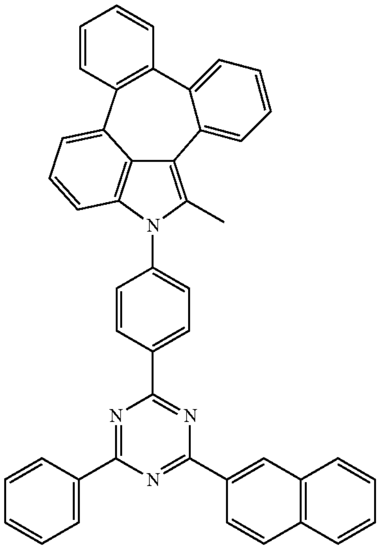

-continued
C-28
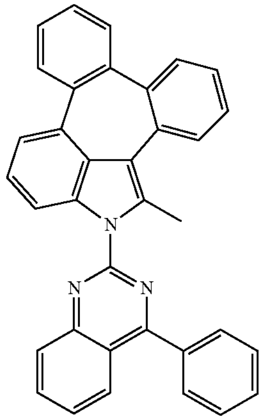
C-29
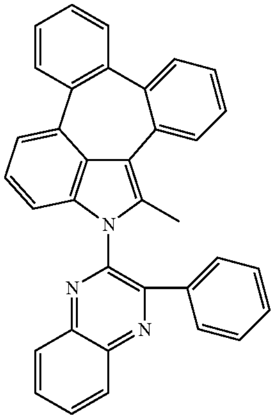
C-30
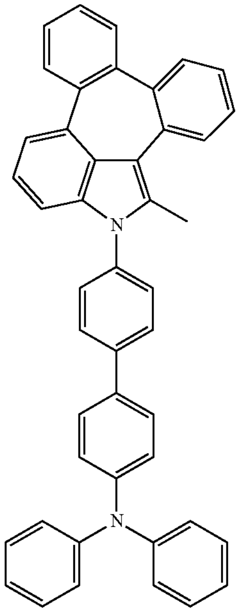
-continued
C-31
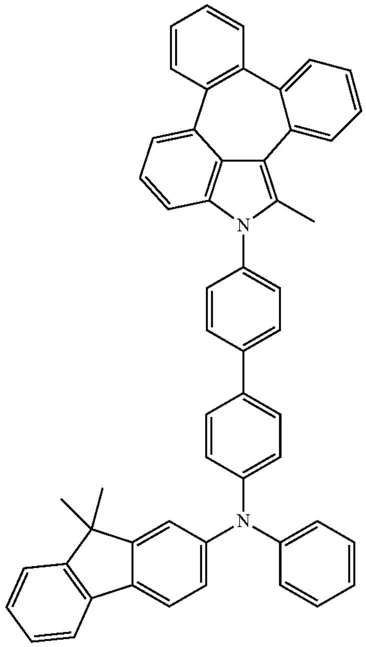
C-32
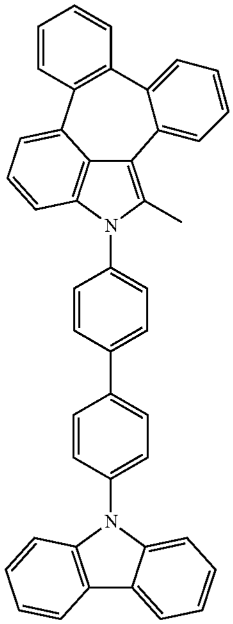
C-33
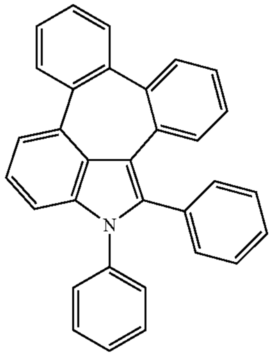

-continued
C-34
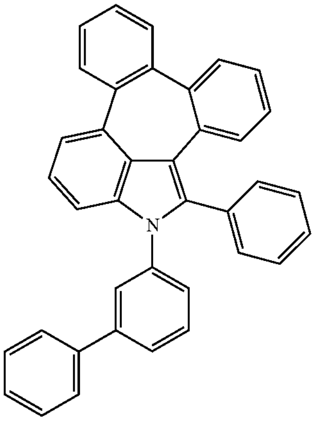
C-35
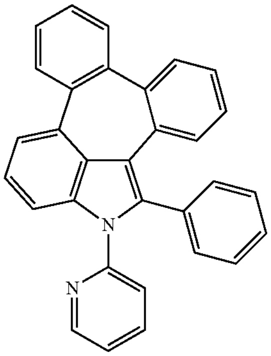
C-36
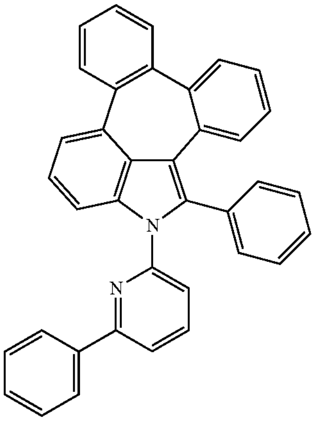
C-37
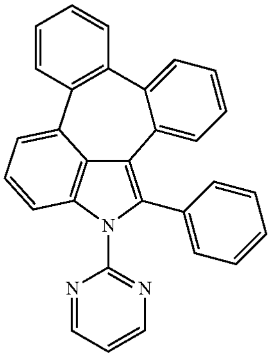
-continued
C-38
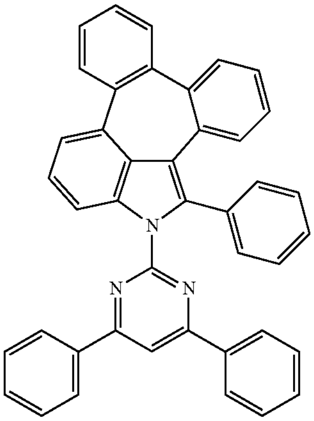
C-39
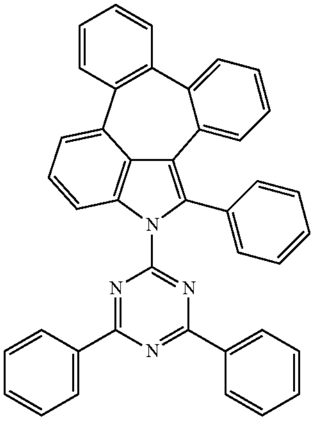
C-40
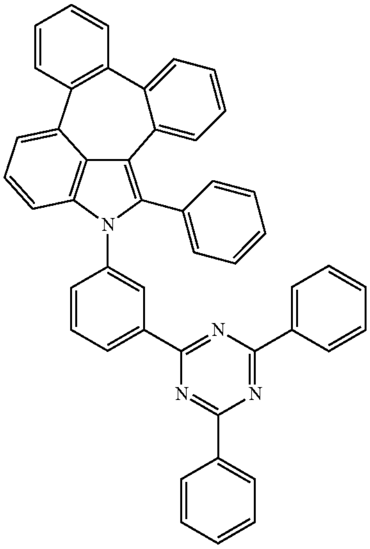

-continued
C-41
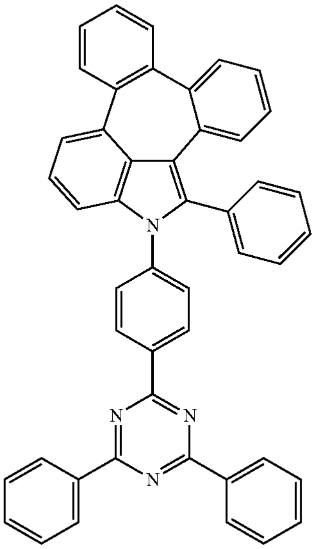
C-42
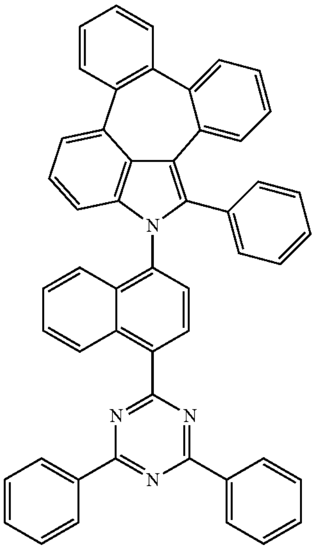
C-43
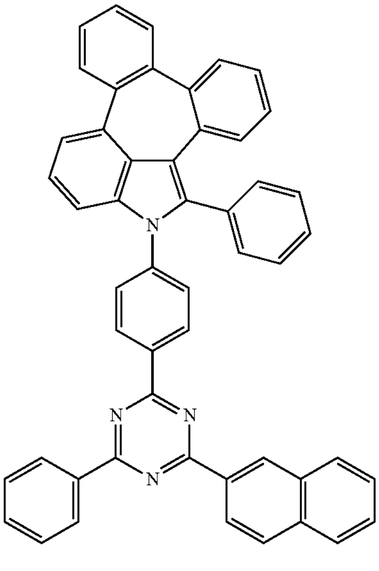
-continued
C-44
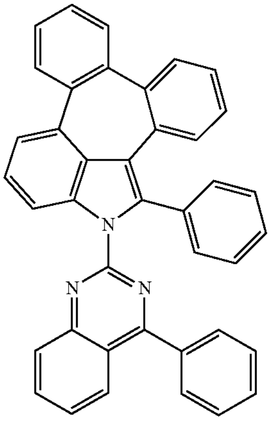
C-45
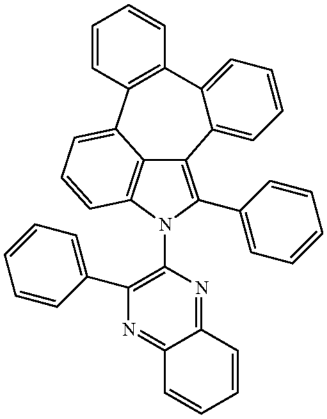
C-46
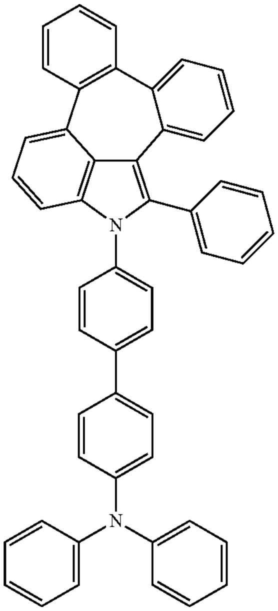

C-47
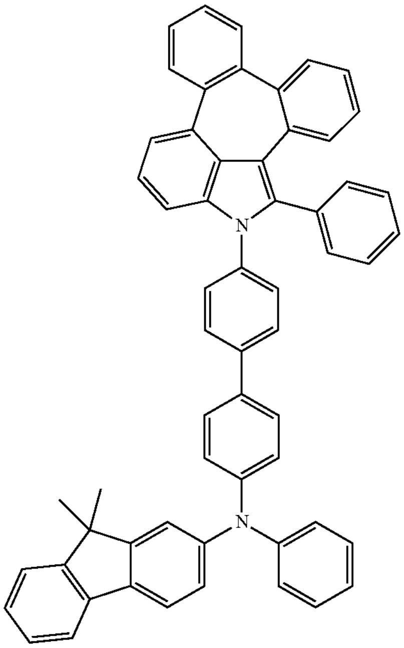
C-48
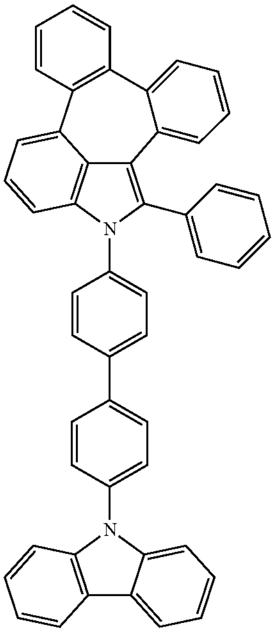
C-49
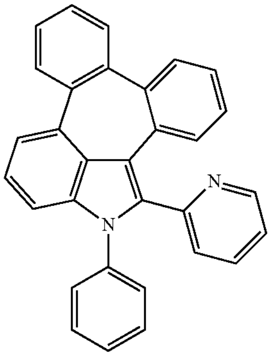
C-50
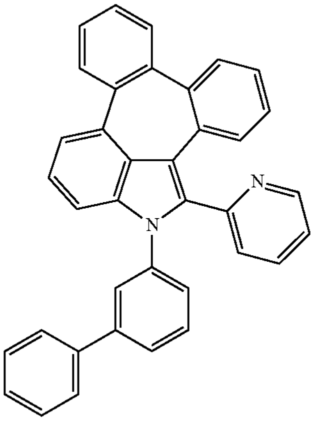
C-51
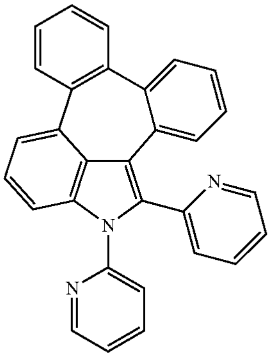
C-52
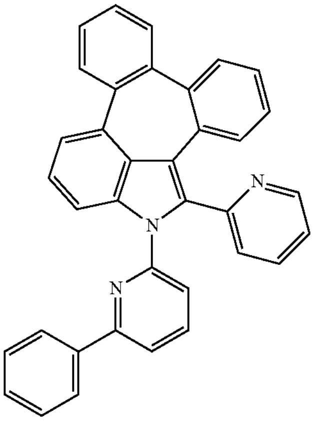
C-53
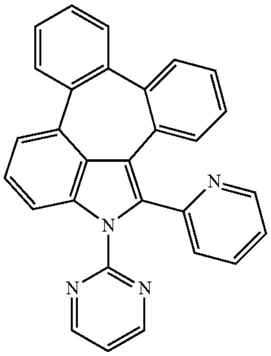

-continued
C-54
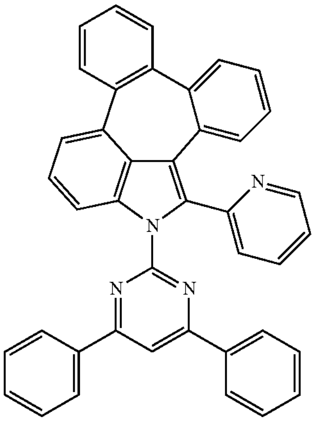
C-55
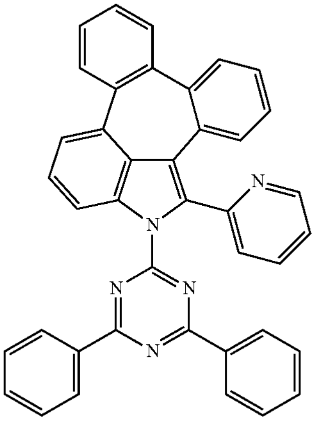
C-56
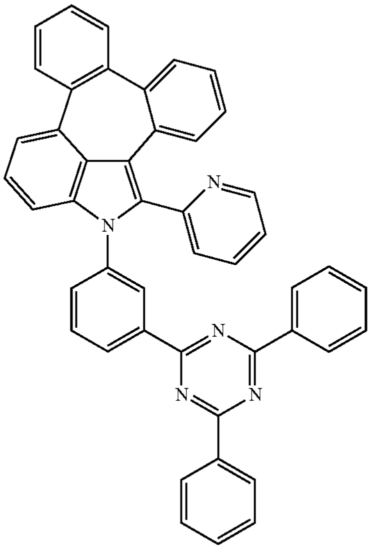
-continued
C-57
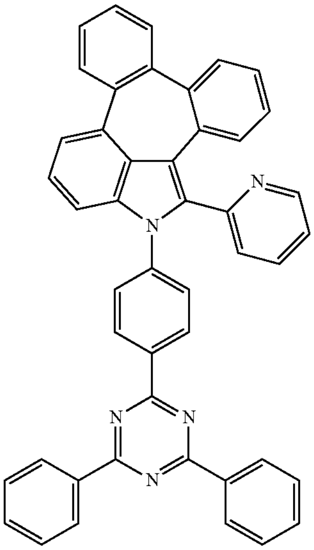
C-58
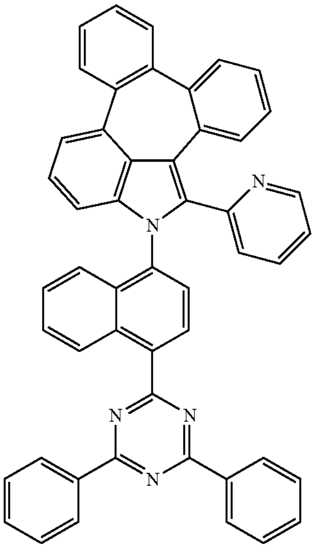
C-59
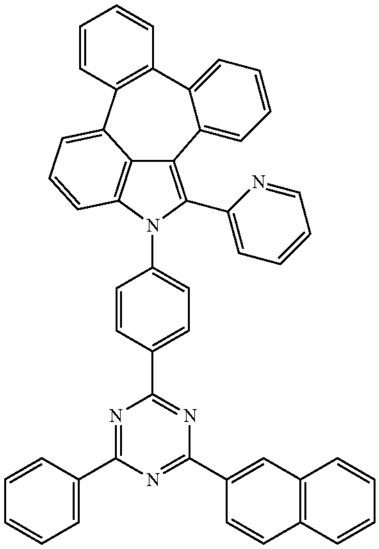

-continued
C-60
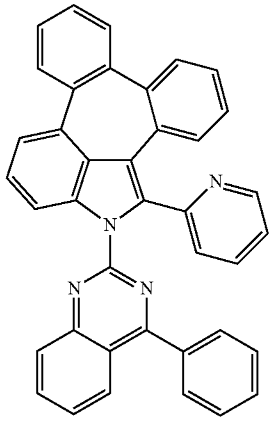
C-61
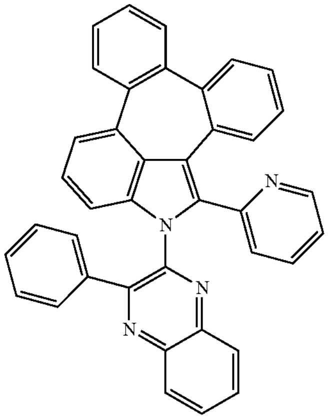
C-62
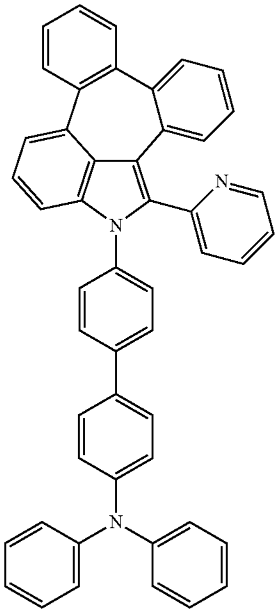
-continued
C-63
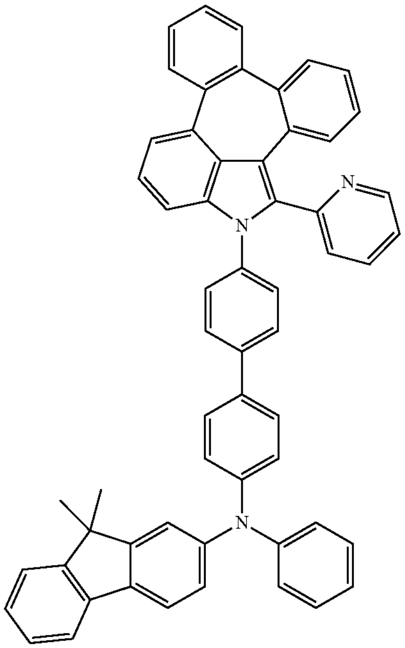
C-64
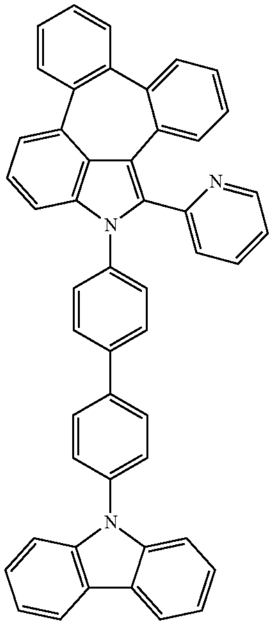
C-65
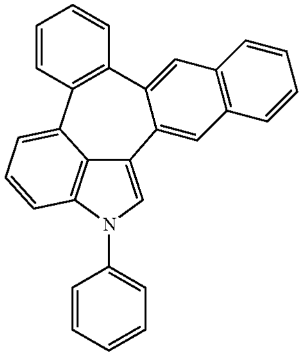

-continued
C-66
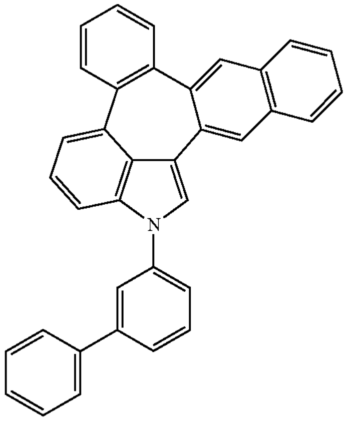
C-67
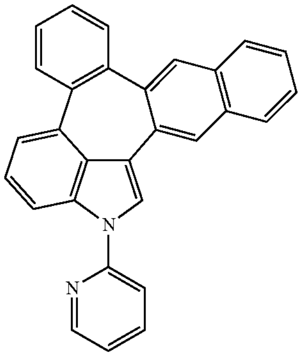
C-68
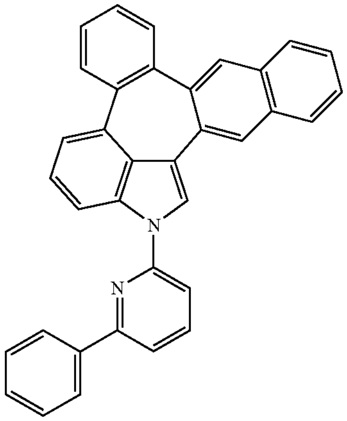
C-69
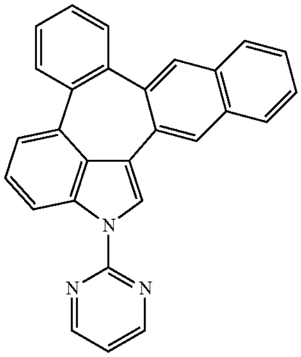
-continued
C-70
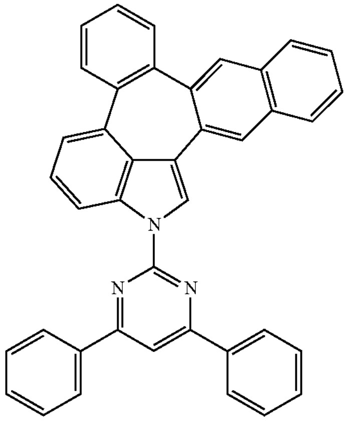
C-71
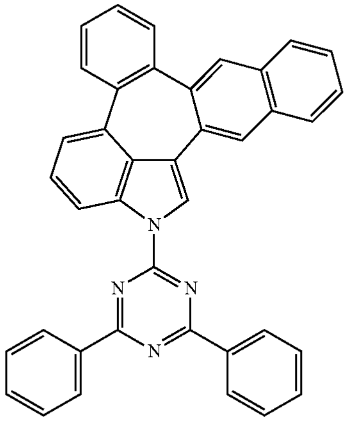
C-72
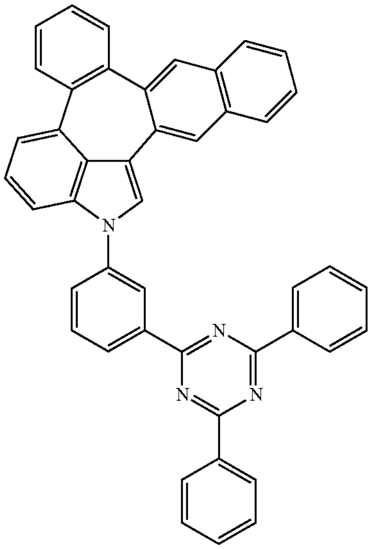

-continued
C-73
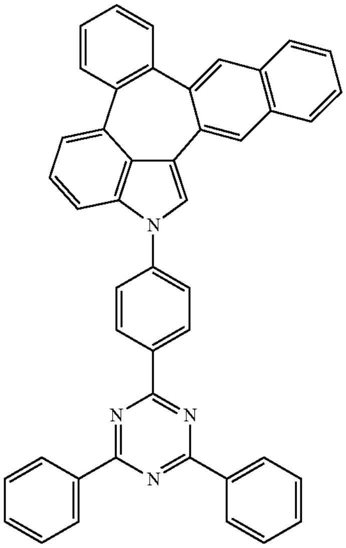
C-74
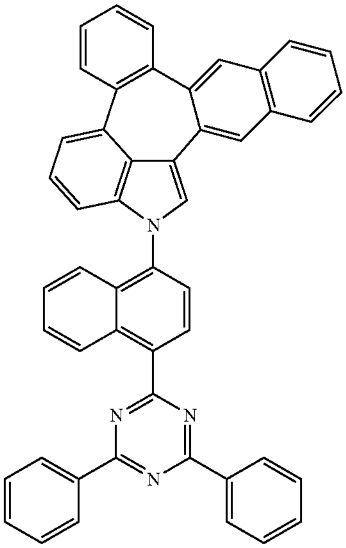
C-75
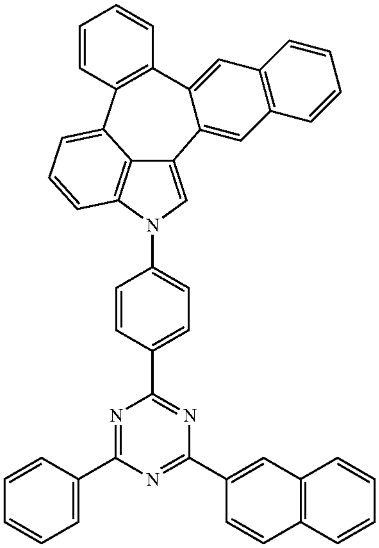
-continued
C-76
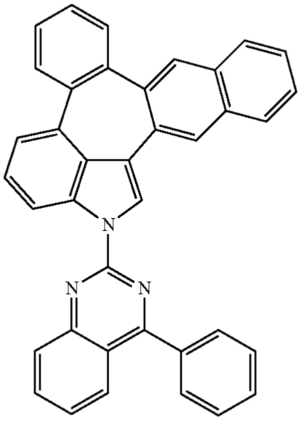
C-77
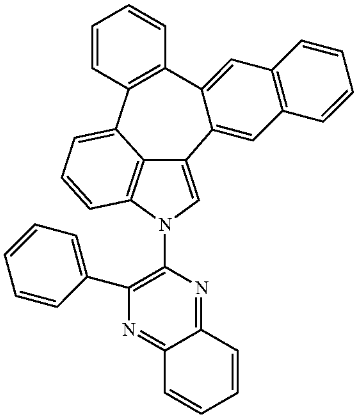
C-78
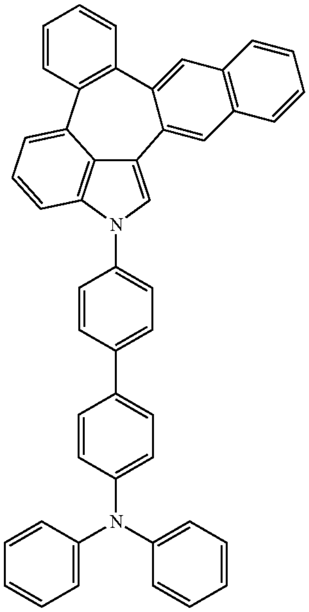

-continued
C-79
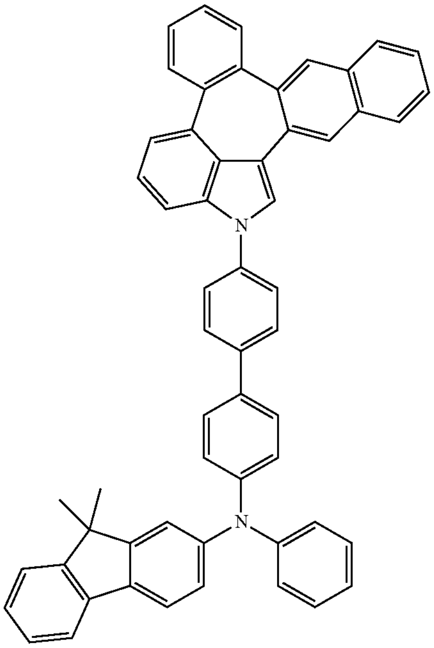
C-80
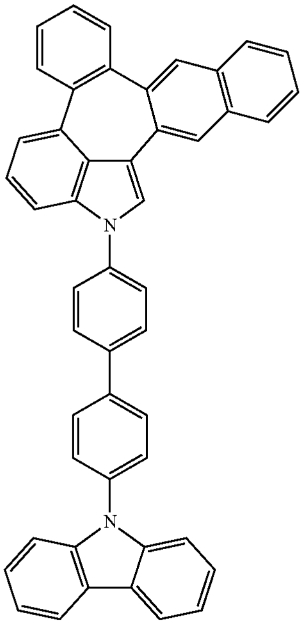
C-81
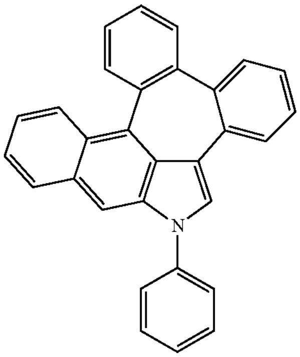
-continued
C-82
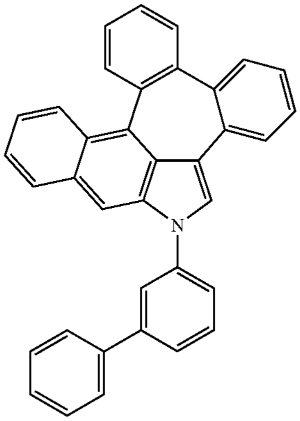
C-83
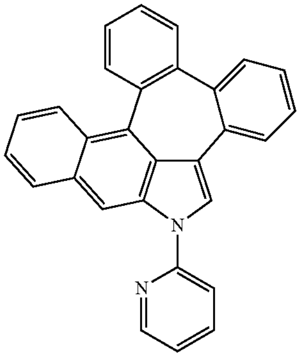
C-84
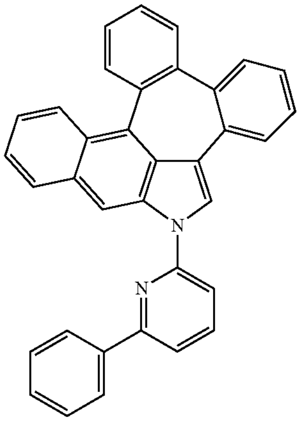
C-85
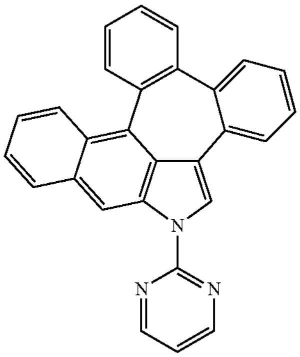

-continued
C-86
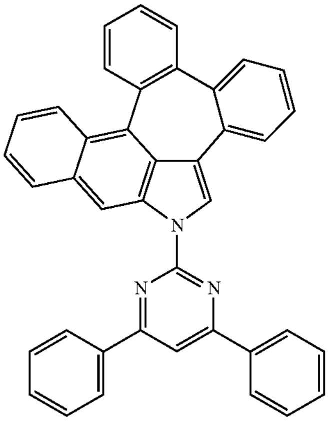
C-87
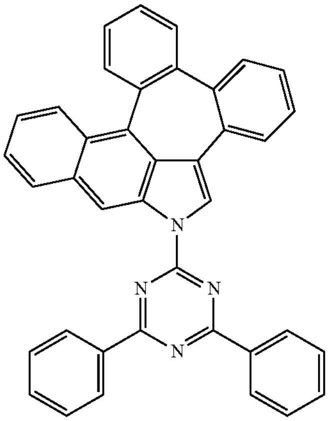
C-88
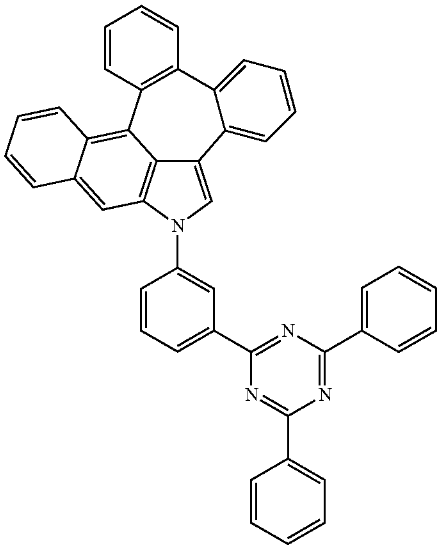
-continued
C-89
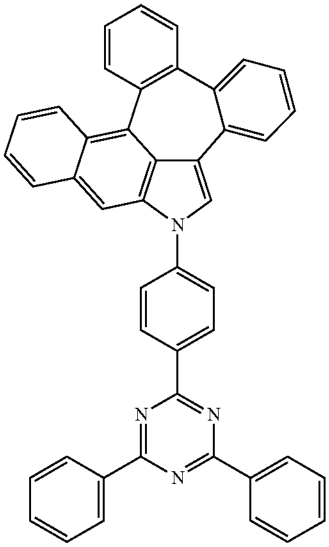
C-90
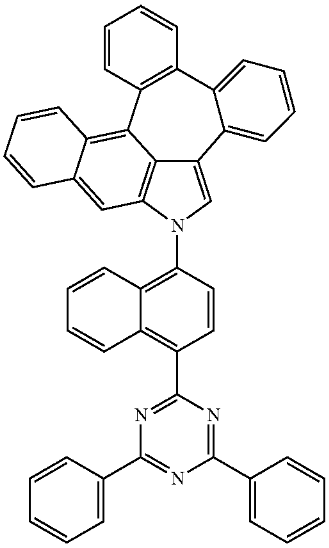
C-91
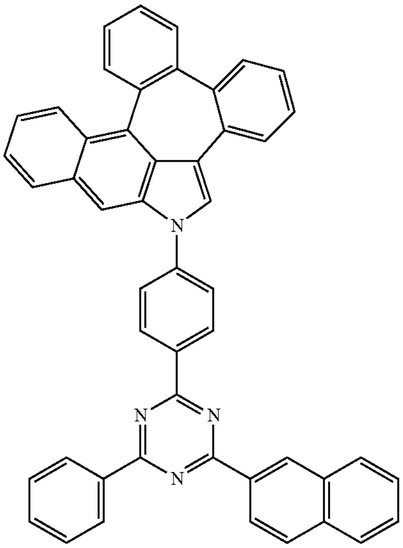

-continued
C-92
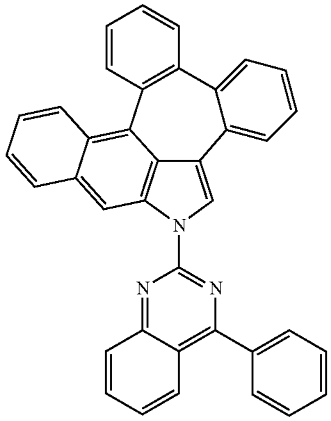
C-93
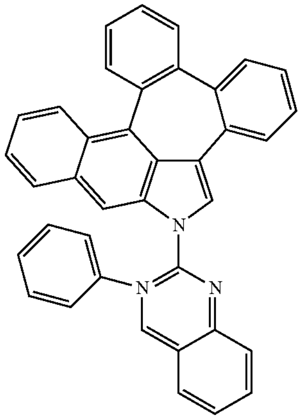
C-94
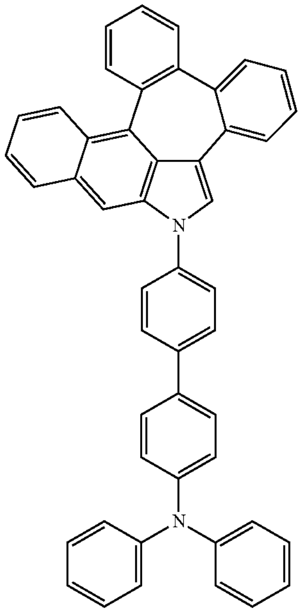
-continued
C-95
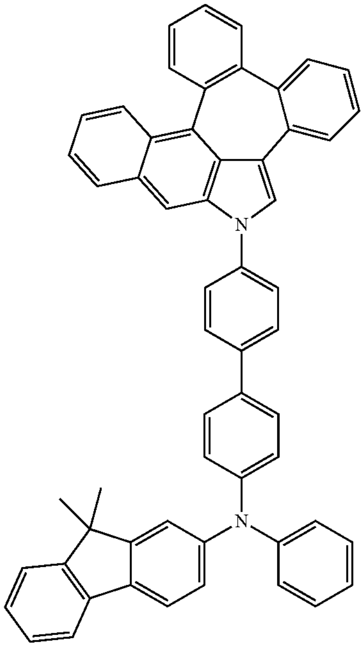
C-96
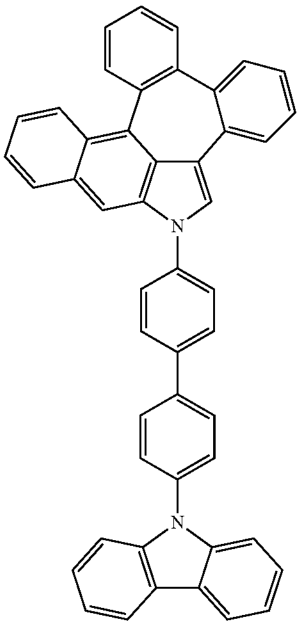

-continued
C-97
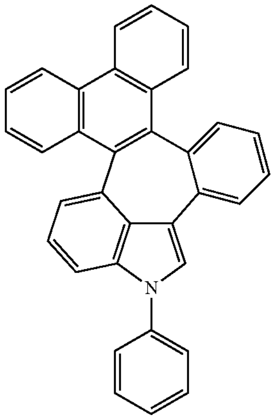
C-98
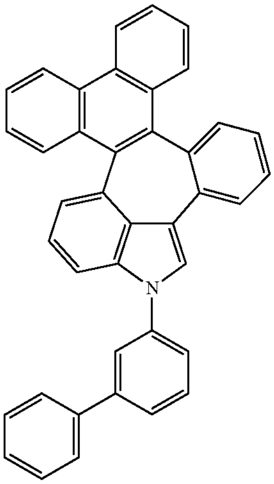
C-99
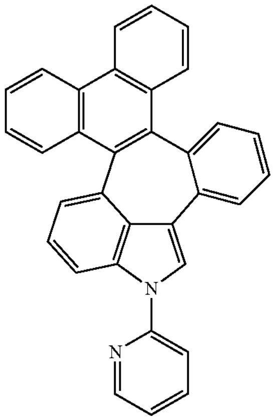
-continued
C-100
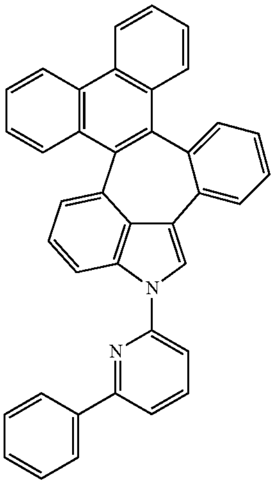
C-101
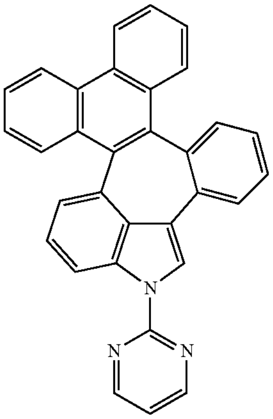
C-102
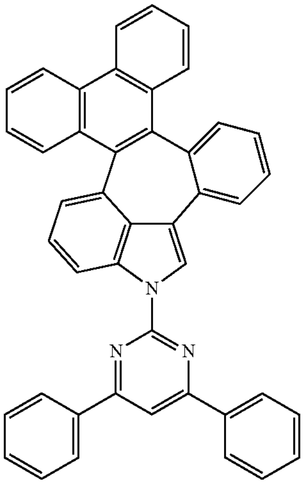

-continued
C-103
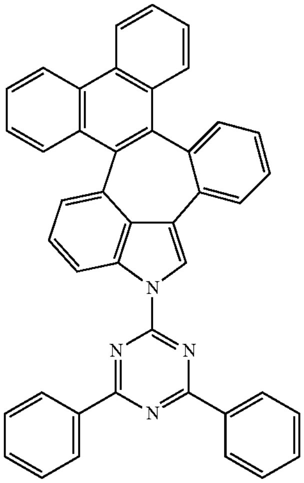
C-104
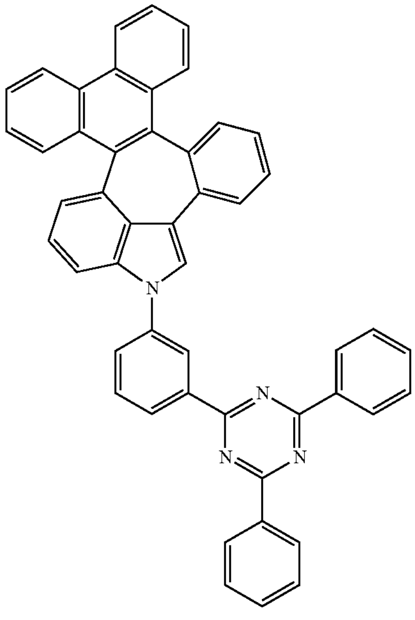
-continued
C-105
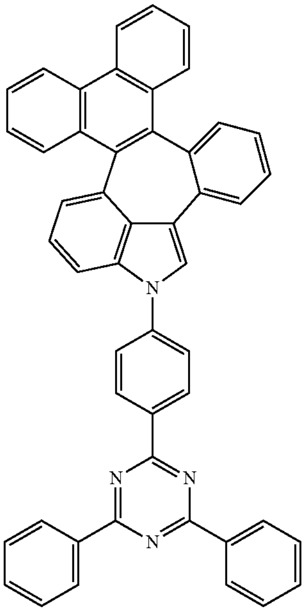
C-106
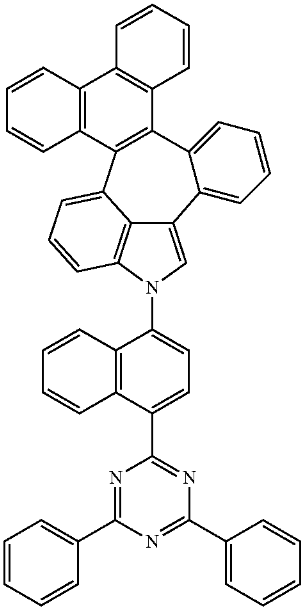

-continued
C-107
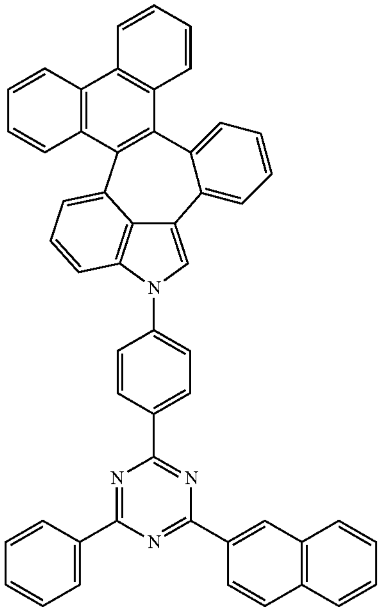
C-108
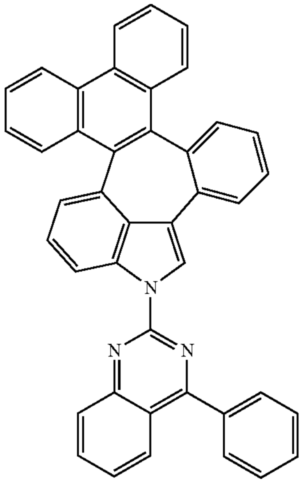
C-109
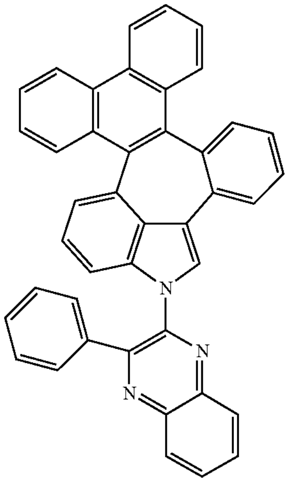
-continued
C-110
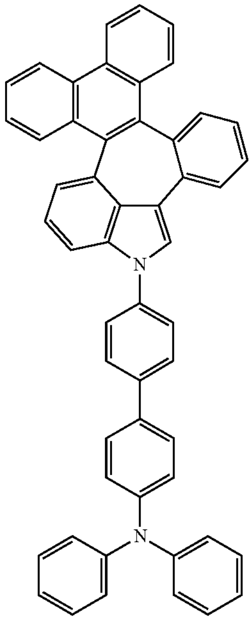
C-111
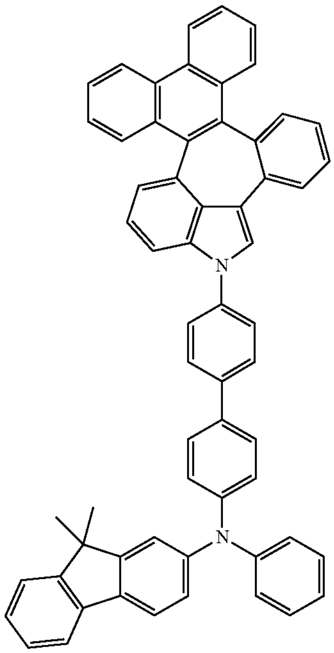

-continued
C-112
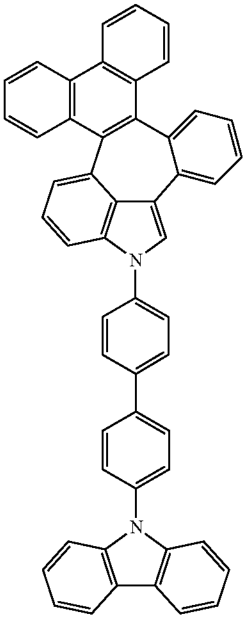
C-113
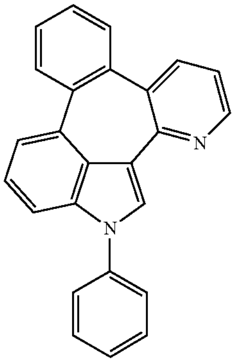
C-114
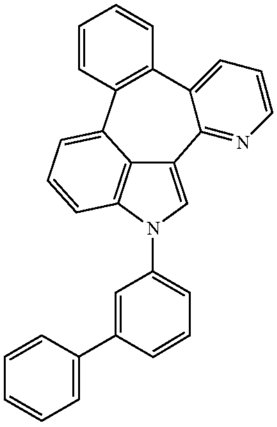
-continued
C-115
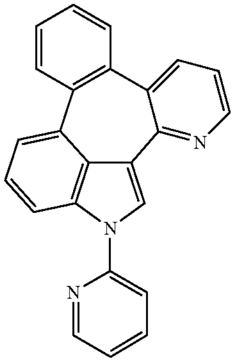
C-116
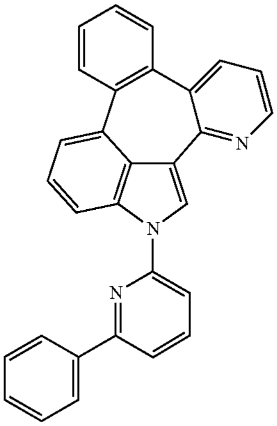
C-117
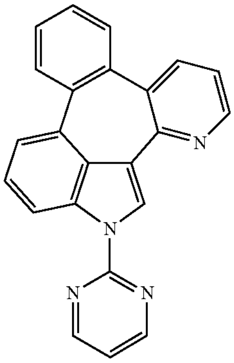
C-118
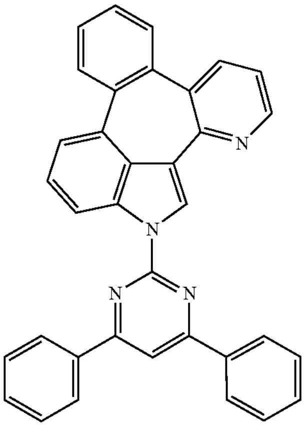

-continued
C-119
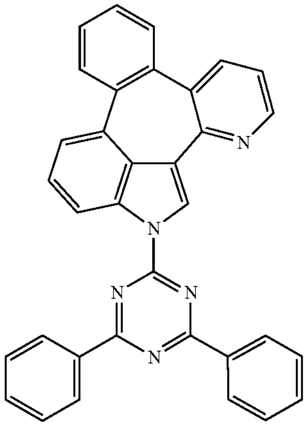
C-120
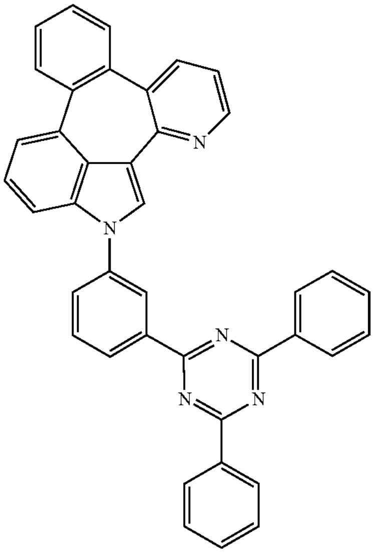
C-121
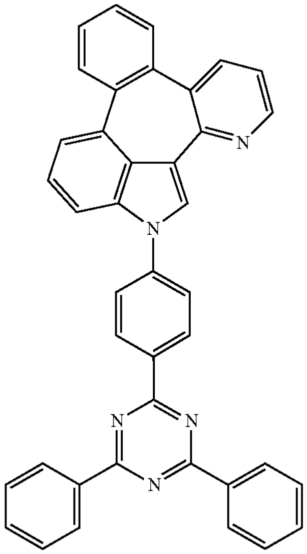
-continued
C-122
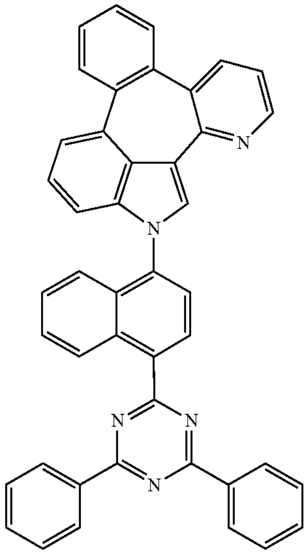
C-123
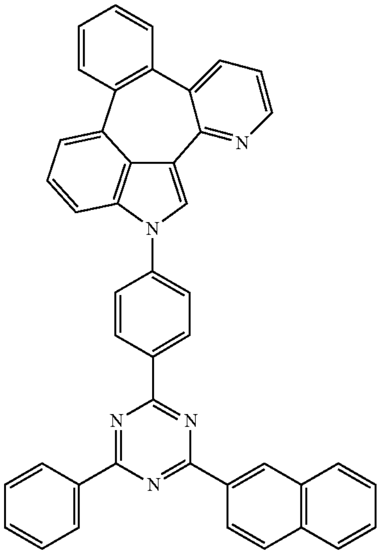
C-124
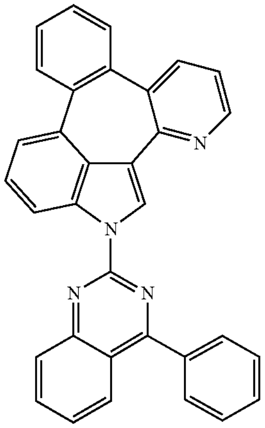

-continued
C-125
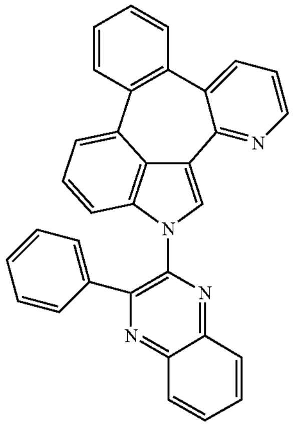
C-126
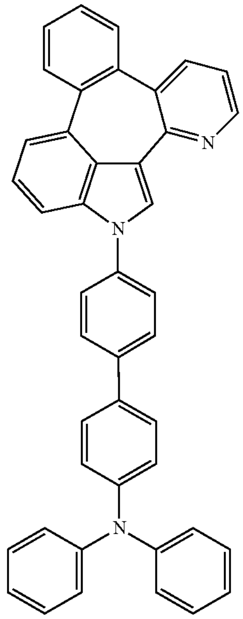
-continued
C-127
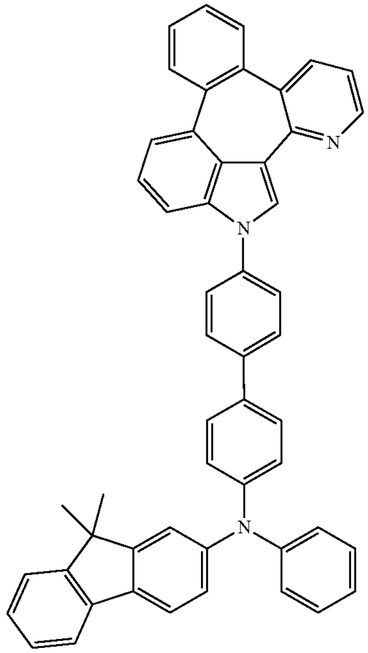
C-128
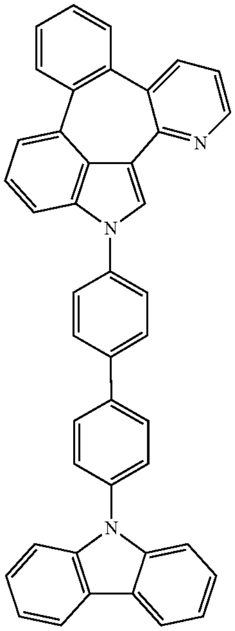

-continued
C-129
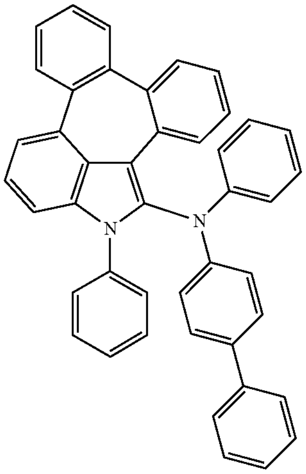
C-130
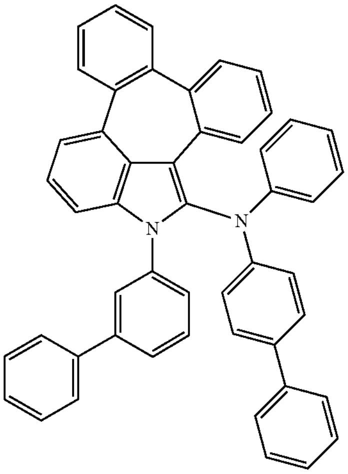
C-131
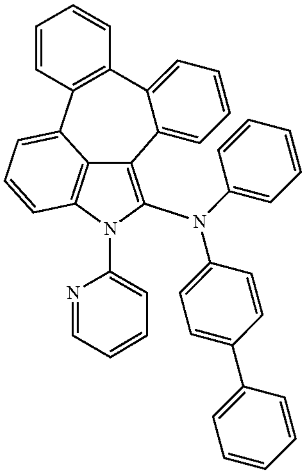
-continued
C-132
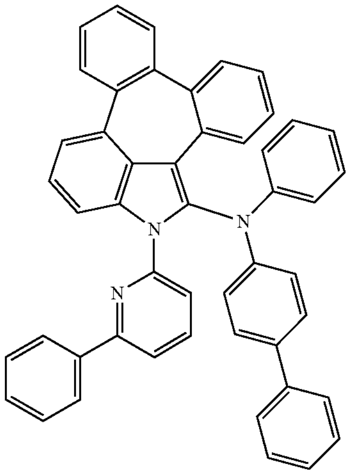
C-133
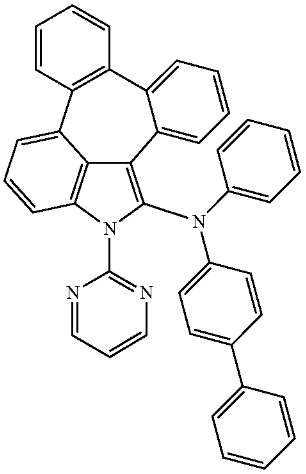
C-134
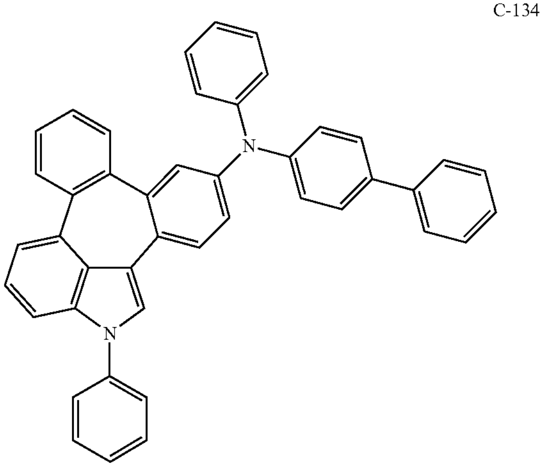

-continued
C-135
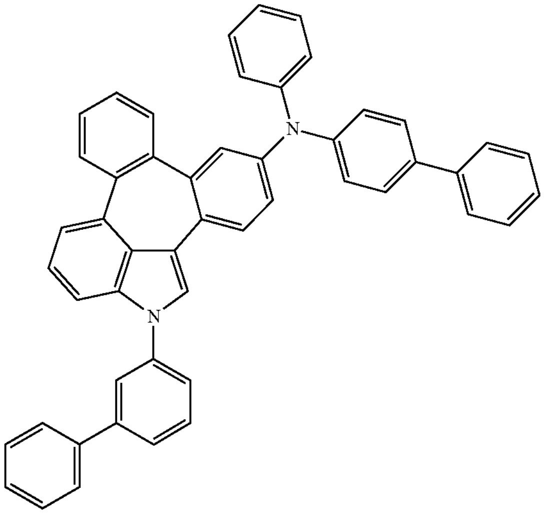
C-136
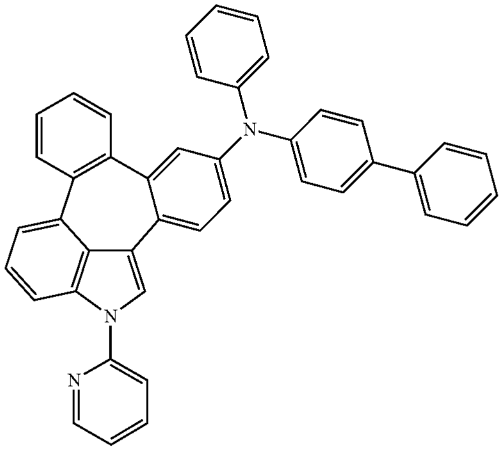
C-137
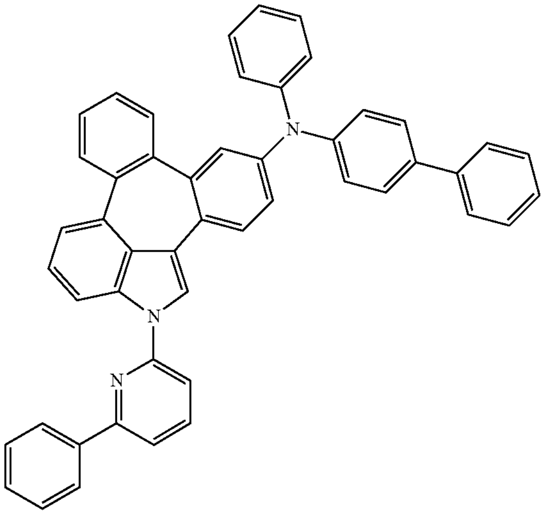
-continued
C-138
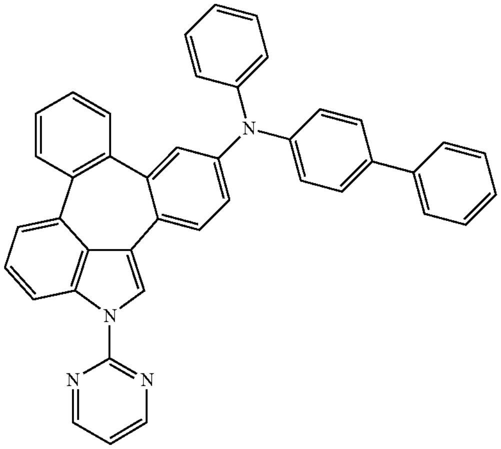
C-139
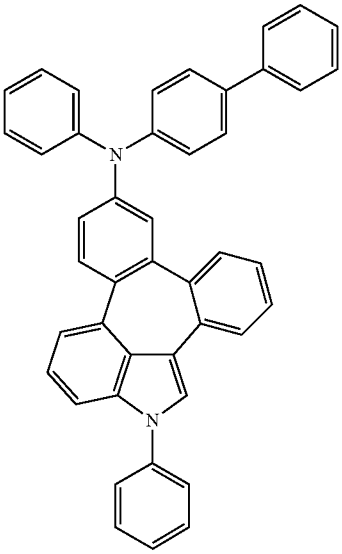
C-140
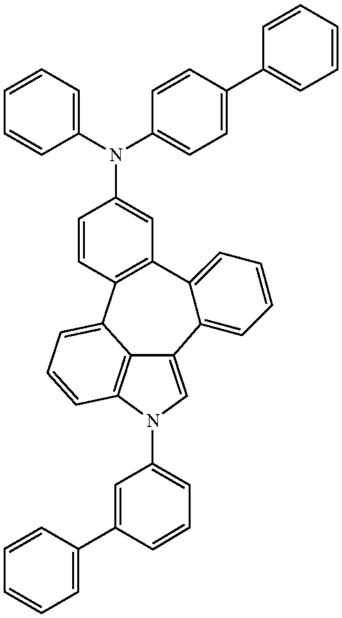

-continued
C-141
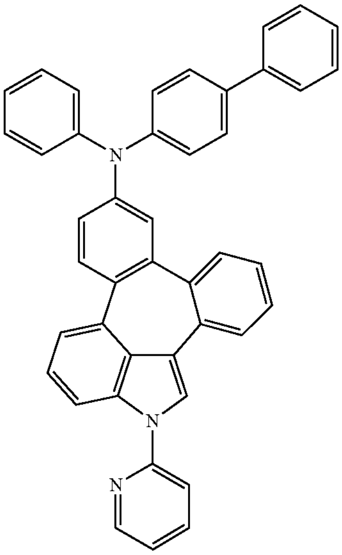
C-142
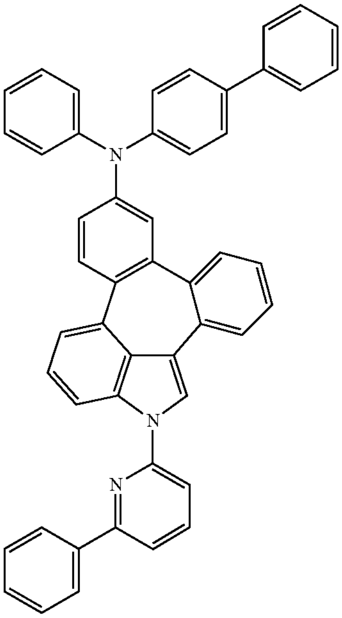
-continued
C-143
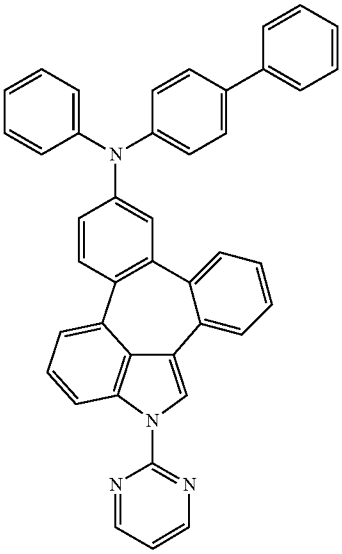
C-144
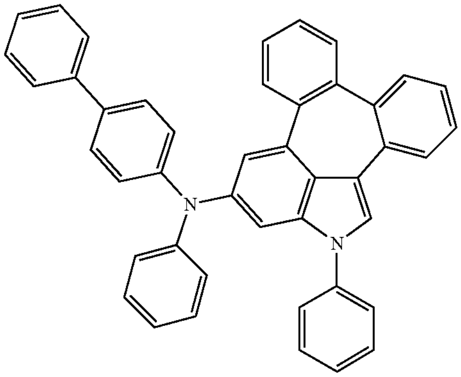
C-145
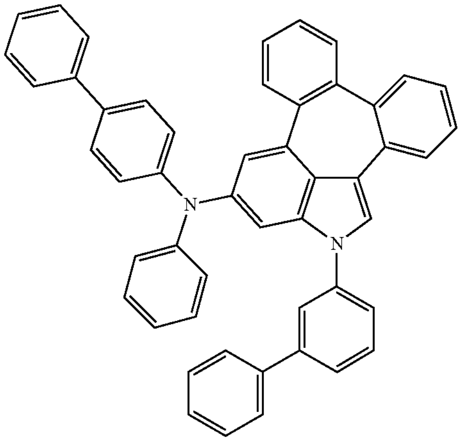

-continued
C-146
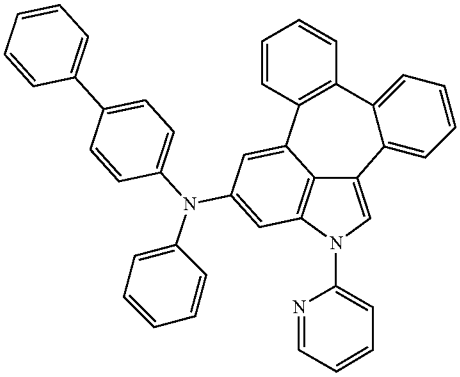
C-147
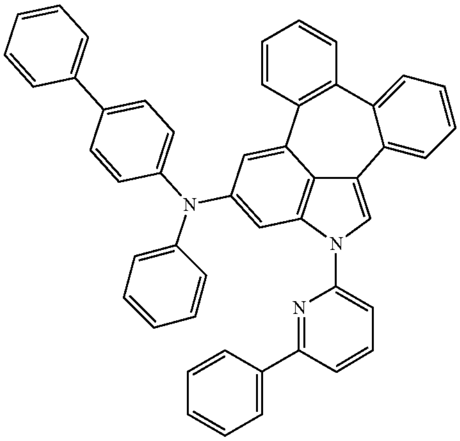
C-148
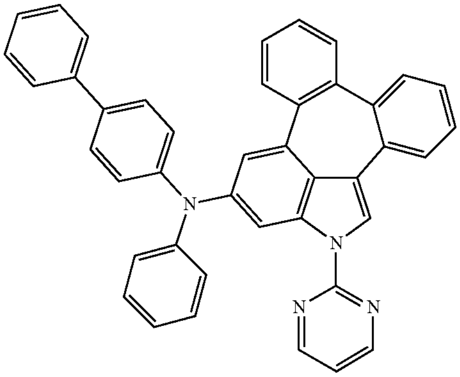
C-149
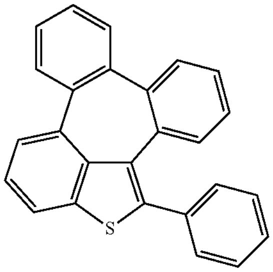
-continued
C-150
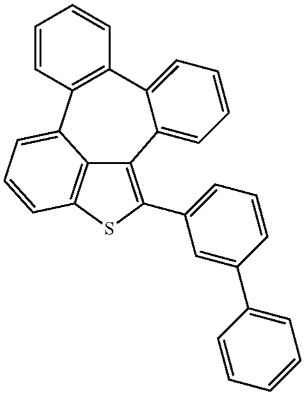
C-151
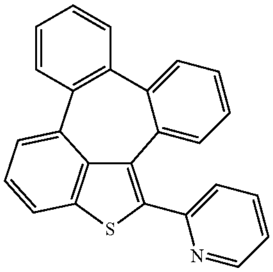
C-152
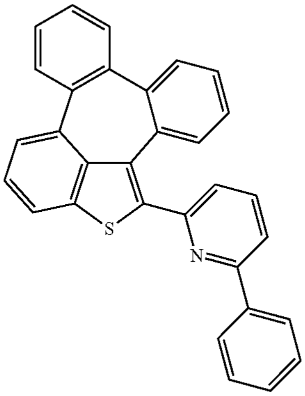
C-153
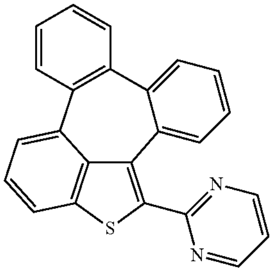

-continued
C-154
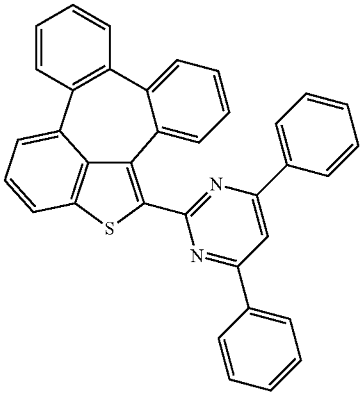
C-155
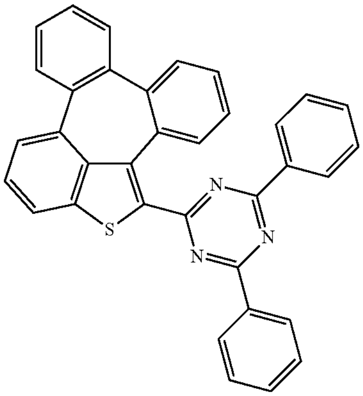
C-156
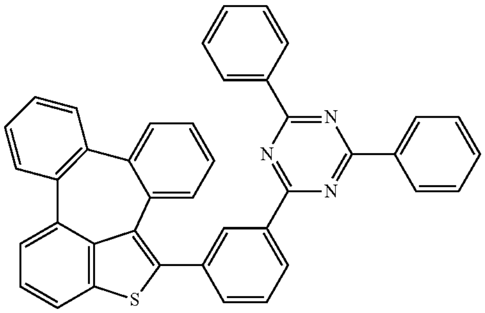
C-157
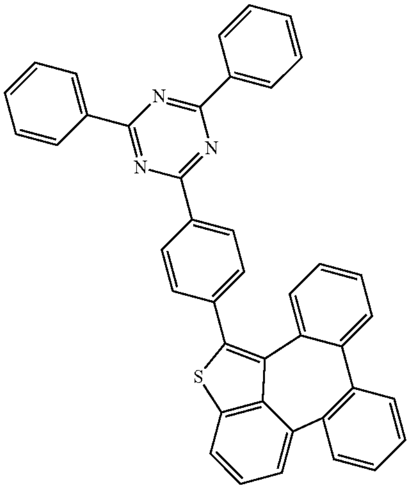
-continued
C-158
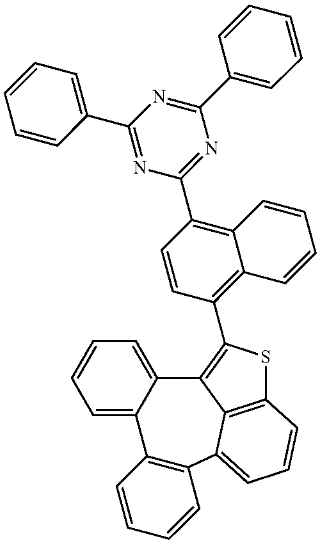
C-159
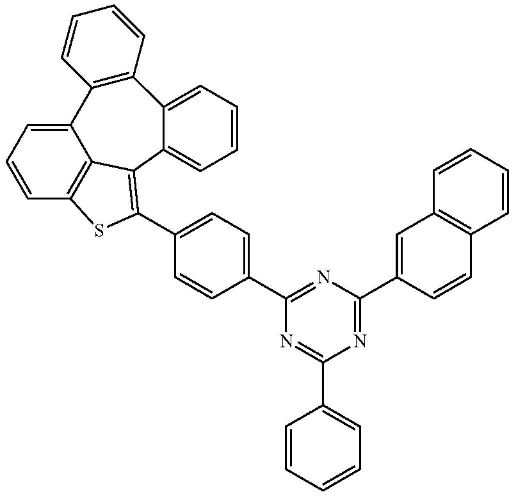
C-160
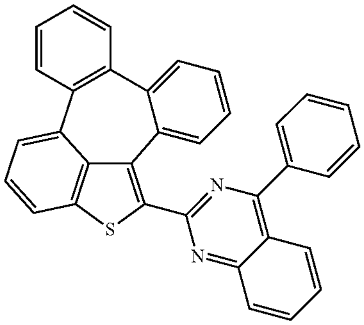

-continued
C-161
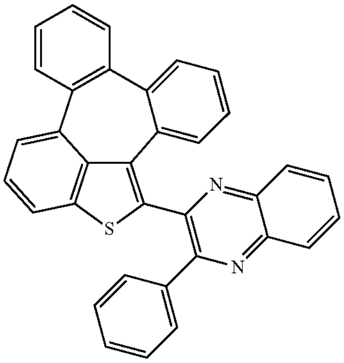
C-162
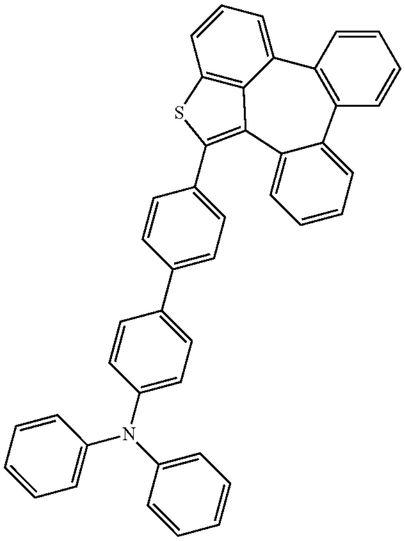
C-163
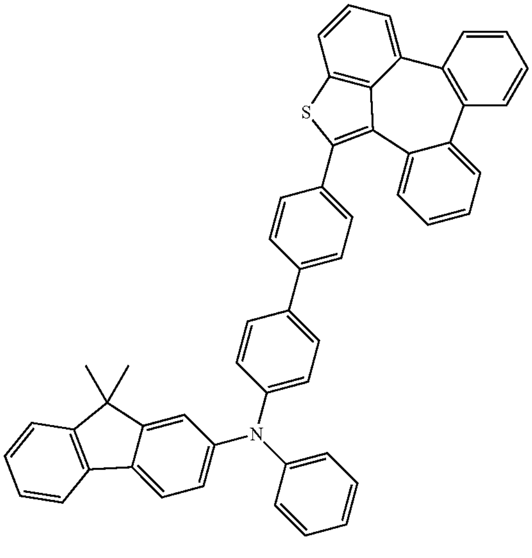
-continued
C-164
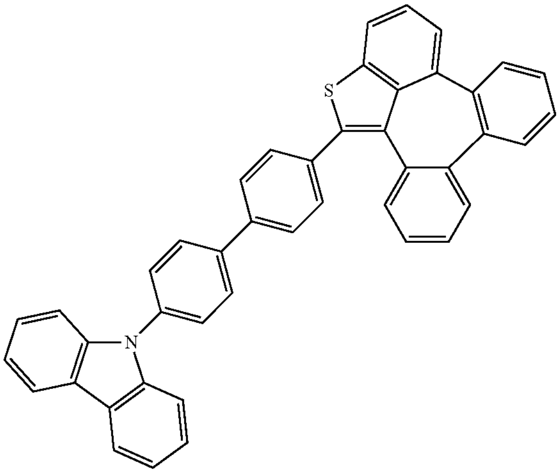
C-165
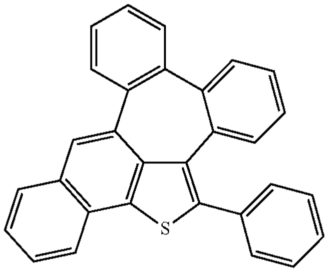
C-166
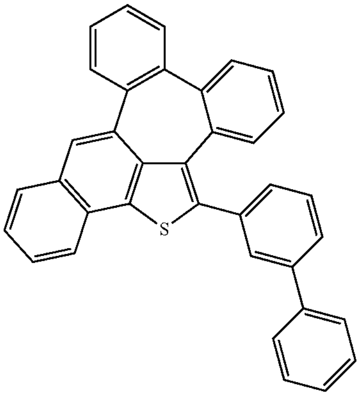
C-167
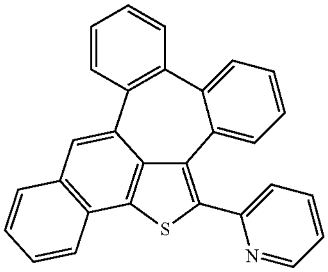

-continued
C-168
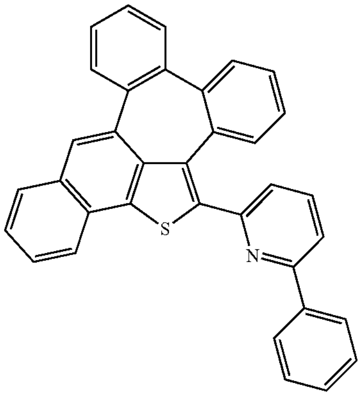
C-169
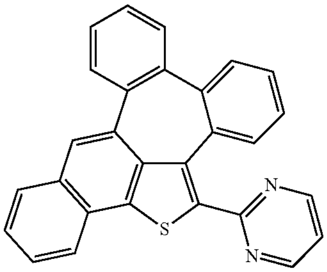
C-170
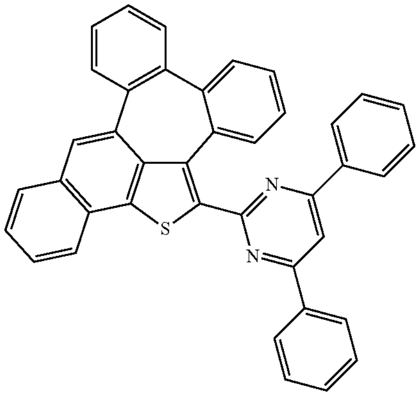
C-171
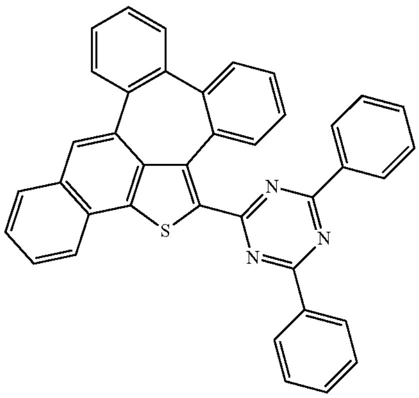
-continued
C-172
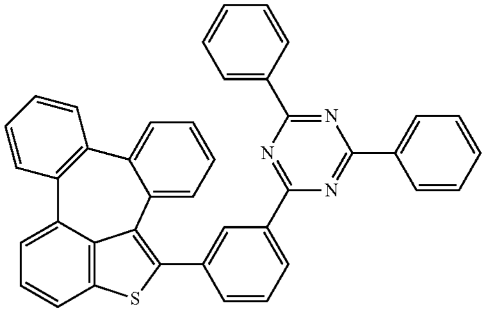
C-173
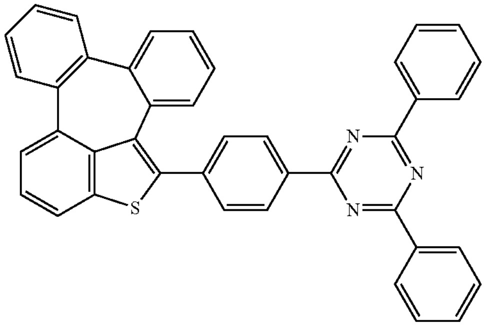
C-174
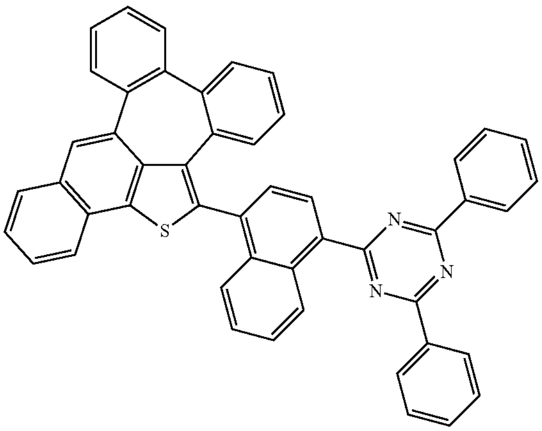
C-175
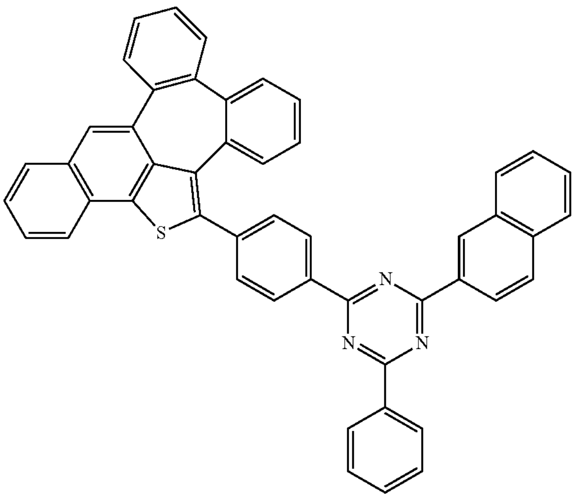

-continued
C-176
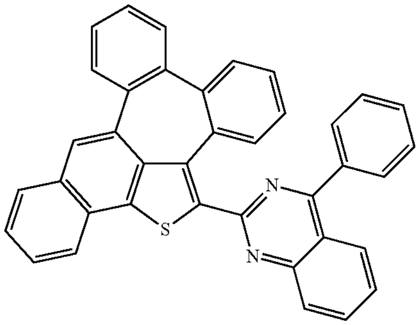
C-177
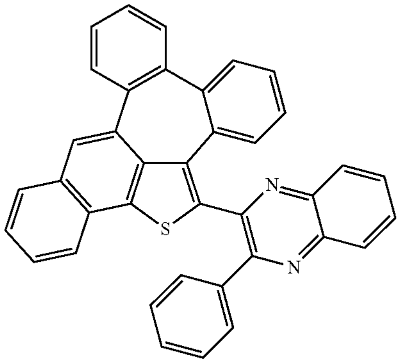
C-178
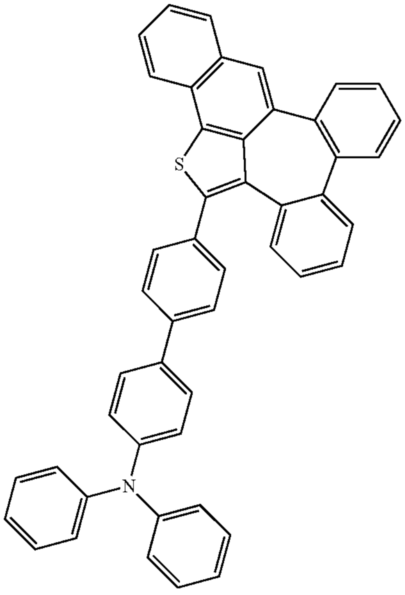
-continued
C-179
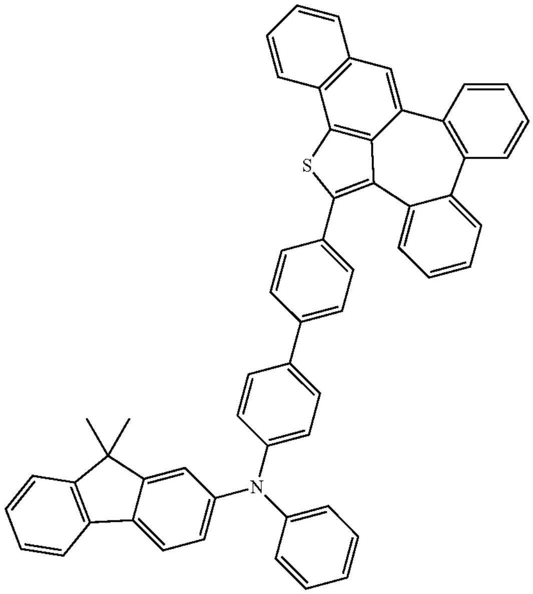
C-180
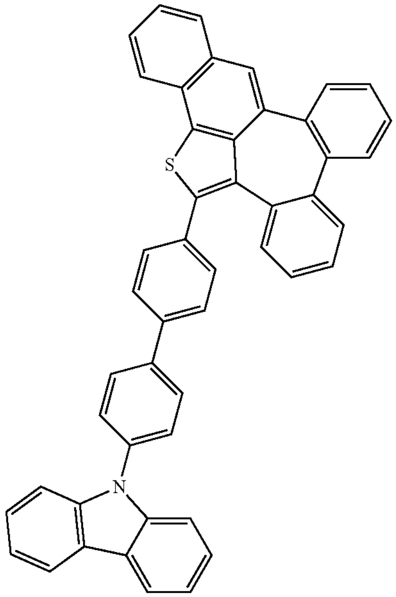
C-181
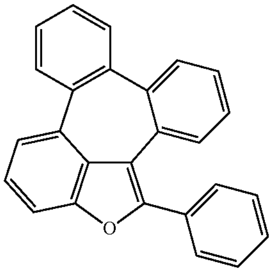

-continued
C-182
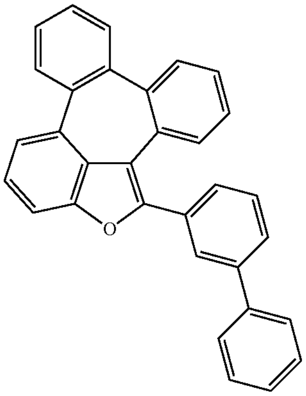
C-183
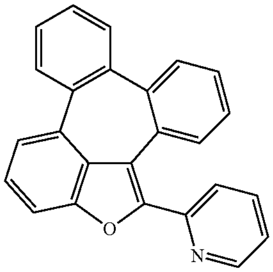
C-184
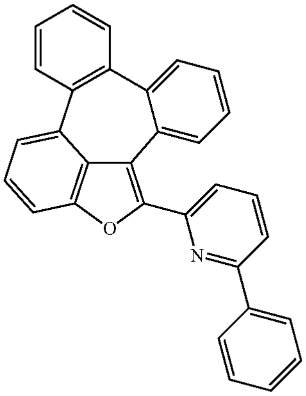
C-185
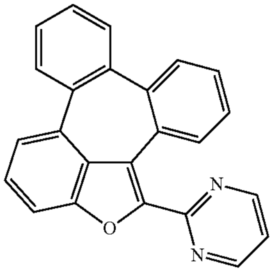
-continued
C-186
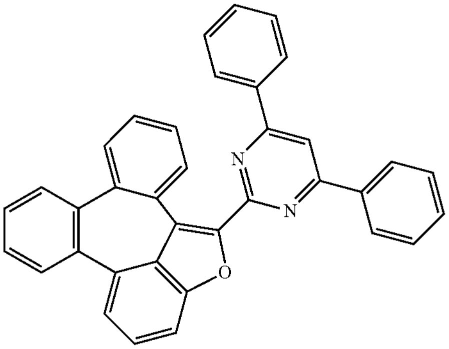
C-187
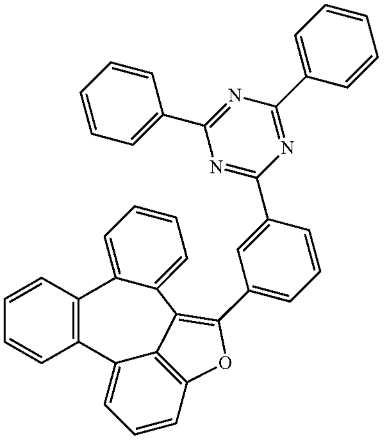
C-188
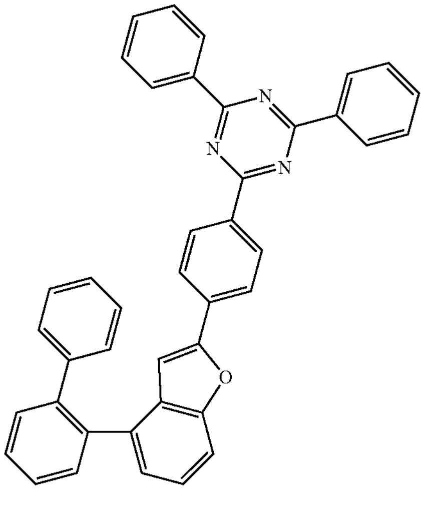

C-189
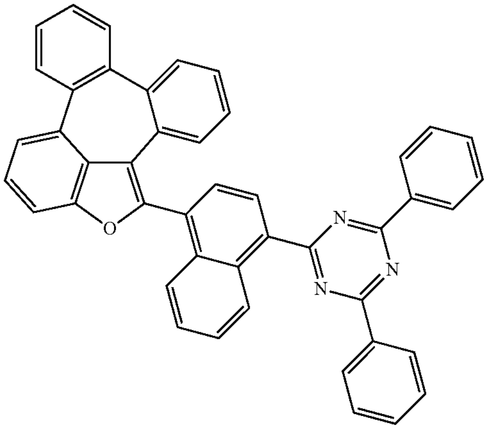
C-190
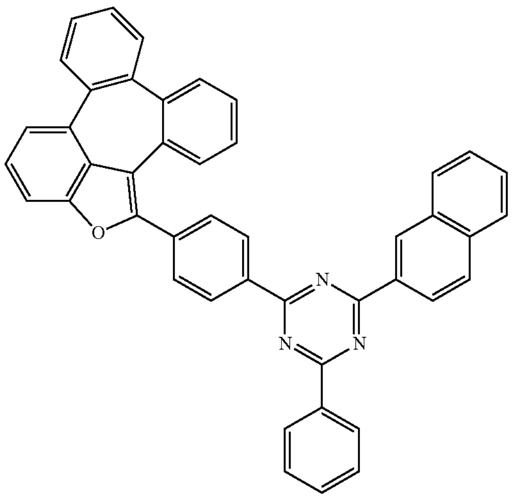
C-191
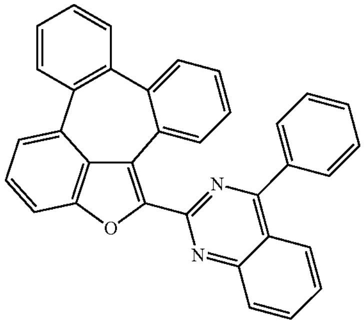
C-192
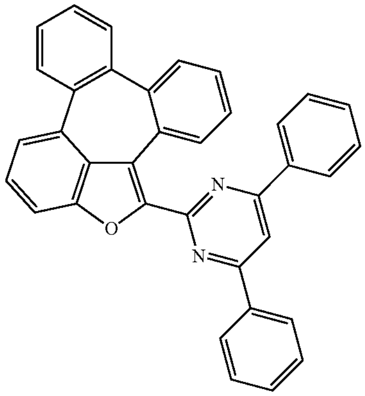
C-193
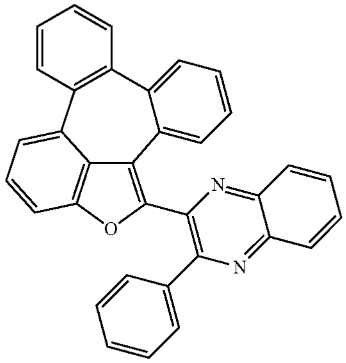
C-194
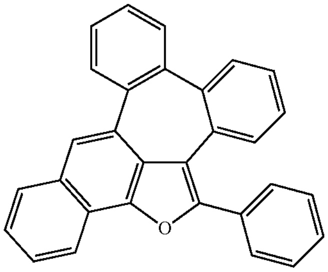
C-195
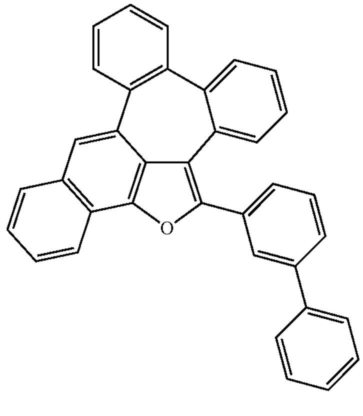

-continued
C-196
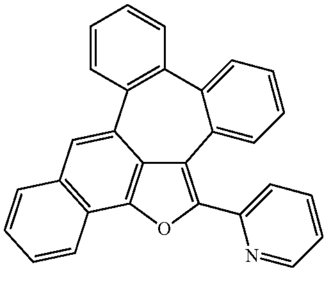
C-197
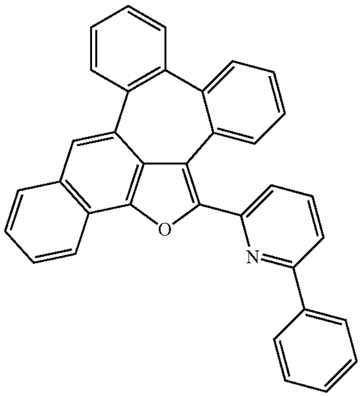
C-198
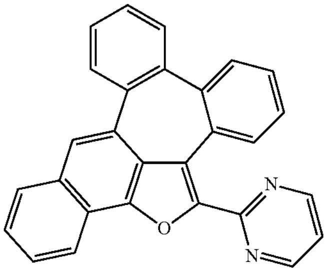
C-199
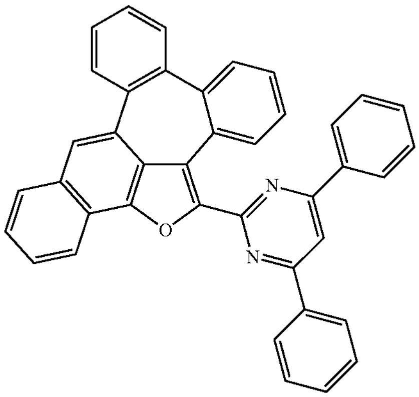
-continued
C-200
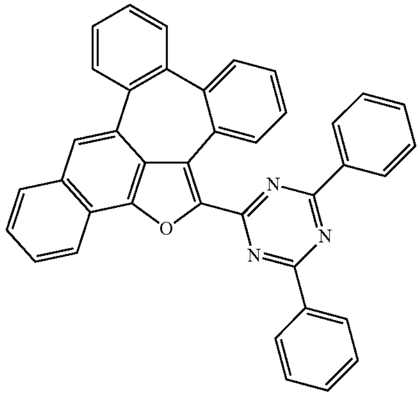
C-201
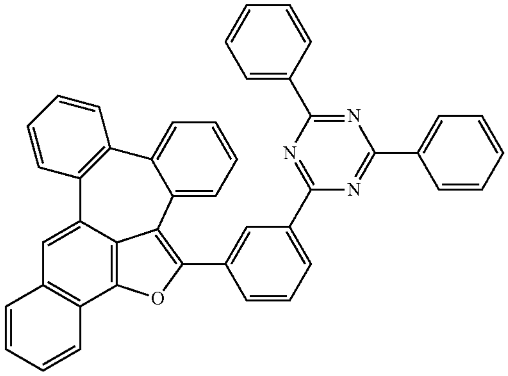
C-202
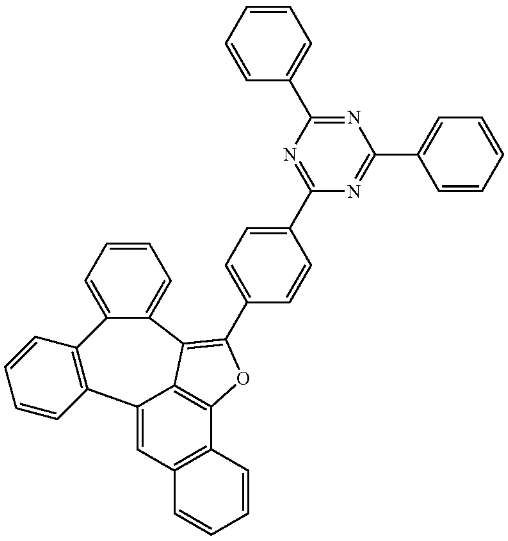

-continued
C-203
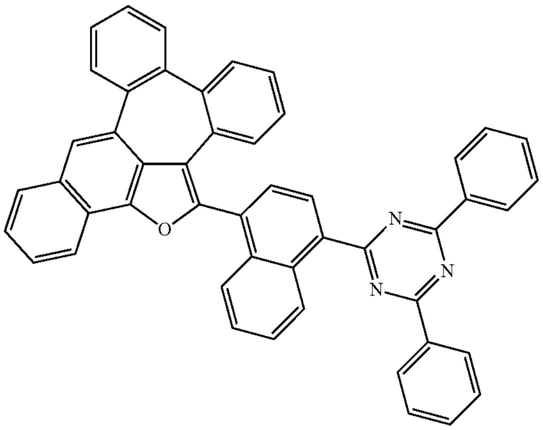
C-204
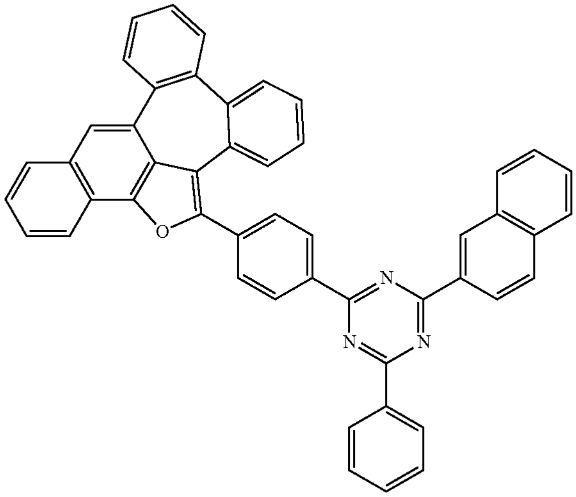
C-205
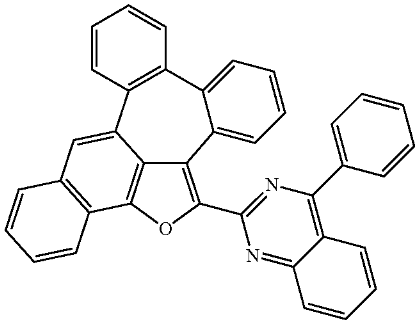
-continued
C-206
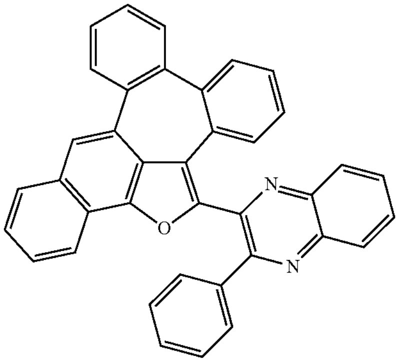
C-207
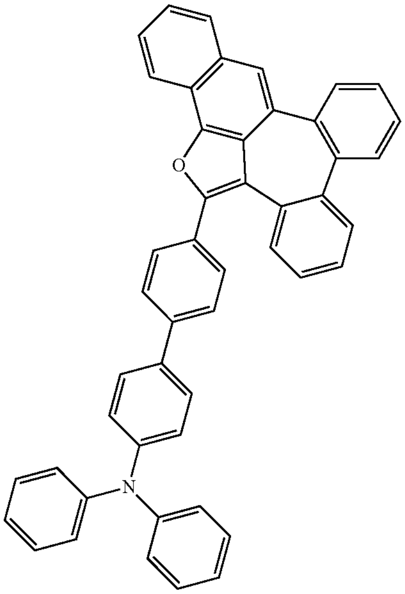
C-208
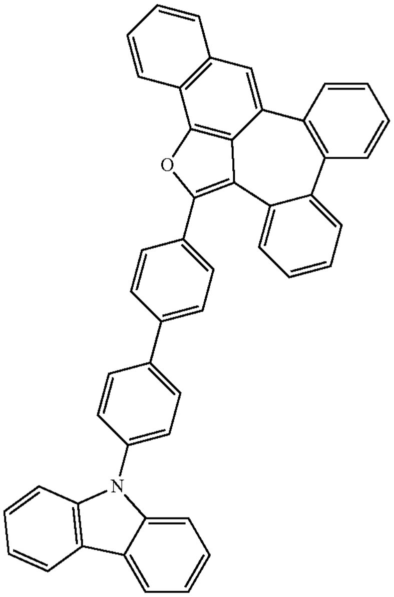

-continued
C-209
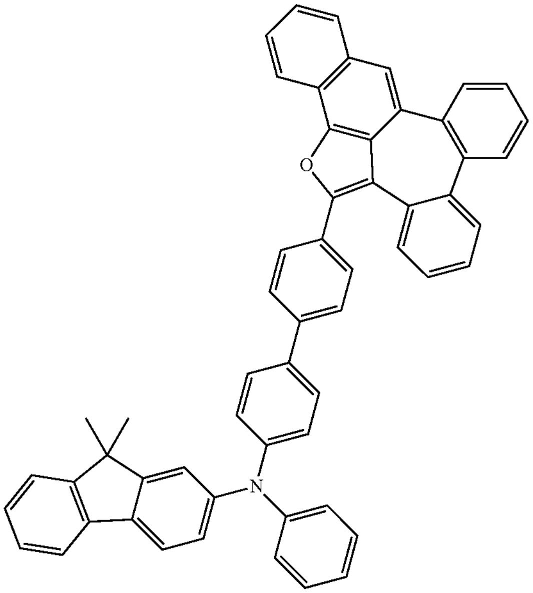
C-210
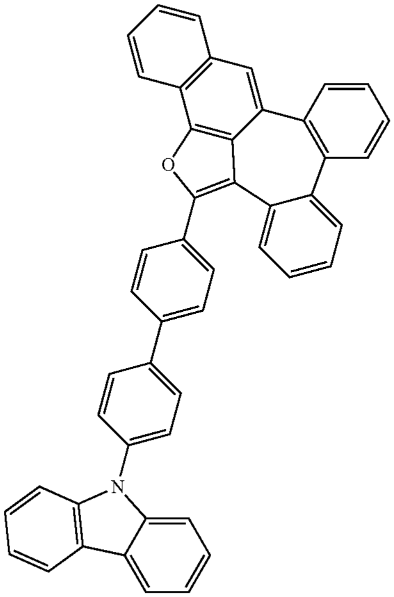
C-211
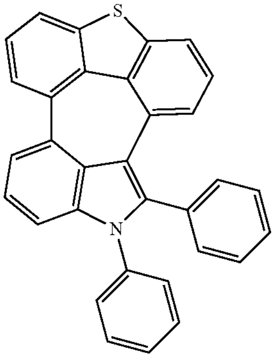
-continued
C-212
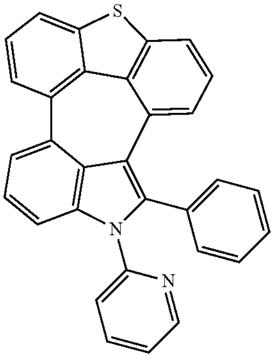
C-213
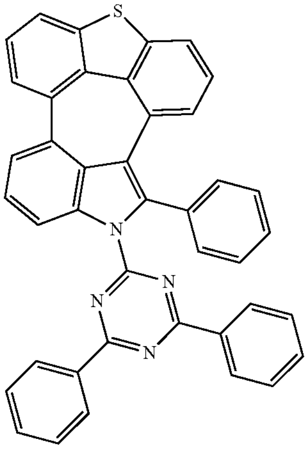
C-214
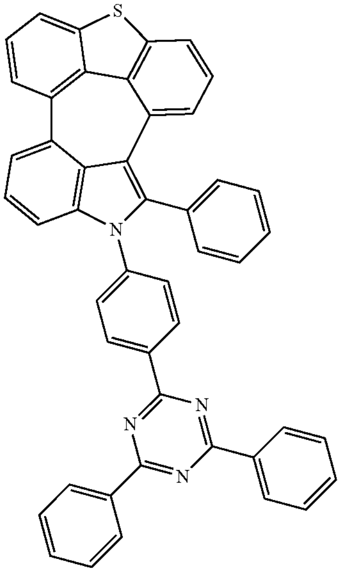

-continued
C-215
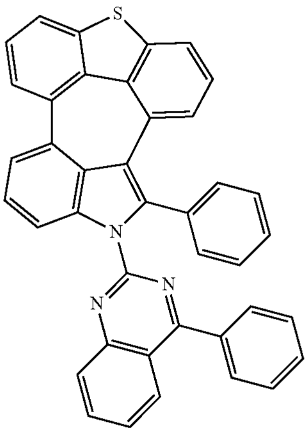
C-216
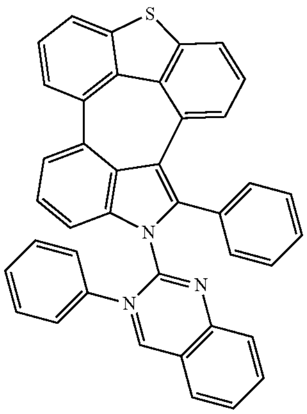
C-217
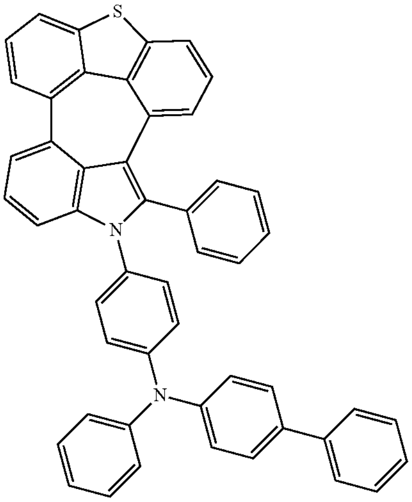
-continued
C-218
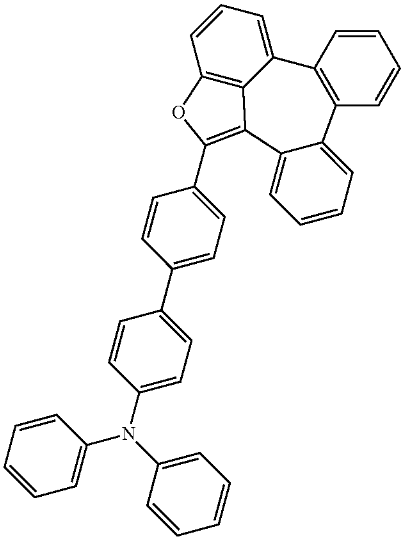
C-219
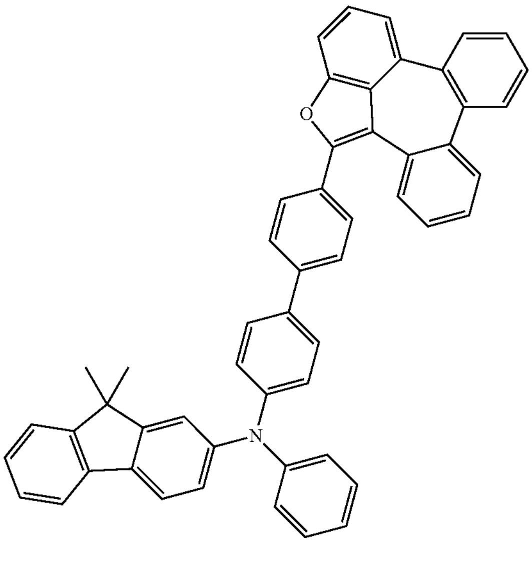
C-220
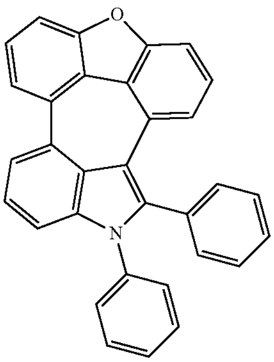

-continued
C-221
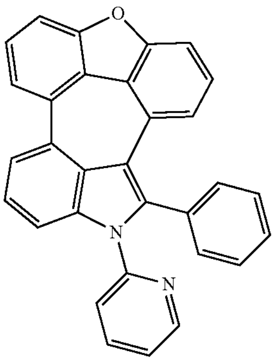
C-222
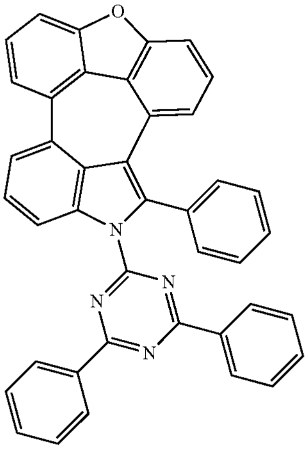
C-223
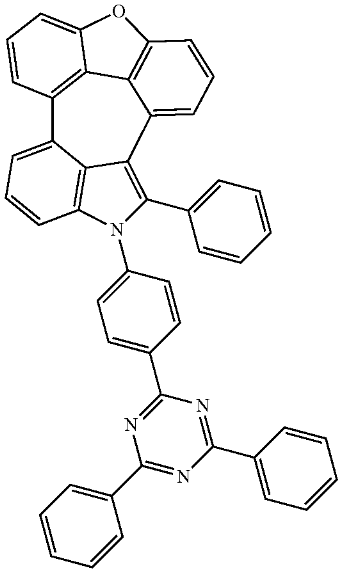
-continued
C-224
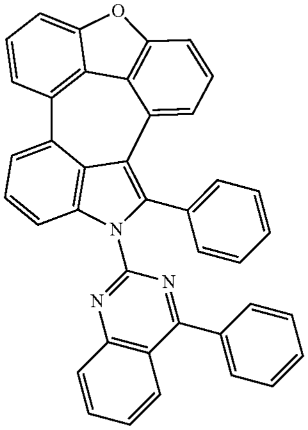
C-225
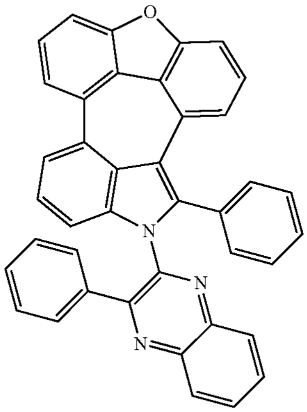
C-226
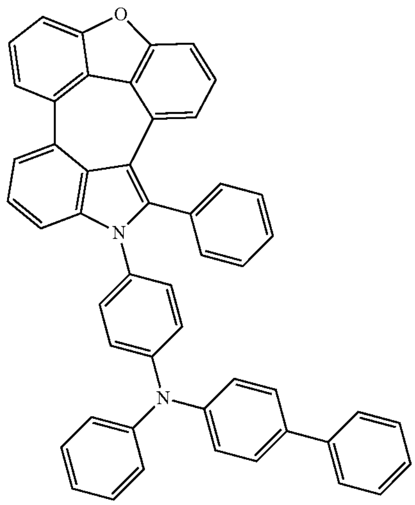

-continued
C-227
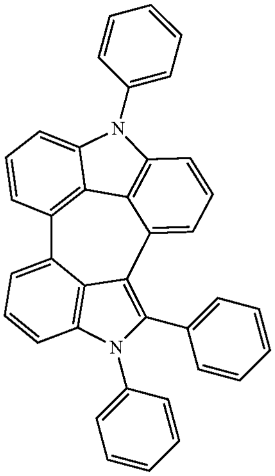
C-228
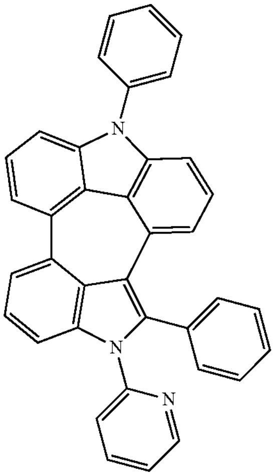
C-229
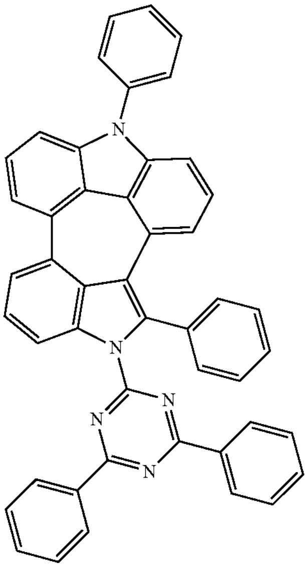
-continued
C-230
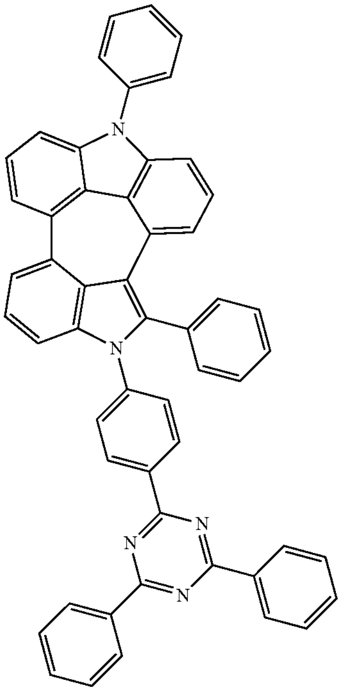
C-231
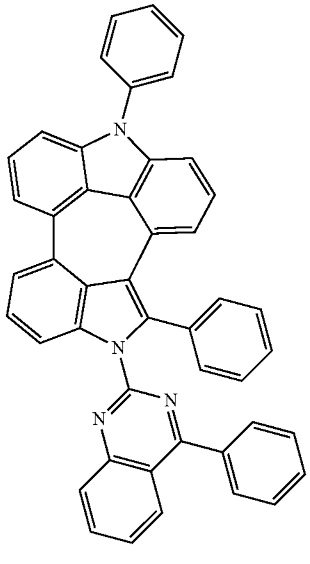

-continued
C-232
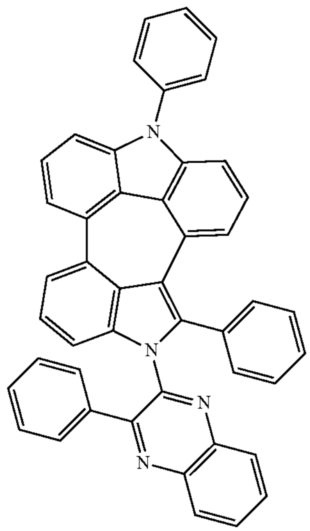
C-233
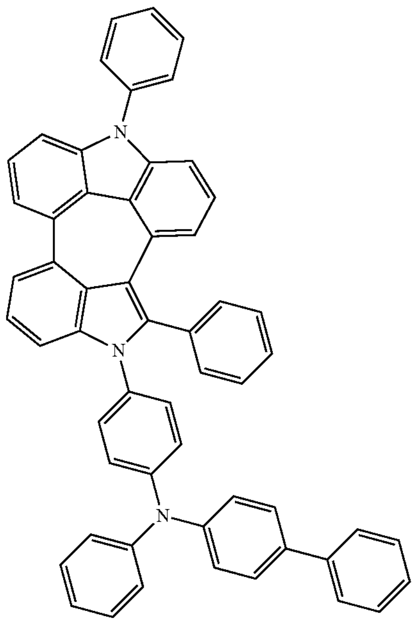
C-234
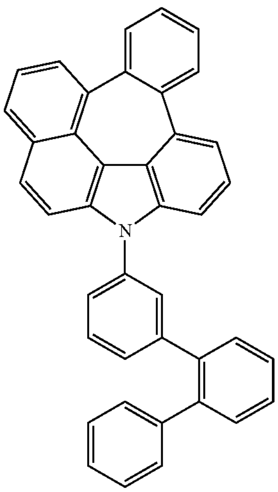
-continued
C-235
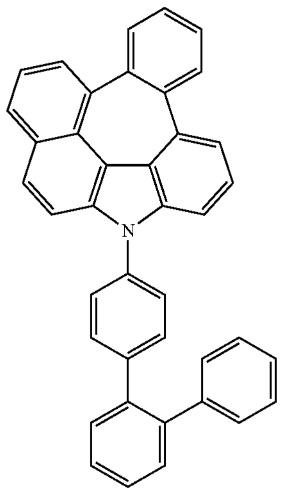
C-236
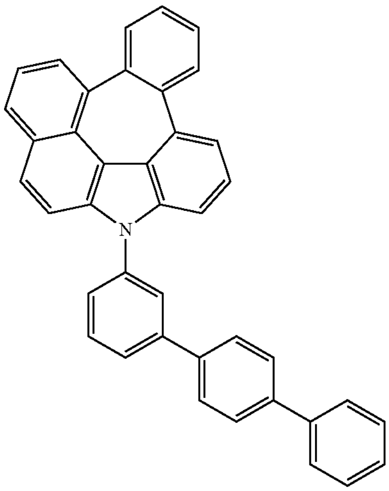
C-237
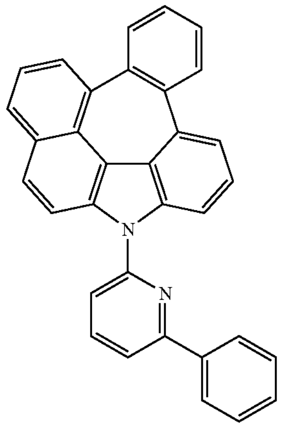

-continued
C-238
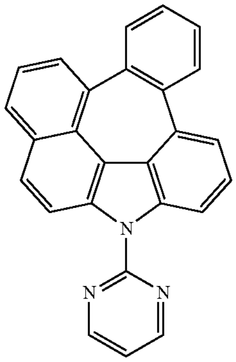
C-239
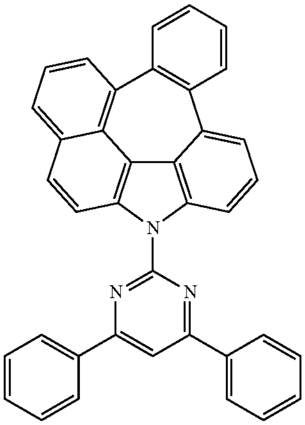
C-240
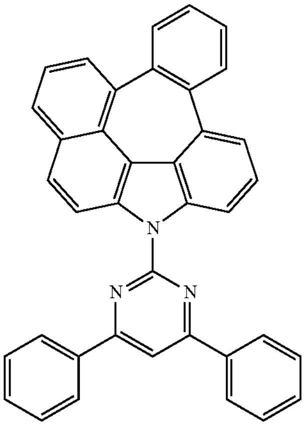
-continued
C-241
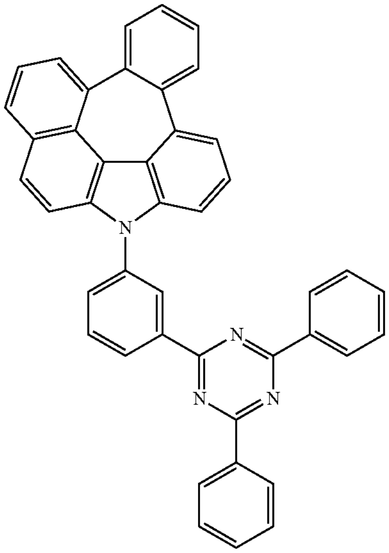
C-242
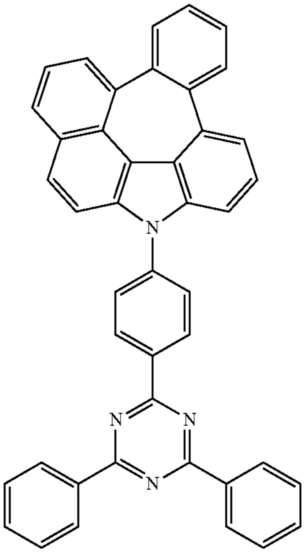

-continued
C-243
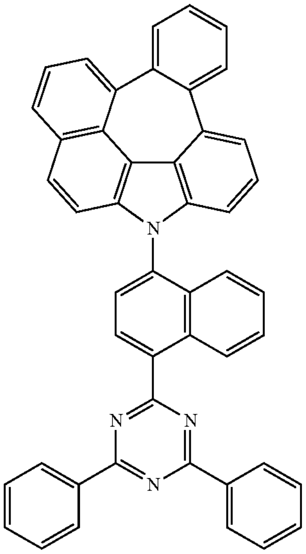
C-244
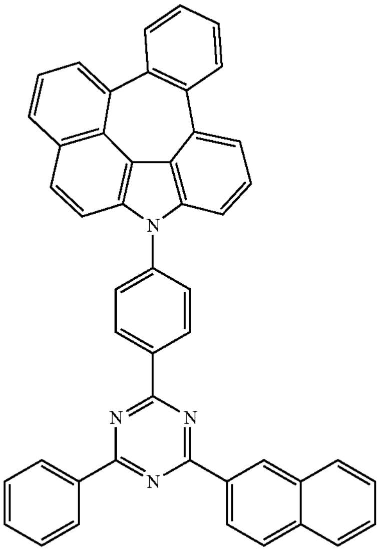
C-245
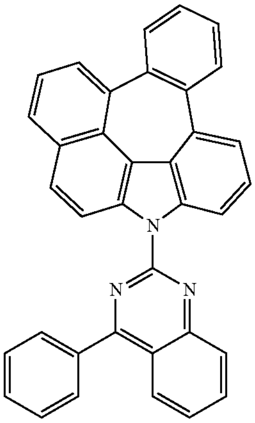
-continued
C-246
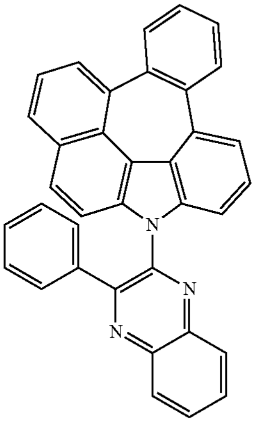
C-247
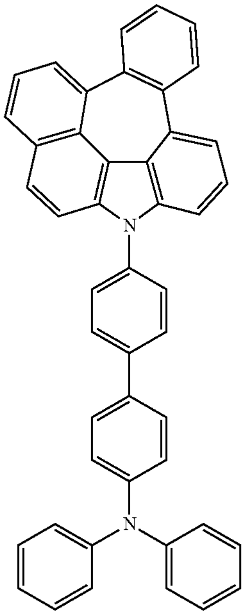

C-248
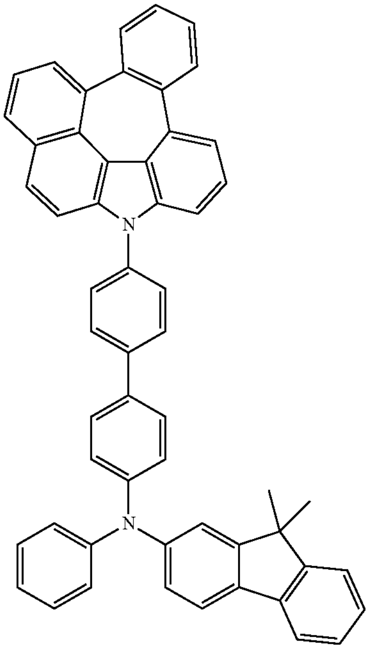
C-249
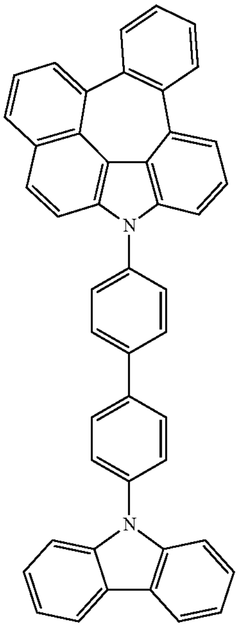
C-250
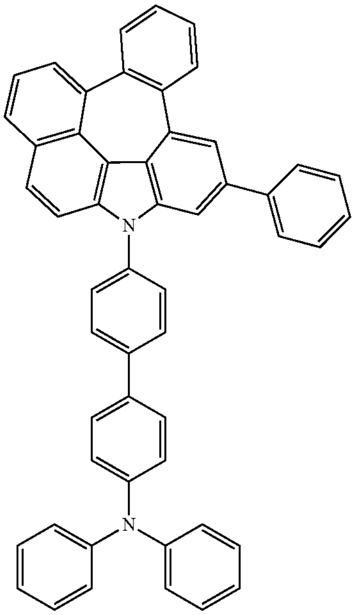
C-251
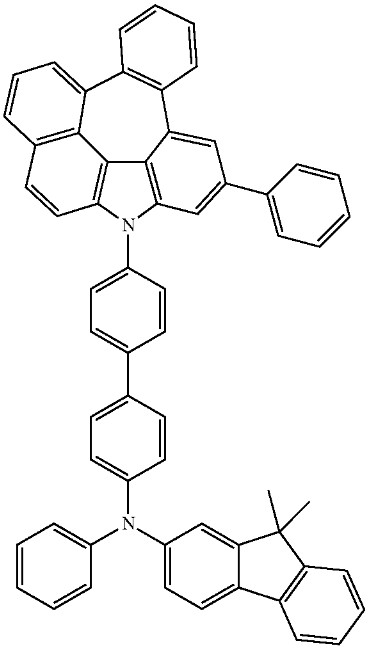

-continued
C-252
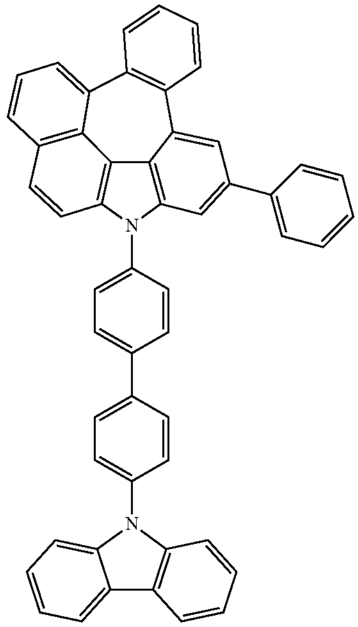
C-253
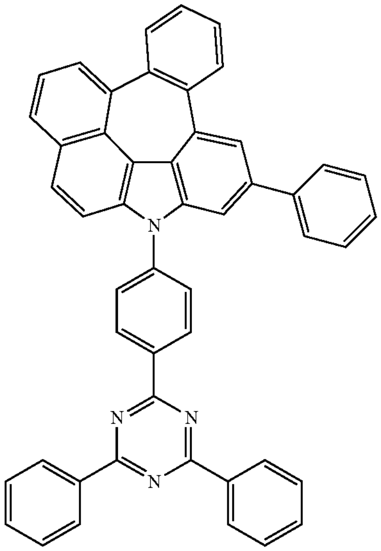
-continued
C-254
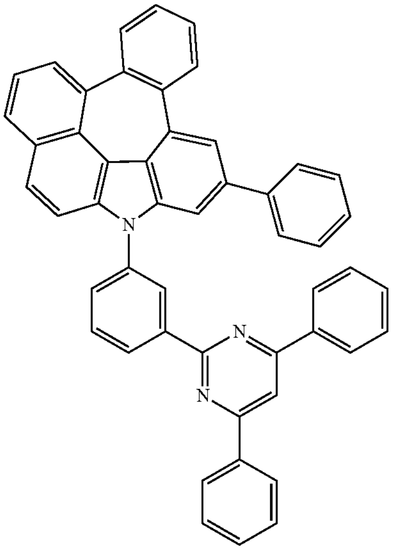
C-255
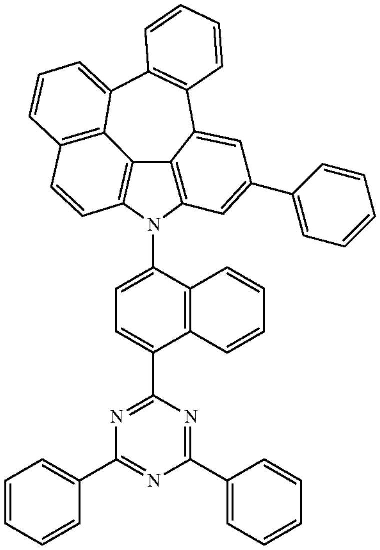
C-256
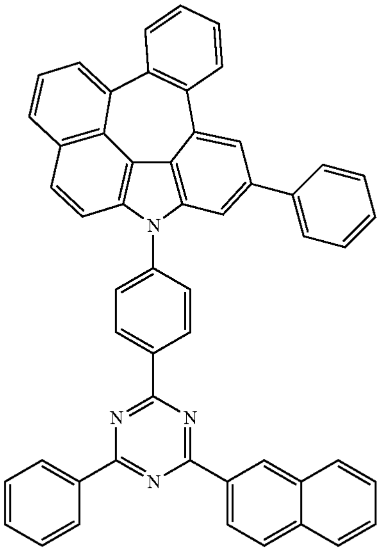

-continued
C-257
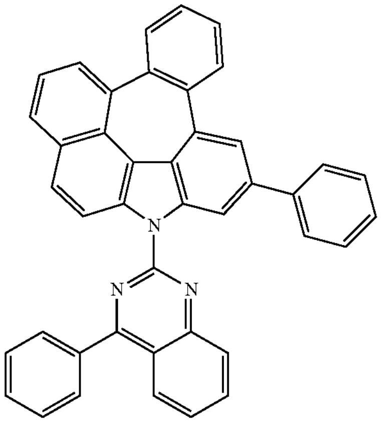
C-258
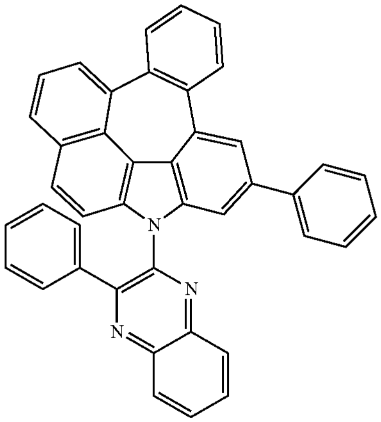
C-259
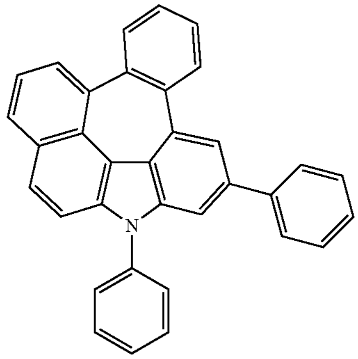
C-260
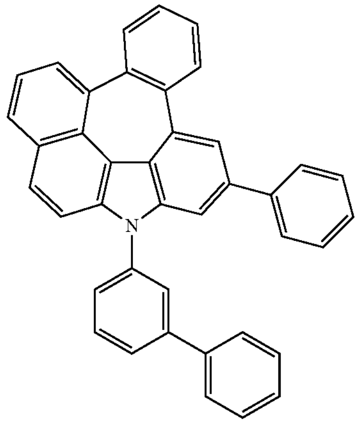
-continued
C-261
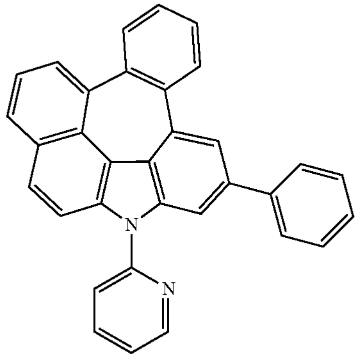
C-262
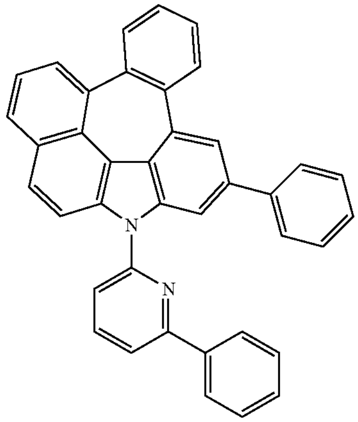
C-263
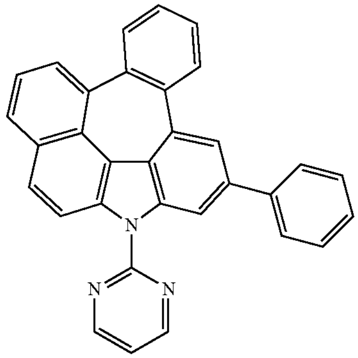
C-264
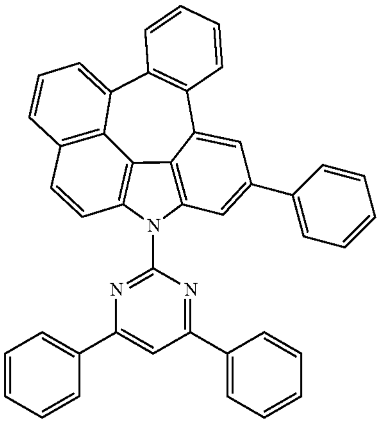

-continued
C-265
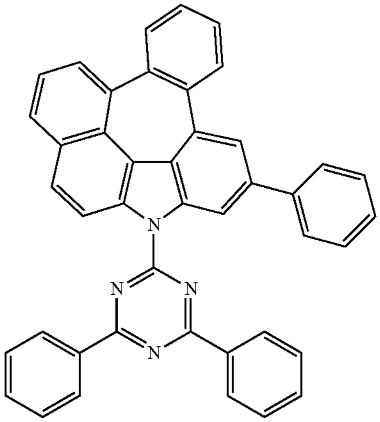
C-266
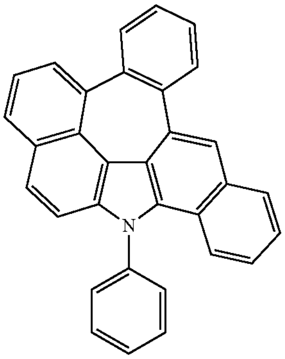
C-267
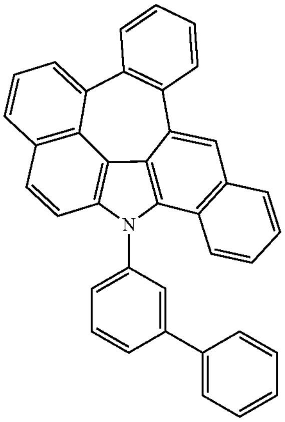
C-268
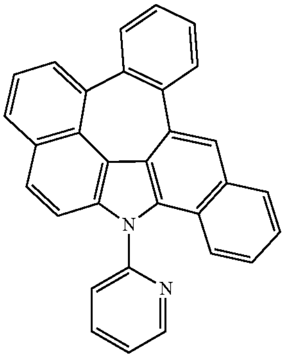
-continued
C-269
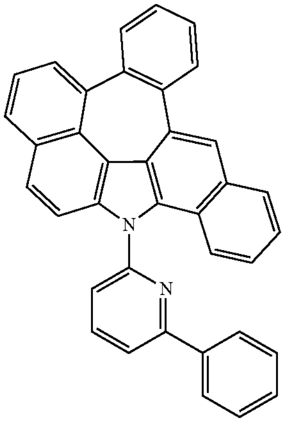
C-270
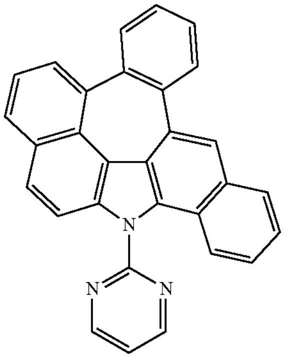
C-271
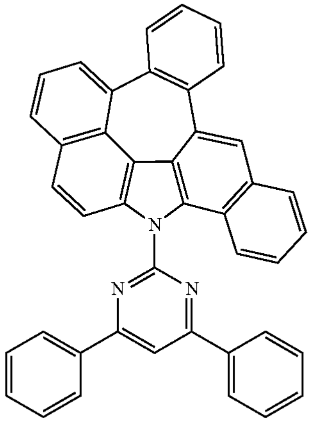
C-272
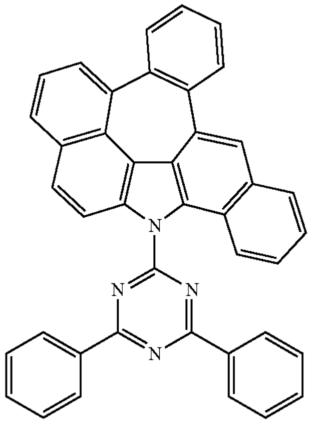

-continued
C-273
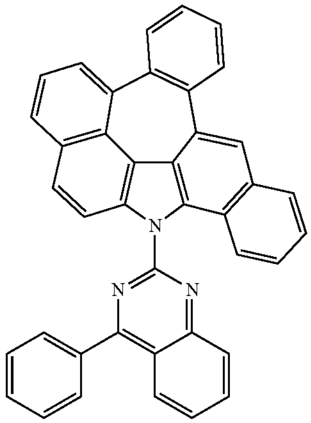
C-274
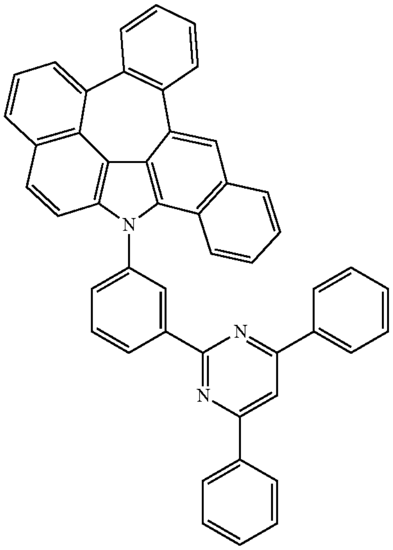
C-275
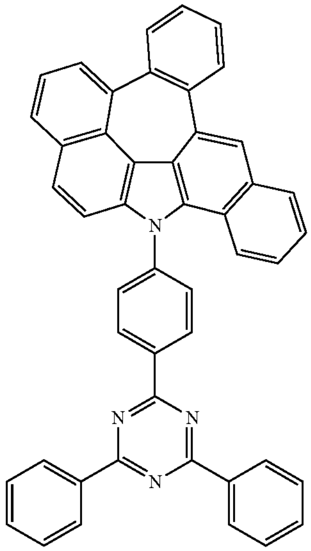
-continued
C-276
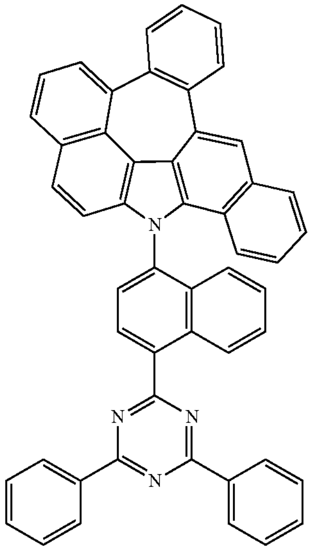
C-277
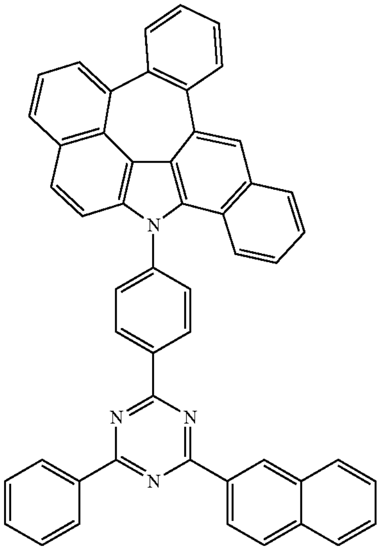
C-278
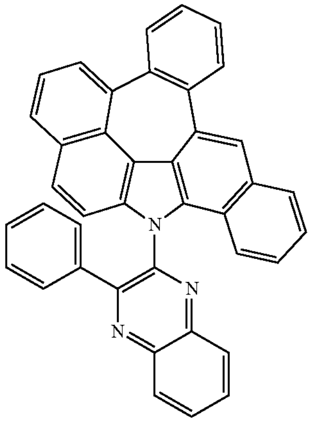

-continued
C-279
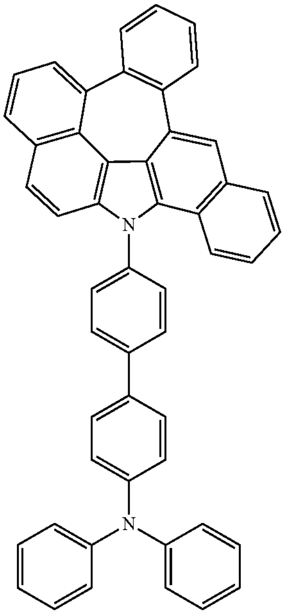
C-280
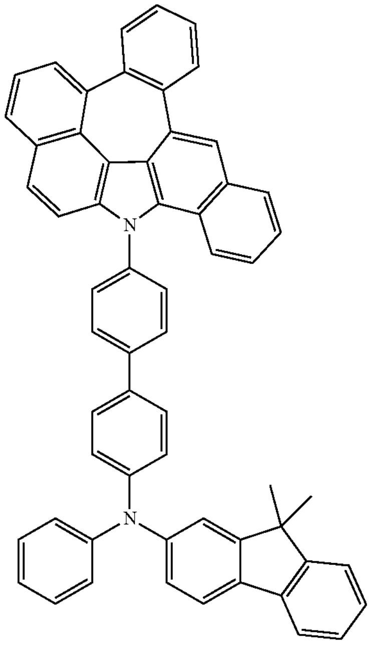
C-281
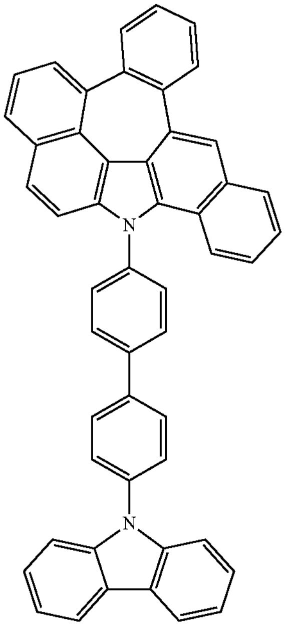
C-282
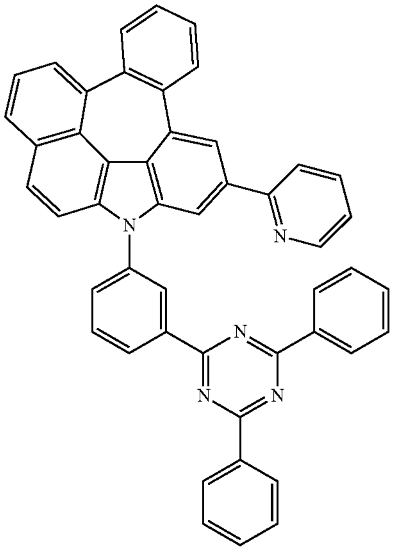

-continued
C-283
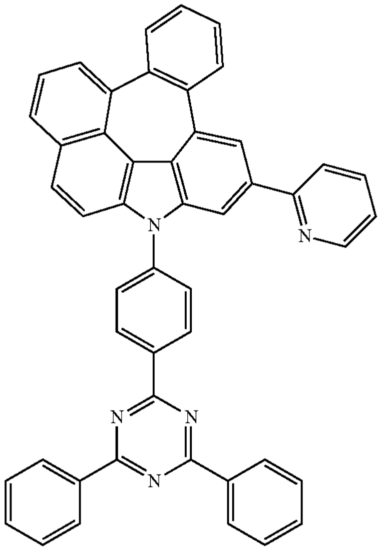
C-284
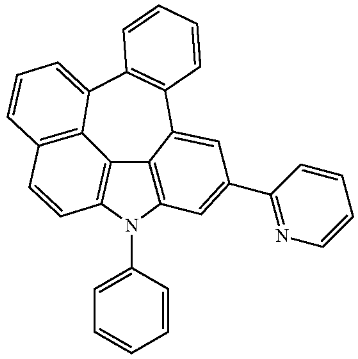
C-285
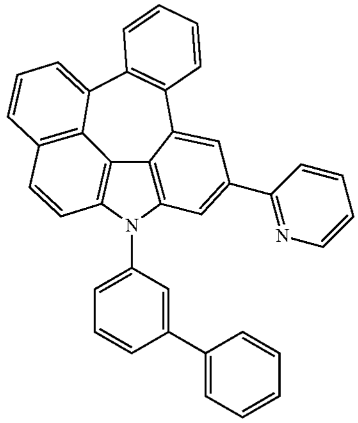
-continued
C-286
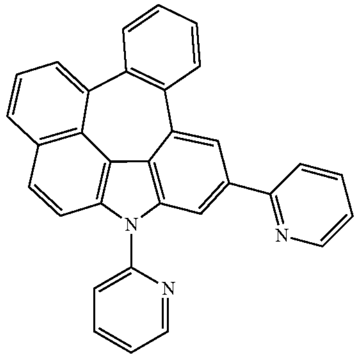
C-287
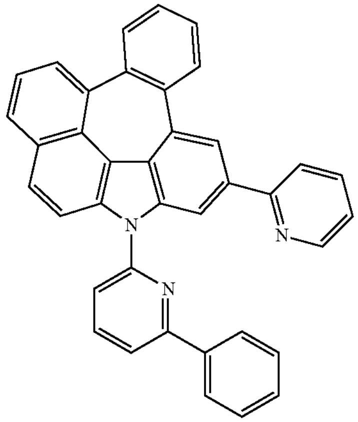
C-288
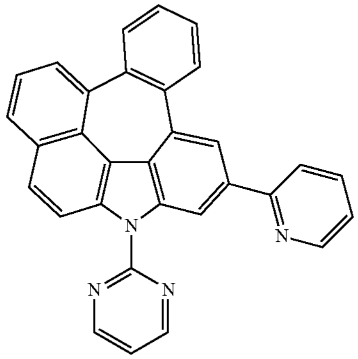

-continued
C-289
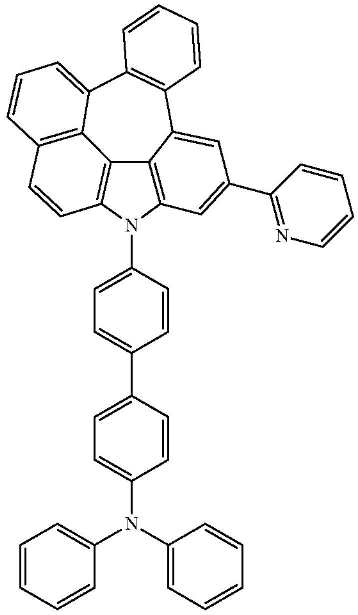
C-290
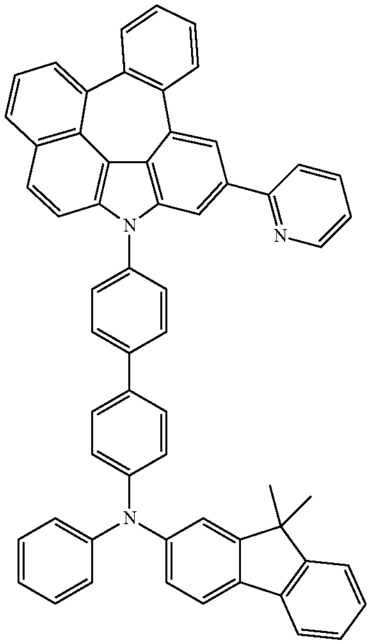
-continued
C-291
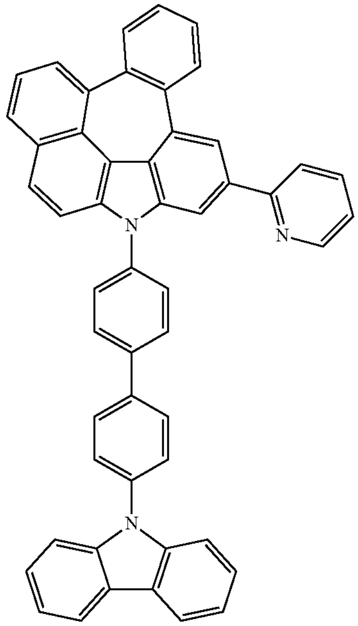
C-292
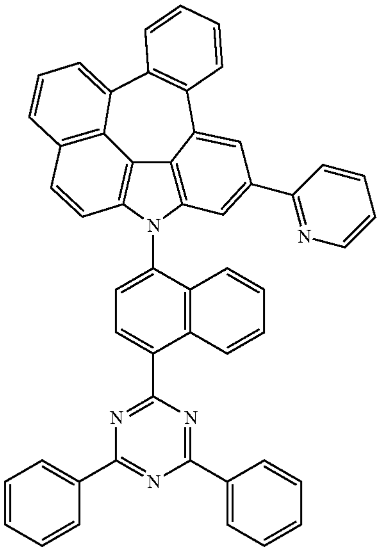

-continued
C-293
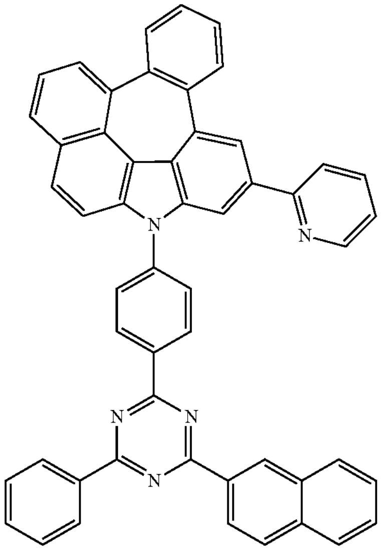
C-294
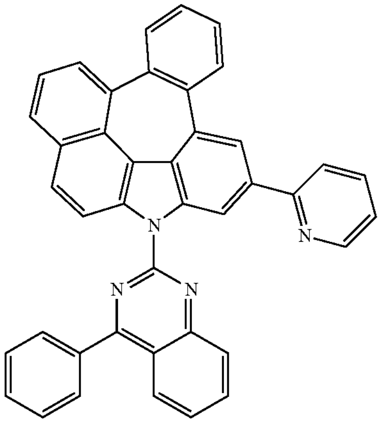
C-295
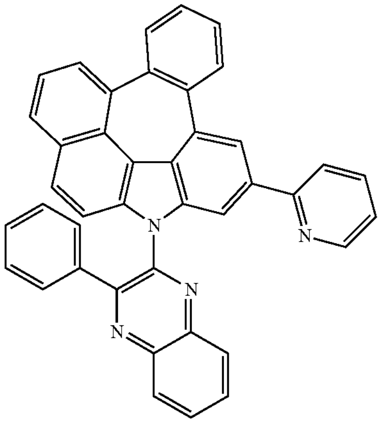
-continued
C-296
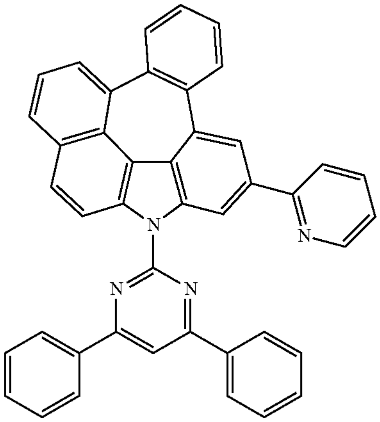
C-297
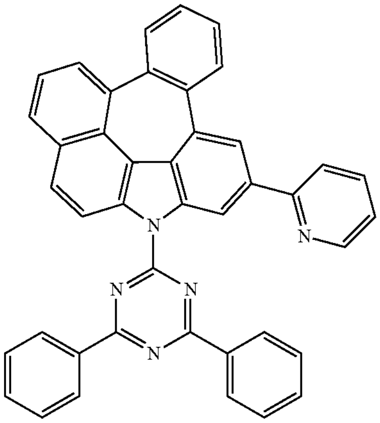
C-298
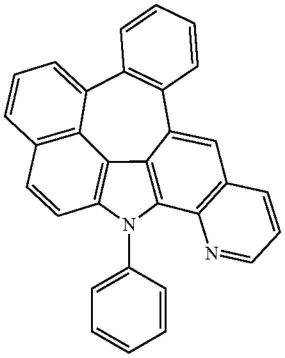
C-299
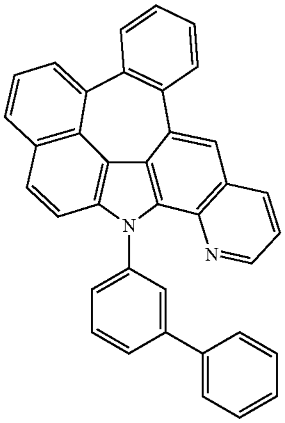

C-300
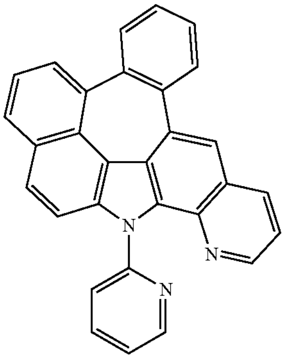
C-301
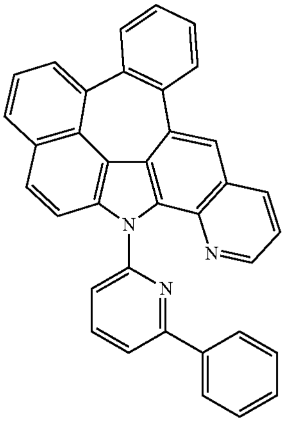
C-302
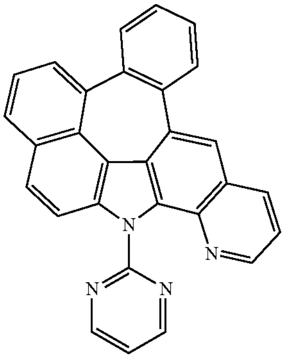
C-303
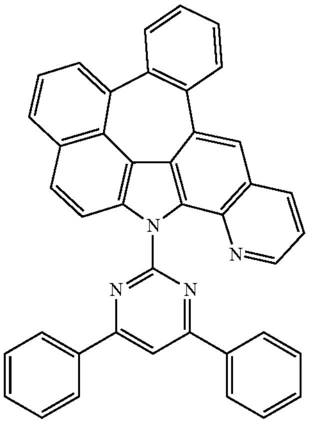
C-304
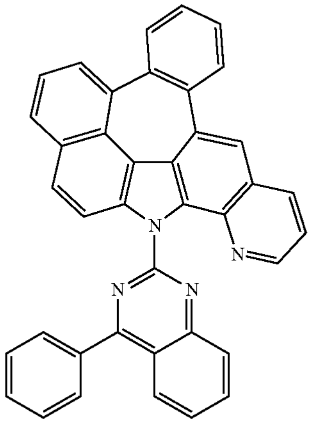
C-305
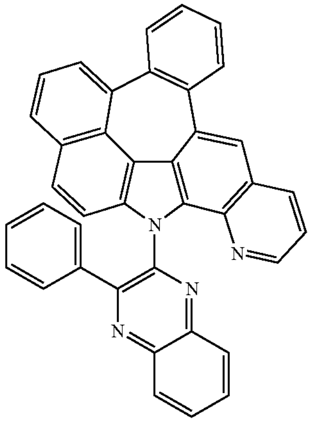
C-306
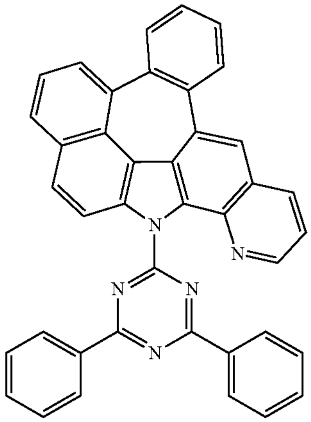

-continued
C-307
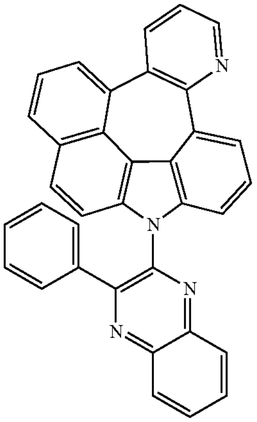
C-308
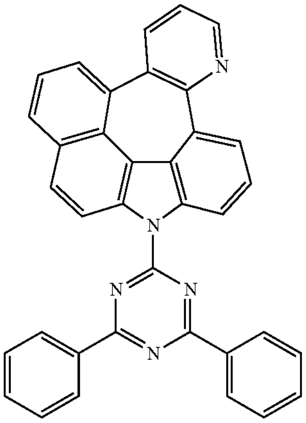
C-309
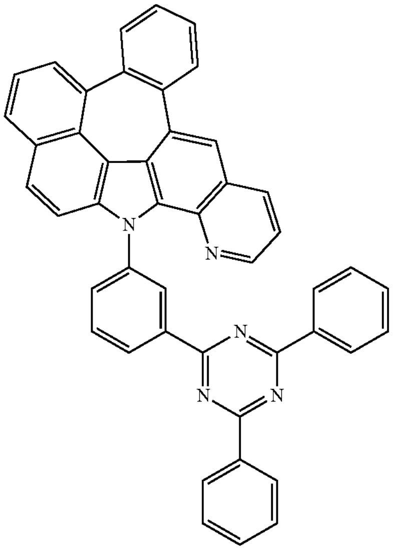
-continued
C-310
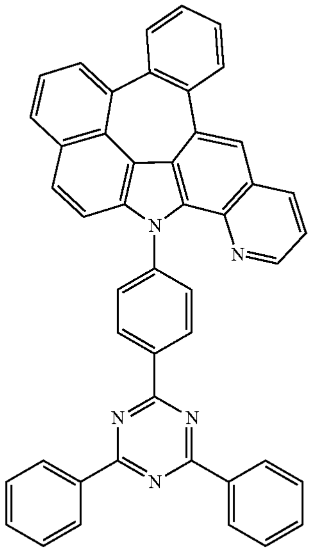
C-311
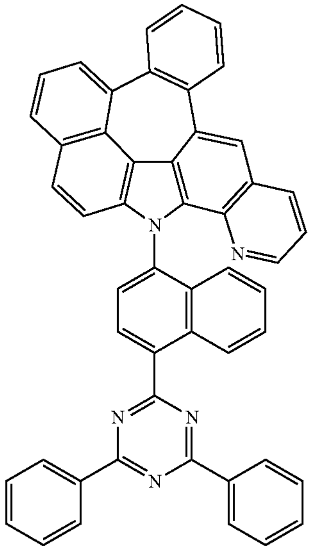
C-312
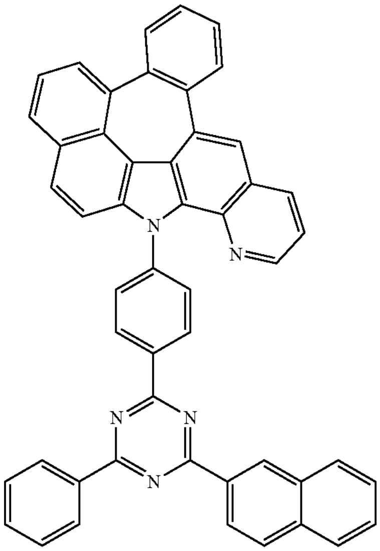

-continued
C-313
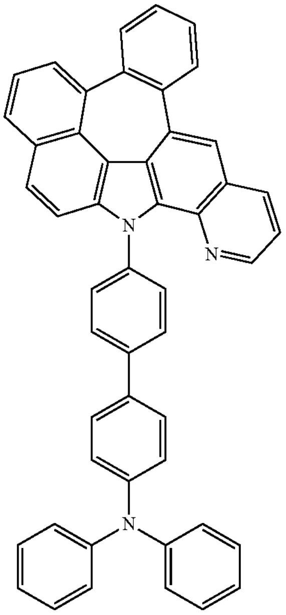
C-314
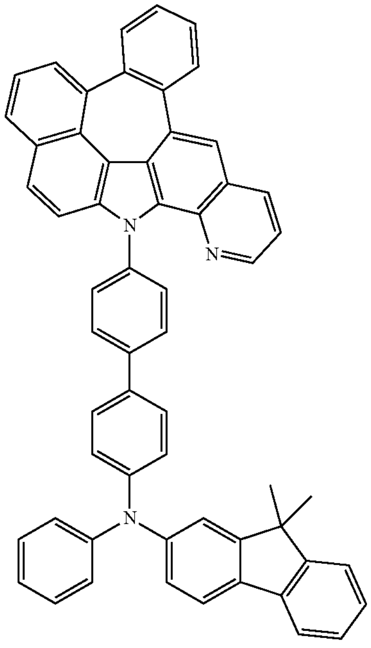
-continued
C-315
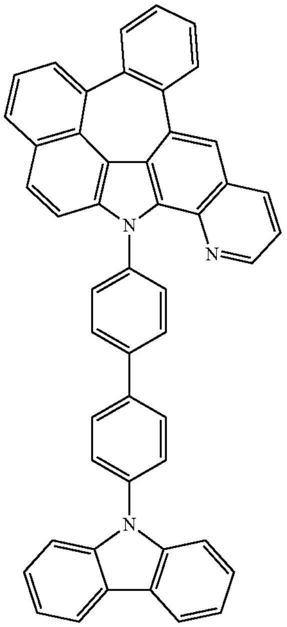
C-316
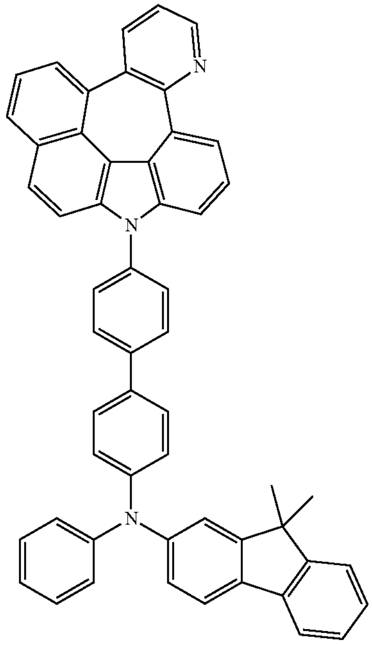

-continued
C-317
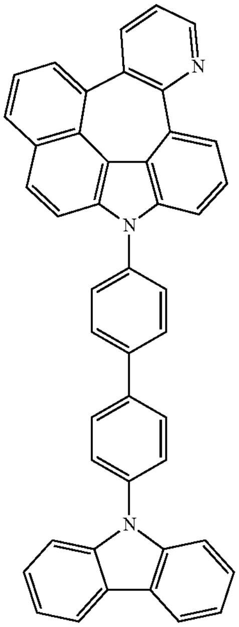
C-318
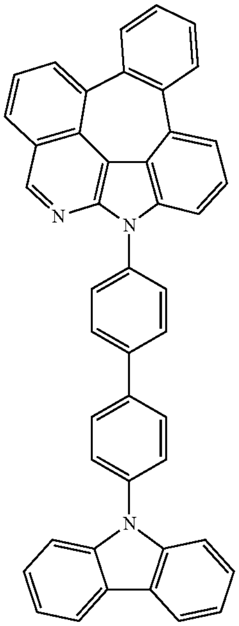
-continued
C-319
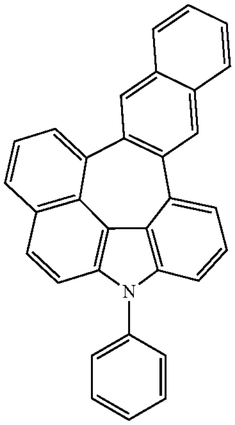
C-320
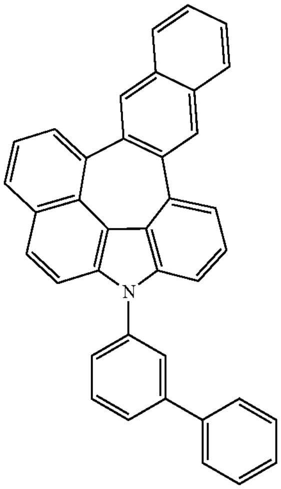
C-321
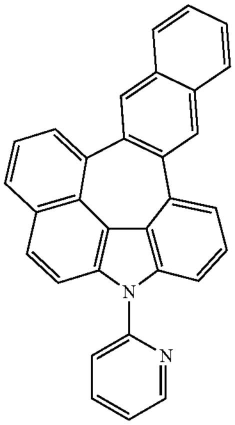

-continued
C-322
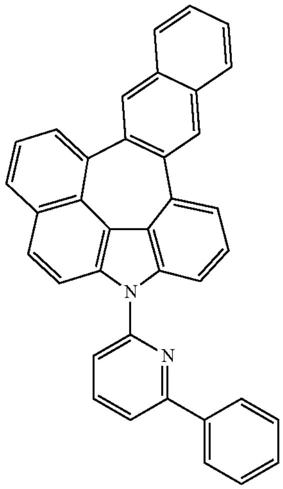
C-323
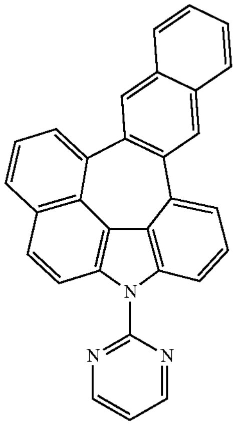
C-324
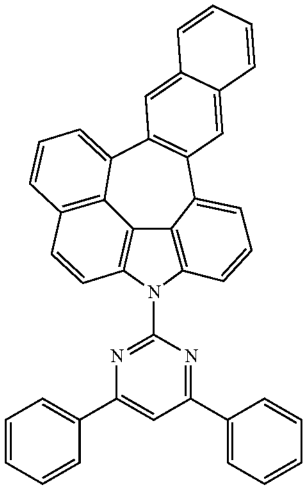
-continued
C-325
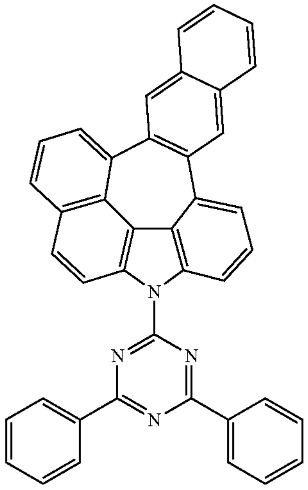
C-326
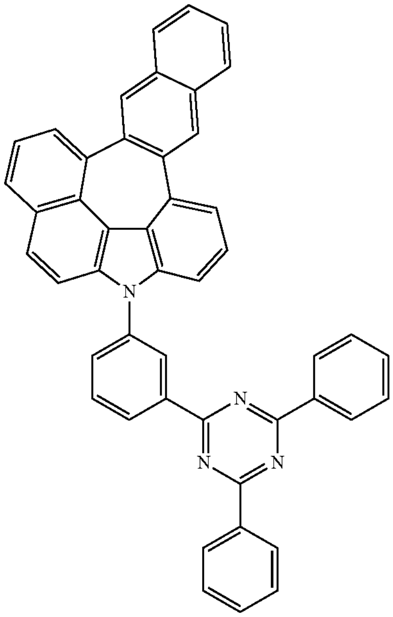

-continued
C-327
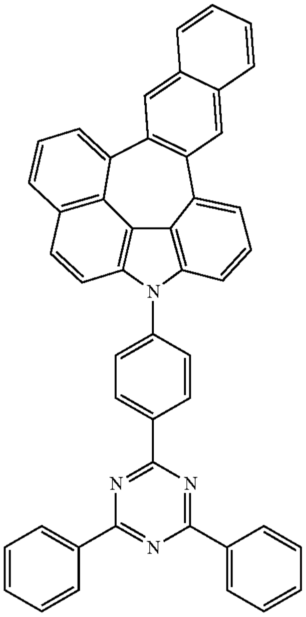
C-328
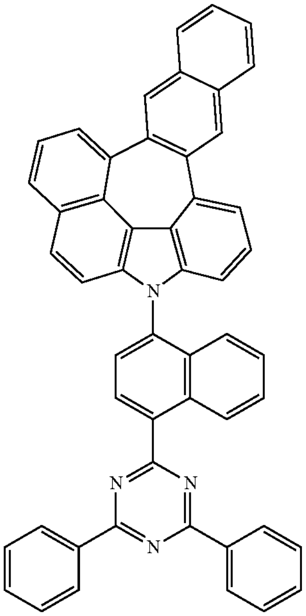
-continued
C-329
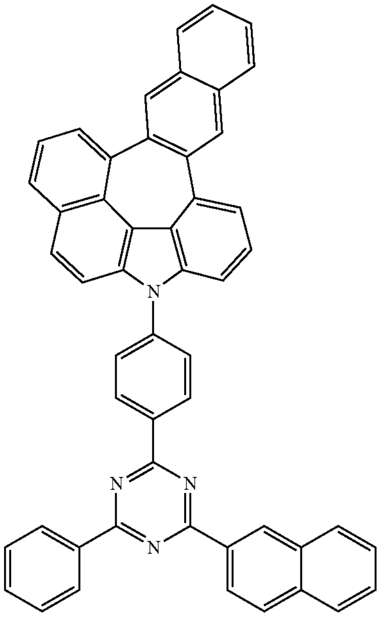
C-330
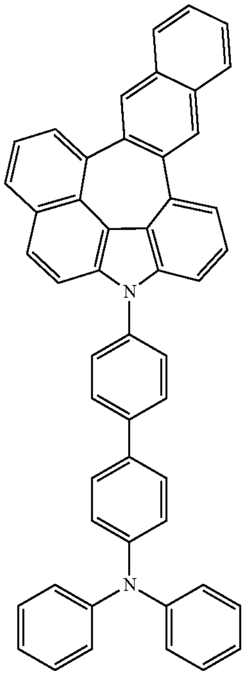

-continued
C-331
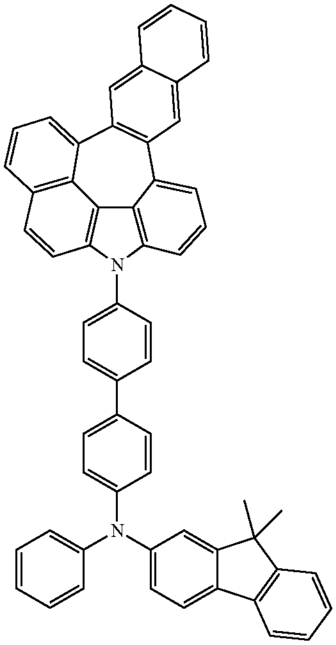
C-332
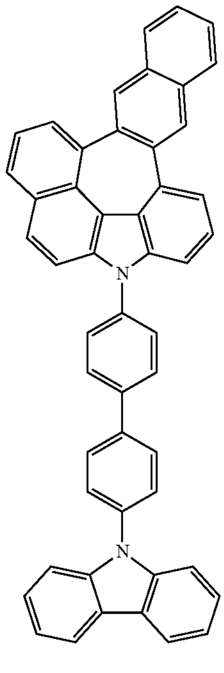
-continued
C-333
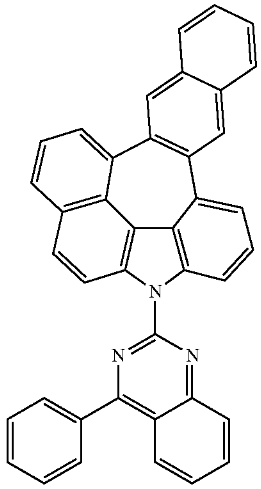
C-334
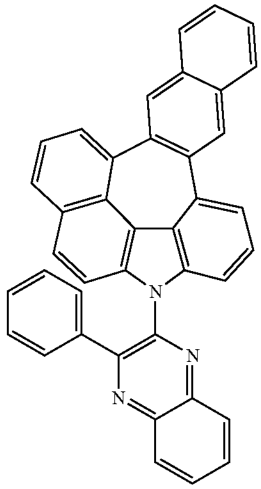
C-335
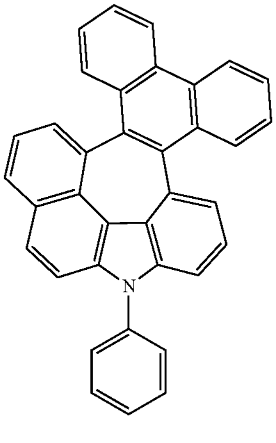

-continued
C-336
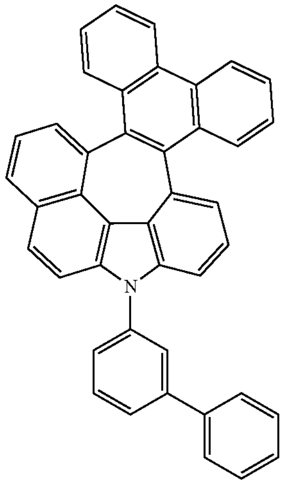
C-337
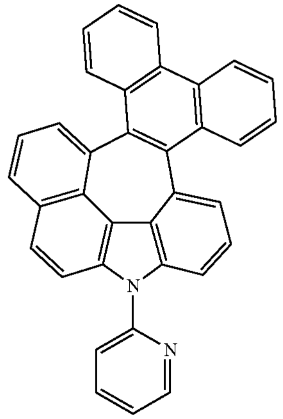
C-338
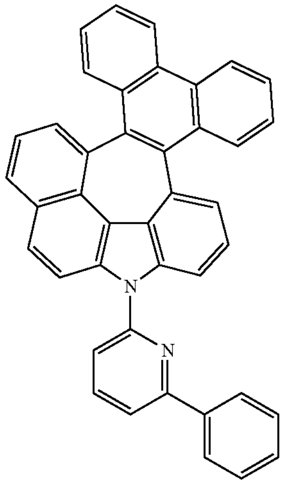
-continued
C-339
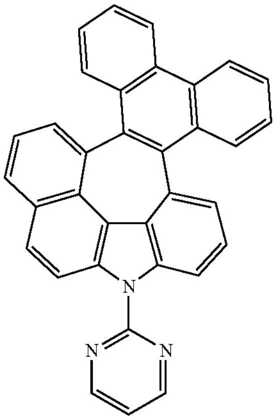
C-340
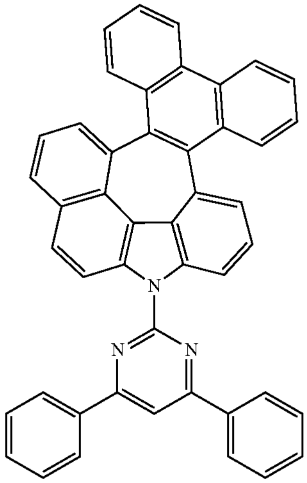
C-341
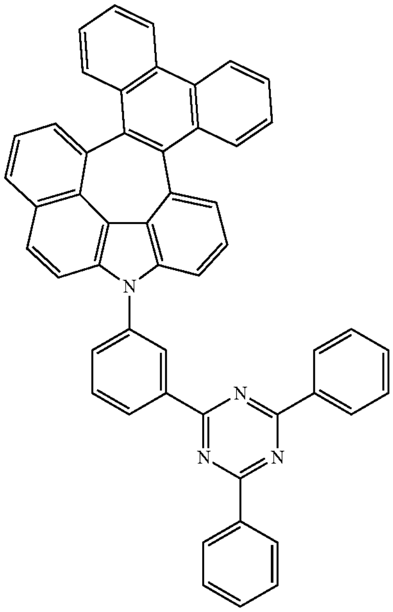

-continued
C-342
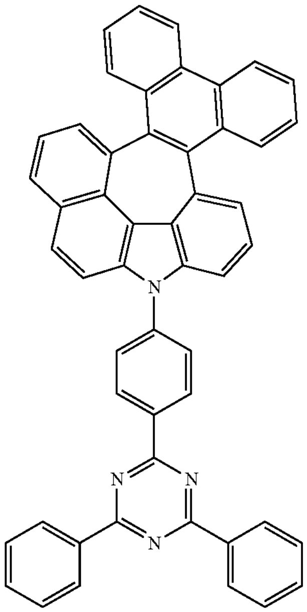
C-343
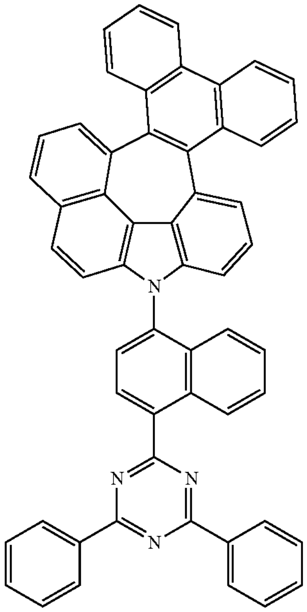
-continued
C-344
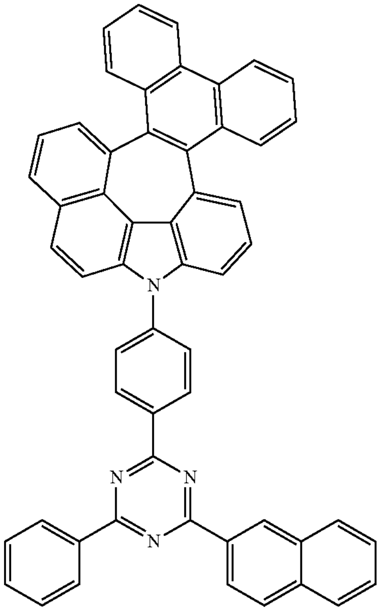
C-345
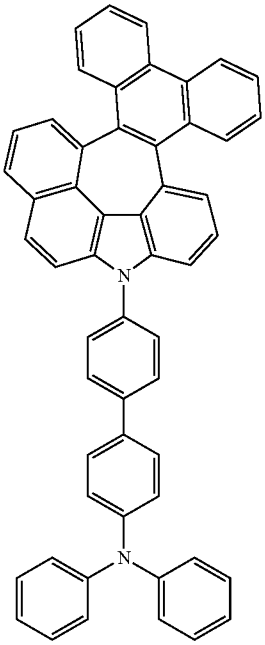

-continued
C-346
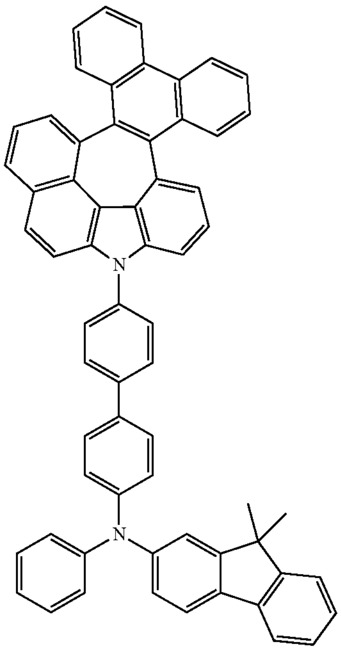
C-347
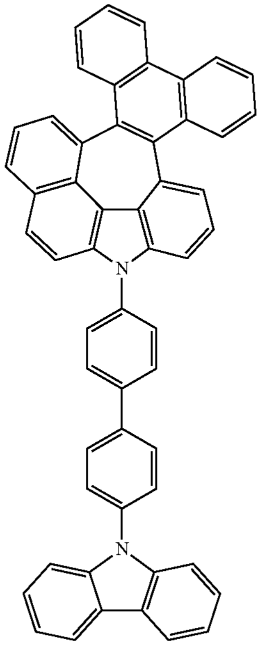
-continued
C-348
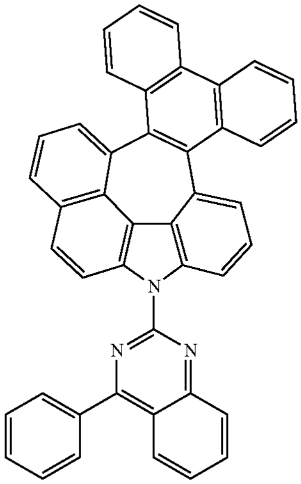
C-349
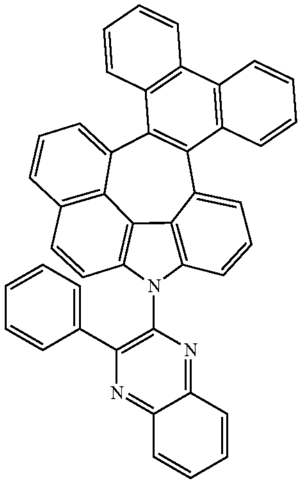
C-350
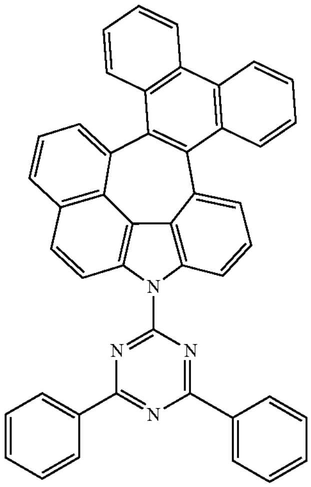

-continued
C-351
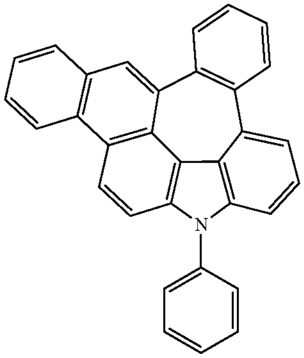
C-352
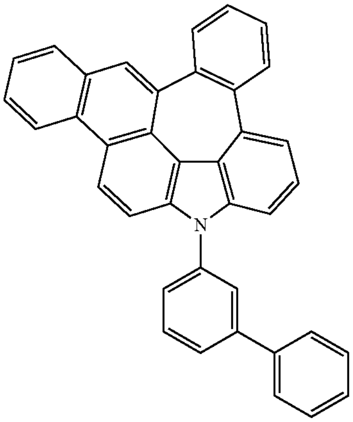
C-353
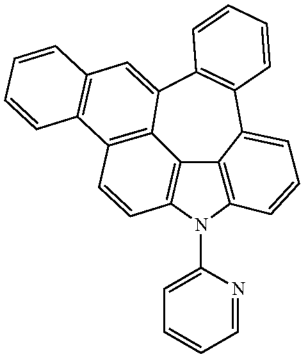
C-354
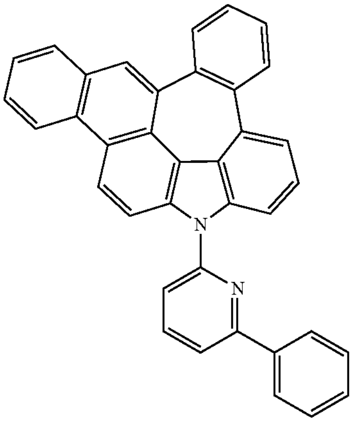
-continued
C-355
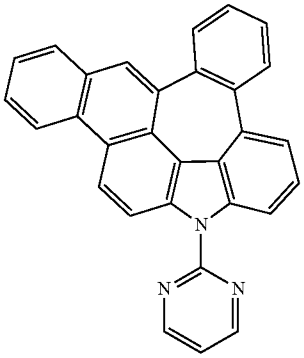
C-356
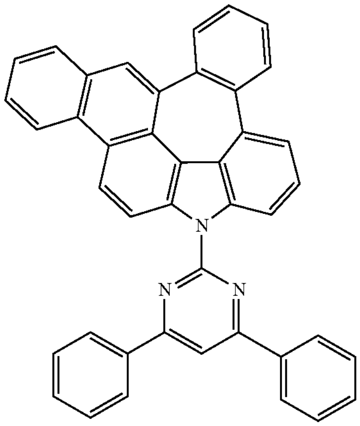
C-357
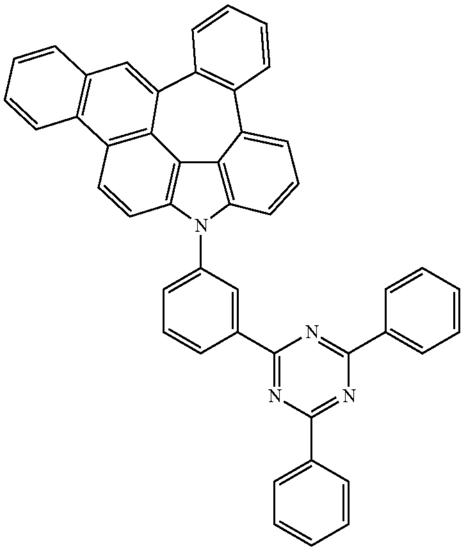

-continued
C-358
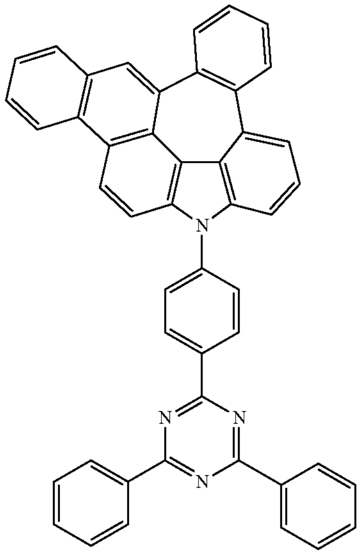
C-359
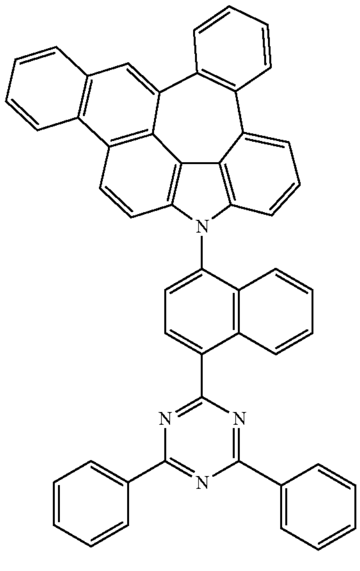
-continued
C-360
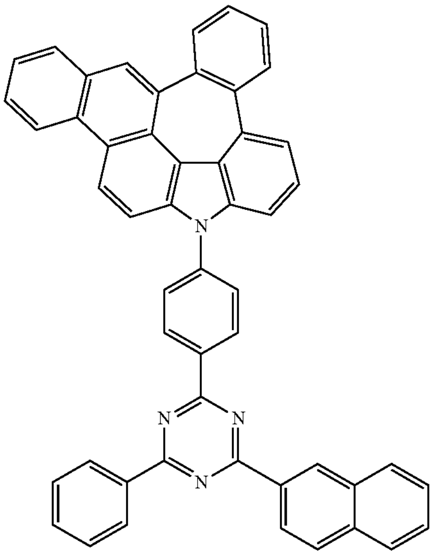
C-361
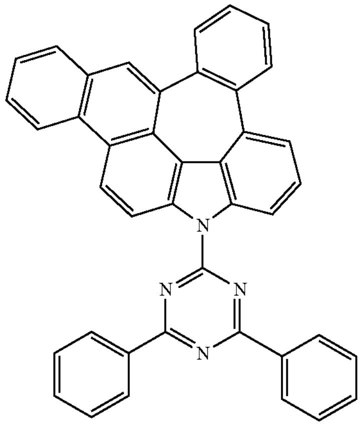
C-362
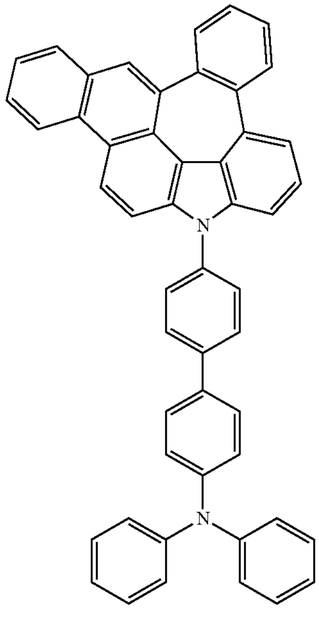

-continued
C-363
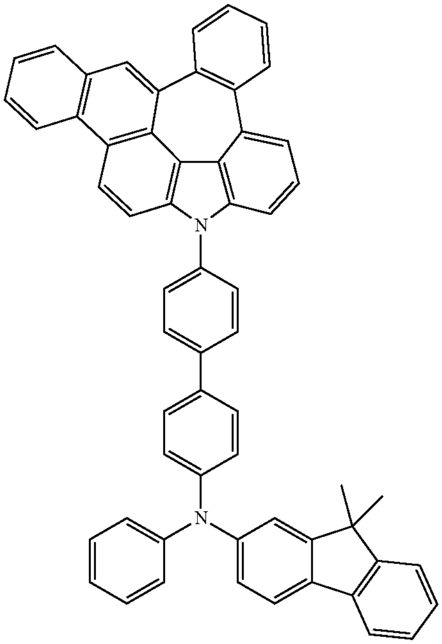
C-364
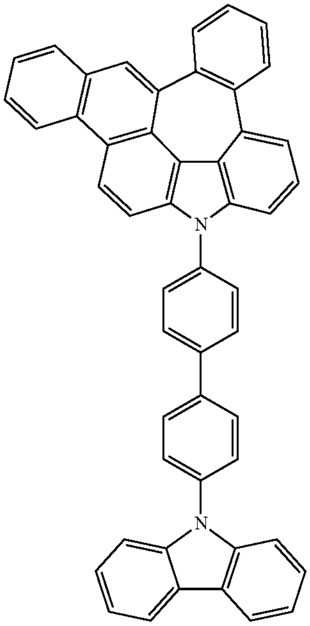
-continued
C-365
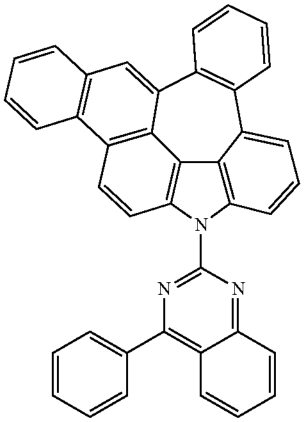
C-366
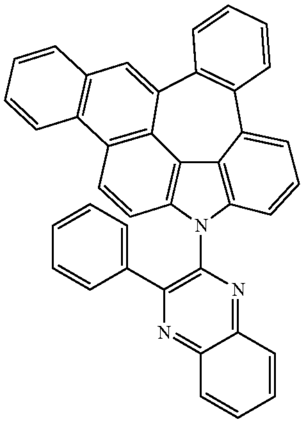
C-367
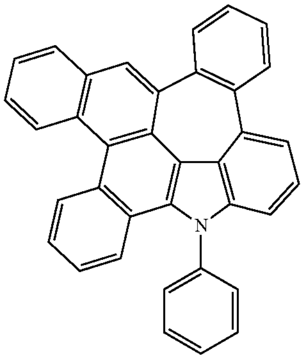
C-368
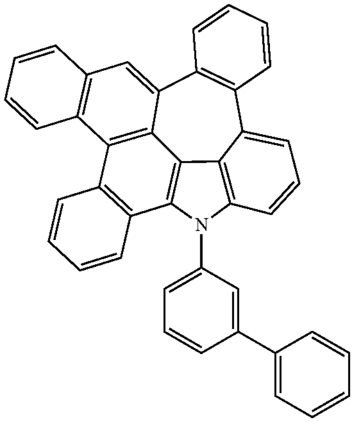

-continued
C-369
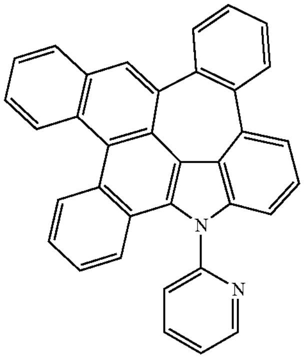
C-370
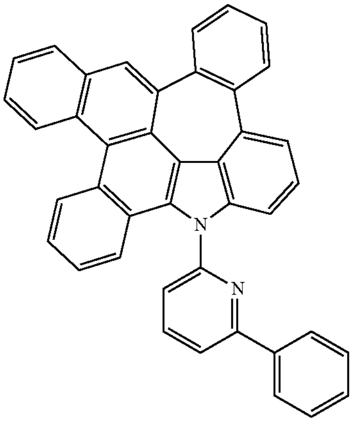
C-371
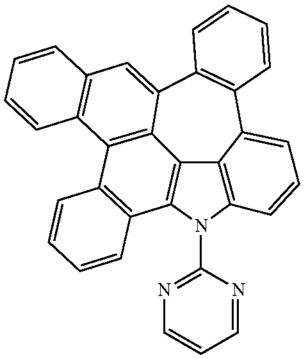
C-372
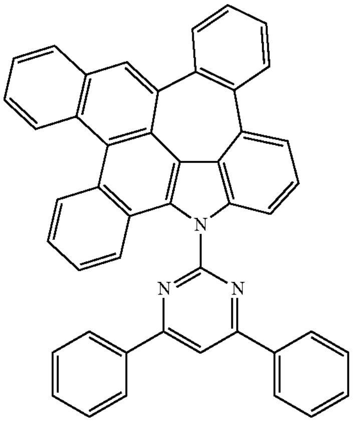
-continued
C-373
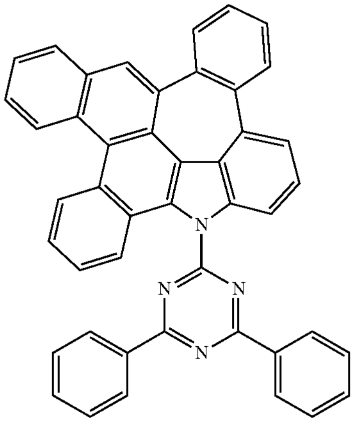
C-374
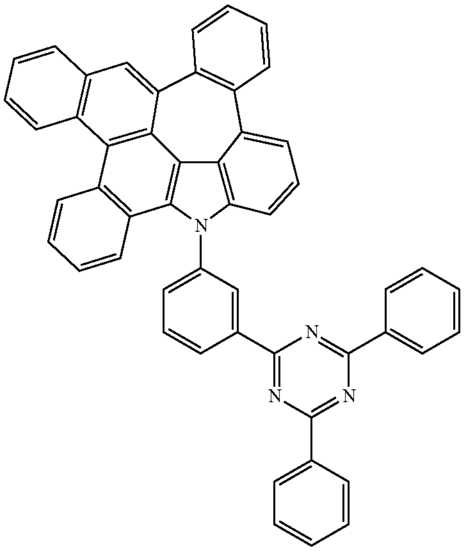
C-375
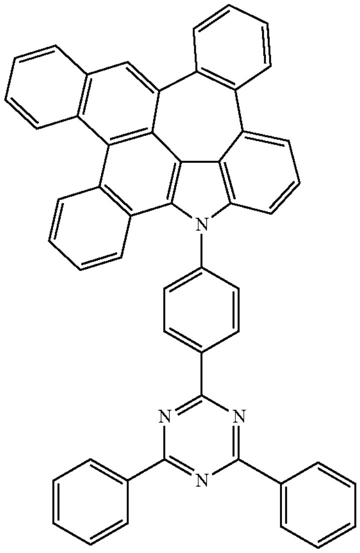

-continued
C-376
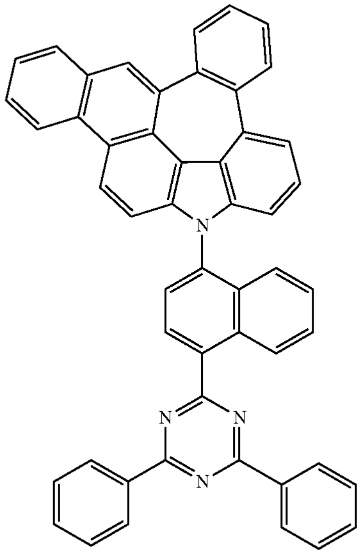
C-377
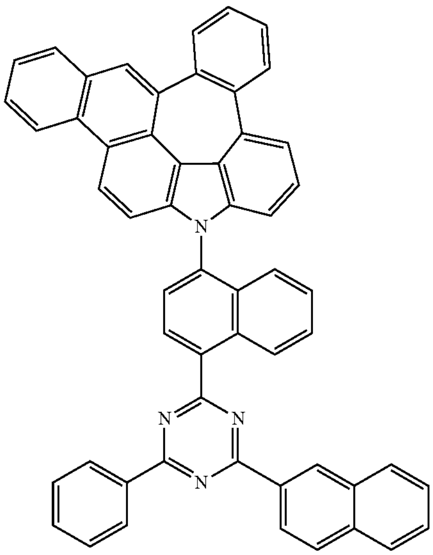
C-378
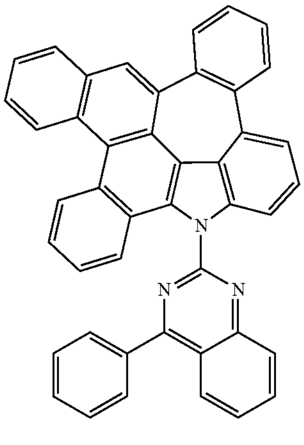
-continued
C-379
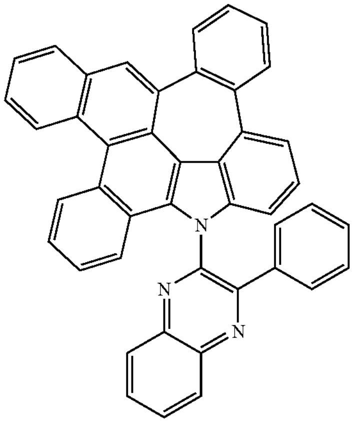
C-380
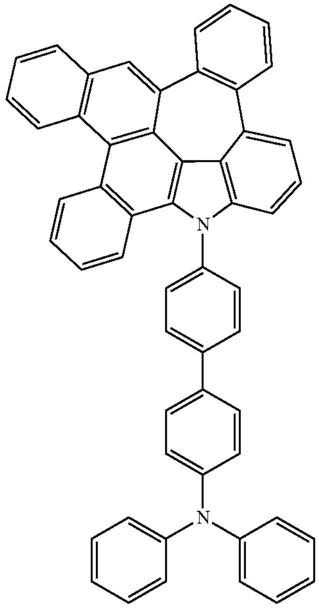

-continued
C-381
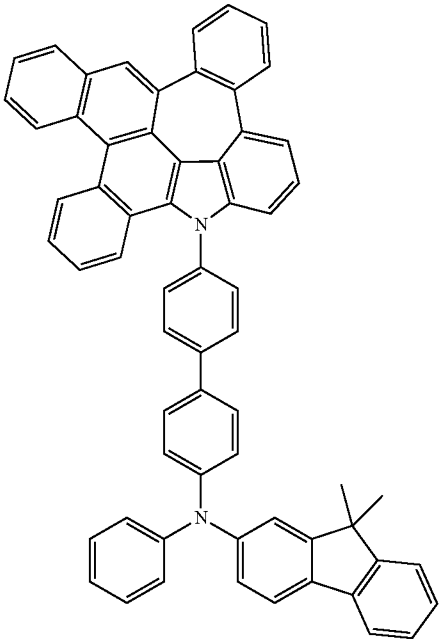
C-382
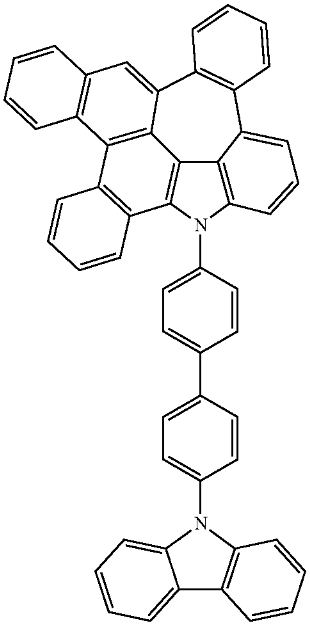
-continued
C-383
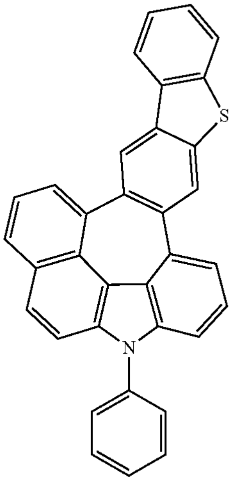
C-384
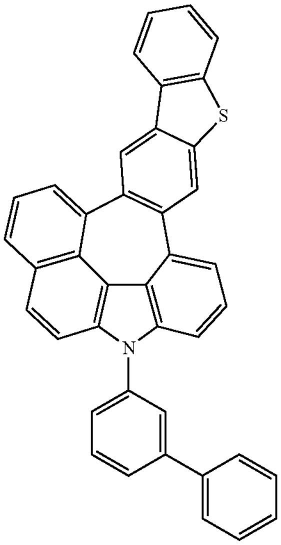
C-385
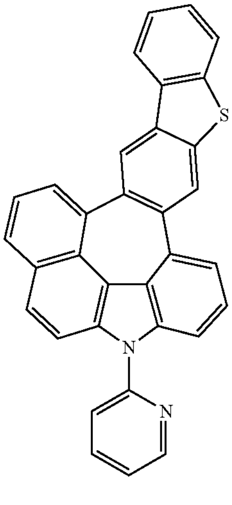

-continued
C-386
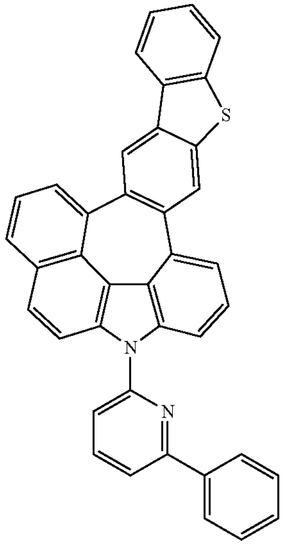
C-387
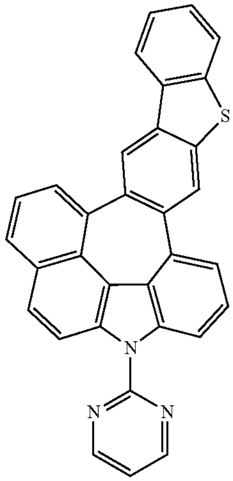
C-388
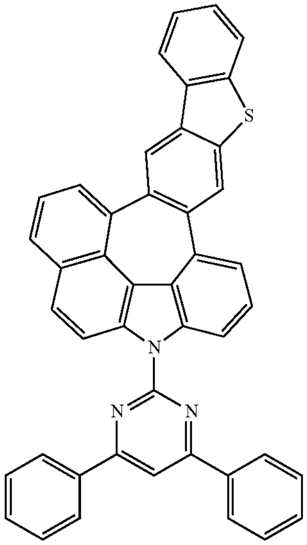
-continued
C-389
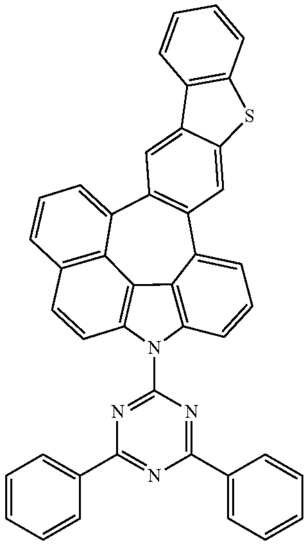
C-390
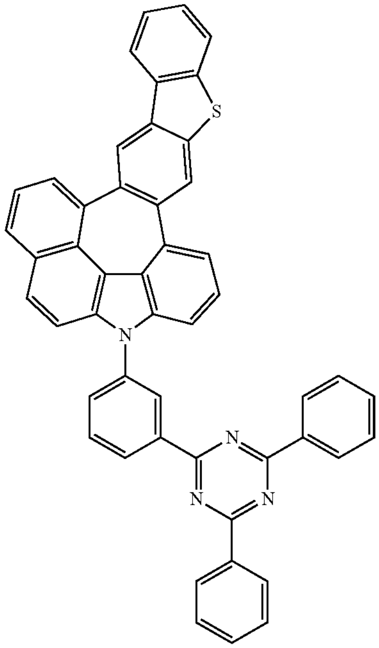

-continued
C-391
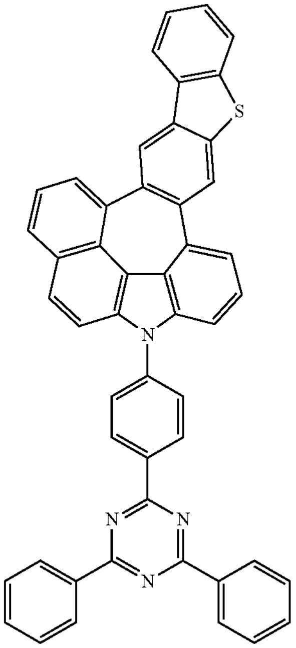
C-392
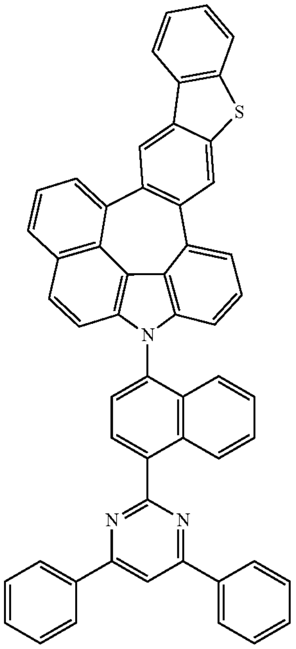
-continued
C-393
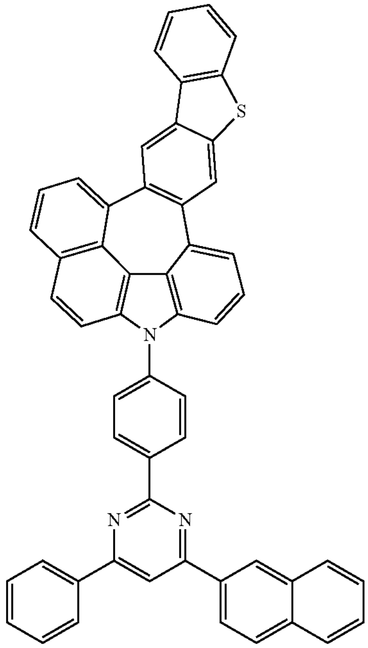
C-394
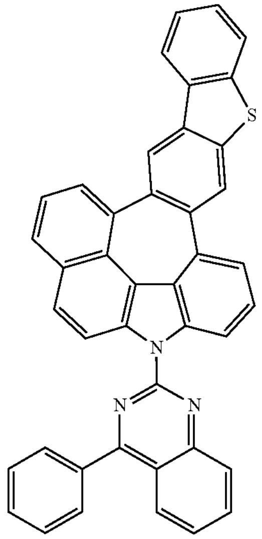

-continued
C-395
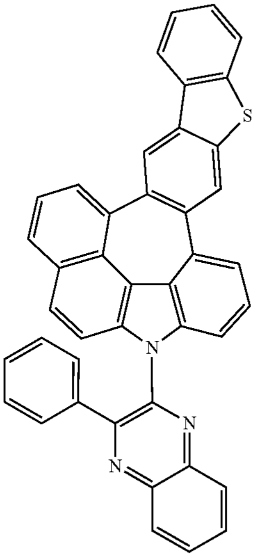
C-396
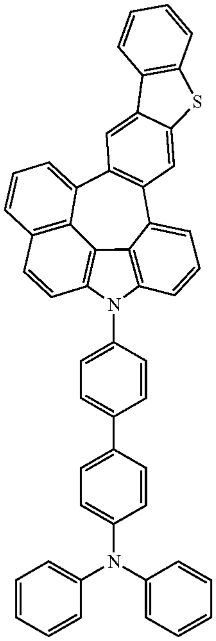
-continued
C-397
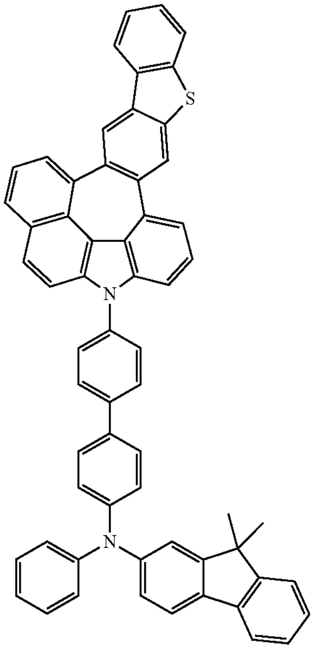
C-398
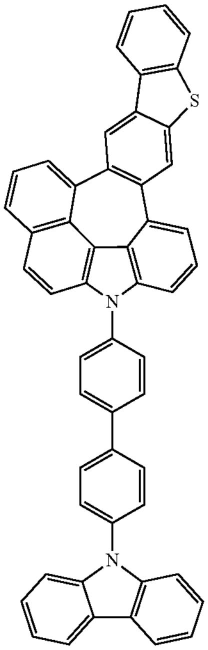

-continued
C-399
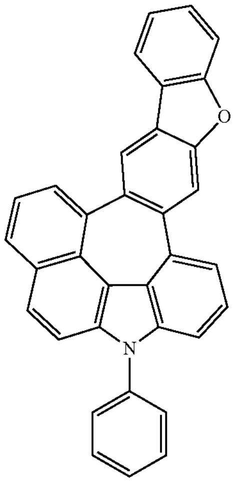
C-400
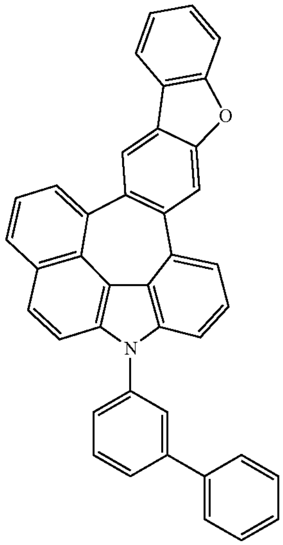
C-401
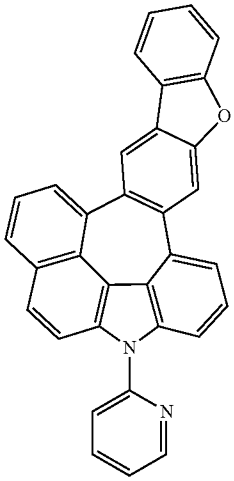
-continued
C-402
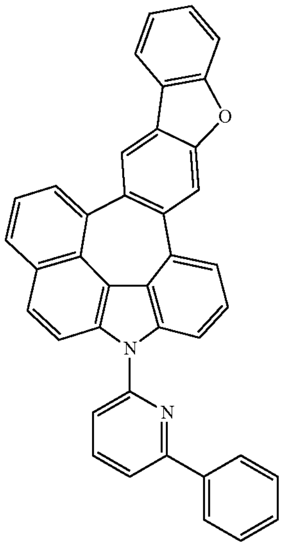
C-403
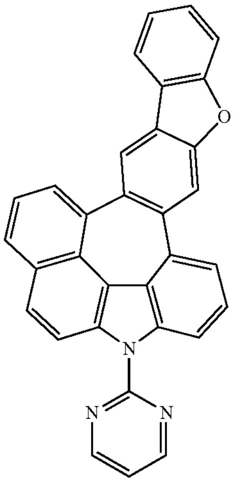
C-404
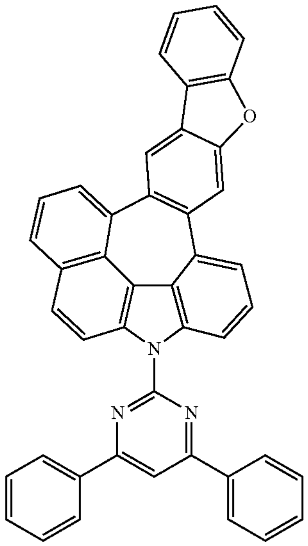

-continued
C-405
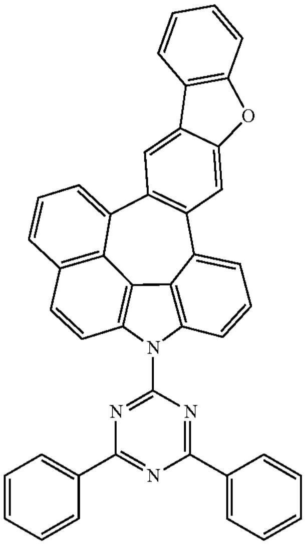
C-406
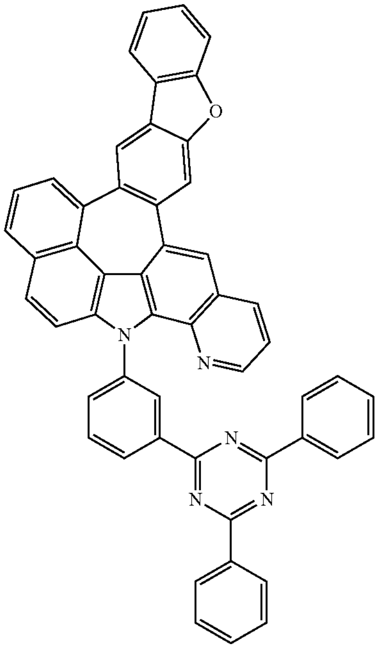
-continued
C-407
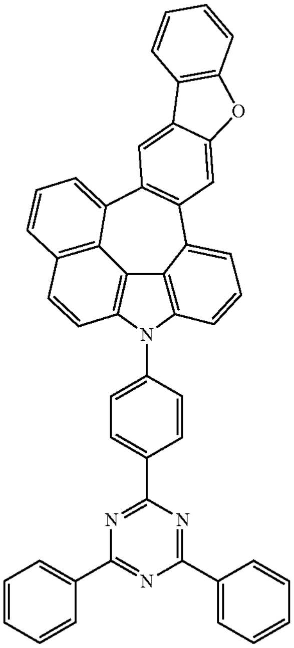
C-408
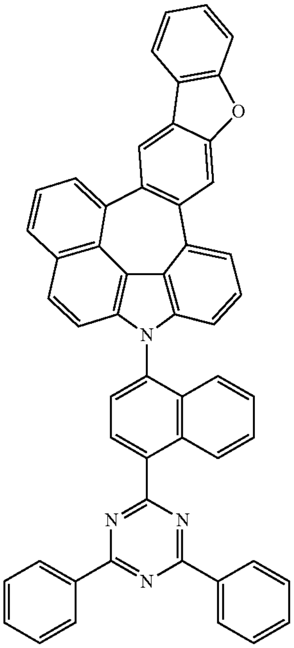

-continued
C-409
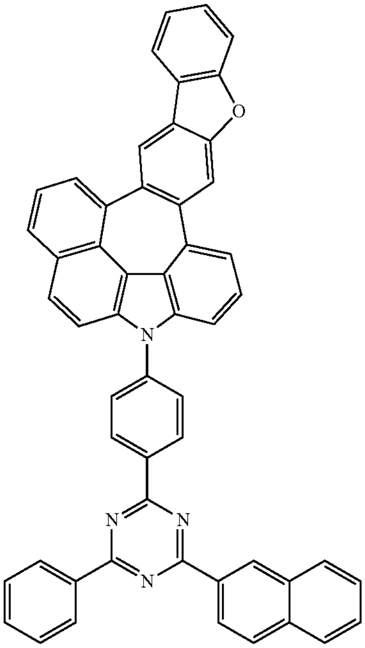
C-410
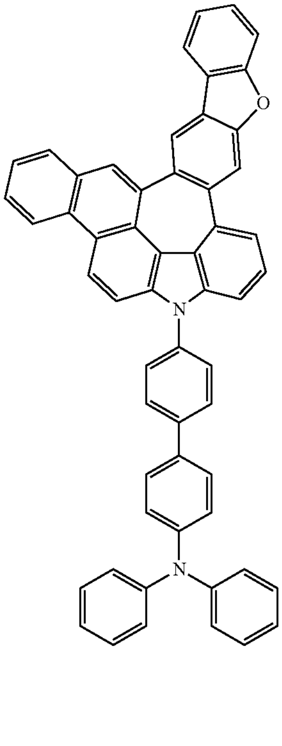
-continued
C-411
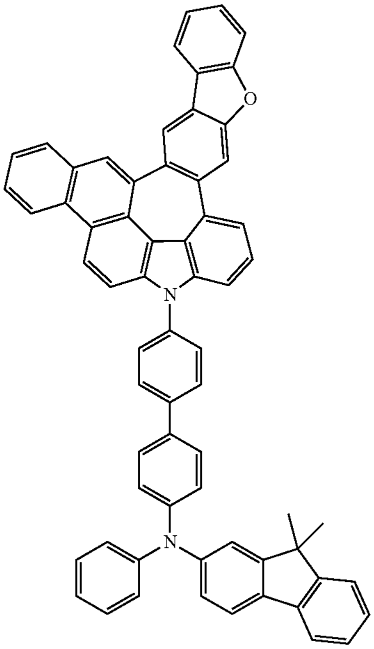
C-412
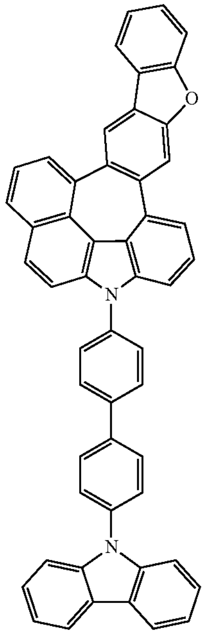

-continued
C-413
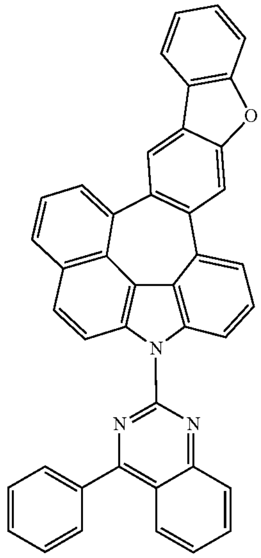
C-414
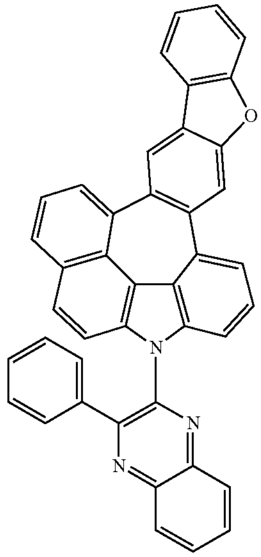
C-415
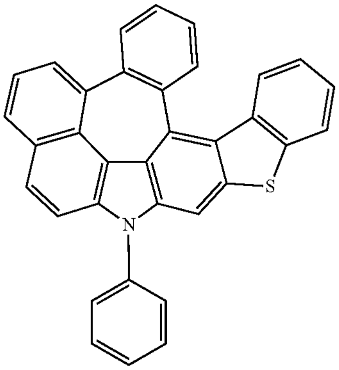
-continued
C-416
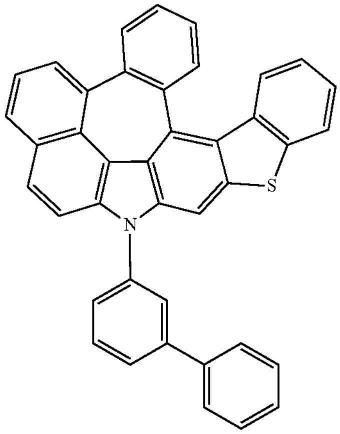
C-417
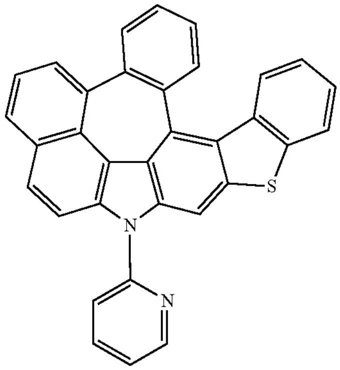
C-417
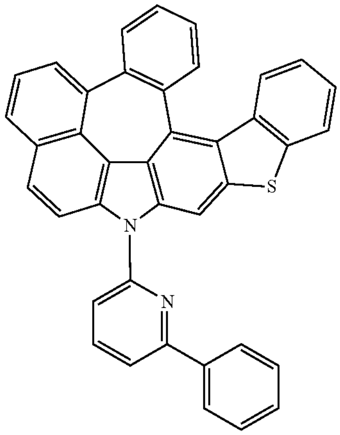
C-419
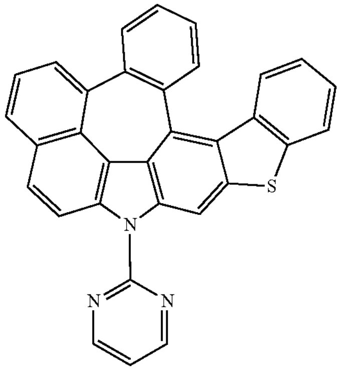

-continued
C-420
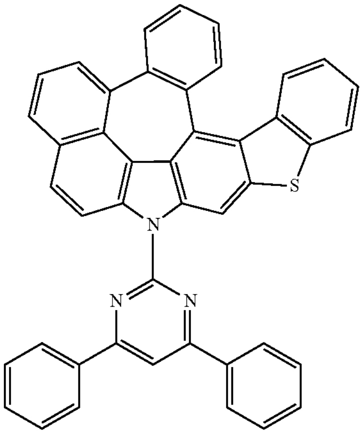
C-421
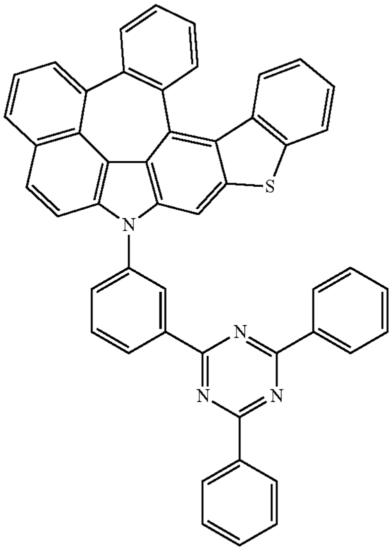
C-422
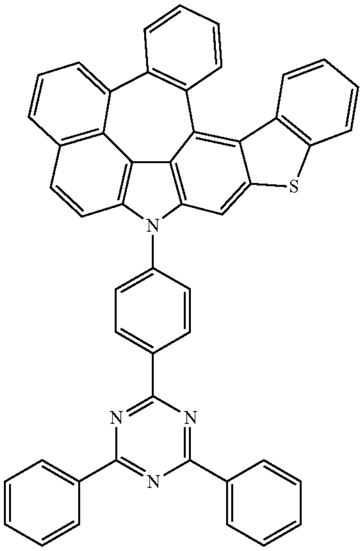
-continued
C-423
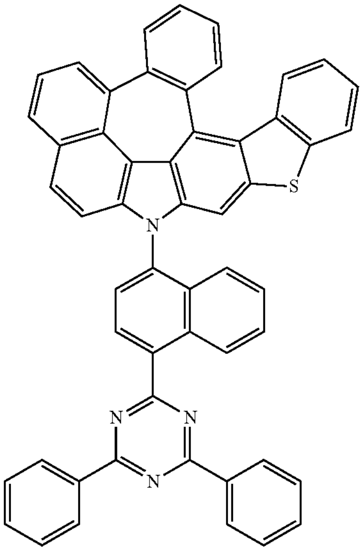
C-424
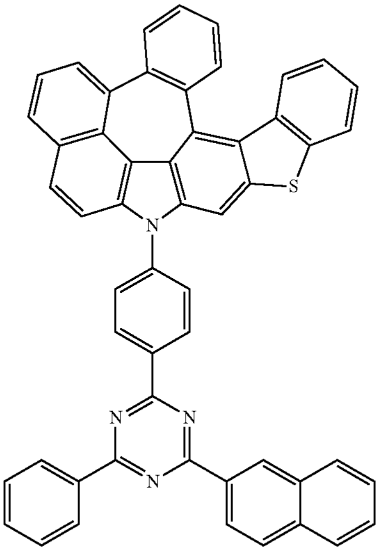
C-425
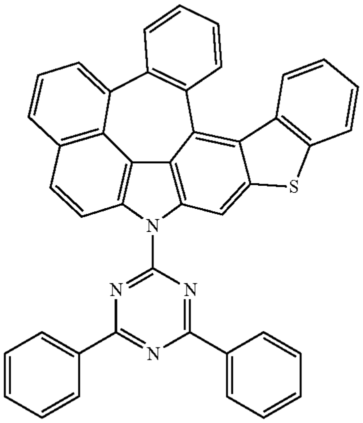

-continued
C-426
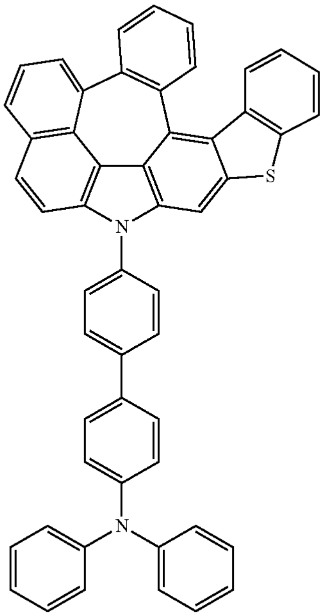
C-427
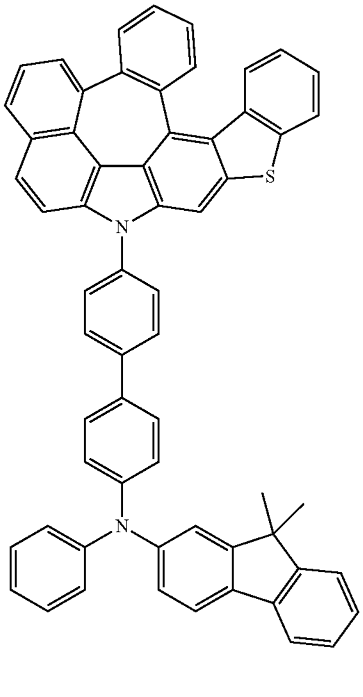
C-428
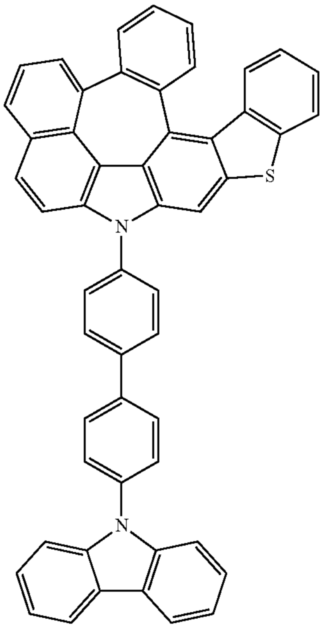
C-429
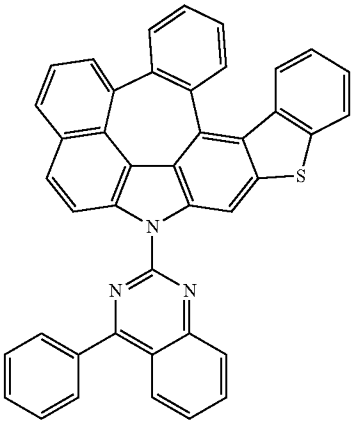
C-430
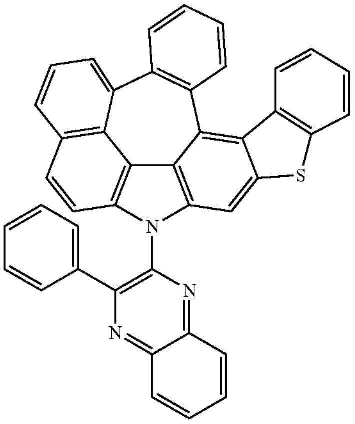

-continued
C-431
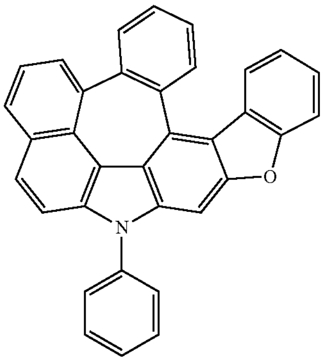
C-432
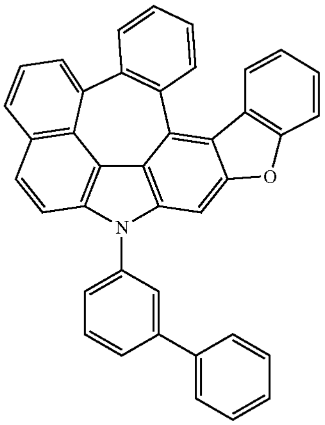
C-433
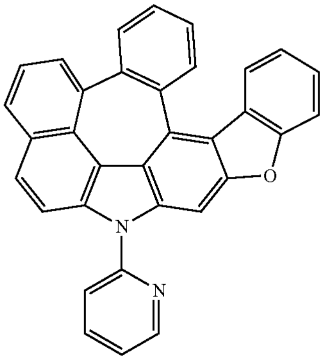
C-434
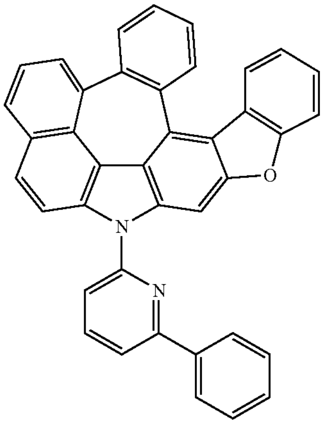
-continued
C-435
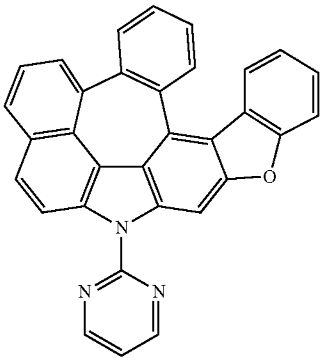
C-436
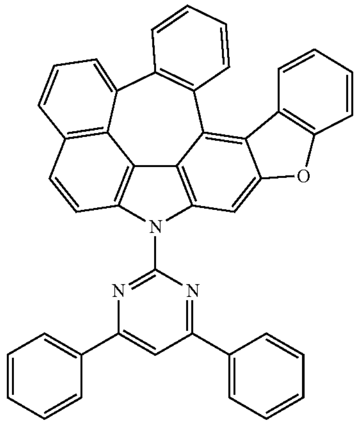
C-437
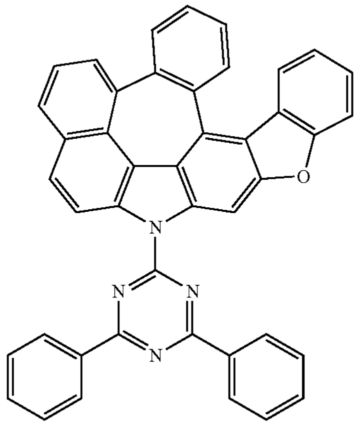

-continued
C-438
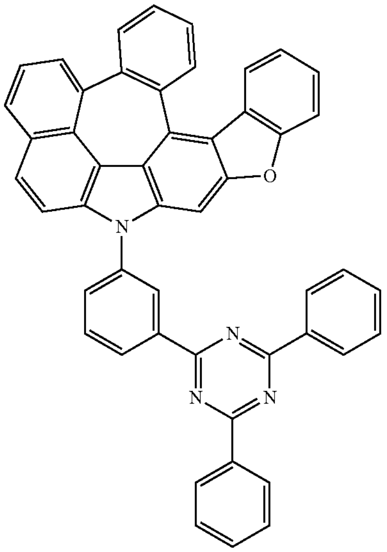
C-439
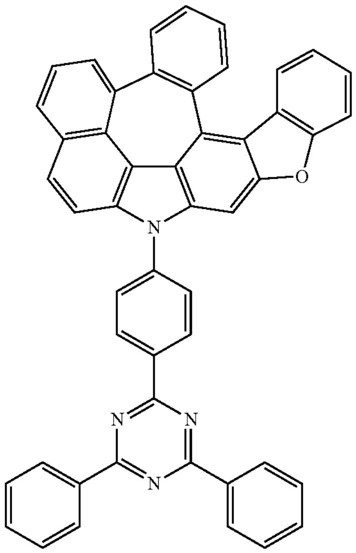
C-440
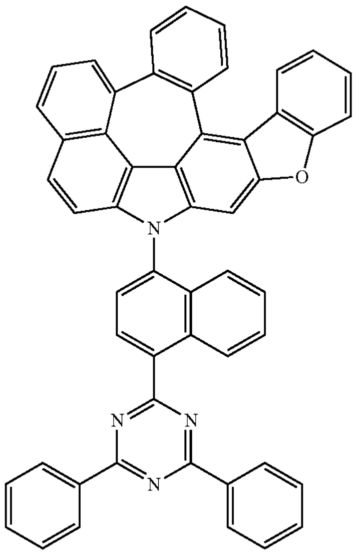
-continued
C-441
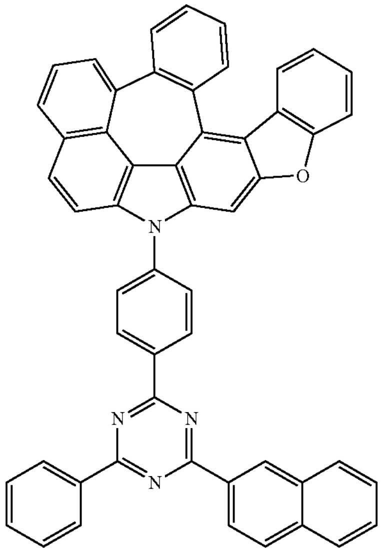
C-442
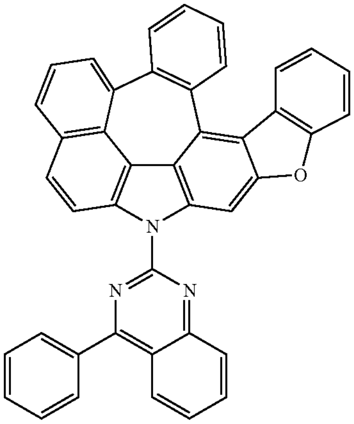
C-443
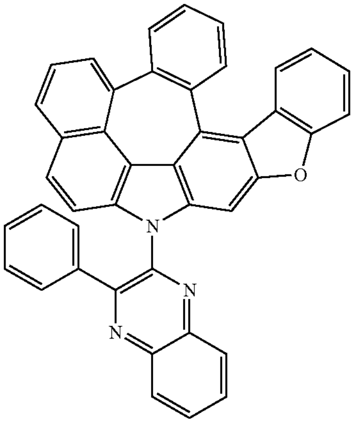

-continued
C-444
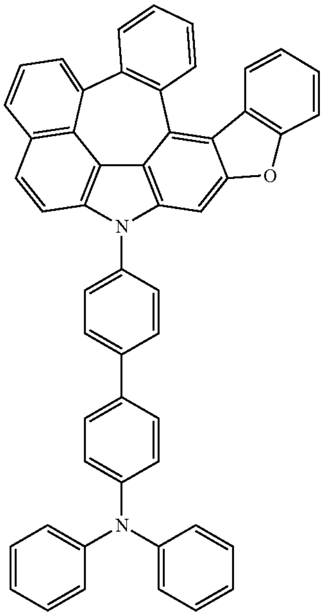
C-445
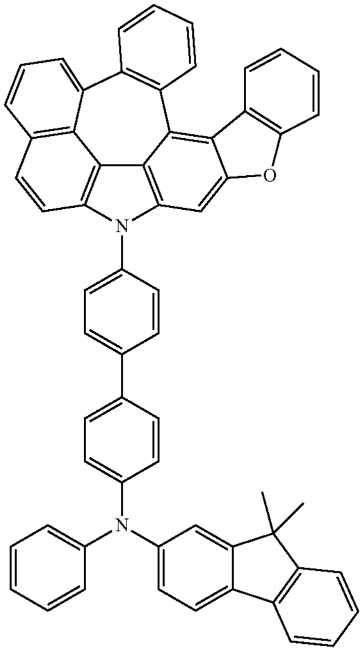
-continued
C-446
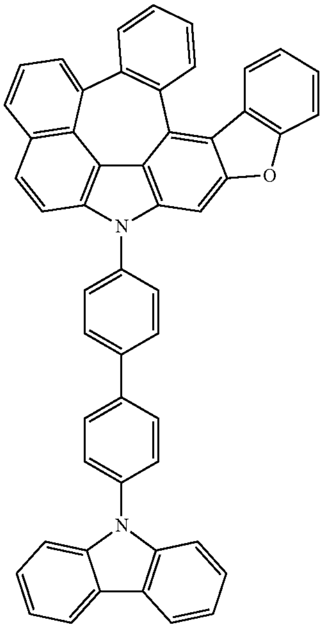
C-447
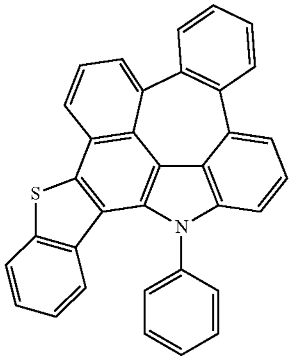
C-448
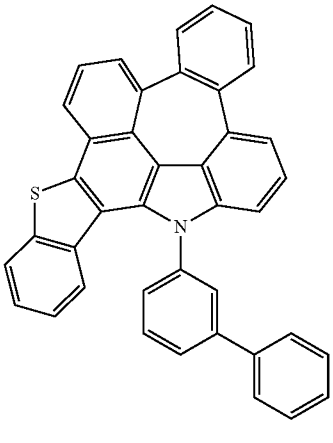

C-449
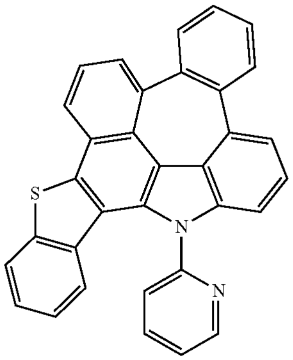
C-450
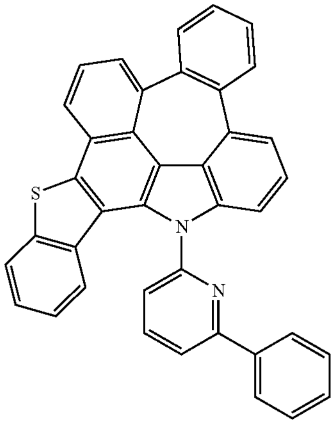
C-451
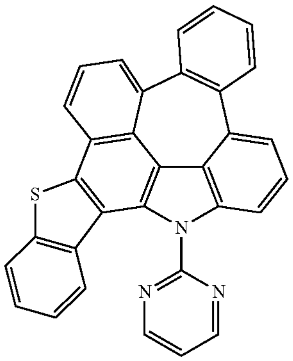
C-452
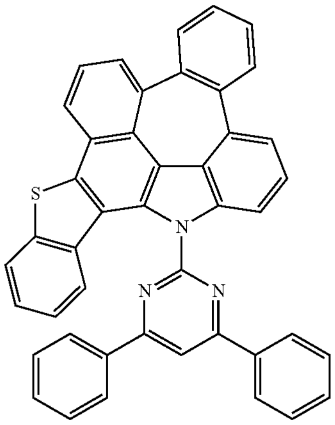
C-453
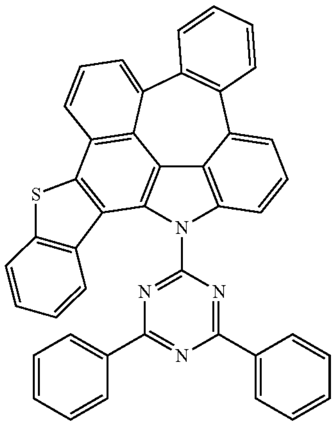
C-454
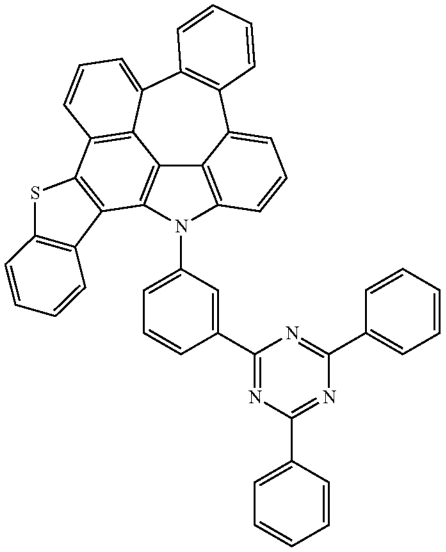
C-455
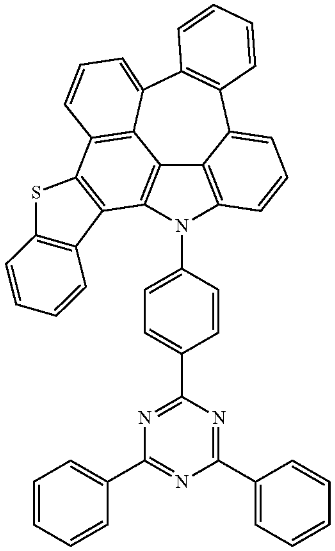

C-456
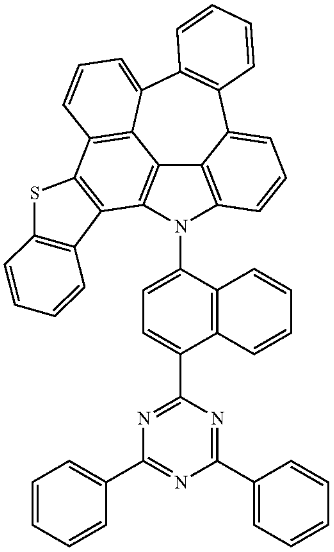
C-457
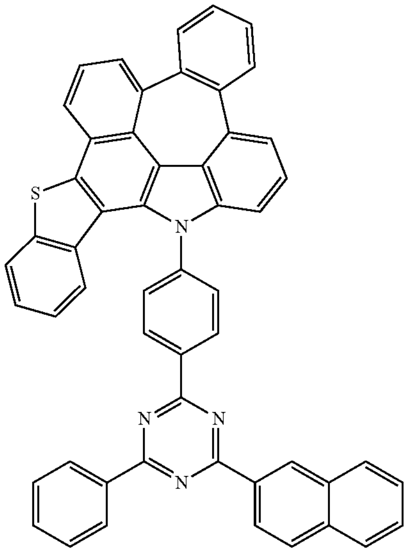
C-458
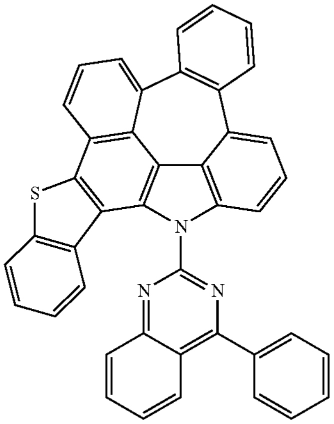
C-459
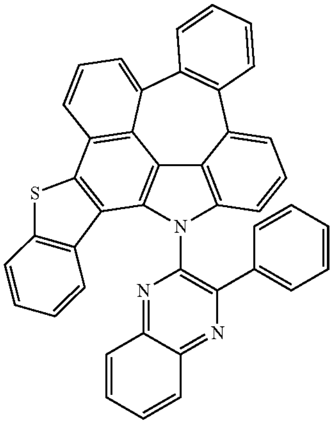
C-460
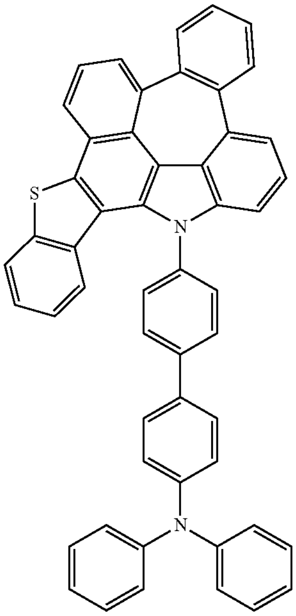

-continued
C-461
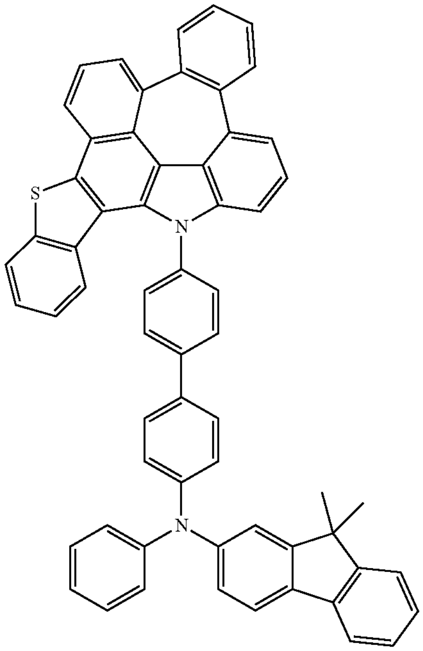
C-462
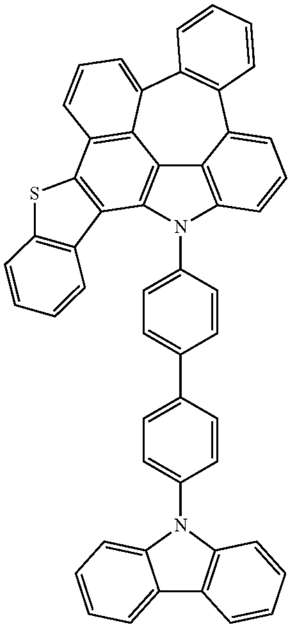
C-463
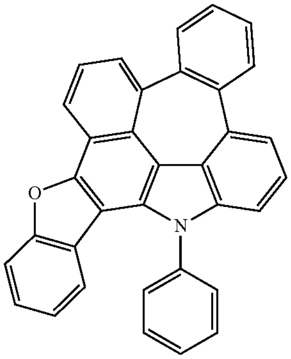
-continued
C-464
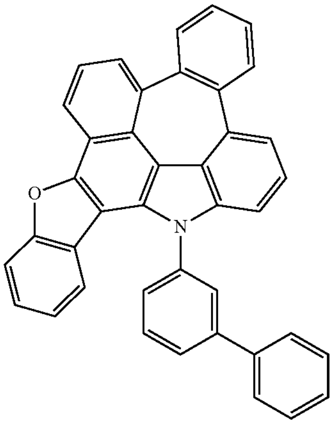
C-465
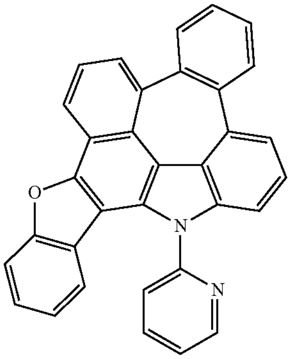
C-466
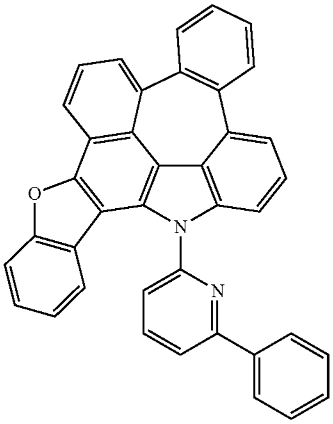
C-467
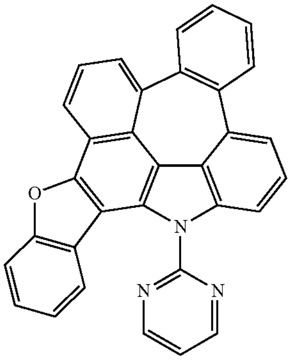

-continued
C-468
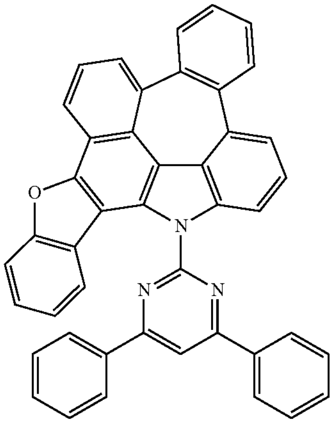
C-469
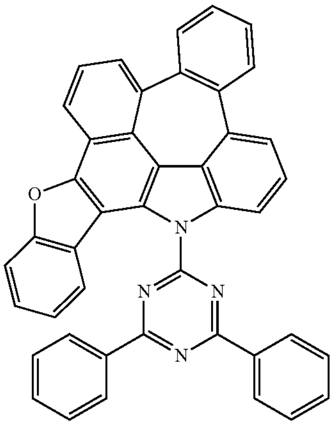
C-470
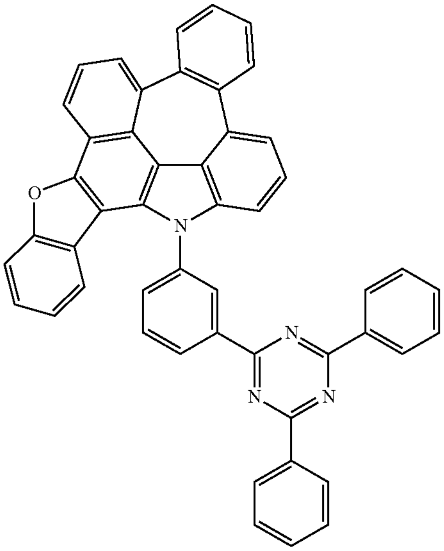
-continued
C-471
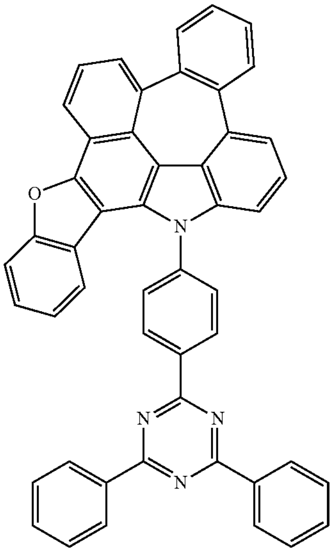
C-472
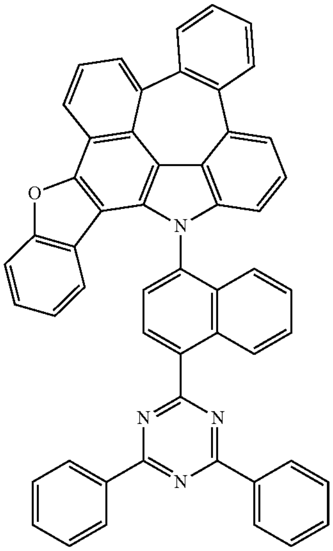
C-473
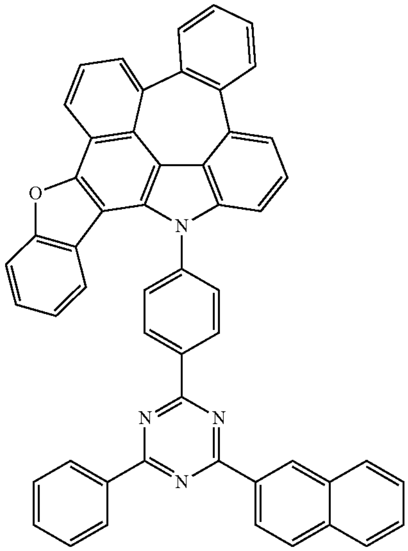

C-474
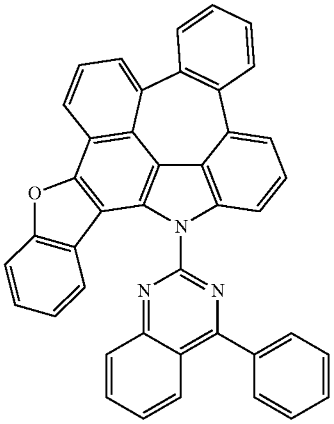
C-475
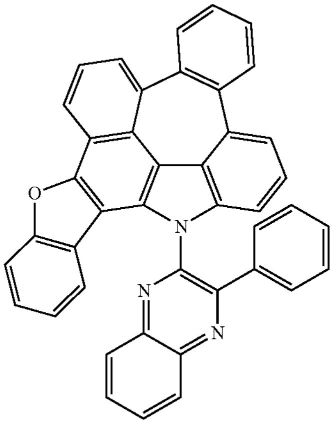
C-476
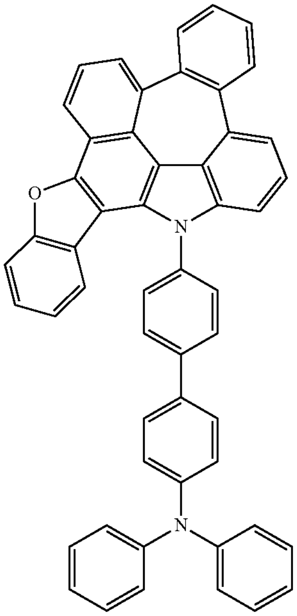
C-477
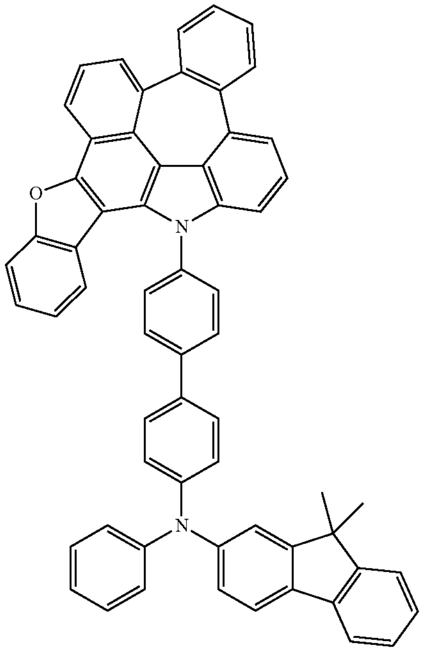
C-478
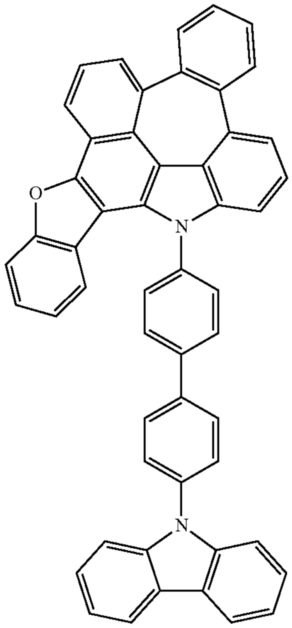

-continued
C-479
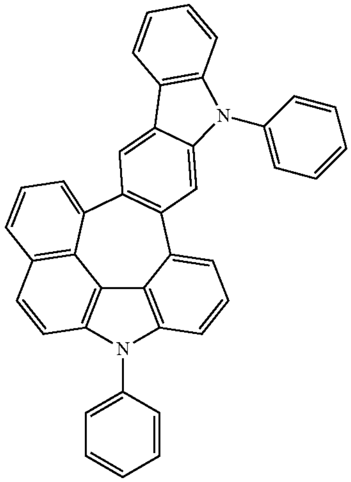
C-480
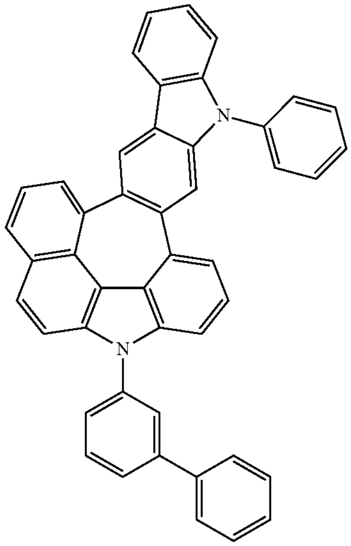
C-481
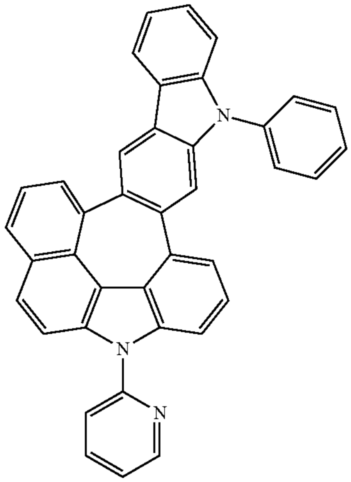
-continued
C-482
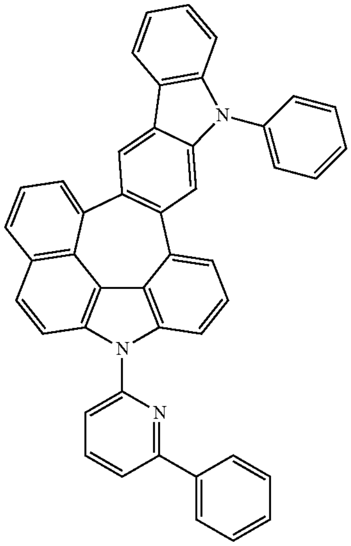
C-483
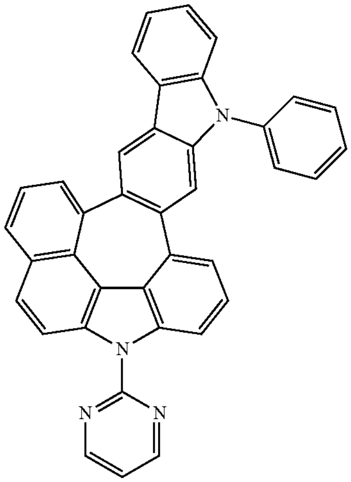
C-484
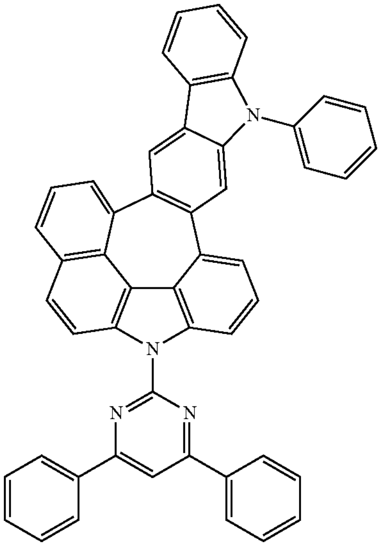

-continued
C-485
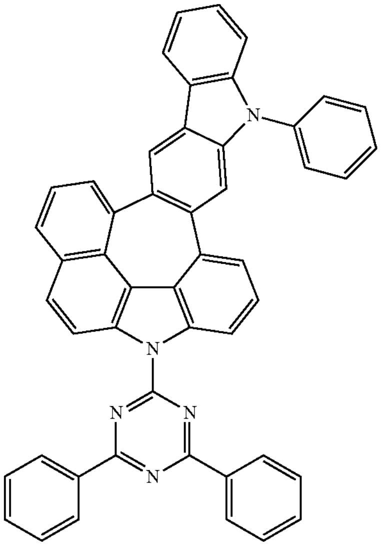
C-486
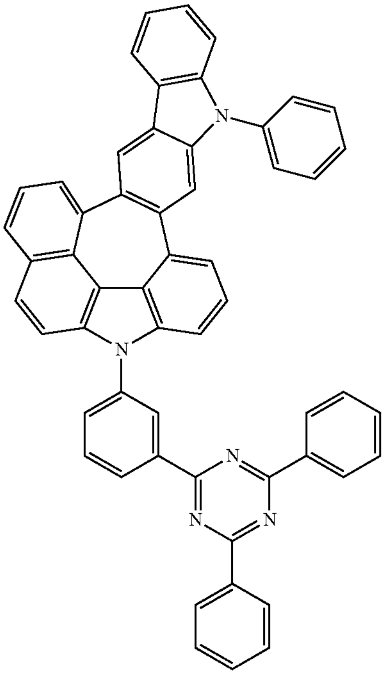
-continued
C-487
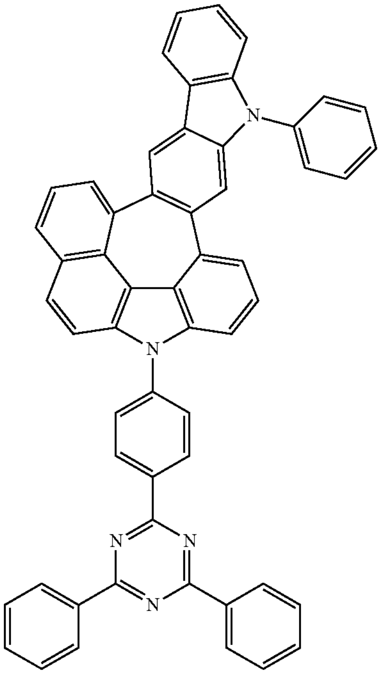
C-488
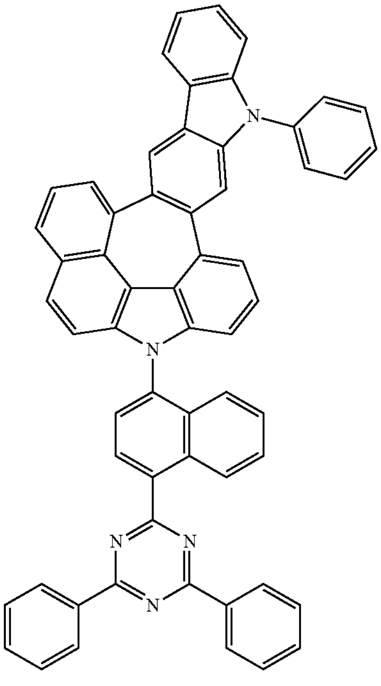

-continued
C-489
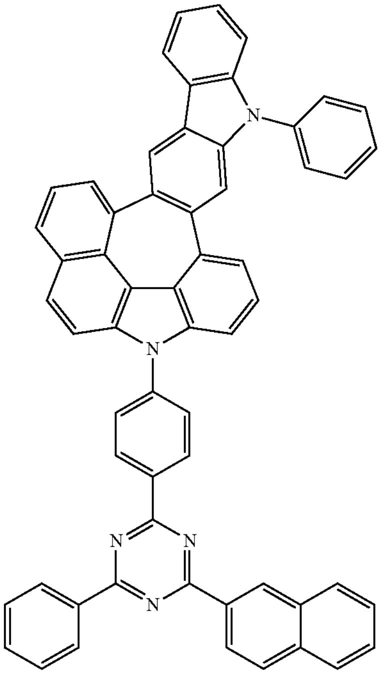
C-490
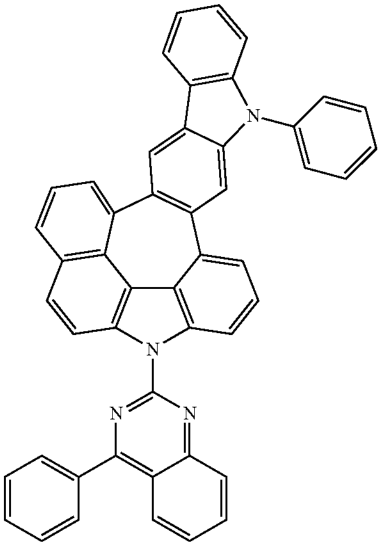
-continued
C-491
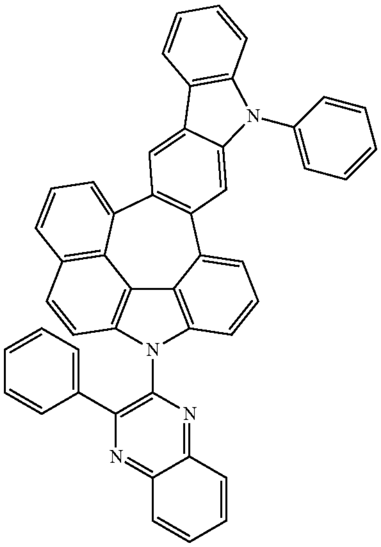
C-492
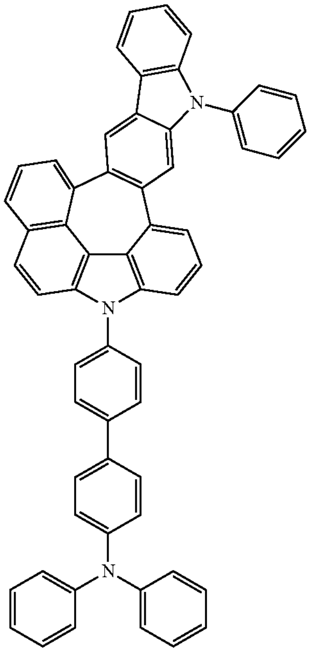

-continued
C-493
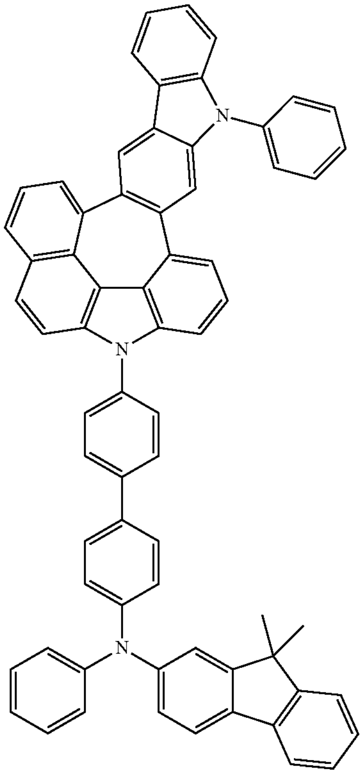
C-494
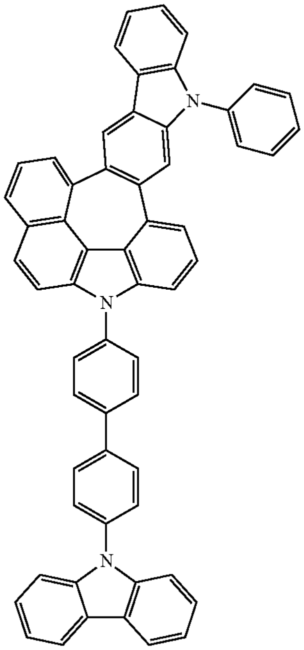
-continued
C-495
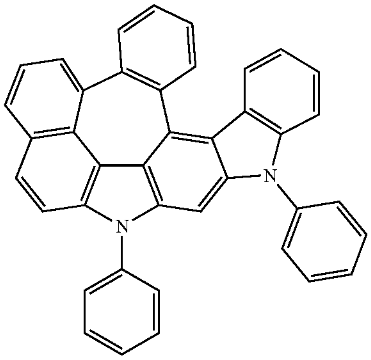
C-496
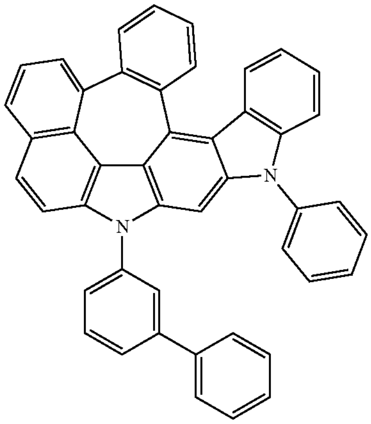
C-497
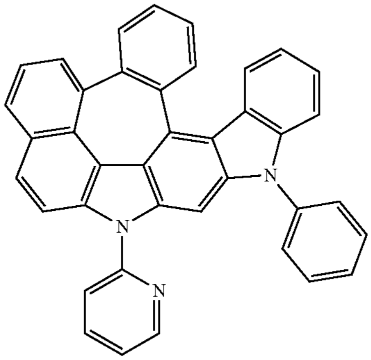
C-498
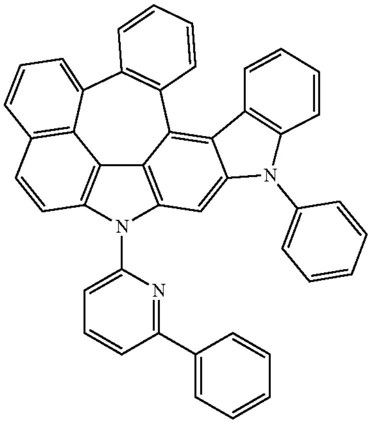

-continued
C-499
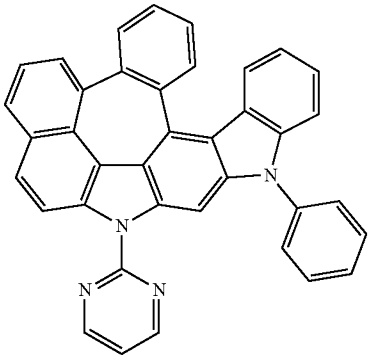
C-500
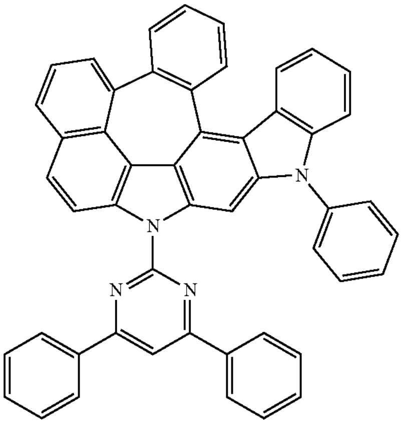
C-501
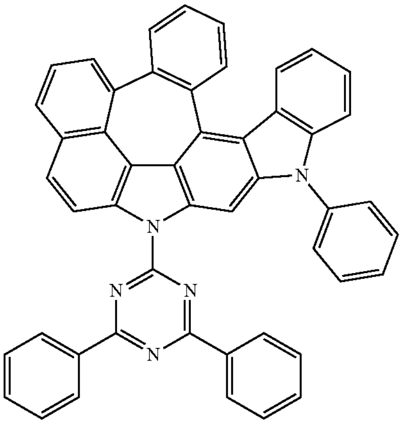
-continued
C-502
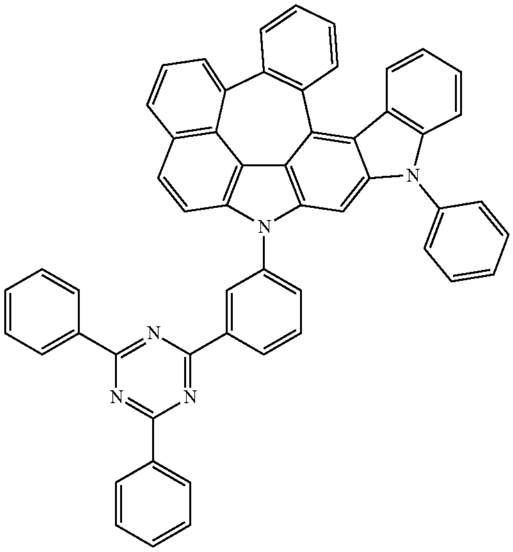
C-503
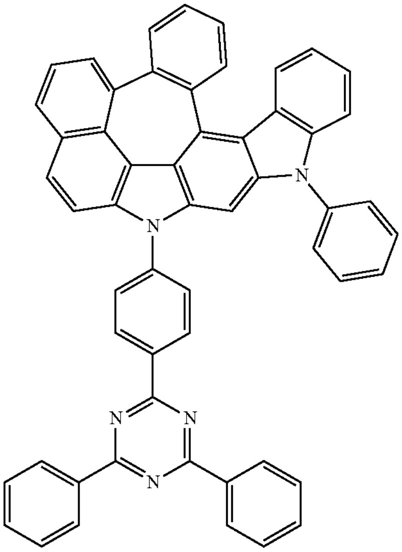

-continued
C-504
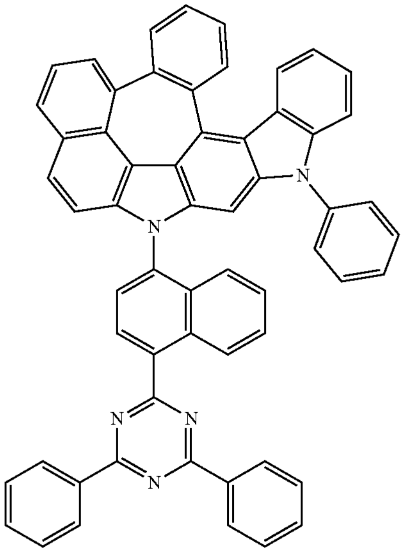
C-505
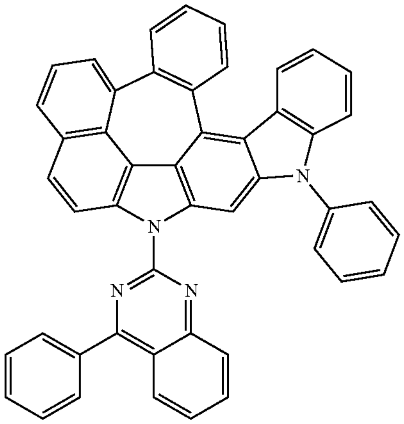
C-506
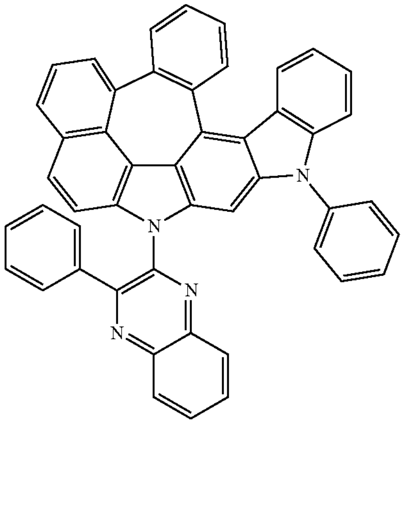
-continued
C-507
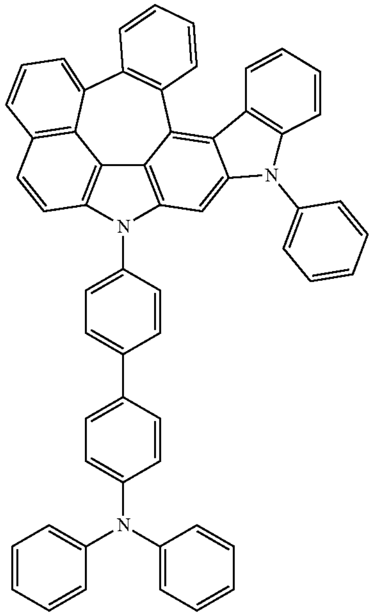
C-508
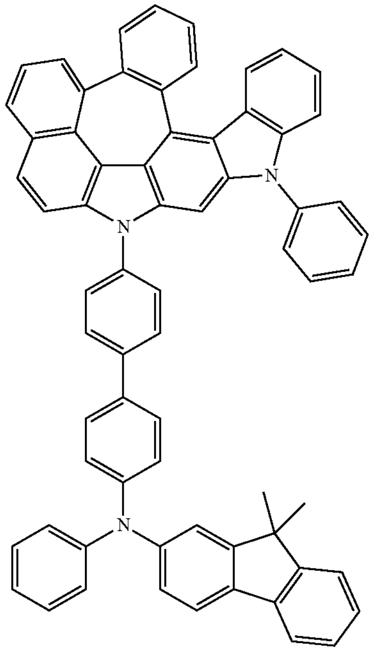

-continued
C-509
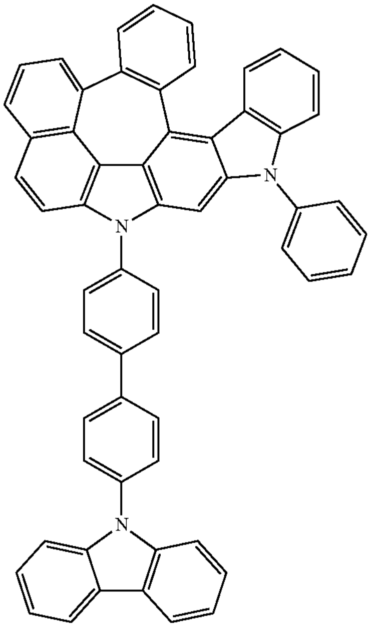
C-510
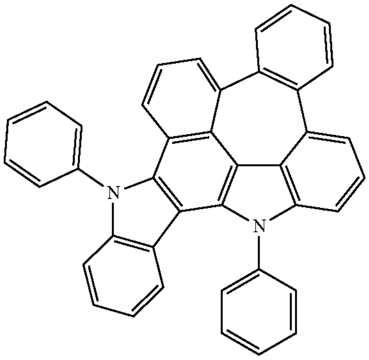
C-511
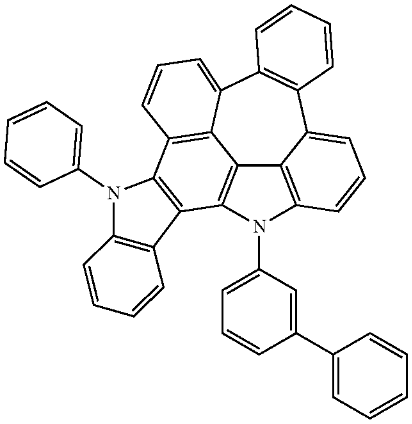
-continued
C-512
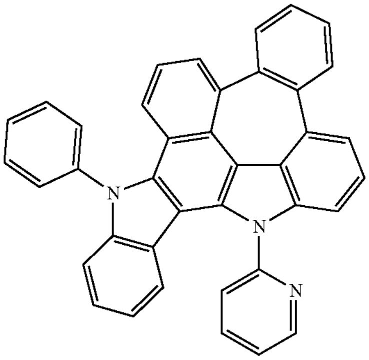
C-513
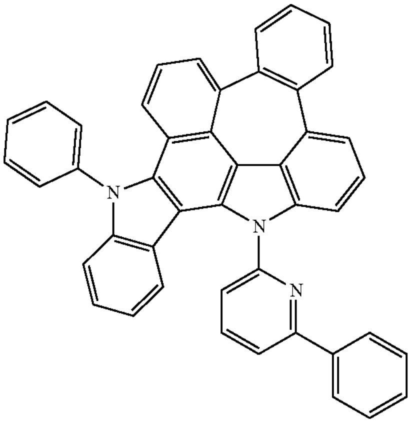
C-514
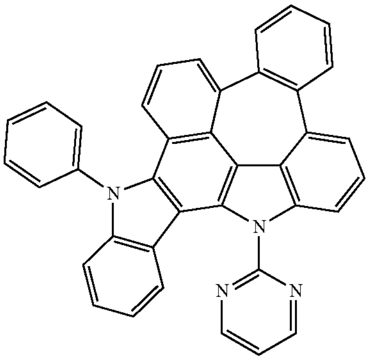
C-515
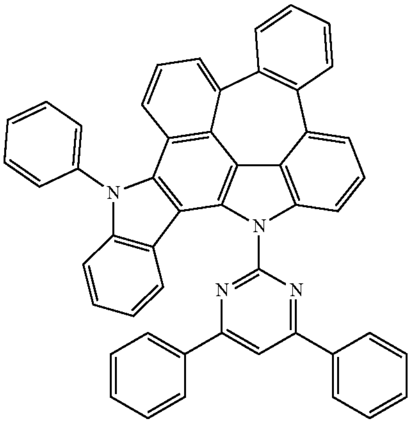

-continued
C-516
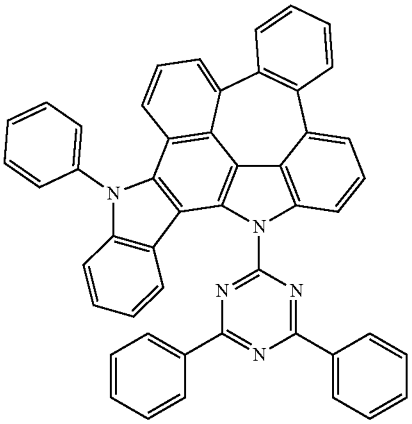
C-517
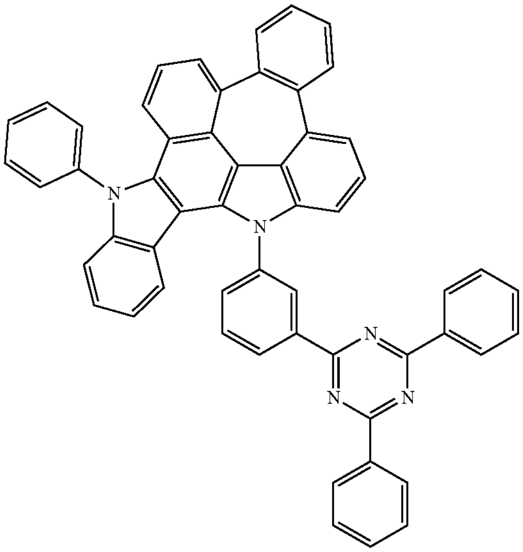
C-518
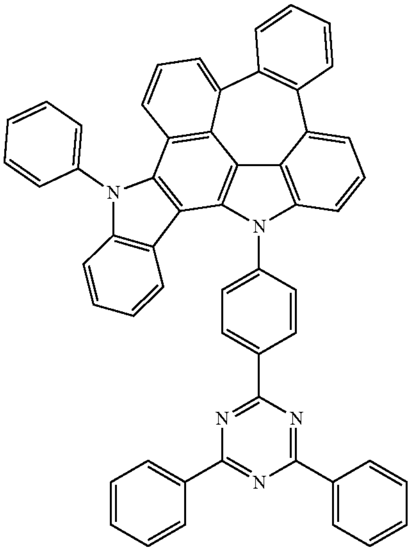
-continued
C-519
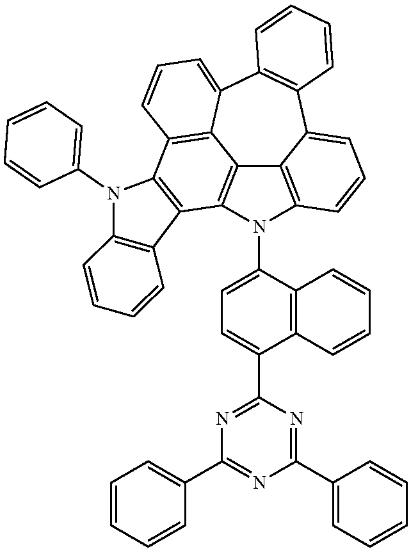
C-520
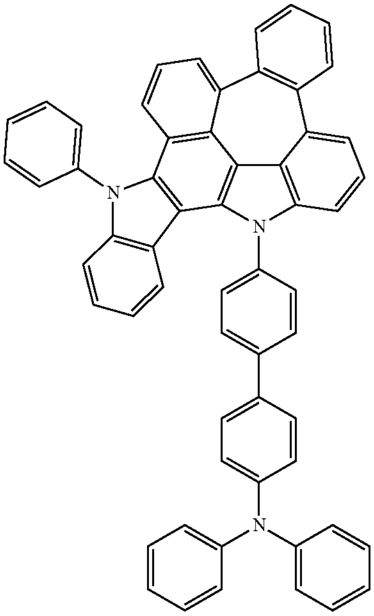

-continued
C-521
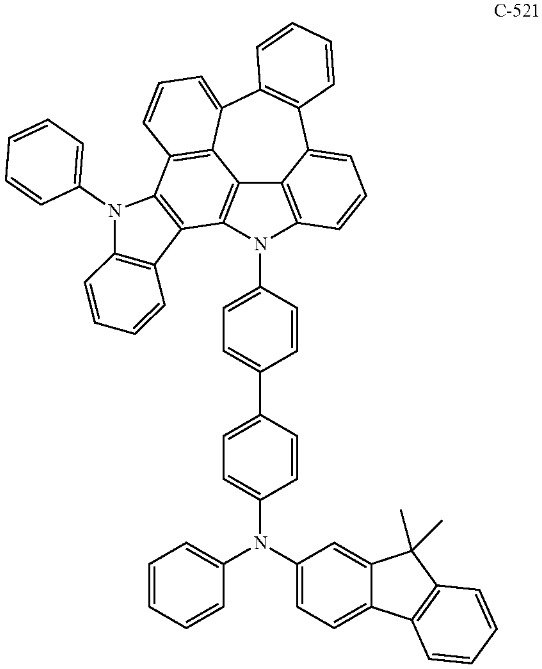
C-522
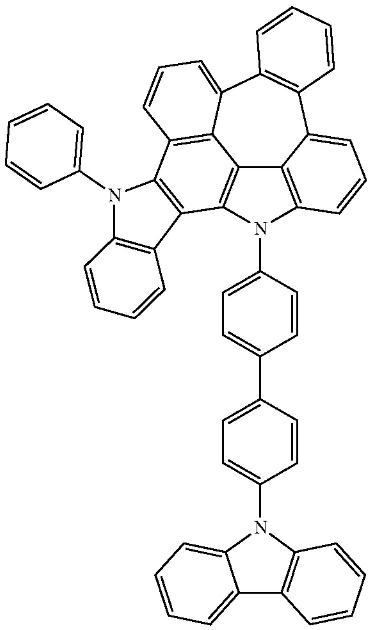
-continued
C-523
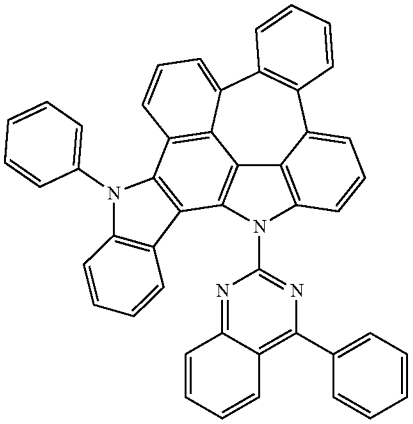
C-524
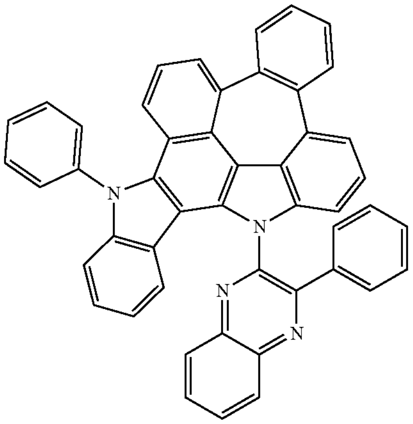
C-525
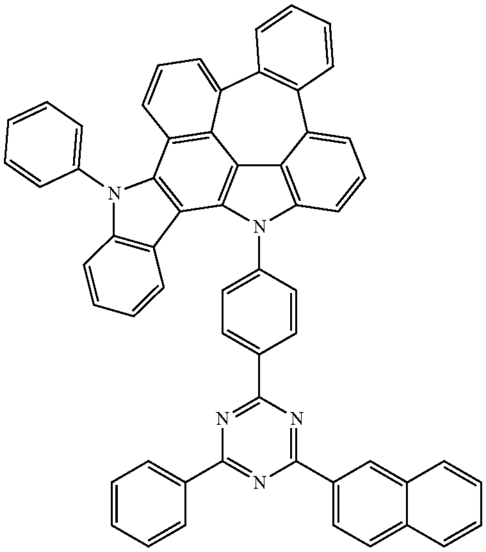

-continued
C-526
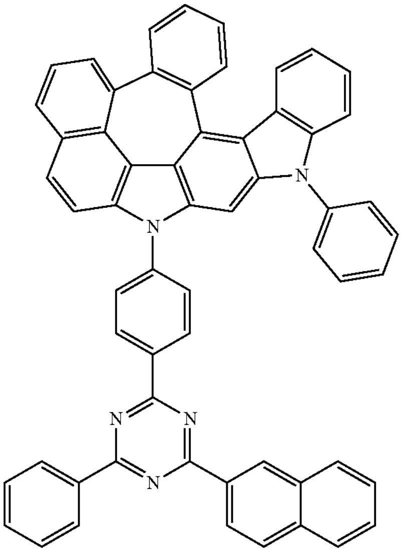
C-527
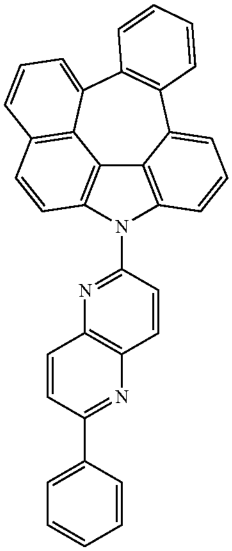
C-528
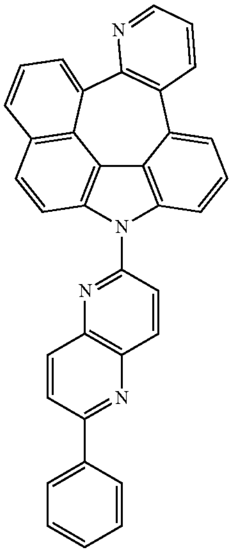
-continued
C-529
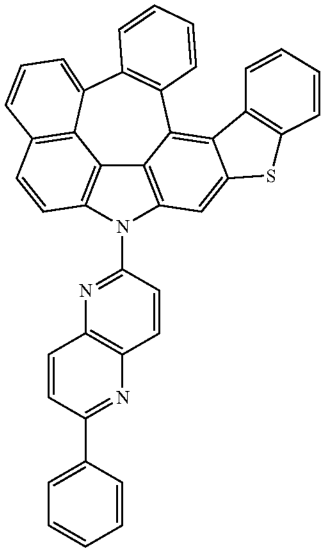
C-530
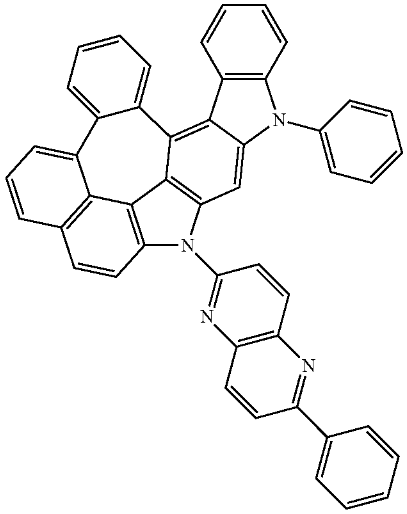
C-531
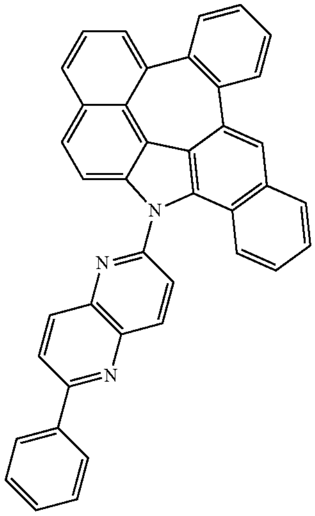

-continued
C-532
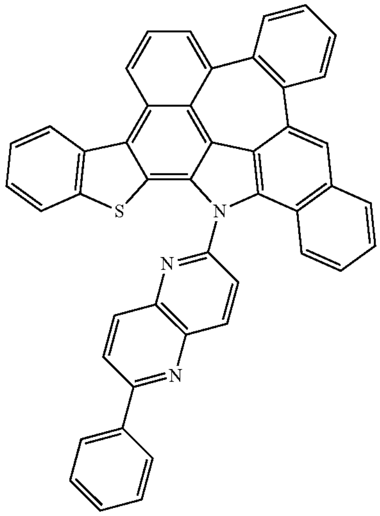
C-533
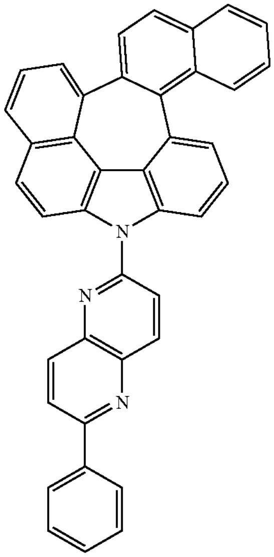
C-534
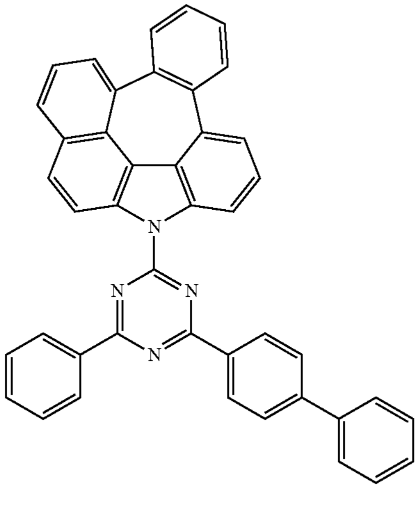
-continued
C-535
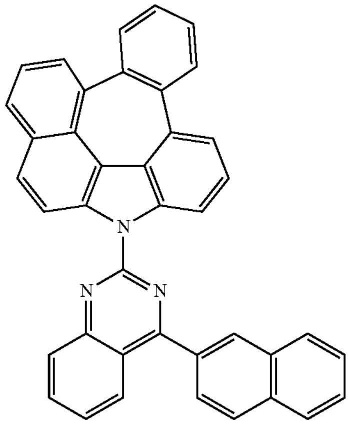
C-536
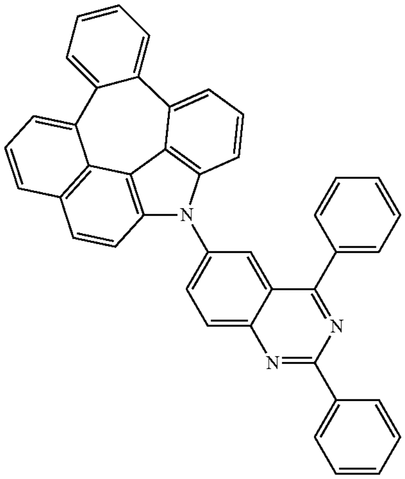
C-537
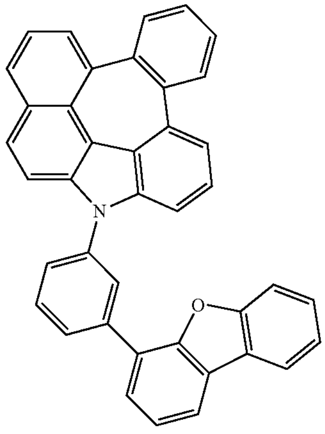

-continued
C-538
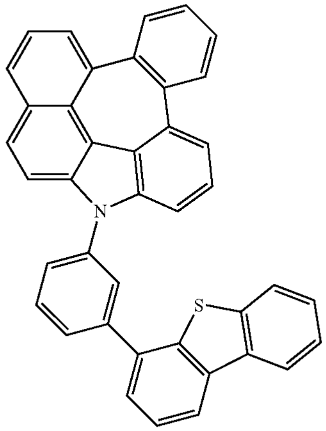
C-539
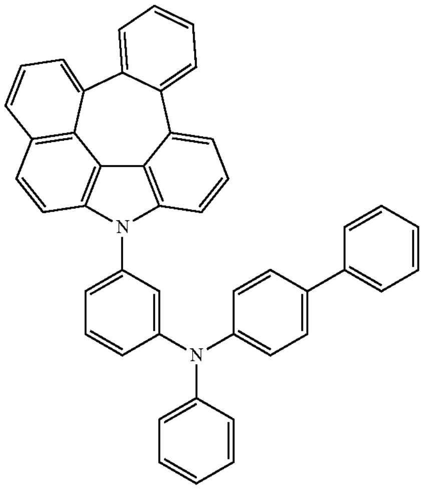
C-540
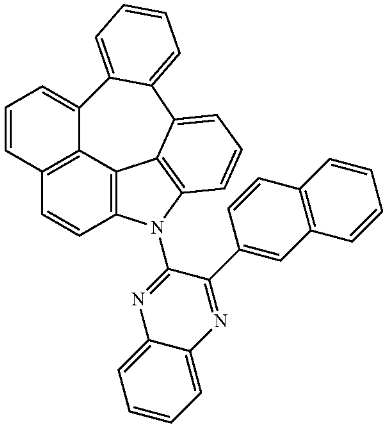
-continued
C-541
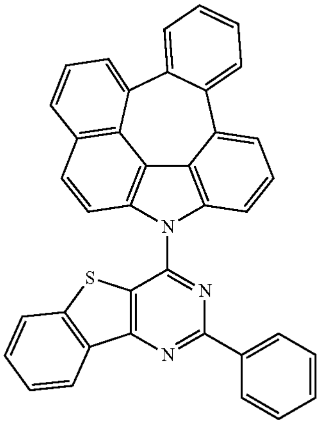
C-542
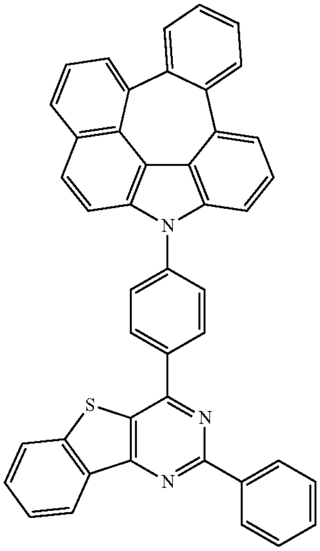
C-543
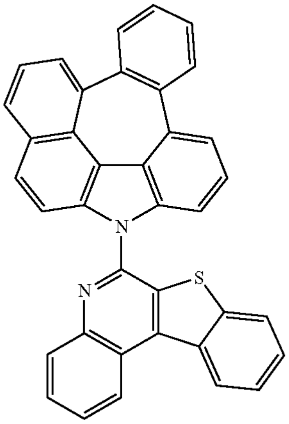

-continued
C-544
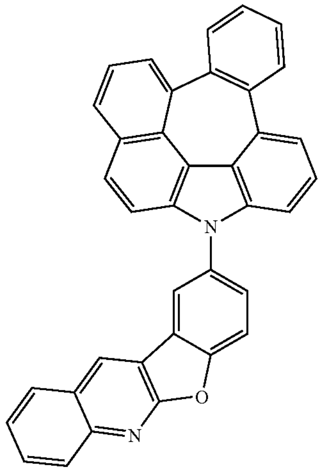
C-545
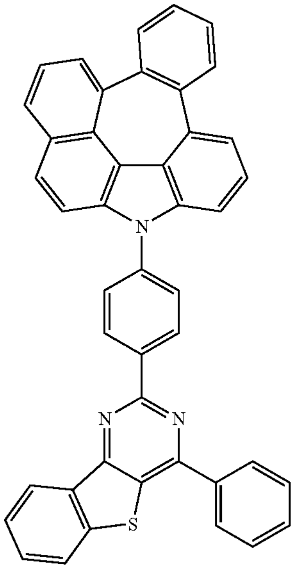
C-546
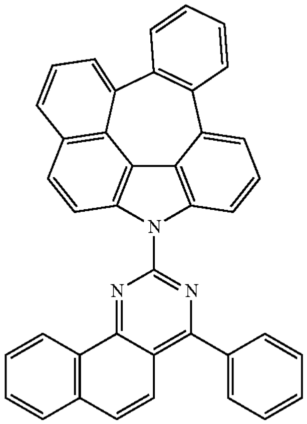
-continued
C-547
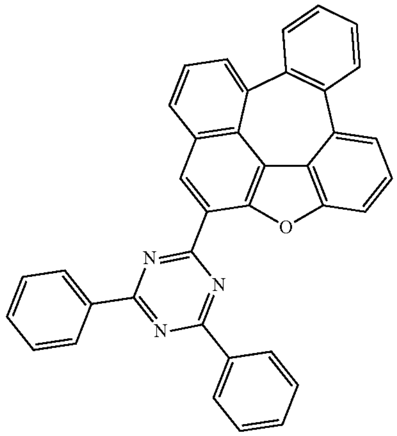
C-548
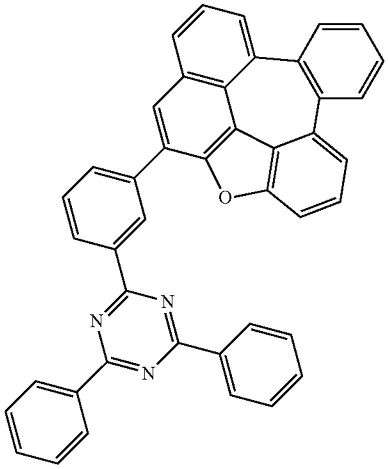
C-549
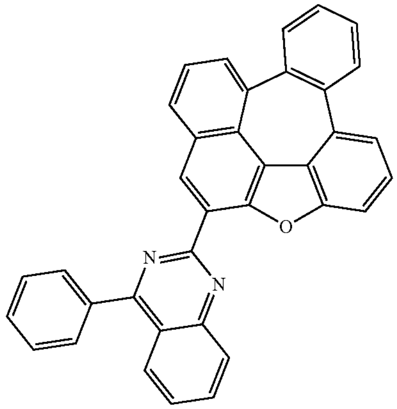

-continued
C-550
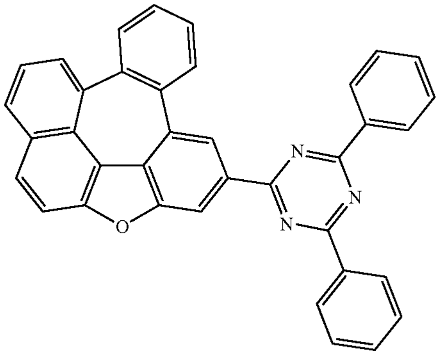
C-551
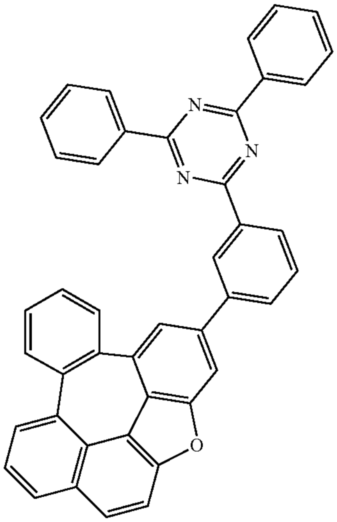
C-552
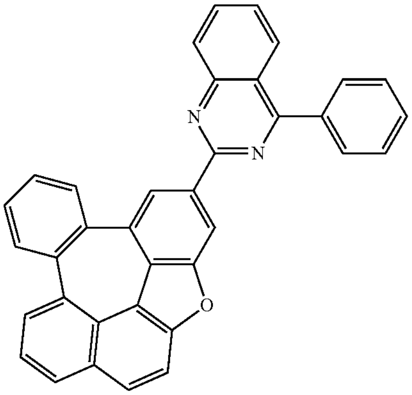
-continued
C-553
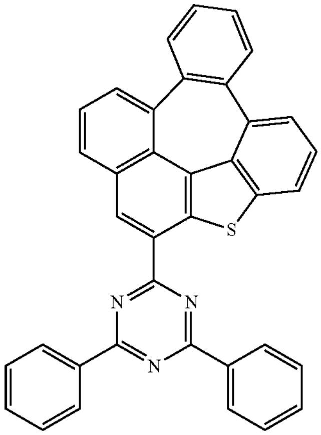
C-554
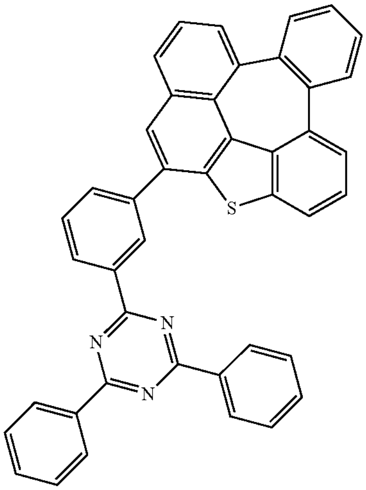
C-555
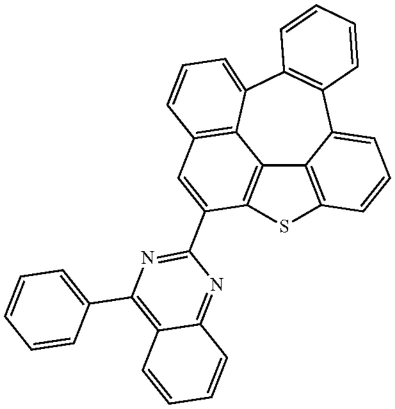

-continued
C-556
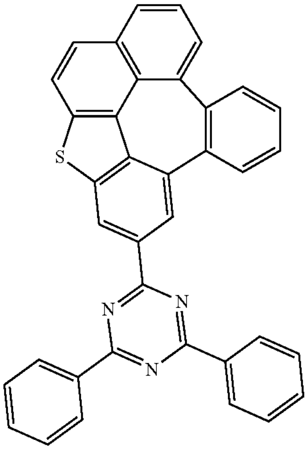
C-557
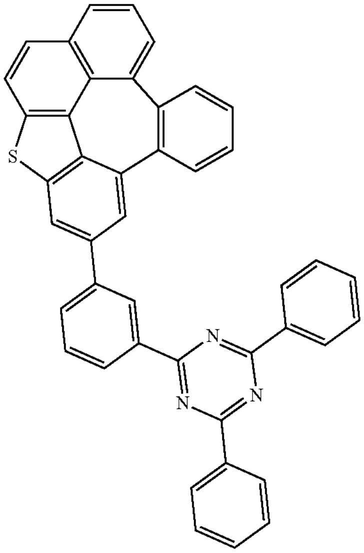
C-558
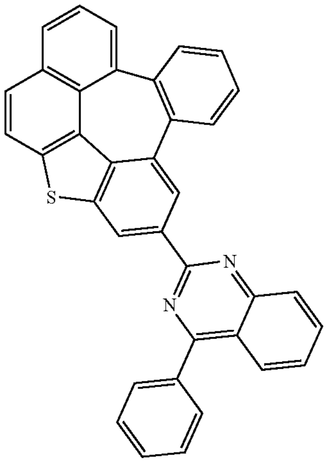
-continued
C-559
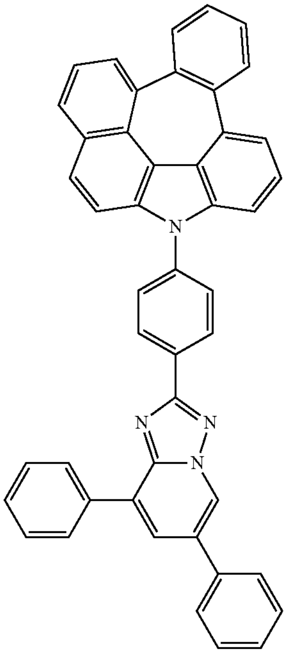
C-560
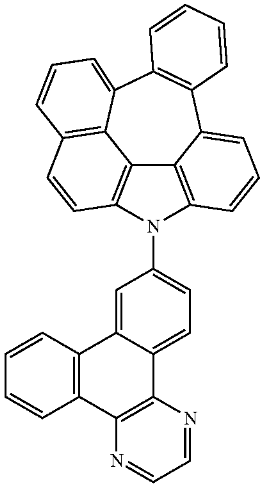

-continued
C-561
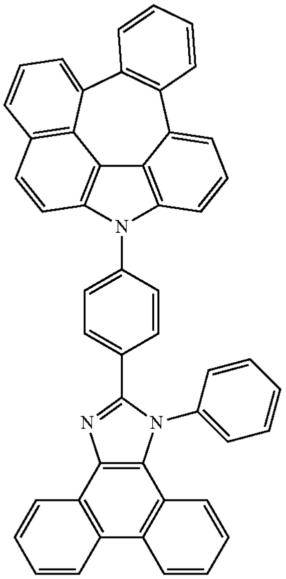
C-562
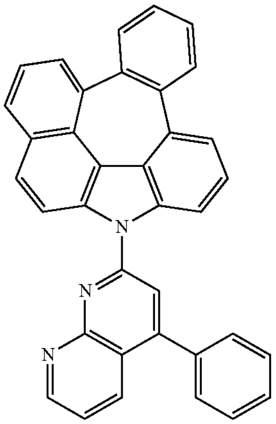
C-563
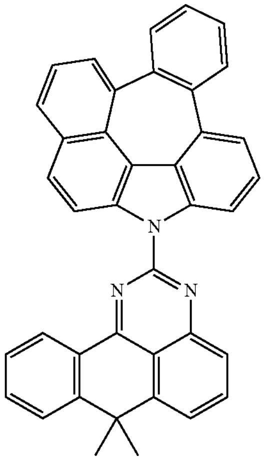
-continued
C-564
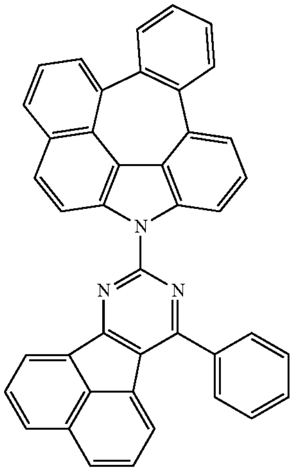
C-565
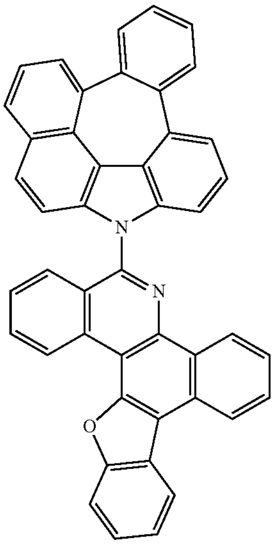
C-566
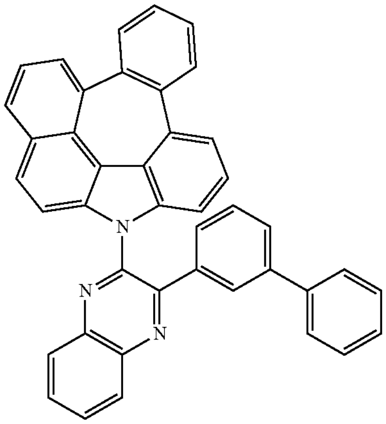

-continued
C-567
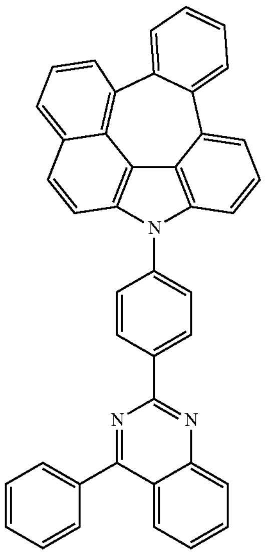
C-568
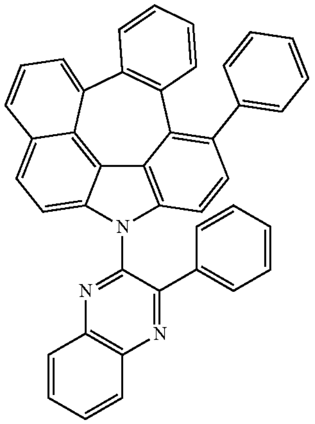
C-569
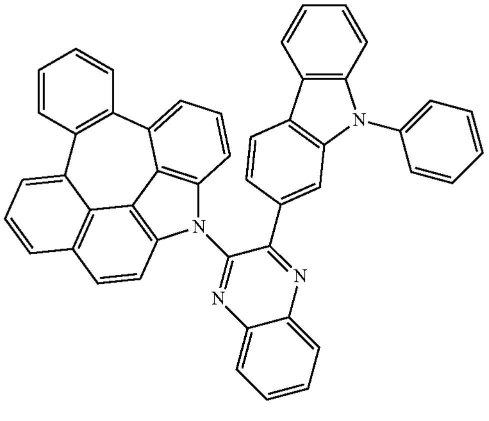
-continued
C-570
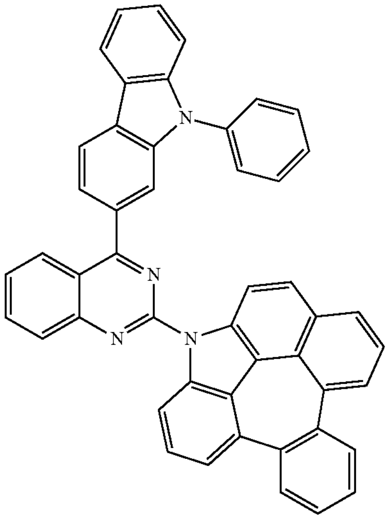
C-571
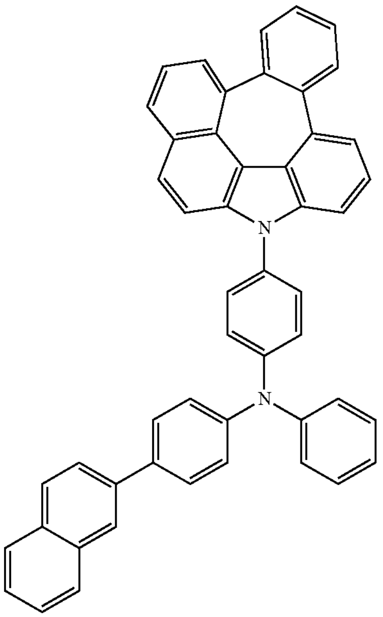

-continued
C-572
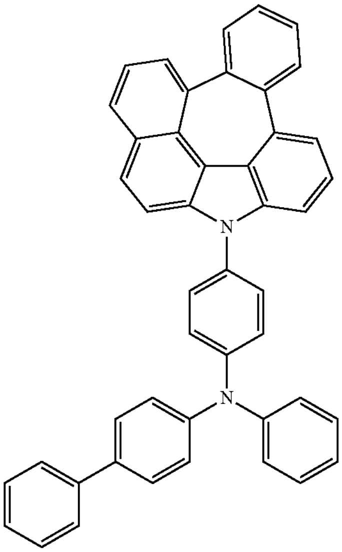
C-573
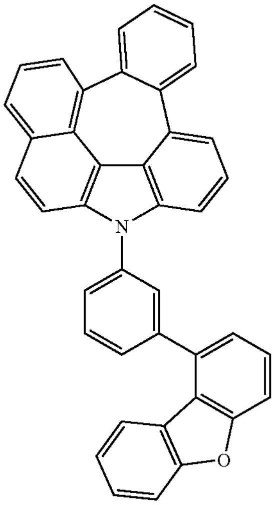
C-574
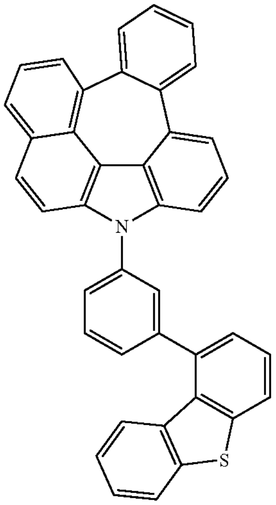
-continued
C-575
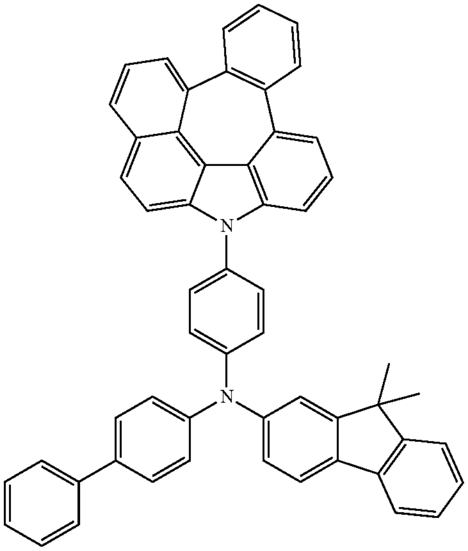
C-576
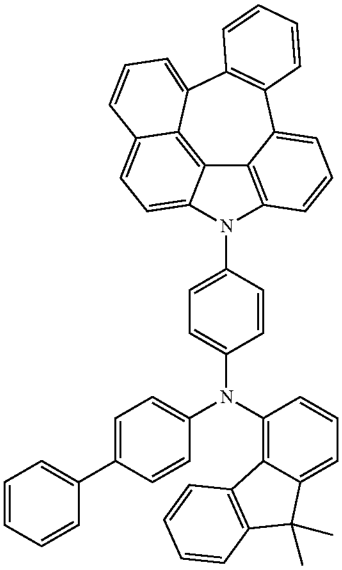

-continued
C-577
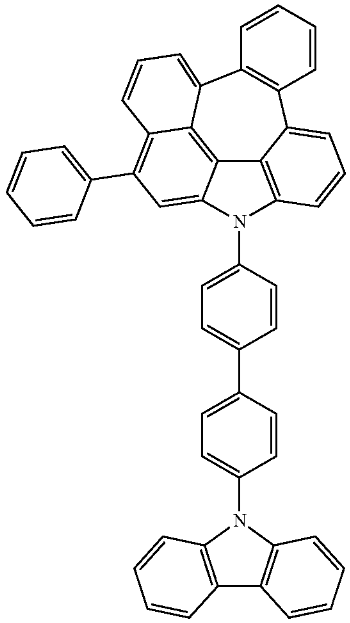
C-578
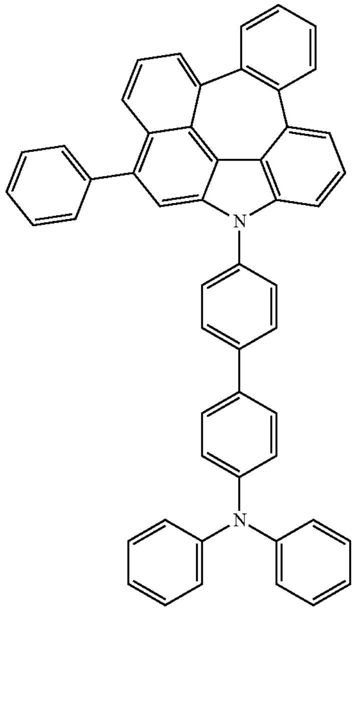
-continued
C-579
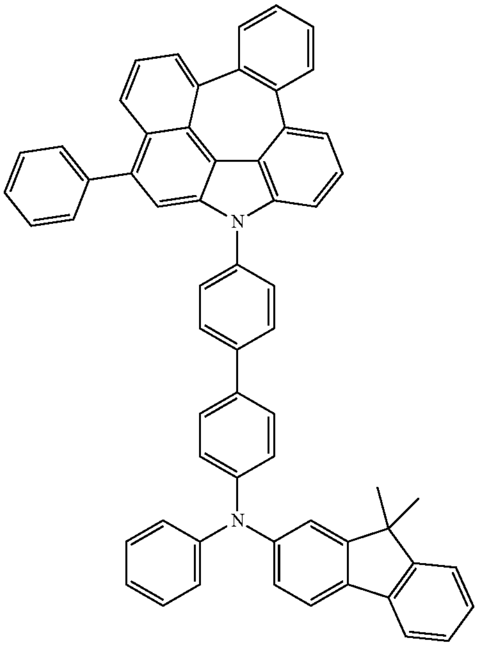
C-580
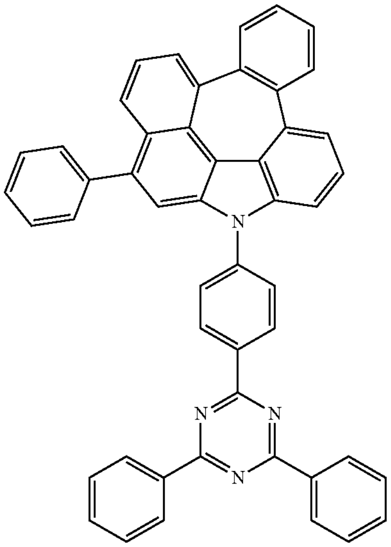

-continued
C-581
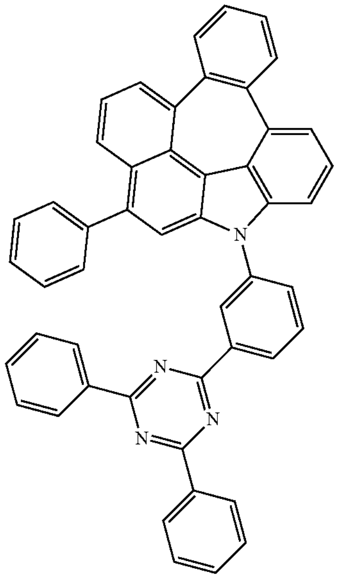
C-582
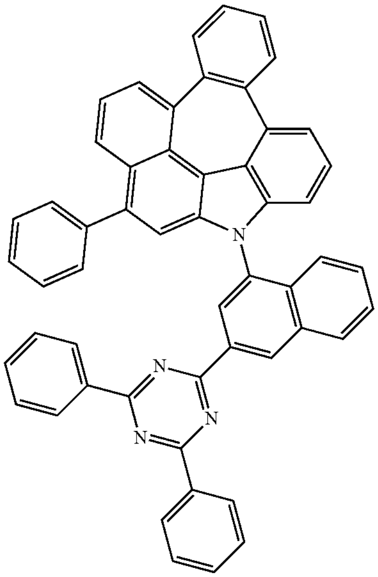
-continued
C-583
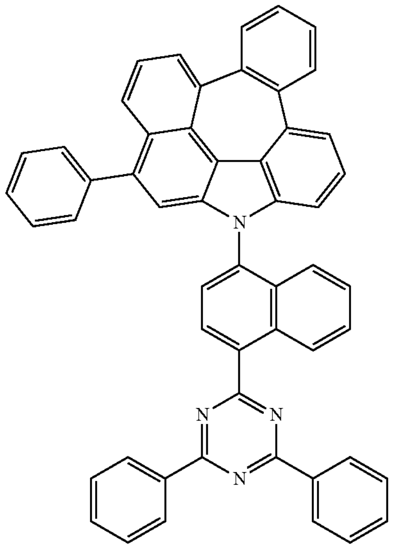
C-584
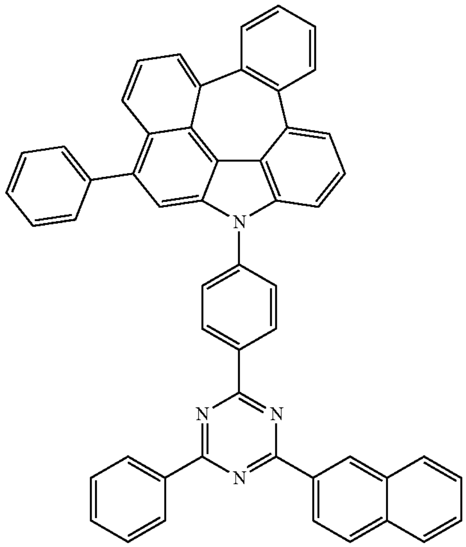

-continued
C-585
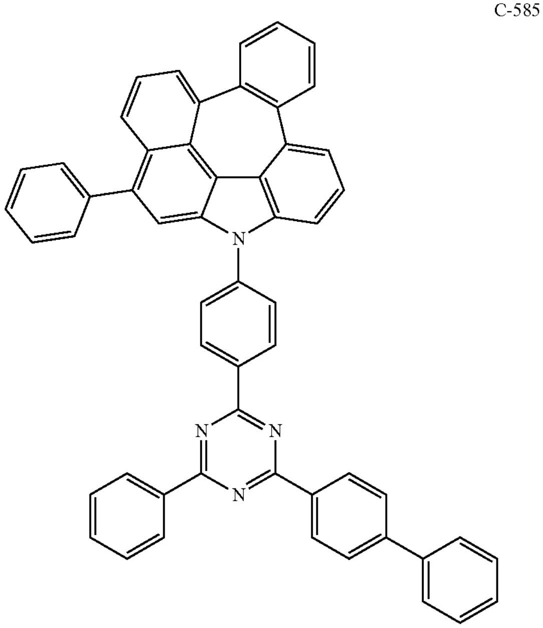
C-586
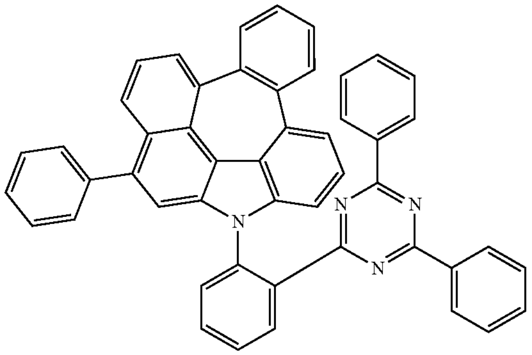
C-587
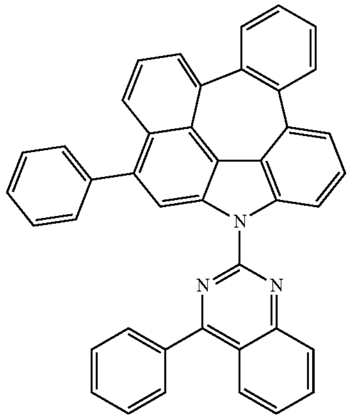
-continued
C-588
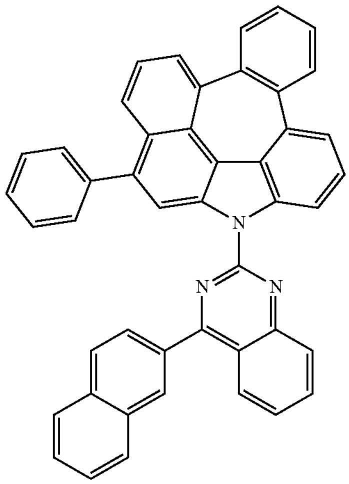
C-589
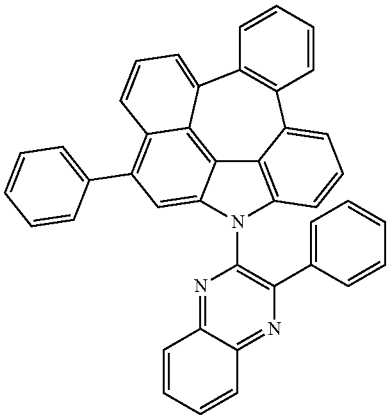
C-590
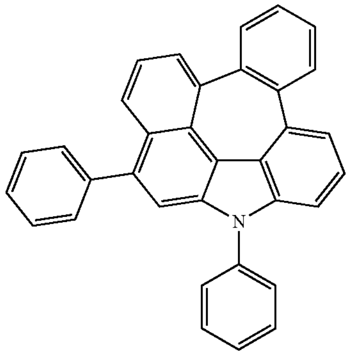

-continued
C-591
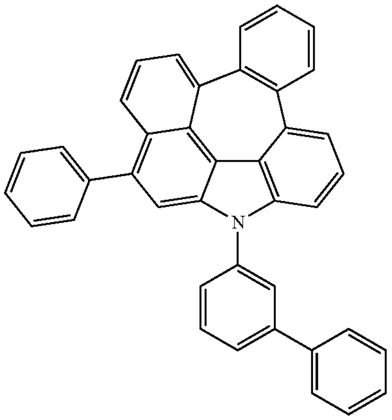
C-592
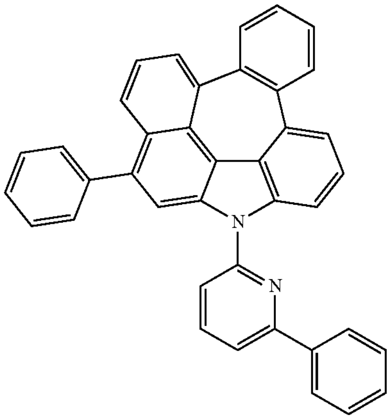
C-593
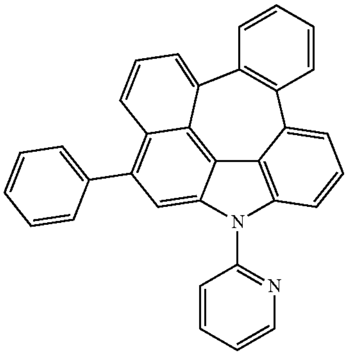
C-594
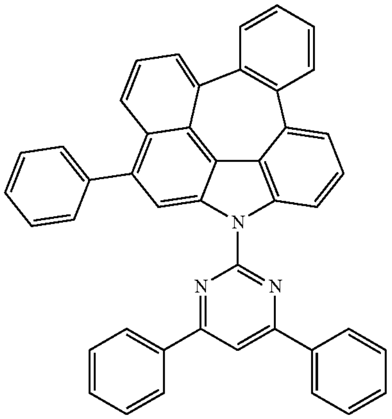
-continued
C-595
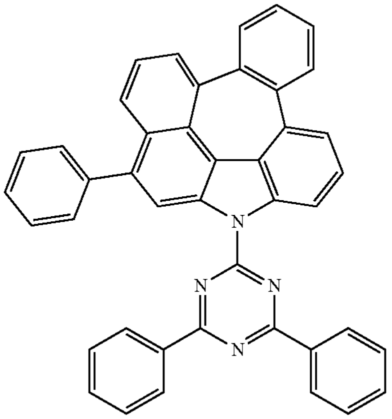
C-596
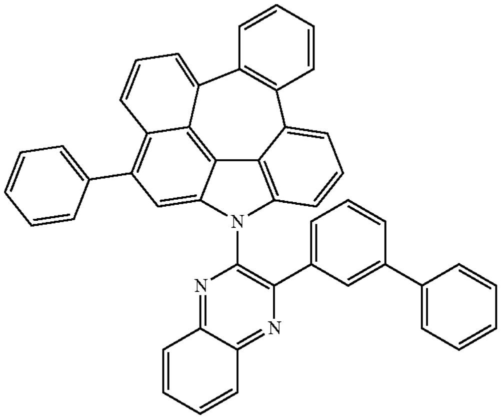
C-597
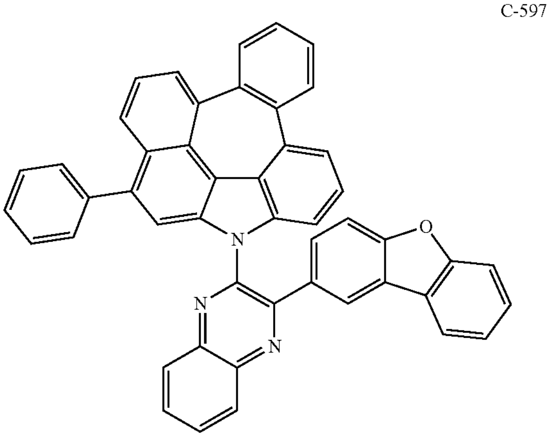

-continued
C-598
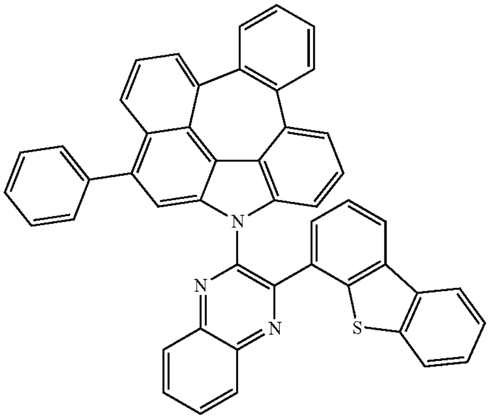
C-599
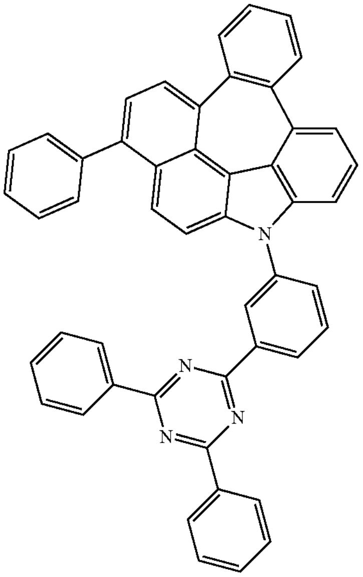
C-600
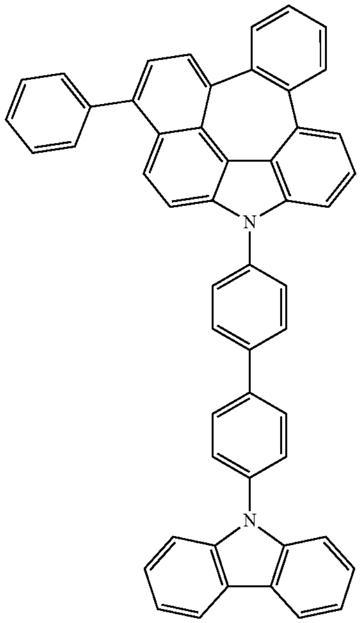
-continued
C-601
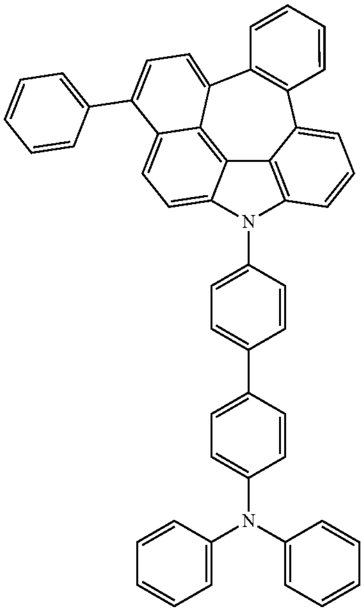
C-602
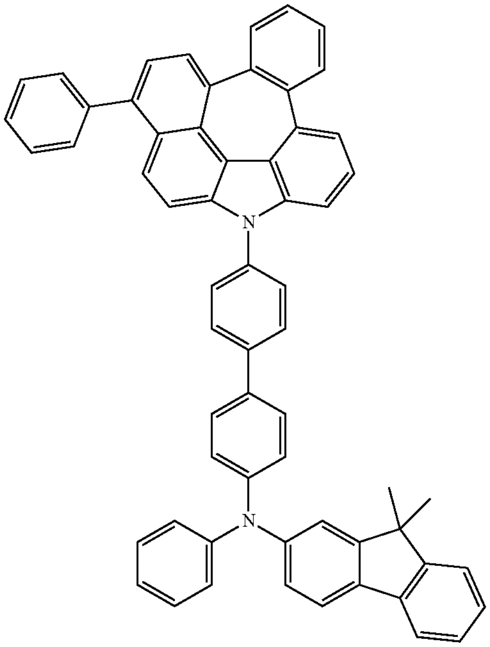

-continued
C-603
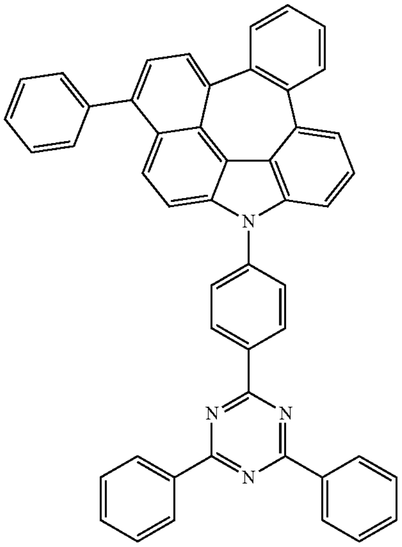
C-604
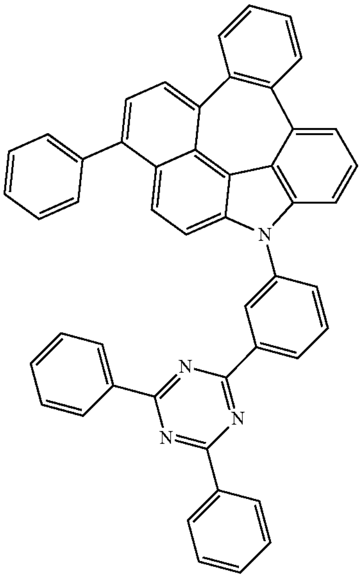
-continued
C-605
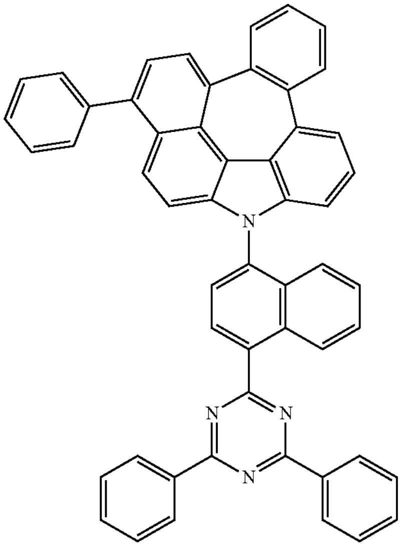
C-606
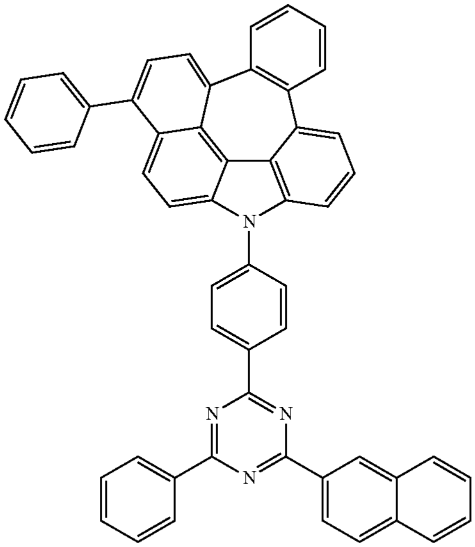

-continued
C-607
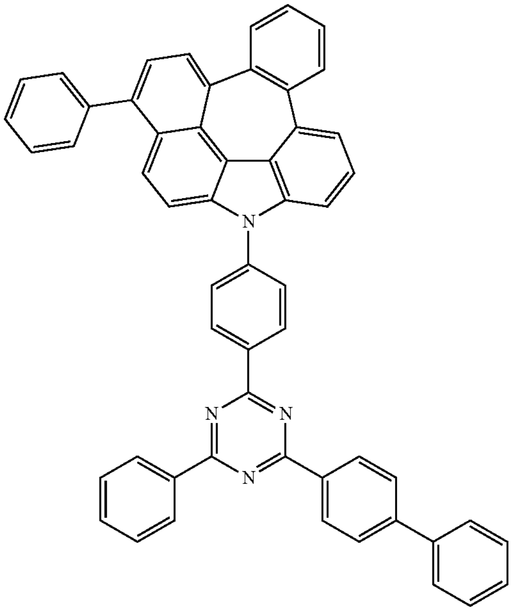
C-608
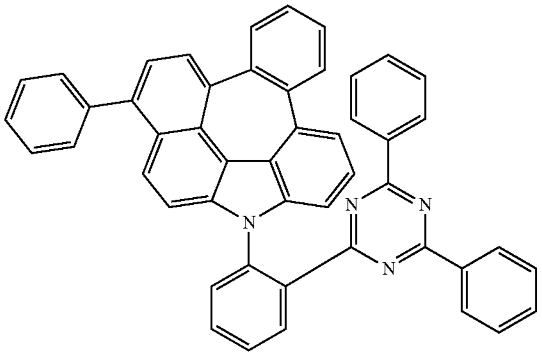
C-609
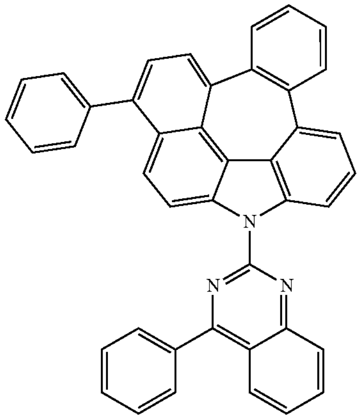
-continued
C-610
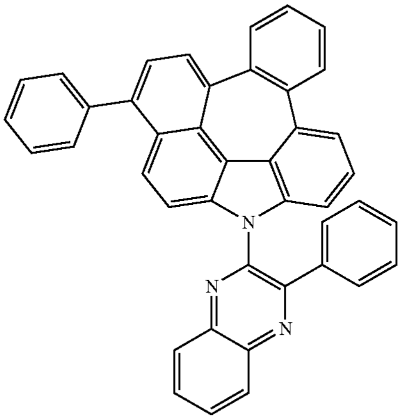
C-611
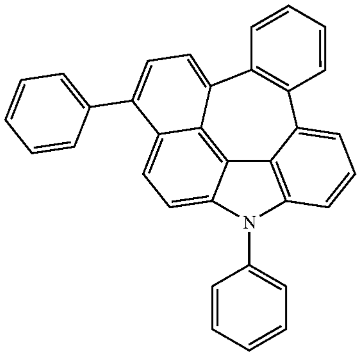
C-612
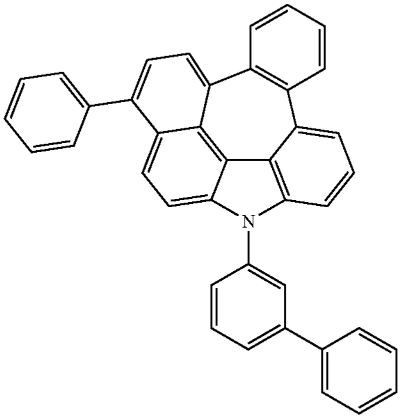
C-613
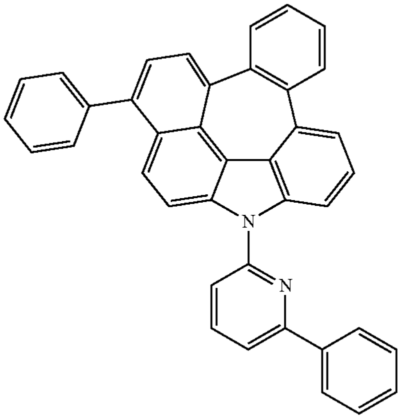

-continued
C-614
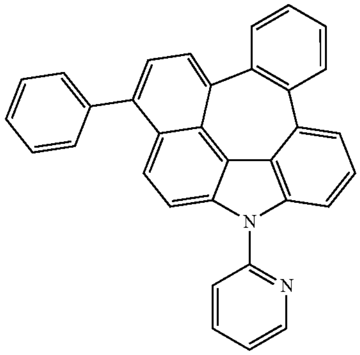
C-615
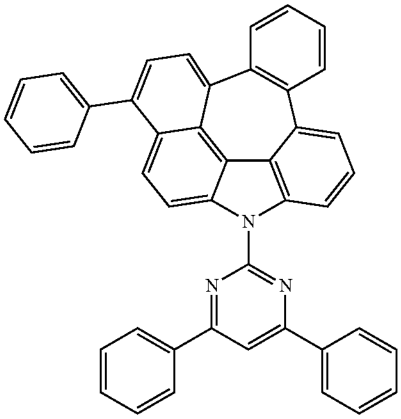
C-616
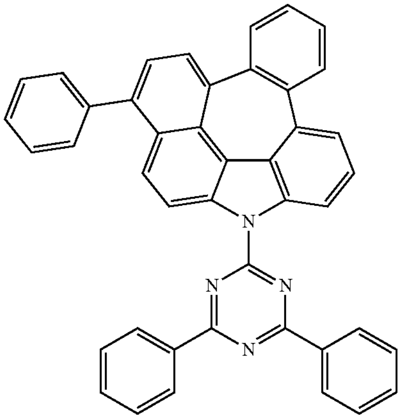
C-617
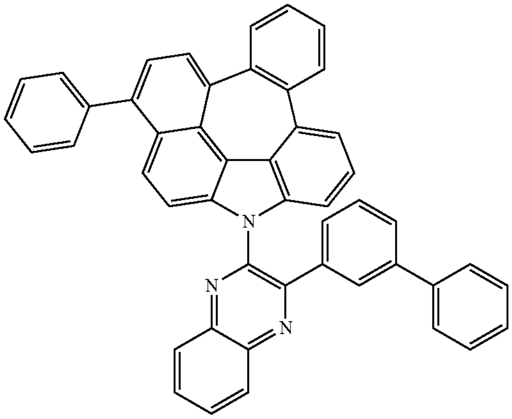
-continued
C-618
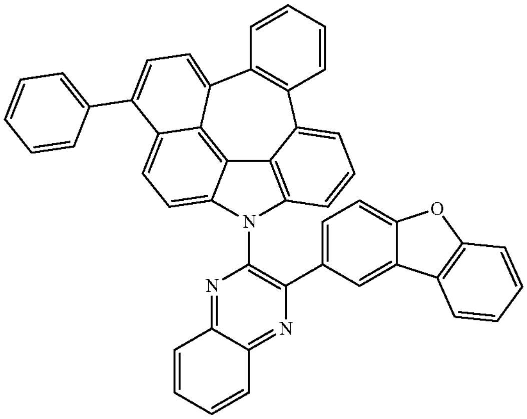
C-619
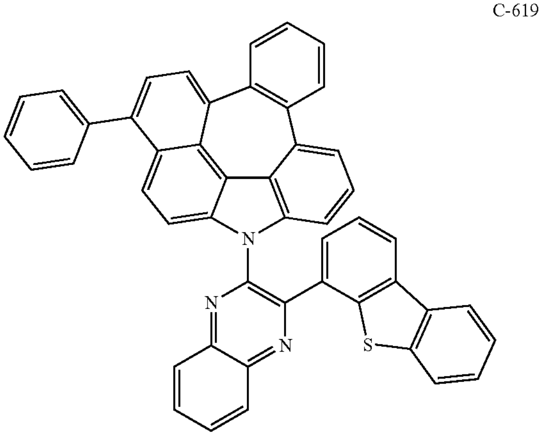
C-620
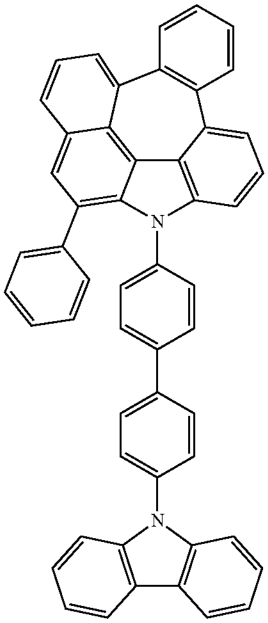

-continued
C-621
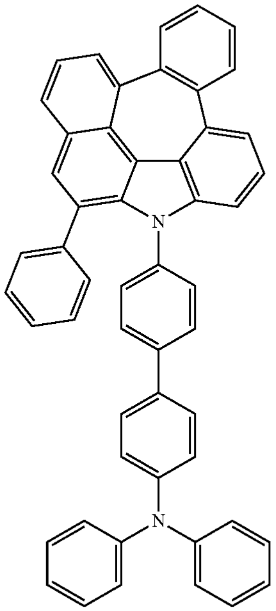
C-622
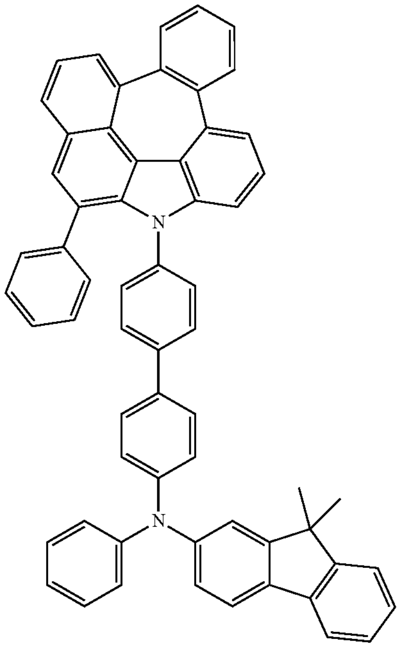
-continued
C-623
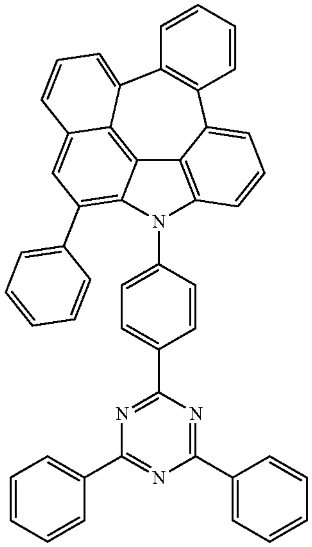
C-624
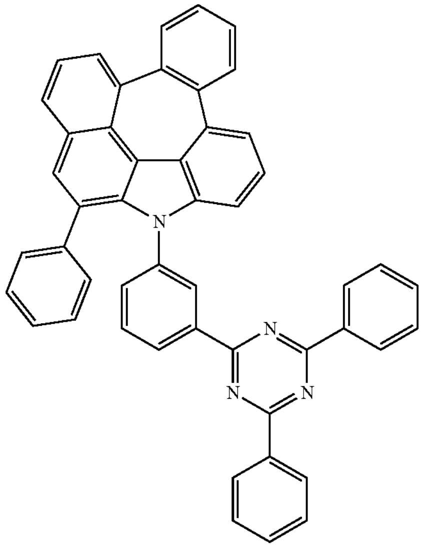
C-625
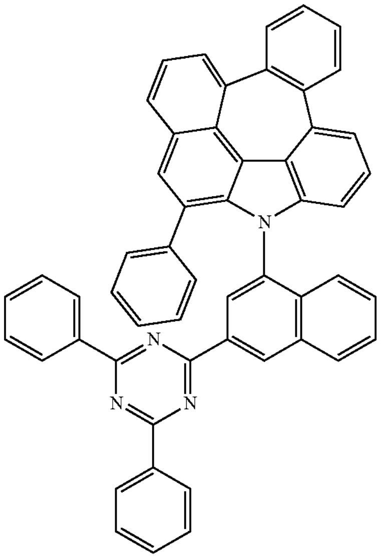

-continued
C-626
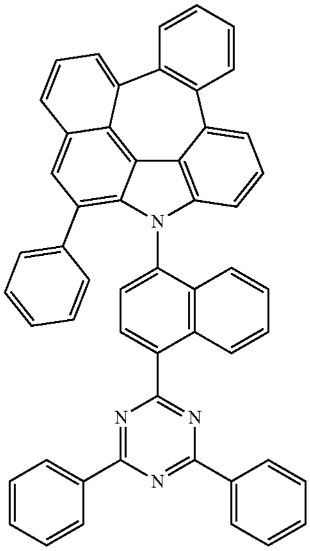
C-627
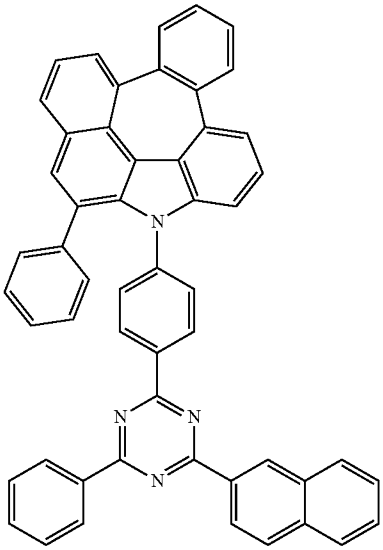
-continued
C-628
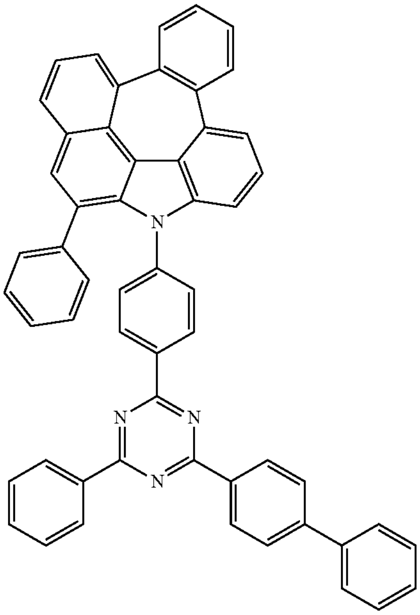
C-629
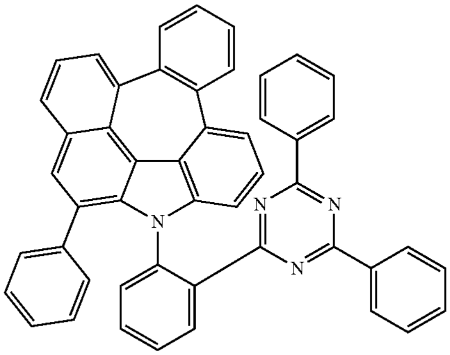
C-630
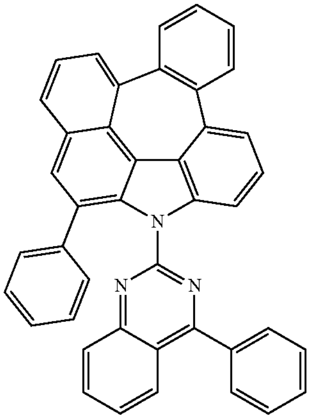

-continued
C-631
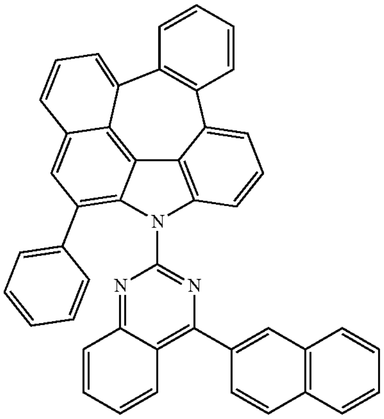
C-632
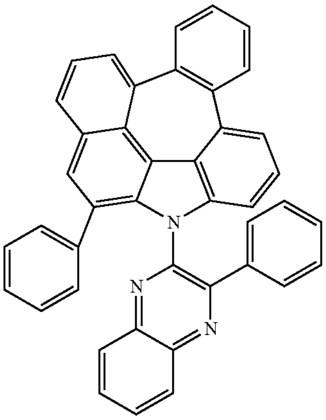
C-633
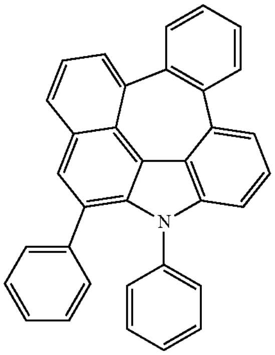
C-634
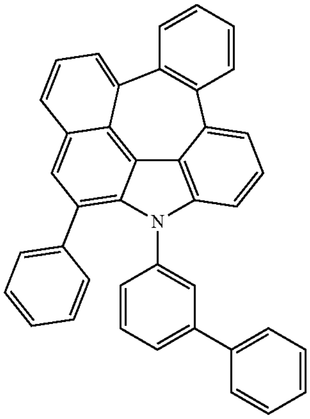
-continued
C-635
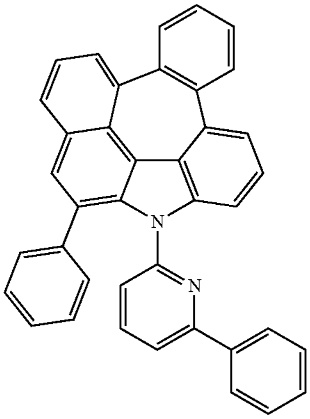
C-636
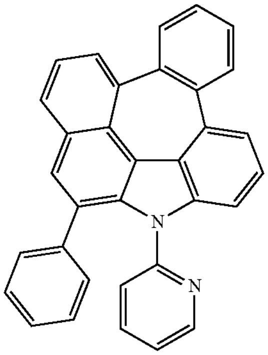
C-637
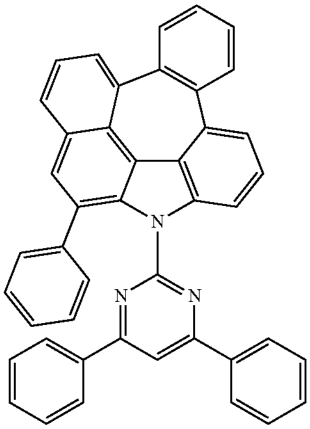
C-638
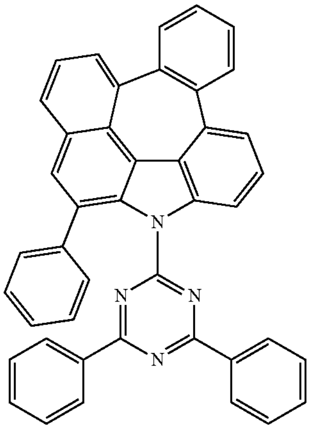

-continued
C-639
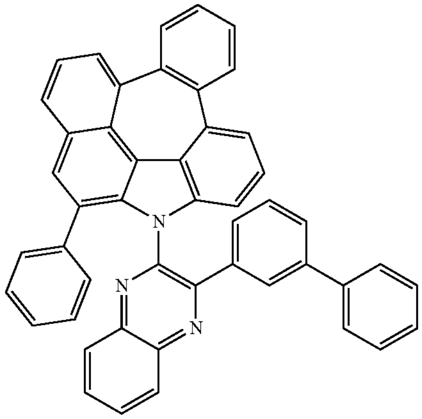
C-640
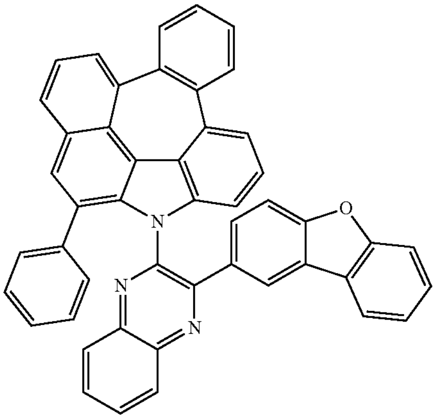
C-641
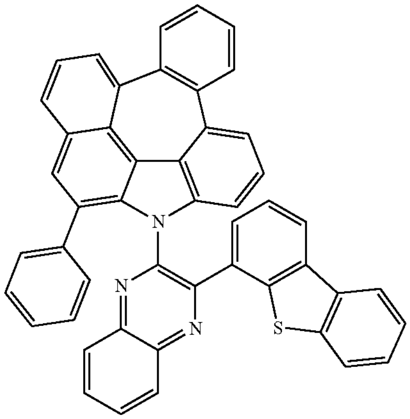
-continued
C-642
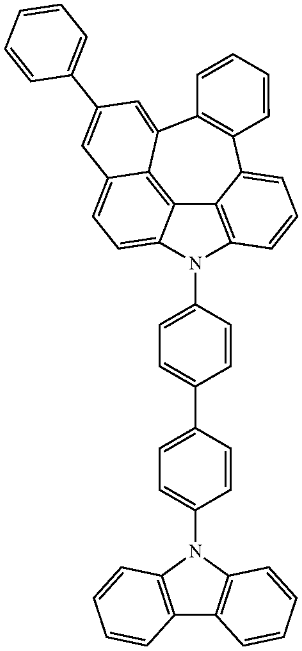
C-643
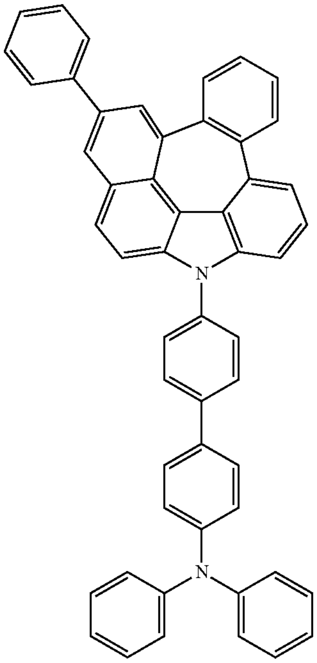

C-644
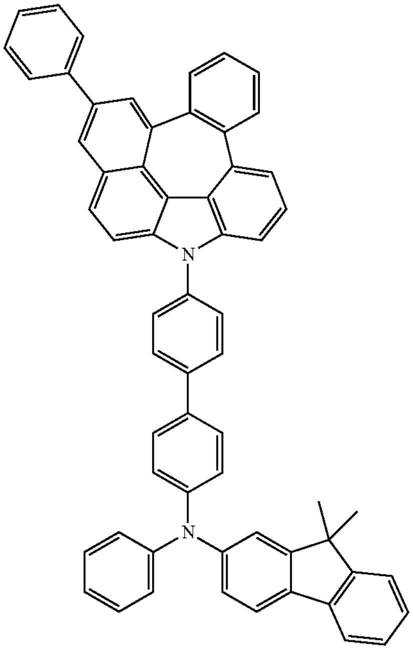
C-645
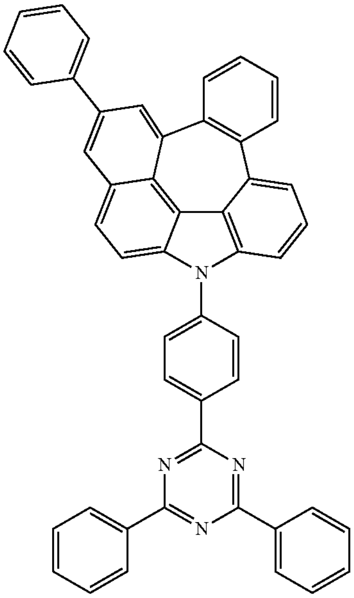
C-646
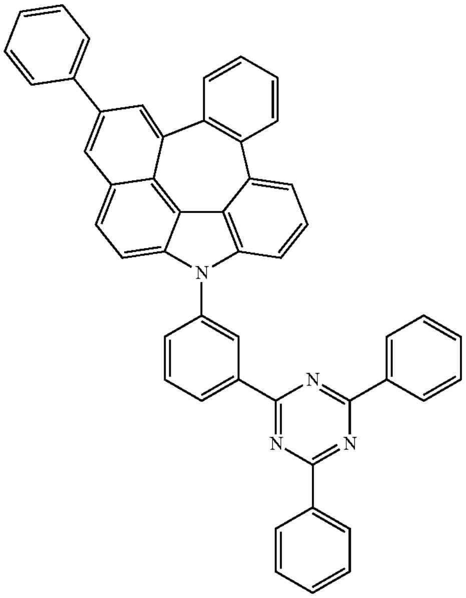
C-647
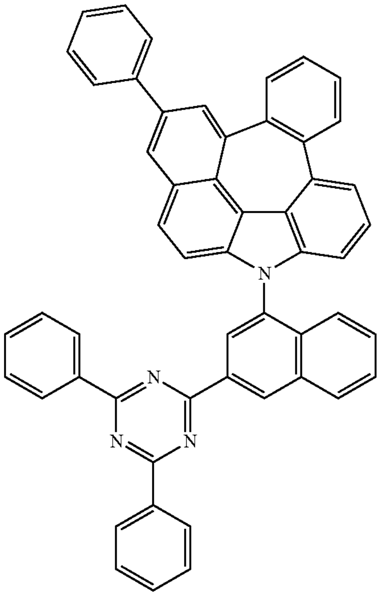

-continued
C-648
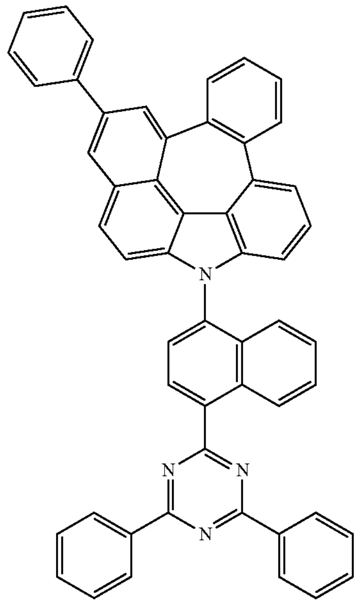
C-649
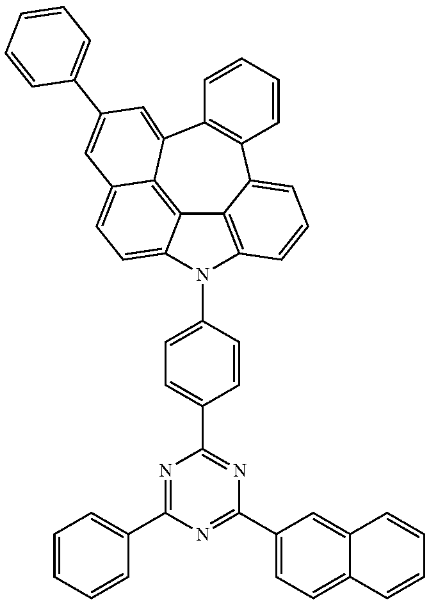
-continued
C-650
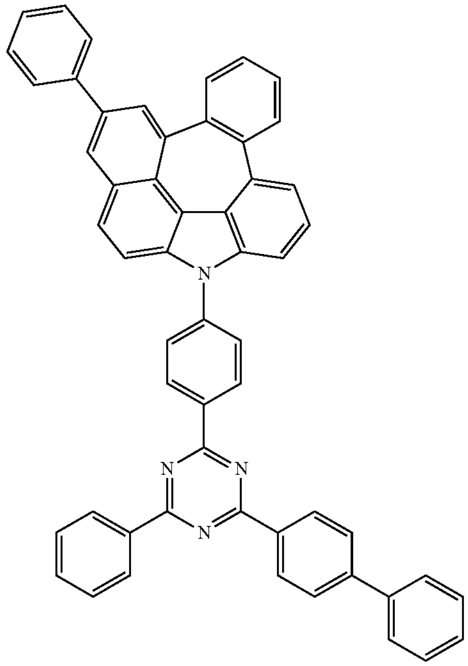
C-651
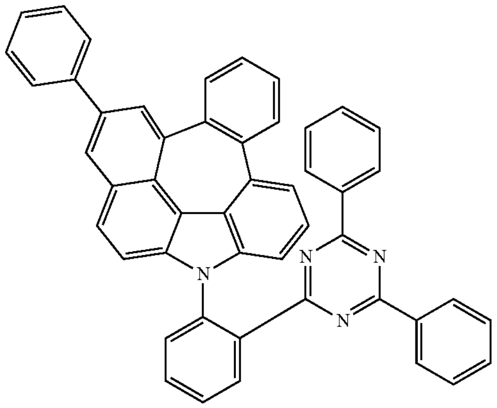
C-652
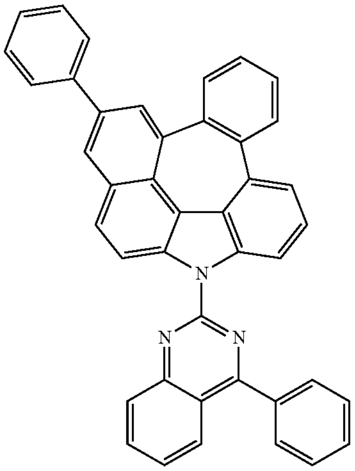

-continued
C-653
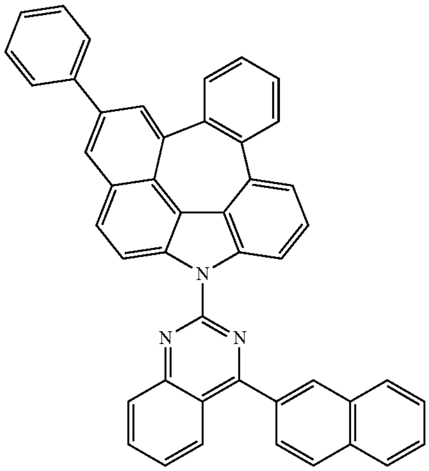
C-654
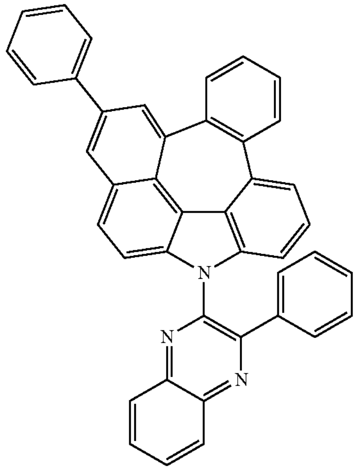
C-655
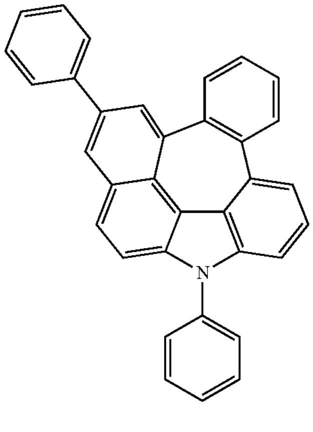
-continued
C-656
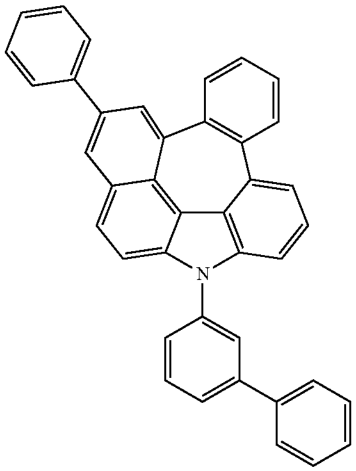
C-657
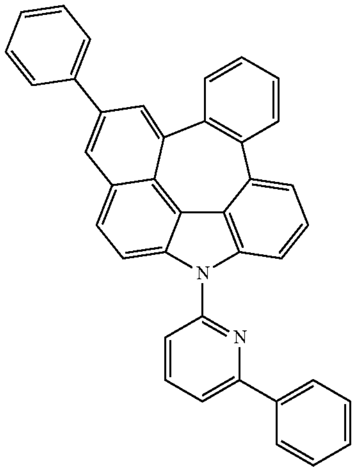
C-658
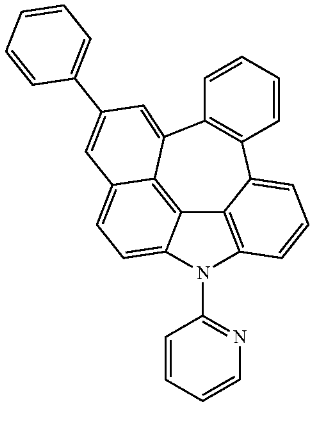

-continued

C-659

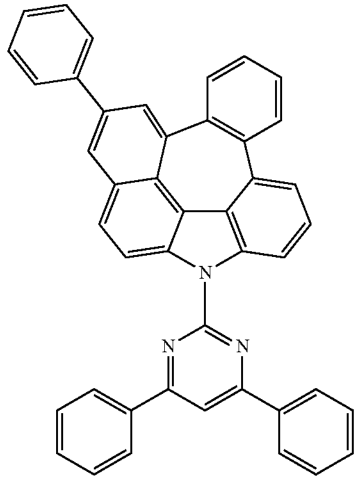

C-660

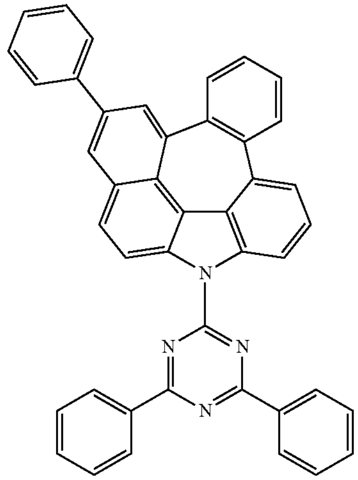

C-661

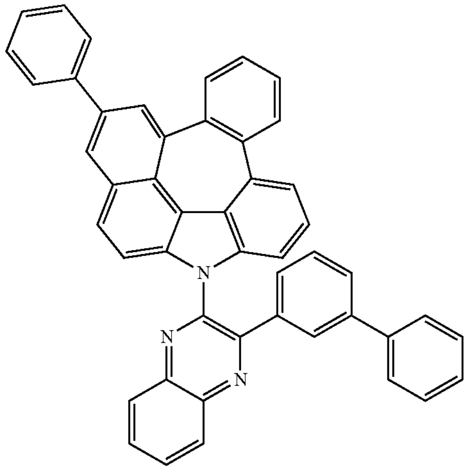

-continued

C-662

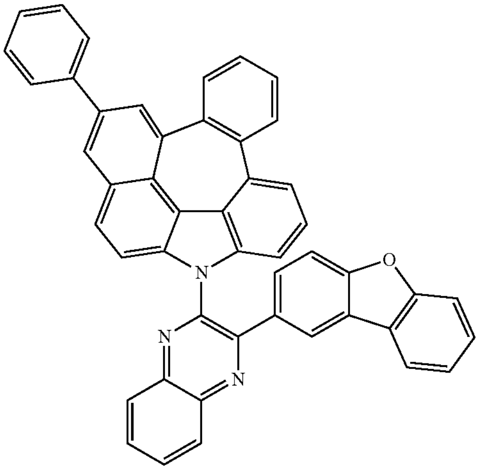

C-663

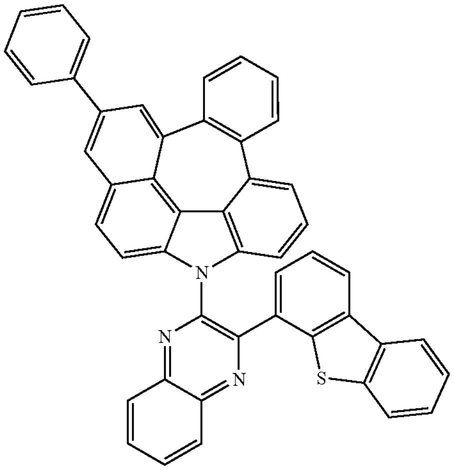

The compound represented by formula 1 according to the present disclosure may be prepared by a synthetic method known to one skilled in the art. For example, it may be prepared by referring to Korean Patent Application Nos. 10-2014-0011428 (filed on Jan. 29, 2014), 10-2012-0099963 (filed on Sep. 10, 2012), 10-2011-0083247 (filed on Aug. 22, 2011), etc. For example, the compound of formula 6 can be prepared by the following reaction scheme 1, but is not limited thereto.

[Reaction Scheme 1]

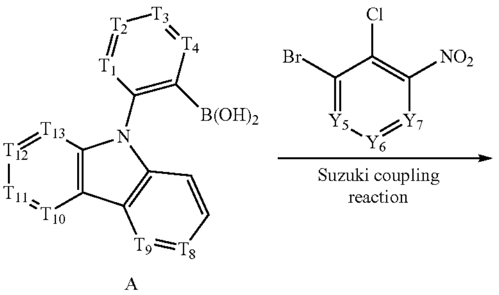

-continued

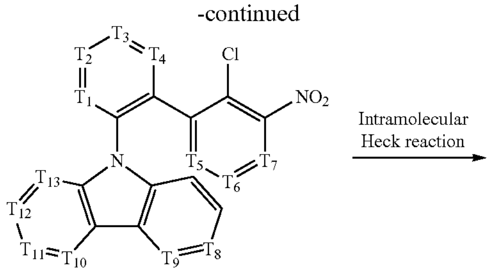

1-1

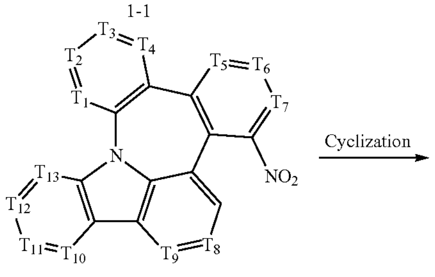

1-2

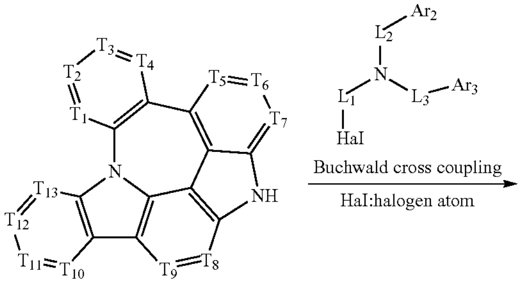

1-3

-continued

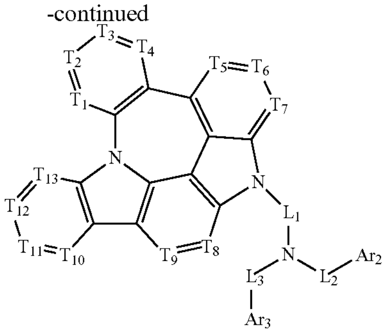

A-1

In reaction scheme 1, $T_1$ to $T_{13}$, $L_1$ to $L_3$, $Ar_2$, and $Ar_3$ are as defined in formula 6.

Also, the compound represented by formula 2 according to the present disclosure may be prepared by a synthetic method known to one skilled in the art. For example, it may be prepared by referring to the following reaction schemes. Further, it may be prepared by referring to Korean Patent Application Nos. 10-2017-0124258 (filed on Sep. 26, 2017), 10-2017-0124285 (filed on Sep. 26, 2017), etc.

[Reaction Scheme 2]

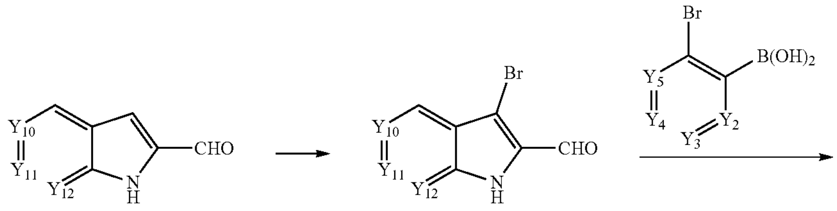

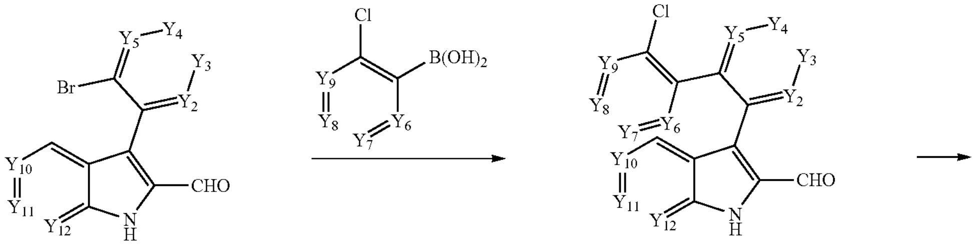

-continued
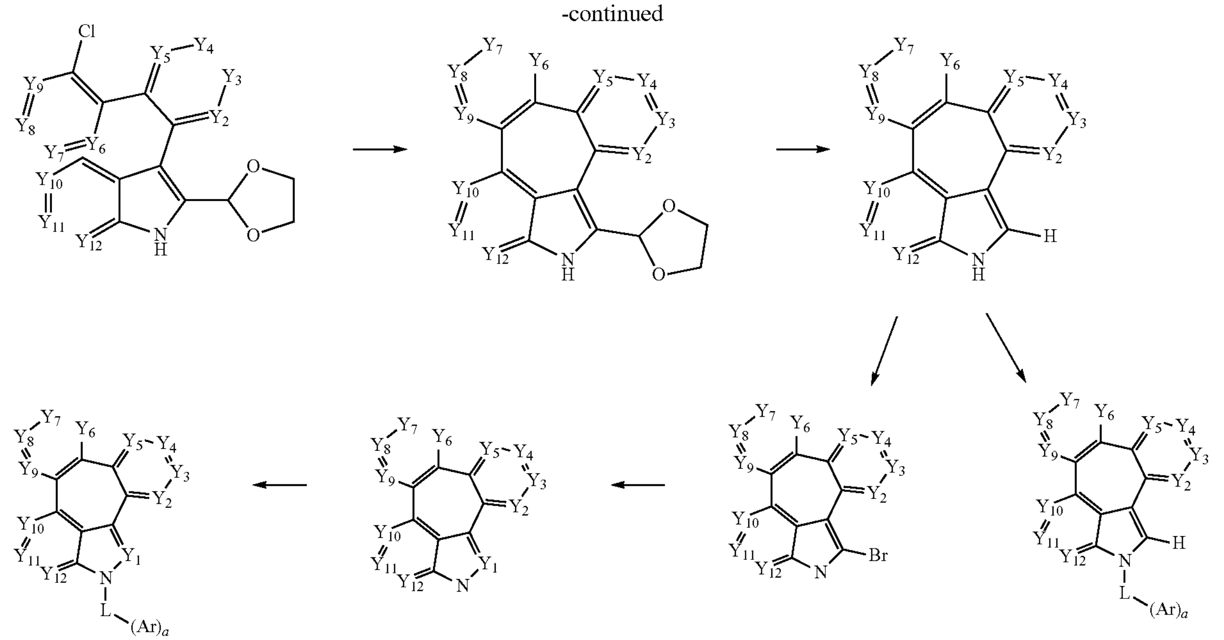
[Reaction Scheme 3]
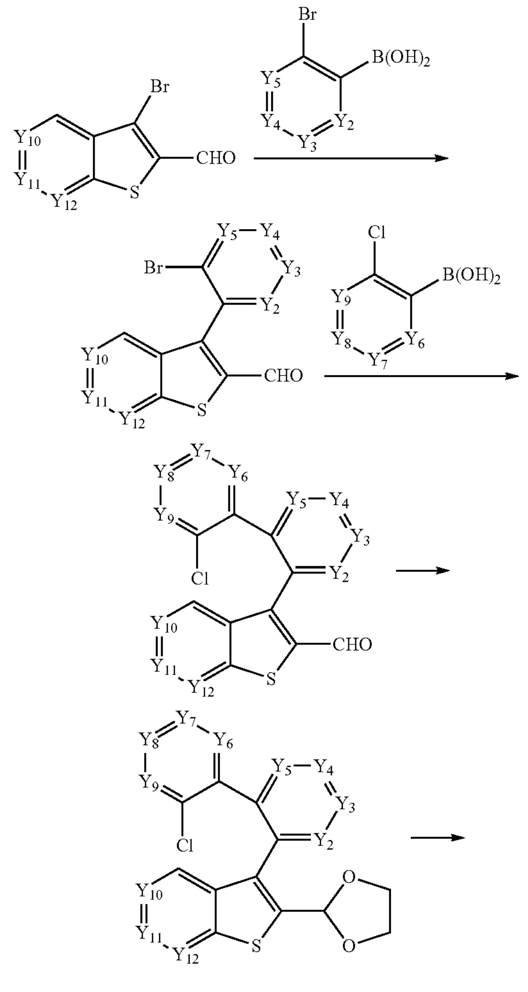
-continued
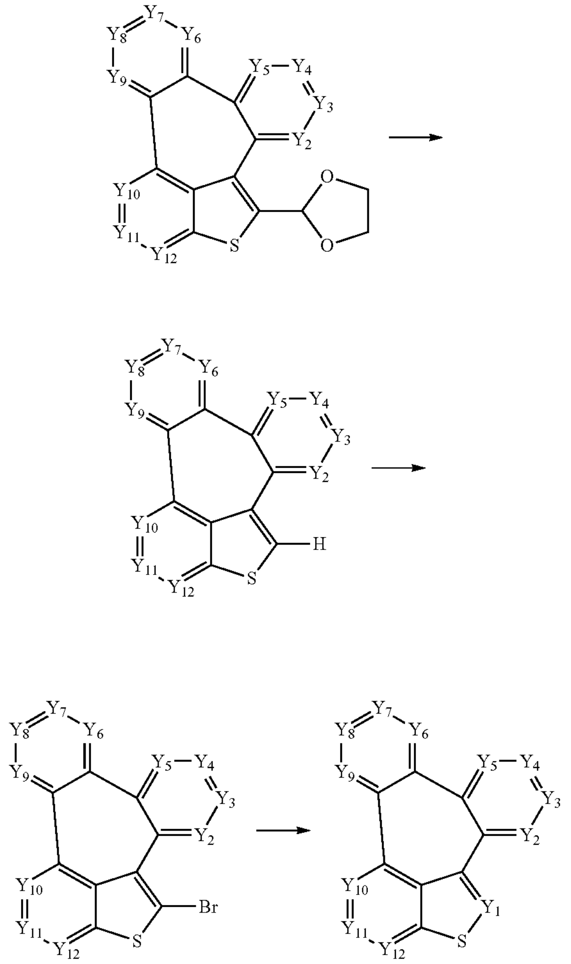

[Reaction Scheme 4]

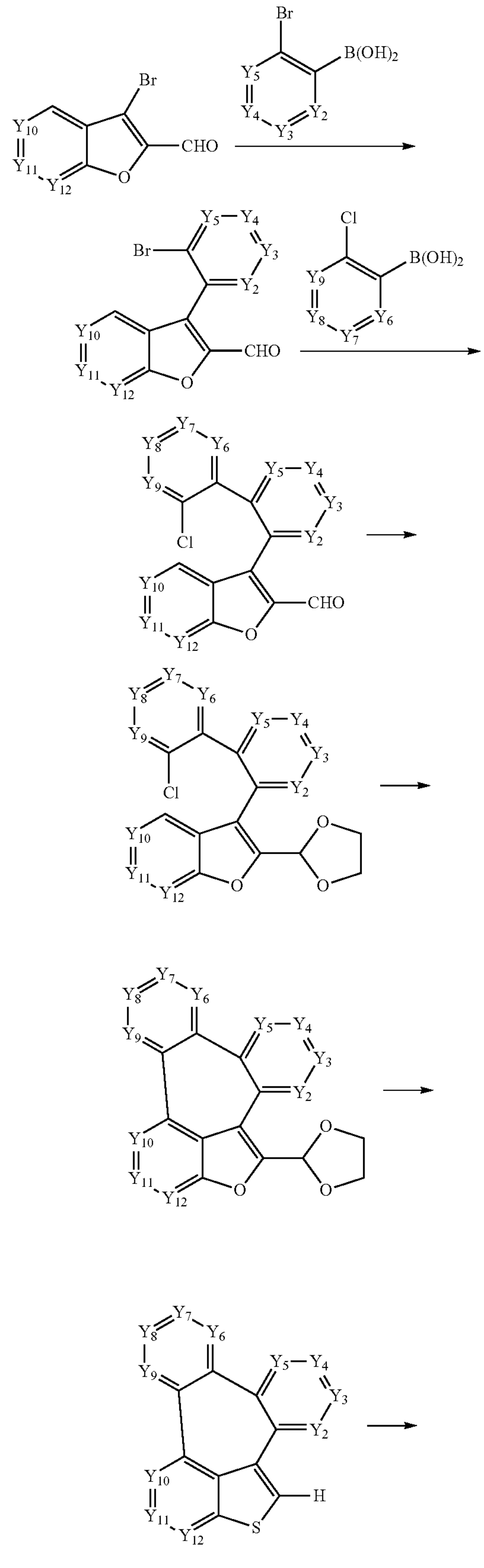

-continued

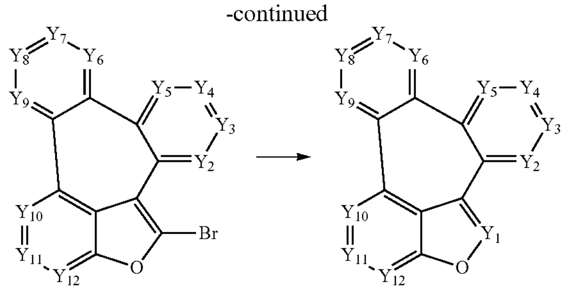

In reaction schemes 2 to 4, L, Ar, $Y_1$ to $Y_{12}$, and a are as defined in formula 2.

According to the present disclosure, an organic electroluminescent device comprising the composition material for an organic electroluminescent device is provided. When the composition material for an organic electroluminescent device is comprised in an organic electroluminescent device, conventional materials comprised in an organic electroluminescent material may be further comprised besides the compounds represented by formulas 1 and 2. In addition, according to an embodiment of the present disclosure, an organic electroluminescent material comprising a plurality of host materials is provided.

The organic electroluminescent device according to the present disclosure comprises a first electrode; a second electrode; and at least one organic layer between the first and second electrodes. The organic layer may comprise the composition material for an organic electroluminescent device comprising compounds of formulas 1 and 2. The organic layer may further comprise at least one compound selected from the group consisting of arylamine-based compounds and styrylarylamine-based compounds. In addition, the organic layer may further comprise at least one metal selected from the group consisting of metals of Group 1, metals of Group 2, transition metals of the $4^{th}$ period, transition metals of the $5^{th}$ period, lanthanides, and organic metals of d-transition elements of the Periodic Table, or at least one complex compound comprising said metal.

One of the first and second electrodes may be an anode, and the other may be a cathode. The organic layer comprises a light-emitting layer, and may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer.

A hole injection layer, a hole transport layer, an electron blocking layer, or a combination thereof can be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. The electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. The hole transport layer and electron blocking layer may be multilayers wherein each of the multilayers may use a plurality of compounds.

An electron buffer layer, a hole blocking layer, an electron transport layer, an electron injection layer, or a combination thereof can be used between the light-emitting layer and the cathode. The electron buffer layer may be multilayers in order to control the injection of the electron and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. When an organic electroluminescent device includes two or more hole transport layers, the hole transport layer, which is further included, may be used as a hole auxiliary layer or an electron blocking layer. The light-emitting auxiliary layer, the hole auxiliary layer, or the electron blocking layer may have an effect of improving the luminous efficiency and/or the lifespan of the organic electroluminescent device.

In one embodiment of the present disclosure, the organic electroluminescent device of the present disclosure may further comprise an azine-based compound, in addition to the organic electroluminescent compound of the present disclosure, as at least one of an electron transport material, an electron injection material, an electron buffer material, and a hole blocking material.

In the organic electroluminescent device according to the present disclosure, at least one layer (hereinafter, "a surface layer") is preferably placed on an inner surface(s) of one or both electrode(s); selected from a chalcogenide layer, a metal halide layer, and a metal oxide layer. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, said chalcogenide includes $SiO_X$ ($1 \le X \le 2$), $AlO_X$ ($1 \le X \le 1.5$), SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

Preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic electroluminescent device having two or more light-emitting layers which emits white light.

The composition material for an organic electroluminescent device of the present disclosure may be comprised in the light-emitting layer. When used in the light-emitting layer, the compound of formula 1 may be comprised as a first host material, and the compound of formula 2 may be comprised as a second host material. Preferably, the light-emitting layer may further comprise one or more dopants.

The dopant compound, which can be used in combination with the host compound of the present disclosure, may comprise the compound represented by the following formula 101, but is not limited thereto.

(101)

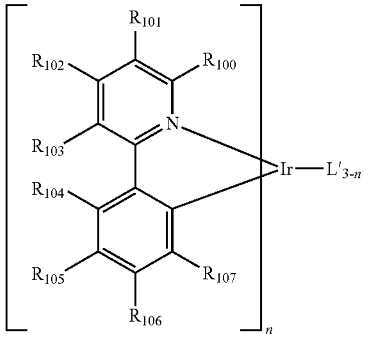

In formula 101, L' is selected from the following structures 1 and 2:

[Structure 1]

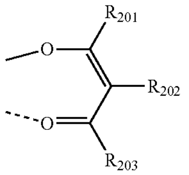

[Structure 2]

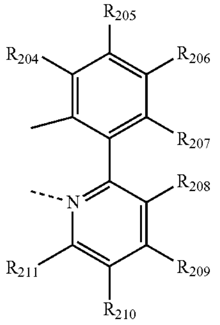

$R_{100}$ to $R_{103}$ each independently represent hydrogen, deuterium, a halogen, a (C1-C30)alkyl unsubstituted or substituted with a halogen, a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to adjacent $R_{100}$ to $R_{103}$ to form a substituted or unsubstituted fused ring together with pyridine, e.g., a substituted or unsubstituted quinoline, a substituted or unsubstituted isoquinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline ring;

$R_{104}$ to $R_{107}$ each independently represent hydrogen, deuterium, a halogen, a (C1-C30)alkyl unsubstituted or substituted with a halogen, a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to adjacent $R_{104}$ to $R_{107}$ to form a substituted or unsubstituted fused ring together with benzene, e.g., a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine ring;

$R_{201}$ to $R_{211}$ each independently represent hydrogen, deuterium, a halogen, a (C1-C30)alkyl unsubstituted or substituted with a halogen, a substituted or unsubstituted (C3-C30)cycloalkyl, or a substituted or unsubstituted (C6-C30)aryl; or may be linked to adjacent $R_{201}$ to $R_{211}$ to form a substituted or unsubstituted fused ring; and n represents an integer of 1 to 3.

The specific examples of the dopant compound are as follows, but are not limited thereto.

D-1

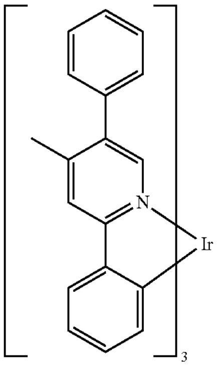

D-2

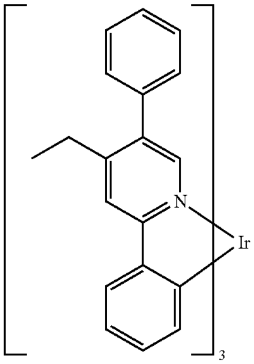

-continued

D-3

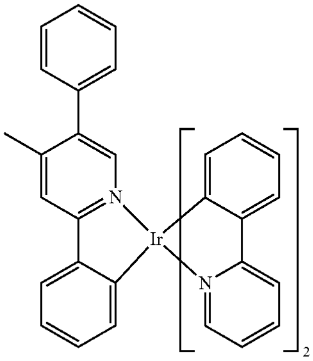

D-4

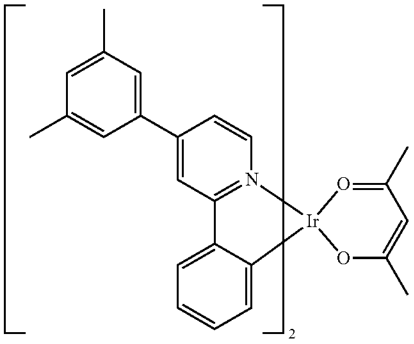

D-5

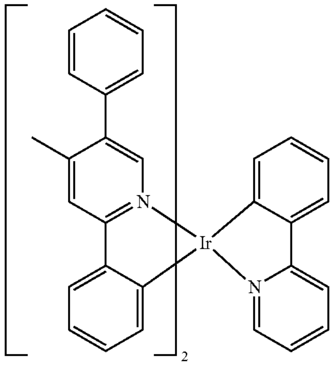

D-6

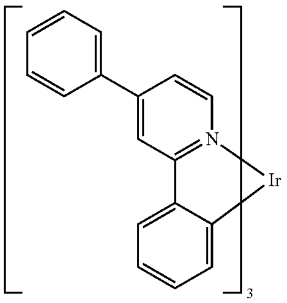

-continued
D-7
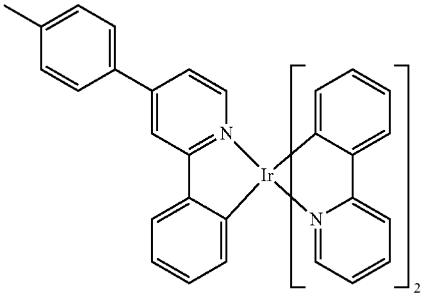
D-8
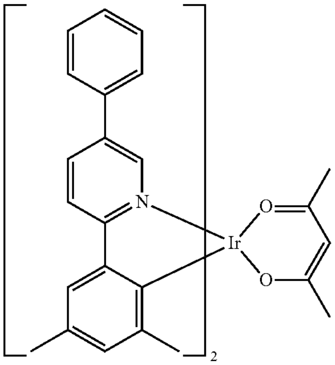
D-9
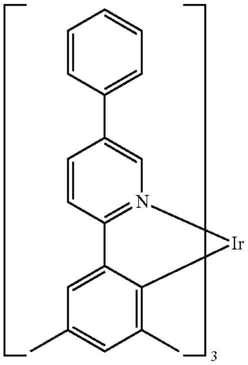
D-10
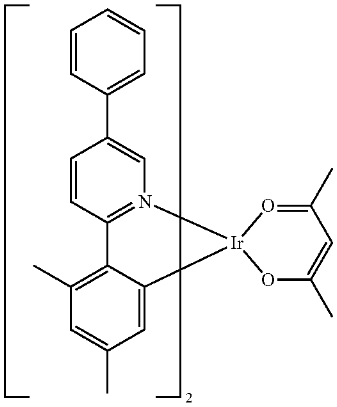
-continued
D-11
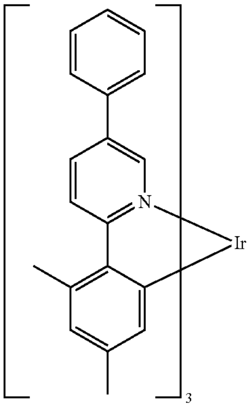
D-12
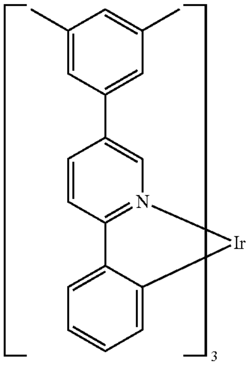
D-13
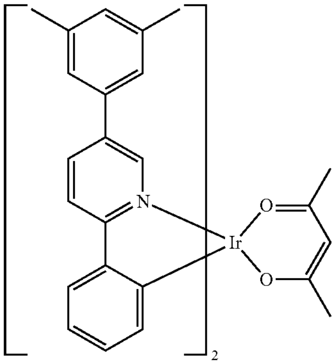
D-14
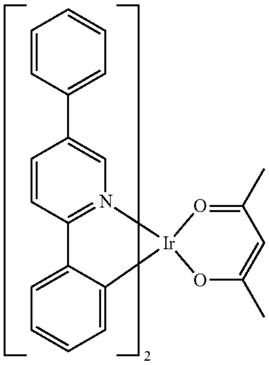

D-15
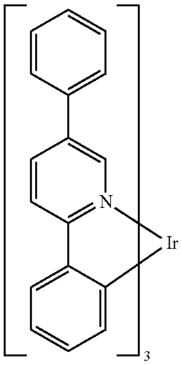
D-16
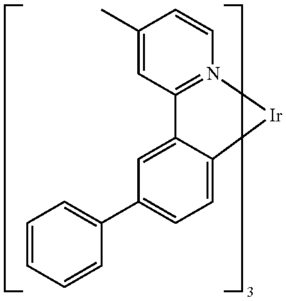
D-17
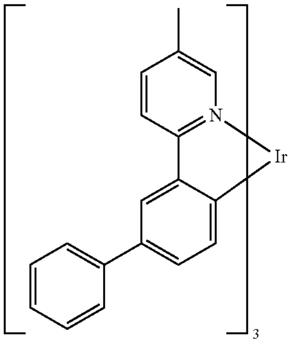
D-18
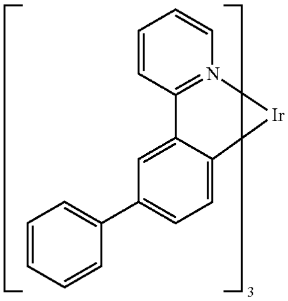
D-19
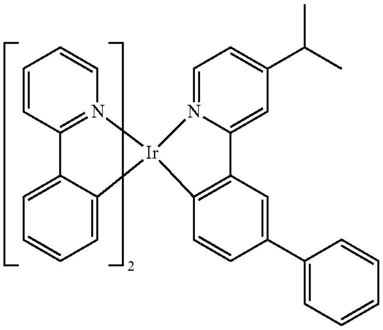
D-20
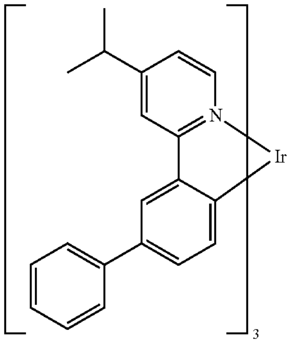
D-21
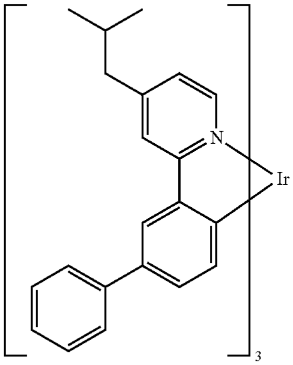
D-22
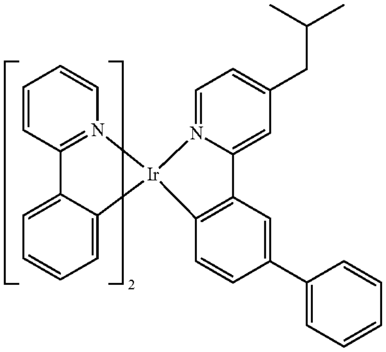

-continued
D-23
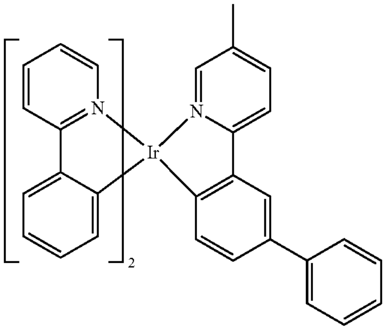
D-24
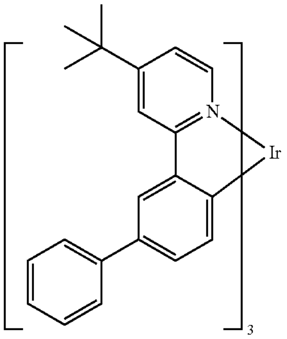
D-25
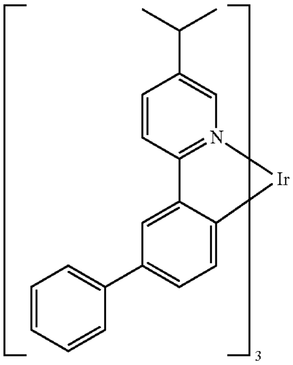
D-26
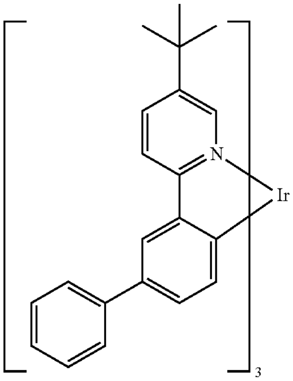
-continued
D-27
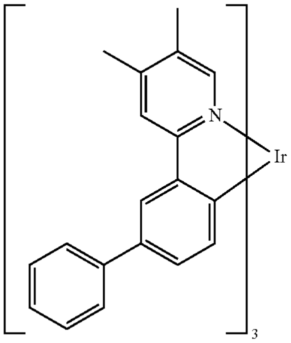
D-28
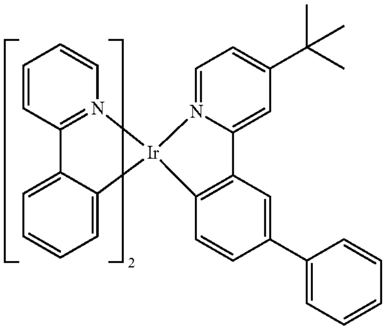
D-29
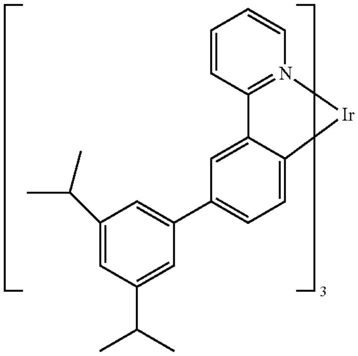
D-30
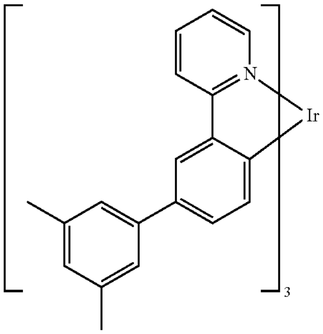

-continued
D-31
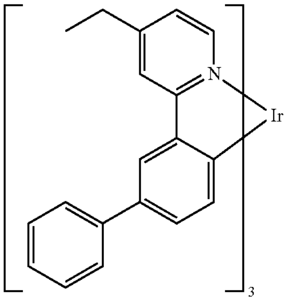
D-32
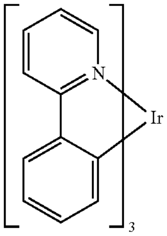
D-33
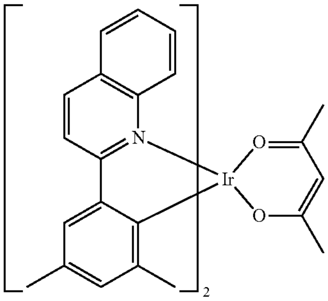
D-34
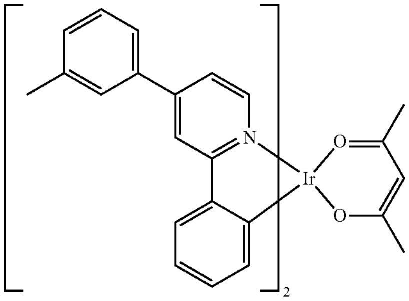
D-35
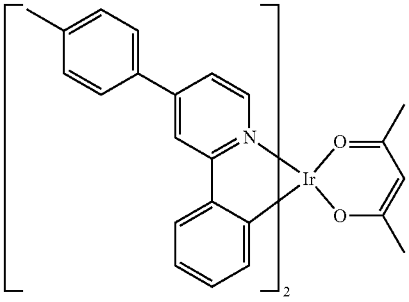
-continued
D-36
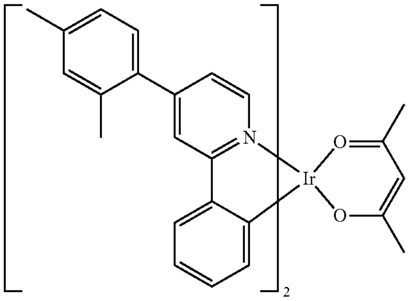
D-37
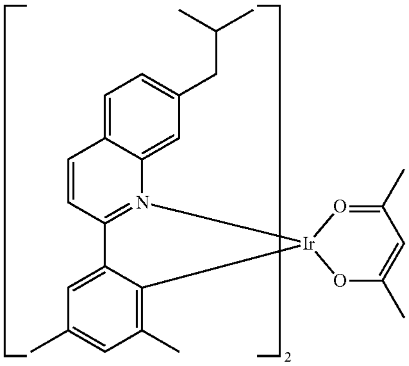
D-38
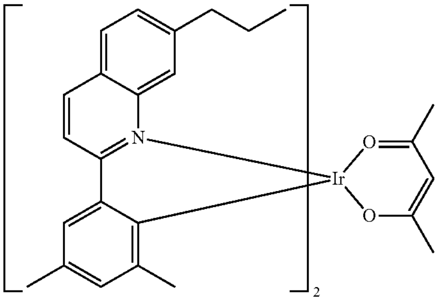
D-39
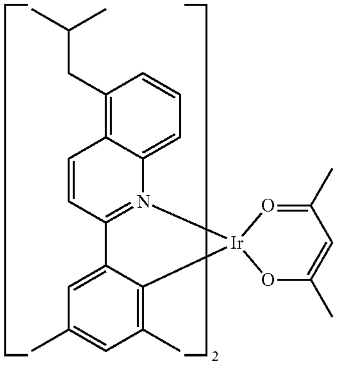

-continued
D-40
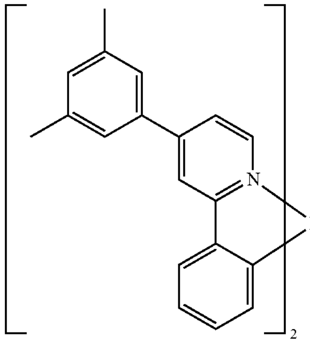
D-41
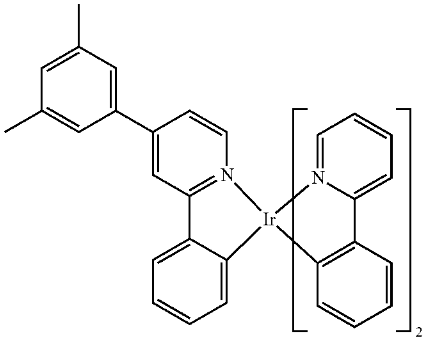
D-42
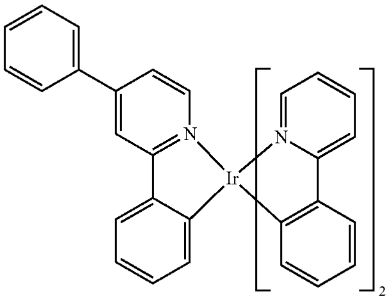
D-43
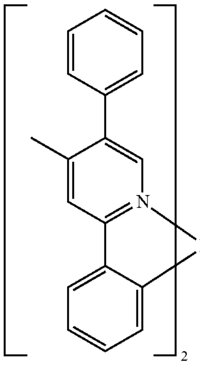
-continued
D-44
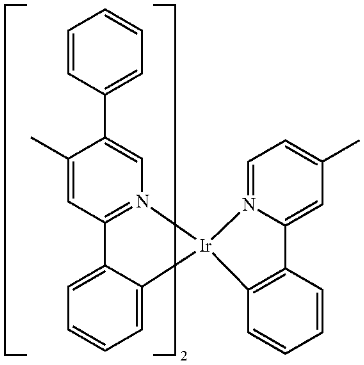
D-45
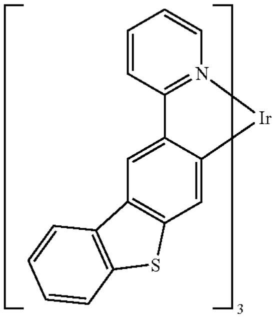
D-46
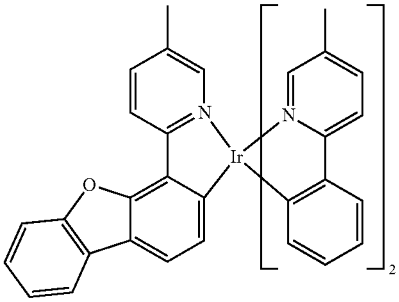
D-47
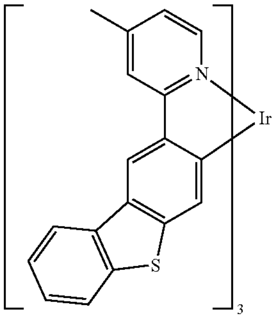
D-48
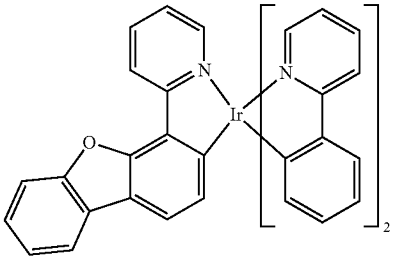

-continued
D-49
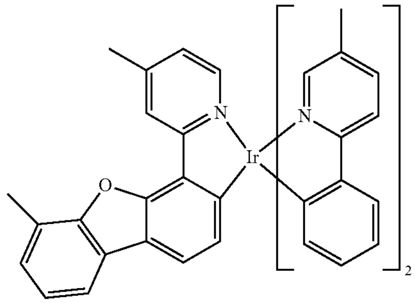
D-50
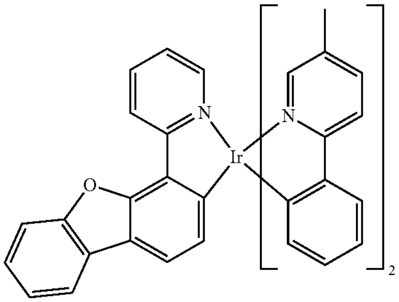
D-51
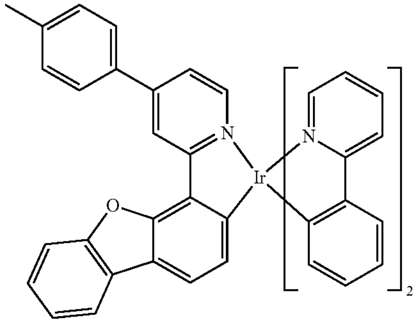
D-52
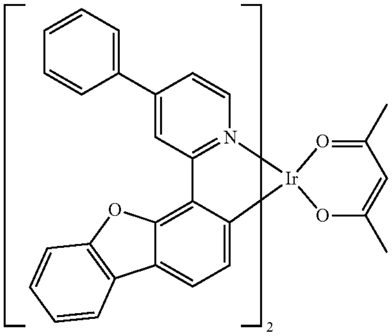
D-53
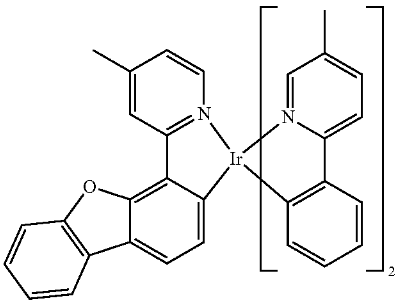
-continued
D-54
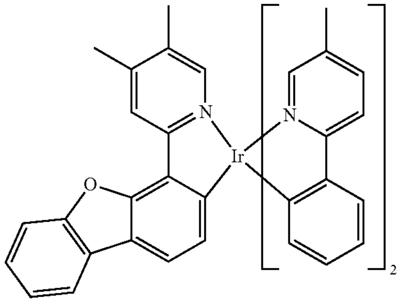
D-55
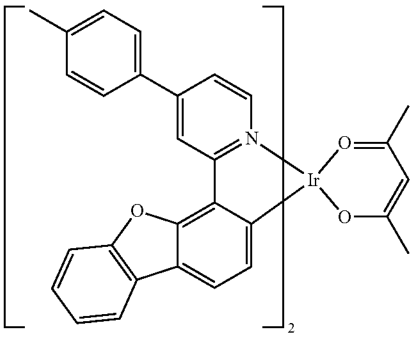
D-56
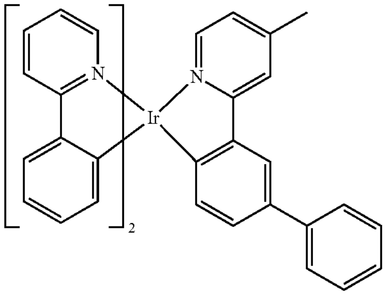
D-57
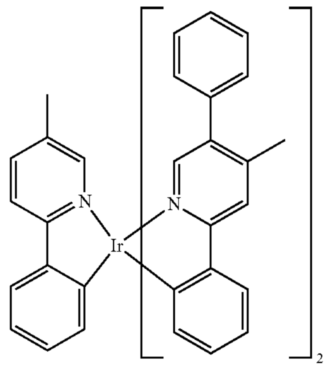

-continued
D-58
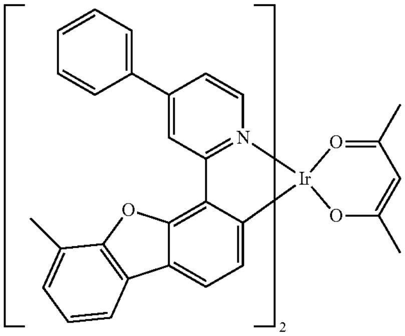
D-59
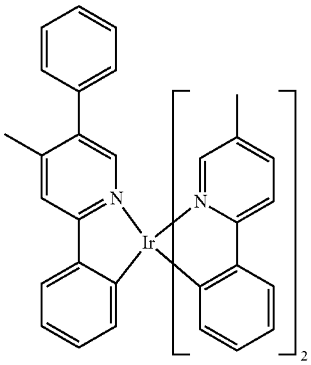
D-60
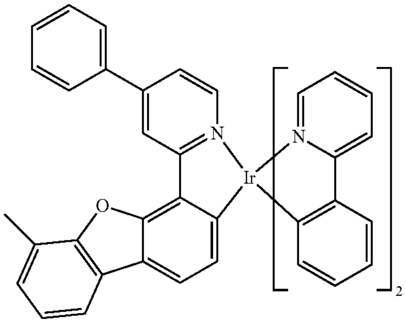
D-61
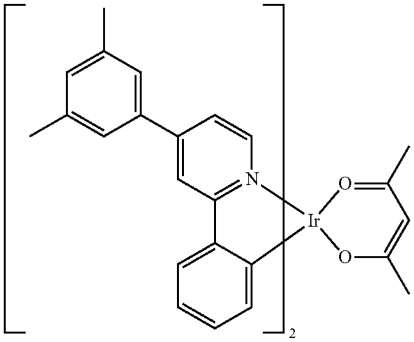
-continued
D-62
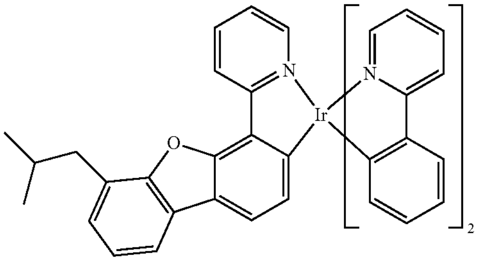
D-63
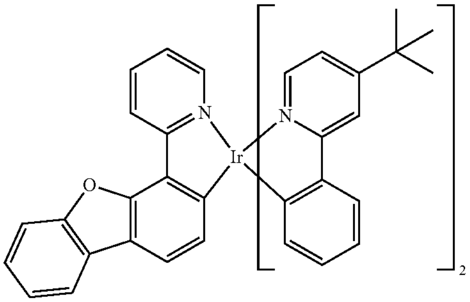
D-64
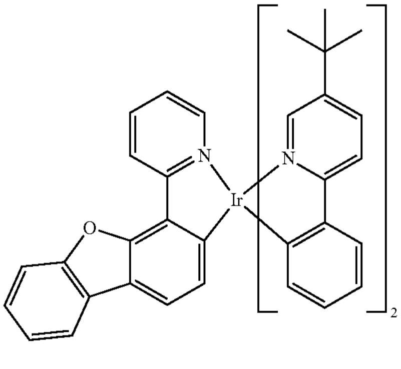
D-65
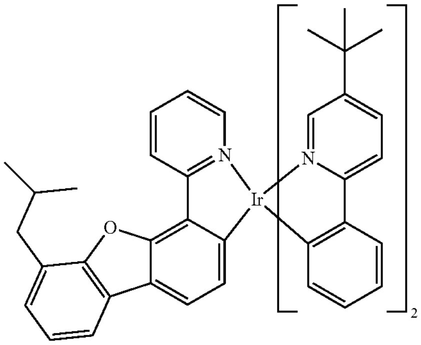

-continued
D-66
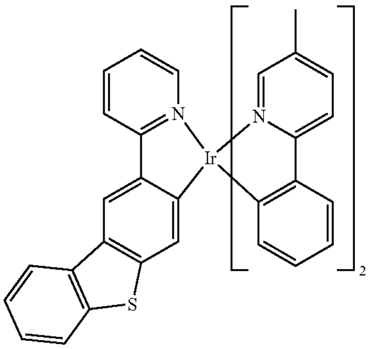
D-67
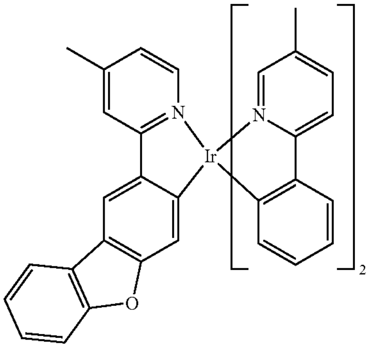
D-68
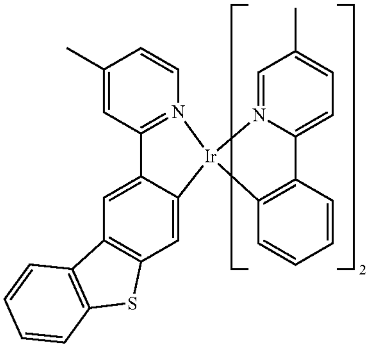
D-69
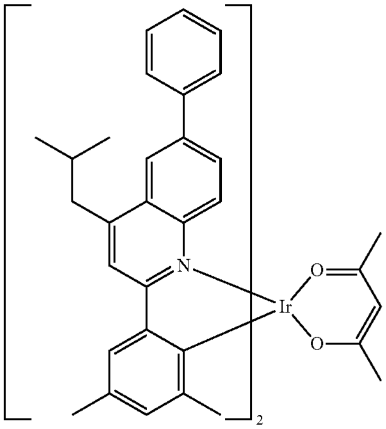
-continued
D-70
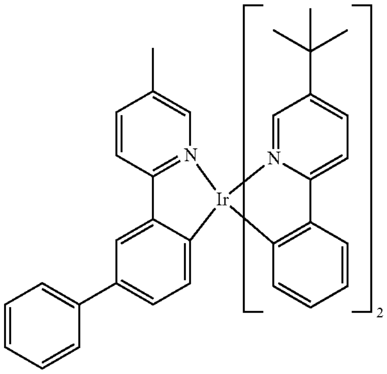
D-71
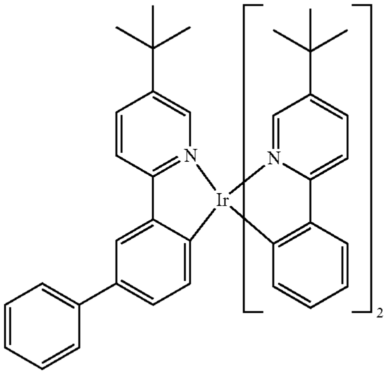
D-72
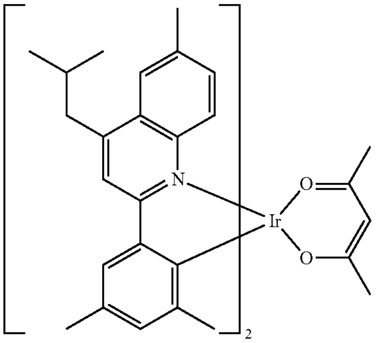
D-73
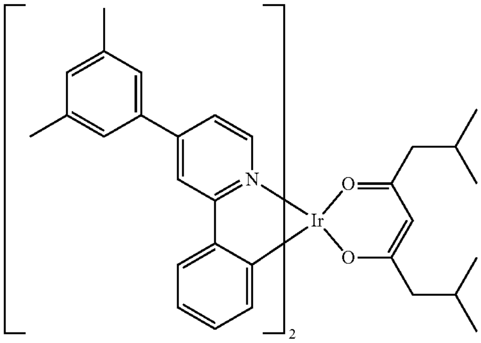

-continued
D-74
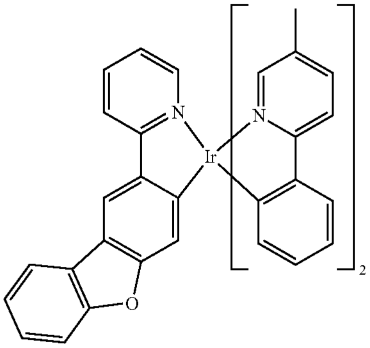
D-75
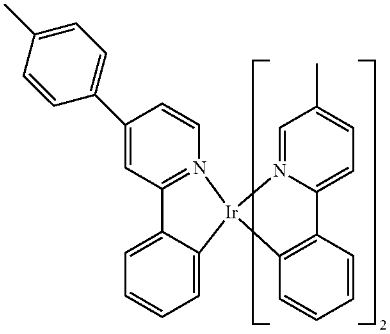
D-76
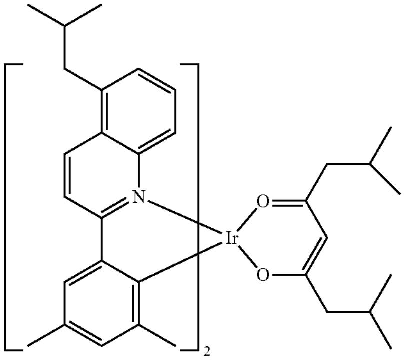
D-77
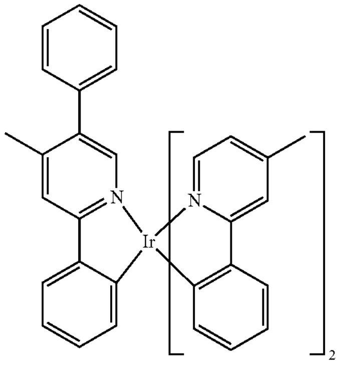
-continued
D-78
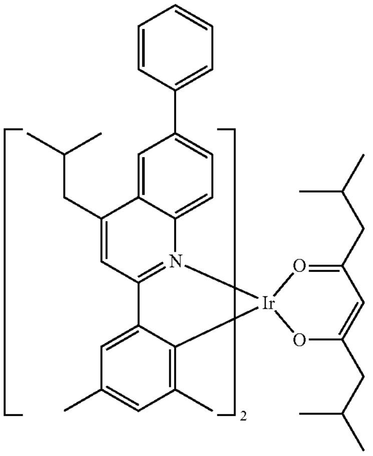
D-79
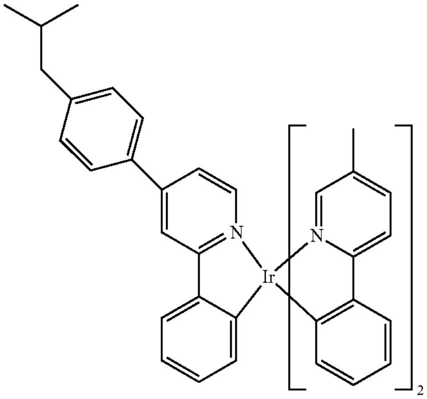
D-80
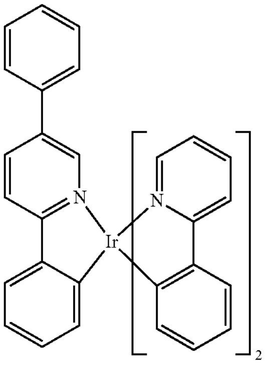

-continued
D-81
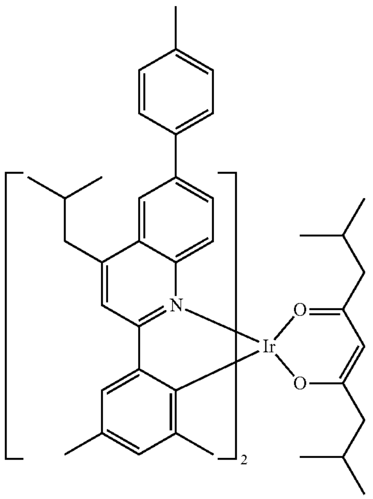
D-82
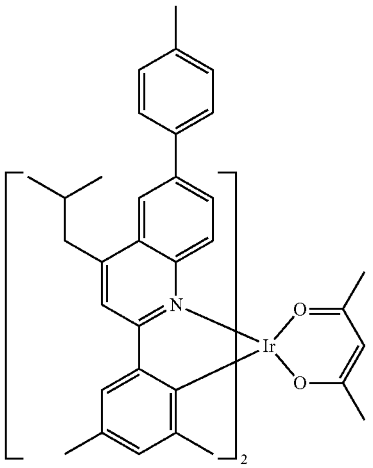
D-83
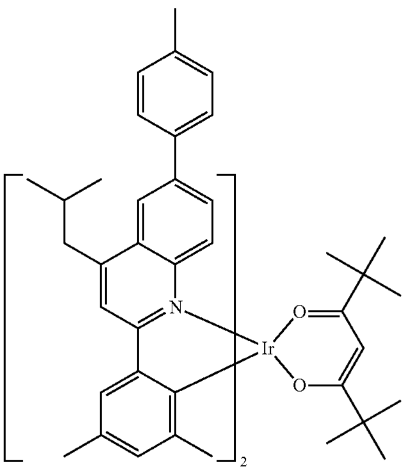
-continued
D-84
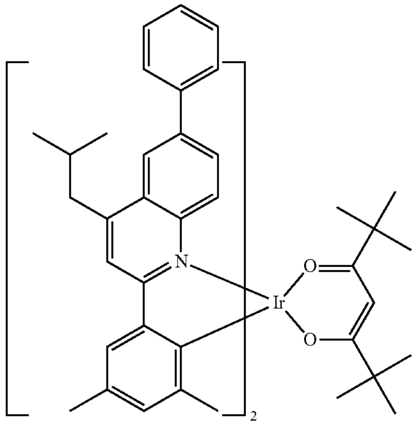
D-85
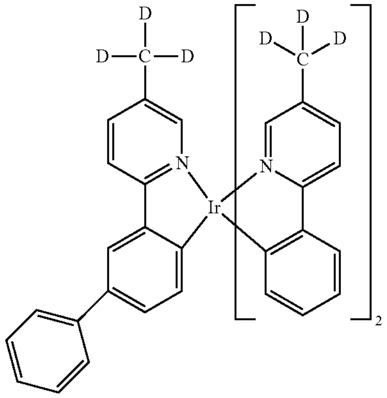
D-86
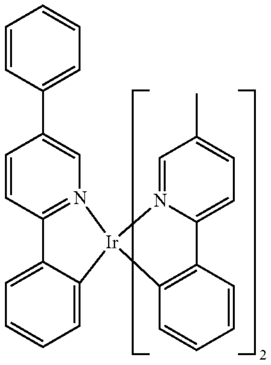
D-87
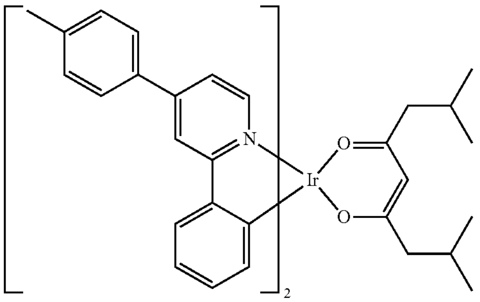

-continued
D-88
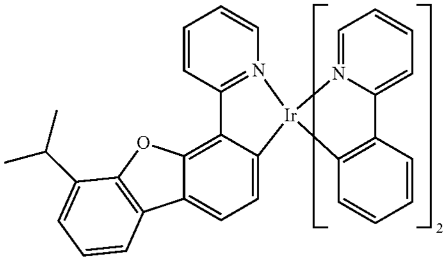
D-89
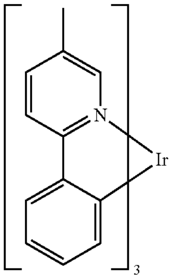
D-90
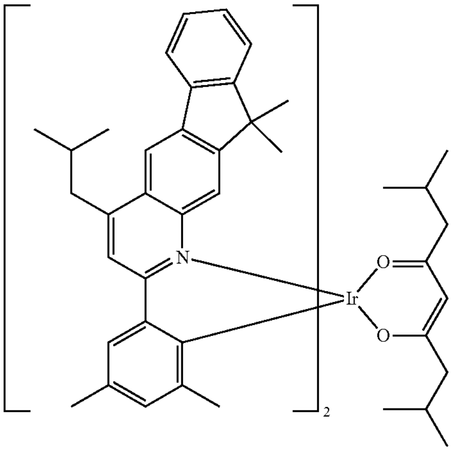
D-91
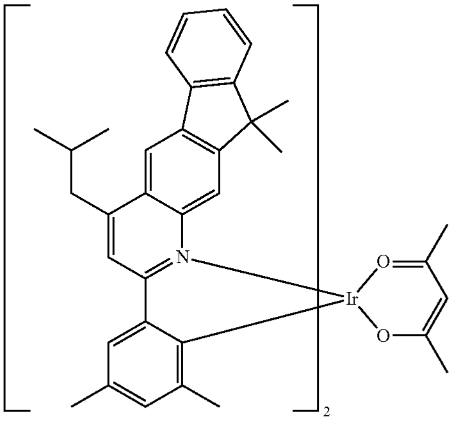
-continued
D-92
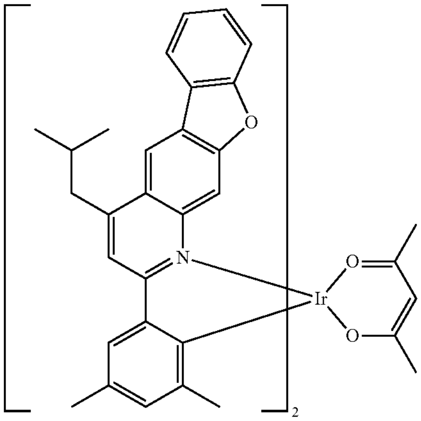
D-93
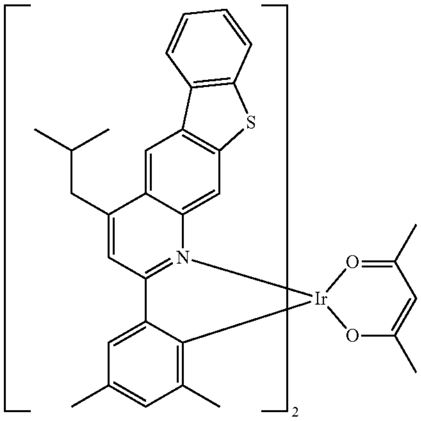
D-94
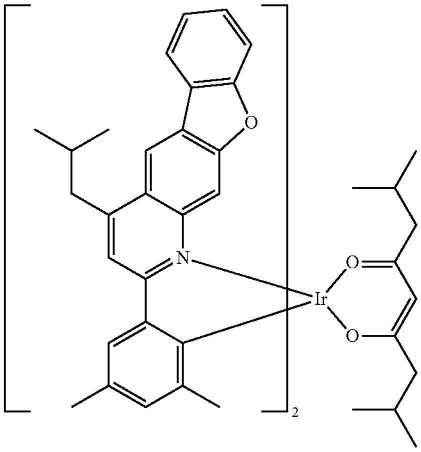

-continued
D-95
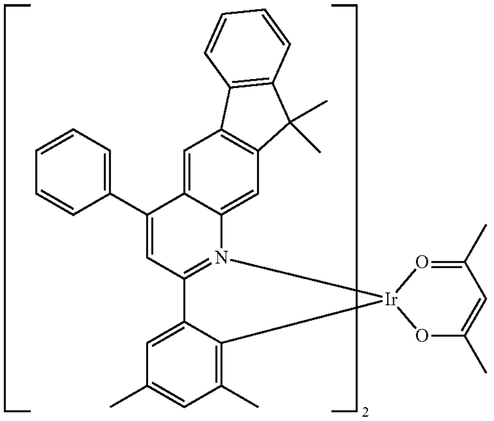
D-96
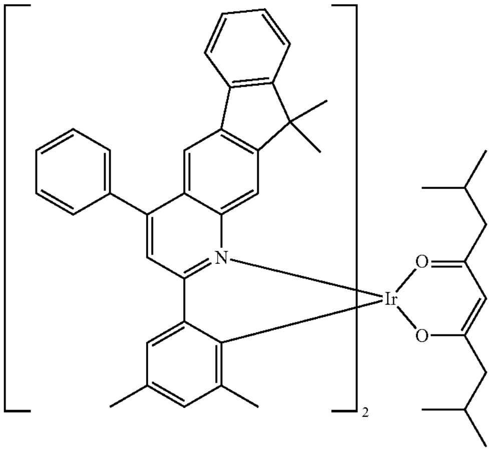
D-97
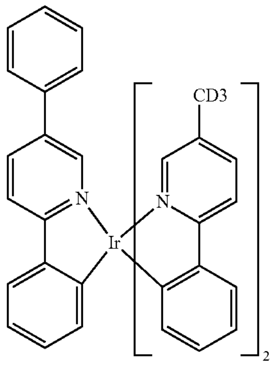
D-98
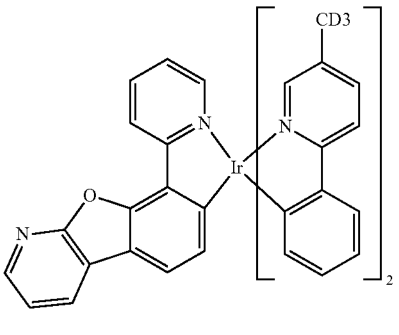
-continued
D-99
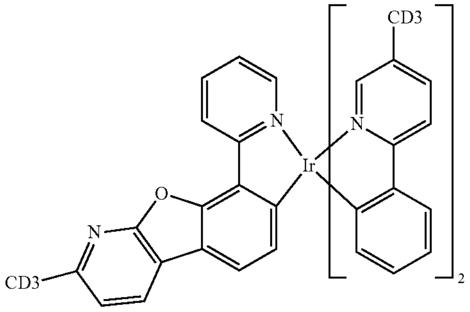
D-100
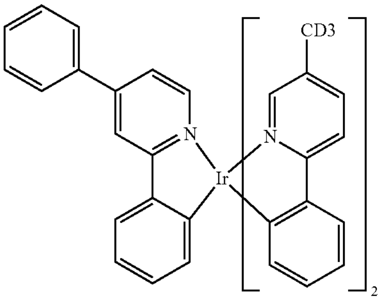
D-101
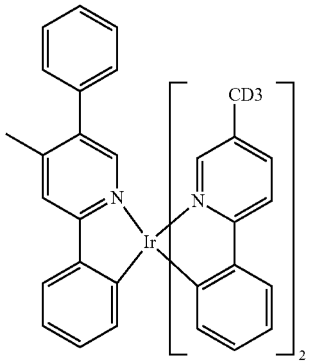
D-102
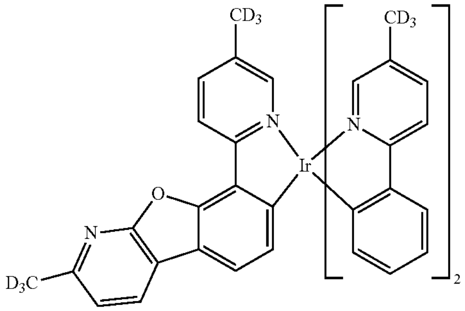
D-103
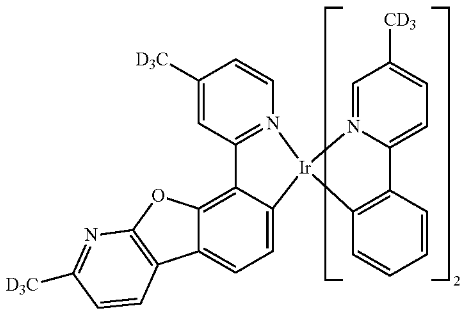

-continued
D-104
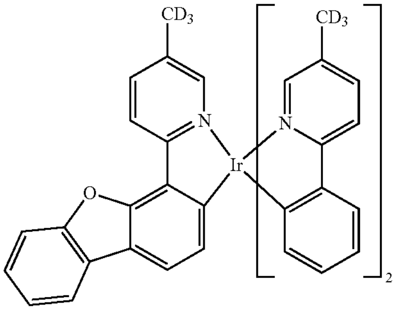
D-105
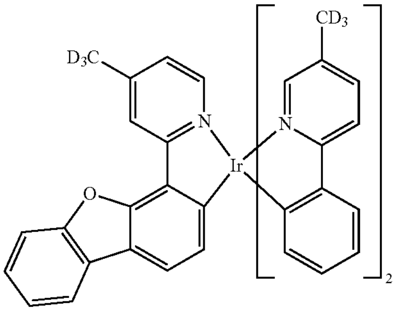
D-106
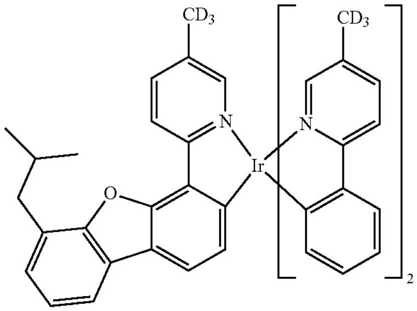
D-107
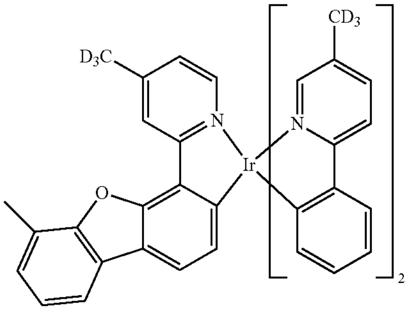
D-108
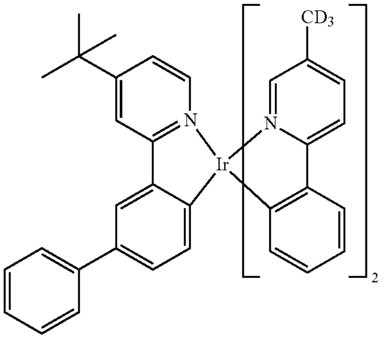
-continued
D-109
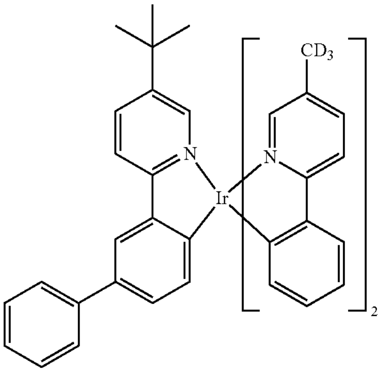
D-110
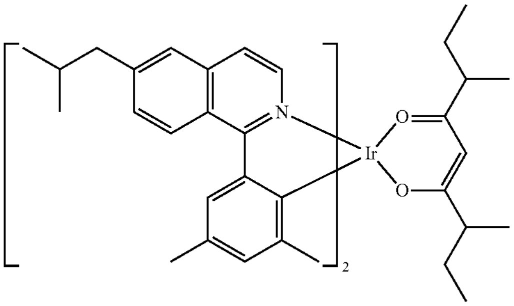
D-111
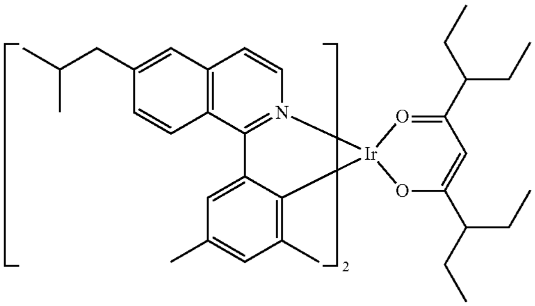
D-112
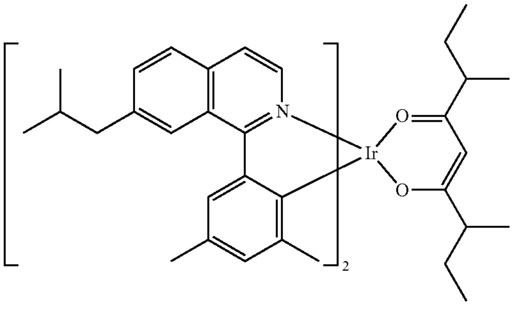

-continued

D-113

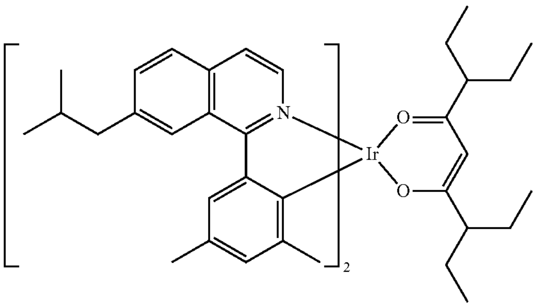

D-114

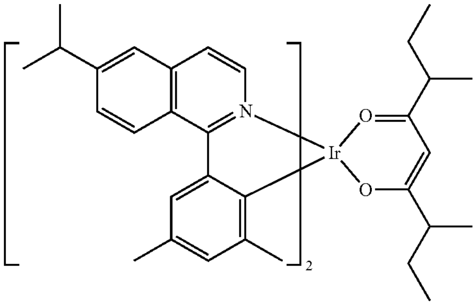

D-115

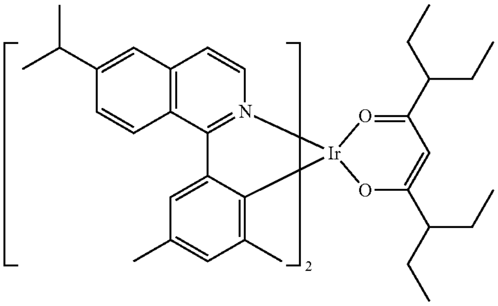

D-116

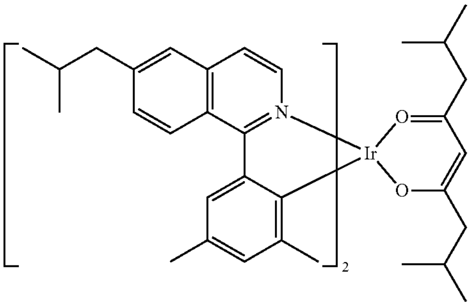

D-117

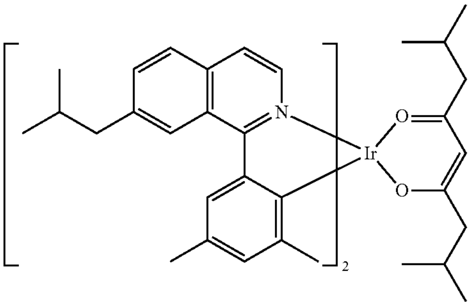

-continued

D-118

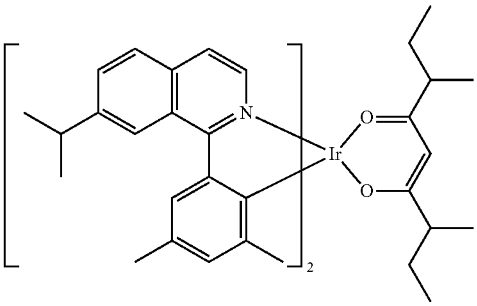

D-119

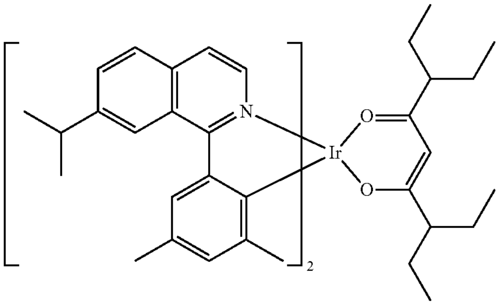

In order to form each layer of the organic electroluminescent device of the present disclosure, dry film-forming methods such as vacuum evaporation, sputtering, plasma and ion plating methods, or wet film-forming methods such as ink jet printing, nozzle printing, slot coating, spin coating, dip coating, and flow coating methods can be used.

When using a solvent in a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

The present disclosure may provide a display device by using the composition material for an organic electroluminescent device comprising the compound represented by formula 1 and the compound represented by formula 2. That is, it is possible to manufacture a display system or a lighting system by using the composition material for an organic electroluminescent device of the present disclosure. Specifically, it is possible to produce a display system, e.g., a display system for smartphones, tablets, notebooks, PCs, TVs, or cars, or a lighting system, e.g., an outdoor or indoor lighting system, by using the composition material for an organic electroluminescent device of the present disclosure.

Hereinafter, the luminous properties of the organic electroluminescent device comprising the composition material for an organic electroluminescent device will be explained in detail. However, the present disclosure is not limited to the following examples.

Device Examples 1 to 10: Production of an OLED Device Comprising the Composition Material for an OLED Device According to the Present Disclosure An organic light-emitting diode (OLED) device was produced comprising the composition material for an OLED device according to the present disclosure. A transparent electrode indium tin oxide (ITO) thin film (10 Ω/sq) on a glass substrate for an OLED device (Geomatec, Japan) was subjected to an ultrasonic washing with trichloroethylene, acetone, ethanol, and distilled water, sequentially, and was then stored in isopropanol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 80 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 10 nm on the second hole injection layer. Compound HT-2 was introduced into another cell of said vacuum vapor depositing apparatus, and was evaporated by applying an electric current to the cell, thereby forming a second hole transport layer having a thickness of 60 nm on the first hole transport layer. After forming the hole injection layers and the hole transport layers, a light-emitting layer was then deposited as follows. The first and second host compounds shown in Table 1 below were introduced into two cells of the vacuum vapor depositing apparatus as a host, and compound D-39 was introduced into another cell. The two host materials were evaporated at a rate of 1:1 and the dopant material was simultaneously evaporated at a different rate and these were deposited in a doping amount of 3 wt % based on the total amount of the host and dopant to form a light-emitting layer having thickness of 40 nm on the second hole transport layer. Compound ET-1 and compound EI-1 were then introduced into two other cells, evaporated at the rate of 1:1, and deposited to form an electron transport layer having a thickness of 35 nm on the light-emitting layer. Next, after depositing compound EI-1 as an electron injection layer having a thickness of 2 nm on the electron transport layer, an Al cathode having a thickness of 80 nm was deposited by another vacuum vapor deposition apparatus. Thus, an OLED device was produced.

TABLE 1

| | First host | Second host |
|---|---|---|
| Device Example 1 | C-1-1 | C-241 |
| Device Example 2 | C-1-7 | C-241 |
| Device Example 3 | C-1-94 | C-536 |
| Device Example 4 | C-1-7 | C-536 |
| Device Example 5 | C-1-7 | C-246 |

TABLE 1-continued

| | First host | Second host |
|---|---|---|
| Device Example 6 | C-1-7 | C-242 |
| Device Example 7 | C-1-90 | C-536 |
| Device Example 8 | C-1-86 | C-536 |
| Device Example 9 | C-1-111 | C-241 |
| Device Example 10 | C-1-106 | C-241 |

Comparative Example 1: Production of an OLED Device not According to the Present Disclosure An OLED device was produced in the same manner as in Device Example 1, except that compound A was used as the first host.

The luminous efficiency at a luminance of 1000 nit, and the time taken for the luminance to decrease from 100% to 97% at a constant current and at a luminance of 5,000 nit (lifespan; T97) of the produced OLED devices in Device Examples 1 to 10 and Comparative Example 1 are provided in Table 2 below.

TABLE 2

| | Luminous efficiency (cd/A) | Increase rate of luminous efficiency (%) | T97 Lifespan (hr) |
|---|---|---|---|
| Comparative Example 1 | 24.3 | — | 138 |
| Device Example 1 | 27.5 | 13.2 | 414 |
| Device Example 2 | 26.7 | 9.9 | 216 |
| Device Example 3 | 28.2 | 16.0 | 292 |
| Device Example 4 | 28.4 | 16.9 | 184 |
| Device Example 5 | 27.7 | 14.0 | 378 |
| Device Example 6 | 27.4 | 12.8 | 273 |
| Device Example 7 | 29.4 | 21.0 | 318 |
| Device Example 8 | 28.4 | 16.9 | 325 |
| Device Example 9 | 26.4 | 8.6 | 158 |
| Device Example 10 | 27.2 | 11.9 | 150 |

From Table 2, it is confirmed that an OLED device comprising the composition material for an organic electroluminescent device of the present disclosure has higher luminous efficiency and improved lifespan characteristics compared to a conventional OLED device. It is confirmed by the present disclosure that both luminous efficiency and lifespan, which have a trade-off relationship, can be increased.

The compounds used in the Device Examples and the Comparative Example are shown in Table 3 below.

TABLE 3
Hole Injection Layer/
Hole Transport Layer
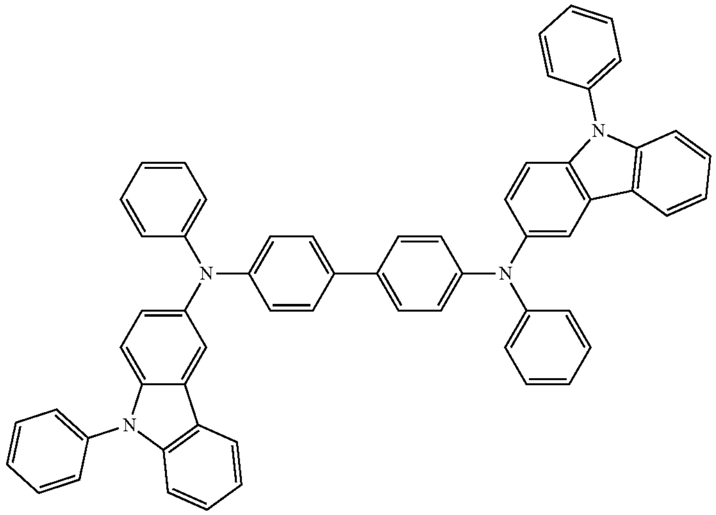
HI-1
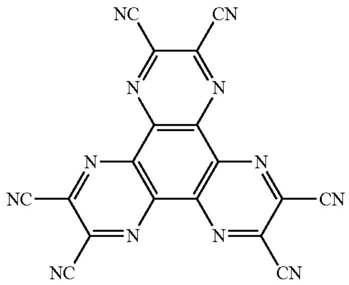
HI-2
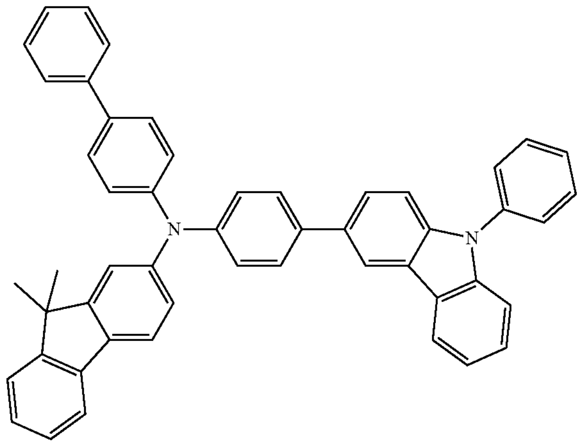
HT-1

TABLE 3-continued
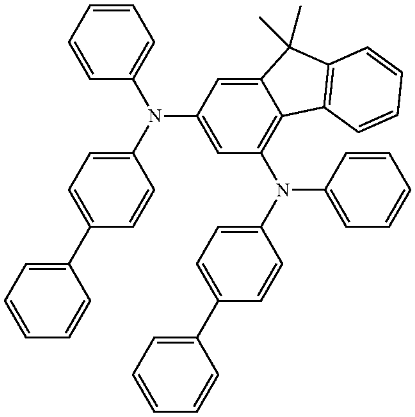
HT-2
Light-Emitting Layer
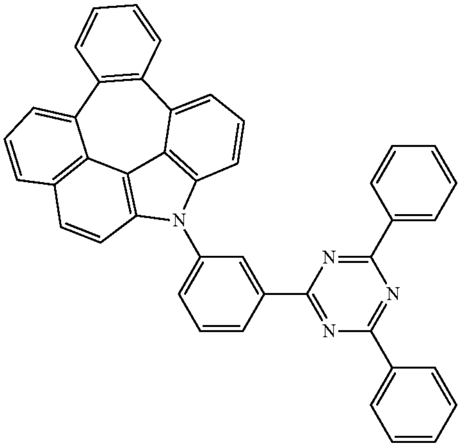
C-241
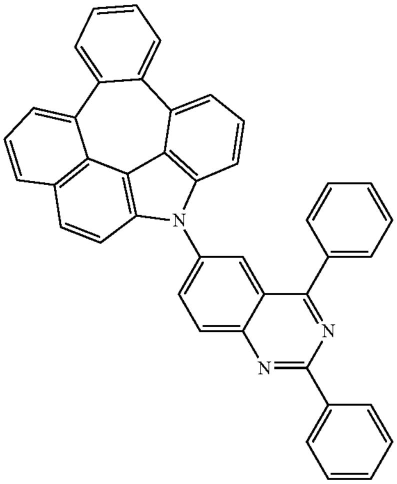
C-536

TABLE 3-continued
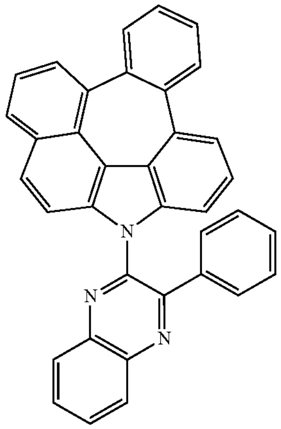
C-246
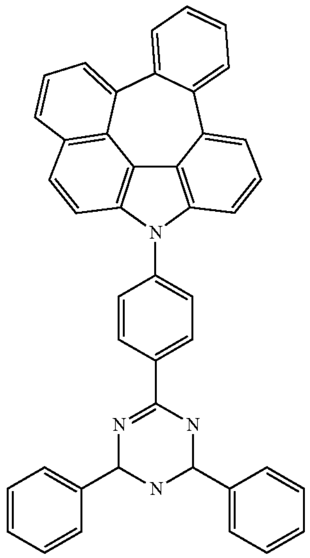
C-242
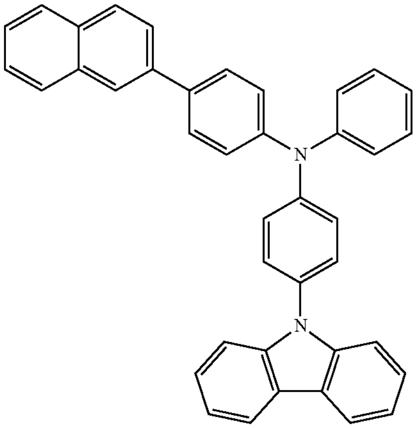
C-1-1

TABLE 3-continued
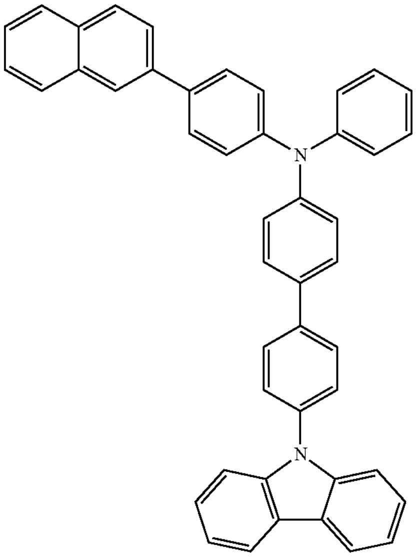
C-1-7
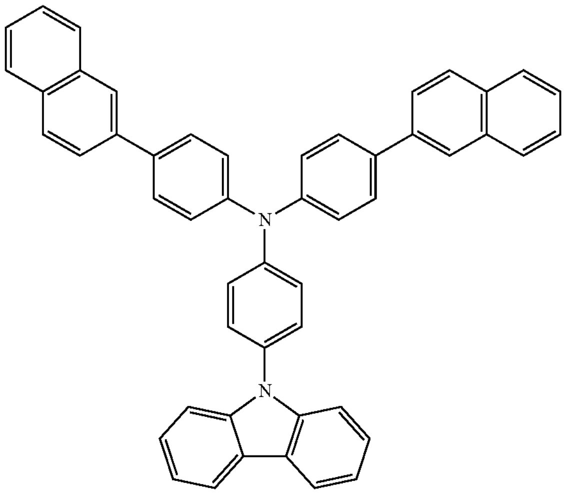
C-1-94
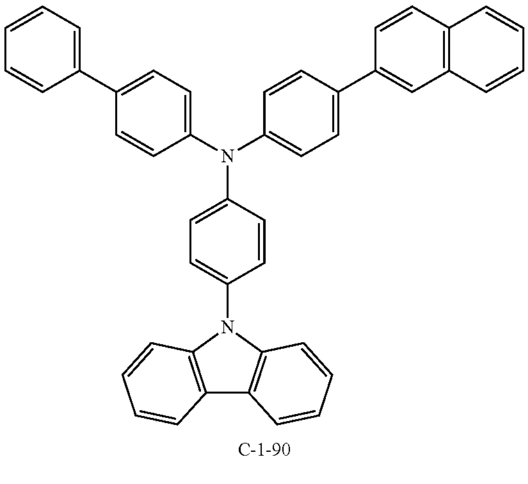 [SMILES: c1ccc(-c2ccc(N(c3ccc(-c4ccc5ccccc5c4)cc3)c3ccc(-n4c5ccccc5c5ccccc54)cc3)cc2)cc1]
C-1-90

TABLE 3-continued
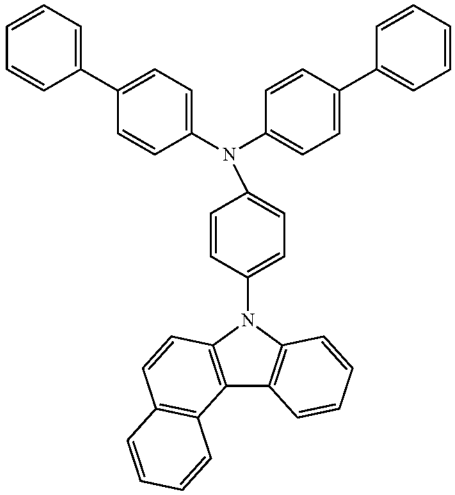
C-1-86
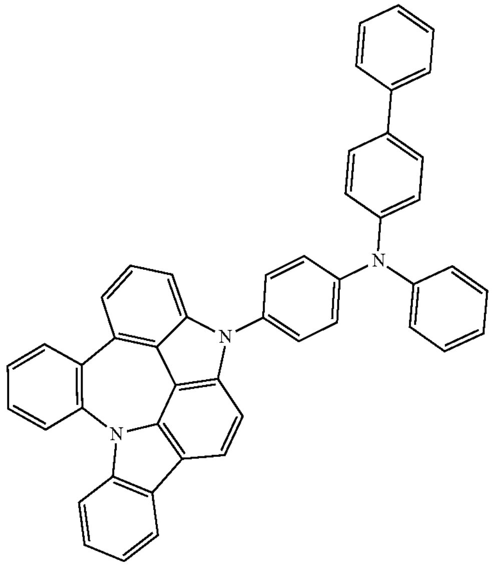
C-1-106

TABLE 3-continued
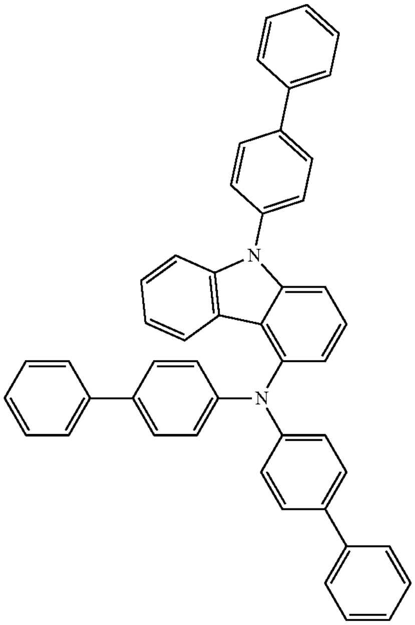
C-1-111
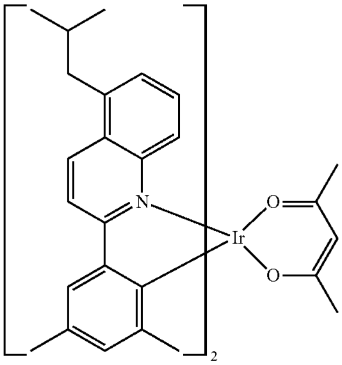
D-39
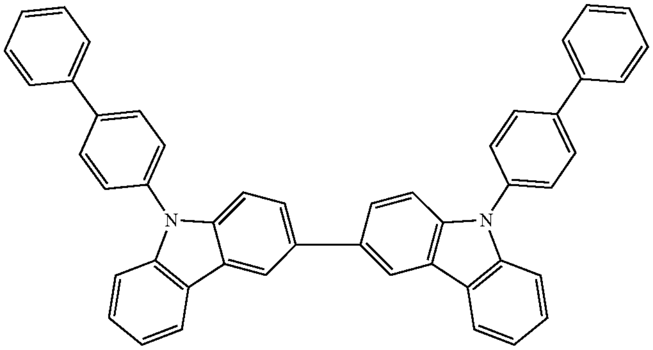
A

TABLE 3-continued

Electron Transport Layer/
Electron Injection Layer

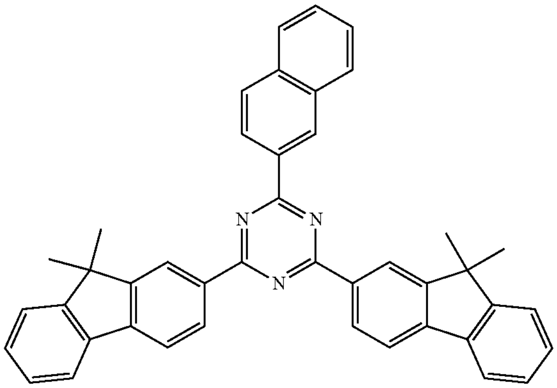

ET-1

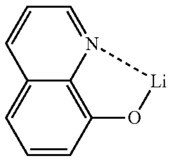

EI-1

The invention claimed is:

1. A composition material for an organic electroluminescent device comprising a compound represented by at least one of the following formulas 3 to 6 and a compound represented by the following formula 2:

(3)

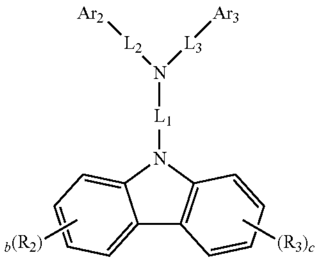

(4)

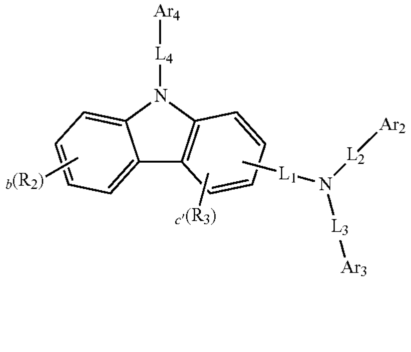

-continued (5)

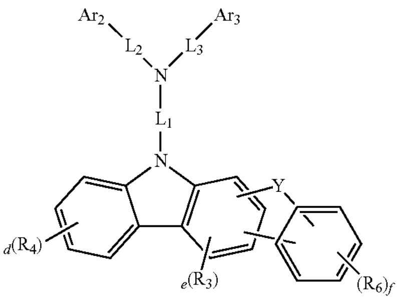

(6)

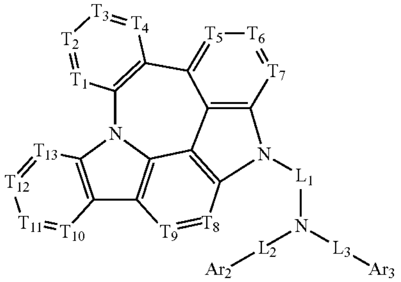

wherein $Ar_2$ and $Ar_3$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino;

$L_1$ to $L_3$ each independently represent a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

Y represents $CR_7R_8$, $NR_9$, O, or S;

$T_1$ to $T_{13}$ each independently represent N or $CV_1$;

$V_1$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or two adjacent $V_1$'s may be linked to each other to form a ring;

$R_2$ to $R_9$ each independently represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or may be linked to an adjacent substituent to form a ring;

$L_4$ represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

$Ar_4$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl;

b, c, d, and f each independently represent an integer of 1 to 4, e represents an integer of 1 or 2, c' represents an integer of 1 to 3, where if b to f and c' each independently are an integer of 2 or more, each of $R_2$ to Re may be the same or different; and

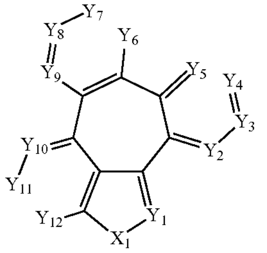

(2)

wherein $X_1$ represents N-L-$(Ar)_a$, S, or O;

L represents a single bond, a substituted or unsubstituted (C6-C30)arylene, or a substituted or unsubstituted (3- to 30-membered)heteroarylene;

Ar represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

$Y_1$ to $Y_{12}$ each independently represent N or $CR_{10}$;

$R_{10}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or may be linked to an adjacent substituent to form a substituted or unsubstituted ring; and a represents an integer of 1 to 4, where if a is an integer of 2 or more, each of Ar may be the same or different.

2. The composition material for an organic electroluminescent device according to claim 1, wherein the substituents of the substituted (C1-C30)alkyl(ene), the substituted (C6-C30)aryl(ene), the substituted (3- to 30-membered) heteroaryl(ene), the substituted (C3-C30)cycloalkyl(ene), the substituted (C1-C30)alkoxy, the substituted tri(C1-C30) alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C1-C30)alkyl(C6-C30)arylamino, and the substituted ring in $Ar_2$ and $Ar_3$, $L_1$ to $L_3$, L, Ar, and $R_{10}$ each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (5- to 30-membered)heteroaryl unsubstituted or substituted with a (C6-C30)aryl, a (C6-C30)aryl unsubstituted or substituted with a (5- to 30-membered)heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino unsubstituted or substituted with a (C1-C30)alkyl, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

3. The composition material for an organic electroluminescent device according to claim 1, wherein in formula 2, at least one adjacent pair among $Y_1$ to $Y_{12}$ is $CR_{10}$, and $R_{10}$'s of the adjacent two $CR_{10}$'s are fused to each other to independently form a ring represented by one of the following formulas 7 to 11:

(7)

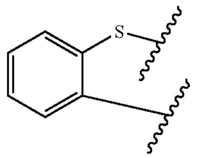

(8)

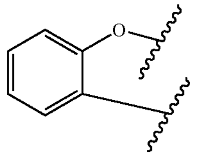

(9)

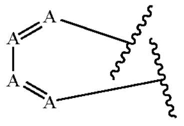

(10)

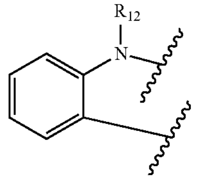

(11)

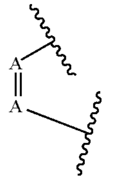

wherein

A each independently represent N or $CR_{11}$;

$R_{11}$ and $R_{12}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; and

 represents a fusing site at the adjacent $CR_{10}$'s.

4. The composition material for an organic electroluminescent device according to claim 1, wherein in formula 2, Ar represents a substituted or unsubstituted phenyl, a substituted or unsubstituted naphthyl, a substituted or unsubstituted biphenyl, a substituted or unsubstituted terphenyl, a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted carbazolyl, a substituted or unsubstituted dibenzothiophenyl, a substituted or unsubstituted benzothiophenyl, a substituted or unsubstituted dibenzofuranyl, a substituted or unsubstituted benzofuranyl, a substituted or unsubstituted naphthyridinyl, a substituted or unsubstituted (9- to 25-membered)heteroaryl containing at least one of nitrogen, oxygen, and sulfur, a substituted or unsubstituted diphenylamino, a substituted or unsubstituted phenylbiphenylamino, a substituted or unsubstituted fluorenylphenylamino, or a substituted or unsubstituted fluorenylbiphenylamino.

5. The composition material for an organic electroluminescent device according to claim 1, wherein the compound represented by at least one of formulas 3 to 6 is selected from the group consisting of the following compounds:

C-1-1

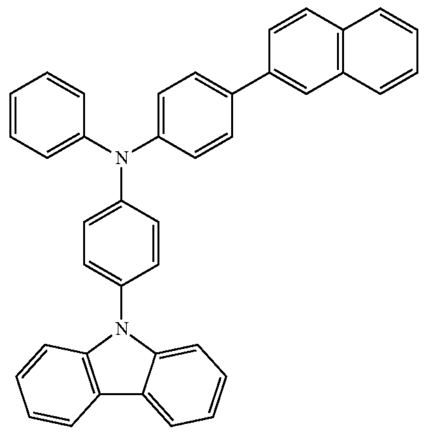

-continued
C-1-2
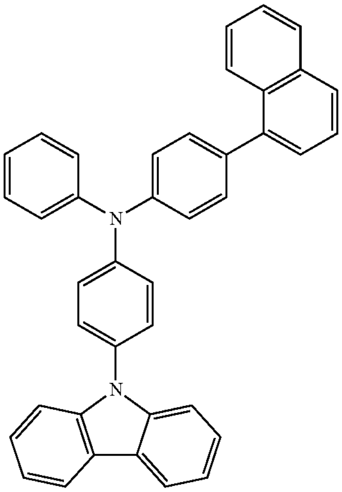
C-1-3
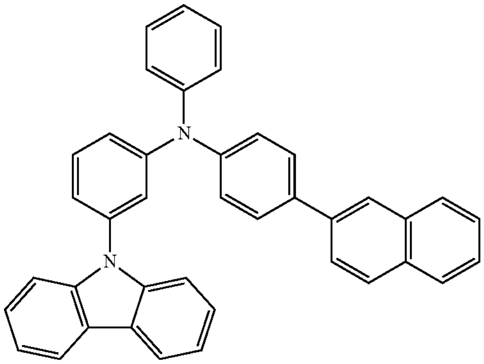
C-1-4
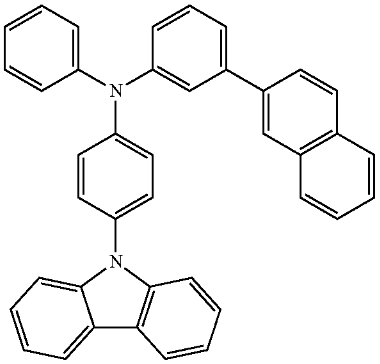
C-1-5
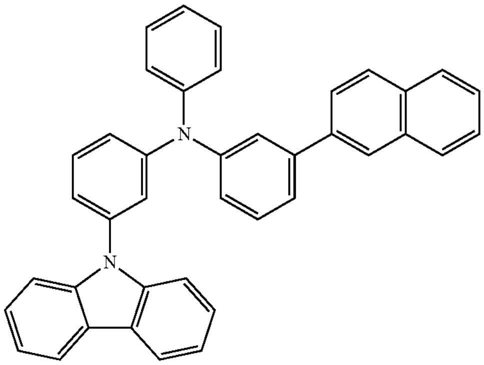
-continued
C-1-6
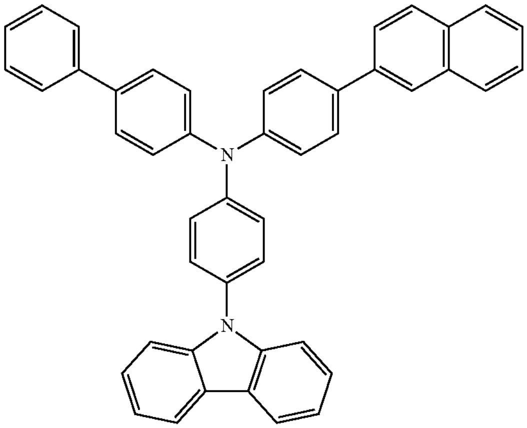
C-1-7
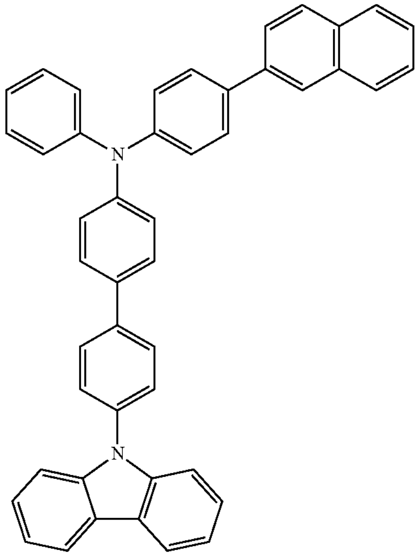
C-1-8
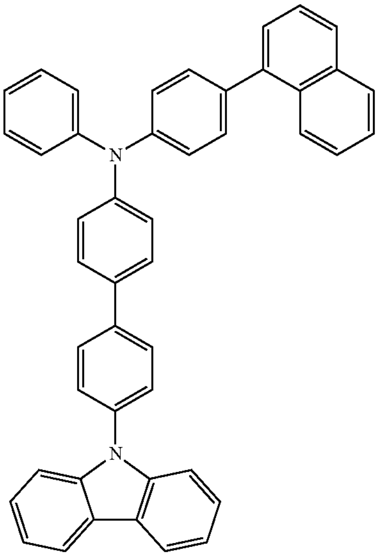

-continued
C-1-9
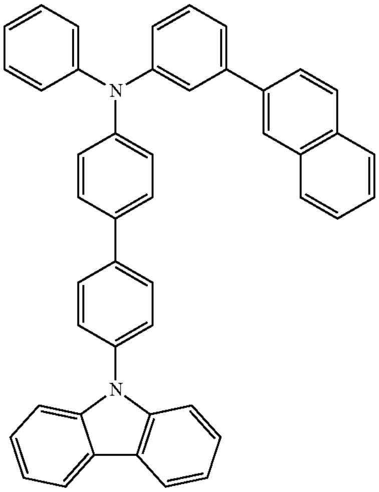
C-1-10
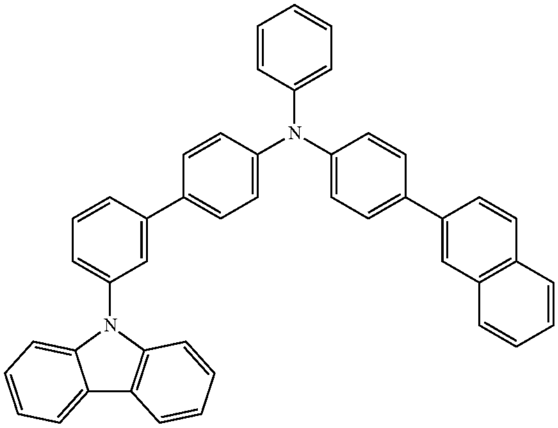
C-1-11
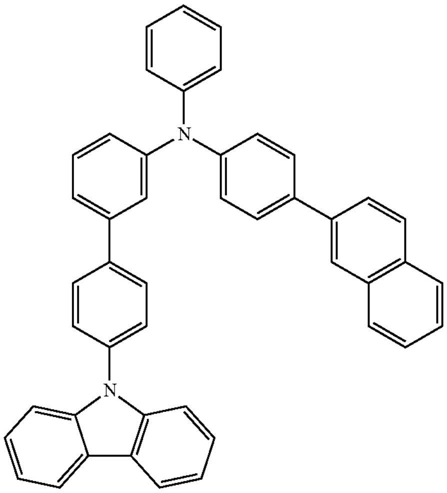
-continued
C-1-12
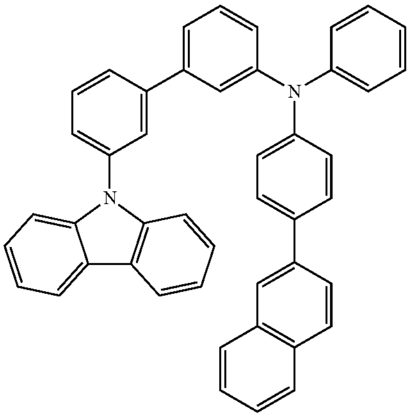
C-1-13
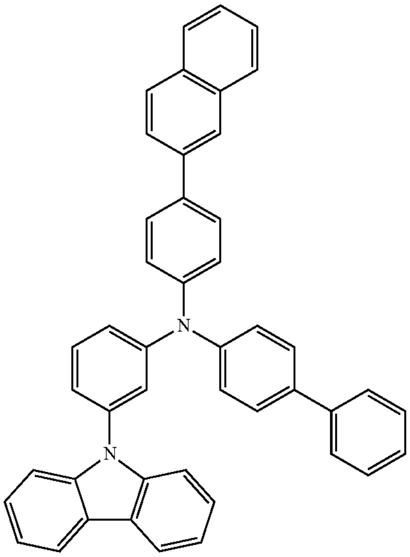
C-1-14
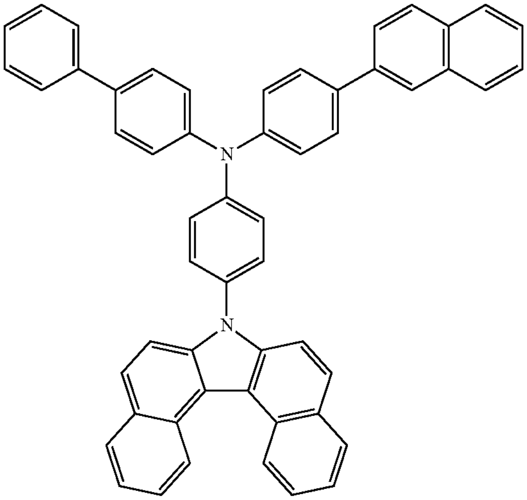

-continued
C-1-15
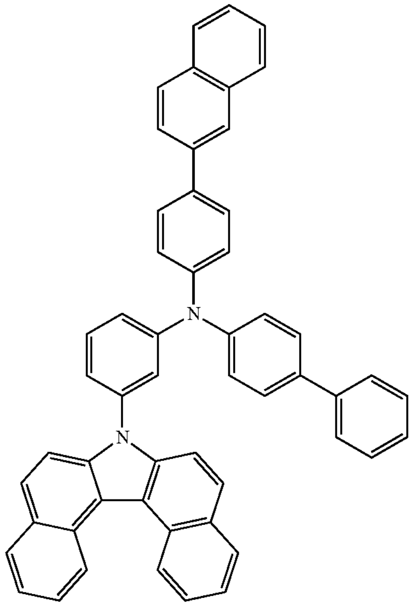
C-1-16
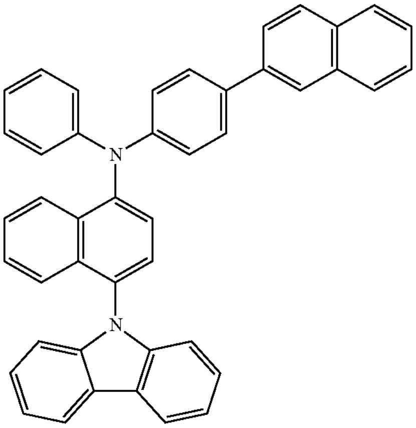
C-1-17
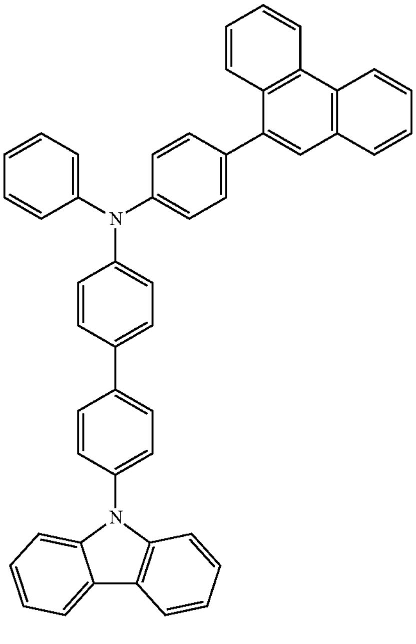
-continued
C-1-18
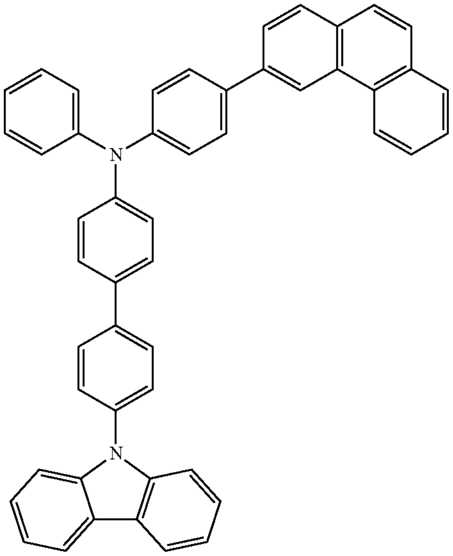
C-1-19
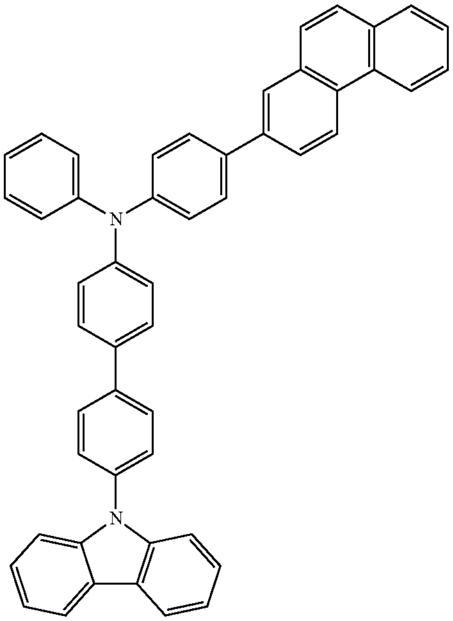
C-1-20
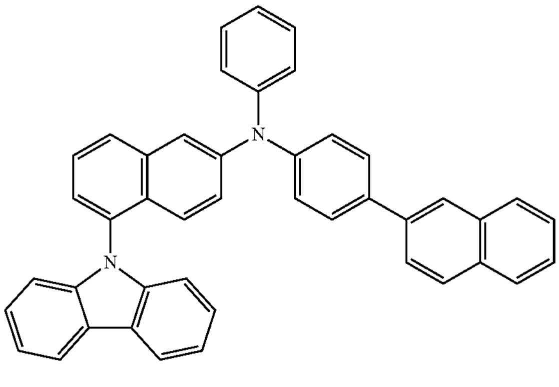

-continued
C-1-21
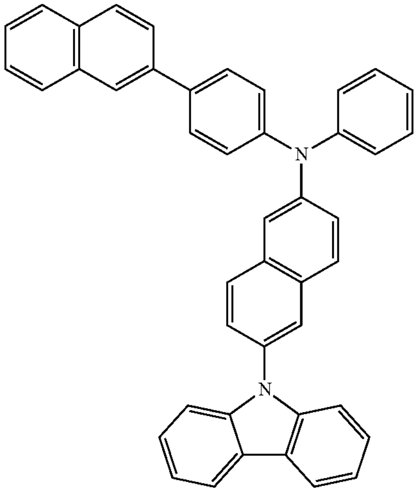
C-1-22
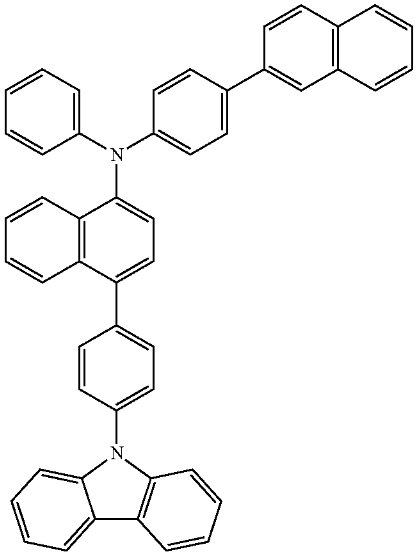
C-1-23
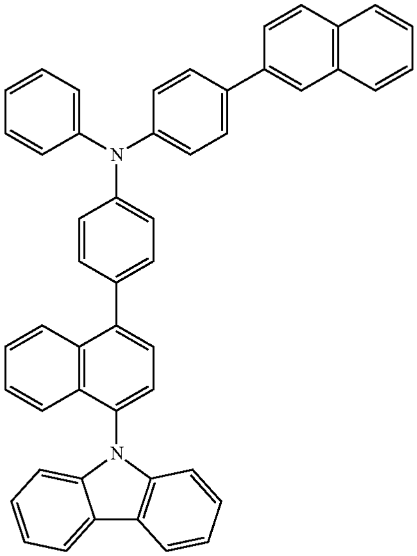
-continued
C-1-24
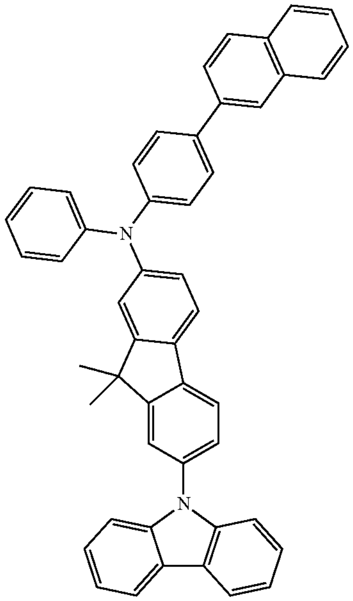
C-1-25
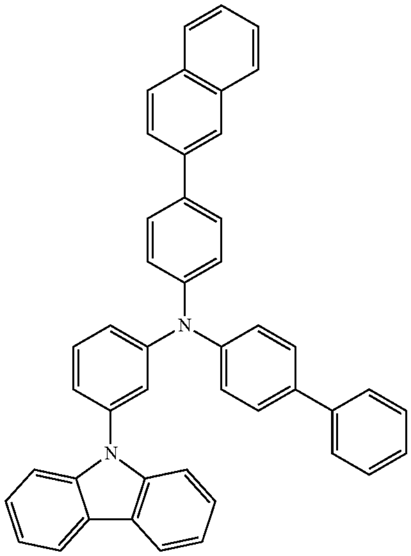

-continued
C-1-26
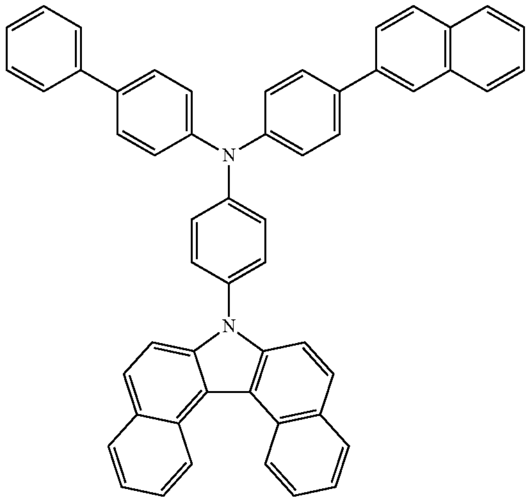
C-1-27
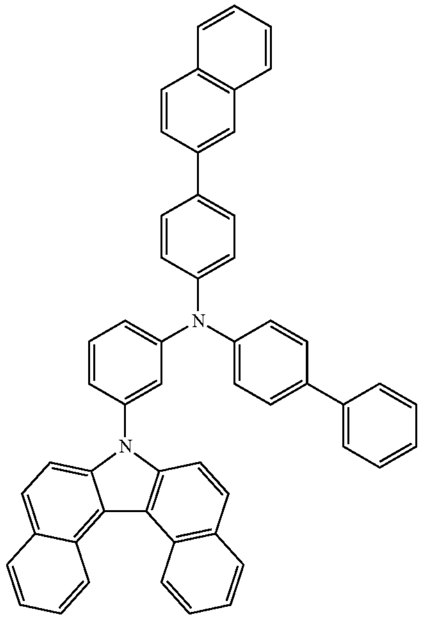
-continued
C-1-28
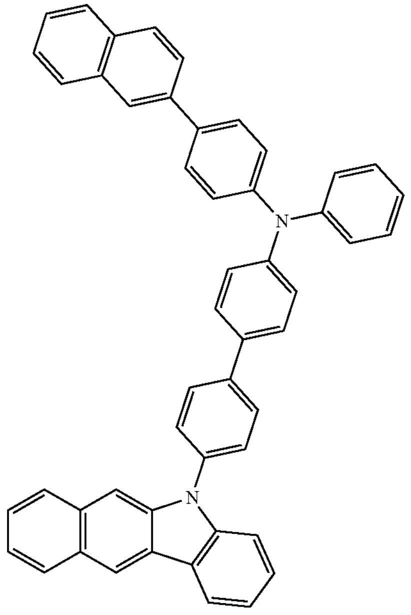
C-1-29
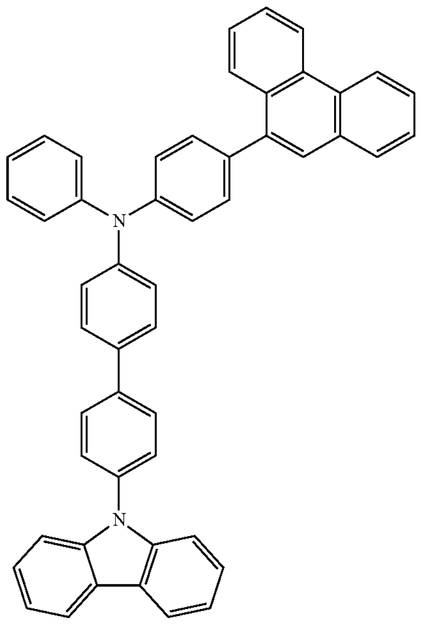

-continued
C-1-30
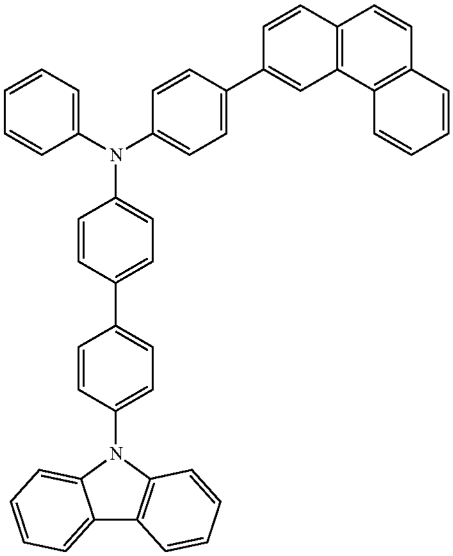
C-1-31
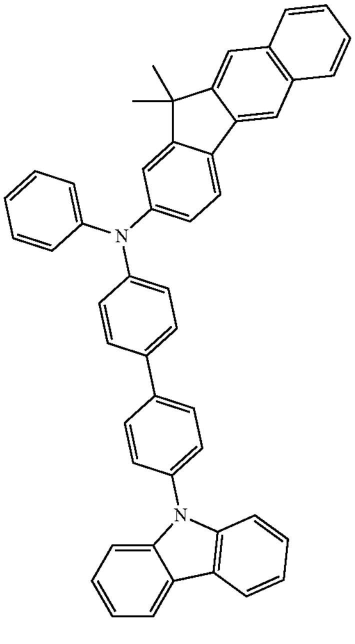
-continued
C-1-32
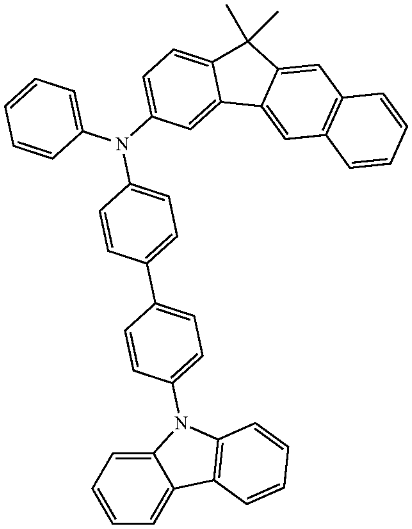
C-1-33
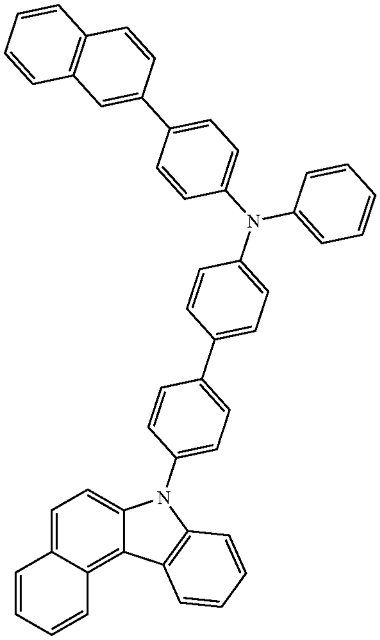

C-1-34
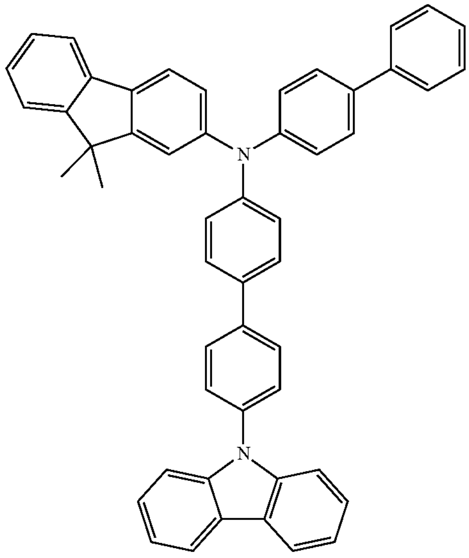
C-1-35
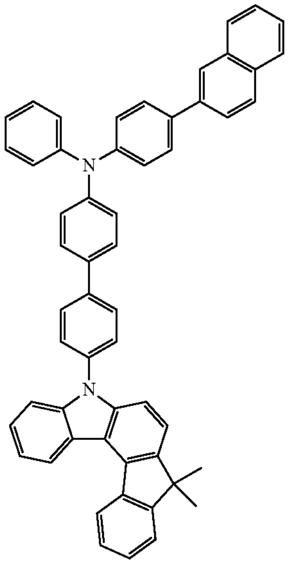
C-1-36
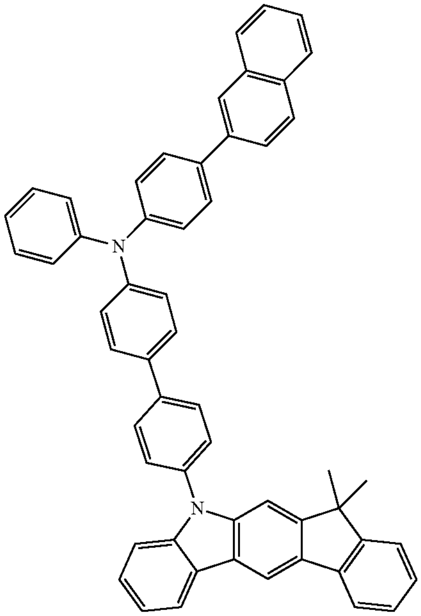
C-1-37
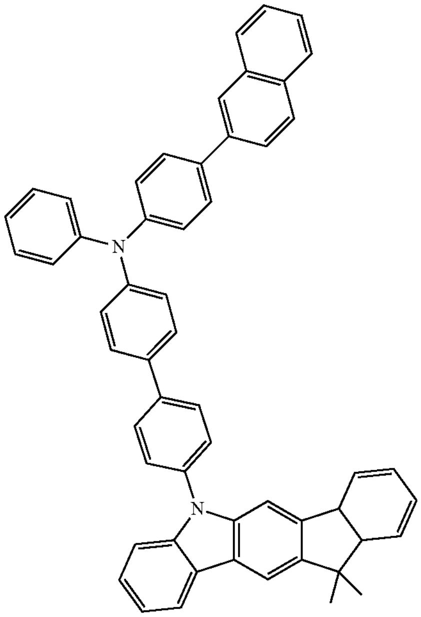
C-1-38
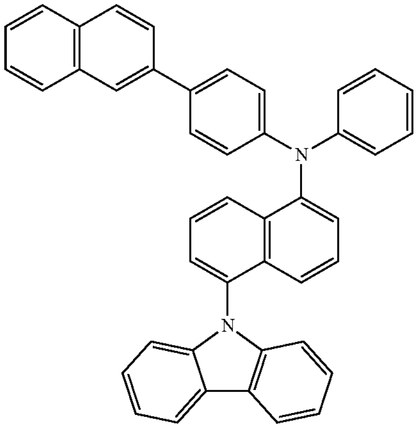

-continued
C-1-39
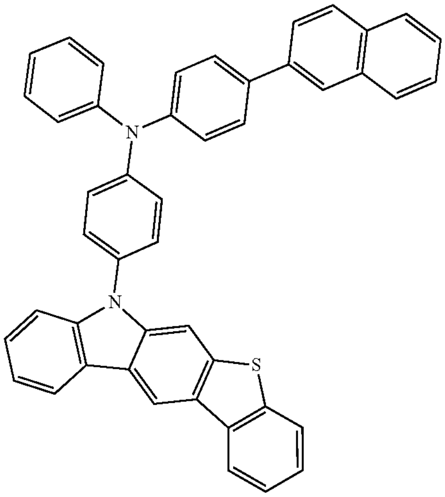
C-1-40
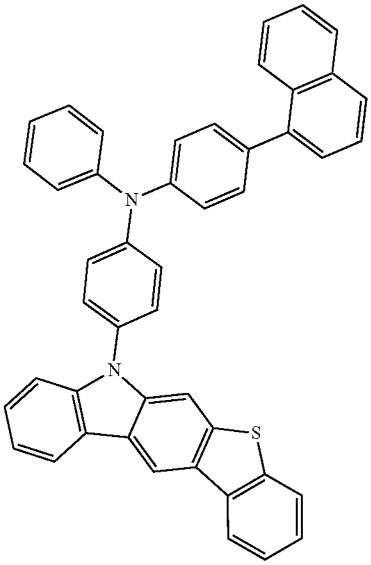
C-1-41
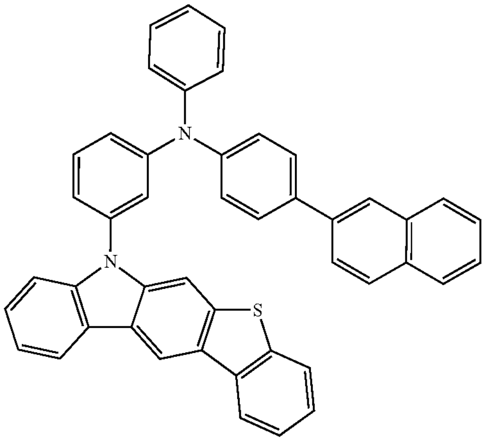
-continued
C-1-42
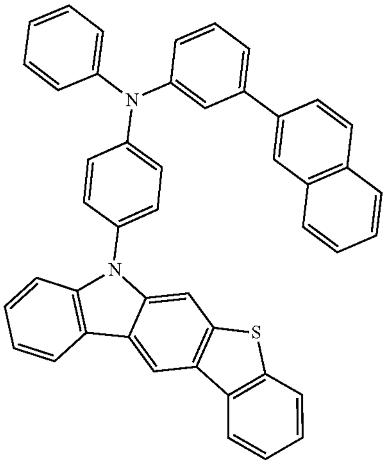
C-1-43
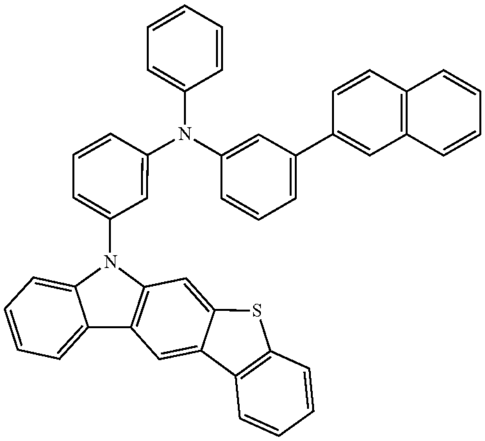
C-1-44
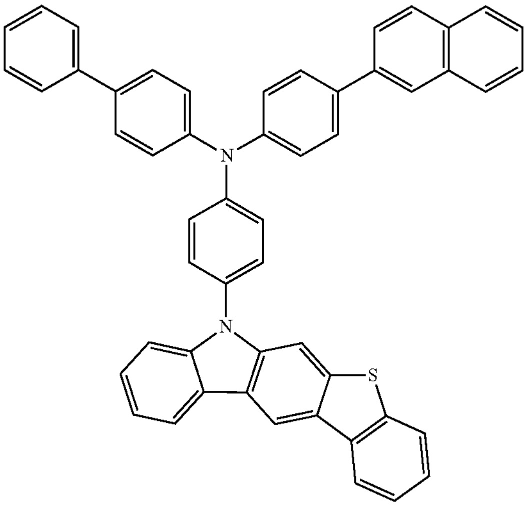

-continued
C-1-45
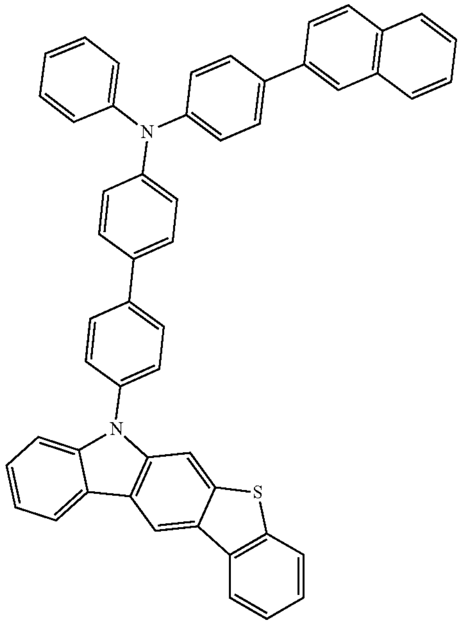
C-1-46
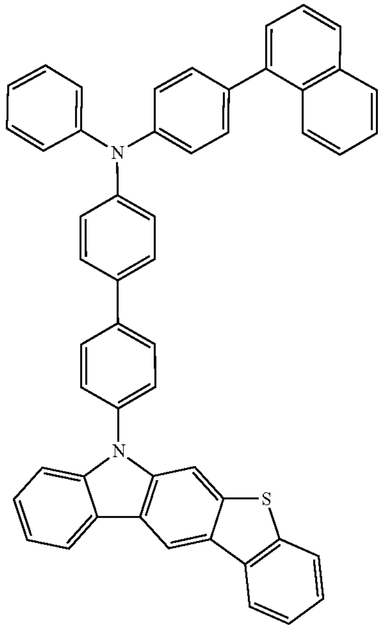
-continued
C-1-47
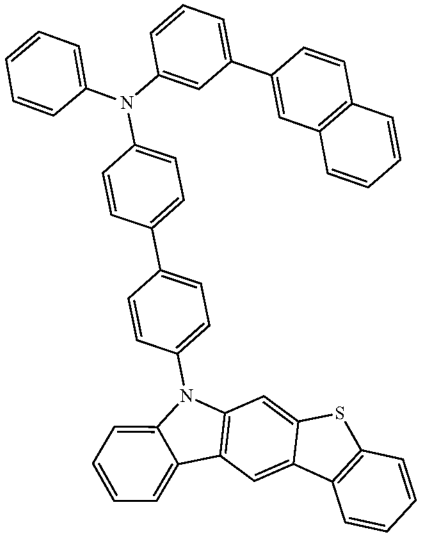
C-1-48
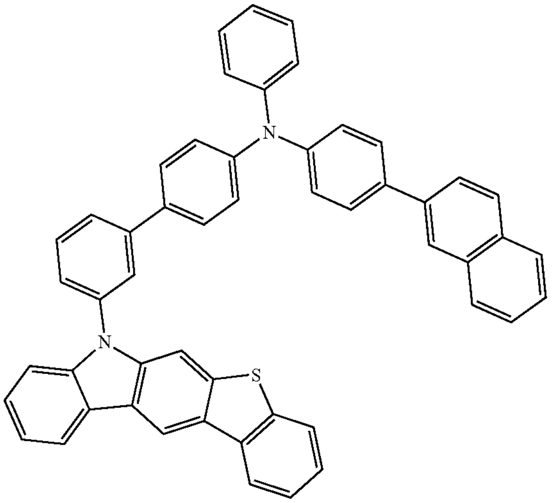
C-1-49
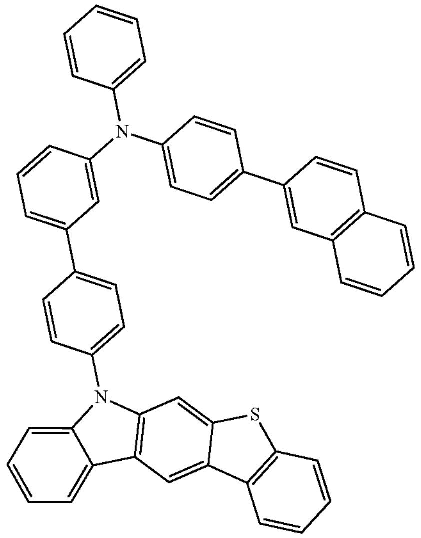

C-1-50
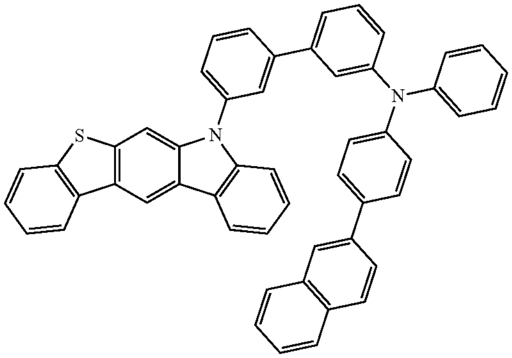
C-1-51
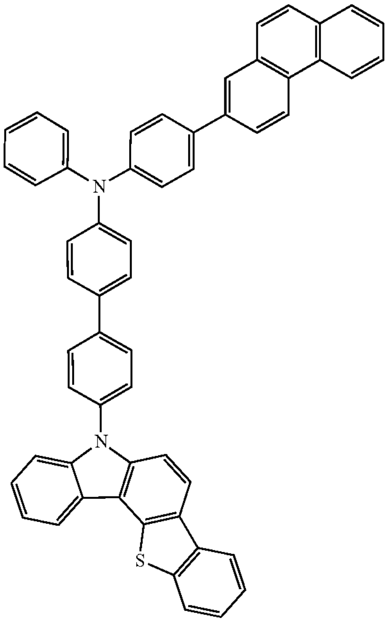
C-1-52
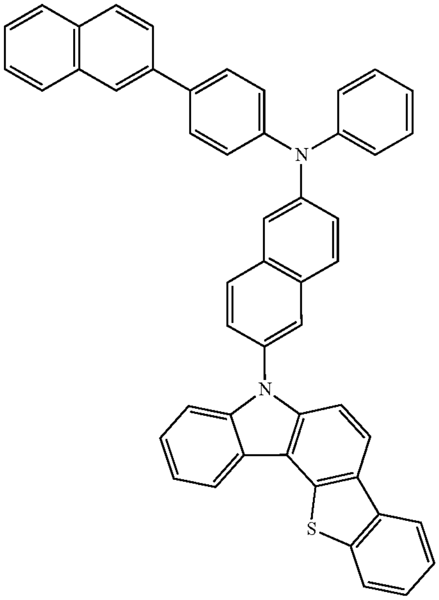
C-1-53
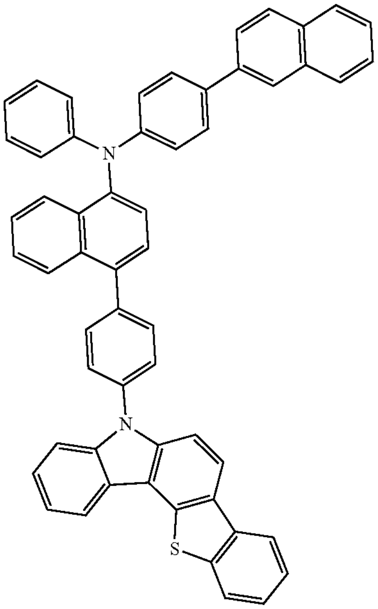
C-1-54
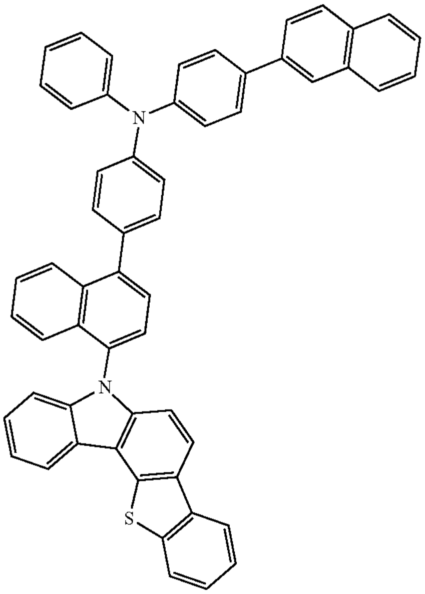

-continued
C-1-55
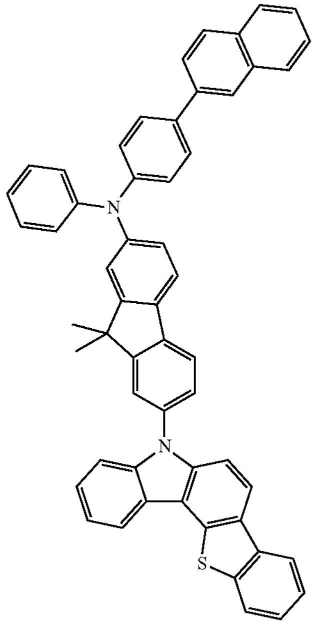
C-1-57
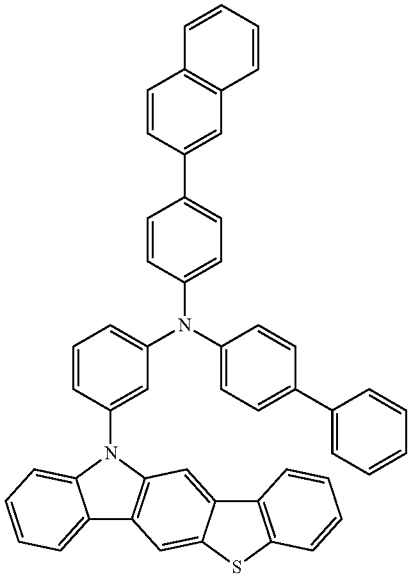
C-1-56
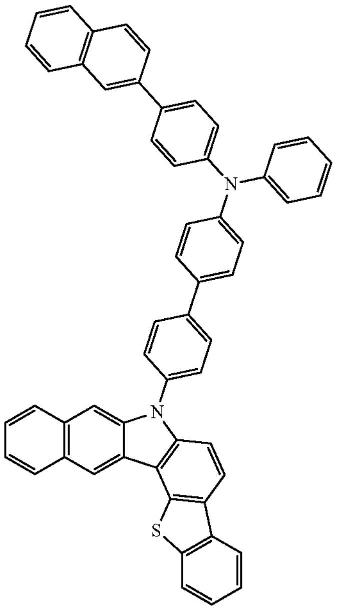
C-1-58
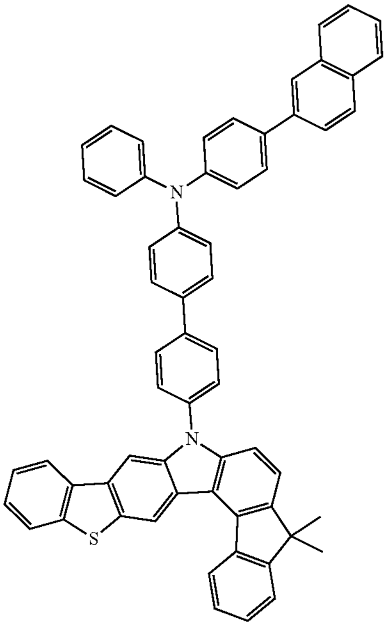

-continued
C-1-59
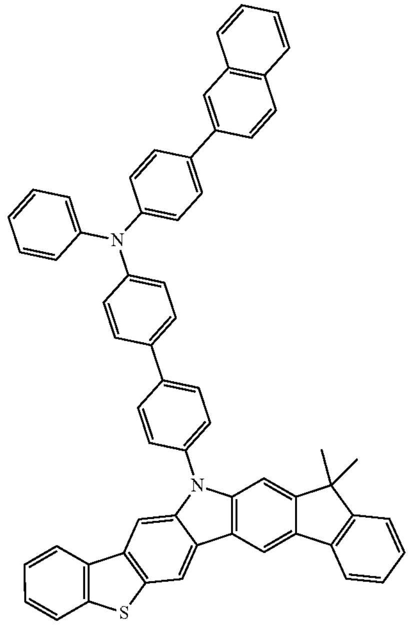
C-1-60
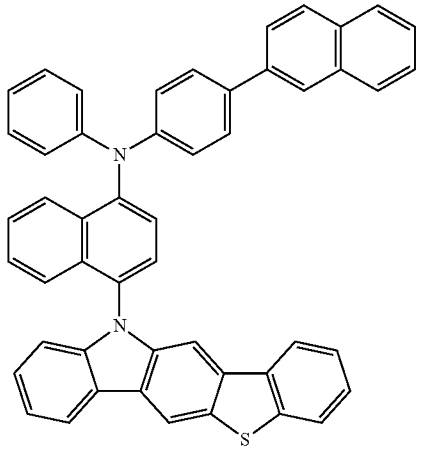
-continued
C-1-61
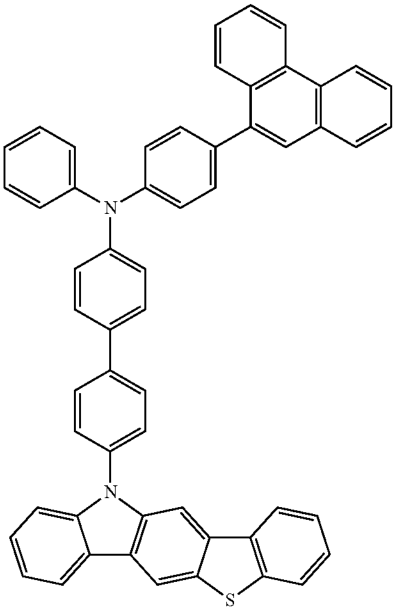
C-1-62
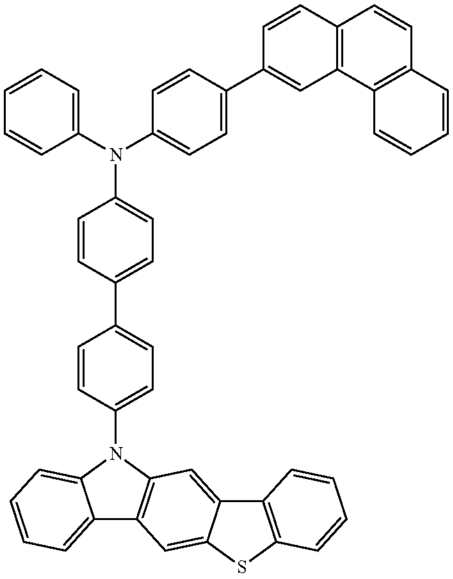
C-1-63
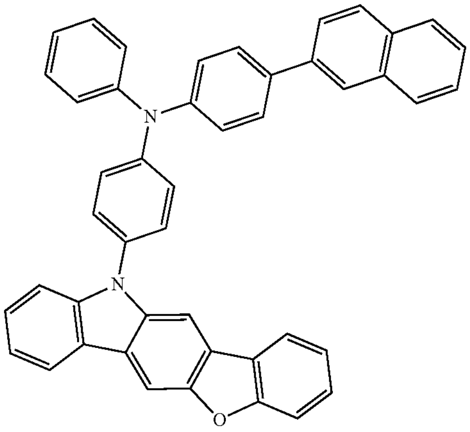

-continued
C-1-64
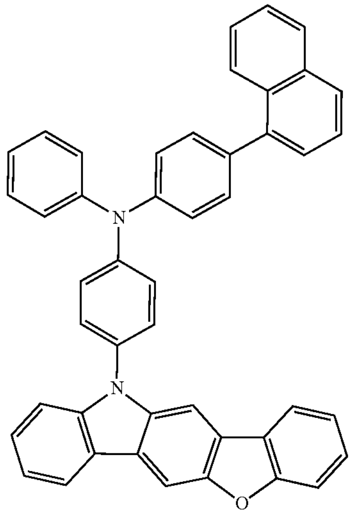
C-1-65
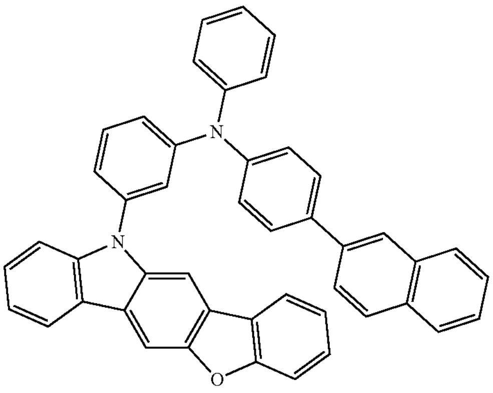
C-1-66
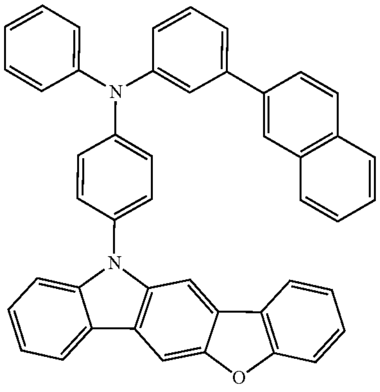
-continued
C-1-67
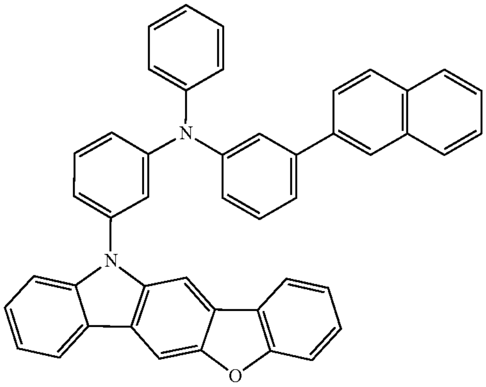
C-1-68
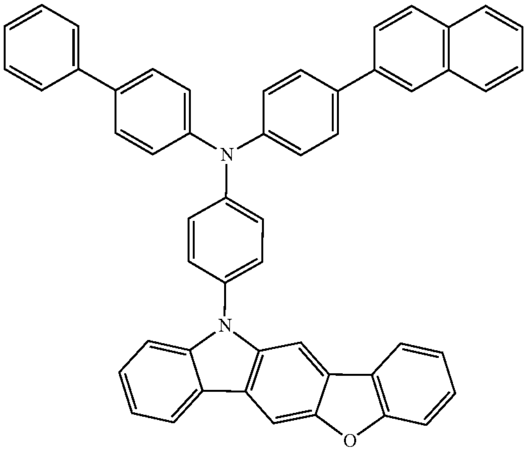
C-1-69
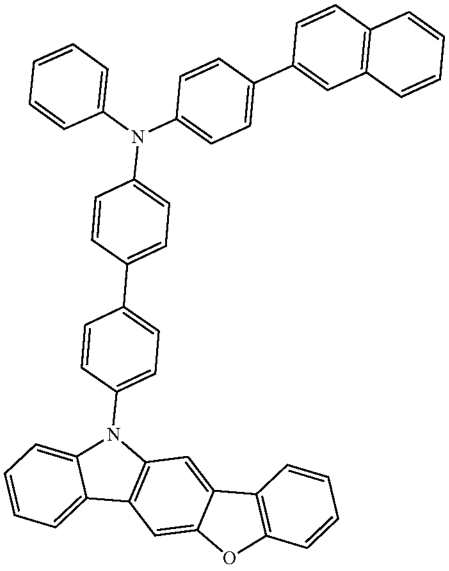

-continued
C-1-70
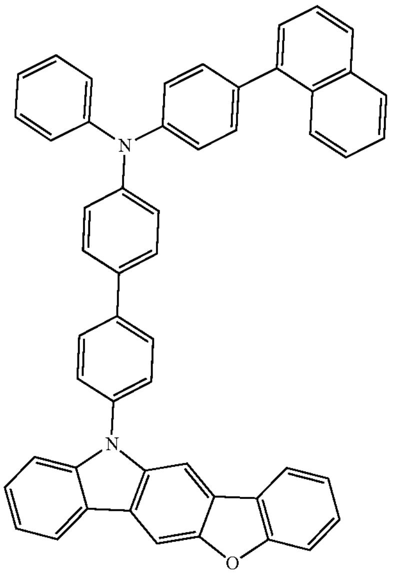
C-1-71
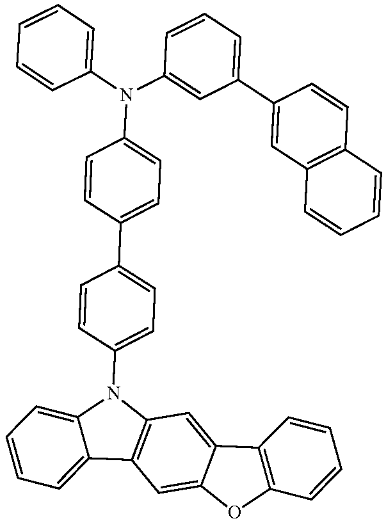
C-1-72
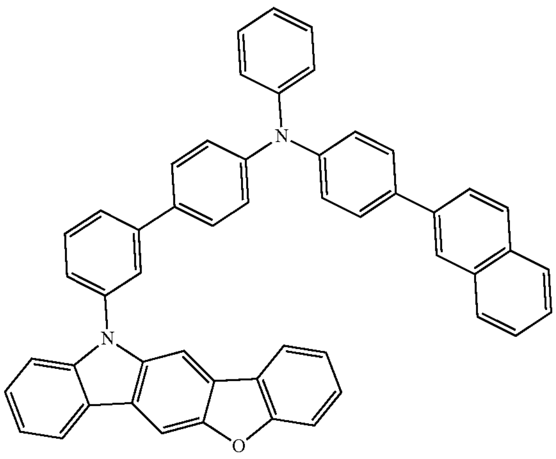
-continued
C-1-73
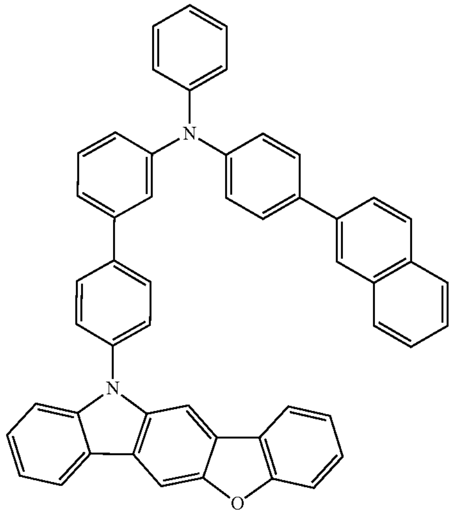
C-1-74
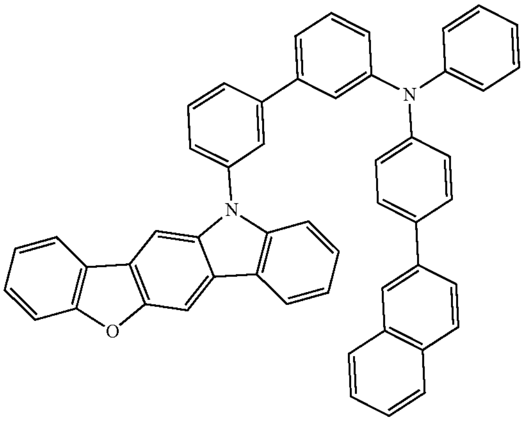
C-1-75
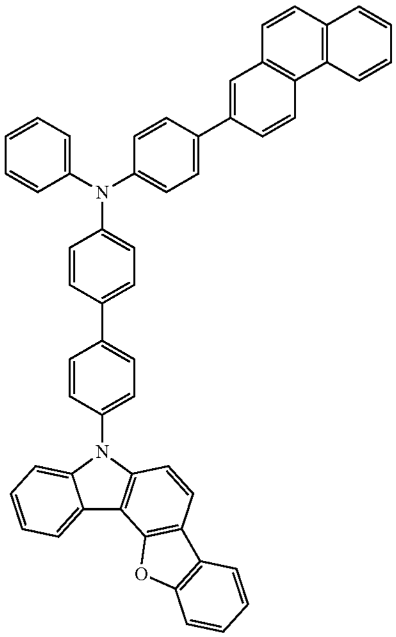

-continued
C-1-76
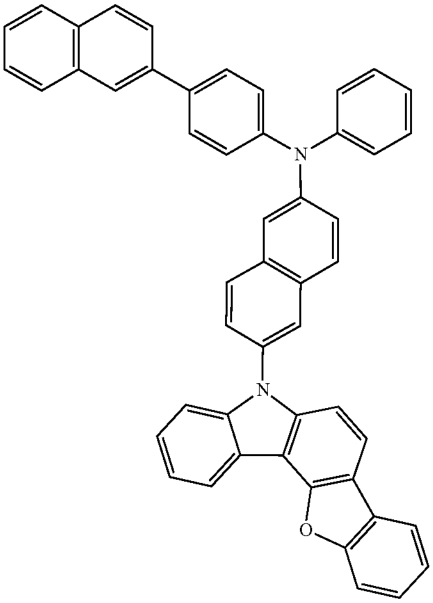
C-1-77
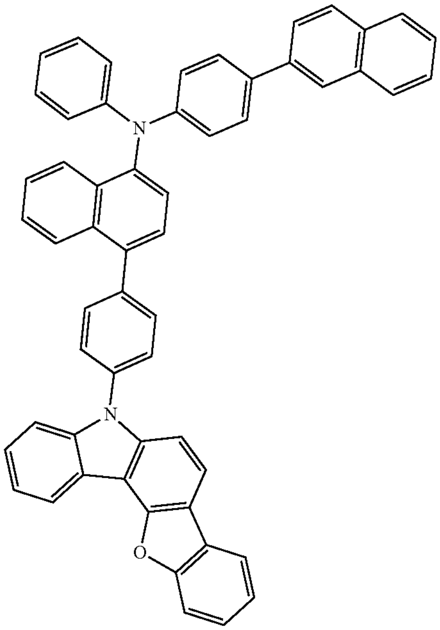
-continued
C-1-78
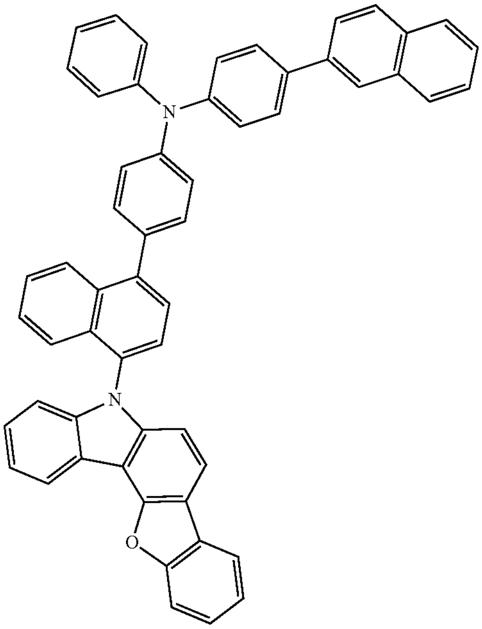
C-1-79
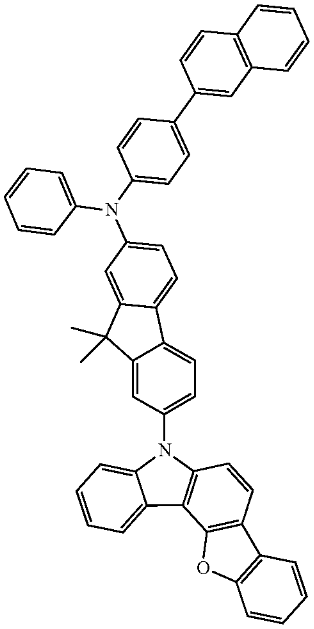

-continued
C-1-80
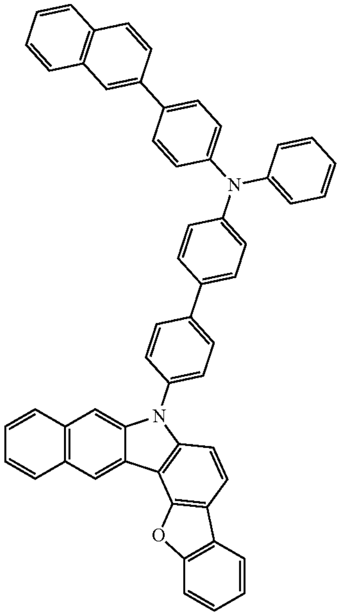
-continued
C-1-82
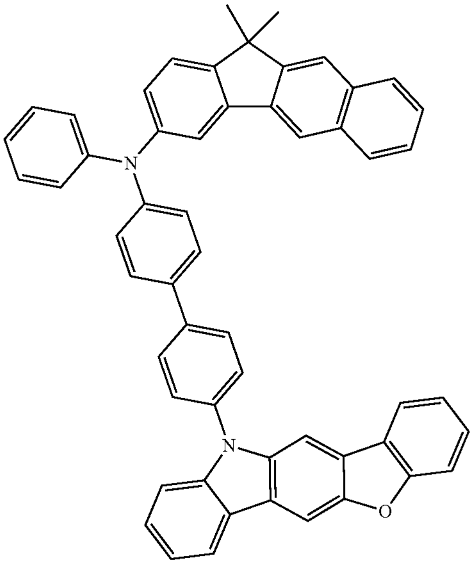
C-1-81
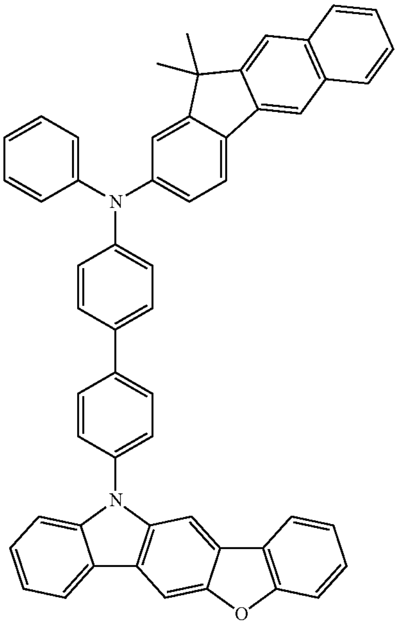
C-1-83
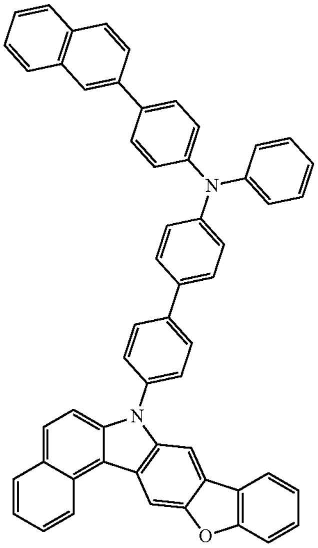

-continued
C-1-84
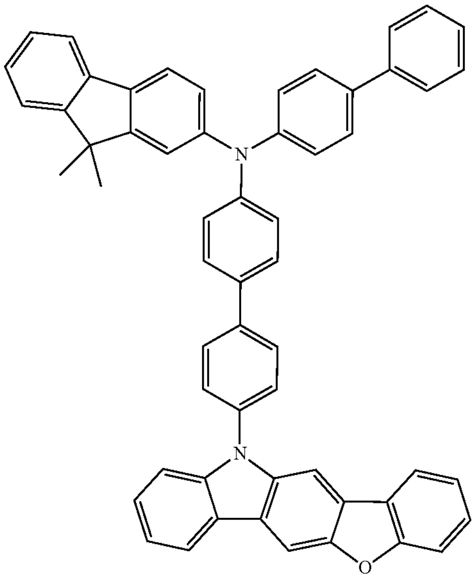
C-1-85
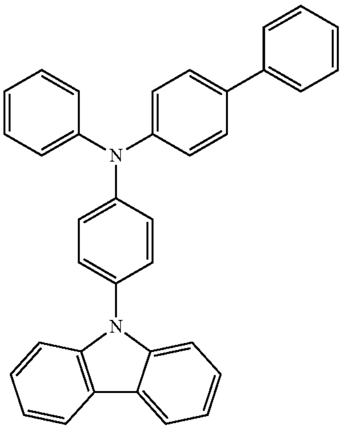
C-1-86
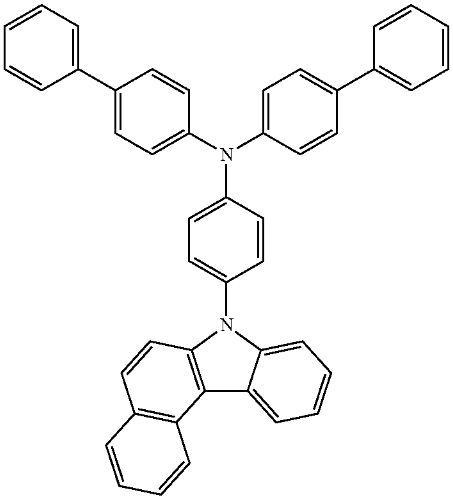
-continued
C-1-87
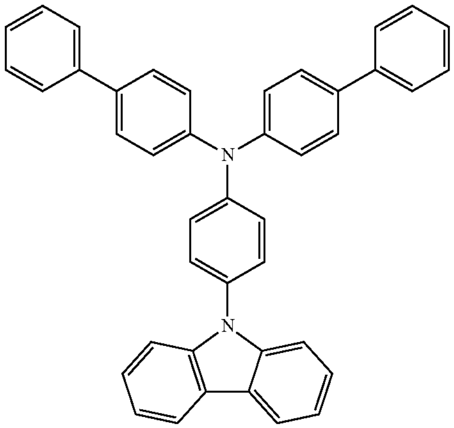
C-1-88
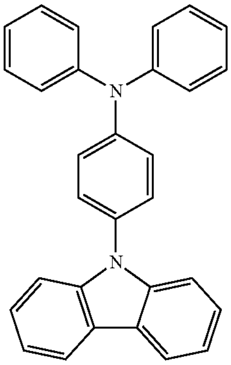
C-1-89
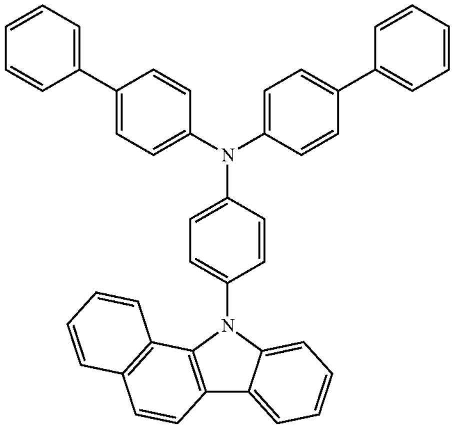

-continued
C-1-90
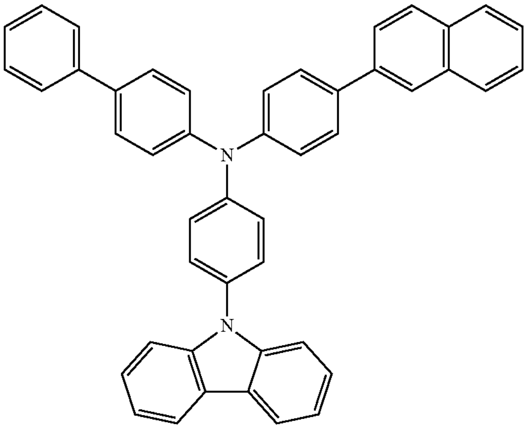
C-1-91
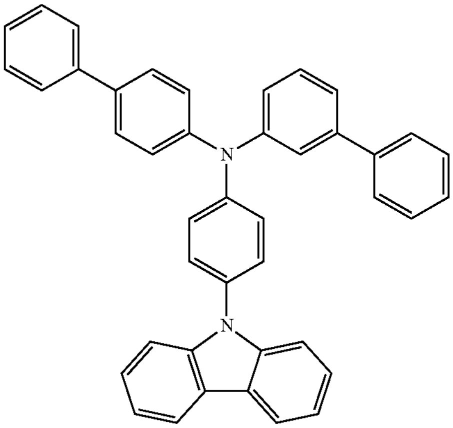
C-1-92
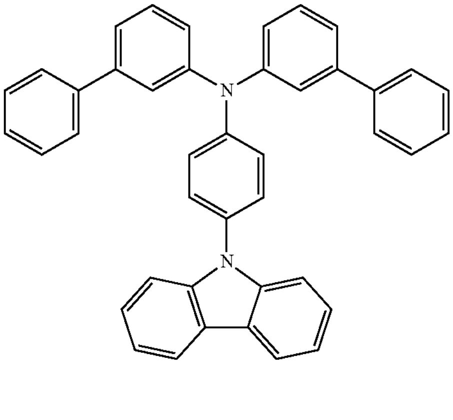
-continued
C-1-93
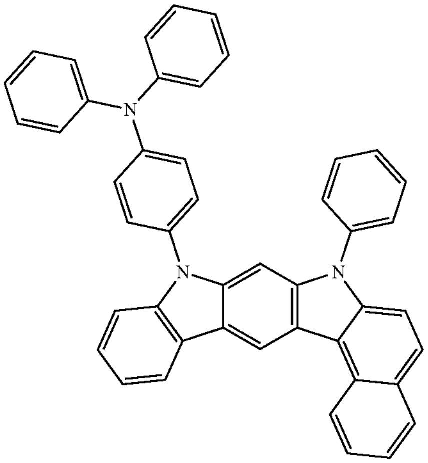
C-1-94
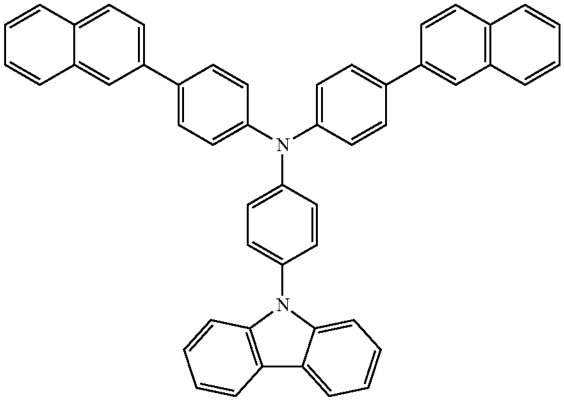
C-1-95
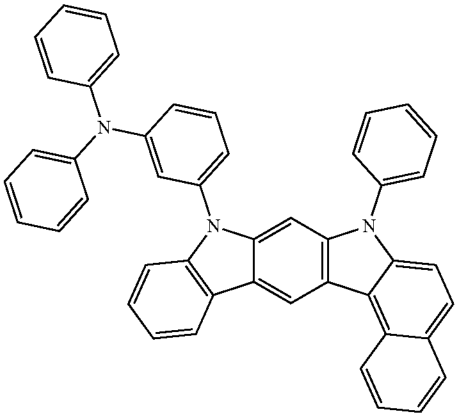

-continued
C-1-96
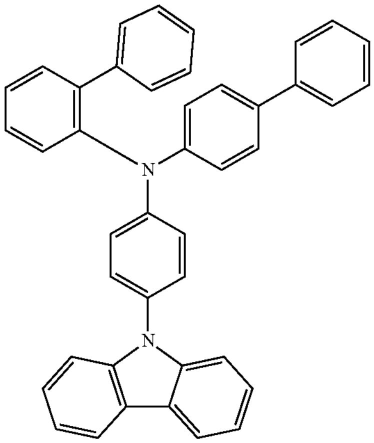
C-1-97
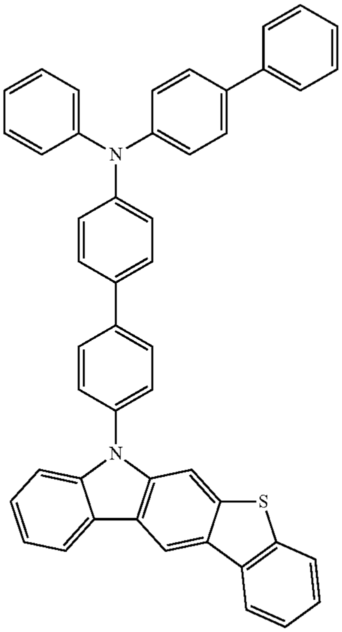
C-1-98
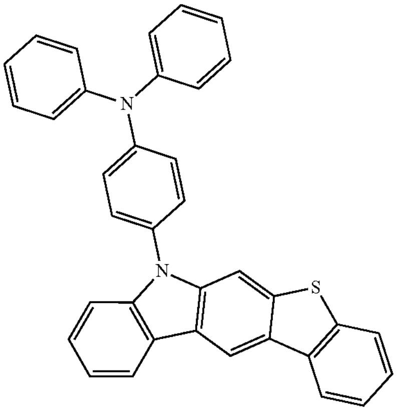
-continued
C-1-99
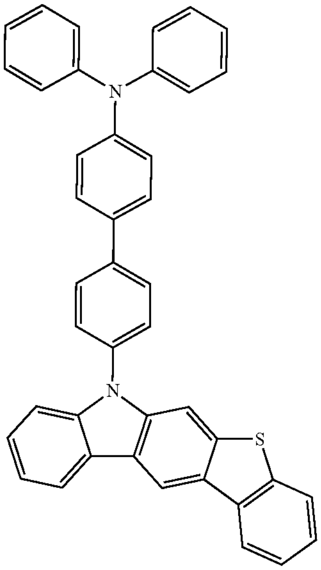
C-1-100
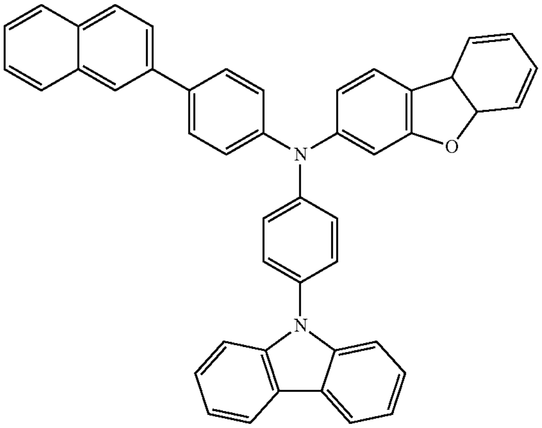
C-1-101
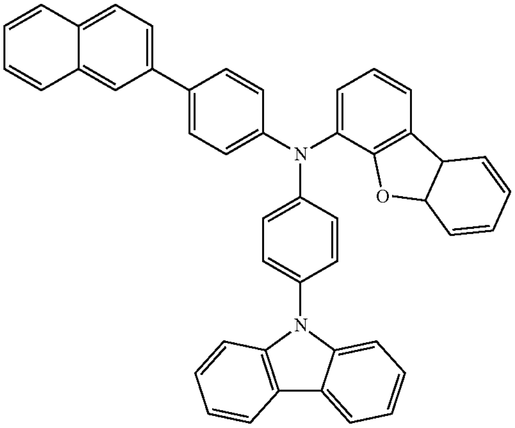

-continued
C-1-102
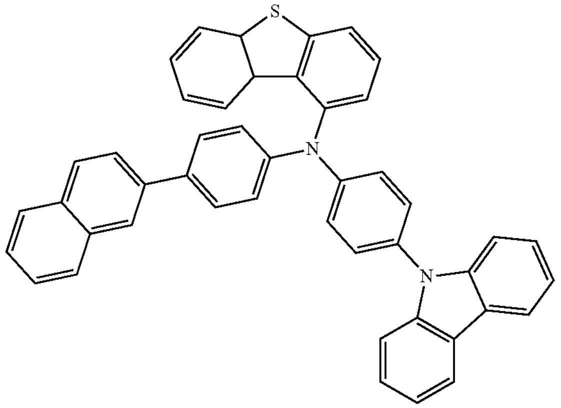
C-1-103
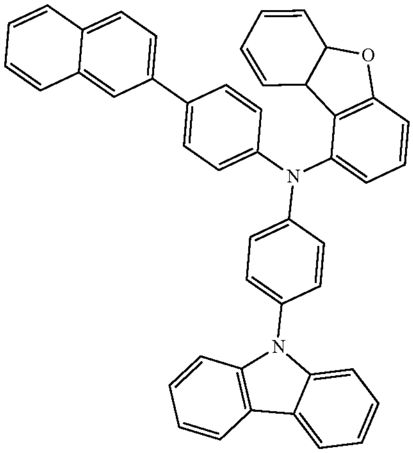
C-1-104
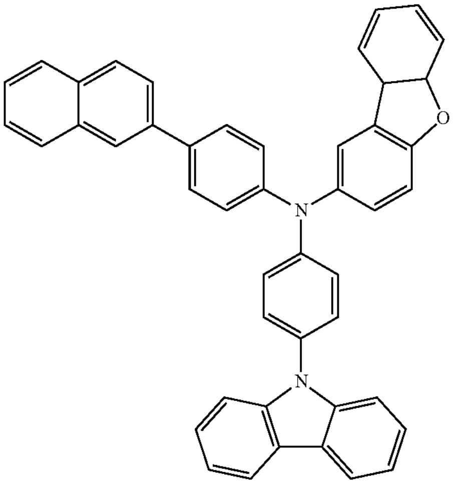
-continued
C-1-105
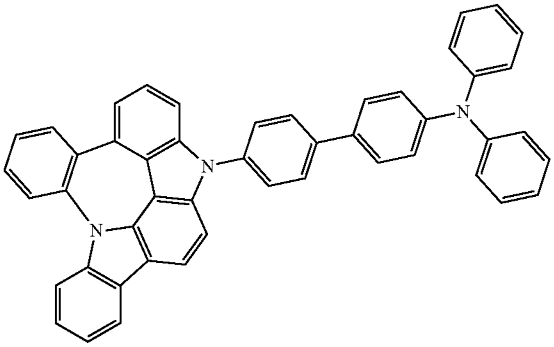
C-1-106
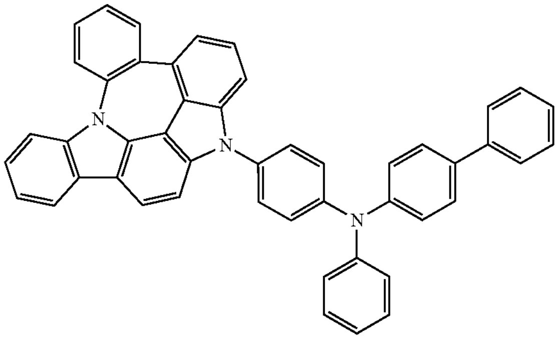
C-1-107
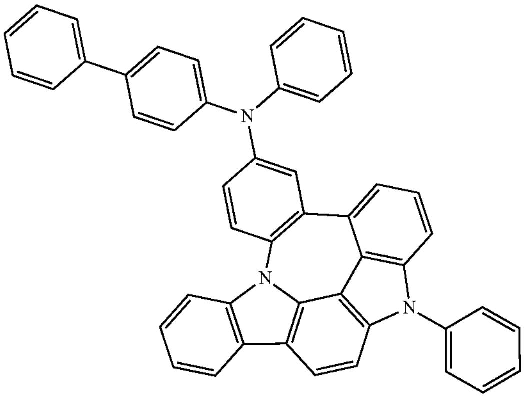
C-1-108
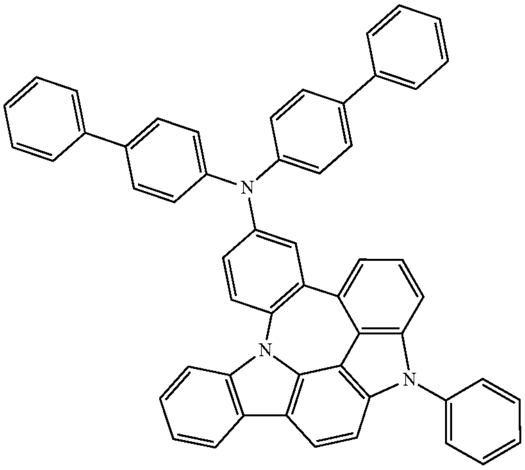

-continued
C-1-109
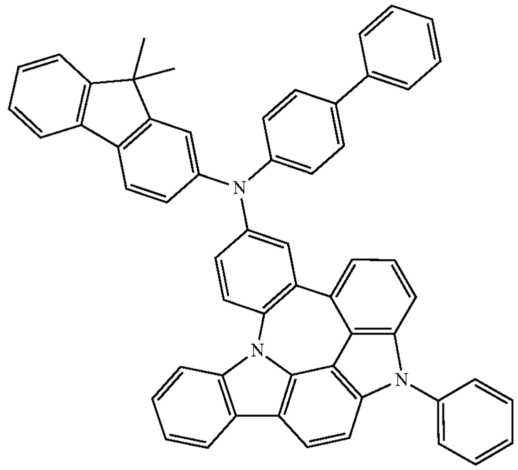
C-1-110
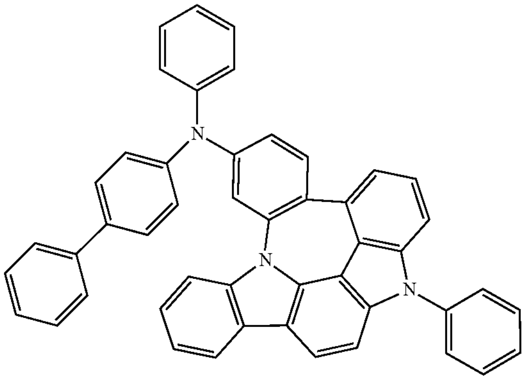
C-1-111
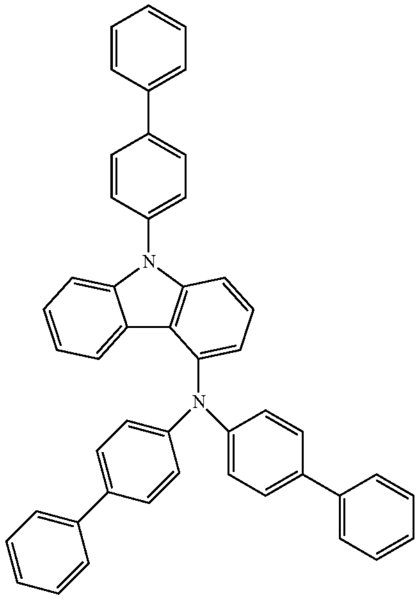
-continued
C-1-112
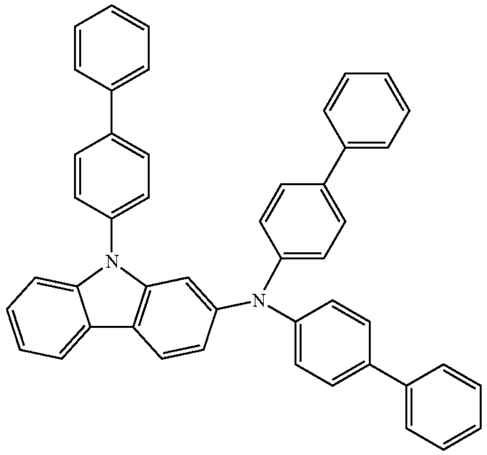
C-1-113
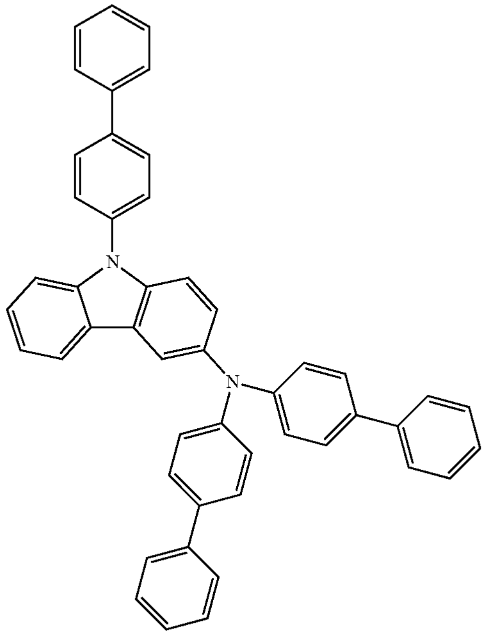

-continued
C-1-114
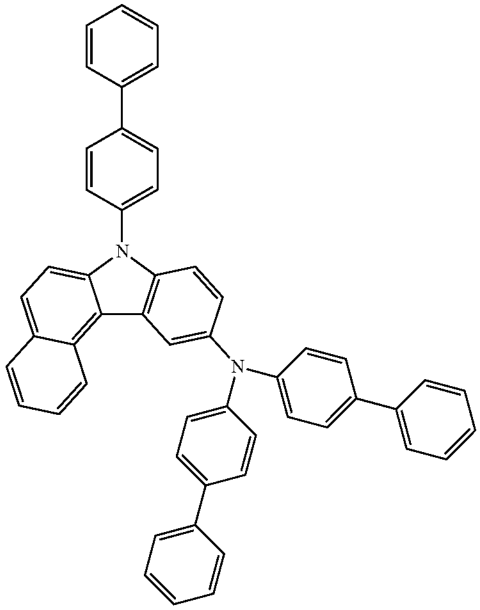
C-1-115
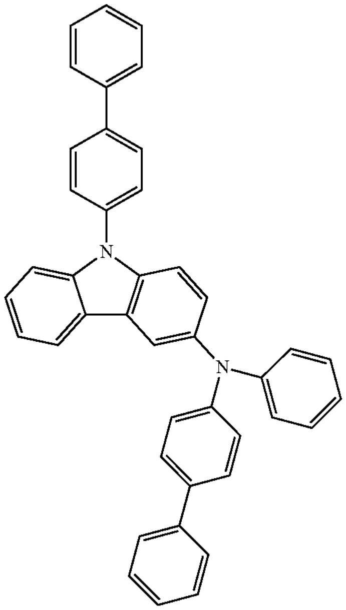
-continued
C-1-116
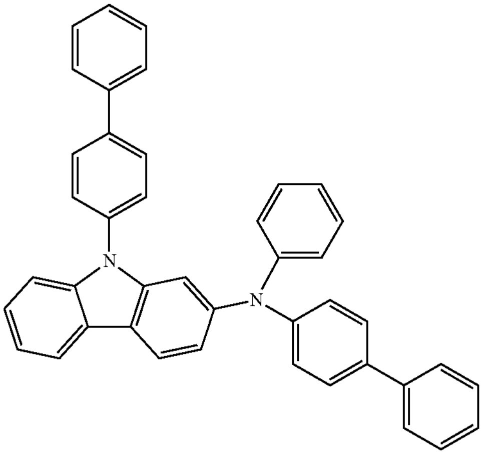
C-1-117
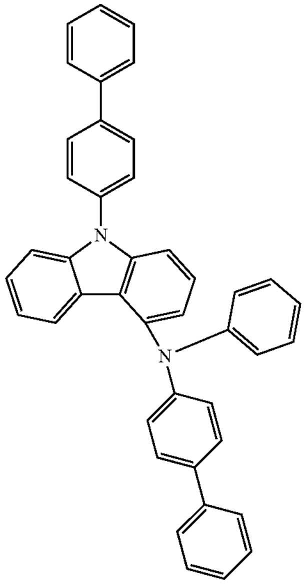
C-1-118
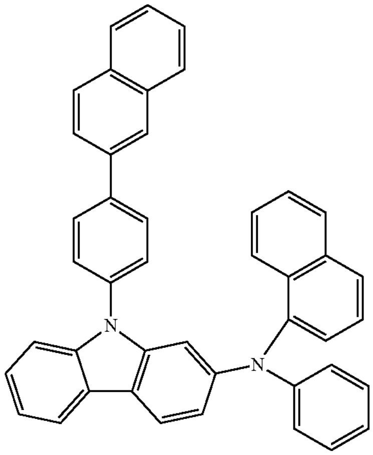

-continued
C-1-119
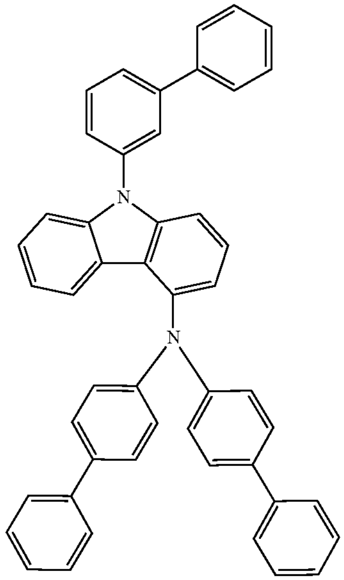
C-1-120
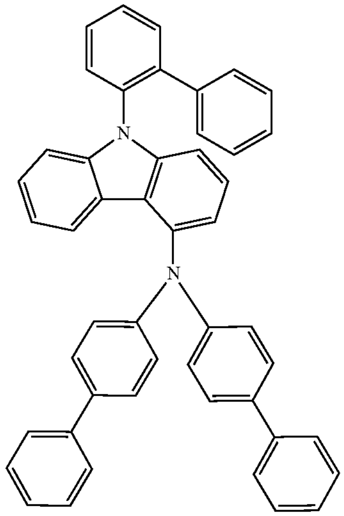
-continued
C-1-121
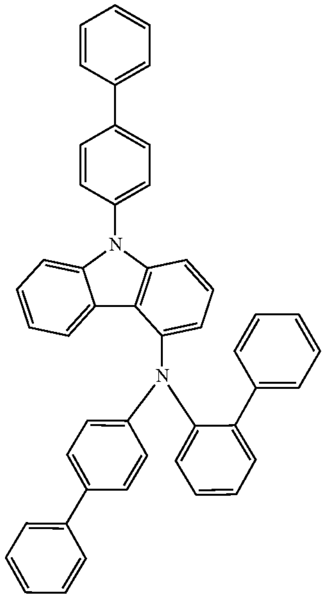
C-1-122
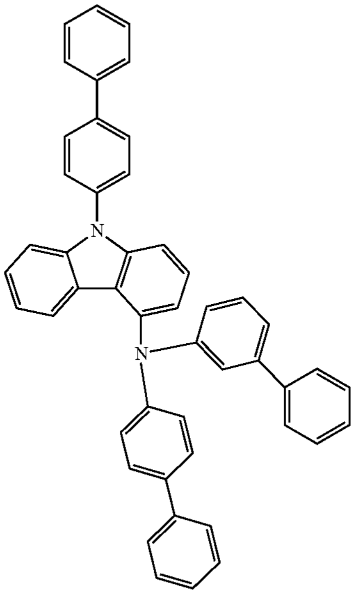

-continued
C-1-123
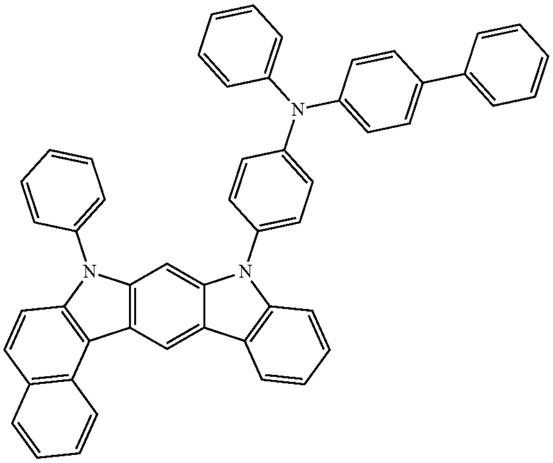
C-1-124
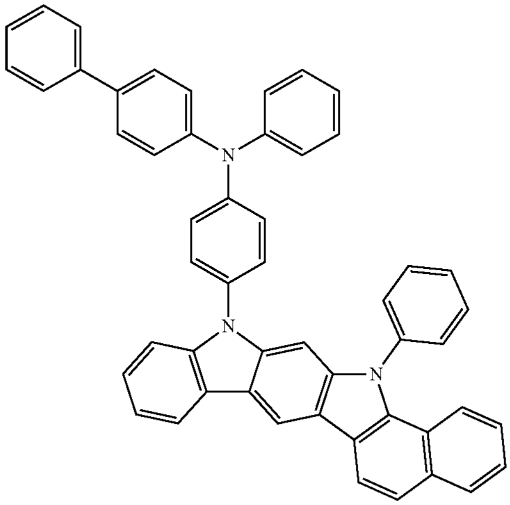
C-1-125
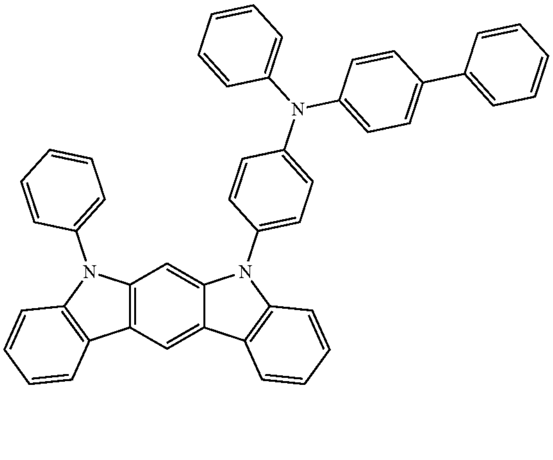
-continued
C-1-126
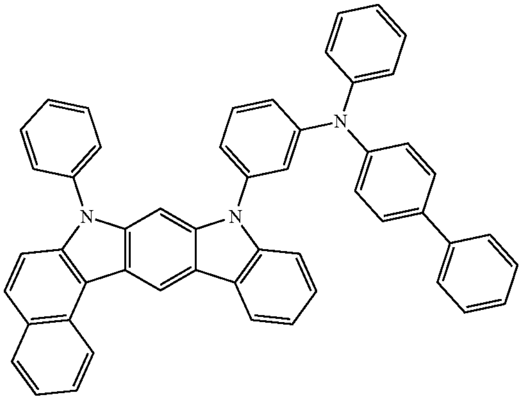
and
C-1-127
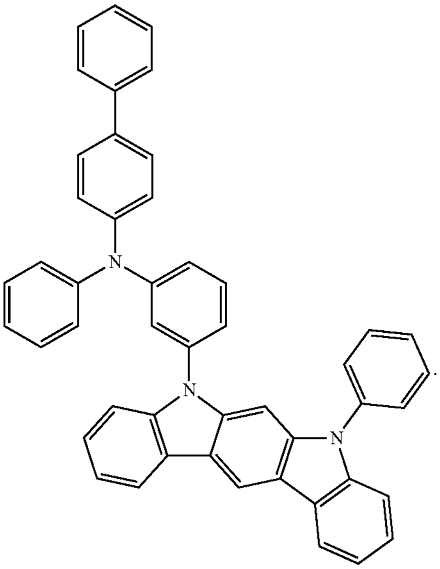
.
6. The composition material for an organic electroluminescent device according to claim 1, wherein the compound represented by formula 2 is selected from the group consisting of the following compounds:
C-1
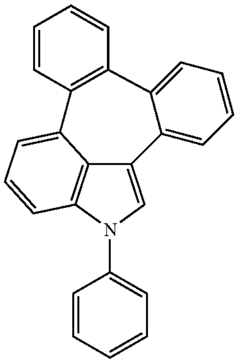

-continued
C-2
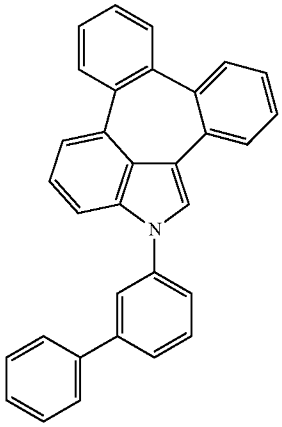
C-3
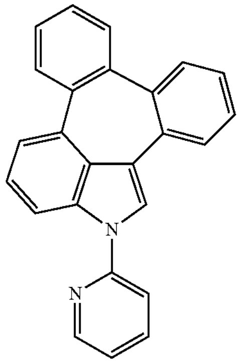
C-4
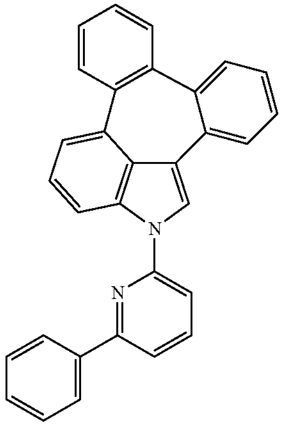
C-5
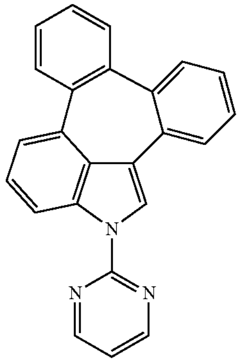
-continued
C-6
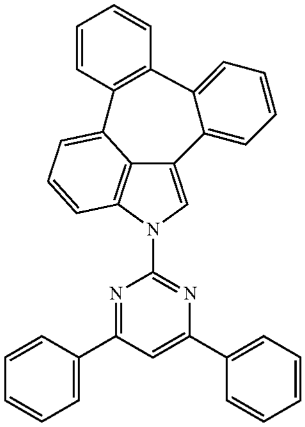
C-7
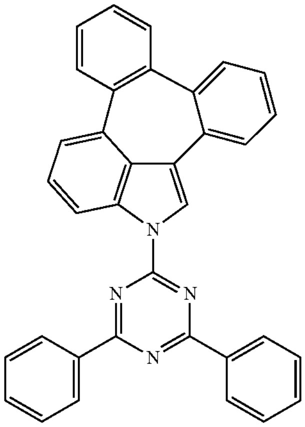
C-8
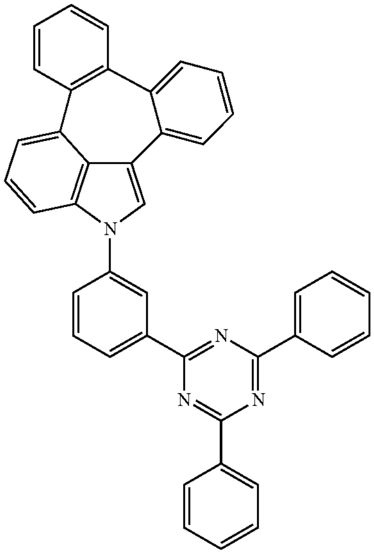

-continued
C-9
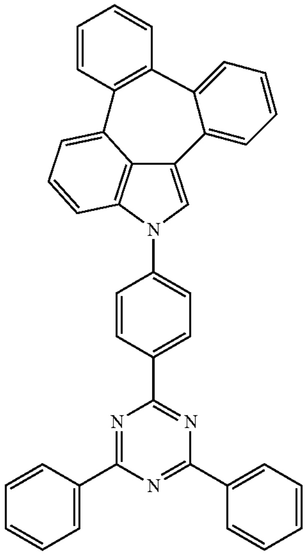
C-10
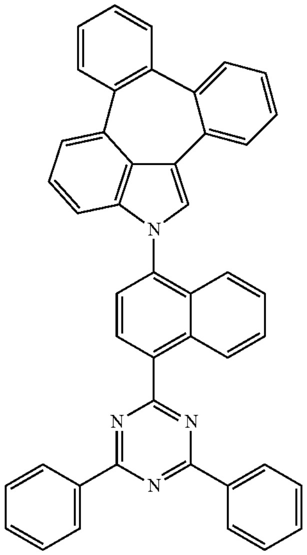
C-11
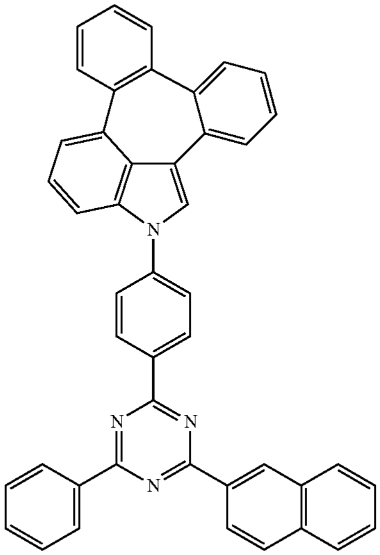
-continued
C-12
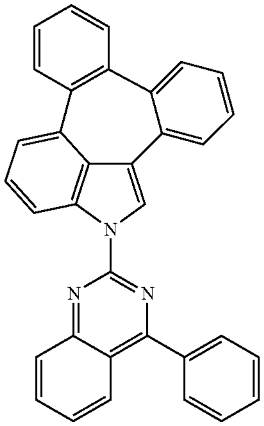
C-13
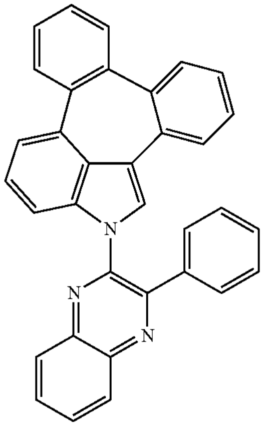
C-14
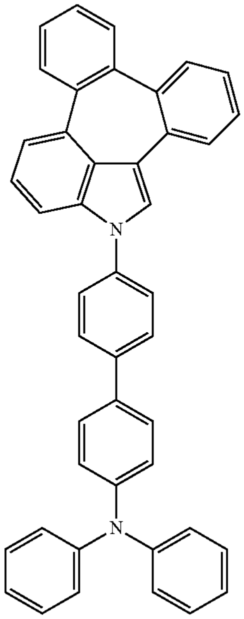

-continued
C-15
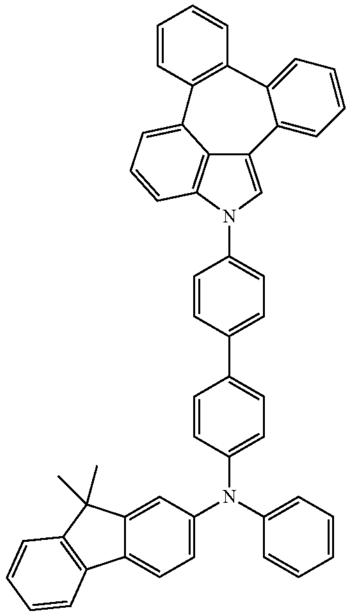
C-16
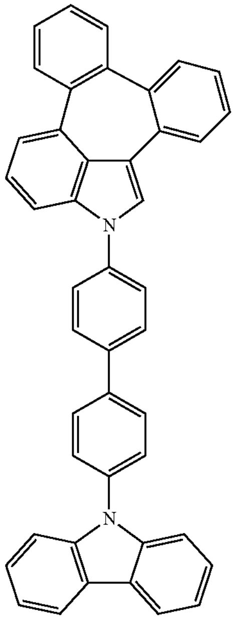
C-17
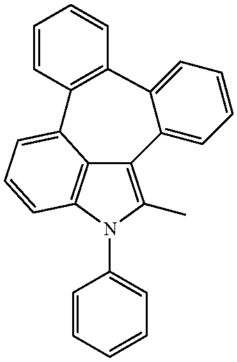
-continued
C-18
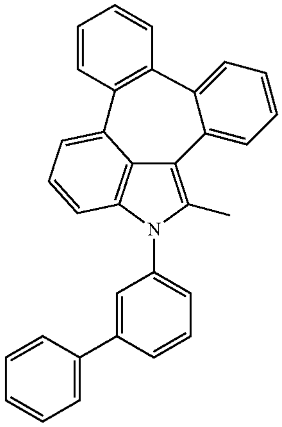
C-19
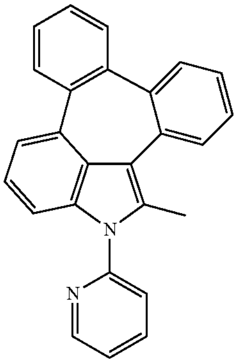
C-20
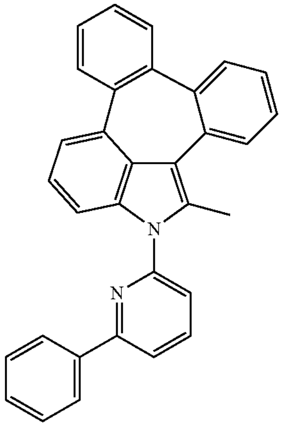
C-21
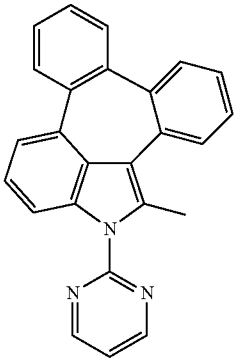

-continued
C-22
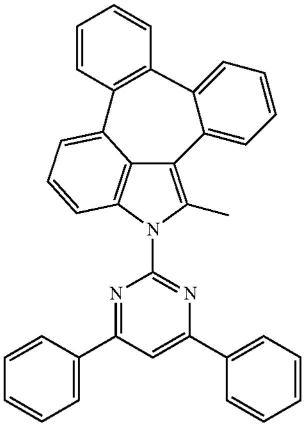
C-23
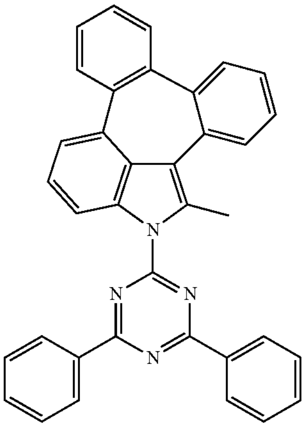
C-24
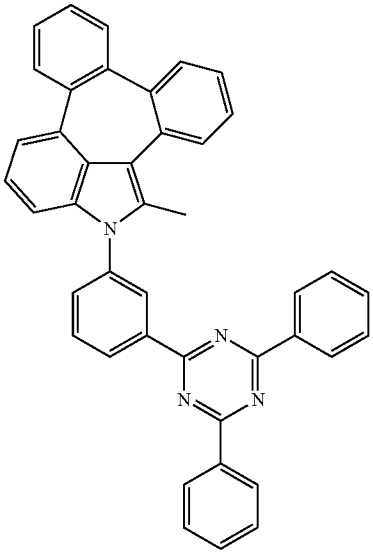
-continued
C-25
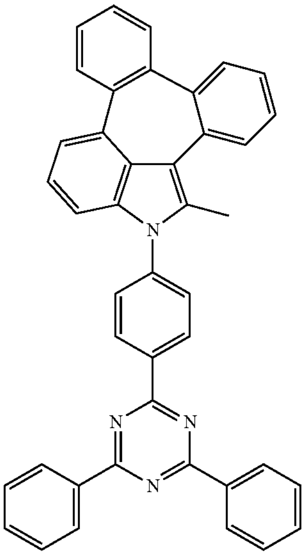
C-26
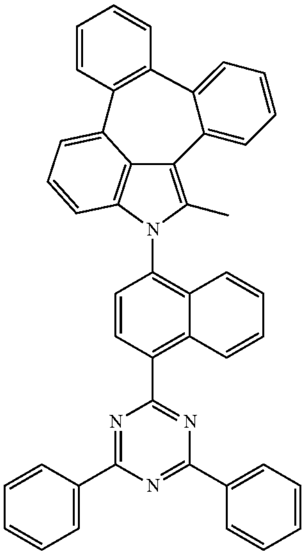
C-27
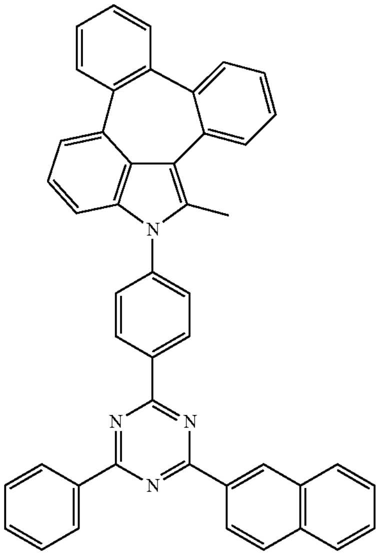

C-28
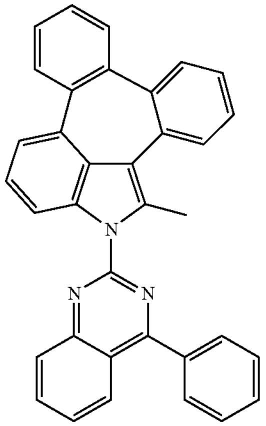
C-29
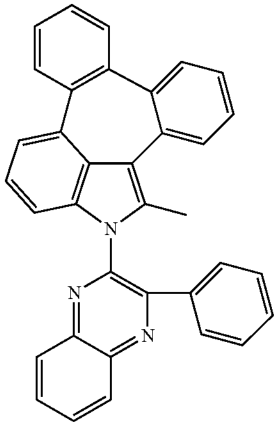
C-30
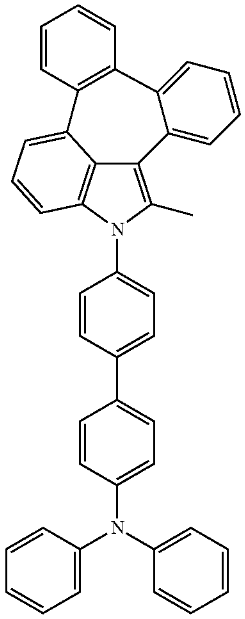
C-31
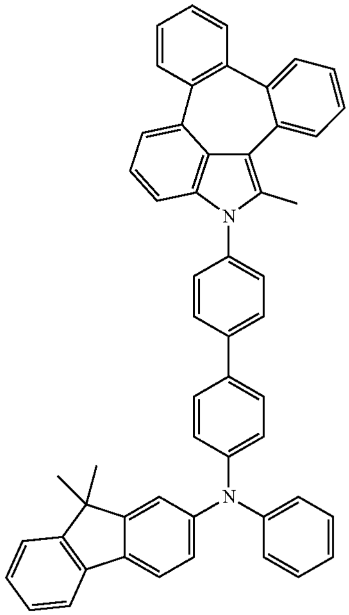
C-32
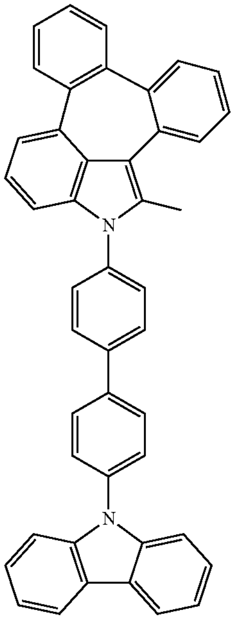
C-33
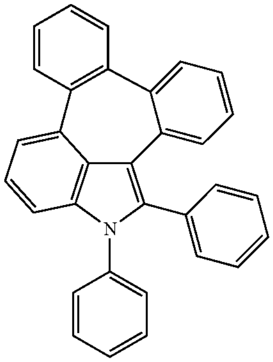

-continued
C-34
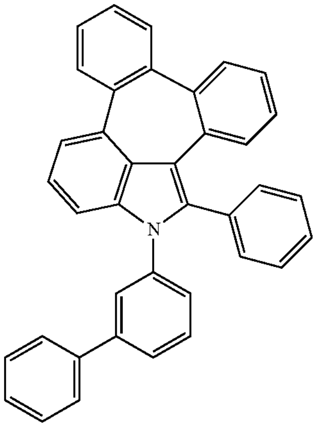
C-35
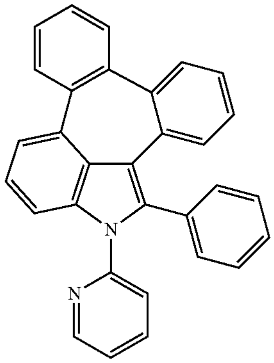
C-36
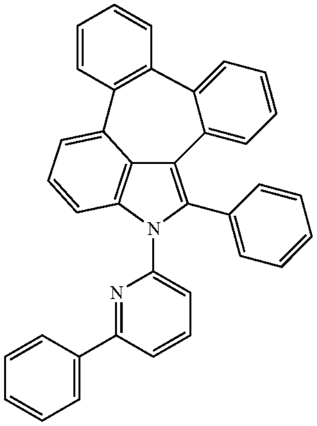
C-37
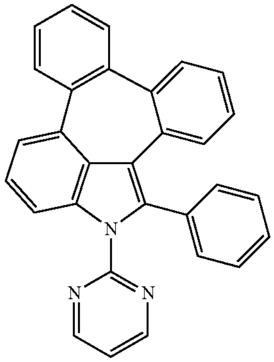
-continued
C-38
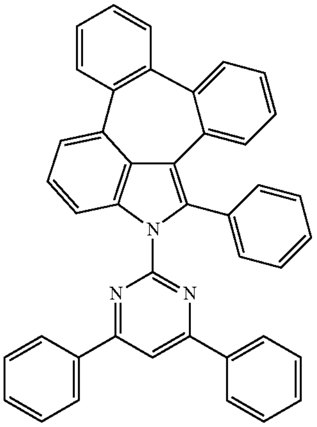
C-39
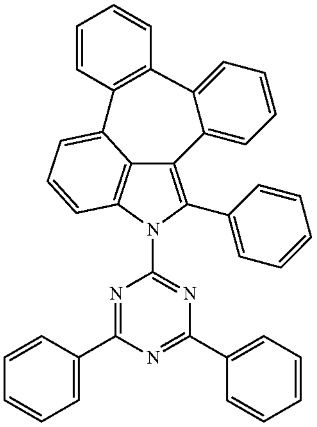
C-40
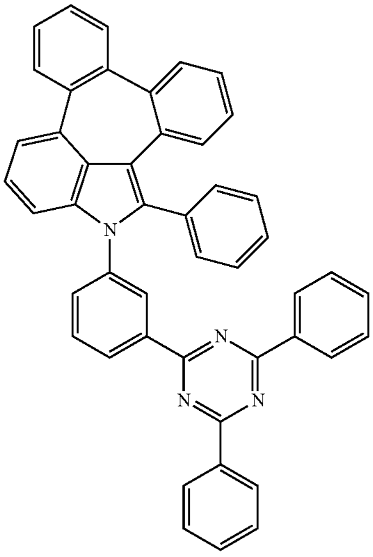

-continued
C-41
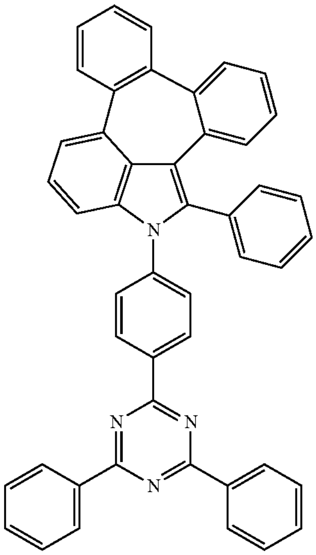
C-42
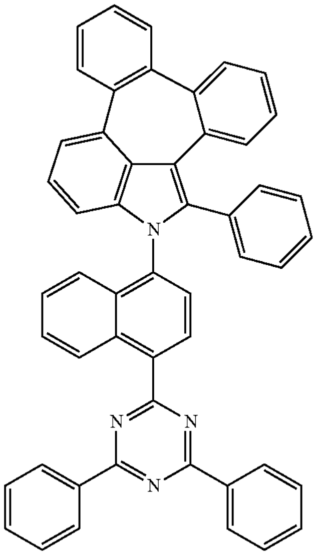
C-43
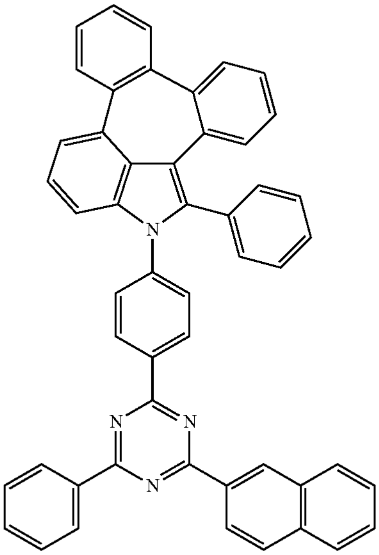
-continued
C-44
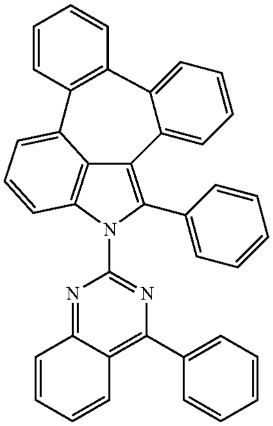
C-45
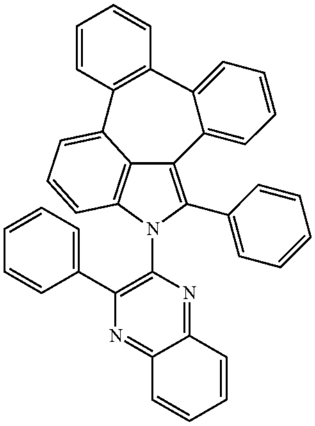
C-46
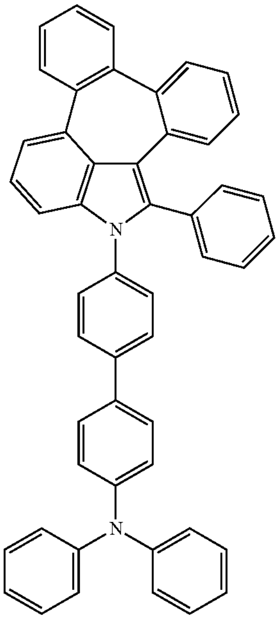

C-47
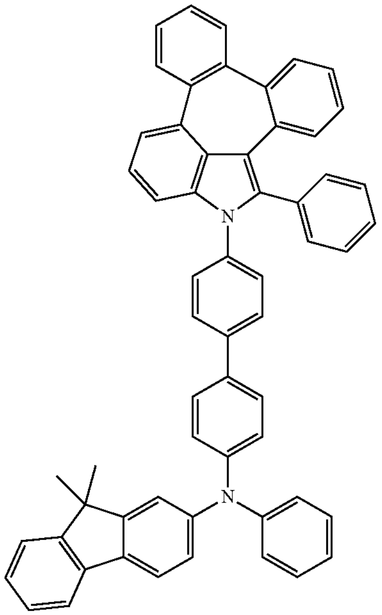
C-48
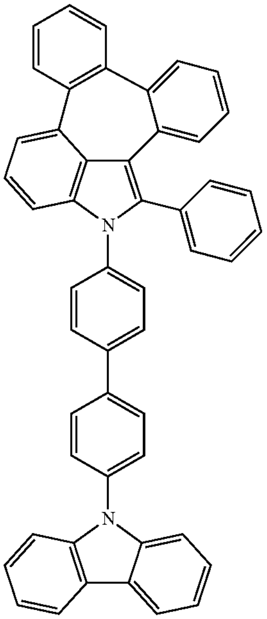
C-49
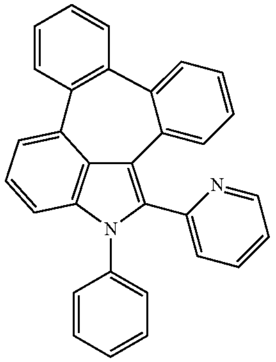
C-50
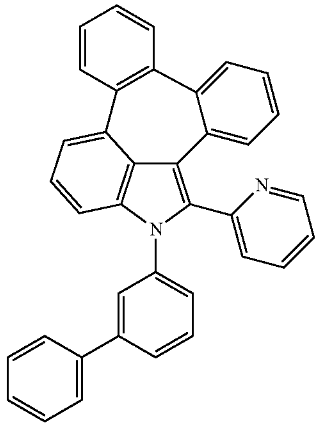
C-51
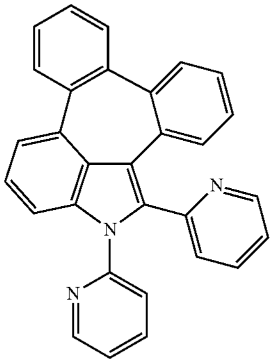
C-52
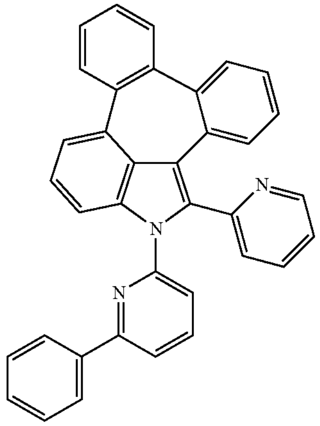
C-53
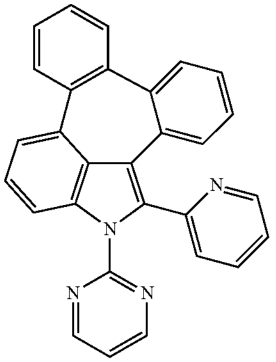

-continued
C-54
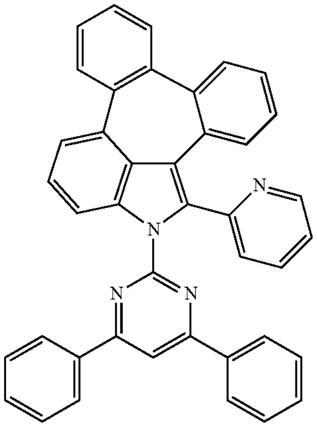
C-55
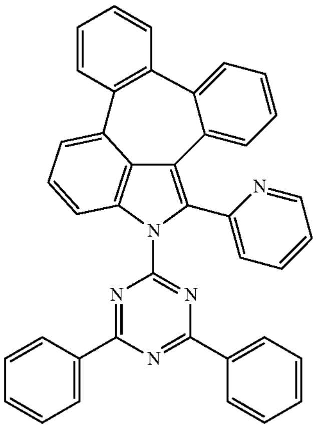
C-56
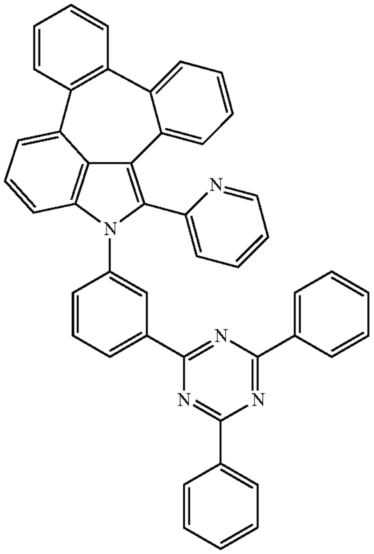
-continued
C-57
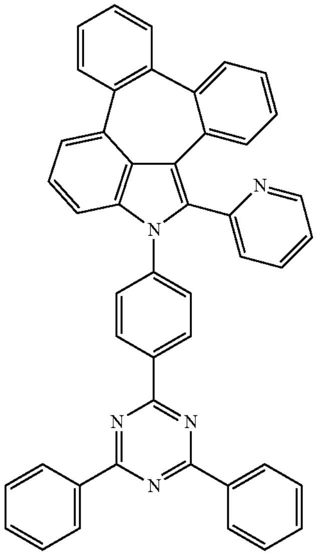
C-58
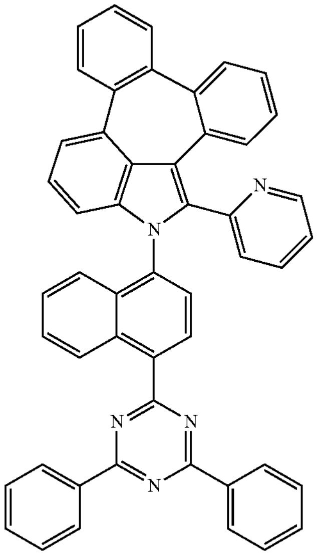
C-59
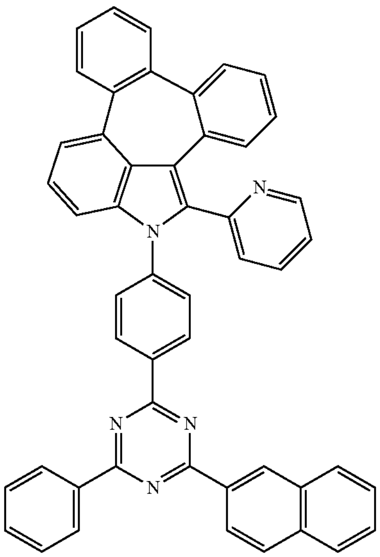

-continued
C-60
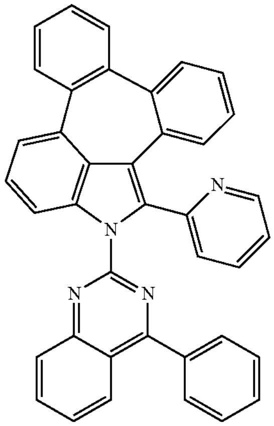
C-61
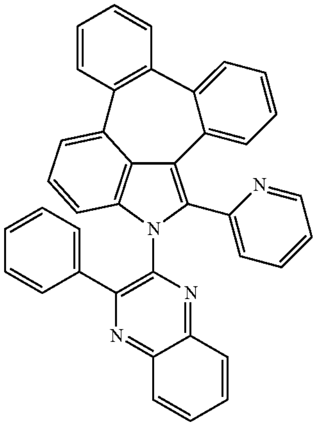
C-62
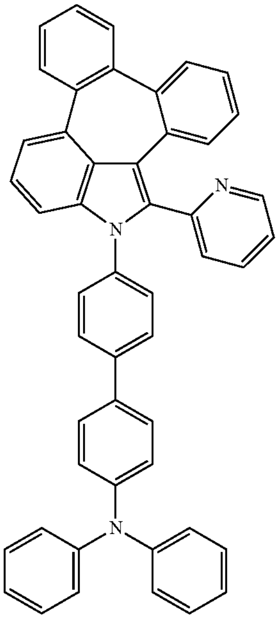
-continued
C-63
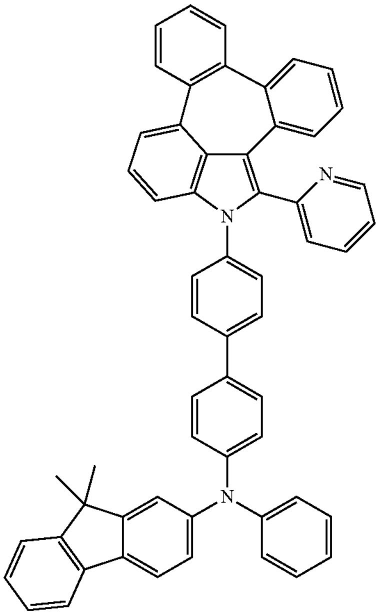
C-64
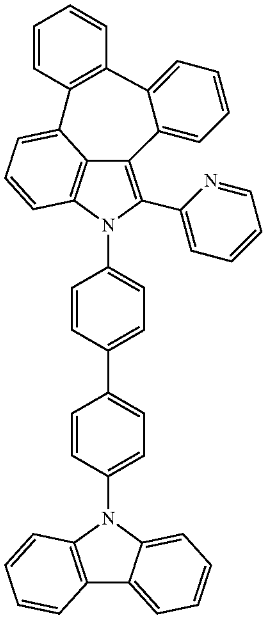
C-65
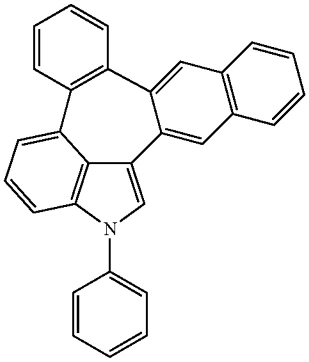

-continued
C-66
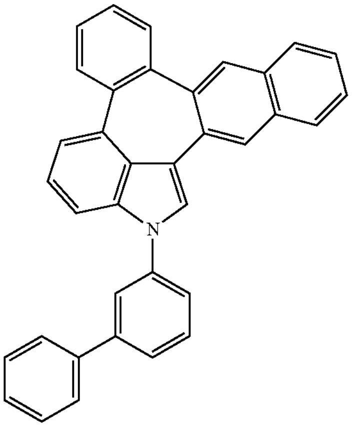
C-67
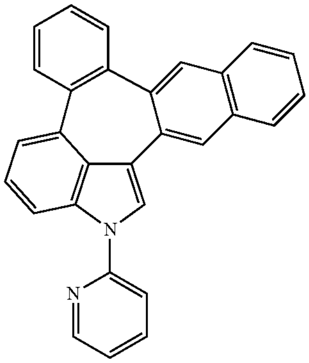
C-68
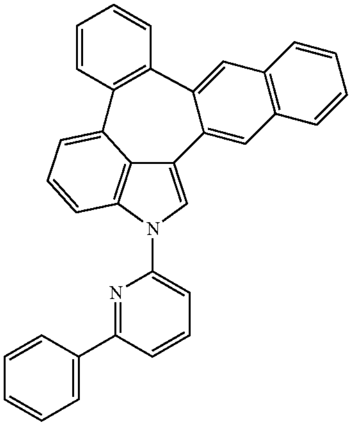
C-69
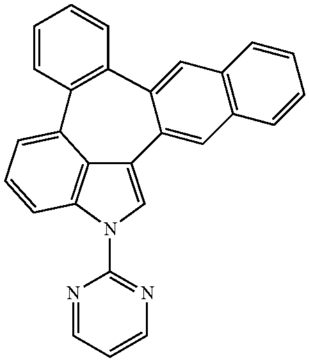
-continued
C-70
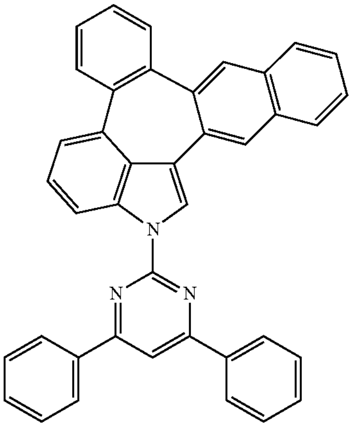
C-71
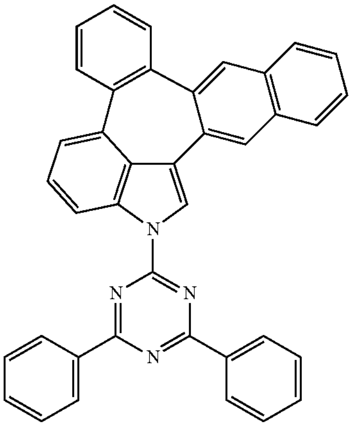
C-72
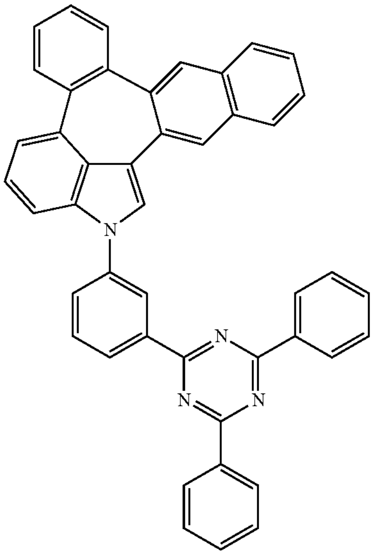

-continued
C-73
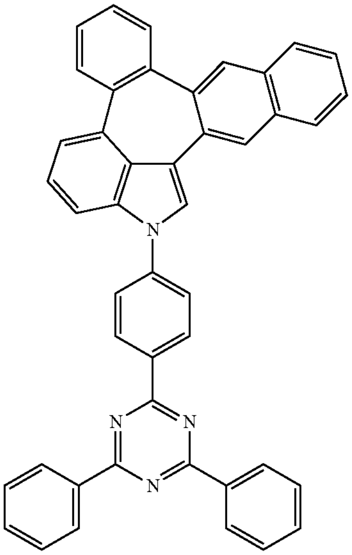
C-74
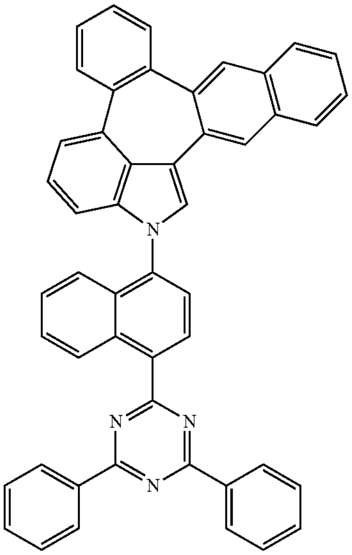
C-75
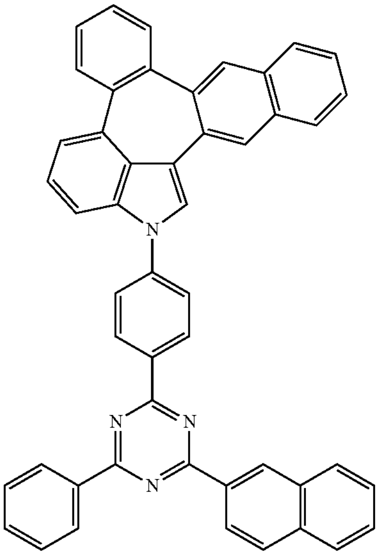
-continued
C-76
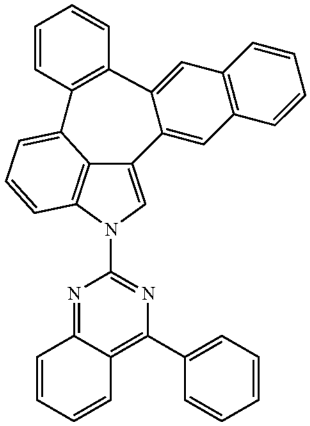
C-77
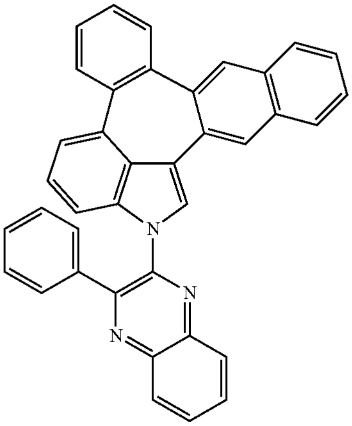
C-78
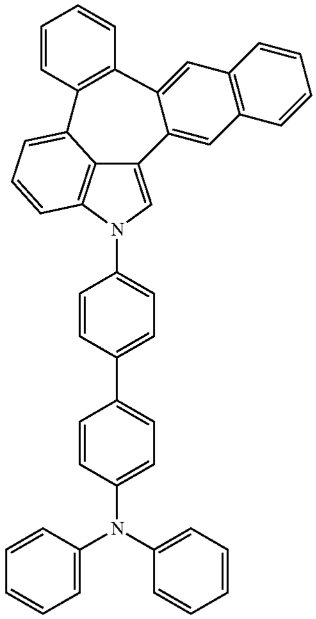

-continued
C-79
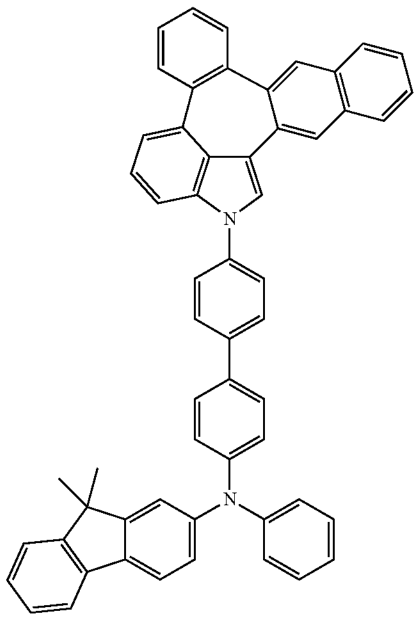
C-80
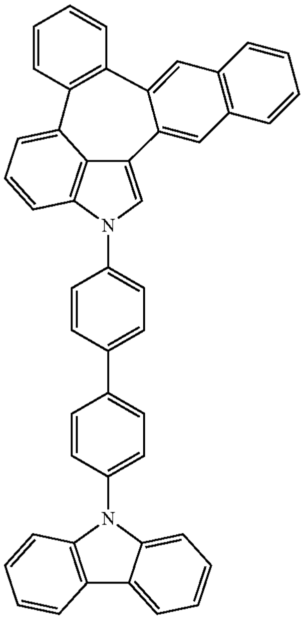
C-81
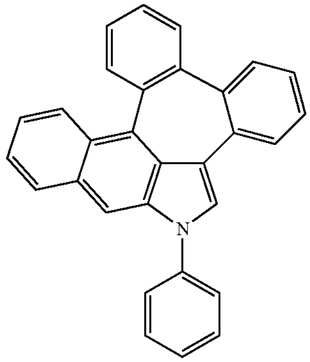
-continued
C-82
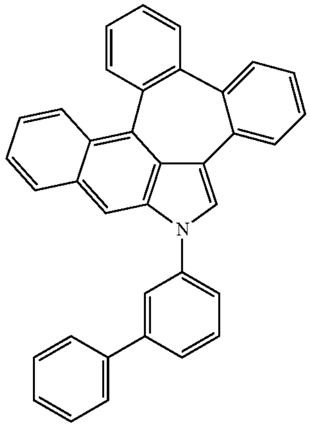
C-83
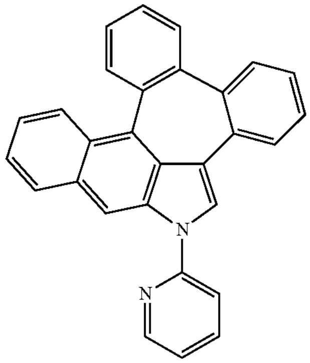
C-84
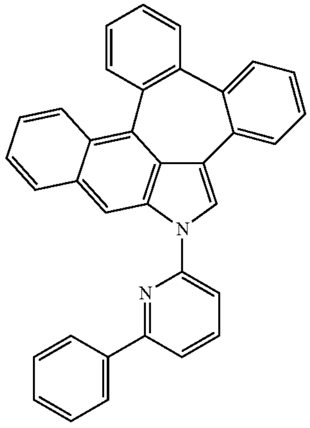
C-85
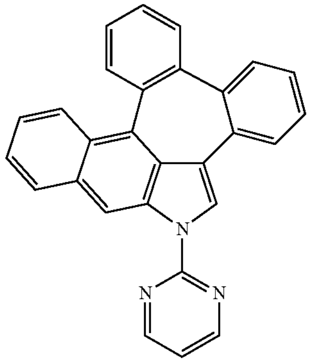

C-86
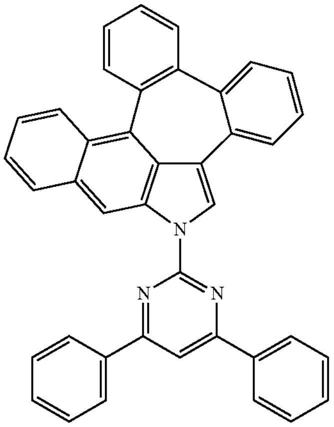
C-87
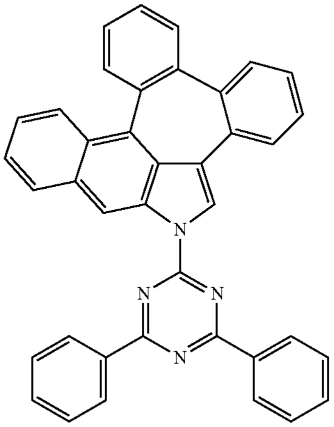
C-88
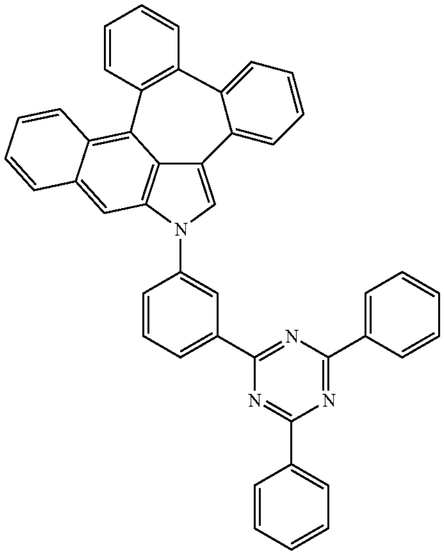
C-89
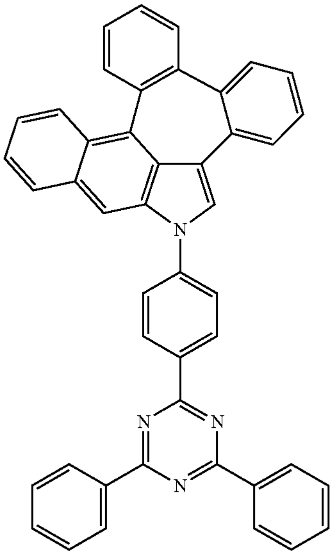
C-90
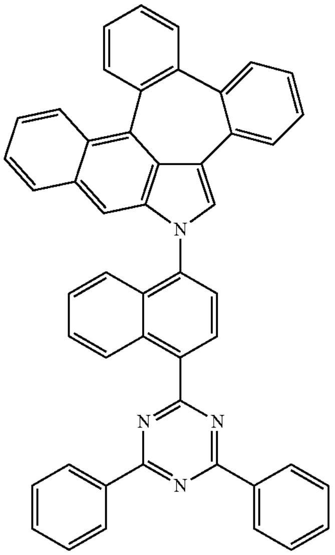
C-91
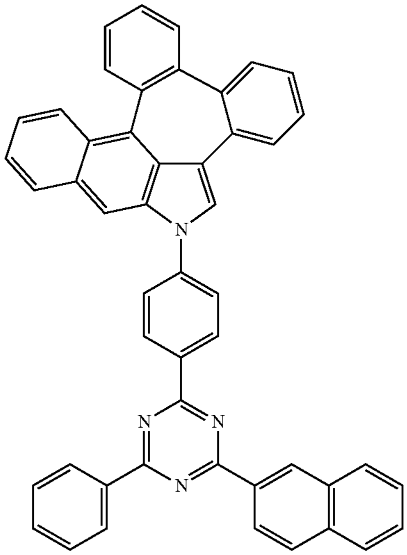

-continued
C-92
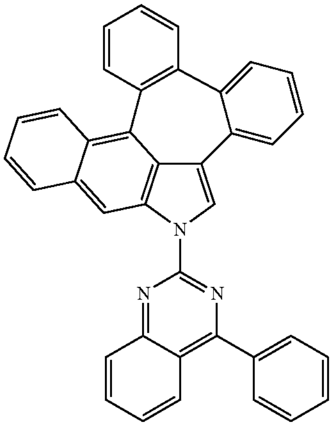
C-93
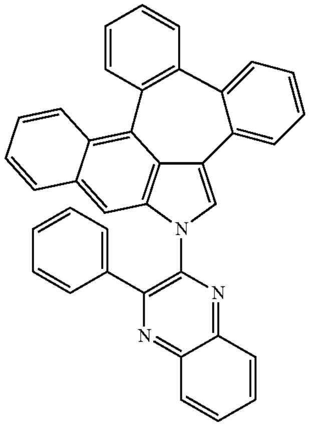
C-94
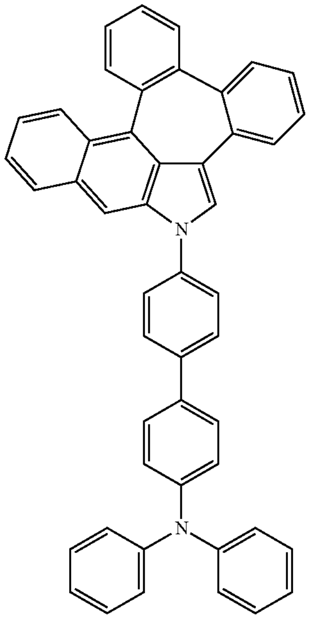
-continued
C-95
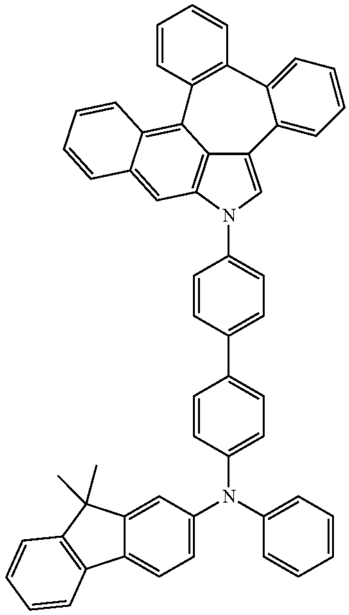
C-96
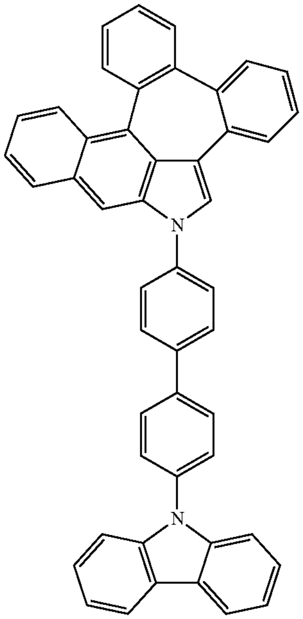
C-97
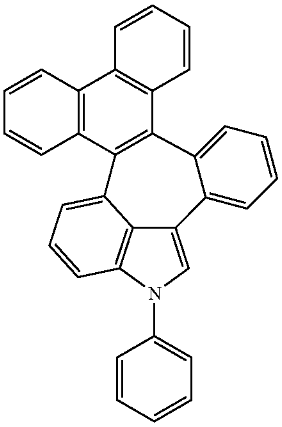

-continued
C-98
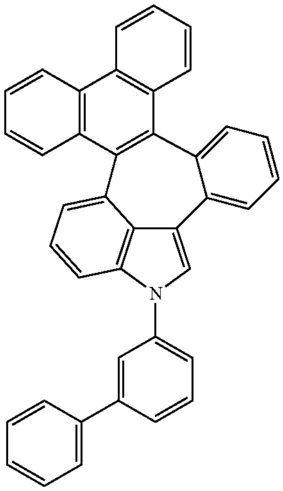
C-99
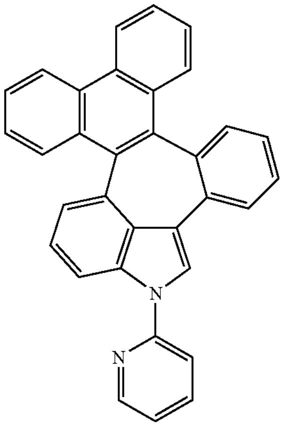
C-100
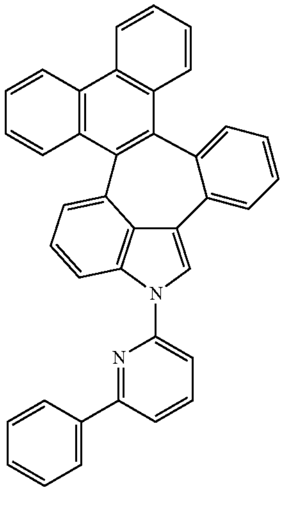
-continued
C-101
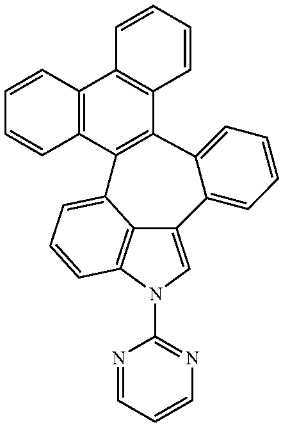
C-102
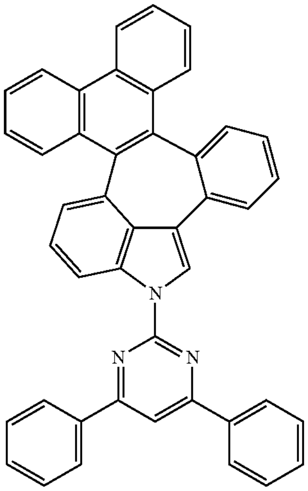
C-103
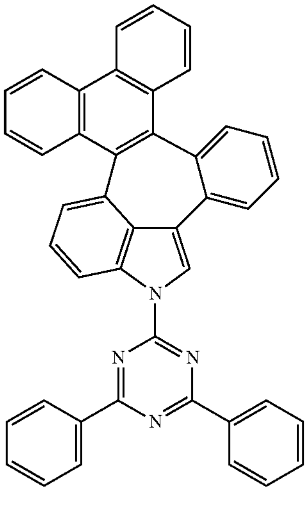

-continued
C-104
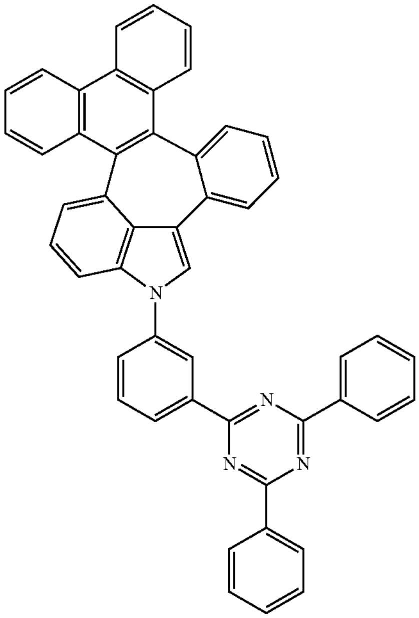
C-105
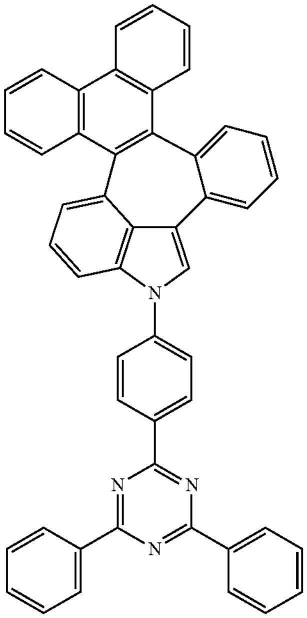
-continued
C-106
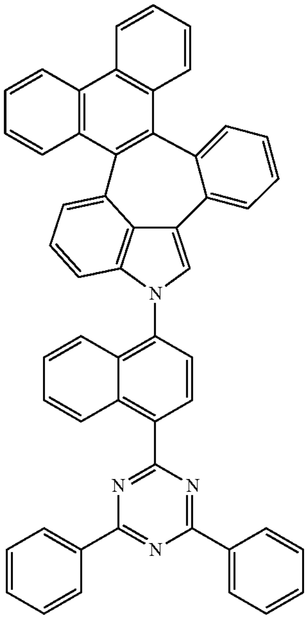
C-107
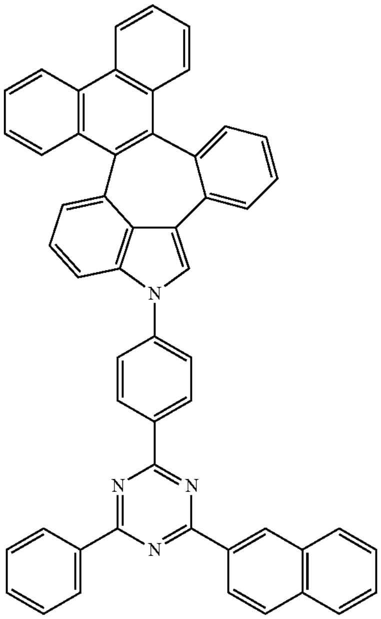

-continued
C-108
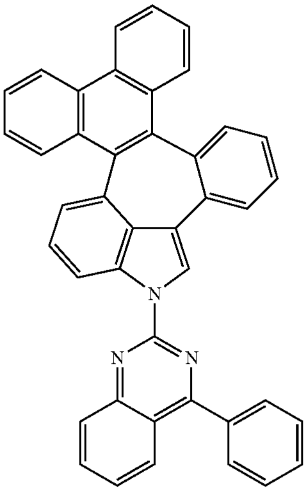
C-109
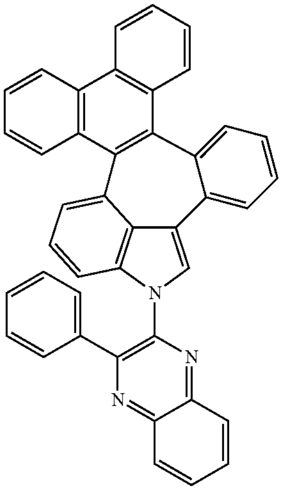
C-110
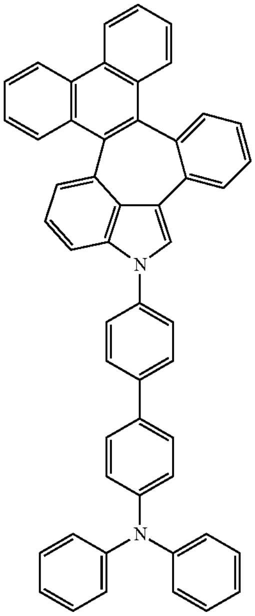
-continued
C-111
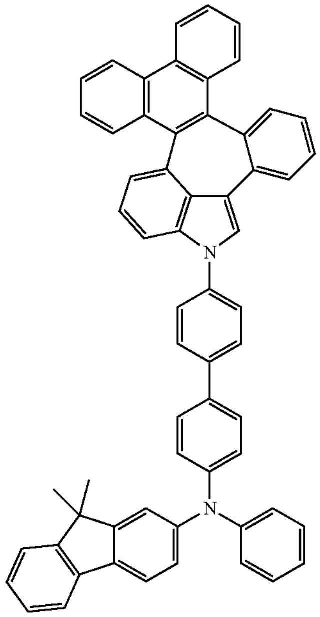
C-112
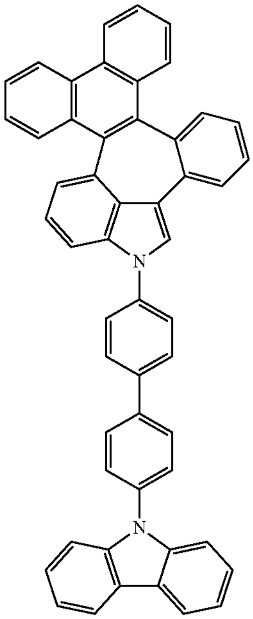
C-113
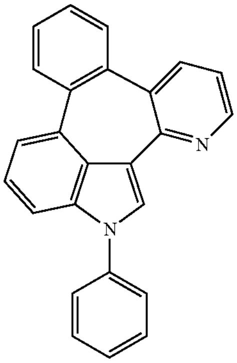

C-114
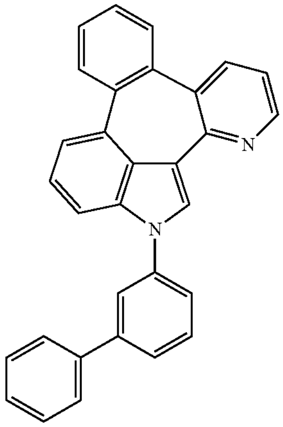
C-115
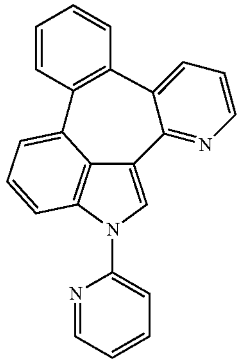
C-116
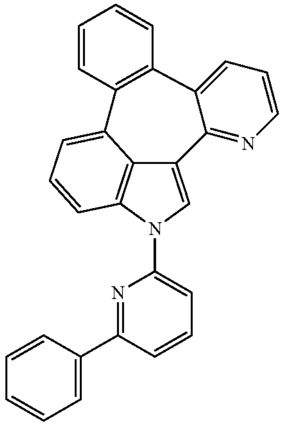
C-117
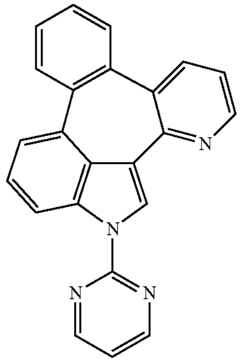
C-118
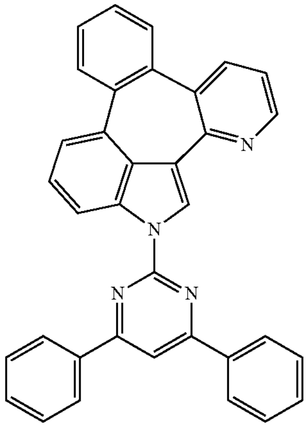
C-119
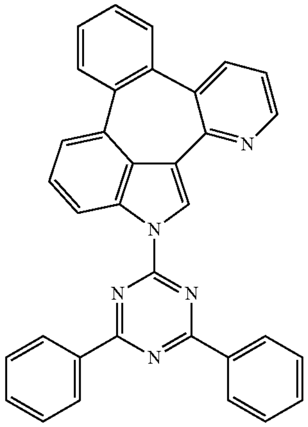
C-120
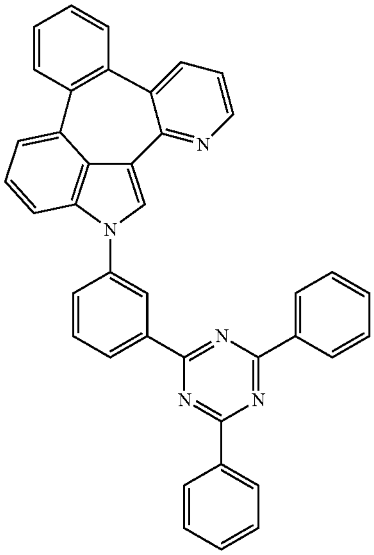

-continued
C-121
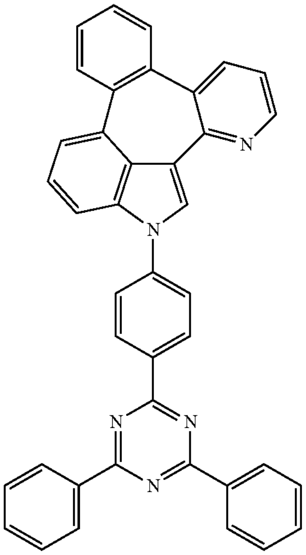
C-122
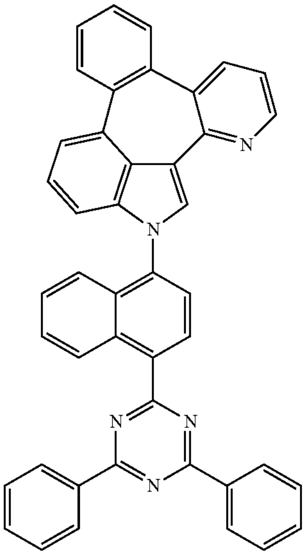
C-123
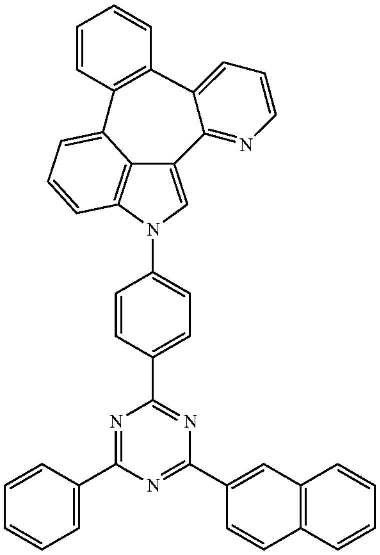
-continued
C-124
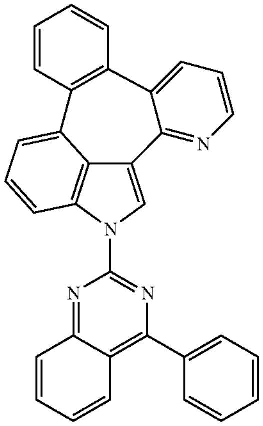
C-125
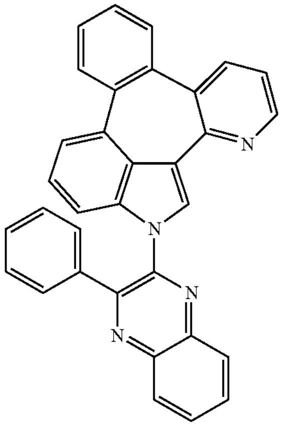
C-126
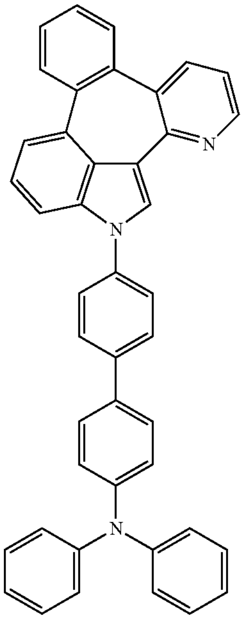

-continued
C-127
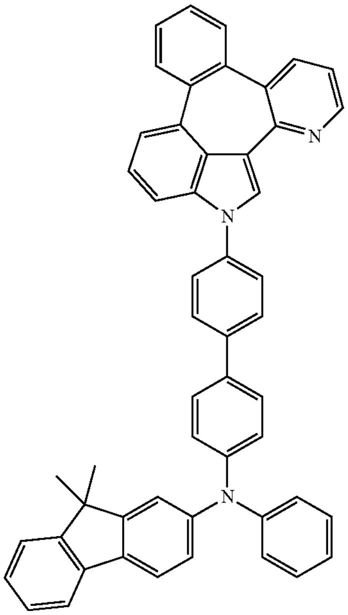
C-128
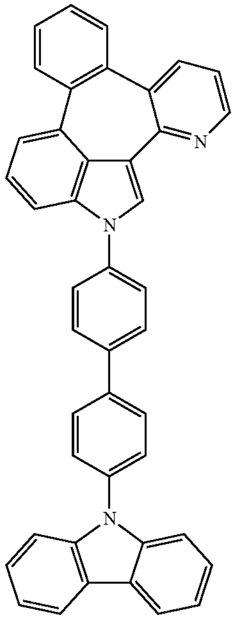
-continued
C-129
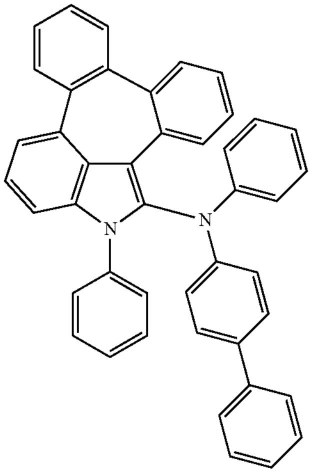
C-130
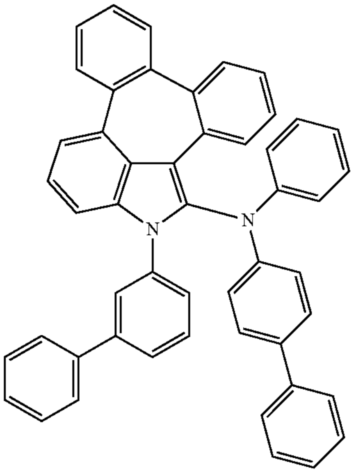
C-131
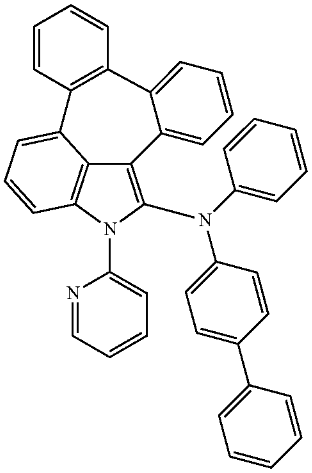

-continued
C-132
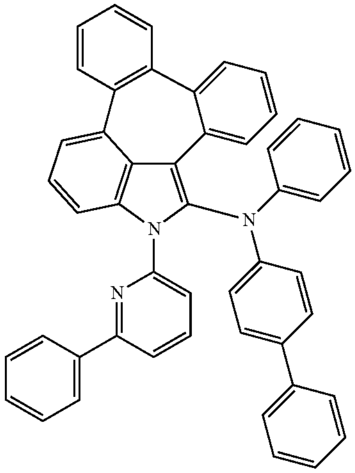
C-133
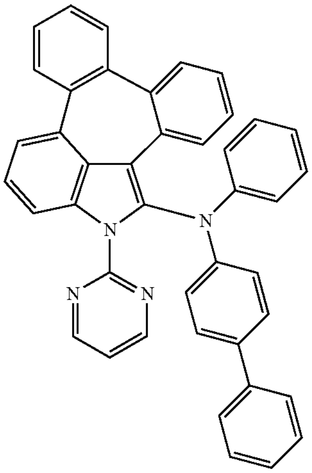
C-134
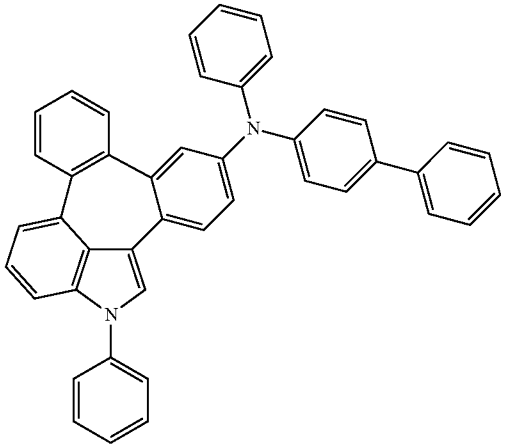
-continued
C-135
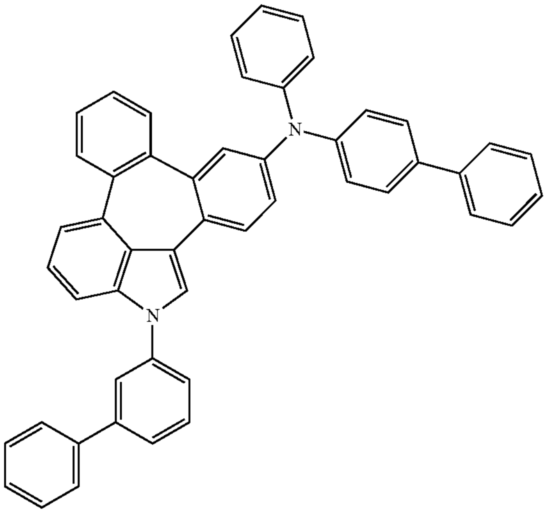
C-136
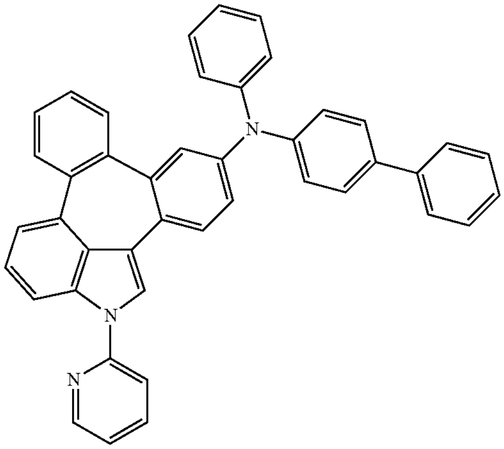
C-137
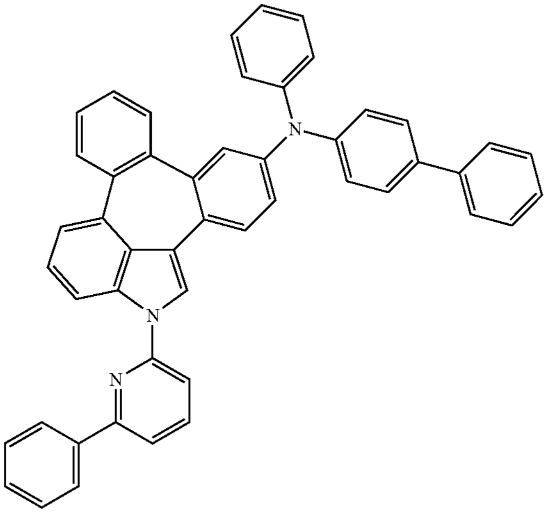

-continued
C-138
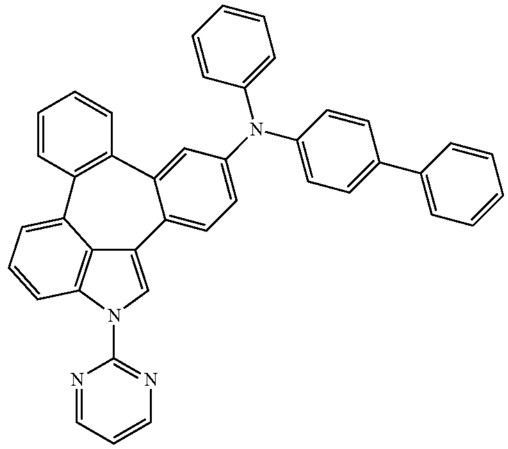
C-139
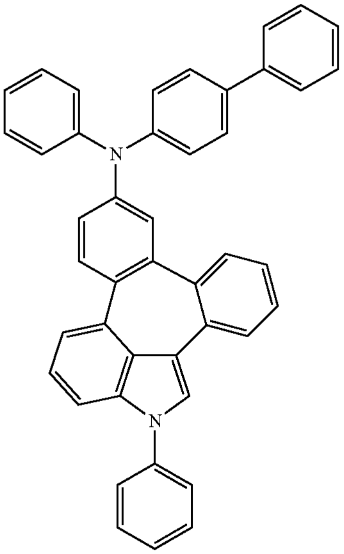
C-140
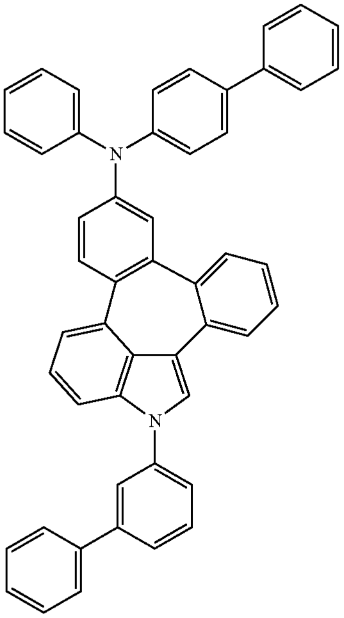
-continued
C-141
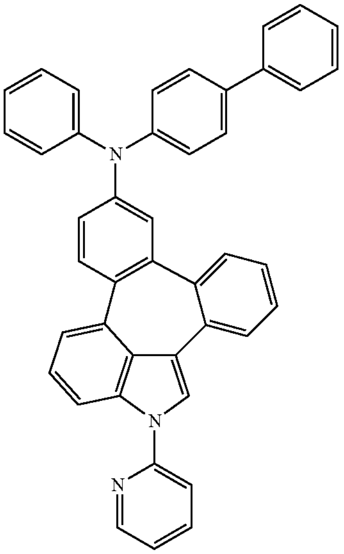
C-142
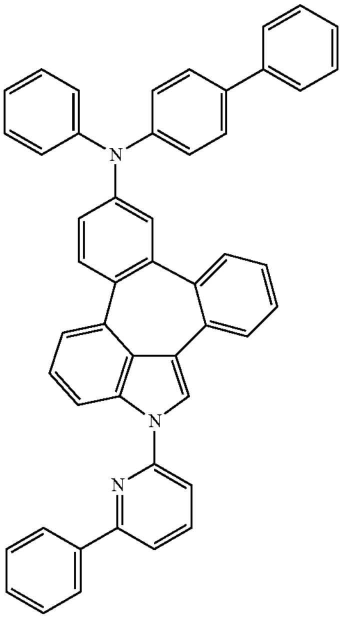

-continued
C-143
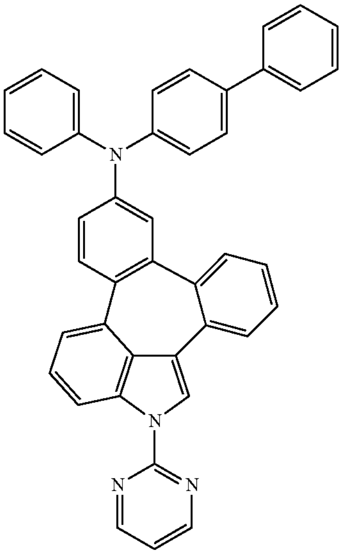
C-144
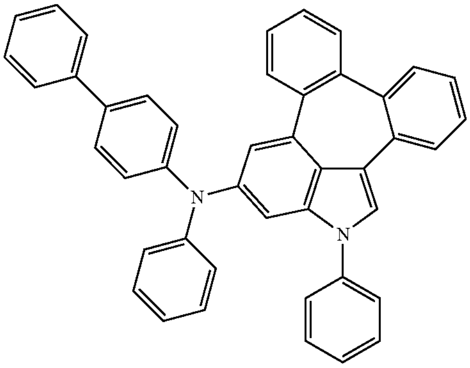
C-145
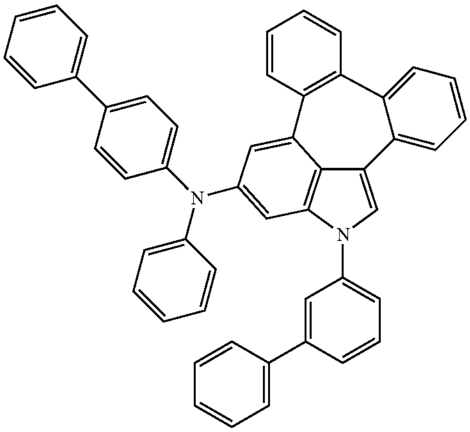
-continued
C-146
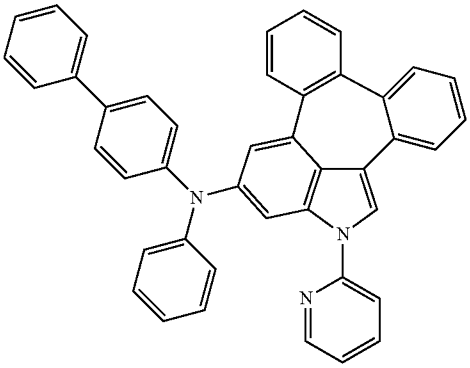
C-147
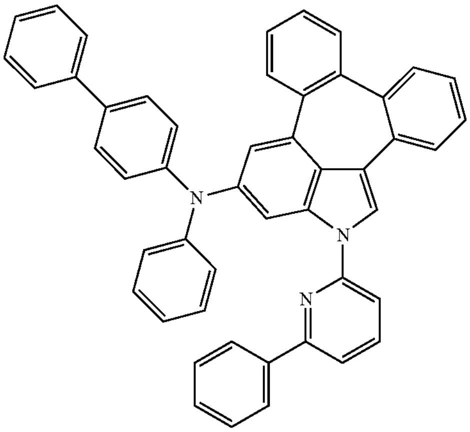
C-148
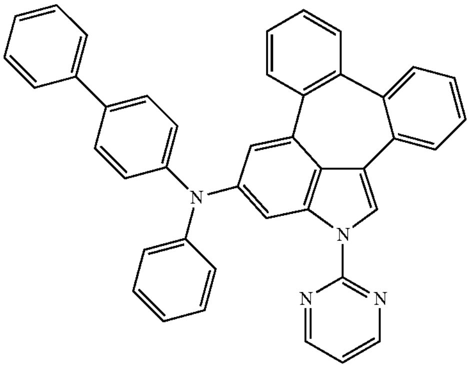
C-149
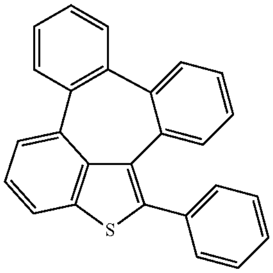

-continued
C-150
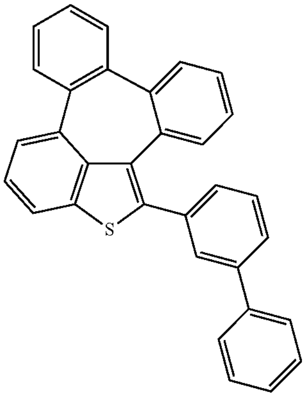
C-151
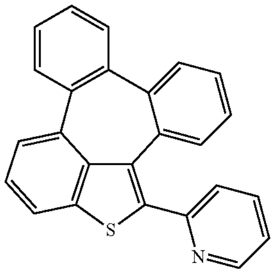
C-152
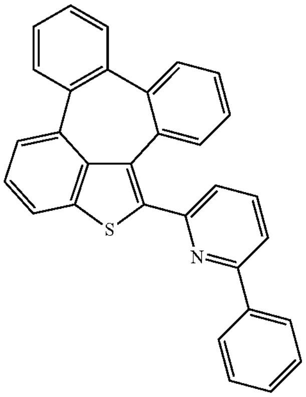
C-153
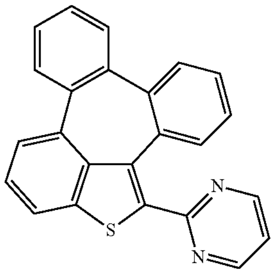
-continued
C-154
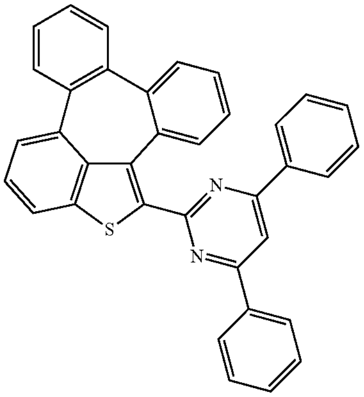
C-155
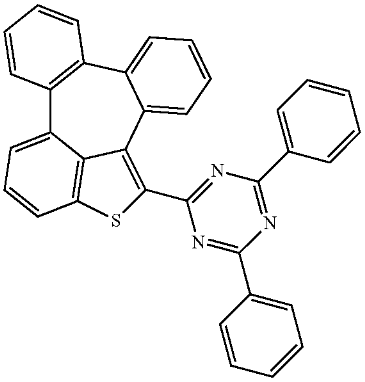
C-156
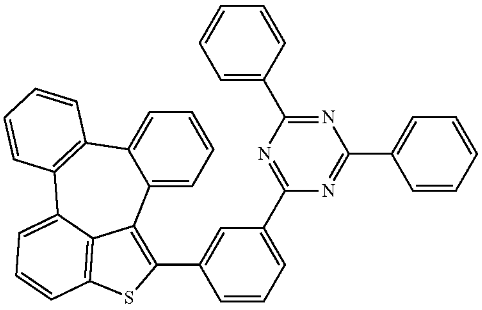
C-157
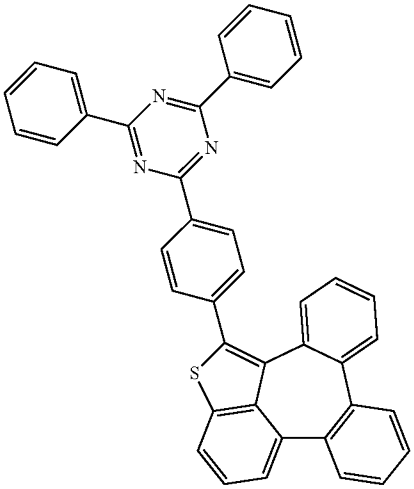

-continued
C-158
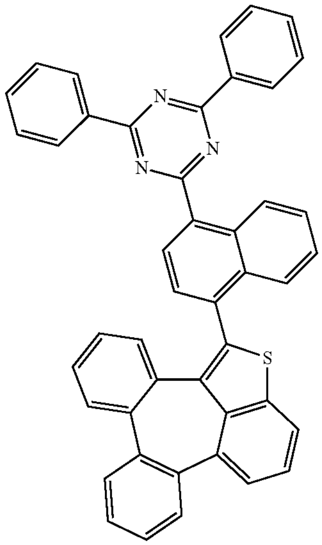
C-159
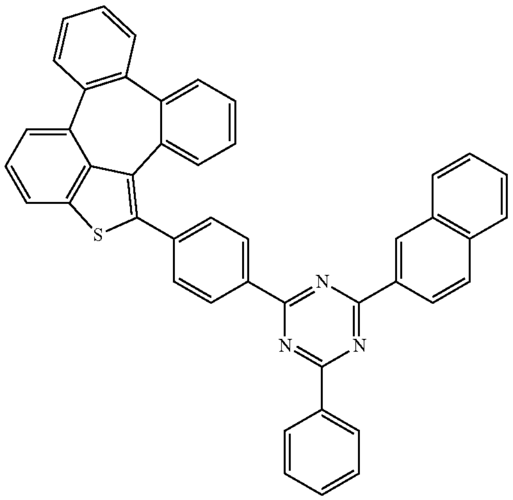
C-160
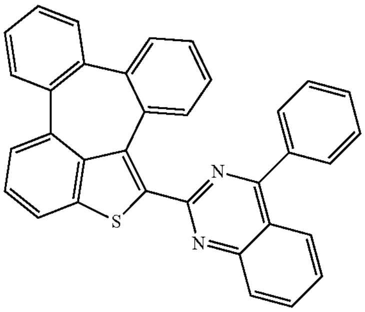
-continued
C-161
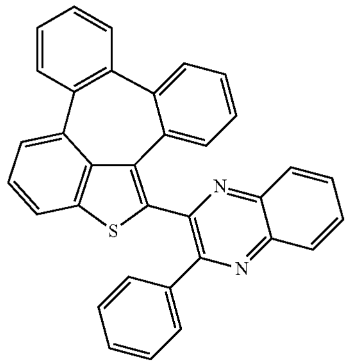
C-162
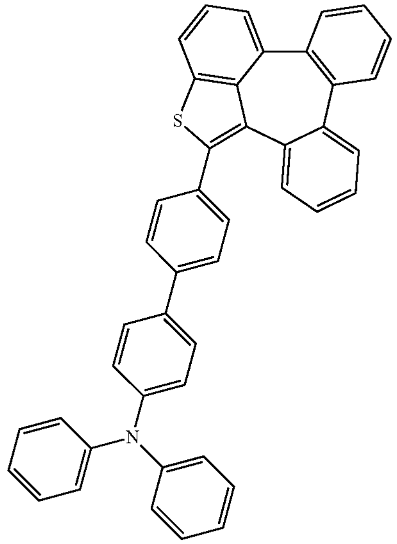
C-163
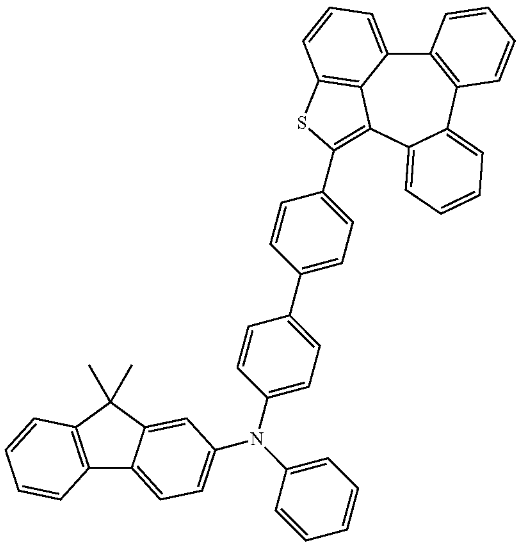

-continued
C-164
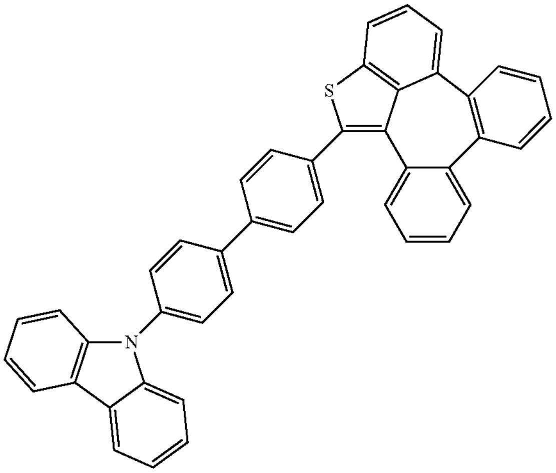
C-165
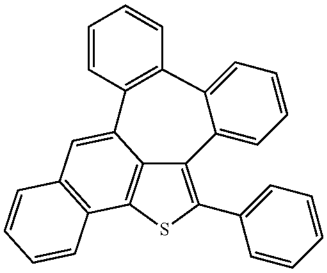
C-166
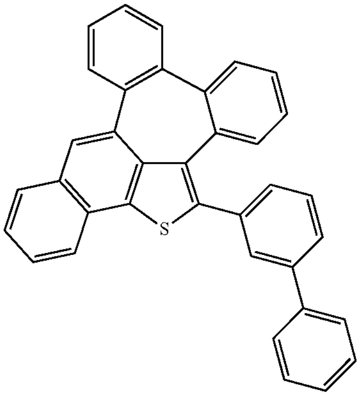
C-167
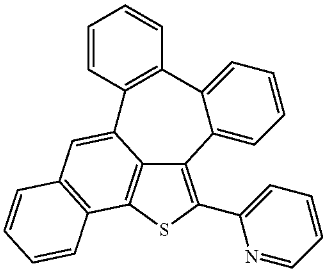
-continued
C-168
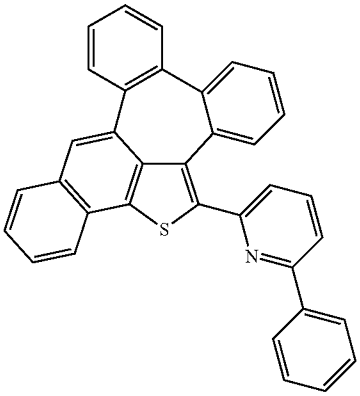
C-169
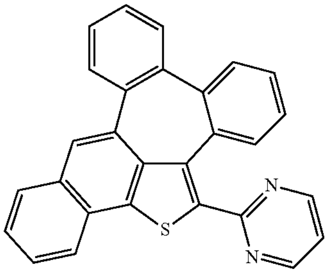
C-170
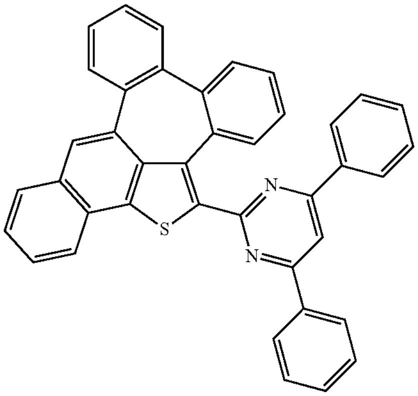
C-171
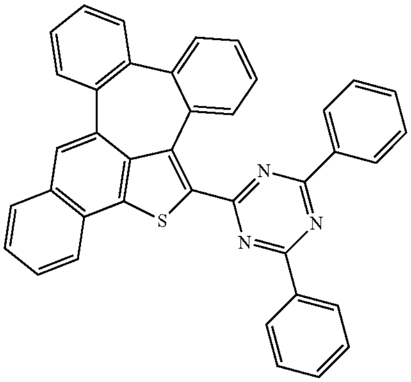

-continued
C-172
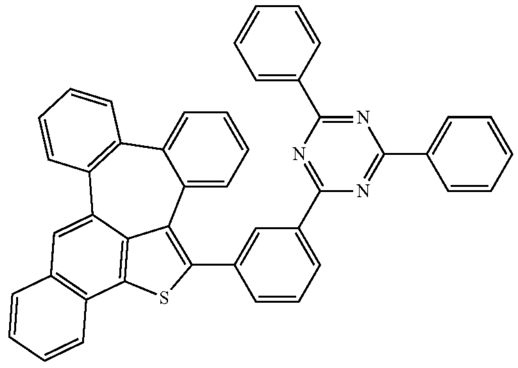
C-173
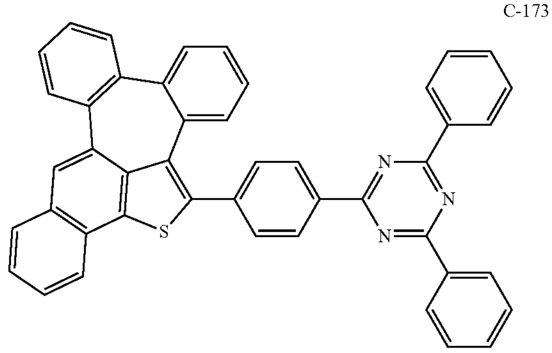
C-174
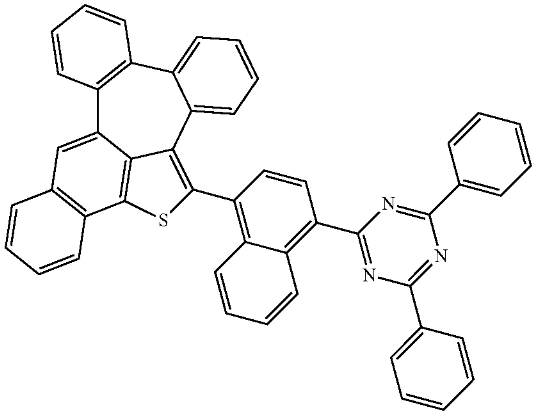
-continued
C-175
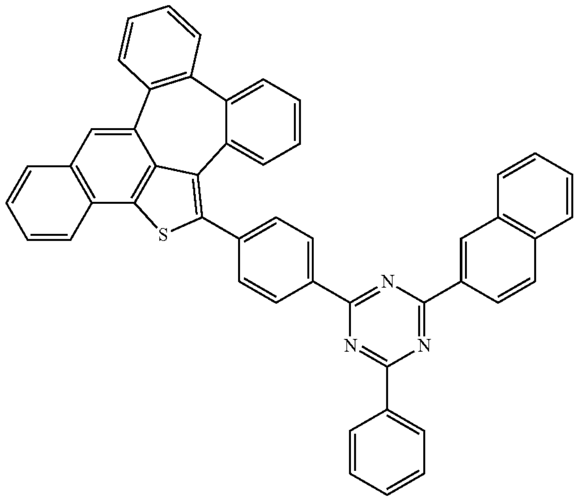
C-176
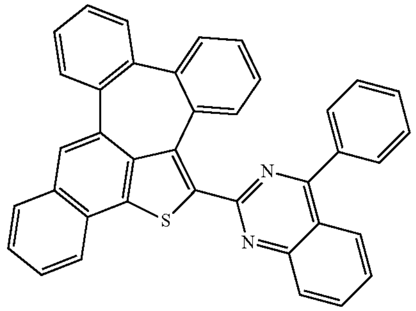
C-177
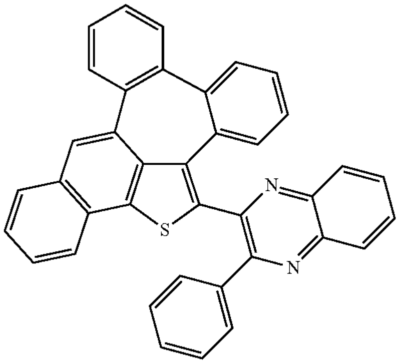

-continued
C-178
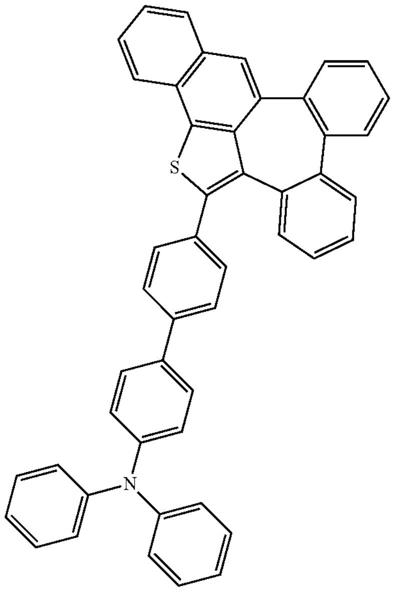
C-179
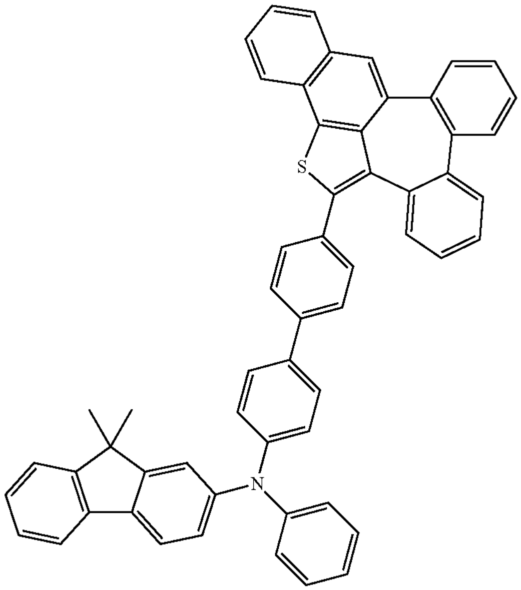
-continued
C-180
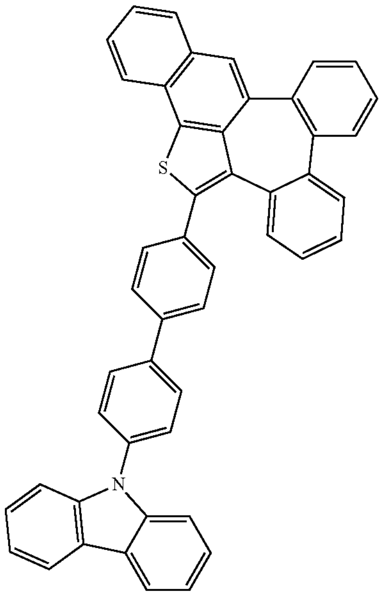
C-181
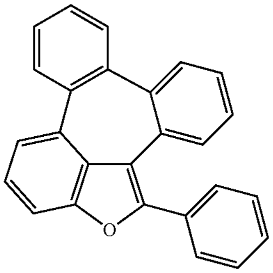
C-182
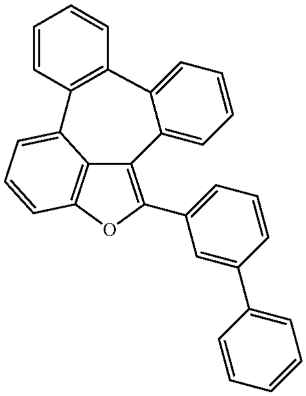
C-183
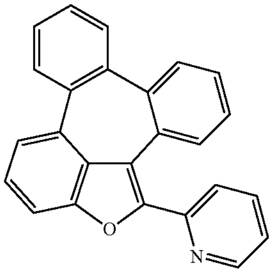

-continued
C-184
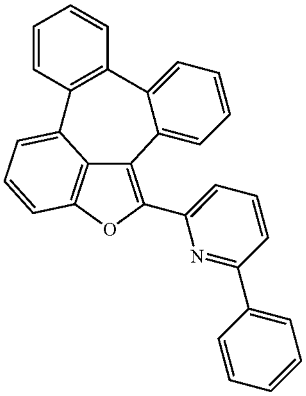
C-185
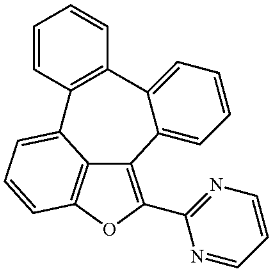
C-186
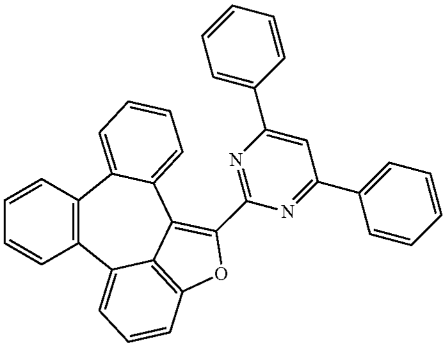
C-187
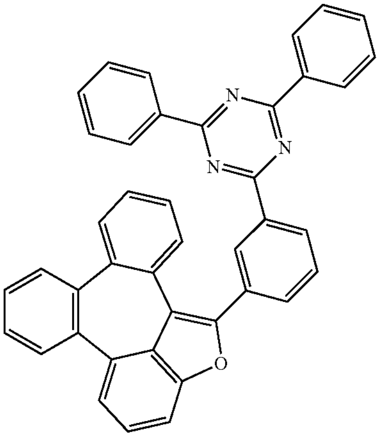
-continued
C-188
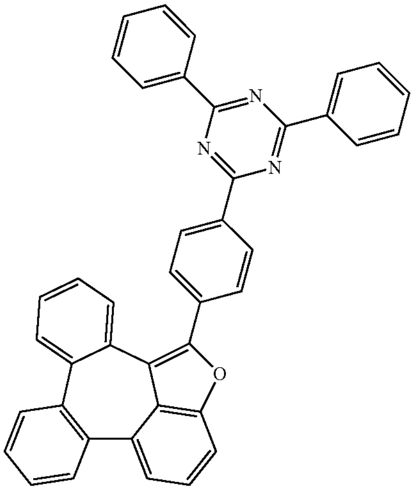
C-189
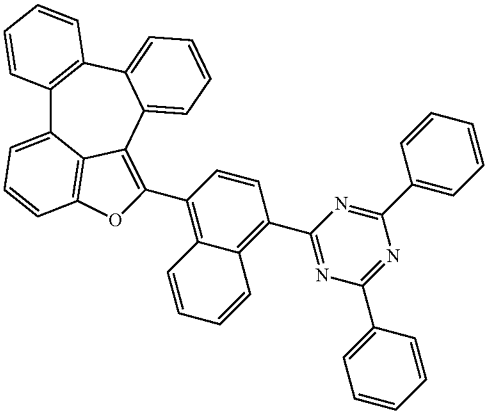
C-190
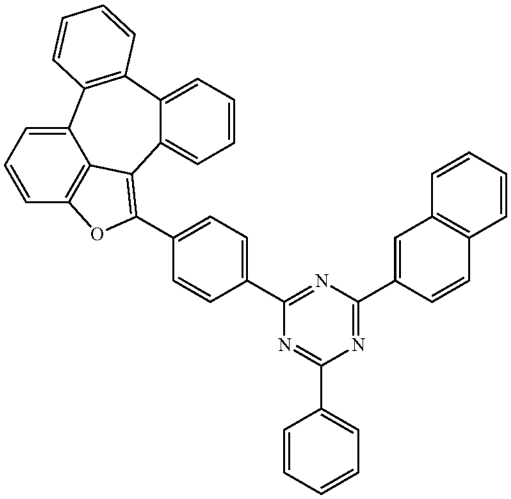

-continued
C-191
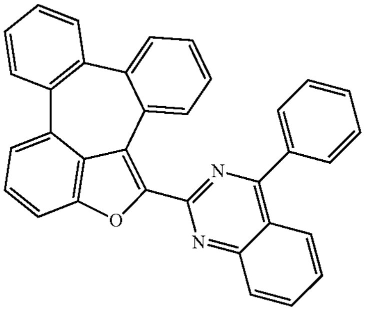
C-192
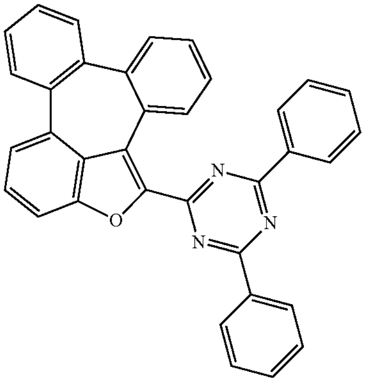
C-193
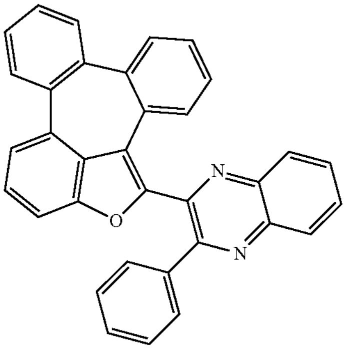
C-194
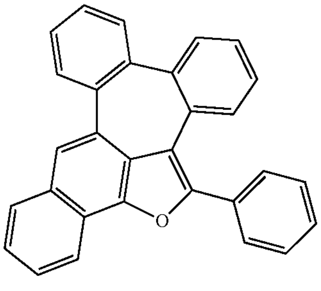
-continued
C-195
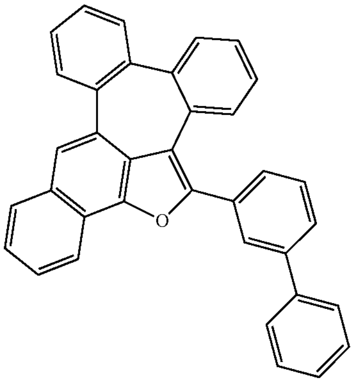
C-196
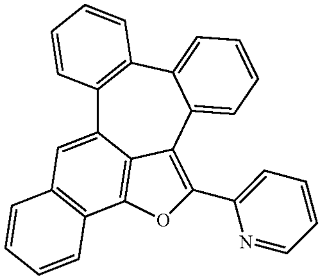
C-197
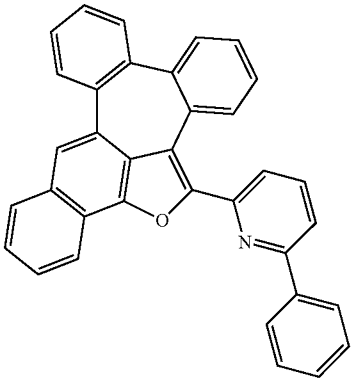
C-198
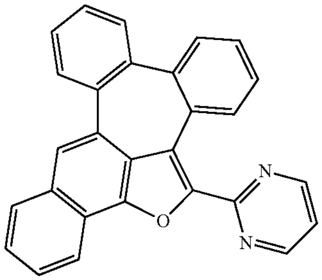

-continued
C-199
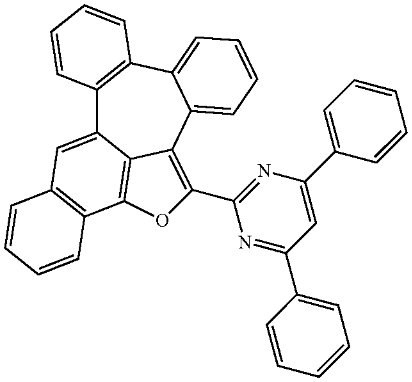
C-200
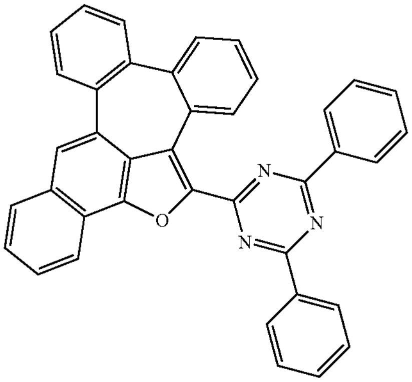
C-201
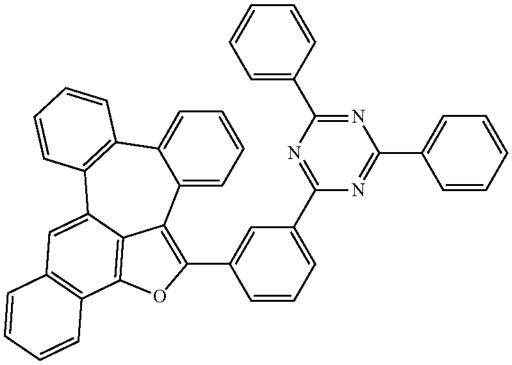
-continued
C-202
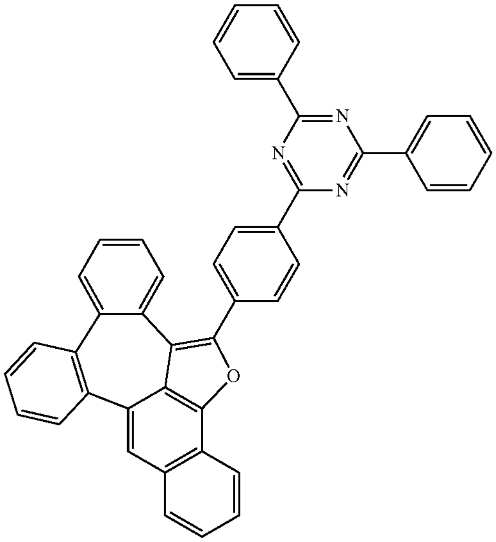
C-203
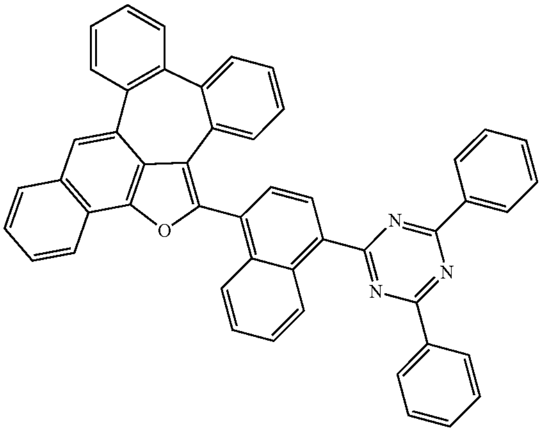
C-204
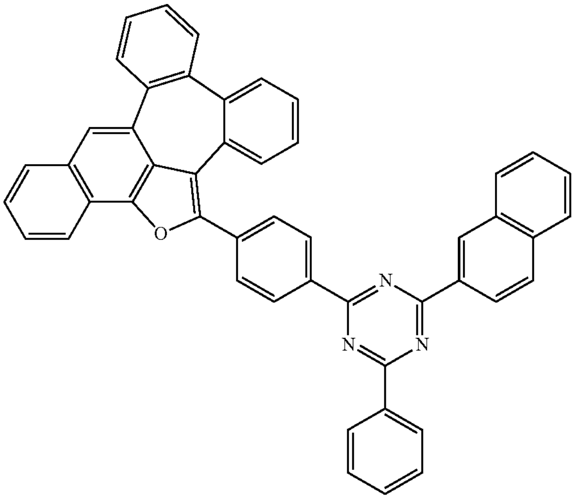

-continued
C-205
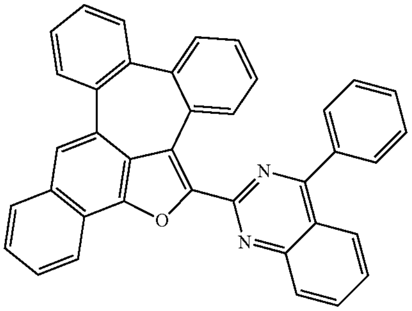
C-206
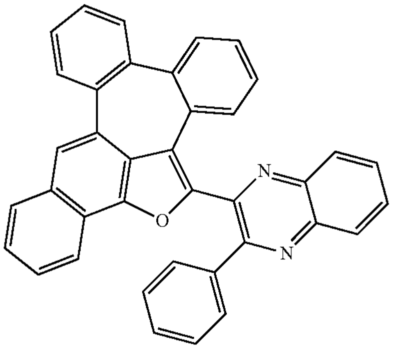
C-207
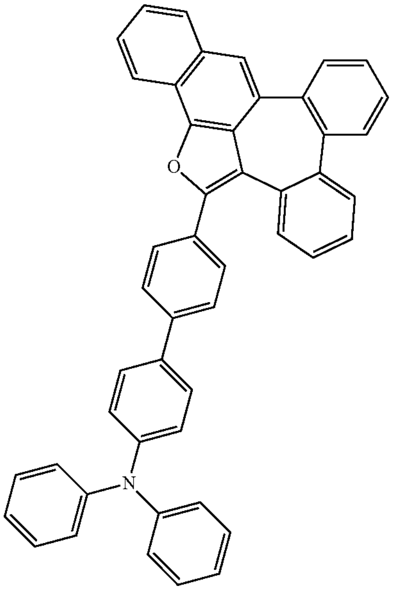
-continued
C-208
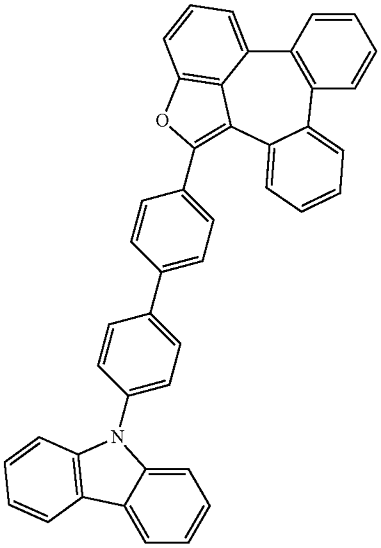
C-209
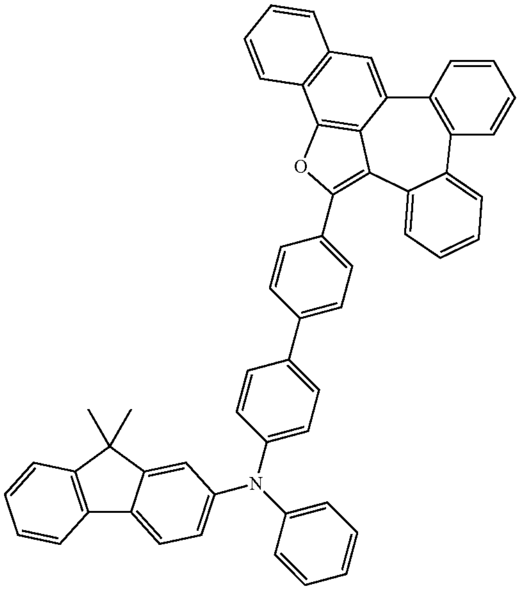

-continued
C-210
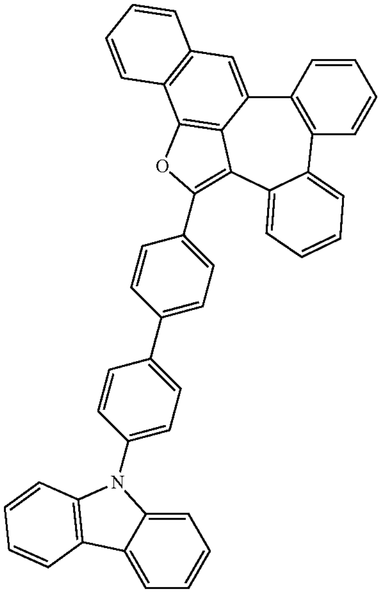
C-211
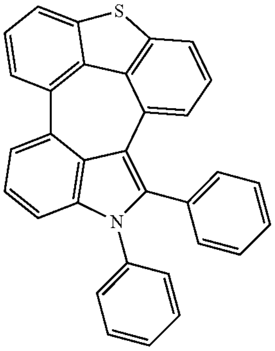
C-212
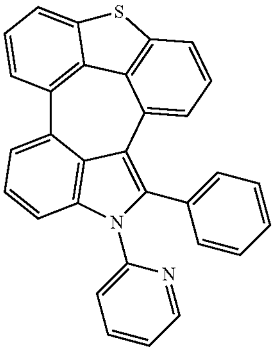
-continued
C-213
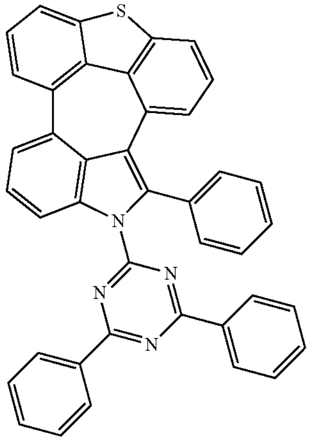
C-214
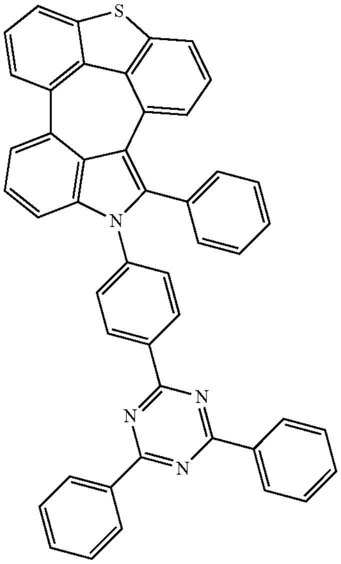
C-215
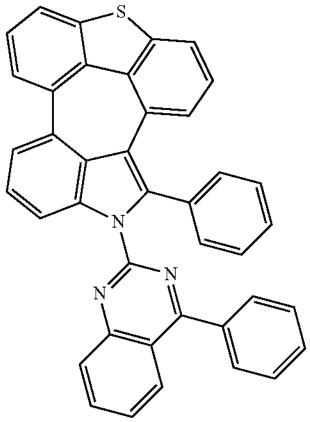

-continued
C-216
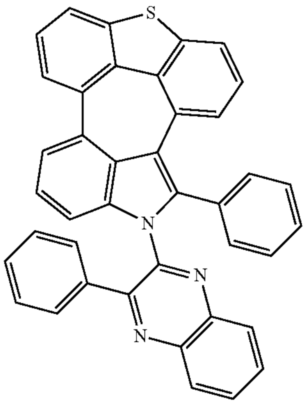
C-217
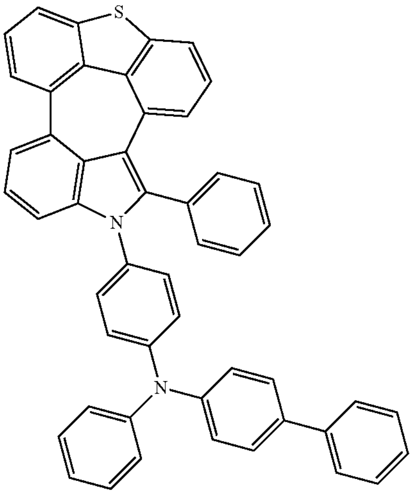
C-218
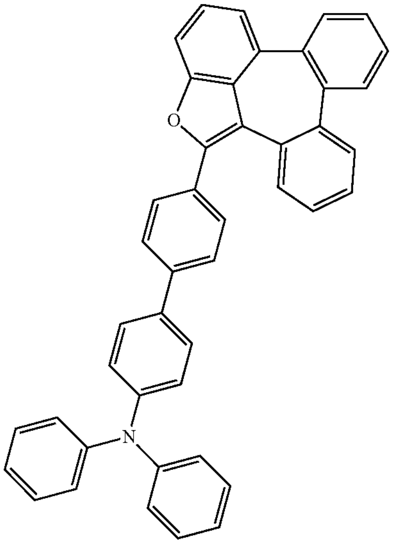
-continued
C-219
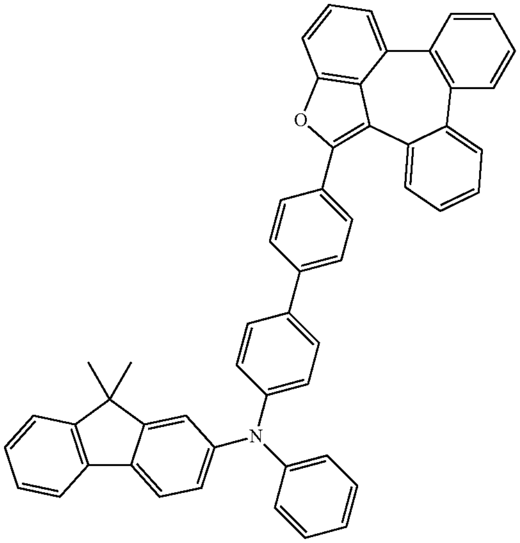
C-220
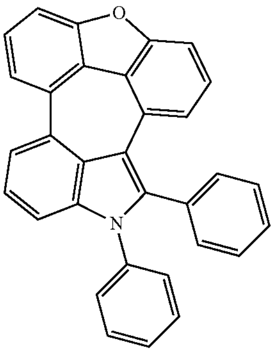
C-221
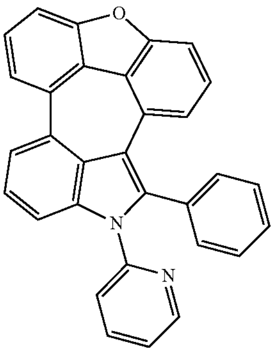

-continued
C-222
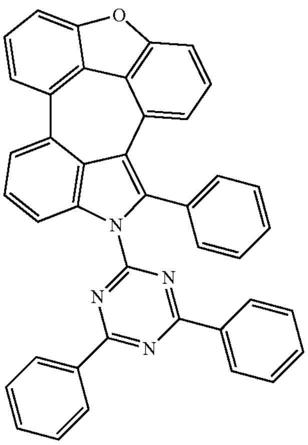
C-223
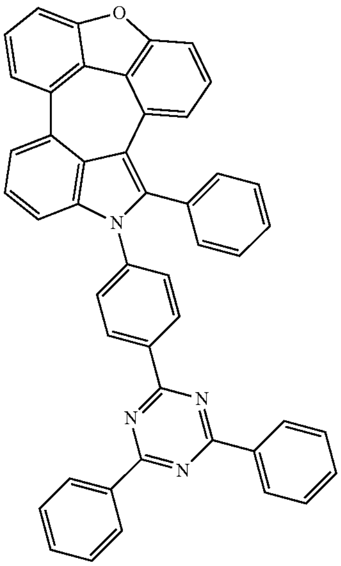
C-224
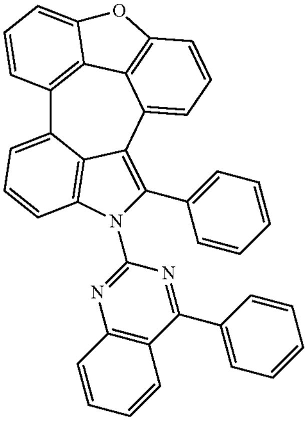
-continued
C-225
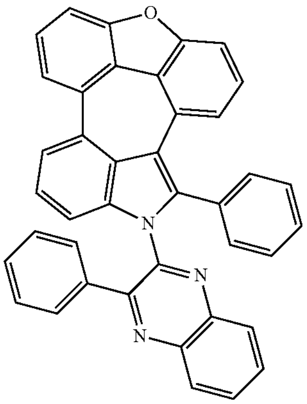
C-226
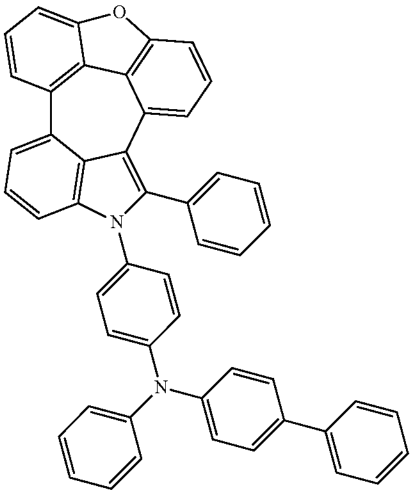
C-227
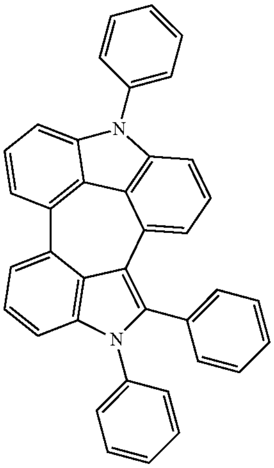

-continued
C-228
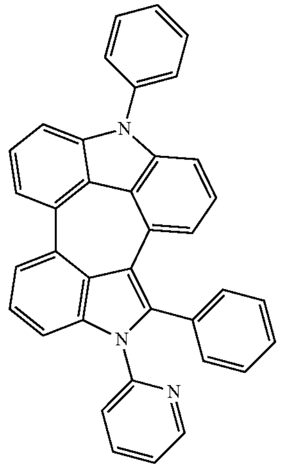
C-229
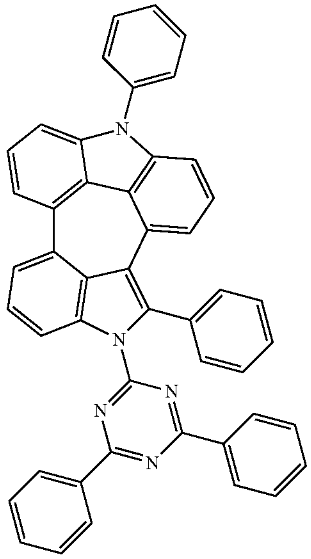
C-230
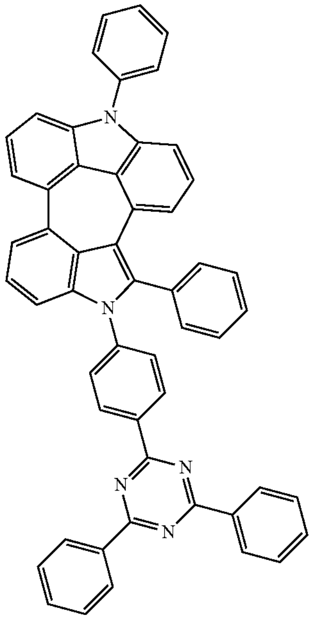
-continued
C-231
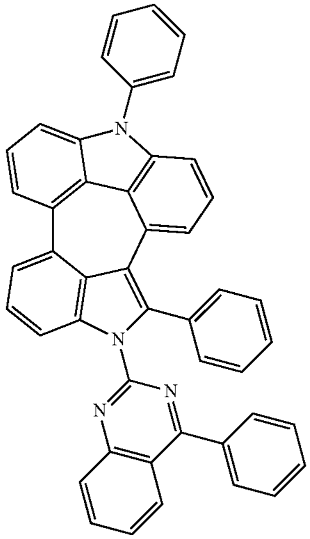
C-232
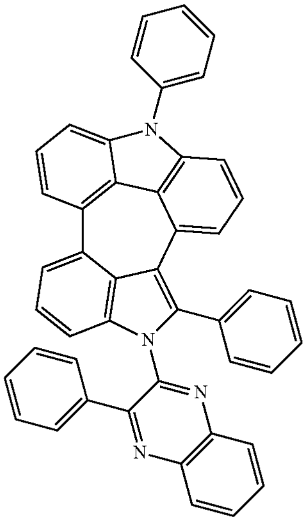

-continued
C-233
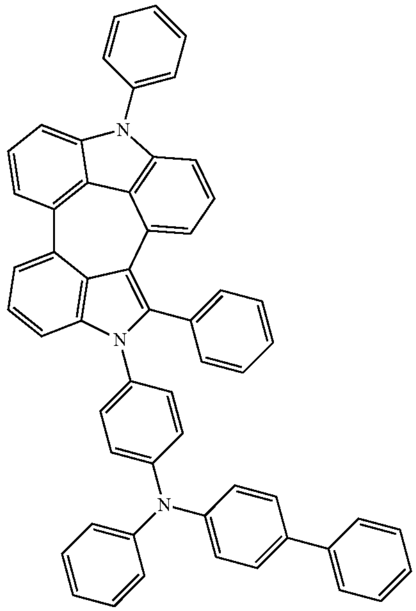
C-234
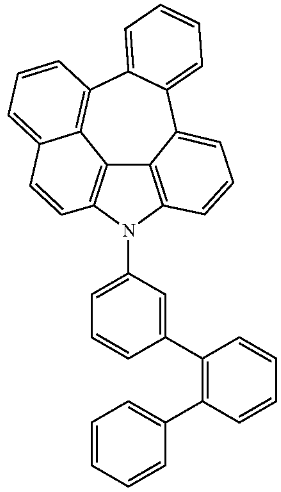
C-235
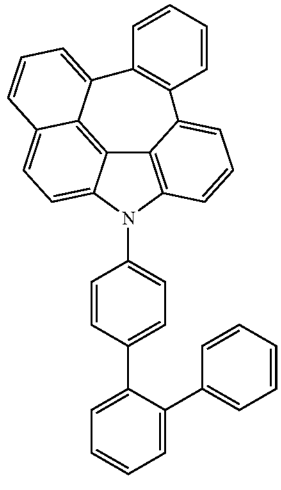
-continued
C-236
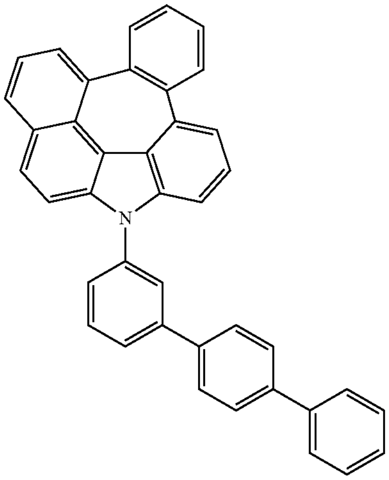
C-237
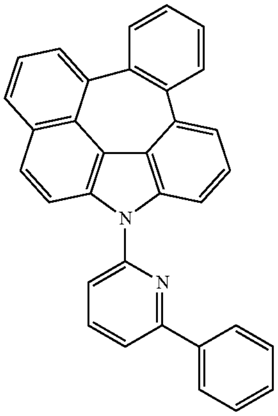
C-238
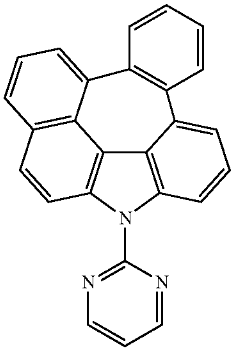

-continued
C-239
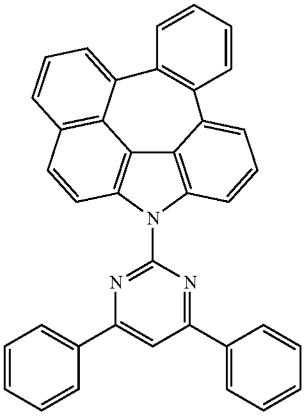
C-240
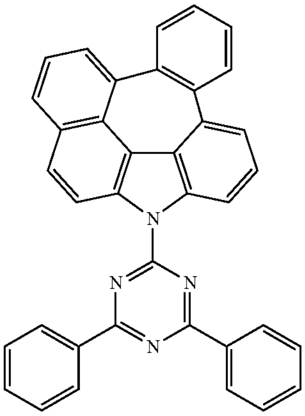
C-241
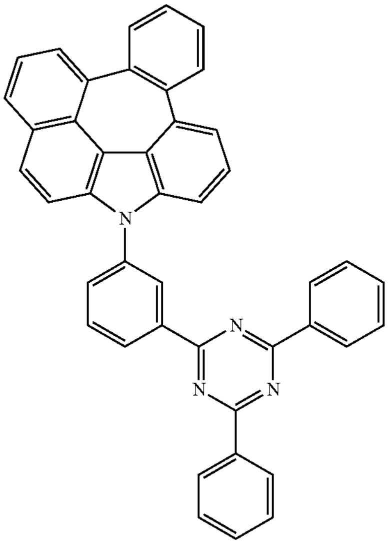
-continued
C-242
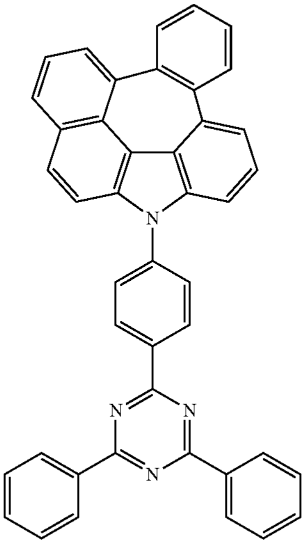
C-243
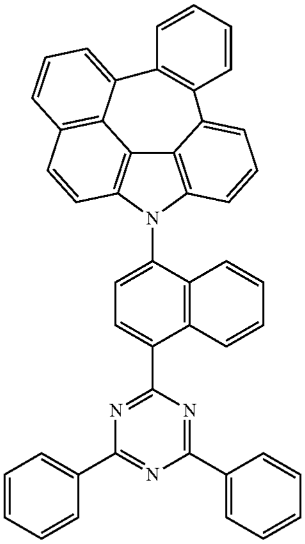

-continued
C-244
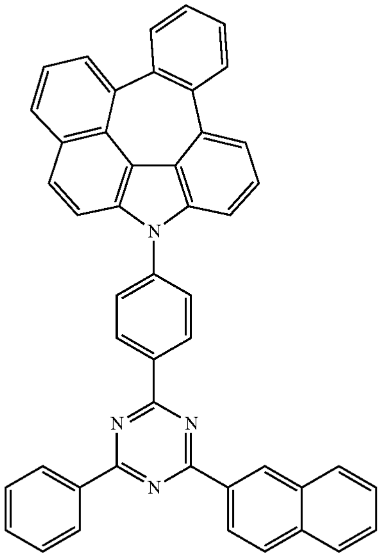
C-245
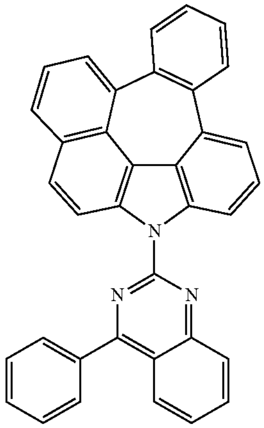
C-246
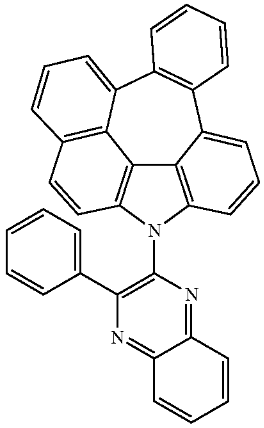
C-247
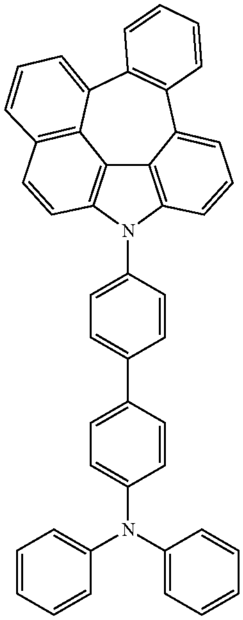
C-248
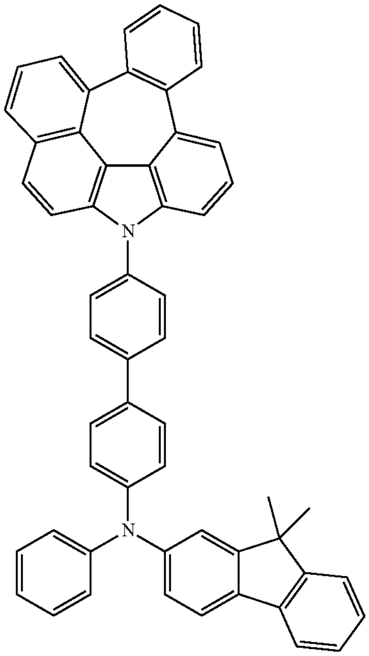

-continued
C-249
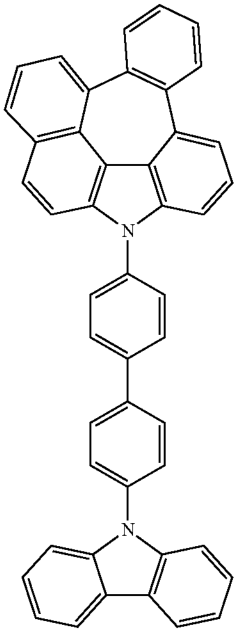
C-250
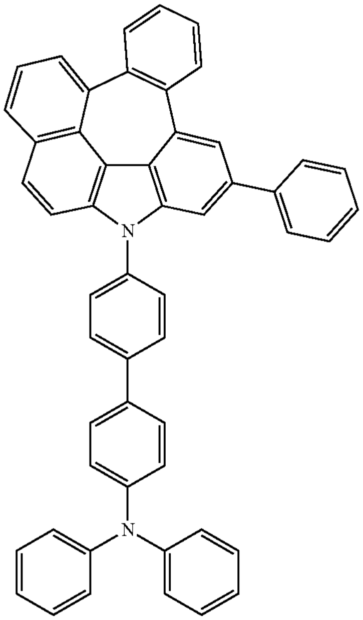
-continued
C-251
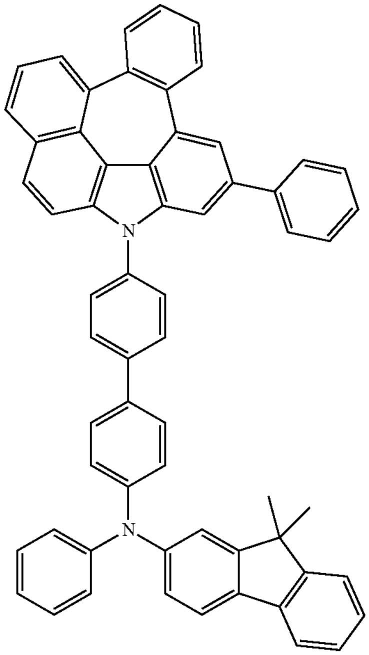
C-252
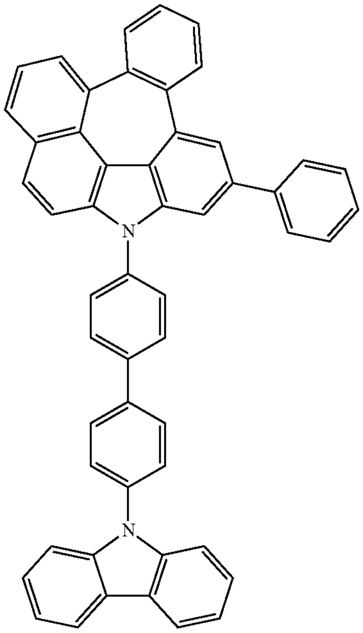

-continued
C-253
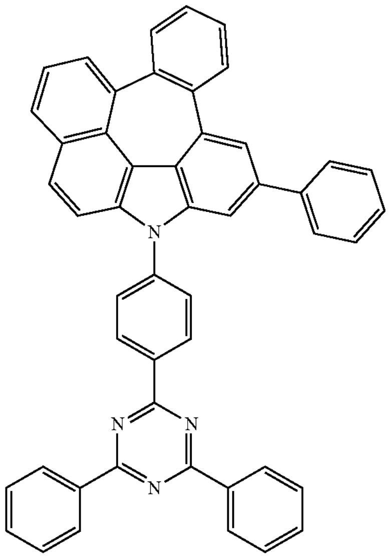
C-254
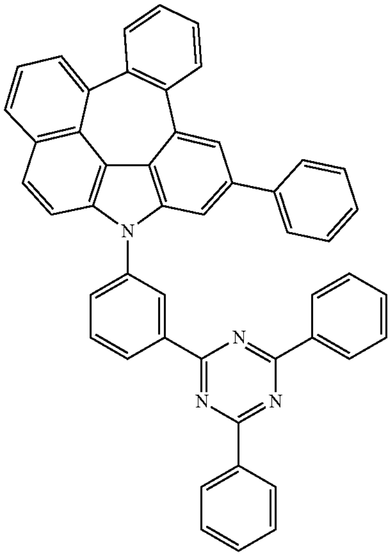
C-255
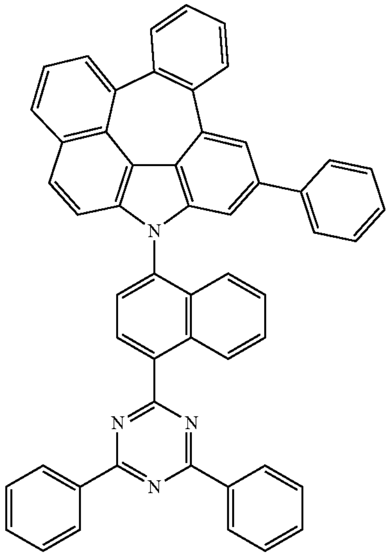
-continued
C-256
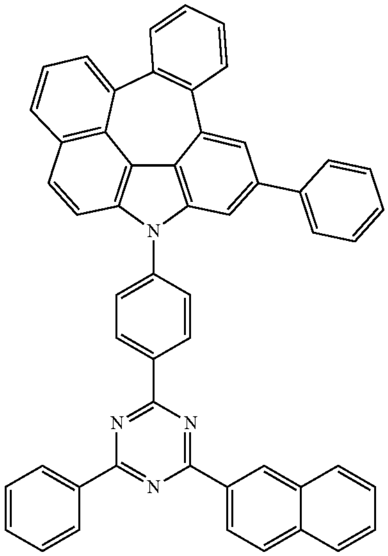
C-257
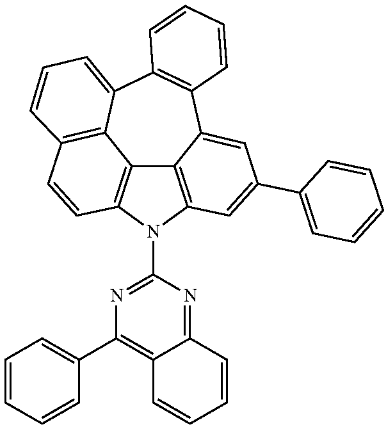
C-258
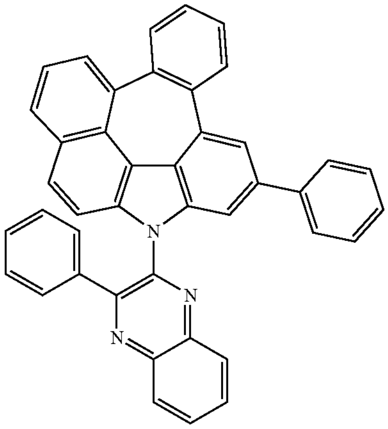

-continued
C-259
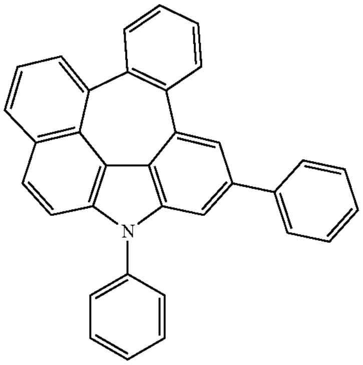
C-260
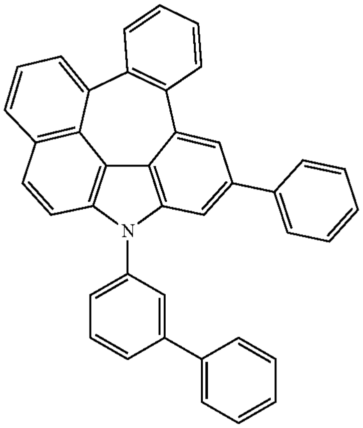
C-261
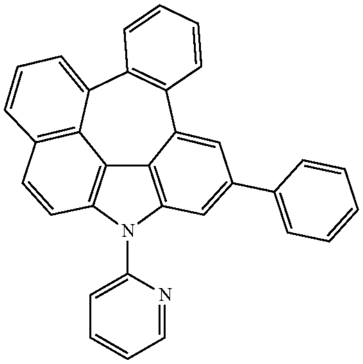
C-262
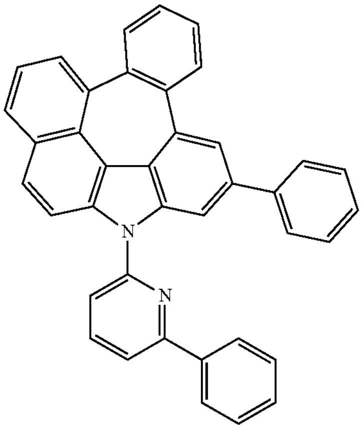
-continued
C-263
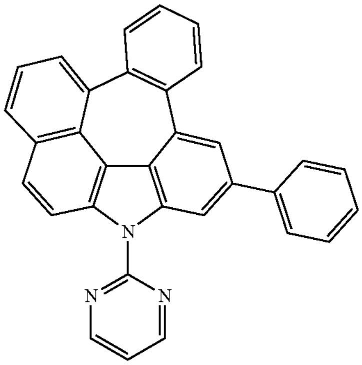
C-264
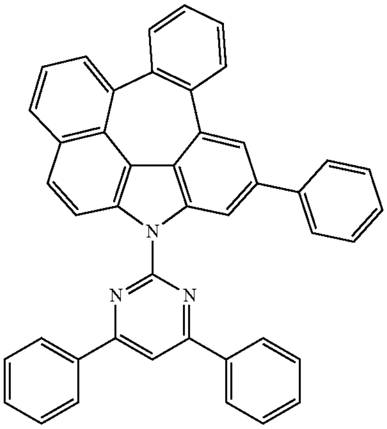
C-265
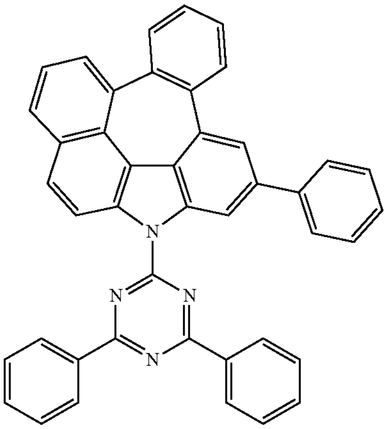
C-266
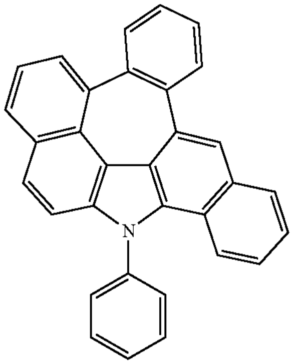

-continued
C-267
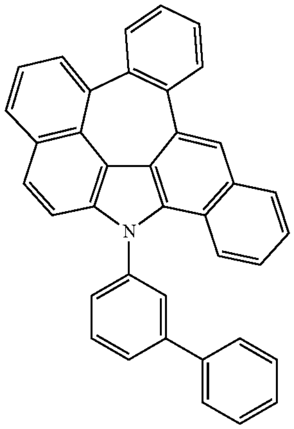
C-268
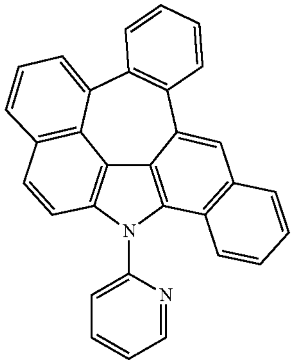
C-269
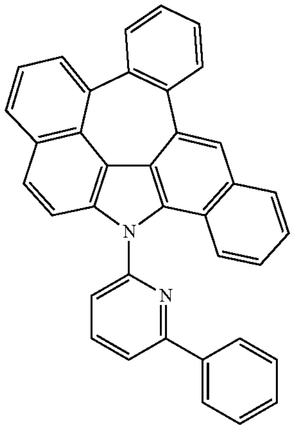
C-270
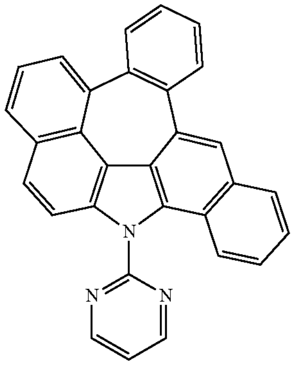
-continued
C-271
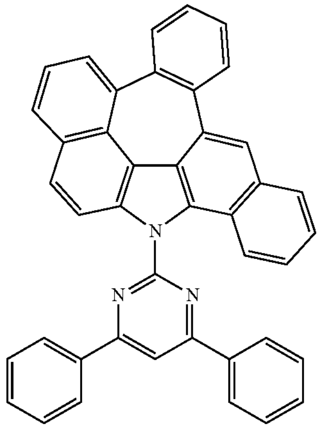
C-272
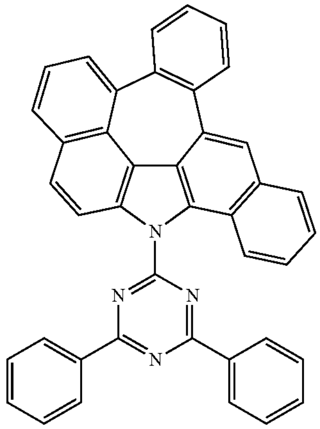
C-273
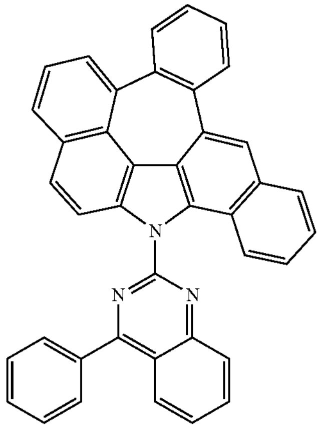

-continued
C-274
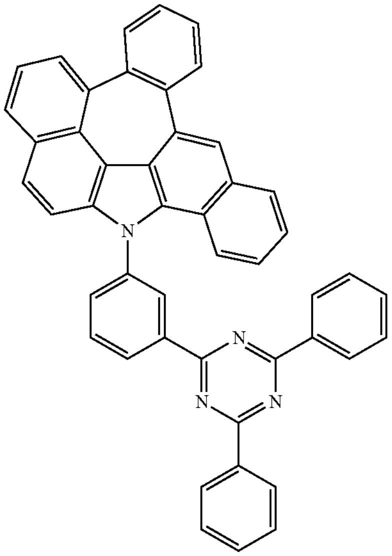
C-275
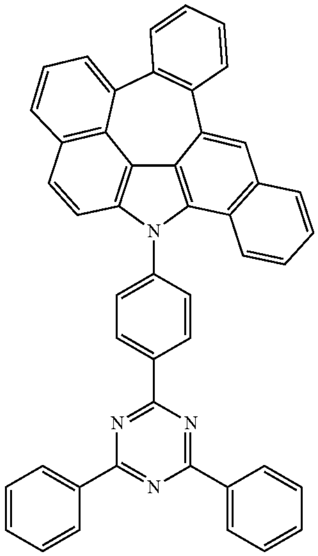
C-276
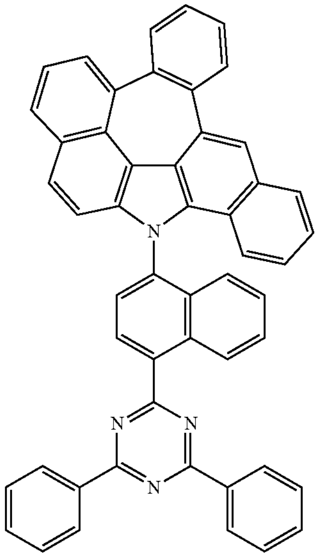
-continued
C-277
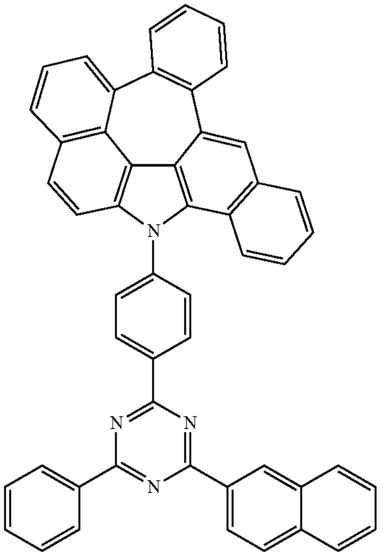
C-278
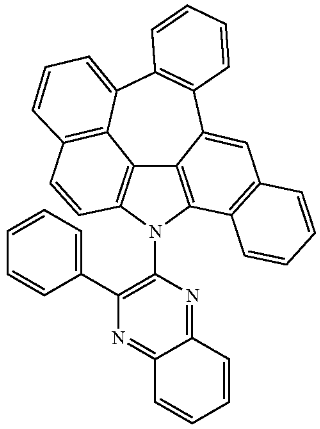
C-279
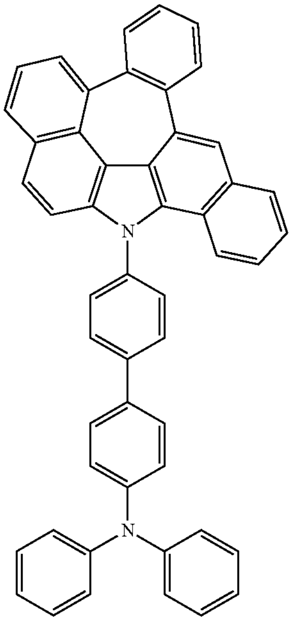

-continued
C-280
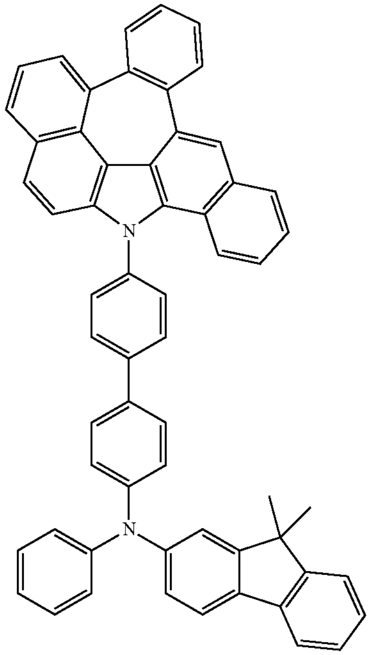
C-281
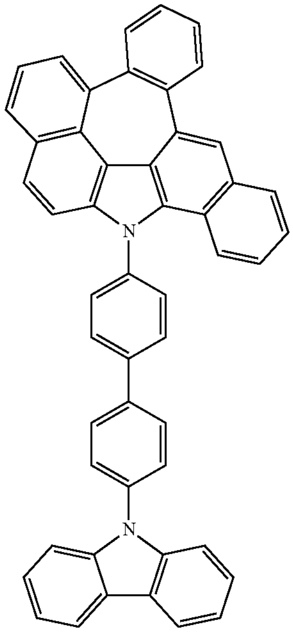
-continued
C-282
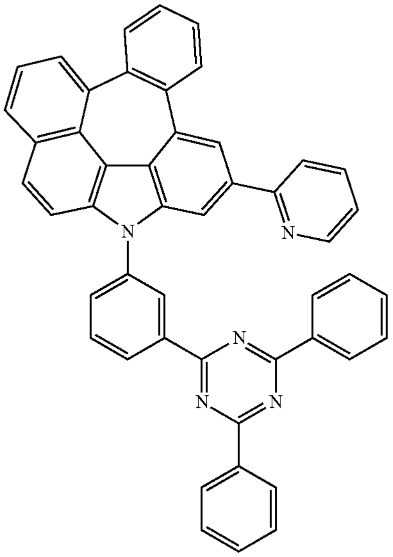
C-283
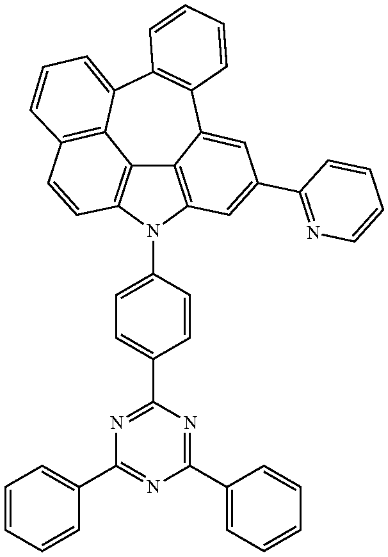
C-284
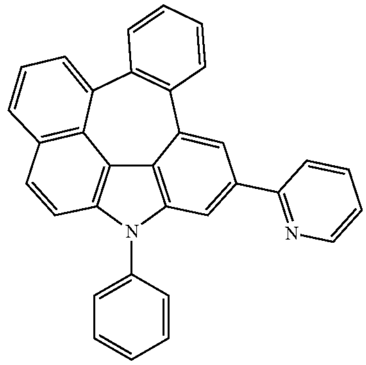

-continued
C-285
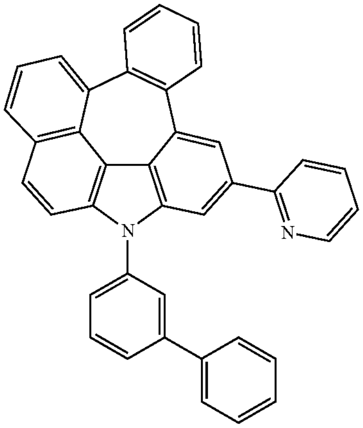
C-286
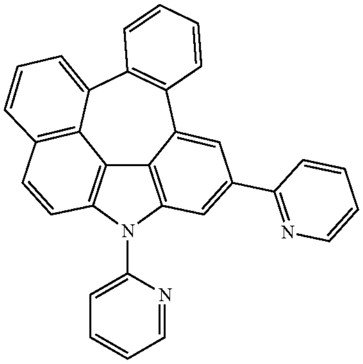
C-287
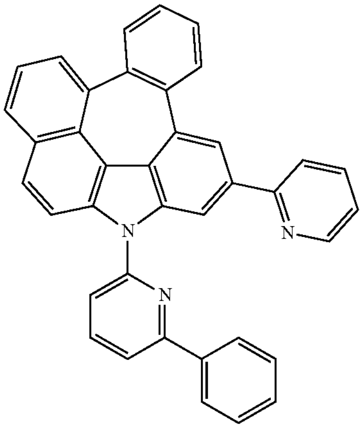
C-288
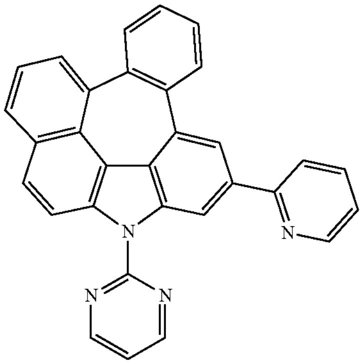
-continued
C-289
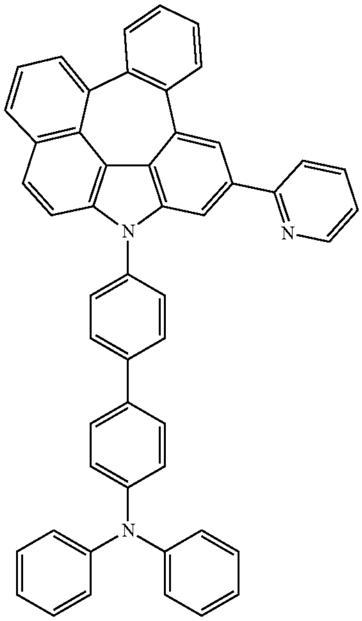
C-290
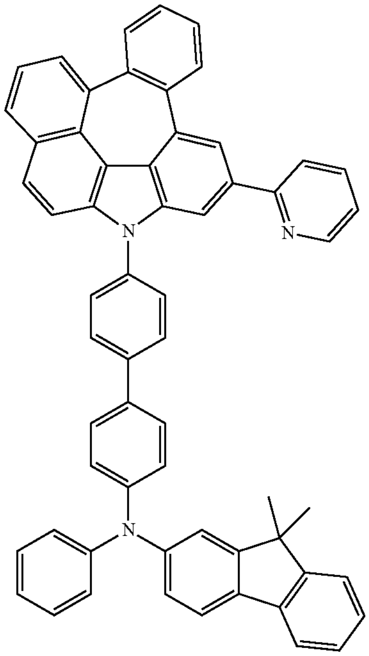

-continued
C-291
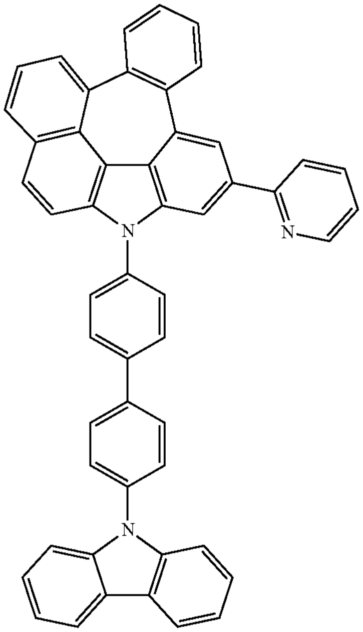
C-292
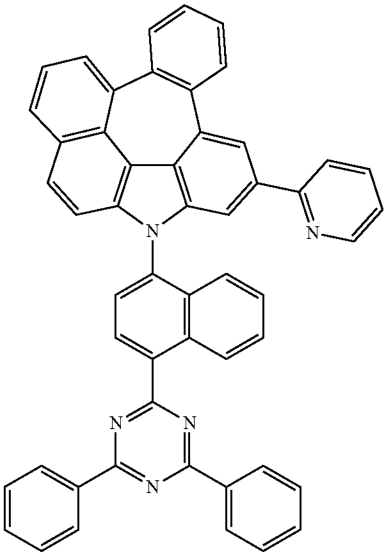
-continued
C-293
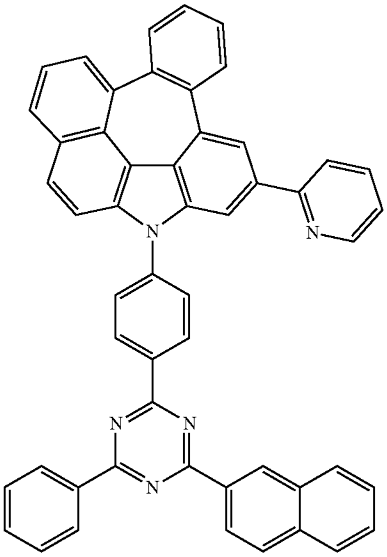
C-294
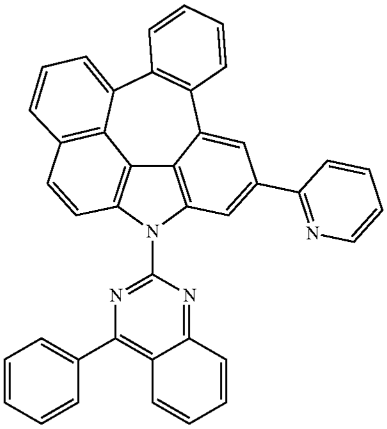
C-295
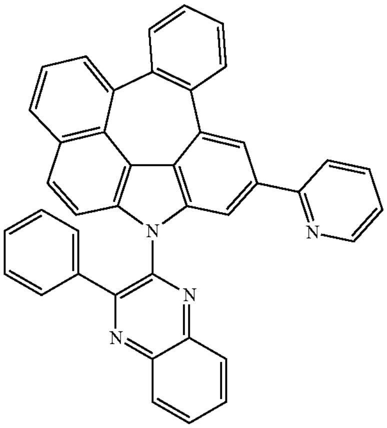

-continued
C-296
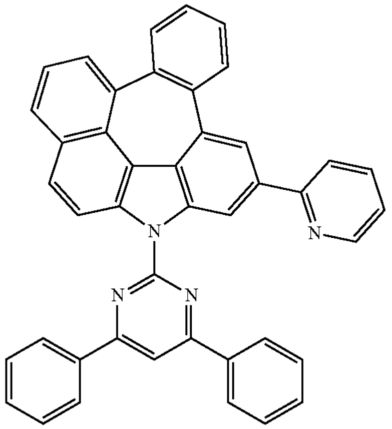
C-297
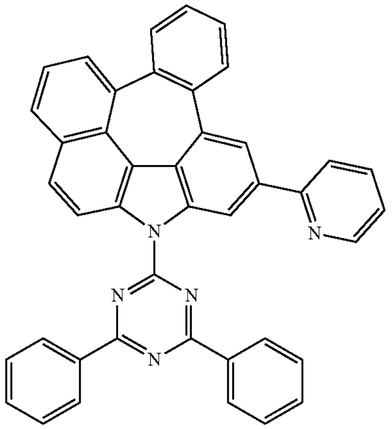
C-298
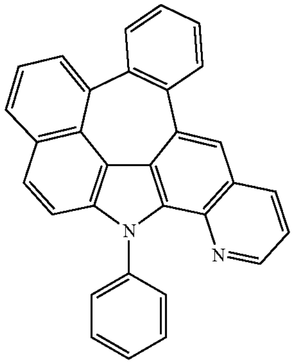
-continued
C-299
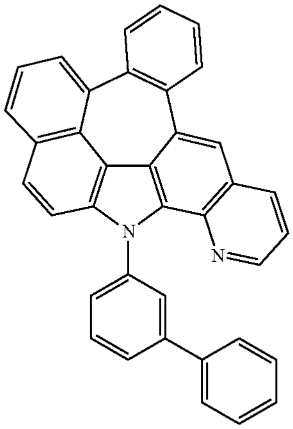
C-300
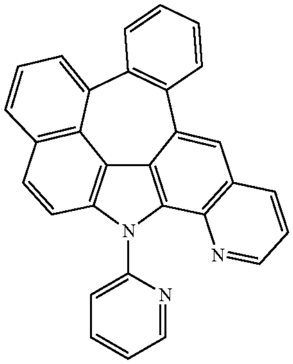
C-301
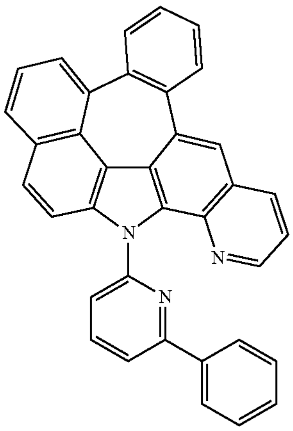
C-302
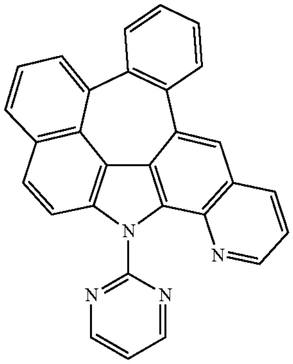

-continued
C-303
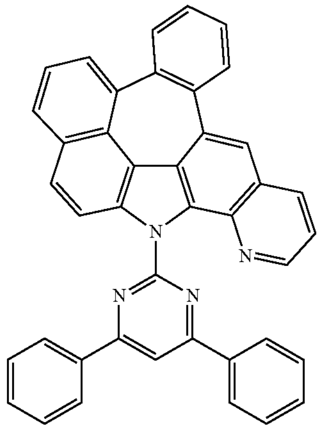
C-304
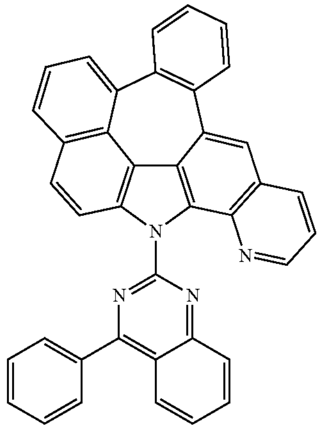
C-305
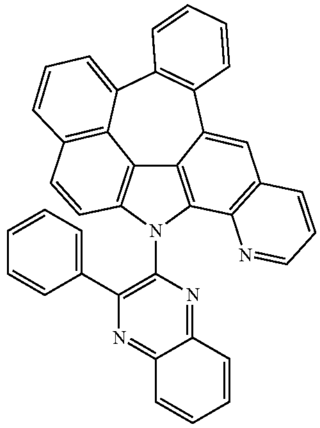
-continued
C-306
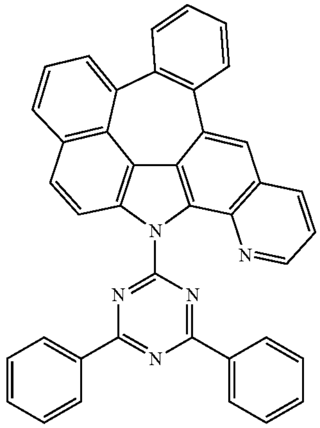
C-307
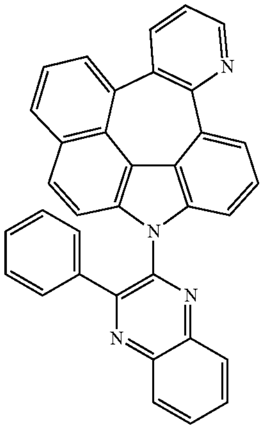
C-308
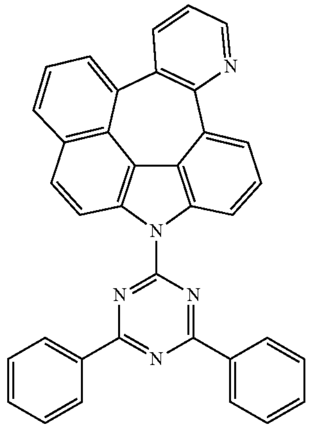

-continued
C-309
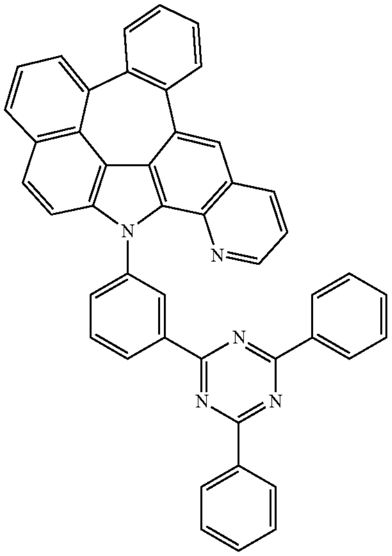
C-310
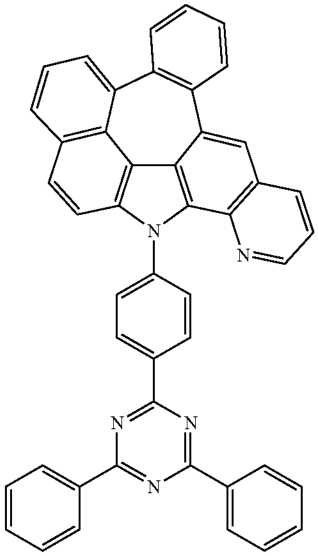
C-311
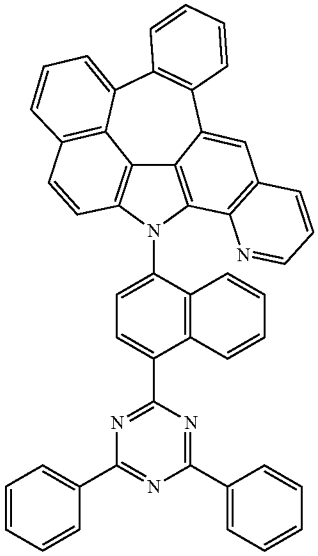
-continued
C-312
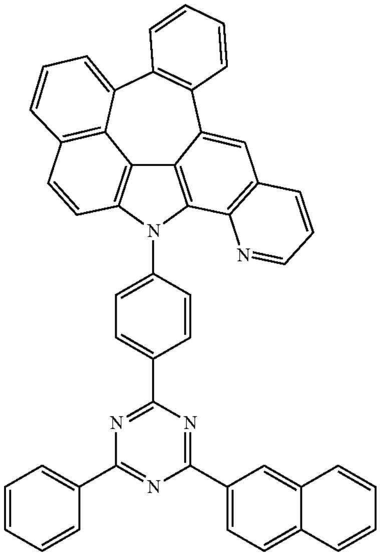
C-313
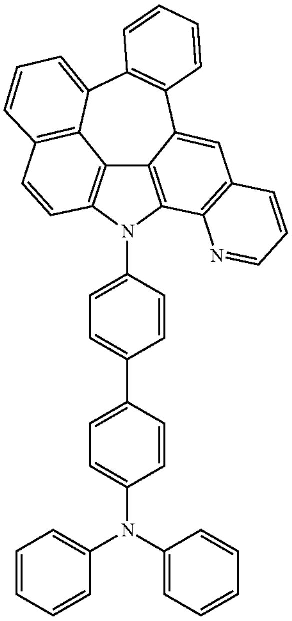

-continued
C-314
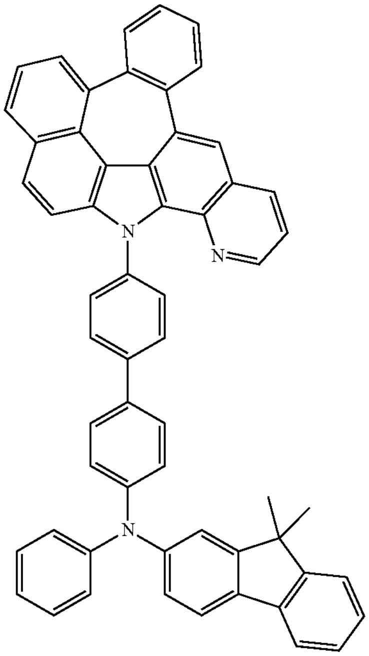
C-315
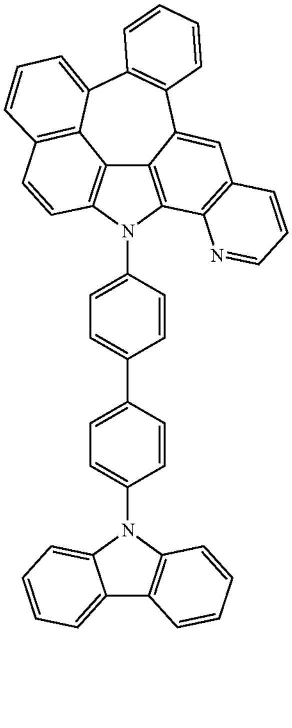
-continued
C-316
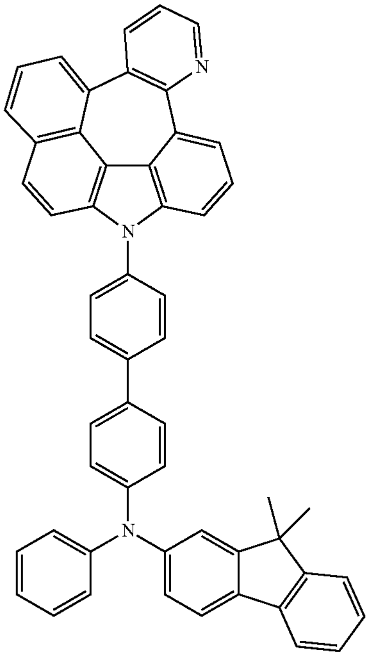
C-317
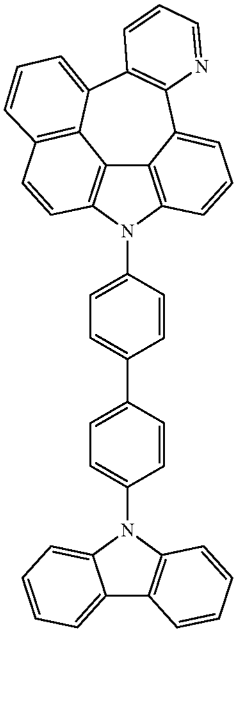

-continued
C-318
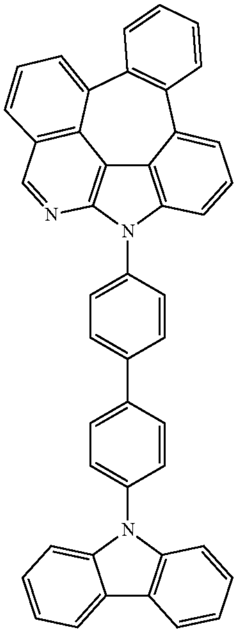
C-319
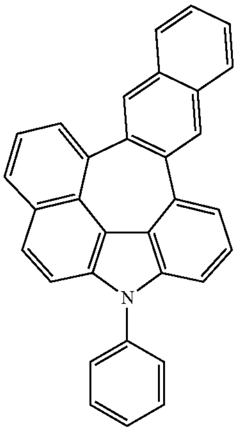
C-320
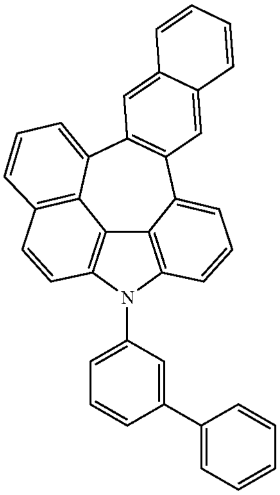
-continued
C-321
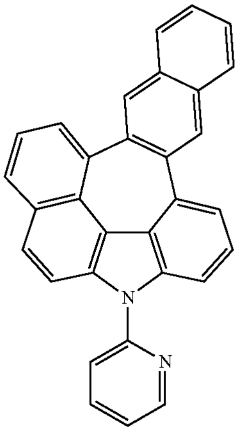
C-322
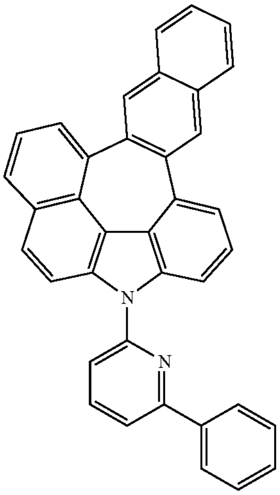
C-323
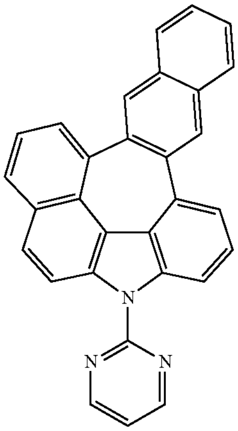

-continued
C-324
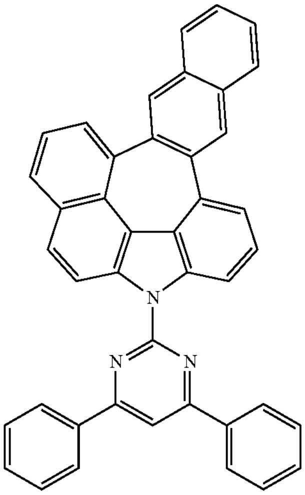
C-325
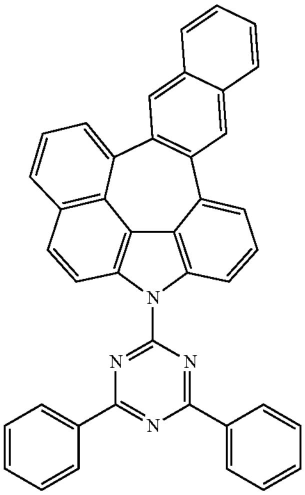
C-326
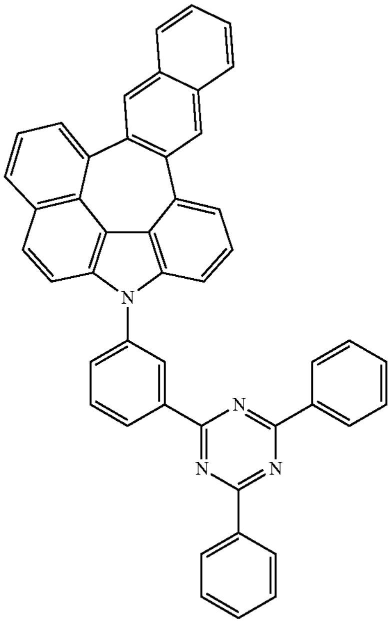
-continued
C-327
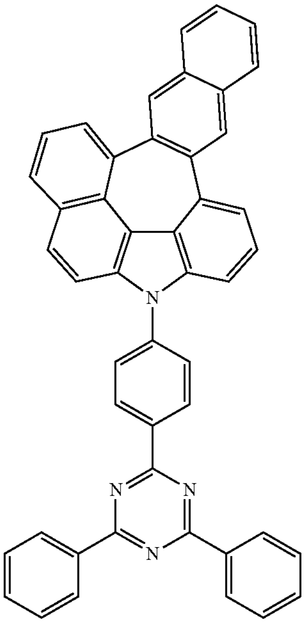
C-328
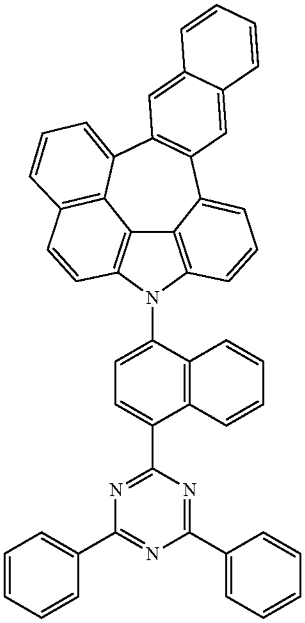

-continued
C-329
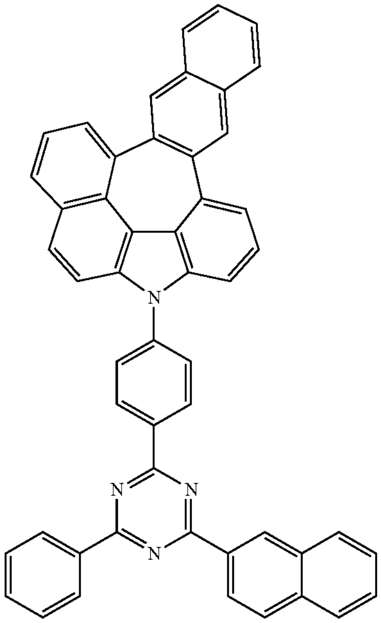
C-330
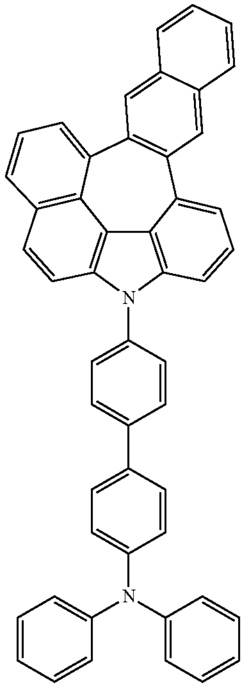
-continued
C-331
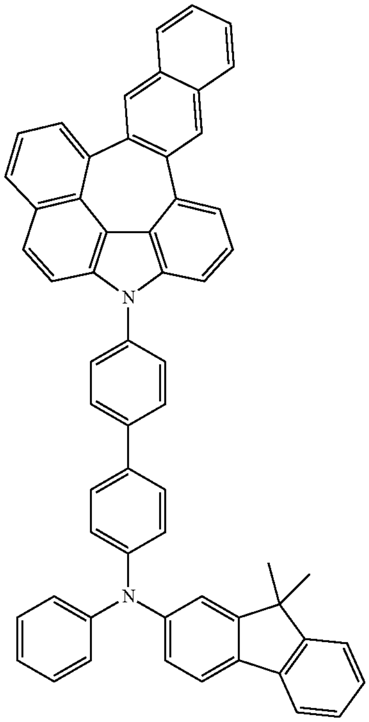
C-332
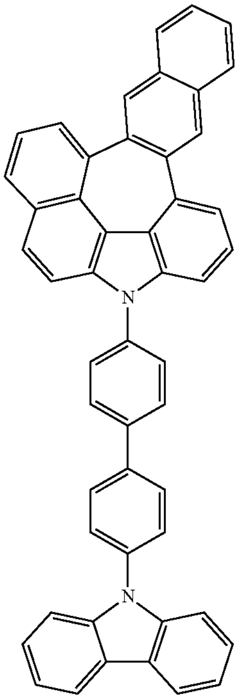

-continued
C-333
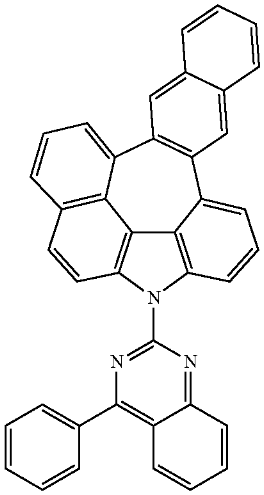
C-334
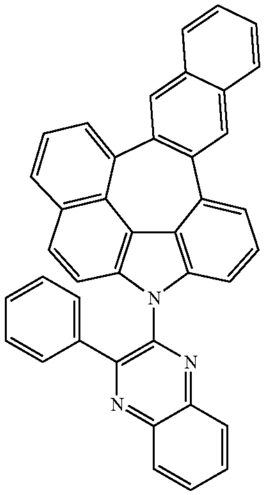
C-335
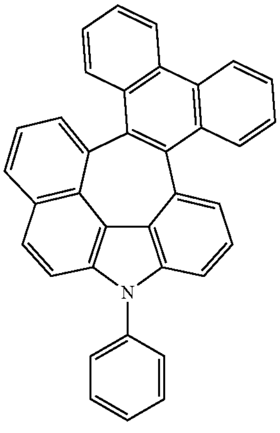
-continued
C-336
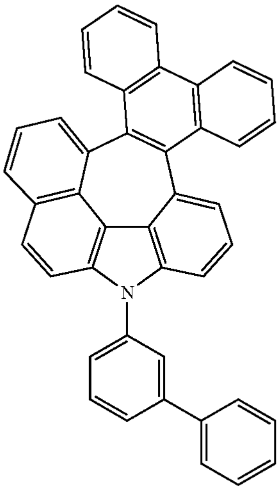
C-337
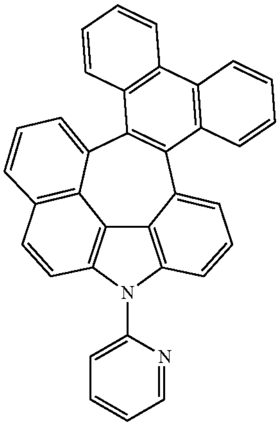
C-338
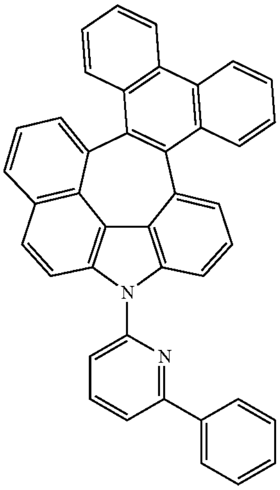

-continued
C-339
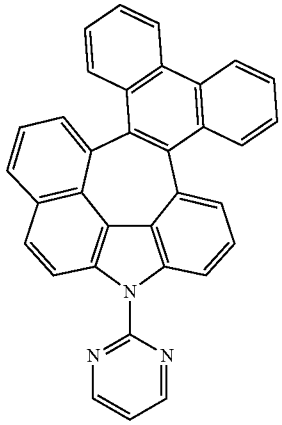
C-340
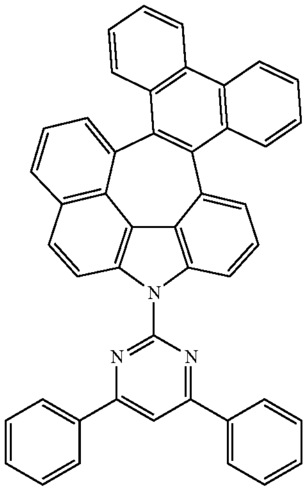
C-341
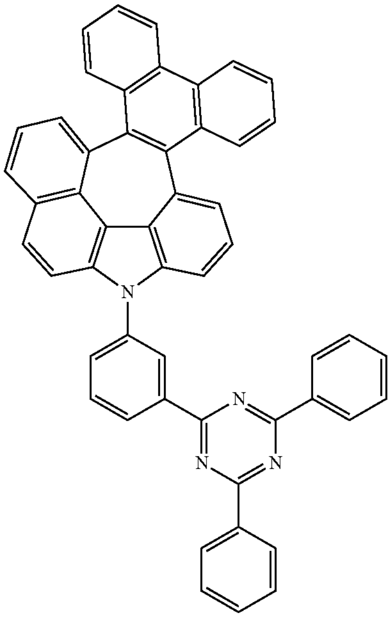
-continued
C-342
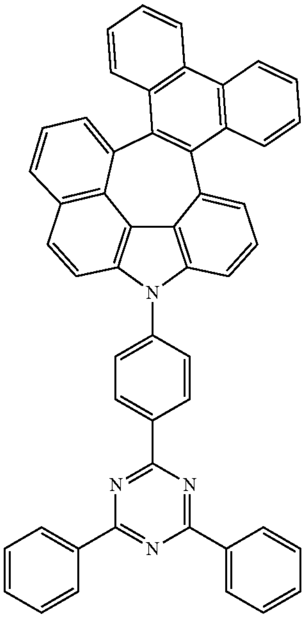
C-343
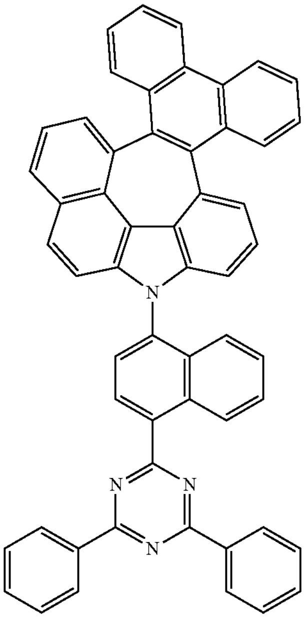

-continued
C-344
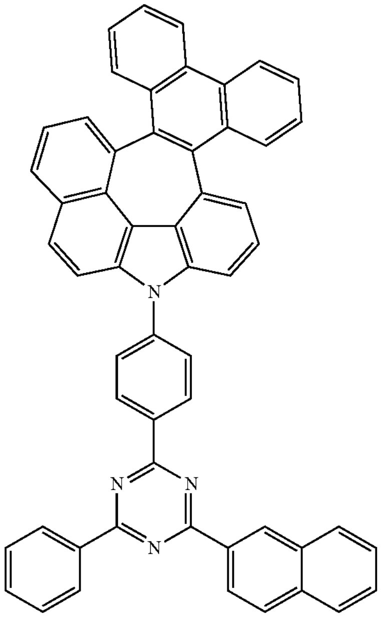
C-345
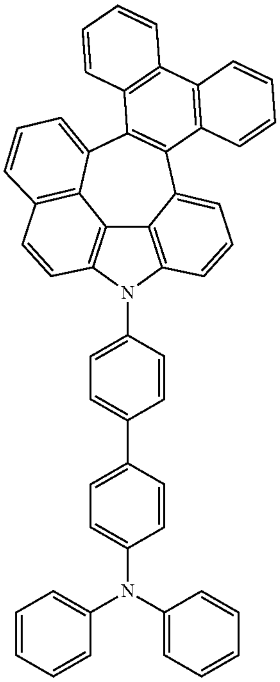
-continued
C-346
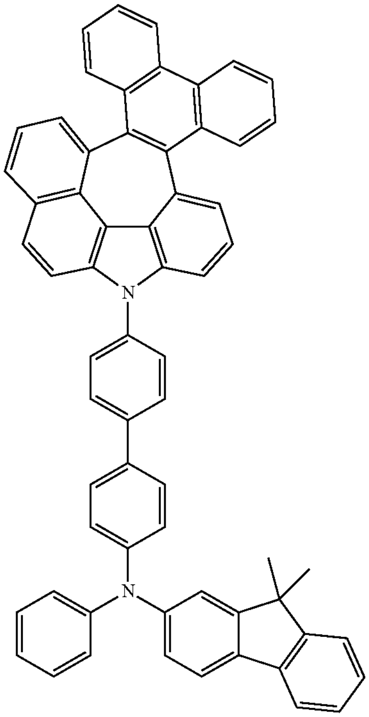
C-347
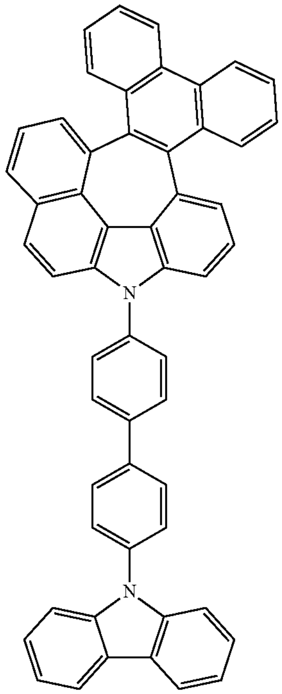

-continued
C-348
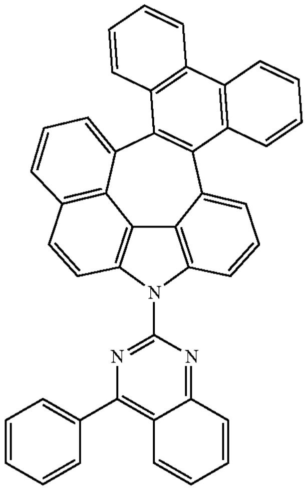
C-349
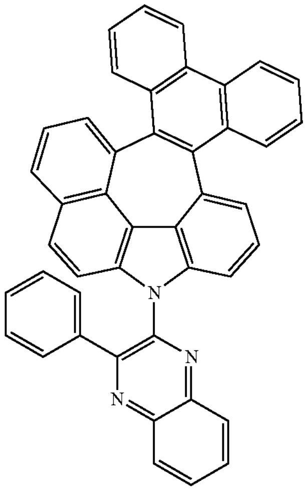
C-350
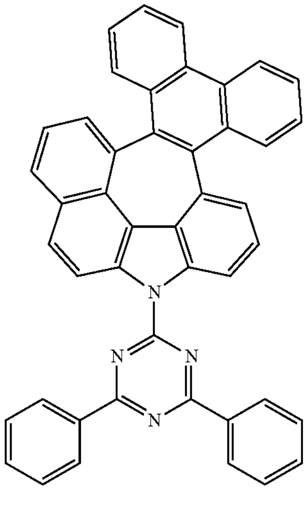
-continued
C-351
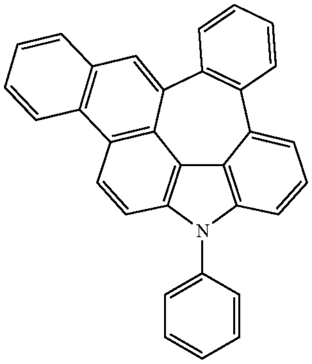
C-352
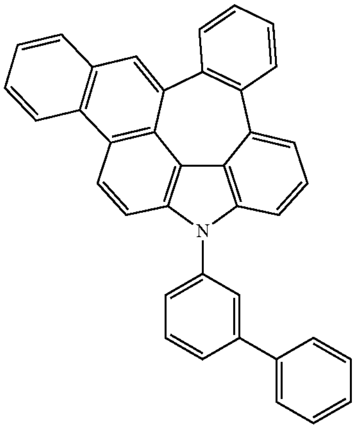
C-353
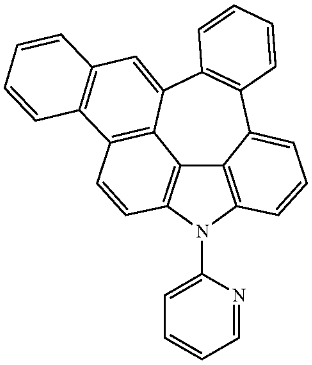
C-354
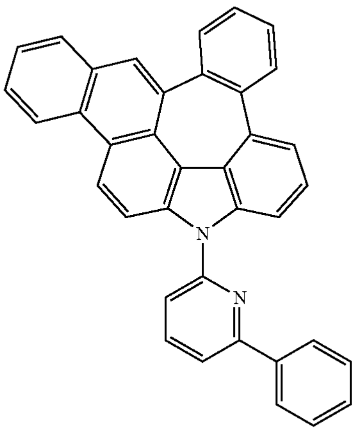

-continued
C-355
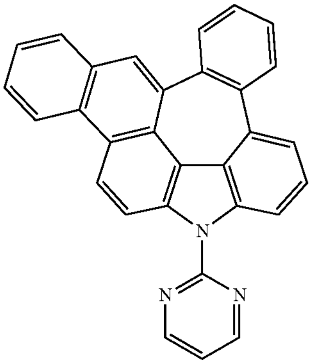
C-356
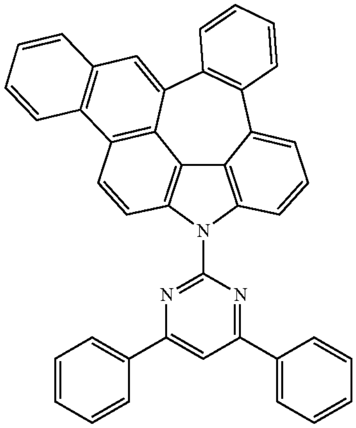
C-357
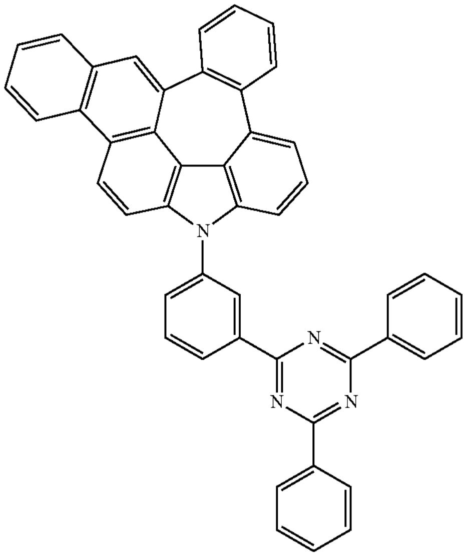
-continued
C-358
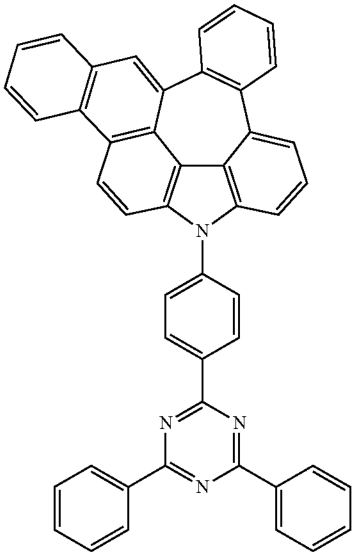
C-359
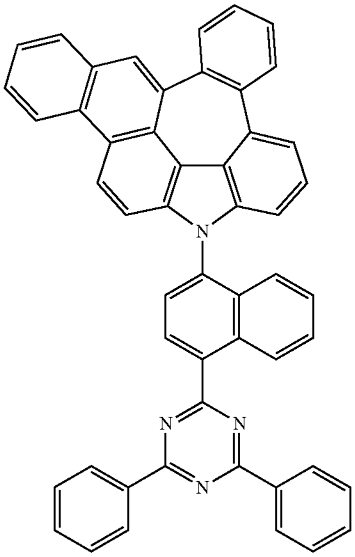

-continued
C-360
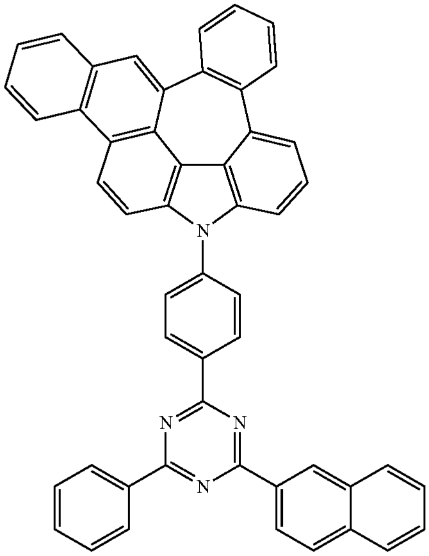
C-361
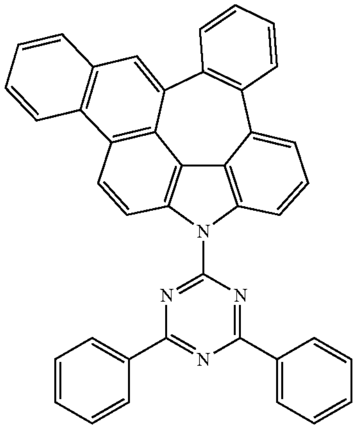
C-362
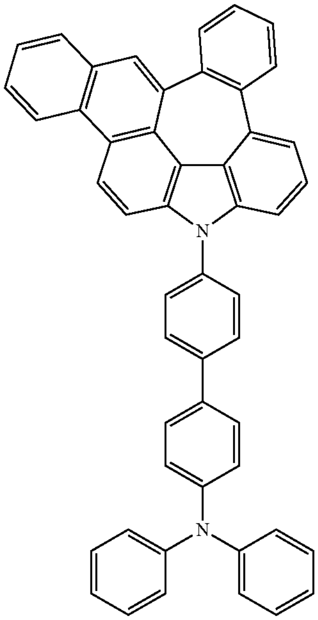
-continued
C-363
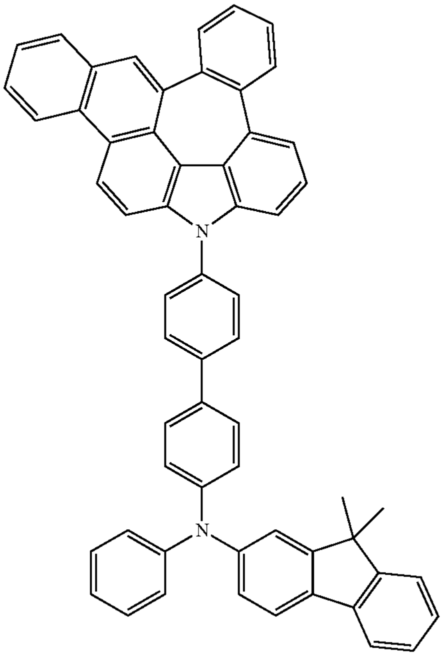
C-364
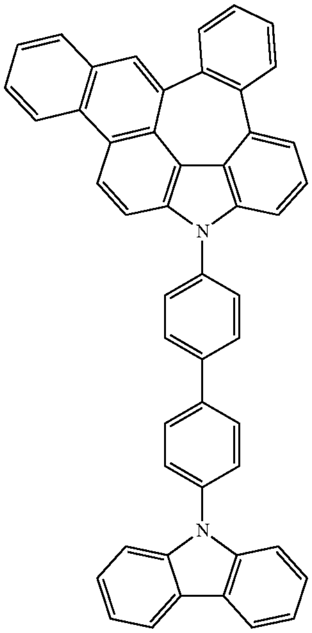

-continued
C-365
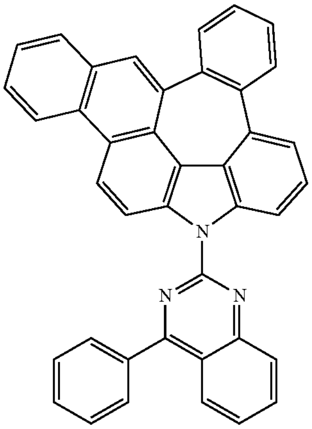
C-366
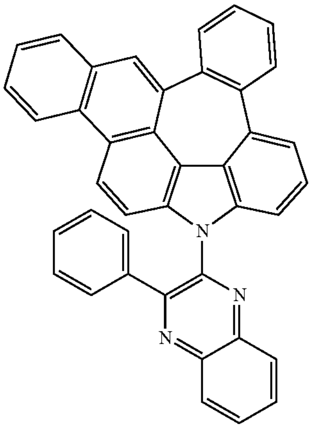
C-367
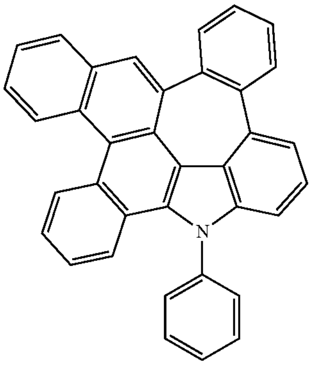
C-368
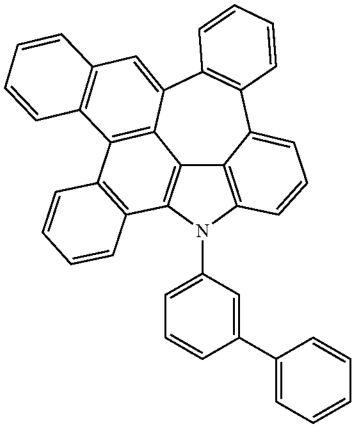
-continued
C-369
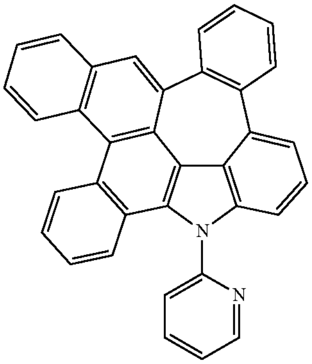
C-370
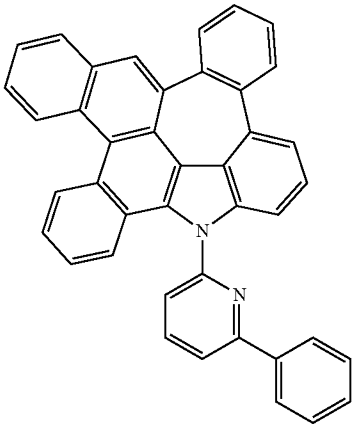
C-371
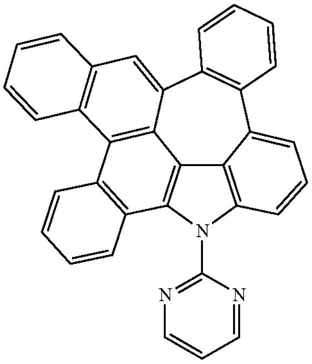
C-372
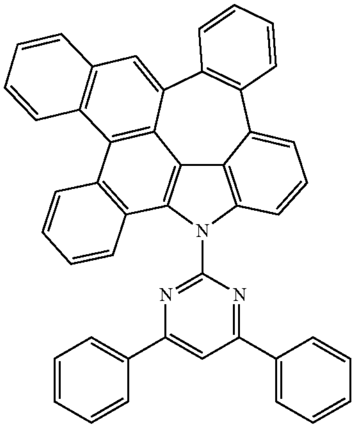

-continued
C-373
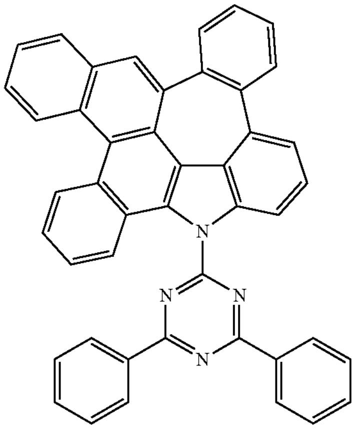
C-374
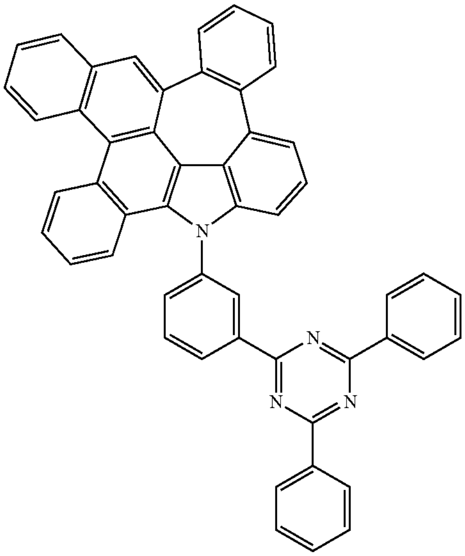
C-375
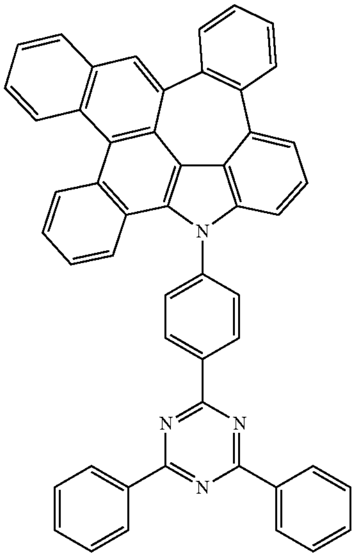
-continued
C-376
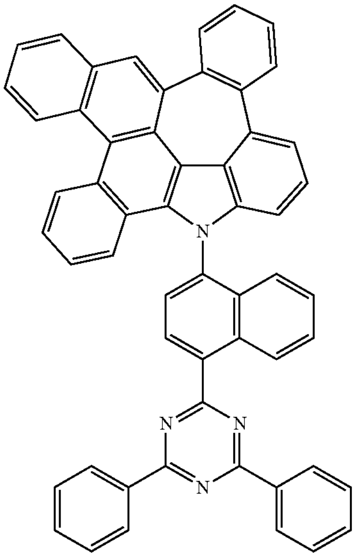
C-377
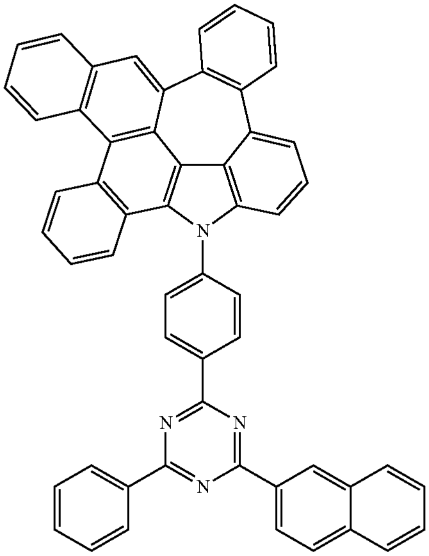
C-378
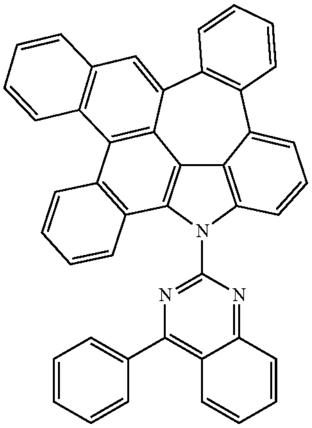

-continued
C-379
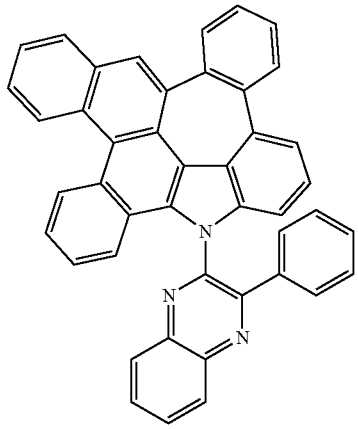
C-380
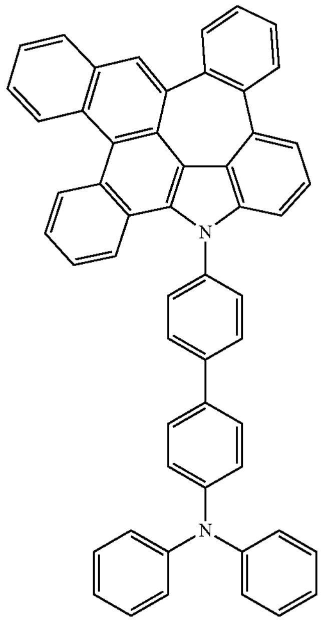
-continued
C-381
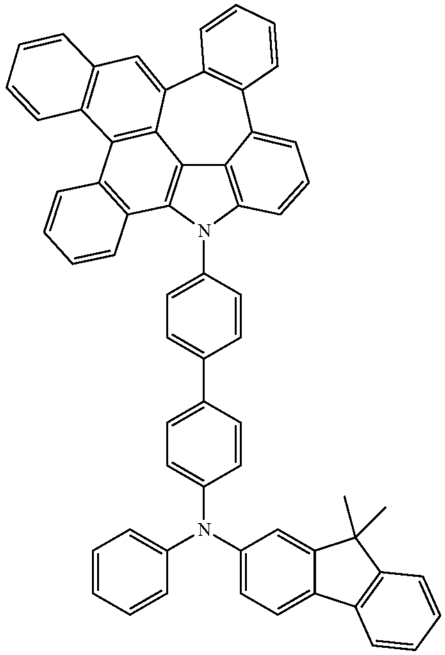
C-382
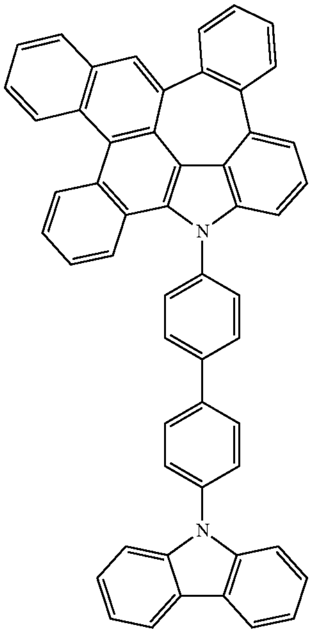

-continued
C-383
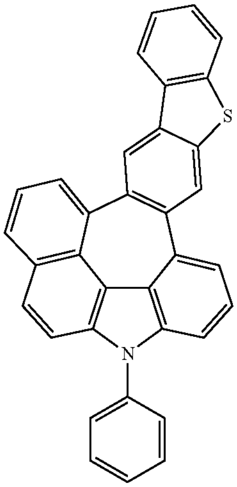
C-384
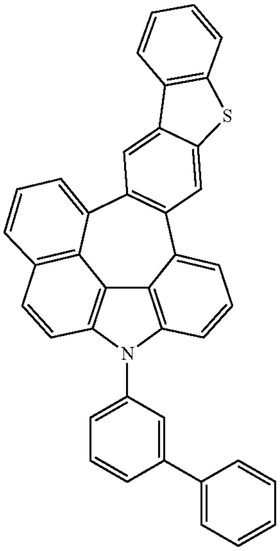
C-385
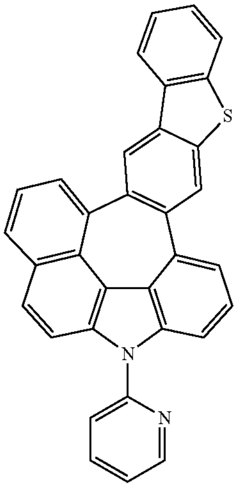
-continued
C-386
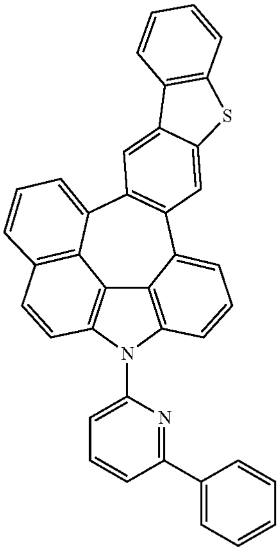
C-387
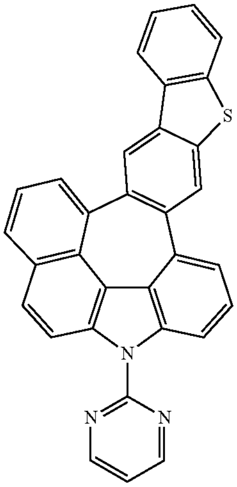
C-388
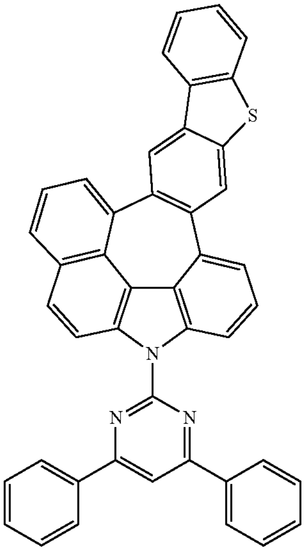

-continued
C-389
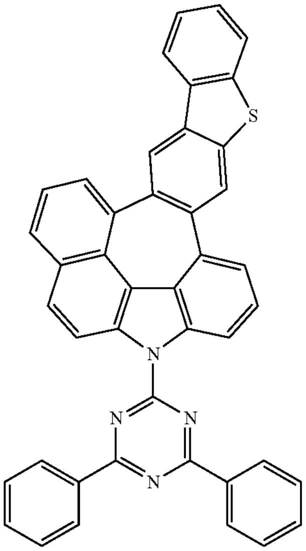
C-390
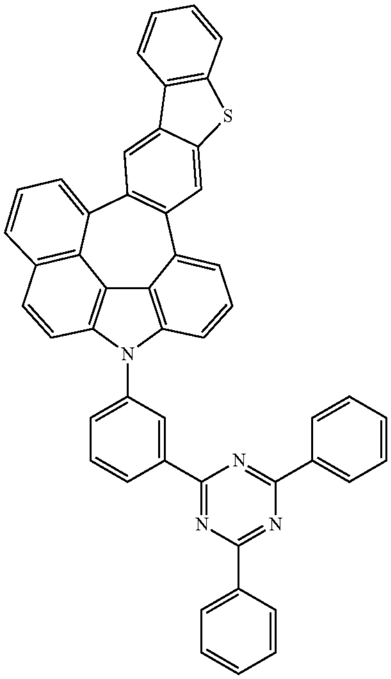
-continued
C-391
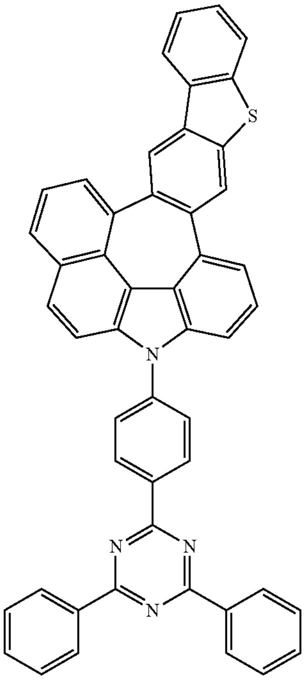
C-392
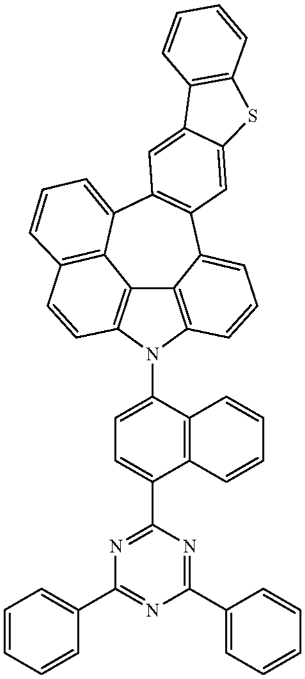

-continued
C-393
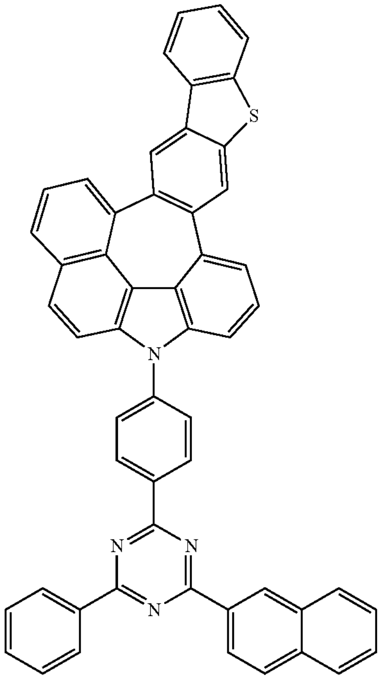
C-394
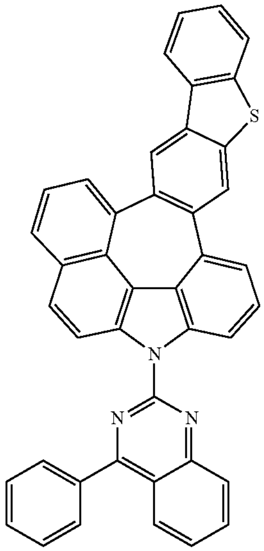
-continued
C-395
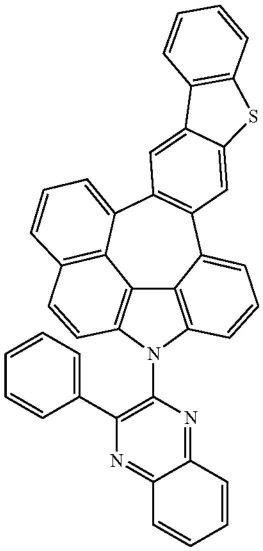
C-396
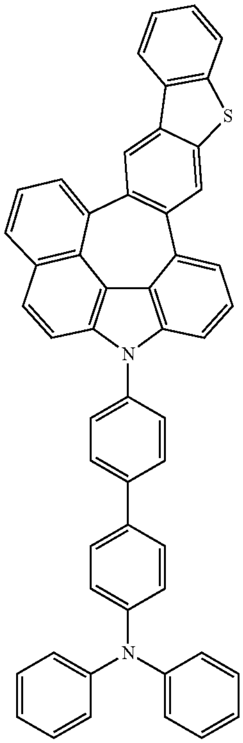

-continued
C-397
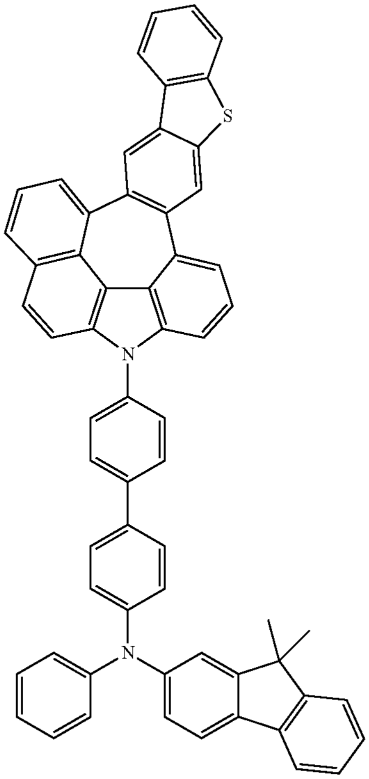
C-398
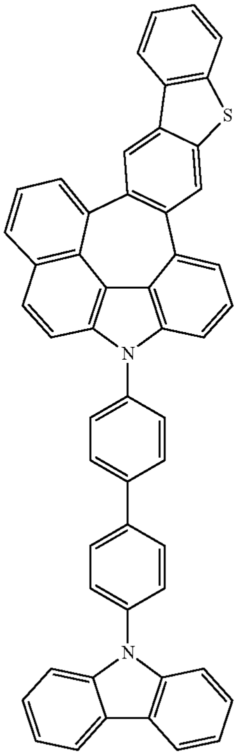
-continued
C-399
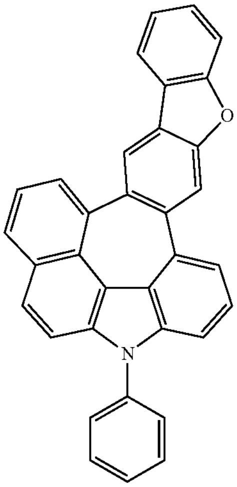
C-400
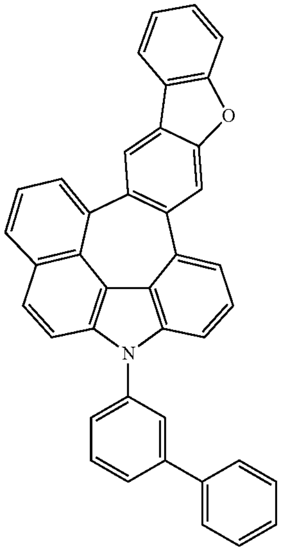
C-401
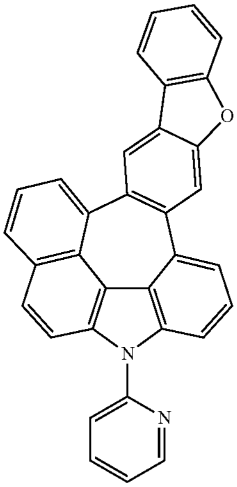

-continued
C-402
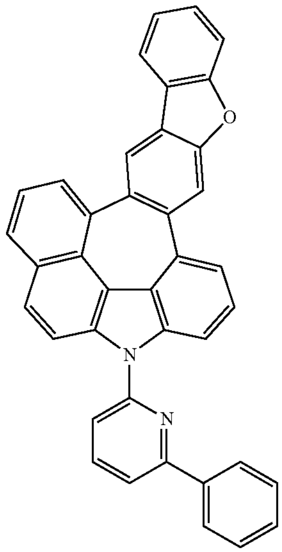
C-403
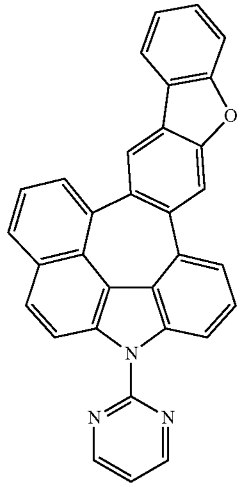
C-404
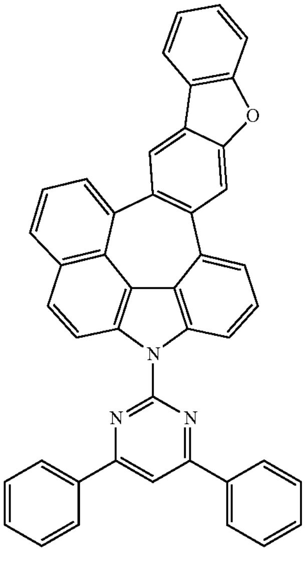
-continued
C-405
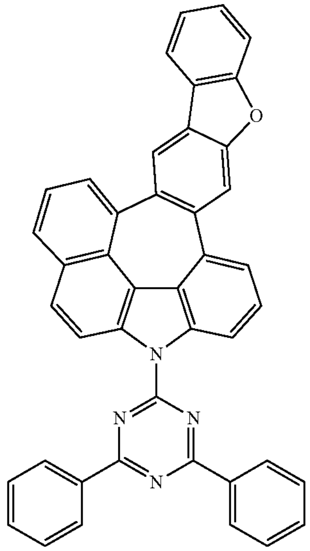
C-406
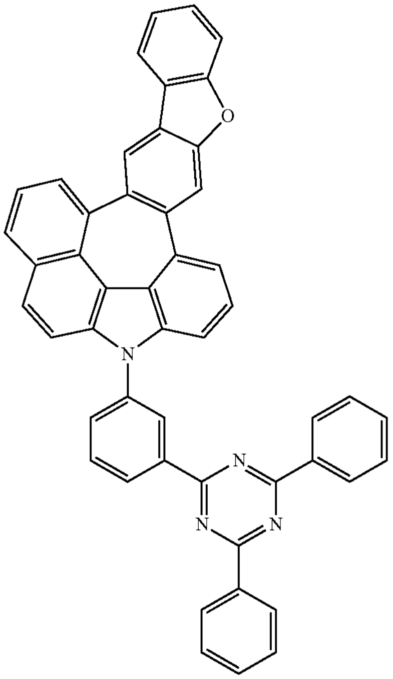

-continued
C-407
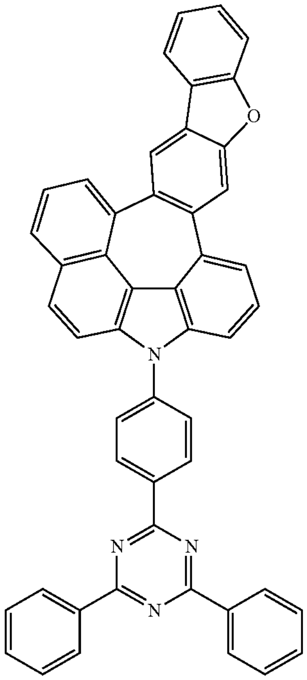
C-408
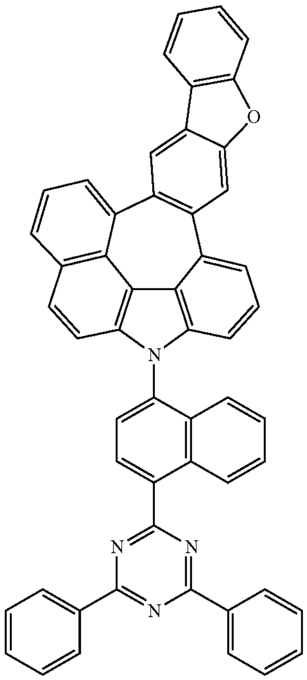
-continued
C-409
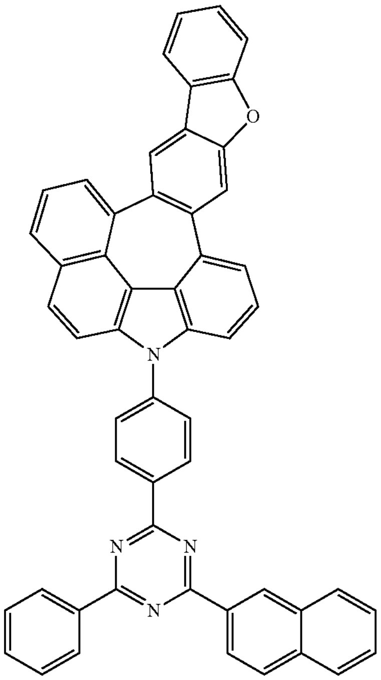
C-410
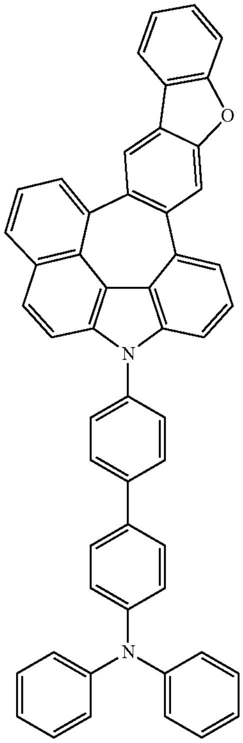

-continued
C-411
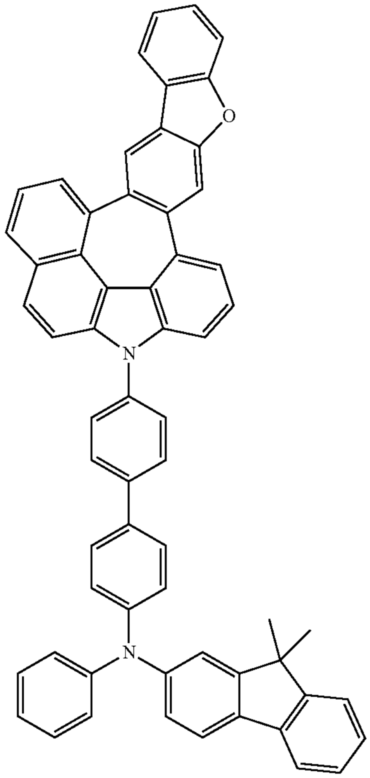
C-412
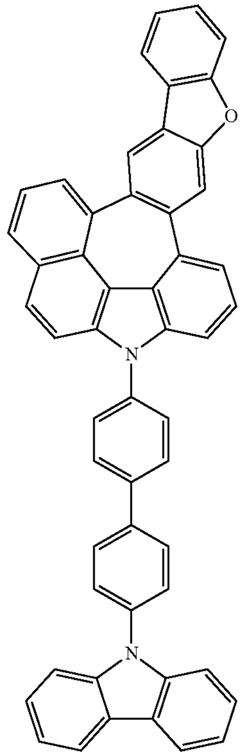
-continued
C-413
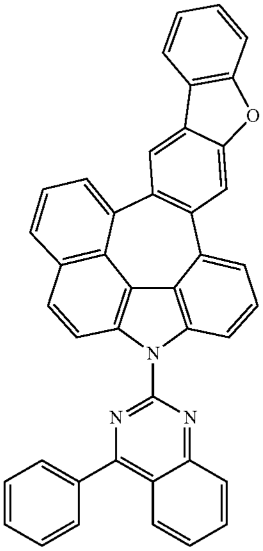
C-414
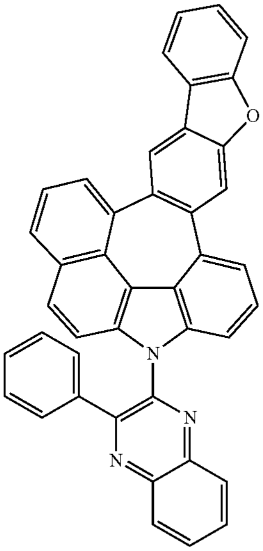
C-415
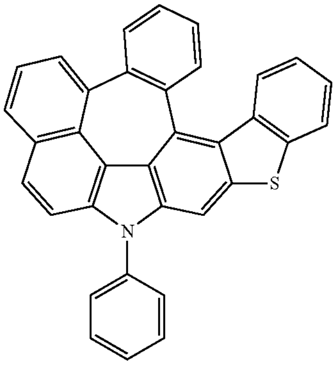

-continued
C-416
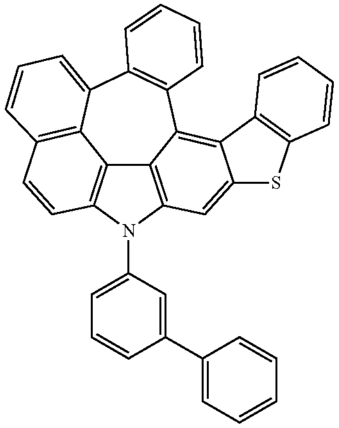
C-417
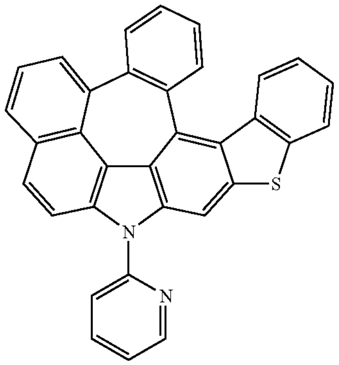
C-418
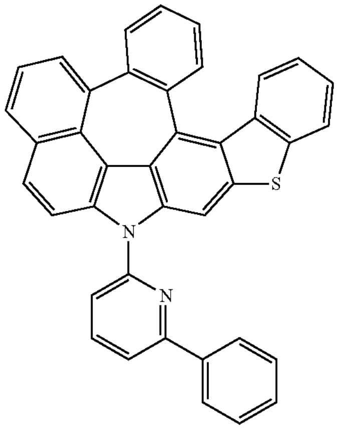
C-419
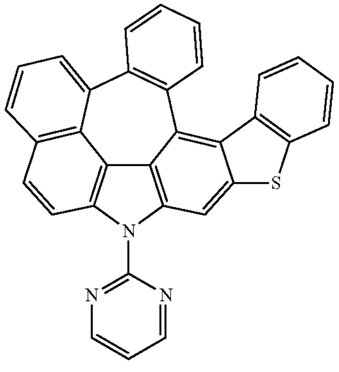
-continued
C-420
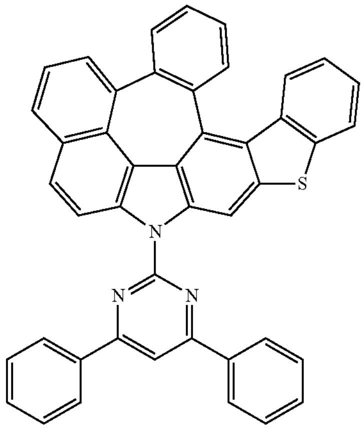
C-421
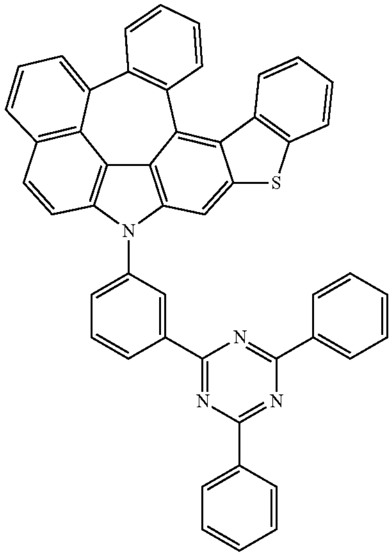
C-422
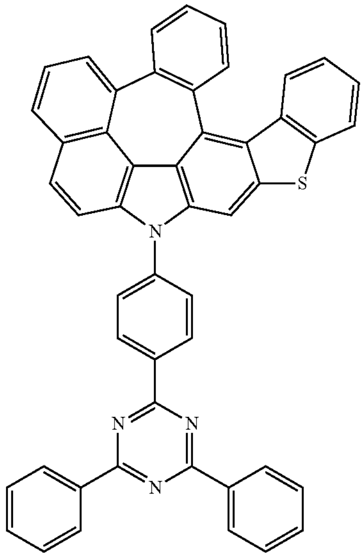

-continued
C-423
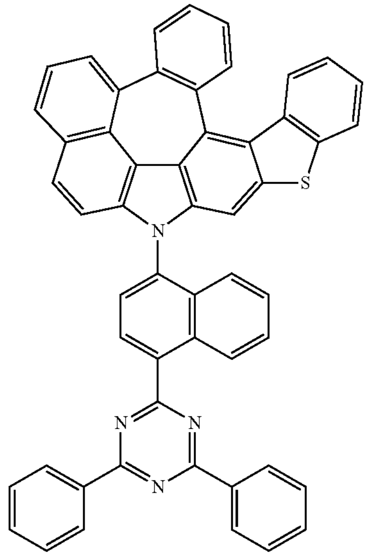
C-424
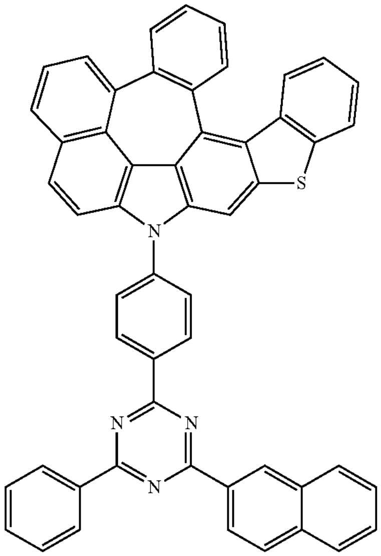
C-425
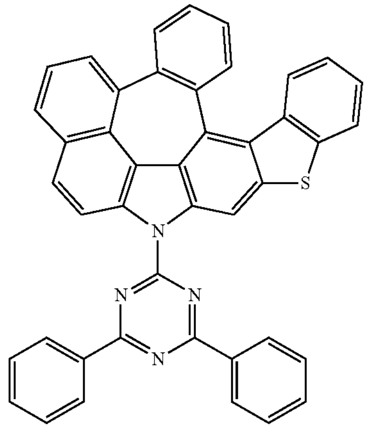
-continued
C-426
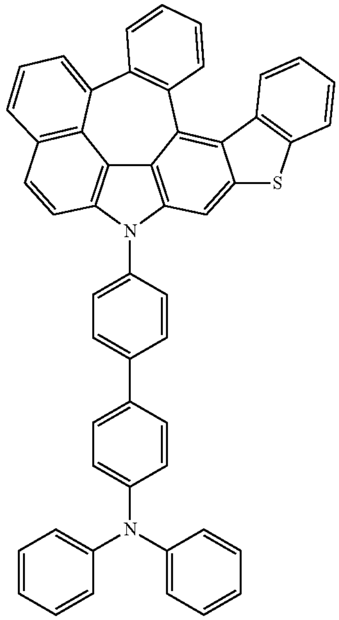
C-427
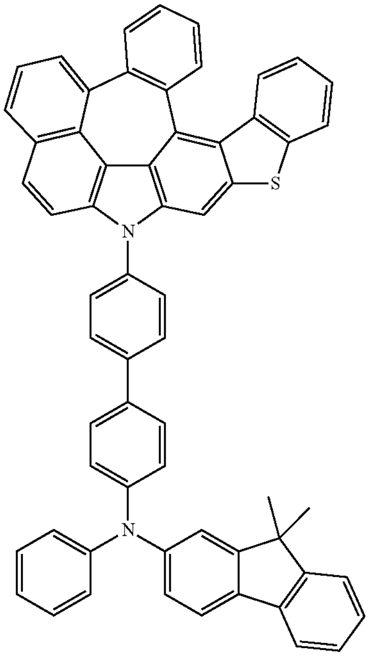

-continued
C-428
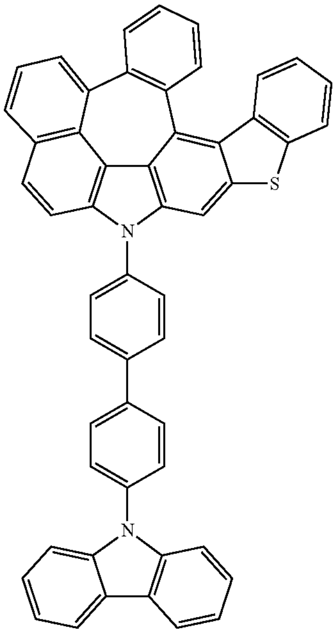
C-429
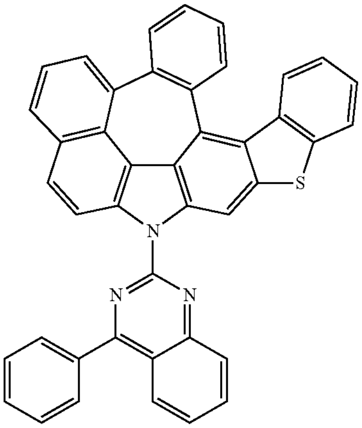
C-430
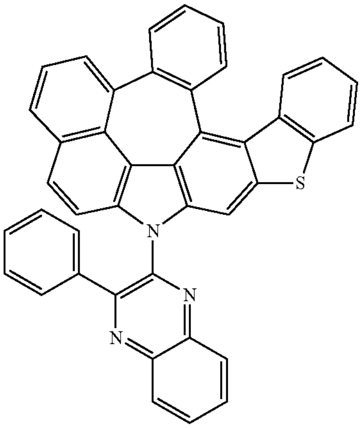
-continued
C-431
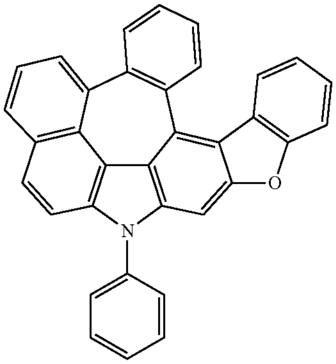
C-432
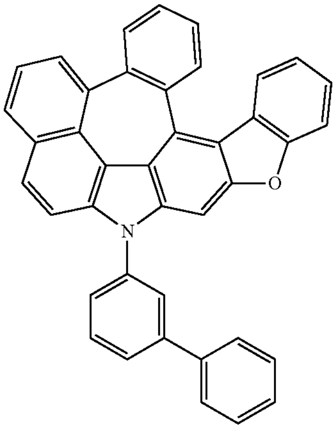
C-433
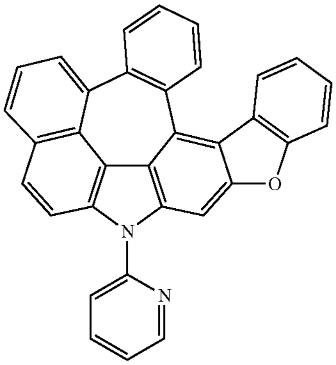
C-434
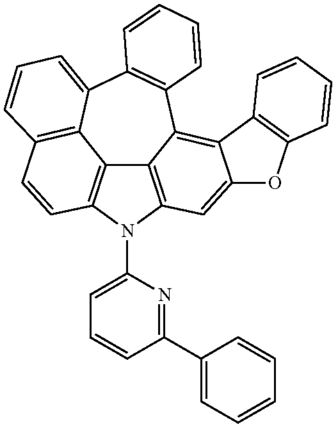

-continued
C-435
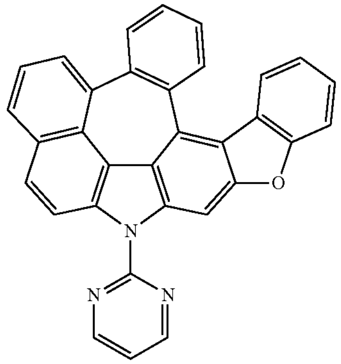
C-436
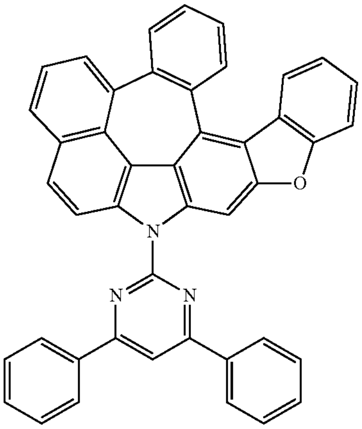
C-437
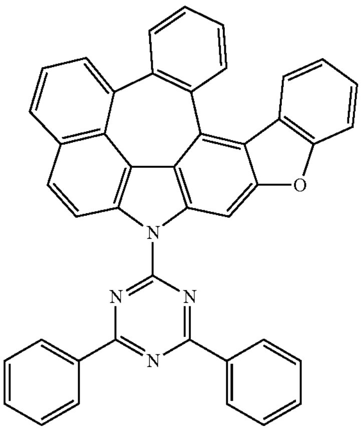
-continued
C-438
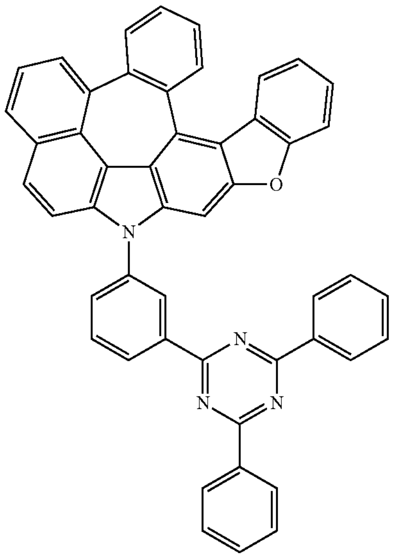
C-439
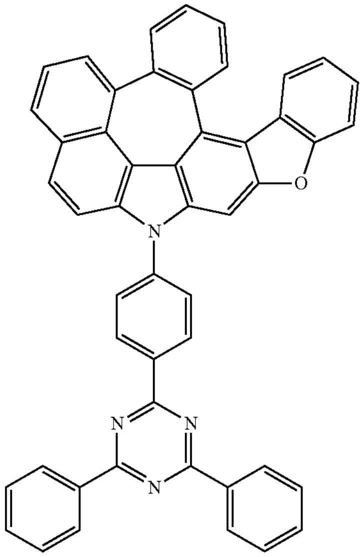
C-440
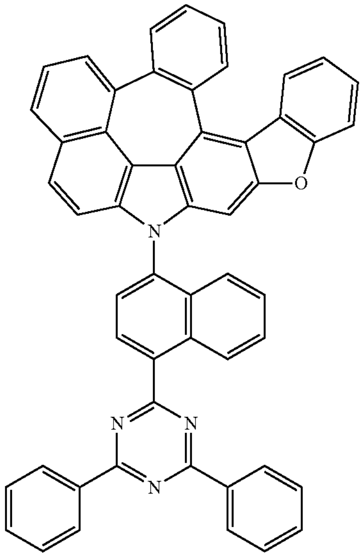

-continued
C-441
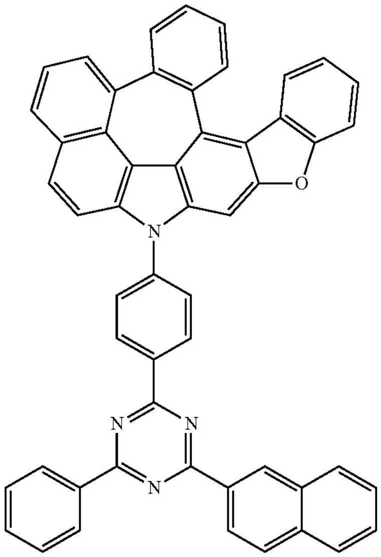
C-442
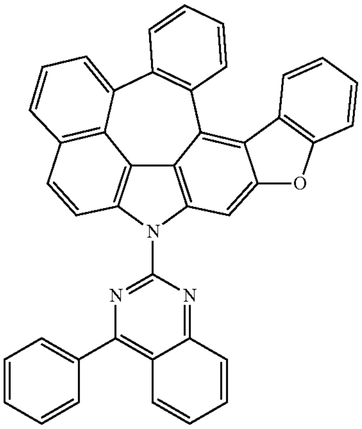
C-443
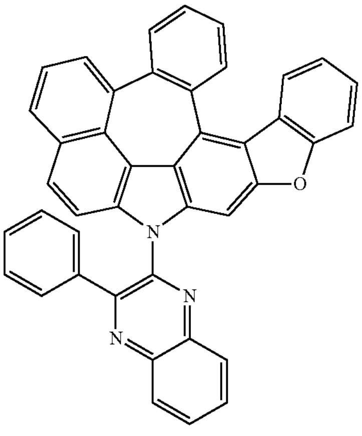
C-444
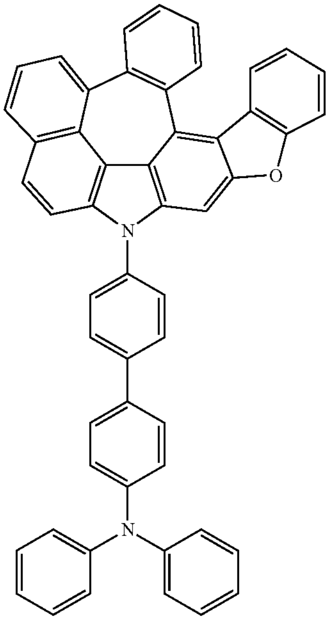
C-445
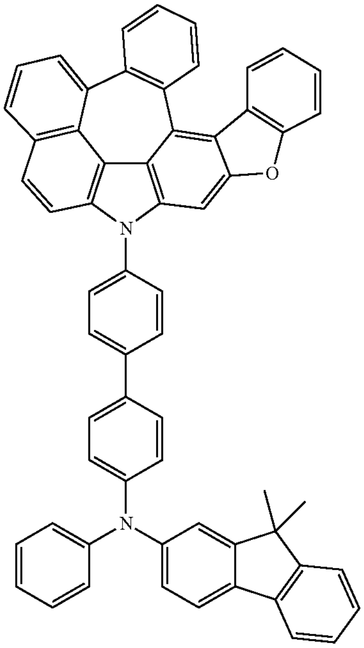

-continued
C-446
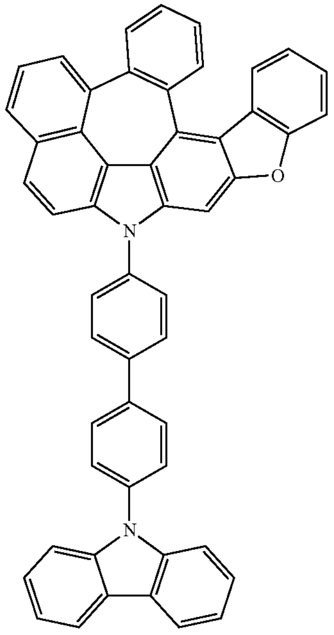
C-447
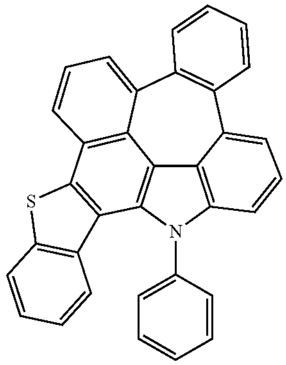
C-448
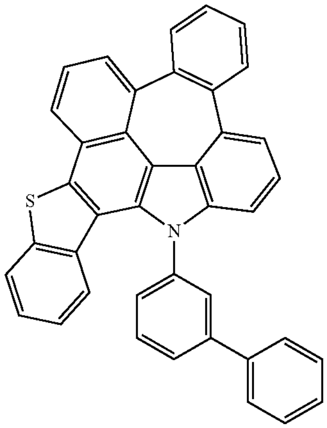
-continued
C-449
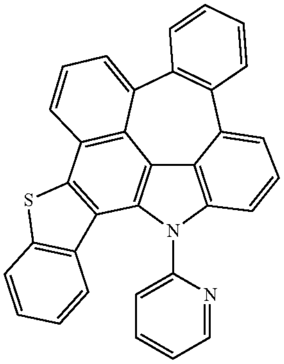
C-450
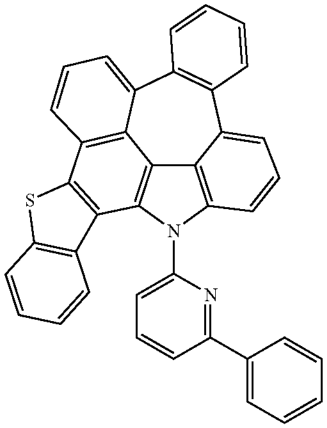
C-451
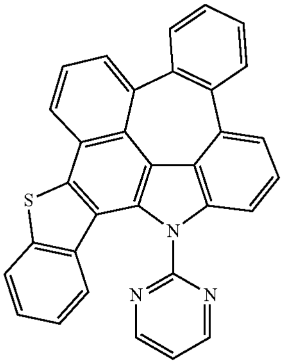
C-452
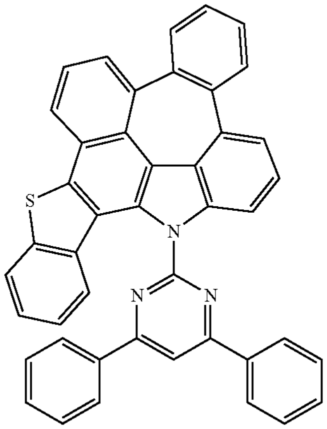

-continued
C-453
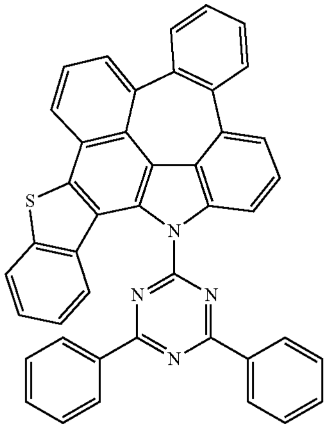
C-454
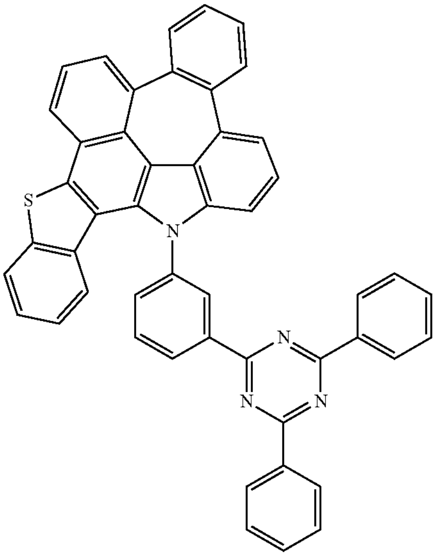
C-455
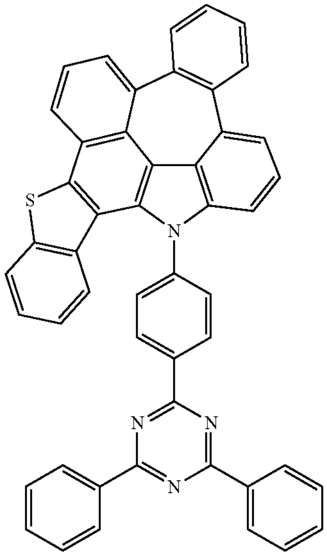
-continued
C-456
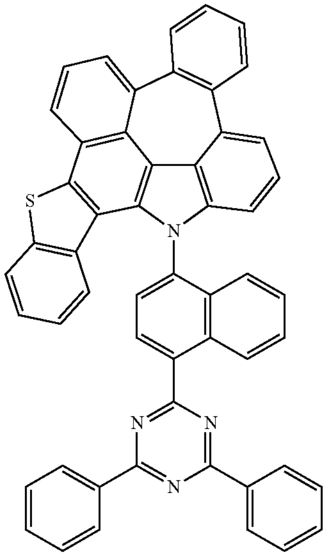
C-457
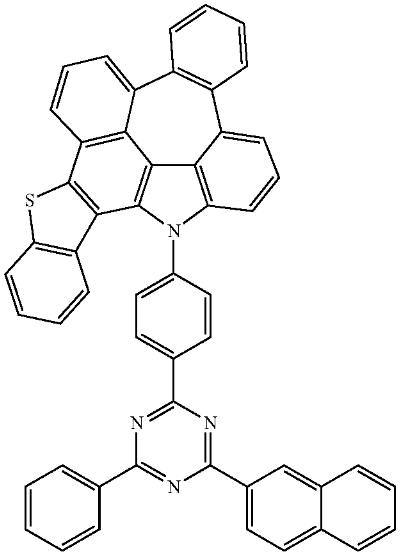
C-458
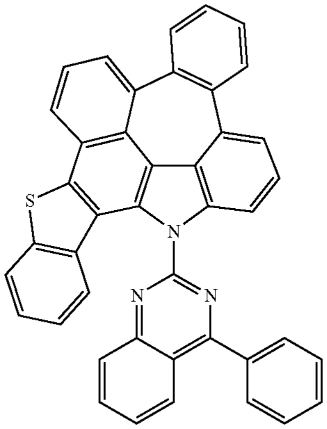

-continued
C-459
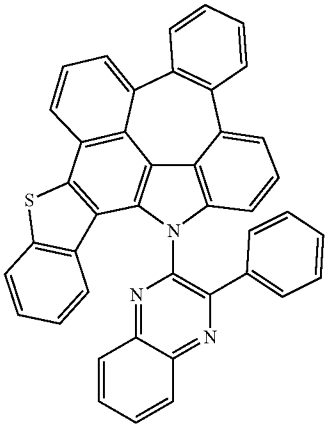
C-460
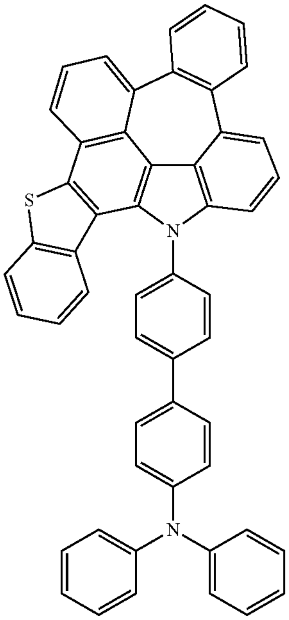
-continued
C-461
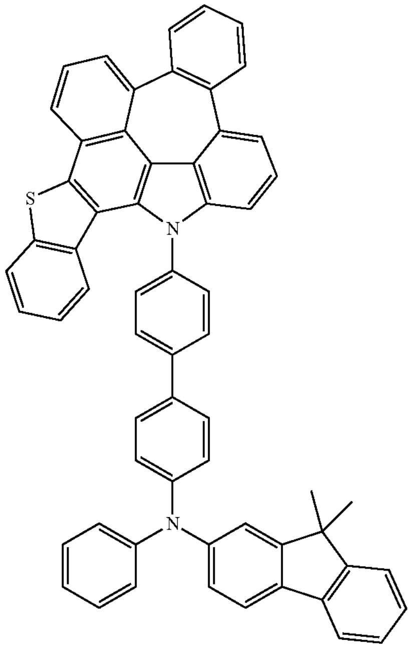
C-462
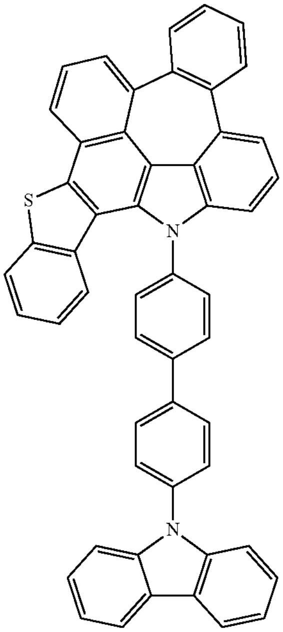
C-463
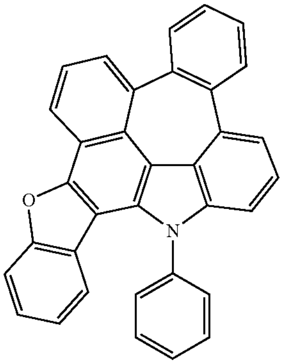

-continued
C-464
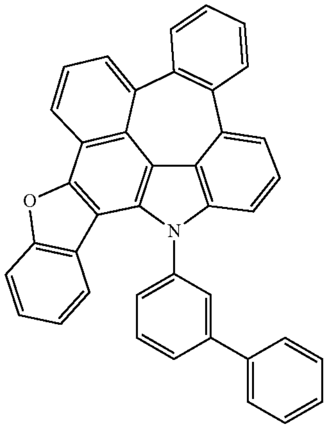
C-465
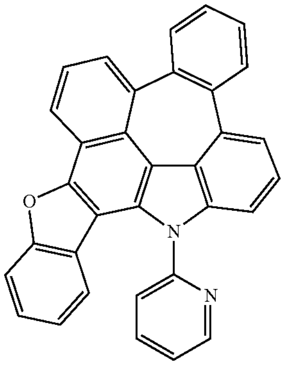
C-466
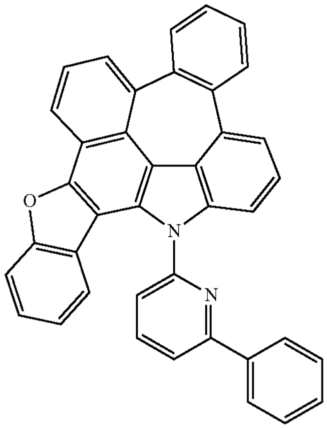
C-467
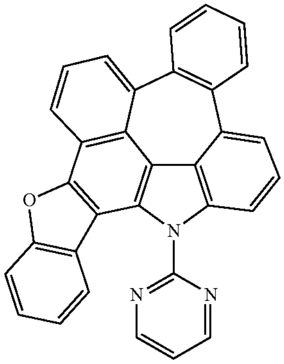
-continued
C-468
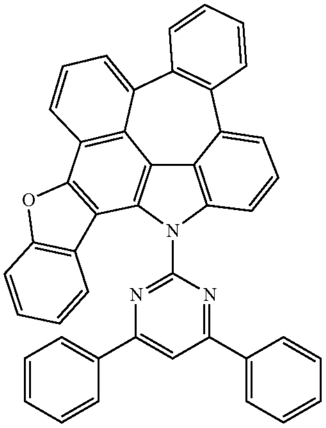
C-469
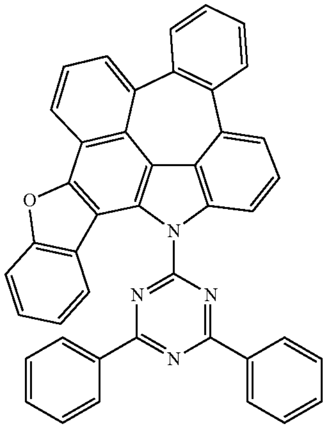
C-470
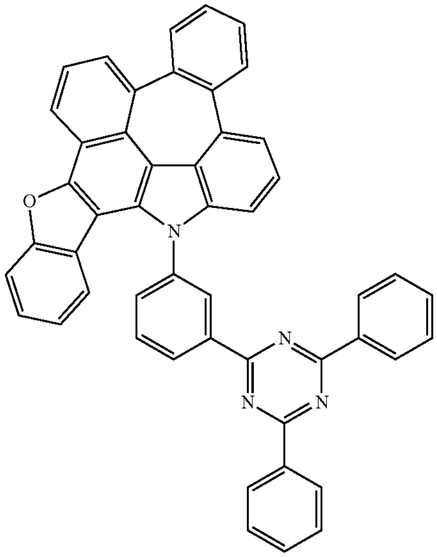

-continued
C-471
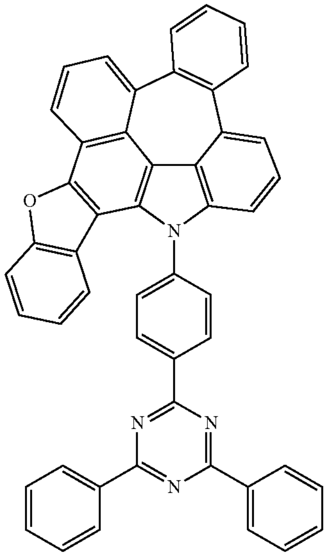
C-472
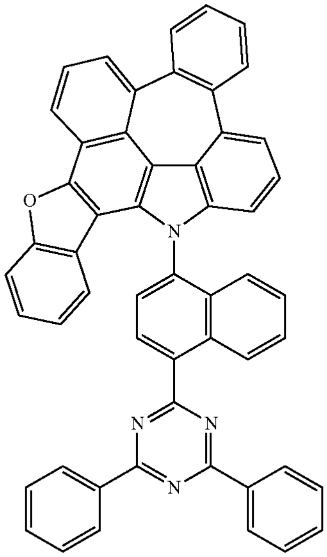
-continued
C-473
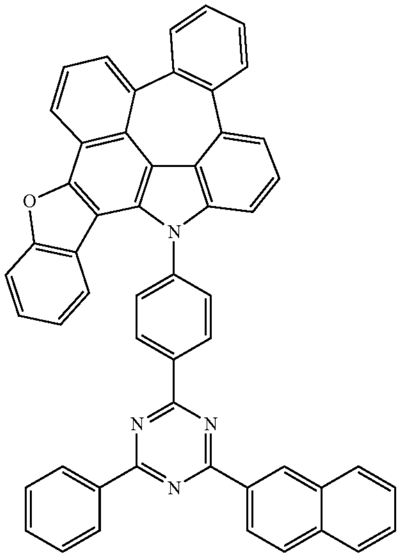
C-474
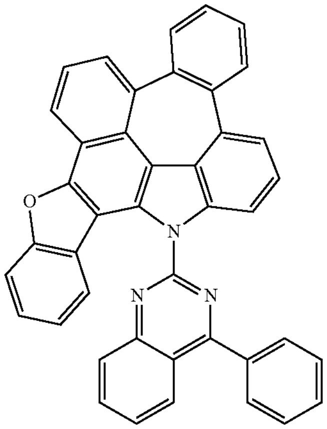
C-475
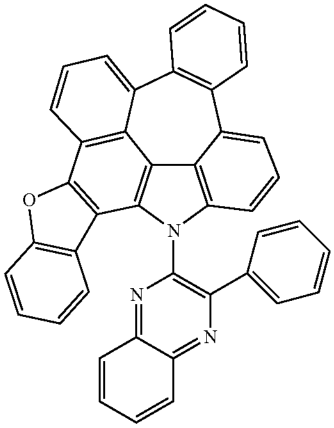

-continued
C-476
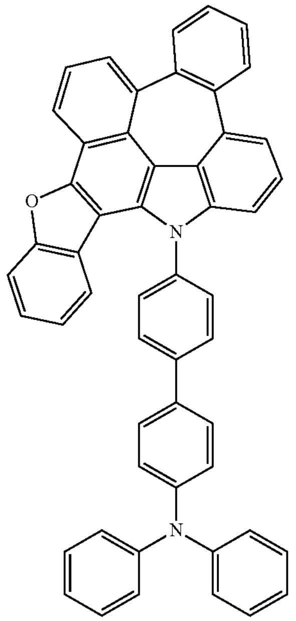
C-477
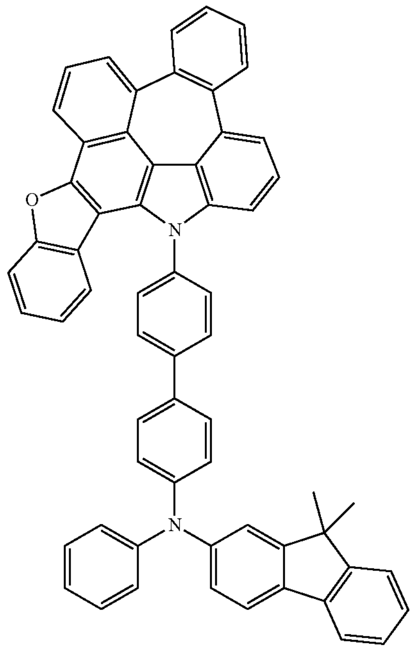
-continued
C-478
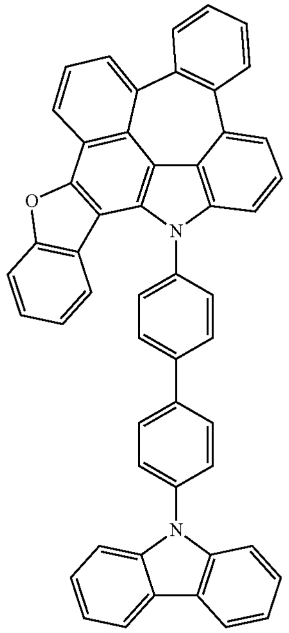
C-479
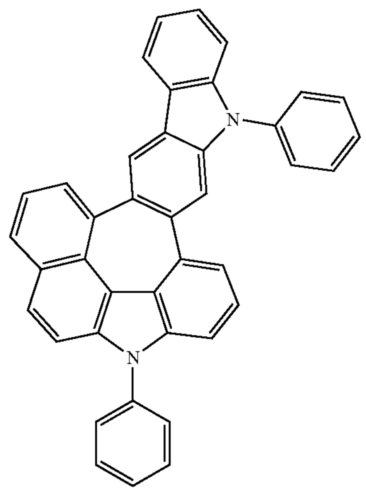

-continued
C-480
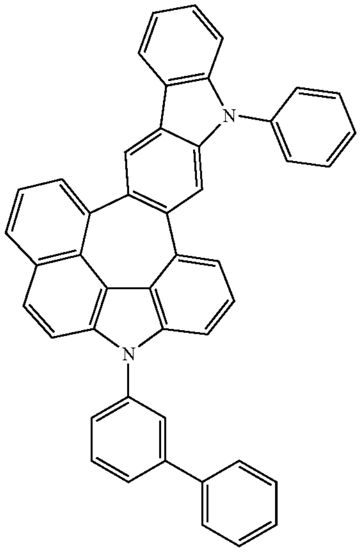
C-481
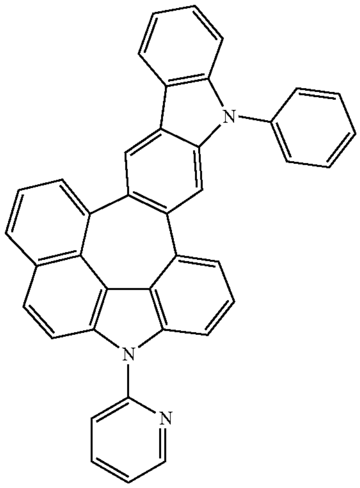
C-482
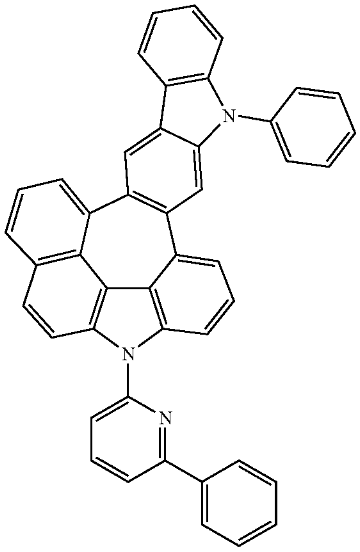
-continued
C-483
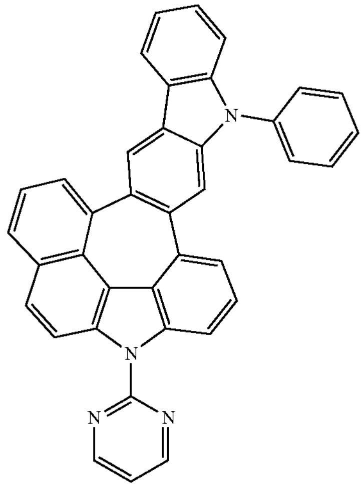
C-484
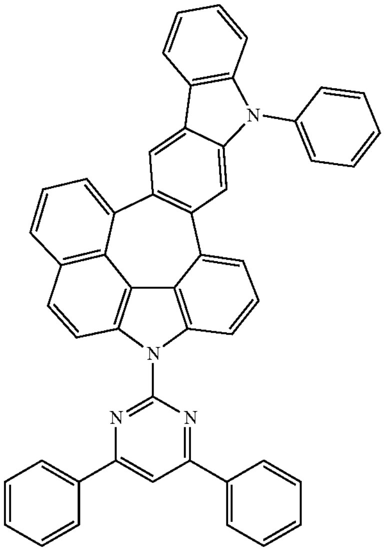
C-485
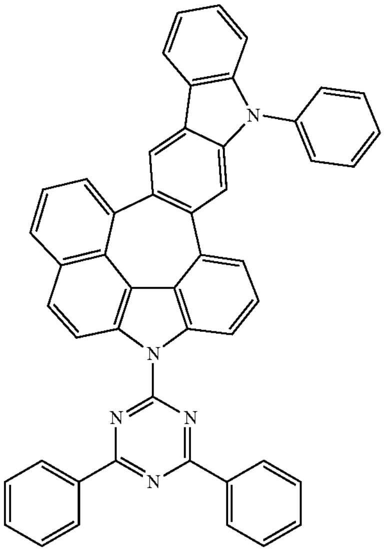

-continued
C-486
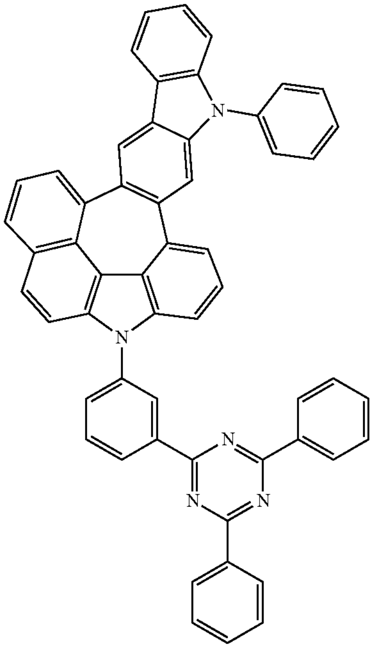
C-487
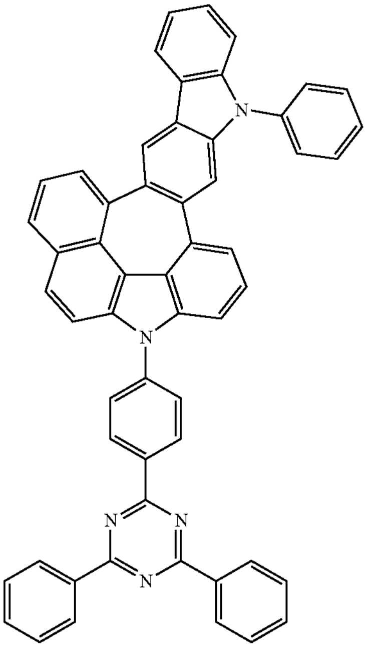
-continued
C-488
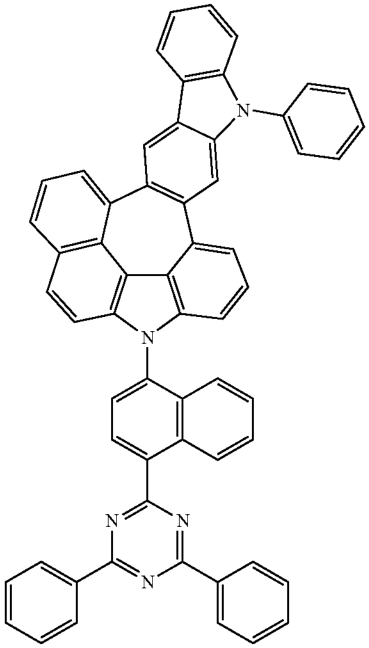
C-489
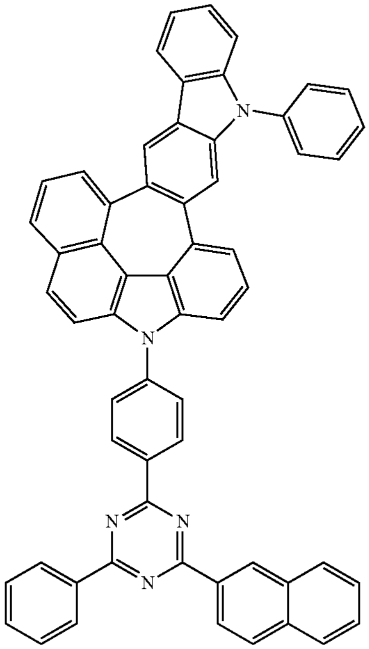

-continued
C-490
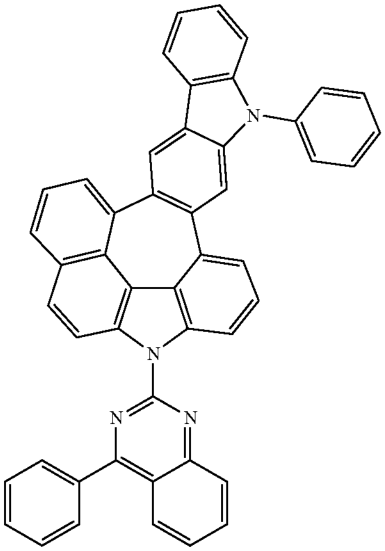
C-491
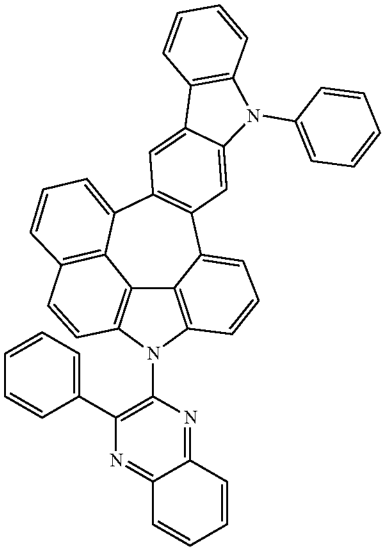
-continued
C-492
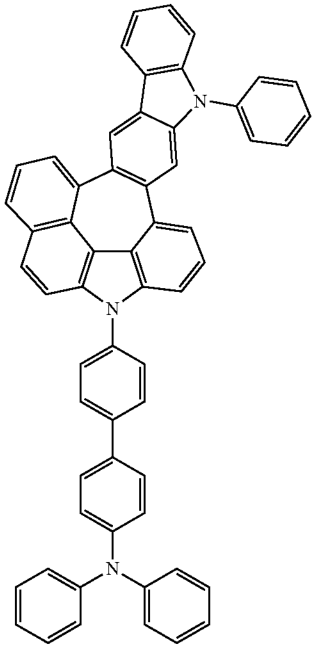
C-493
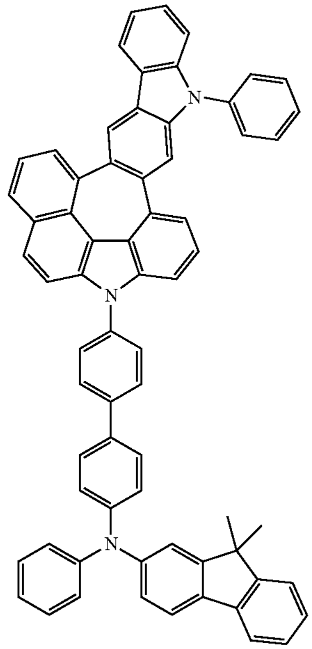

-continued
C-494
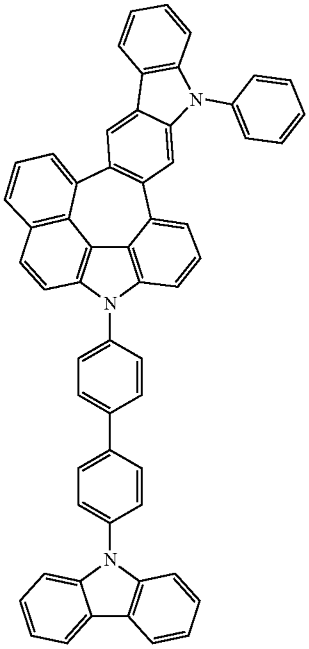
C-495
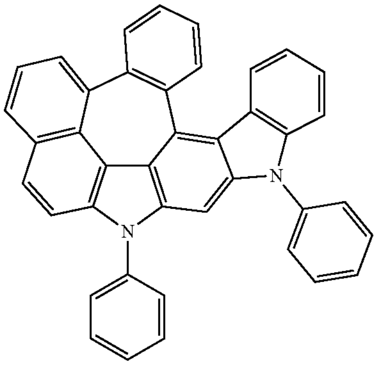
C-496
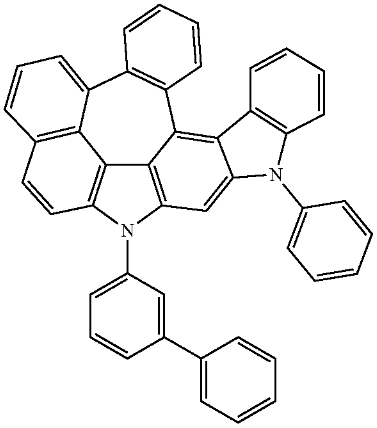
-continued
C-497
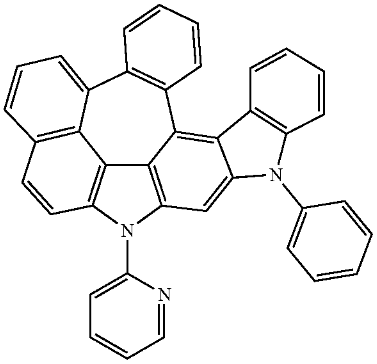
C-498
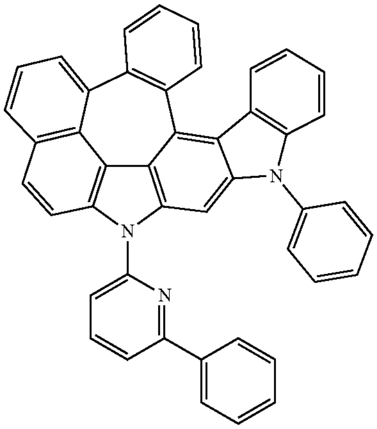
C-499
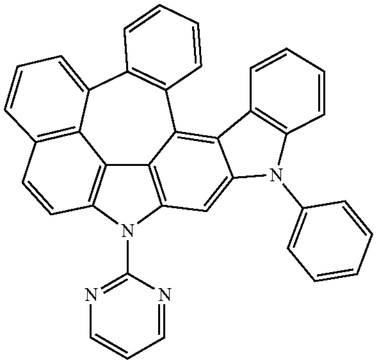
C-500
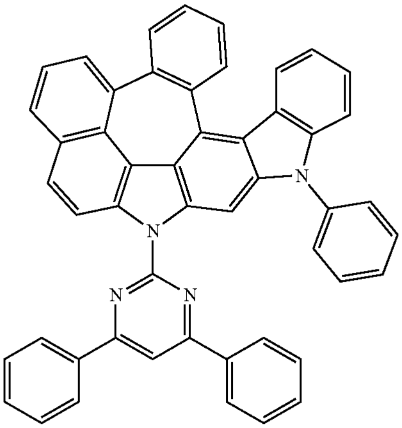

-continued
C-501
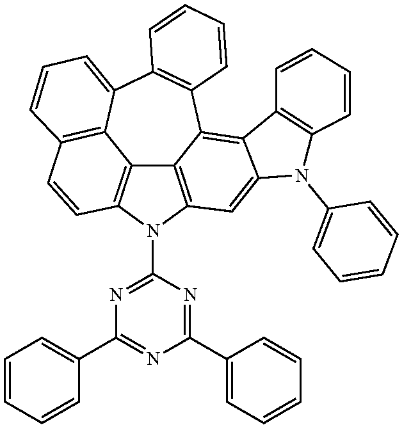
C-502
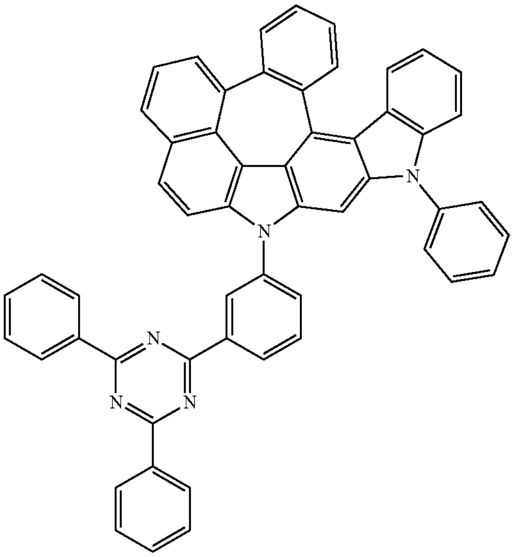
C-503
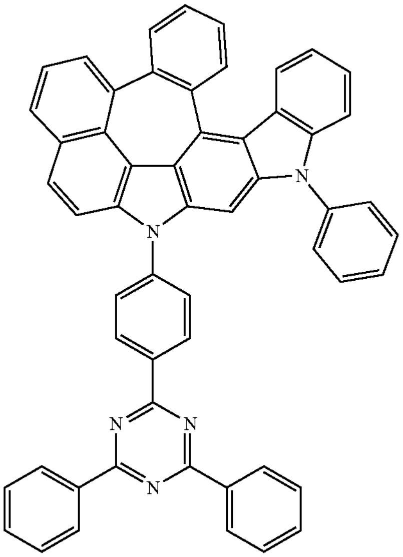
-continued
C-504
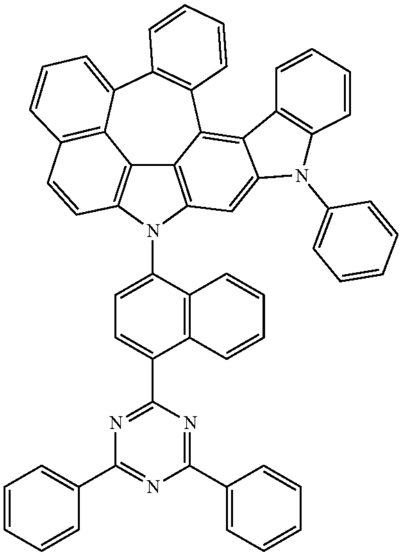
C-505
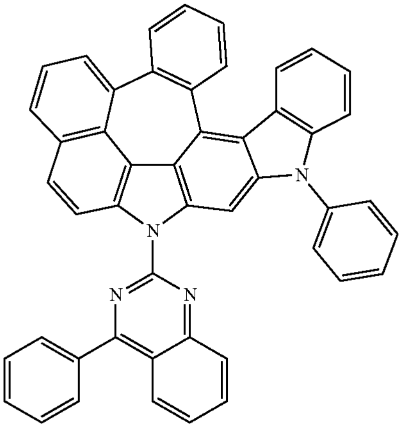
C-506
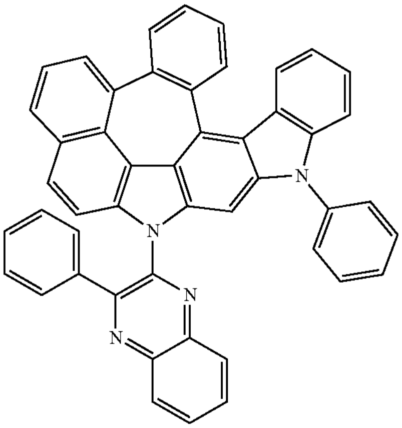

-continued
C-507
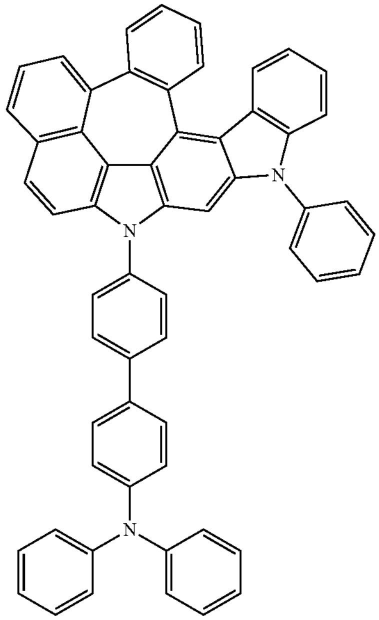
C-508
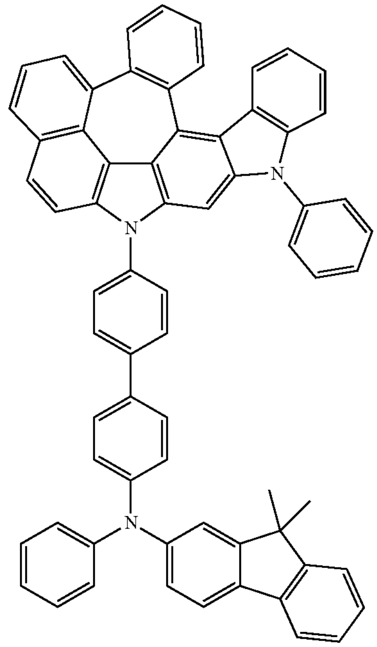
-continued
C-509
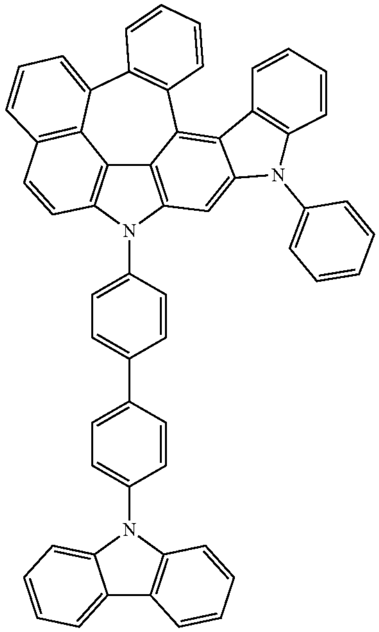
C-510
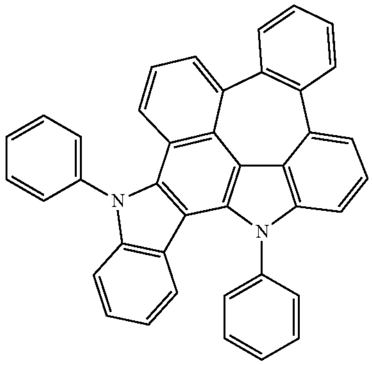
C-511
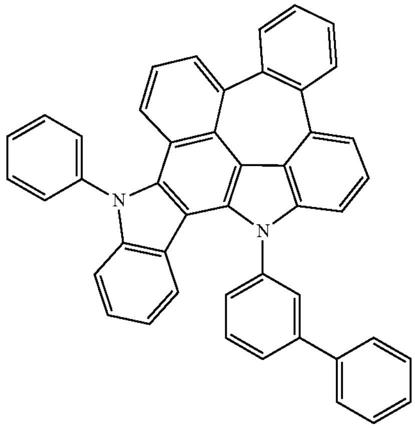

-continued
C-512
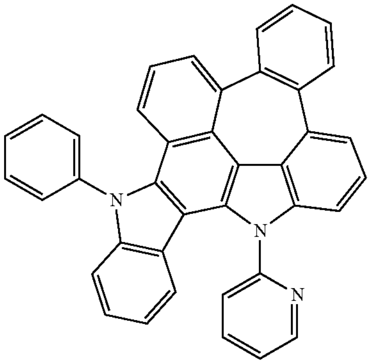
C-513
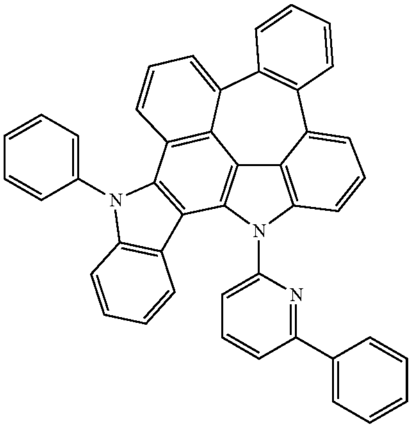
C-514
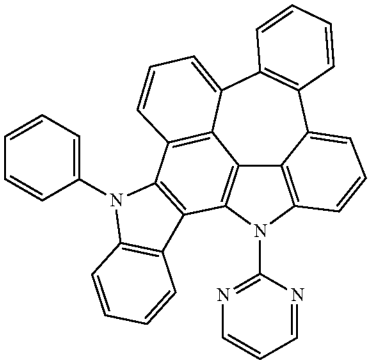
C-515
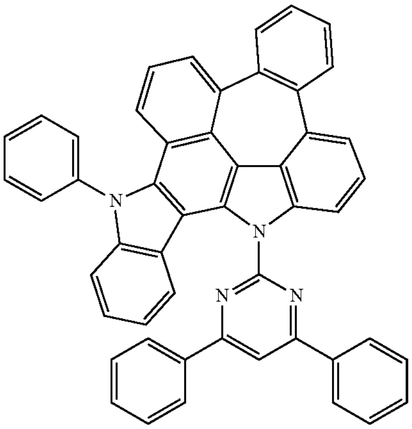
-continued
C-516
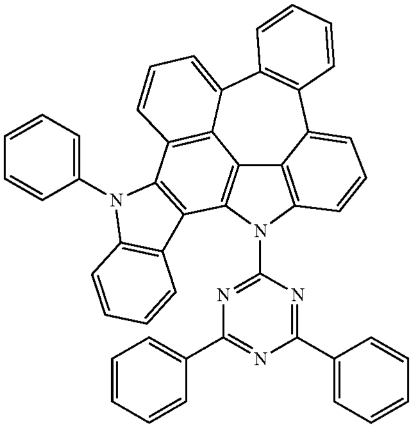
C-517
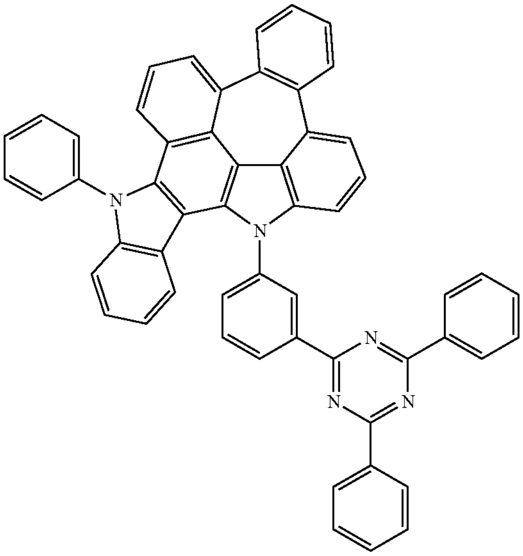
C-518
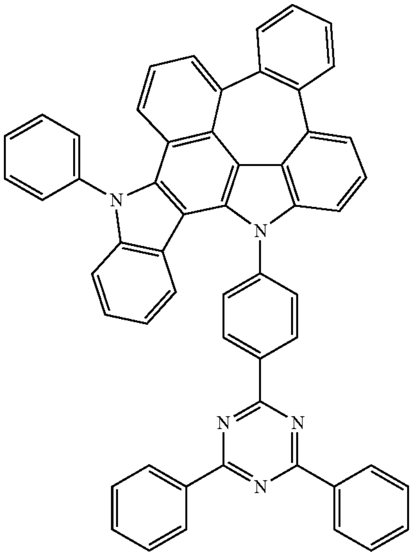

-continued
C-519
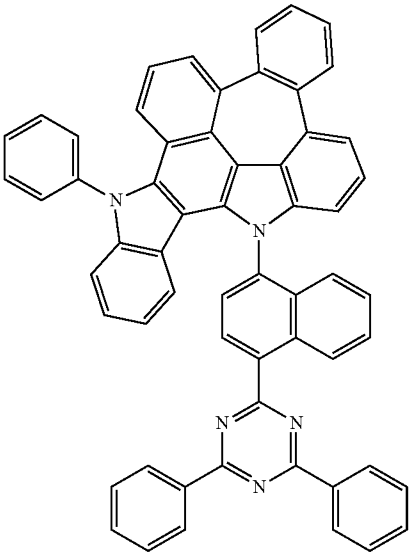
C-520
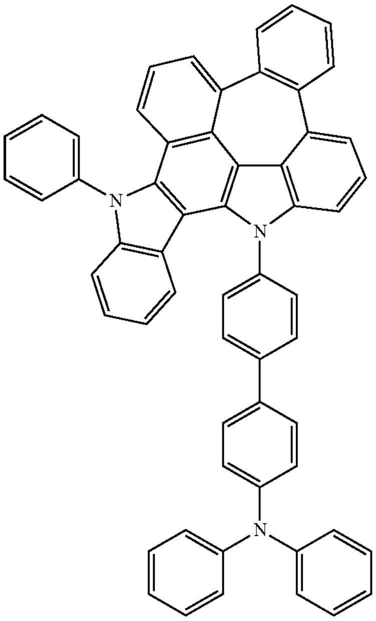
-continued
C-521
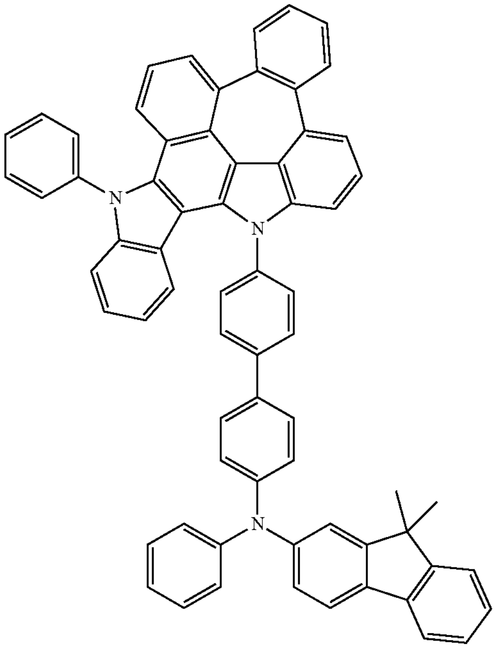
C-522
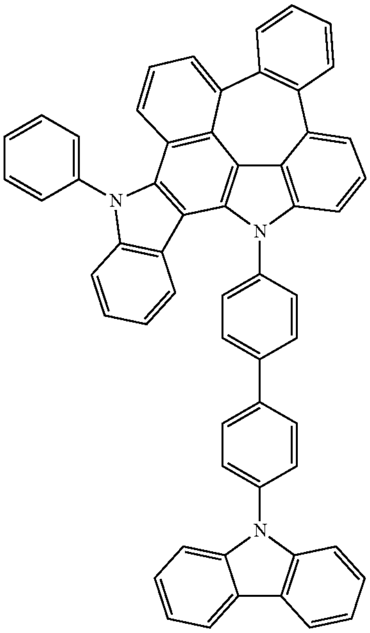

-continued
C-523
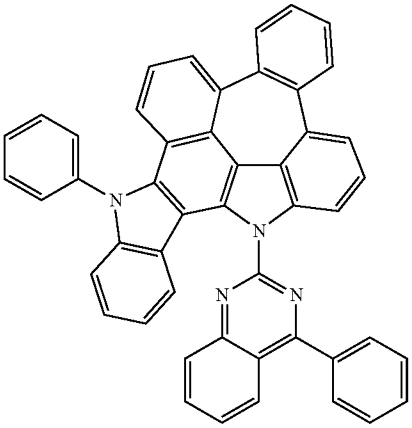
C-524
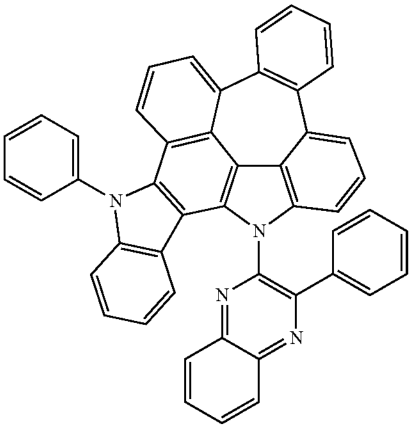
C-525
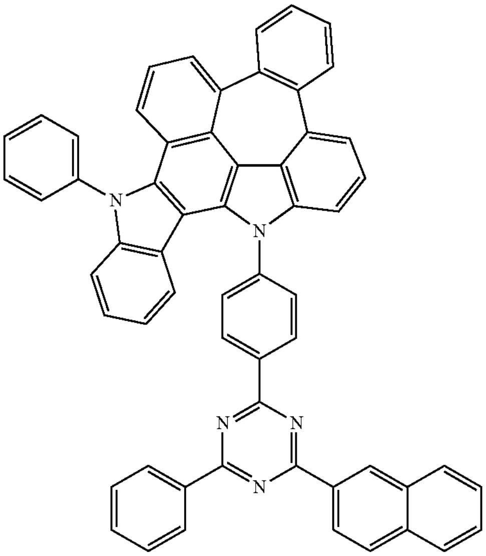
-continued
C-526
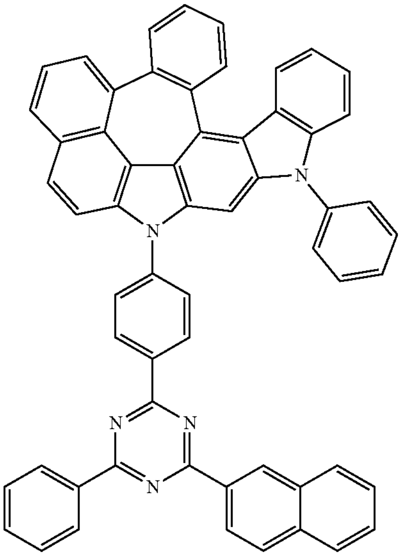
C-527
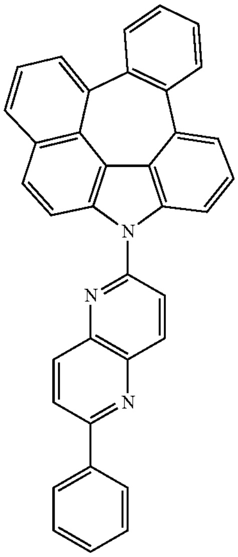
C-528
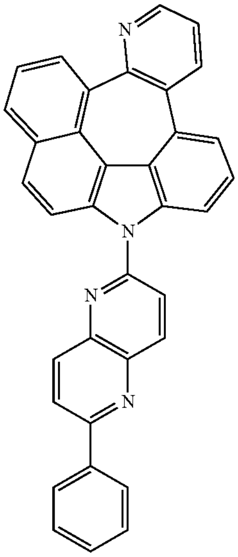

-continued
C-529
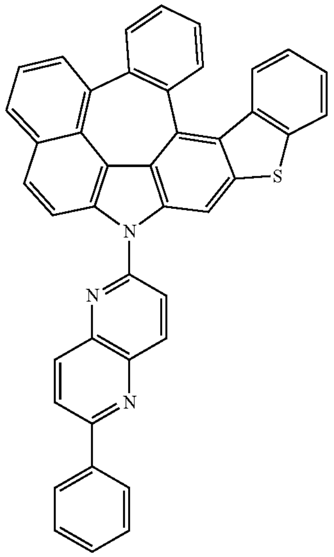
C-530
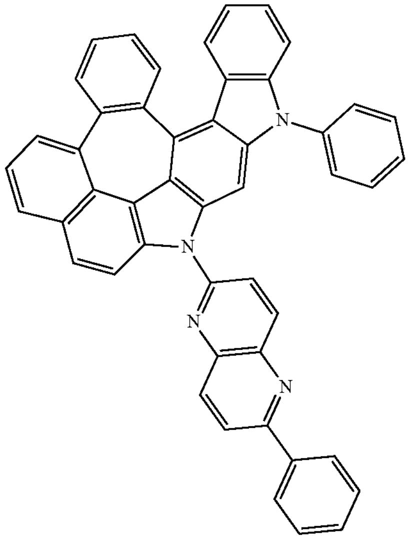
C-531
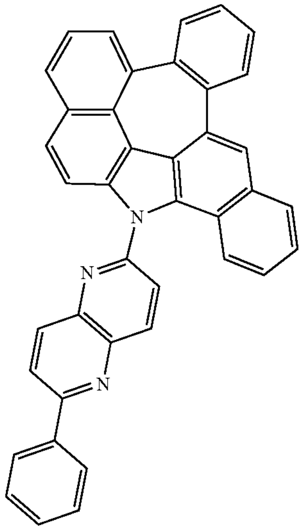
-continued
C-532
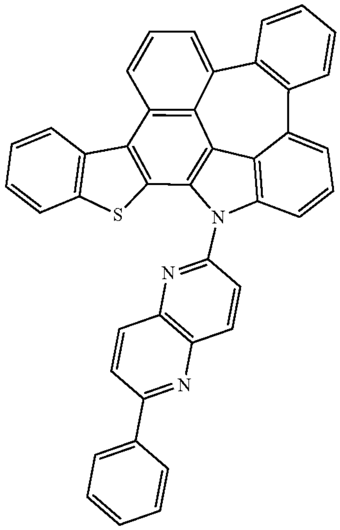
C-533
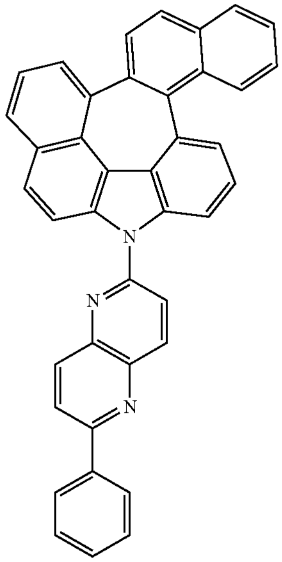
C-534
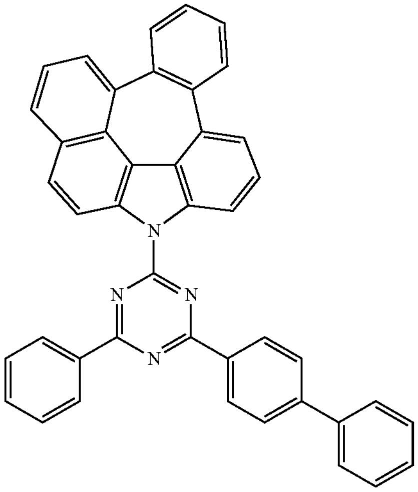

-continued
C-535
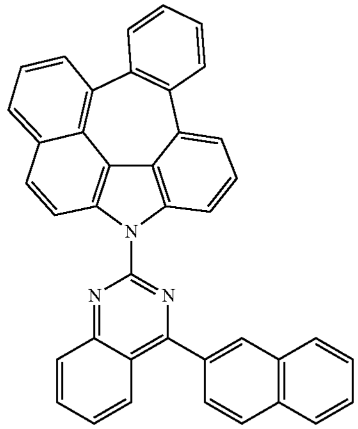
C-536
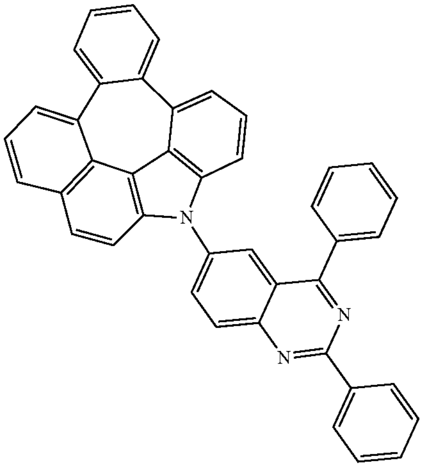
C-537
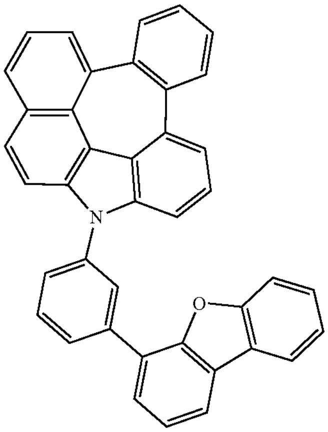
-continued
C-538
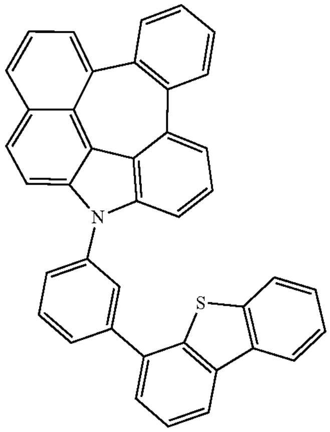
C-539
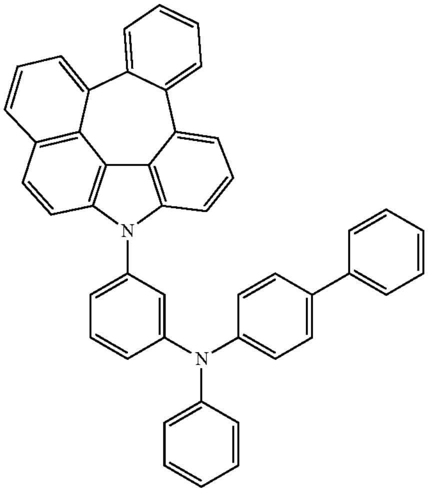
C-540
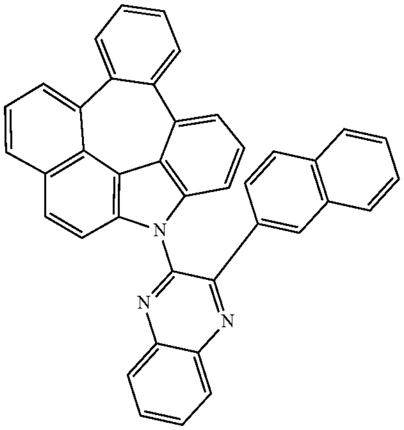

-continued
C-541
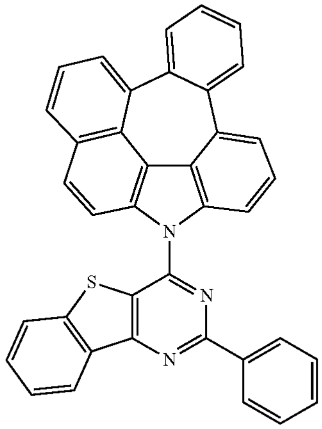
C-542
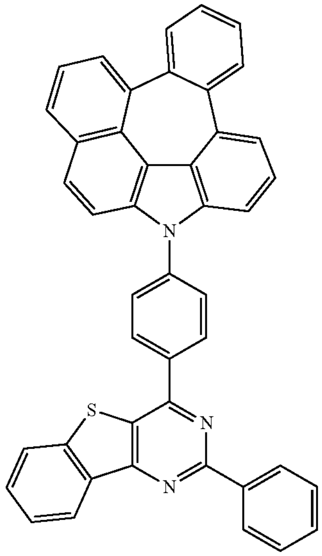
C-543
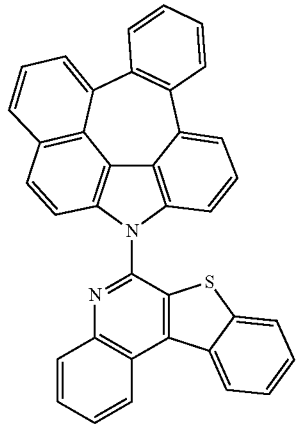
-continued
C-544
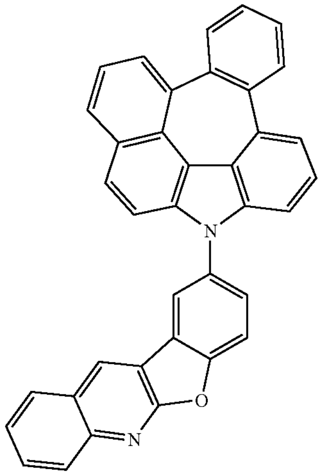
C-545
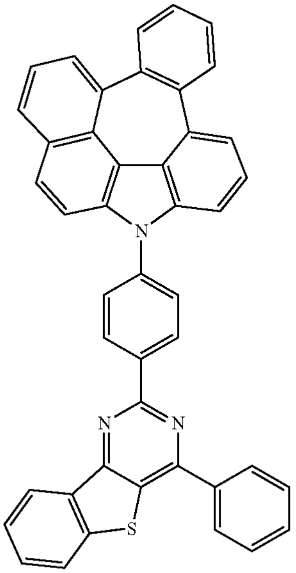
C-546
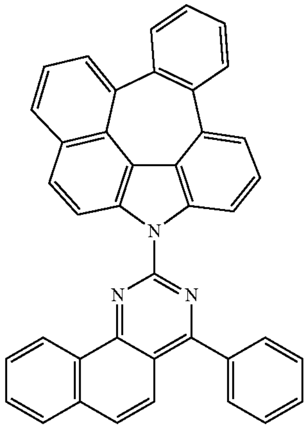

-continued
C-547
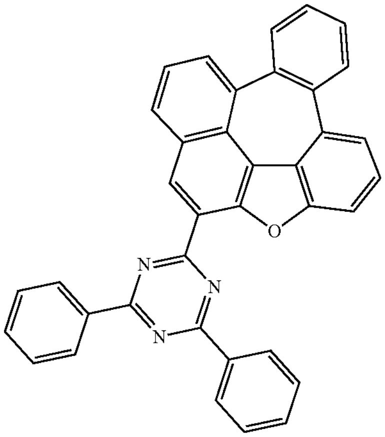
C-548
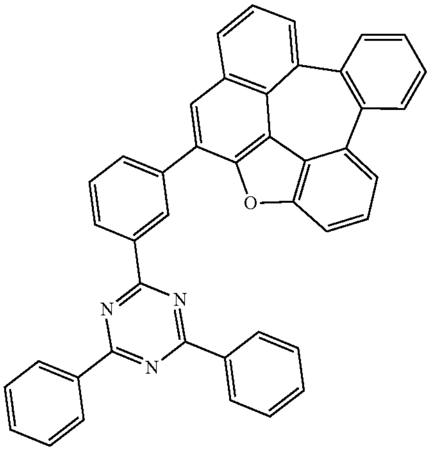
C-549
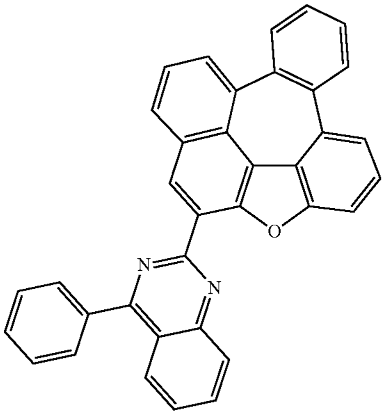
-continued
C-550
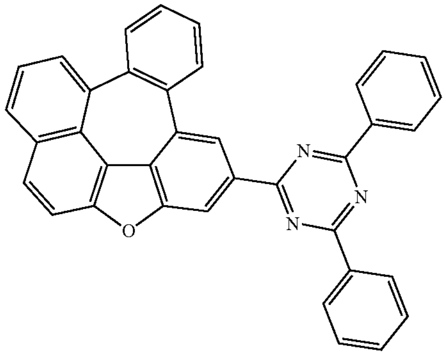
C-551
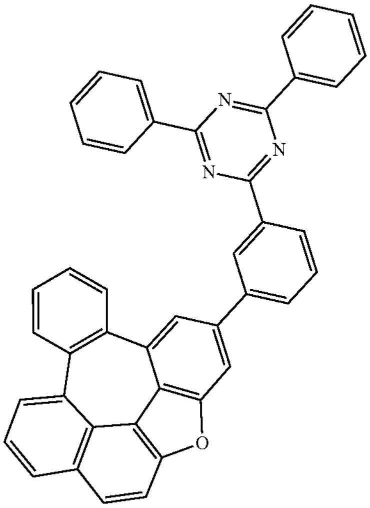
C-552
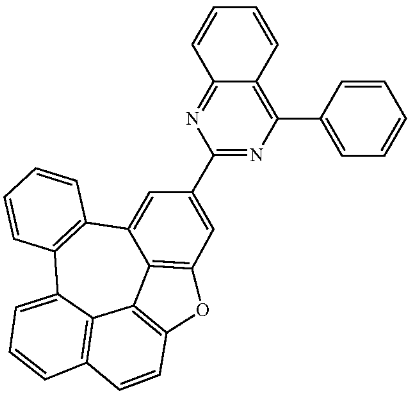

-continued
C-553
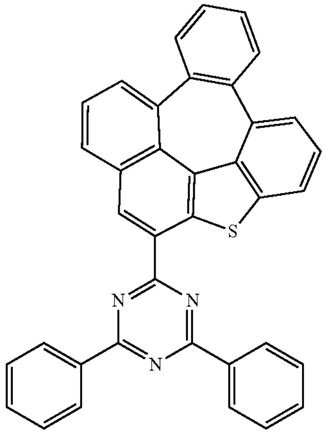
C-554
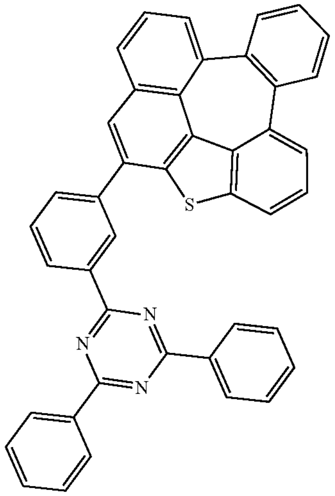
C-555
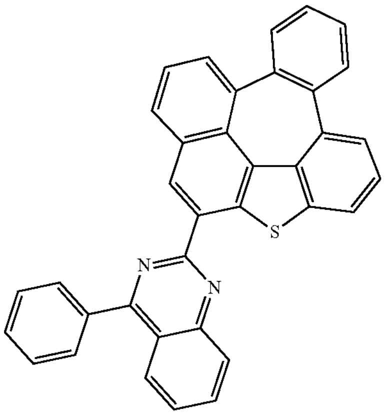
-continued
C-556
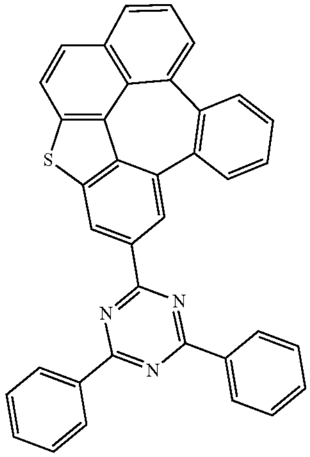
C-557
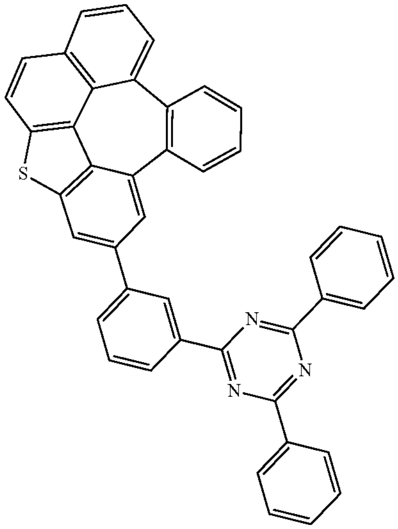
C-558
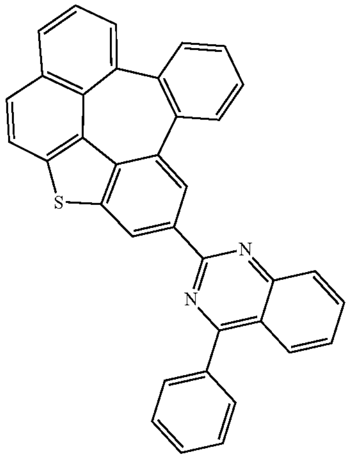

-continued
C-559
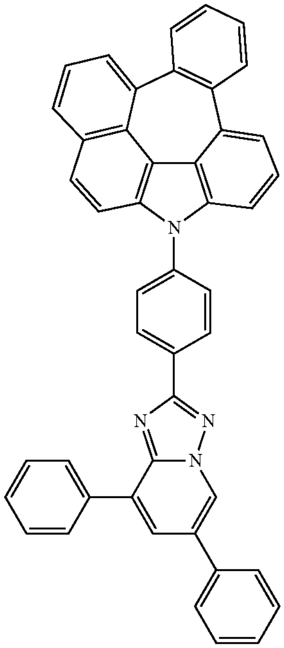
C-560
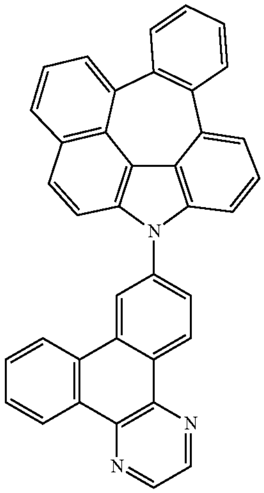
-continued
C-561
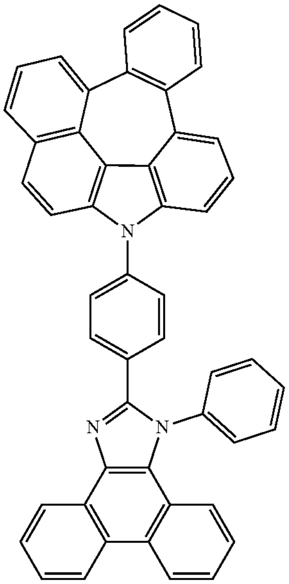
C-562
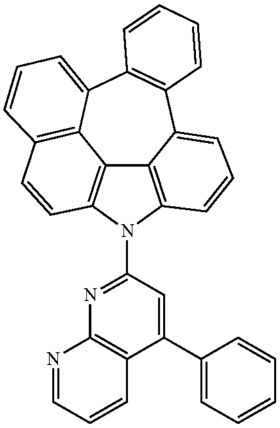
C-563
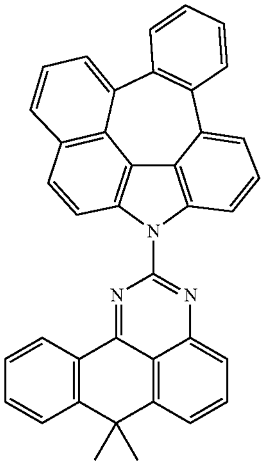

-continued
C-564
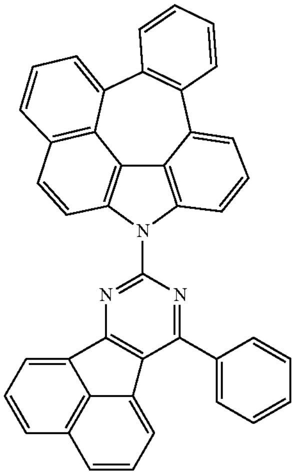
C-565
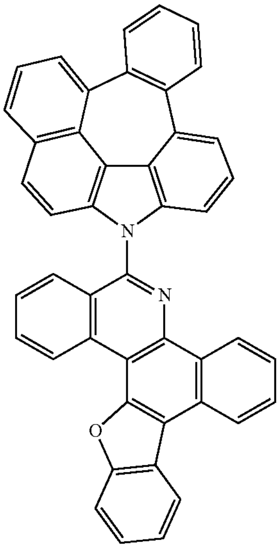
C-566
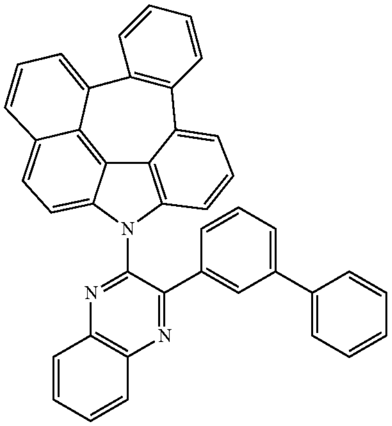
-continued
C-567
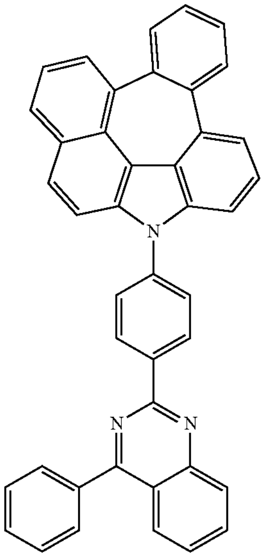
C-568
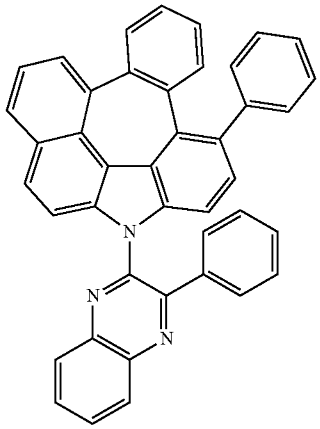
C-569
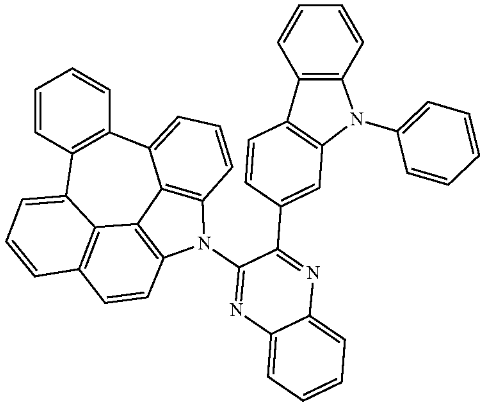

-continued
C-570
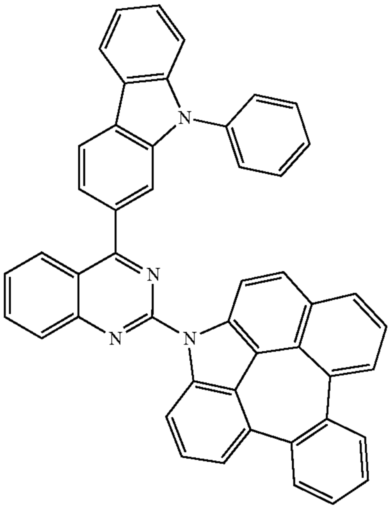
C-571
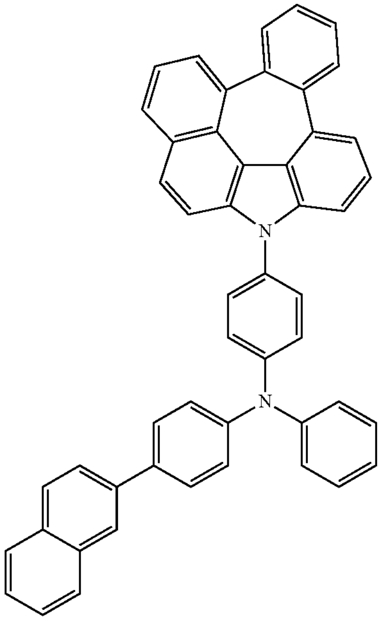
-continued
C-572
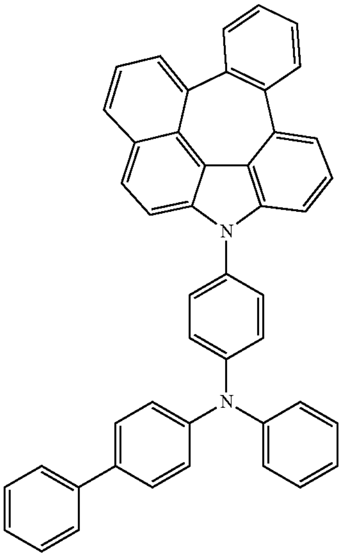
C-573
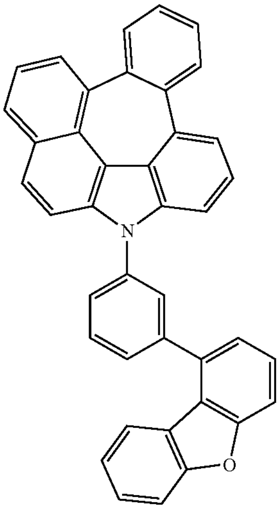
C-574
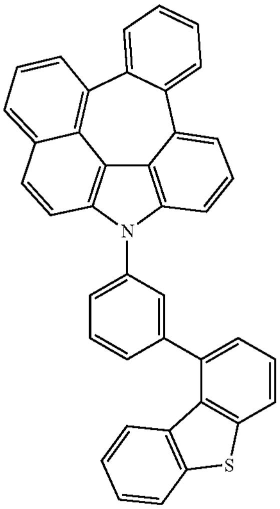

-continued
C-575
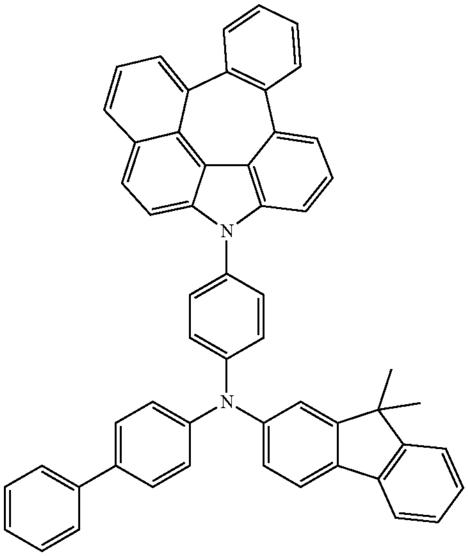
C-576
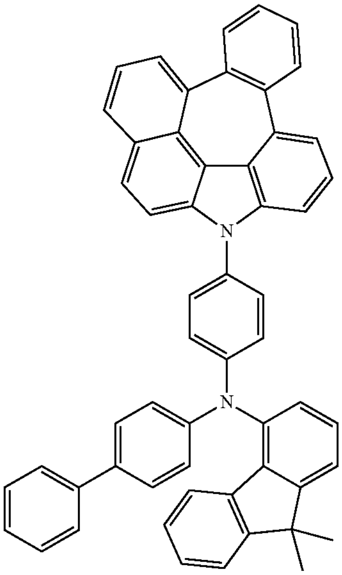
-continued
C-577
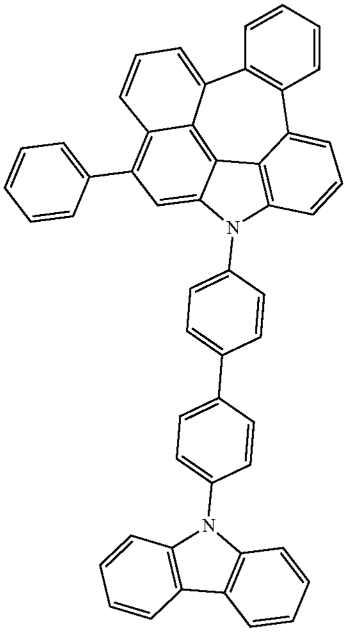
C-578
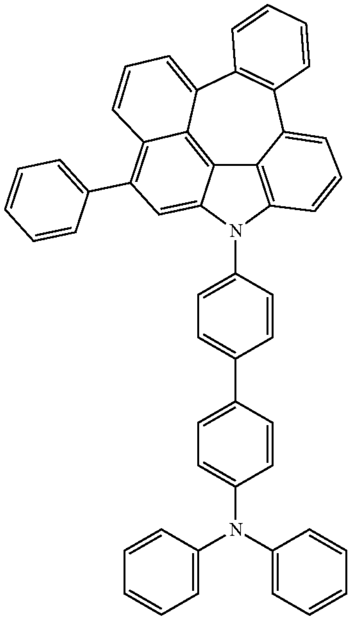

-continued
C-579
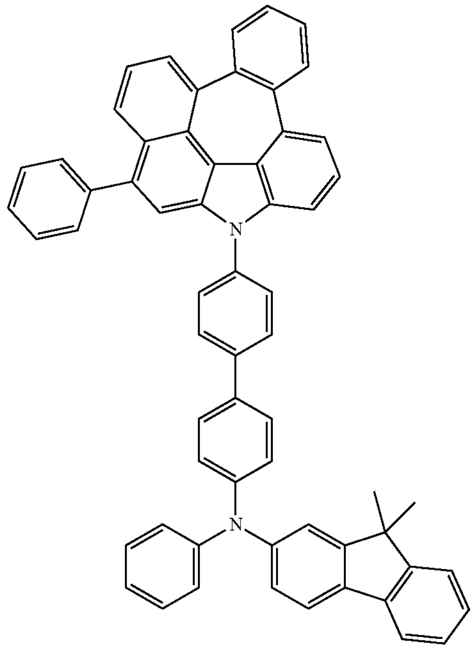
C-580
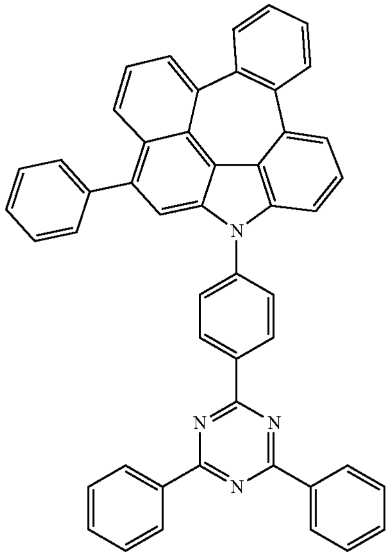
-continued
C-581
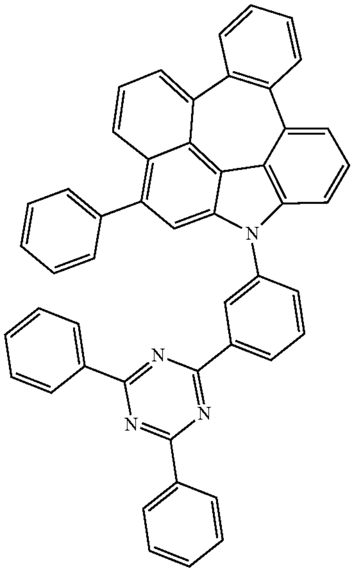
C-582
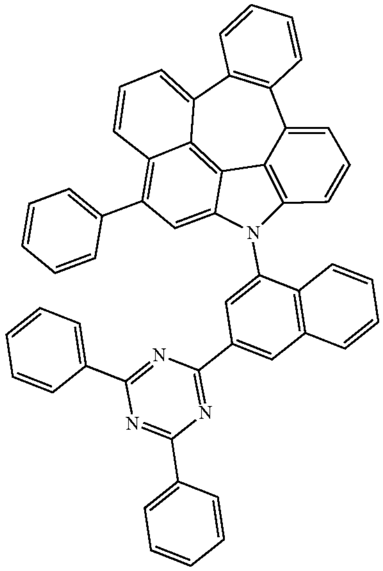

-continued
C-583
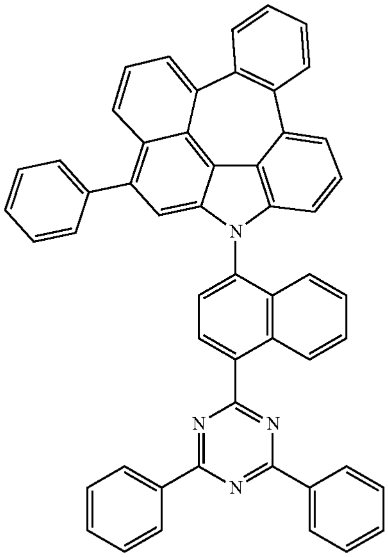
C-584
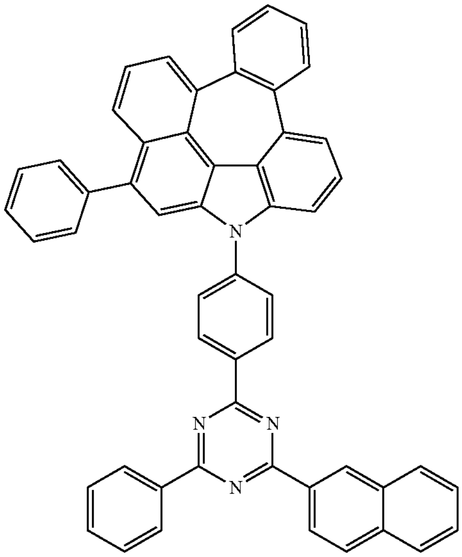
-continued
C-585
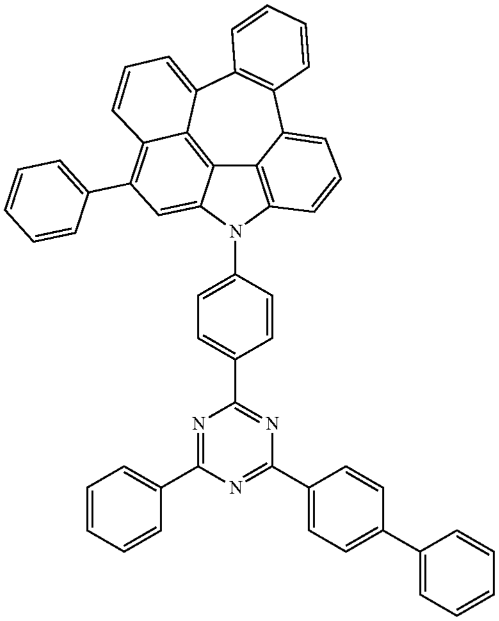
C-586
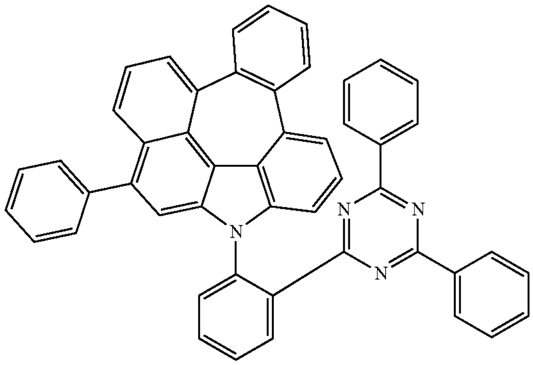
C-587
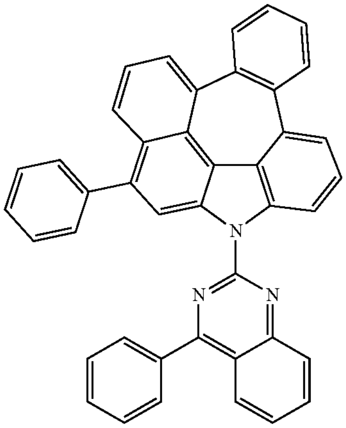

-continued
C-588
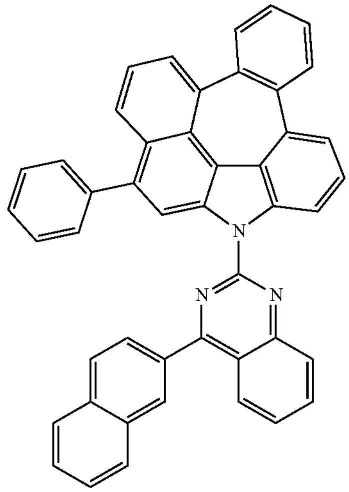
C-589
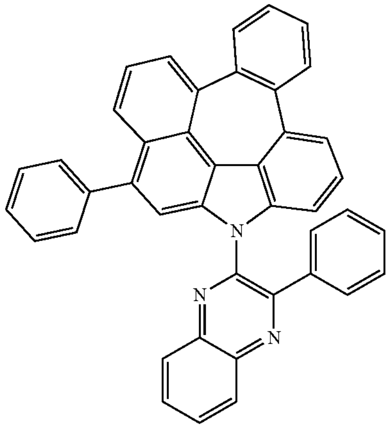
C-590
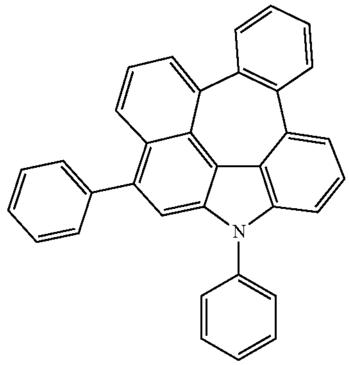
-continued
C-591
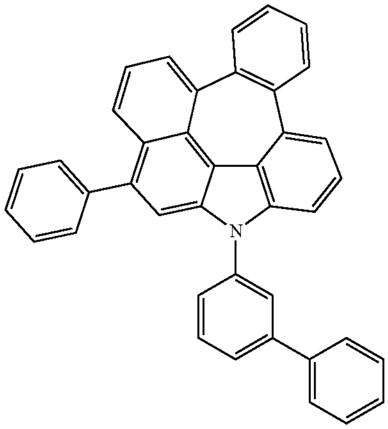
C-592
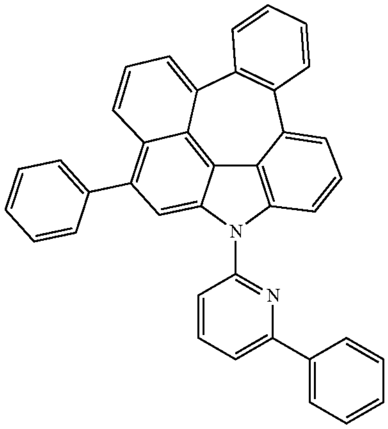
C-593
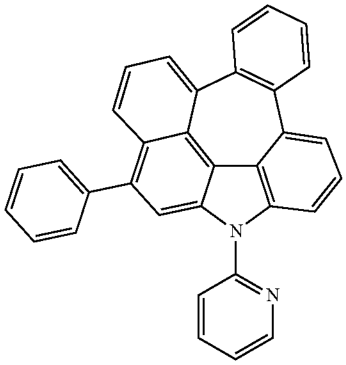

C-594
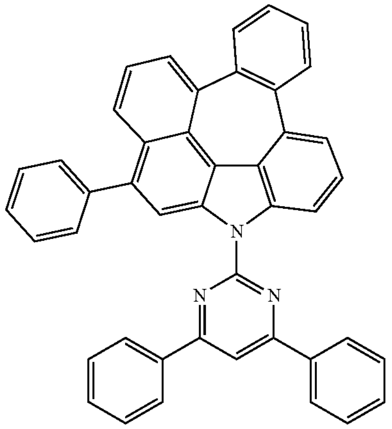
C-595
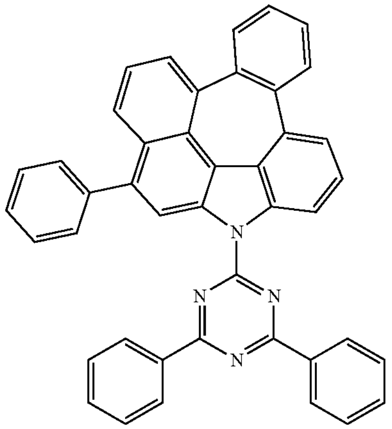
C-596
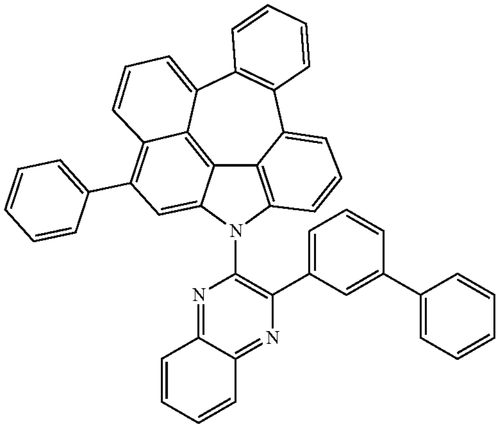
C-597
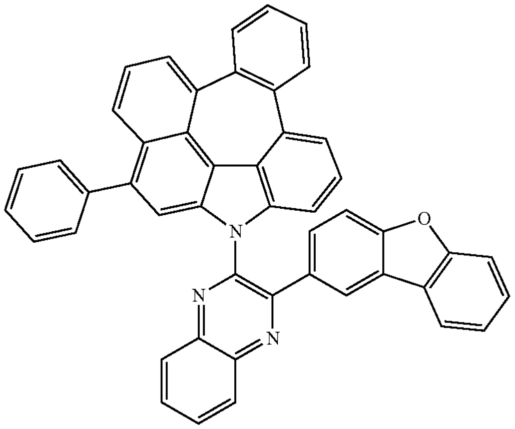
C-598
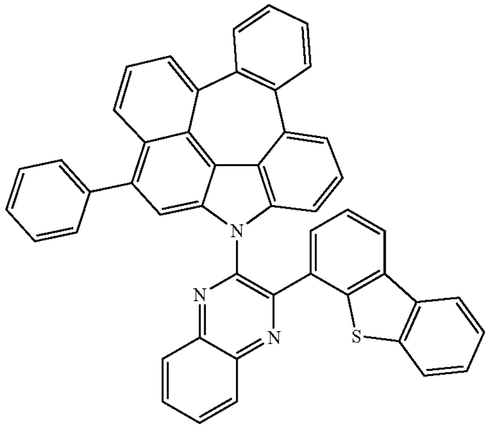
C-599
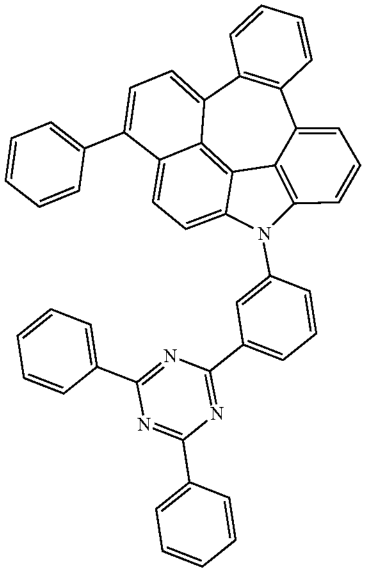

-continued
C-600
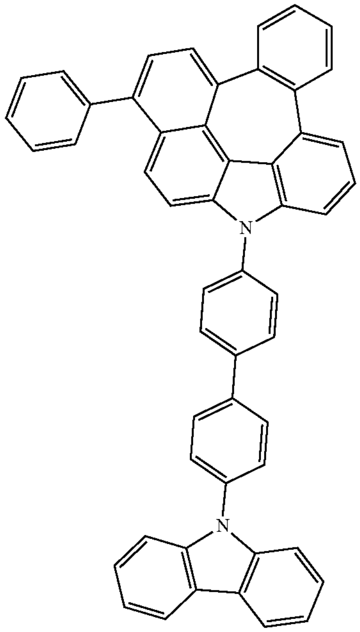
C-601
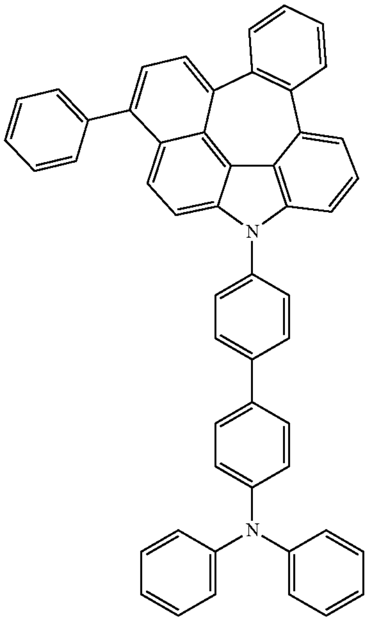
-continued
C-602
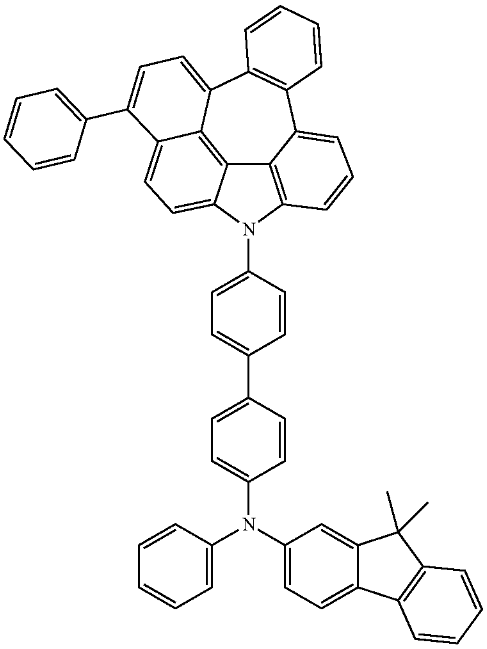
C-603
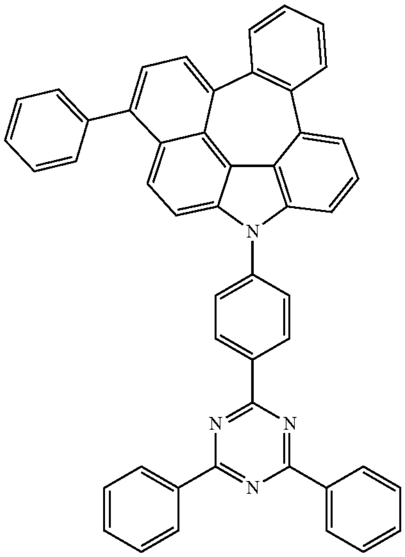

-continued
C-604
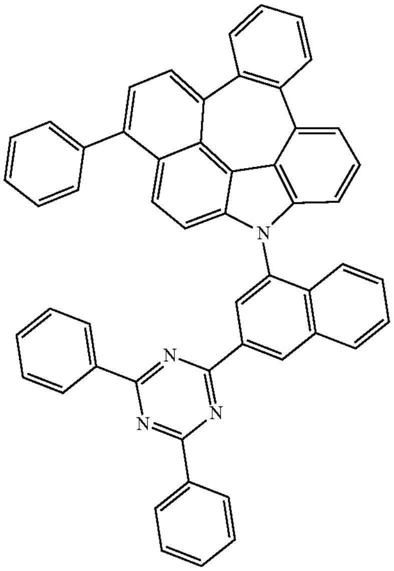
C-605
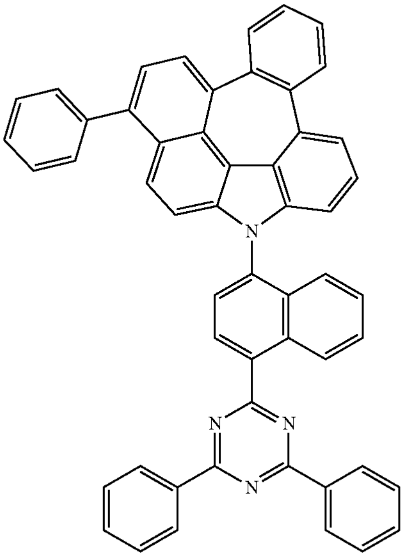
-continued
C-606
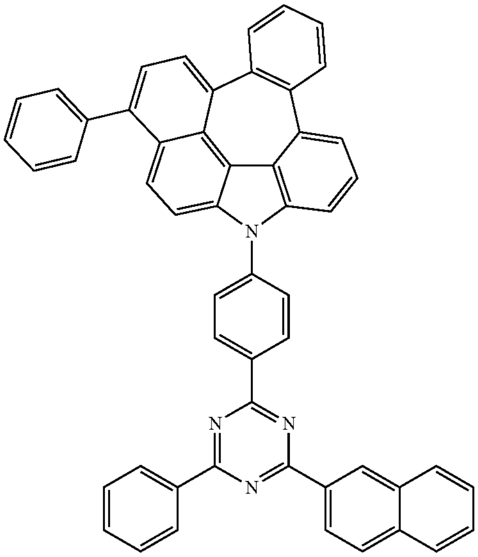
C-607
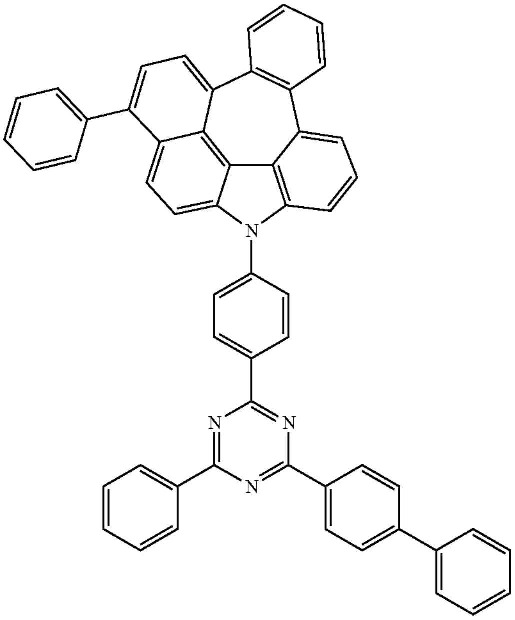
C-608
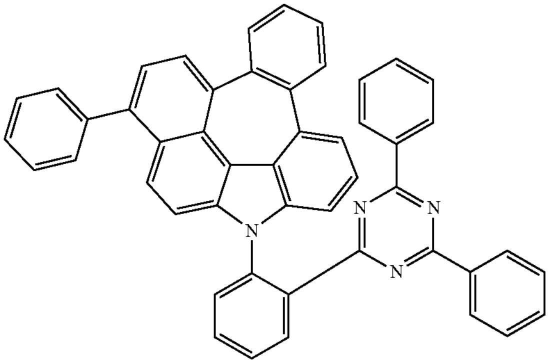

-continued
C-609
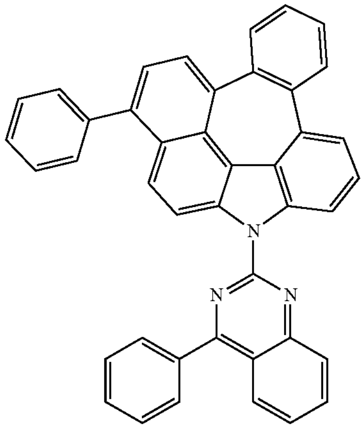
C-610
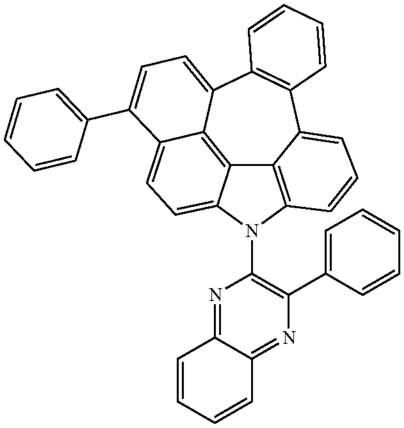
C-611
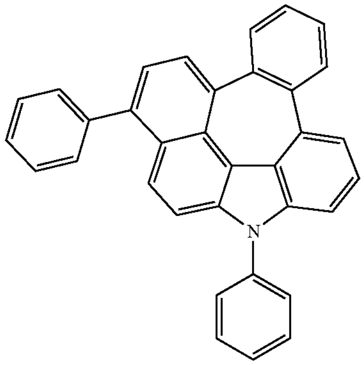
-continued
C-612
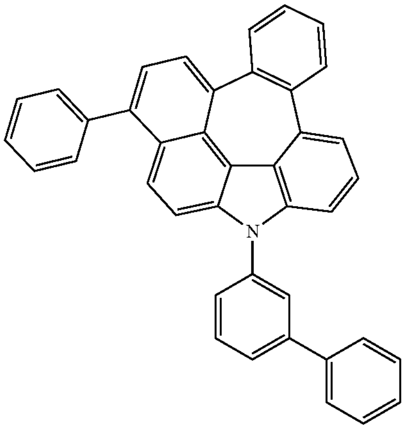
C-613
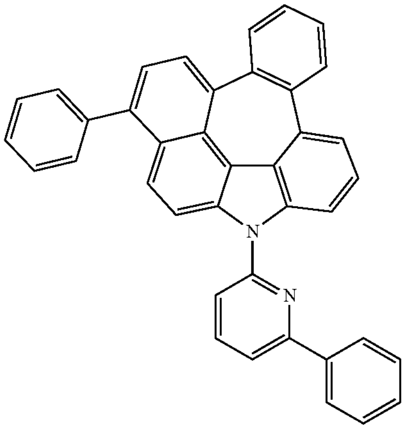
C-614
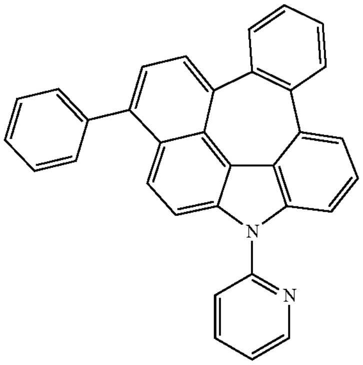

C-615
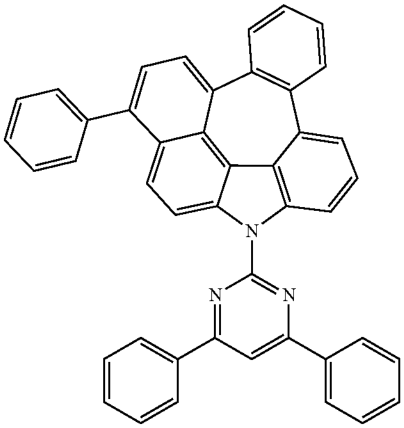
C-616
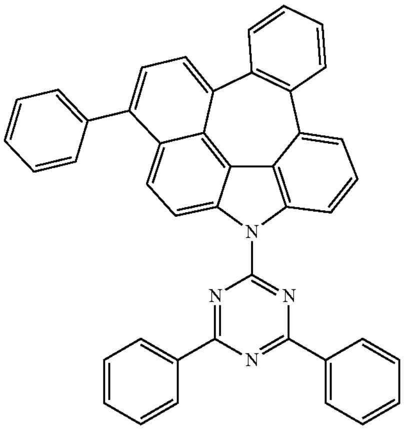
C-617
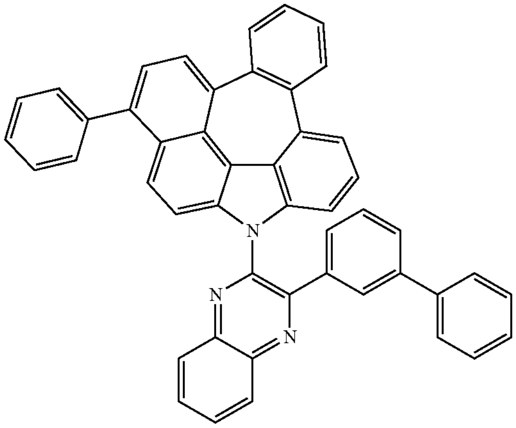
C-618
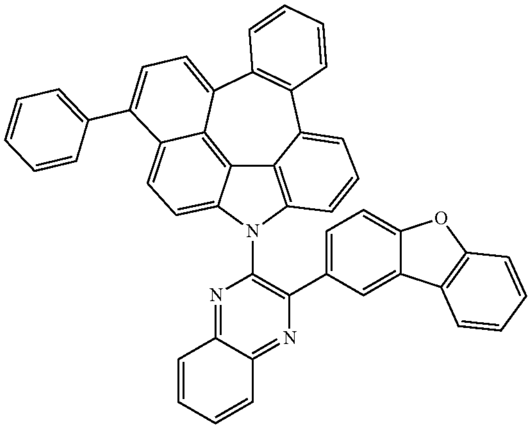
C-619
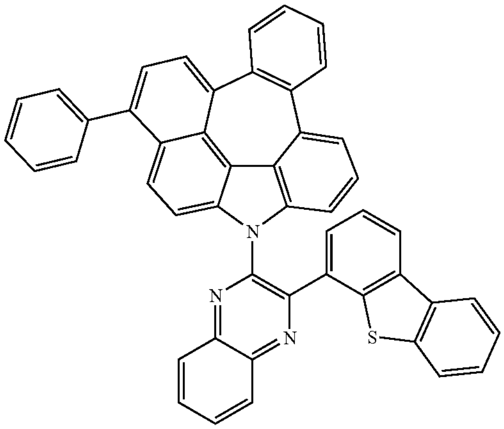
C-620
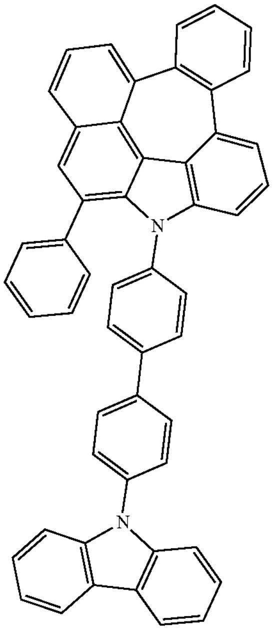

-continued
C-621
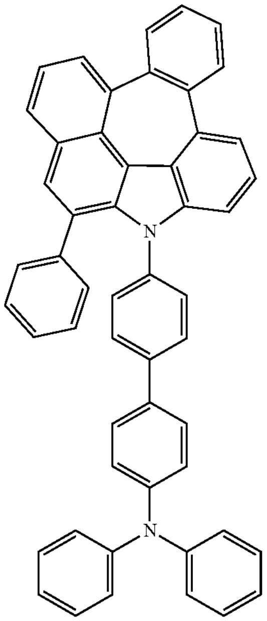
C-622
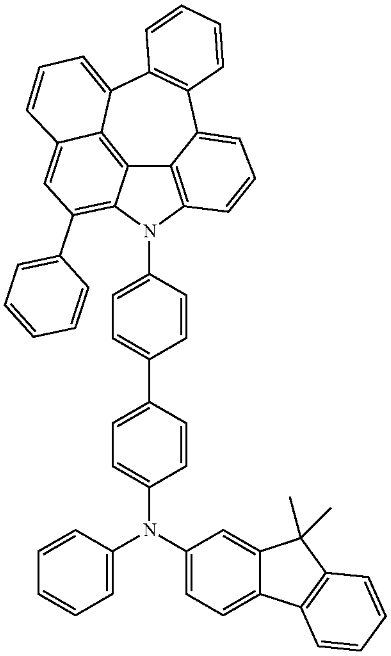
-continued
C-623
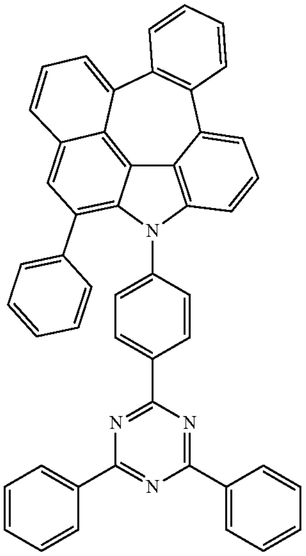
C-624
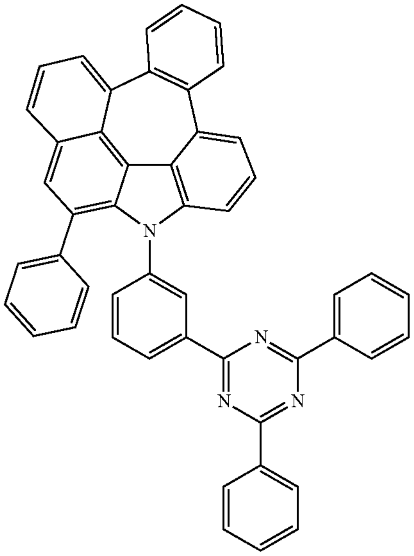

-continued
C-625
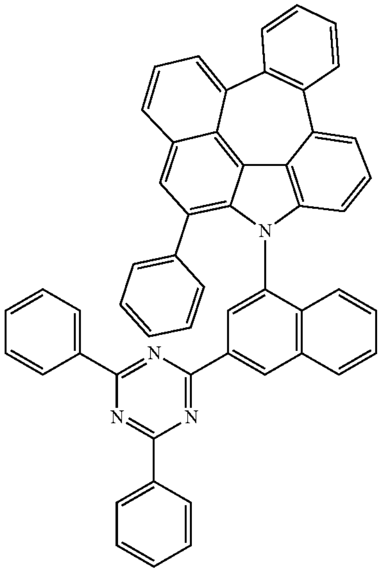
C-626
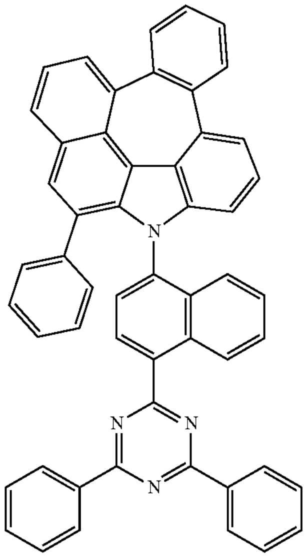
-continued
C-627
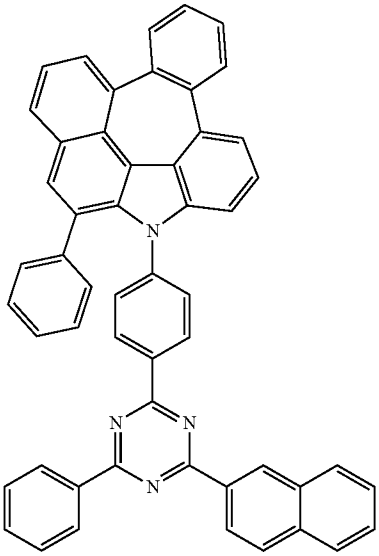
C-628
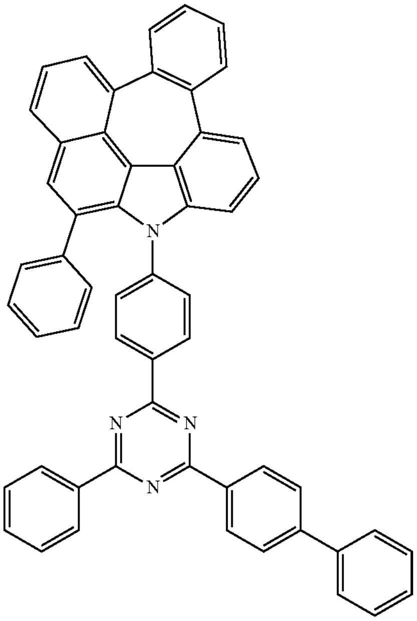
C-629
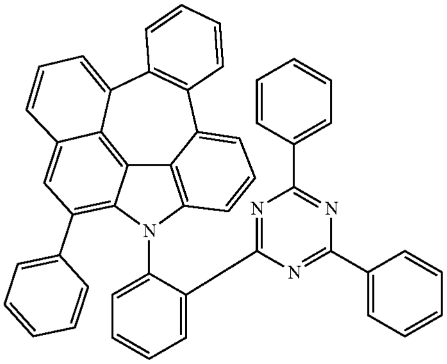

-continued
C-630
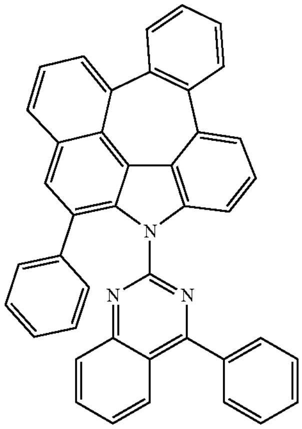
C-631
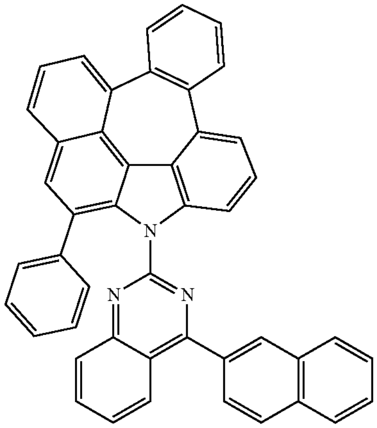
C-632
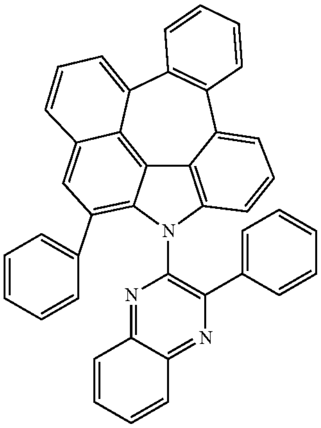
-continued
C-633
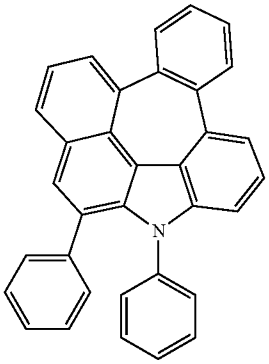
C-634
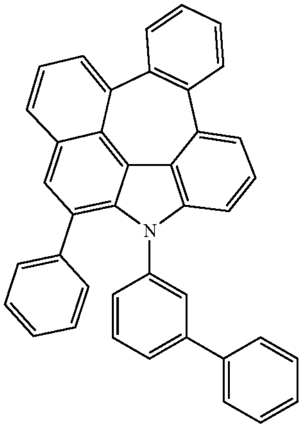
C-635
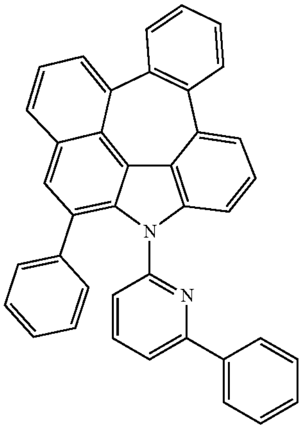
C-636
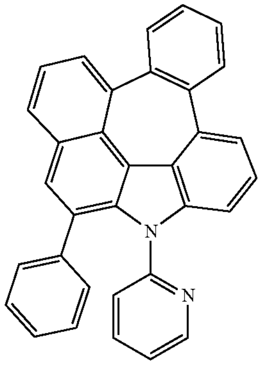

C-637
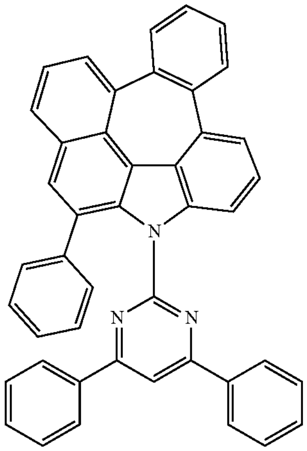
C-638
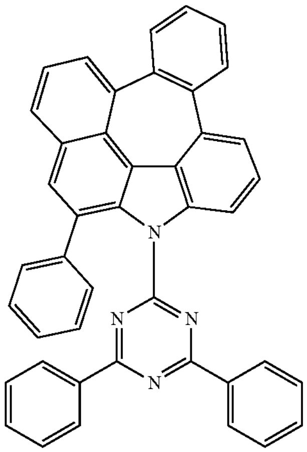
C-639
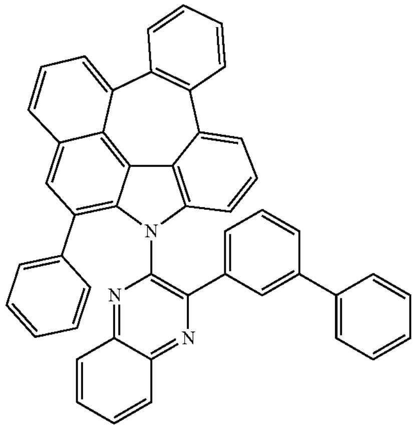
C-640
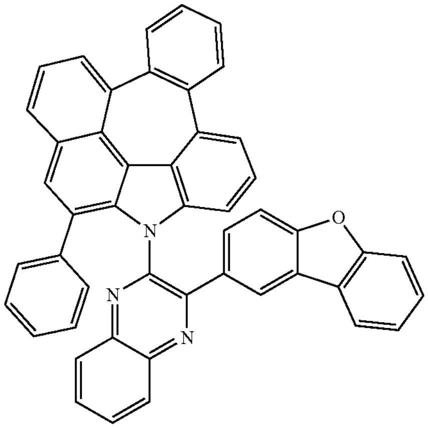
C-641
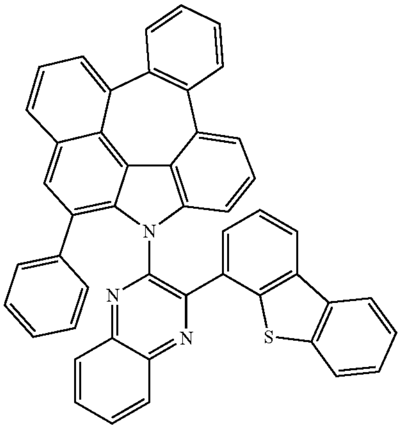
C-642
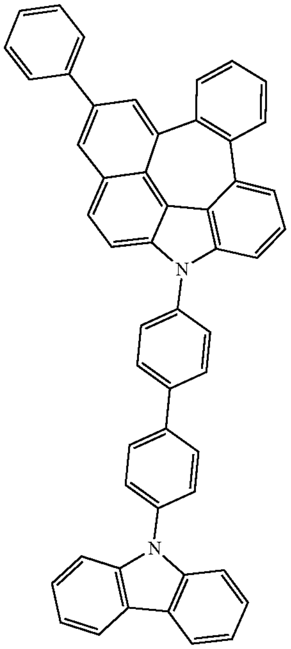

-continued
C-643
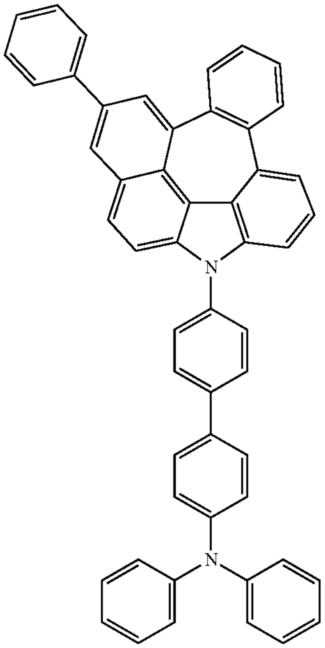
C-644
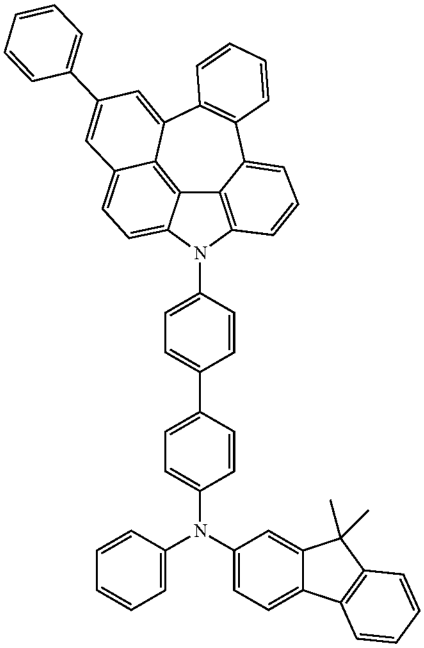
-continued
C-645
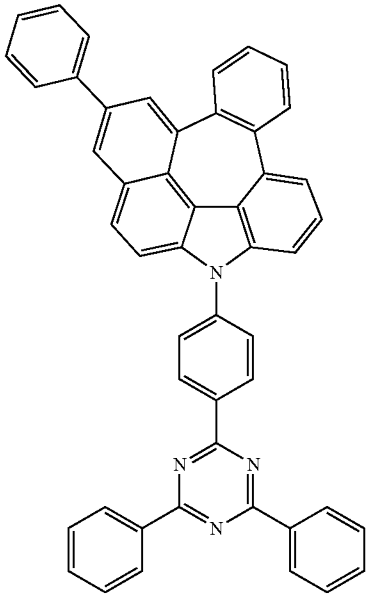
C-646
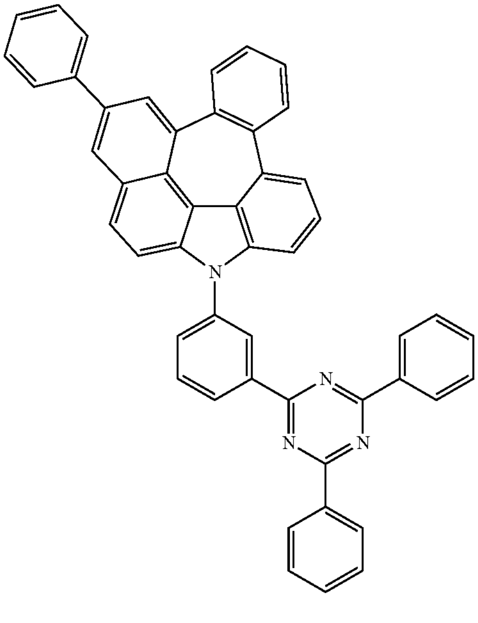

-continued
C-647
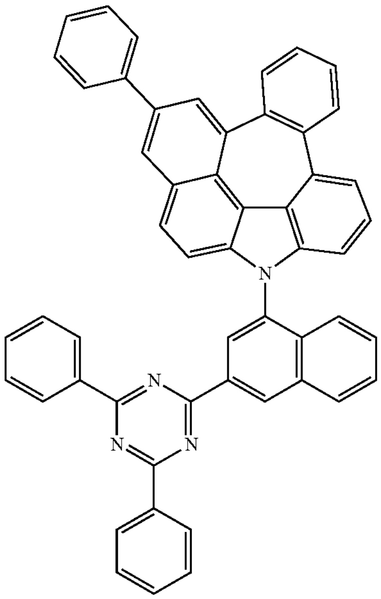
C-648
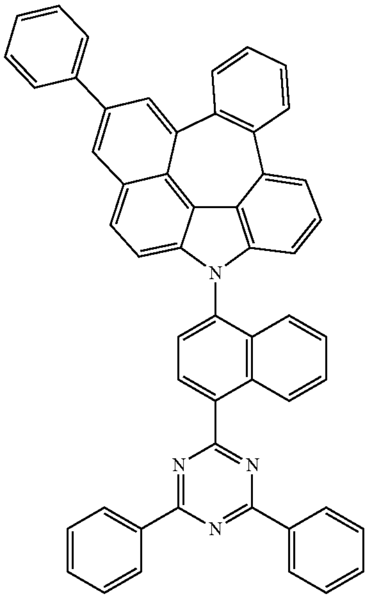
-continued
C-649
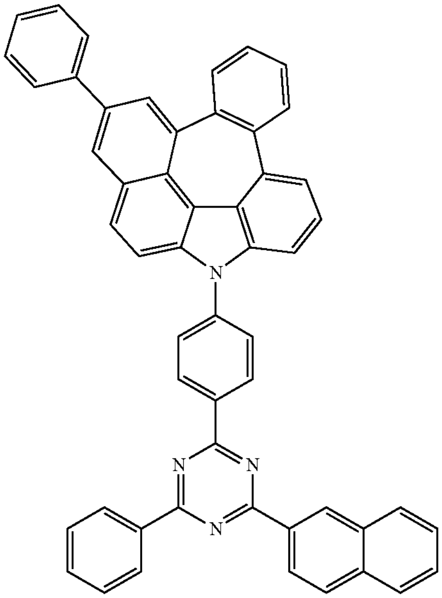
C-650
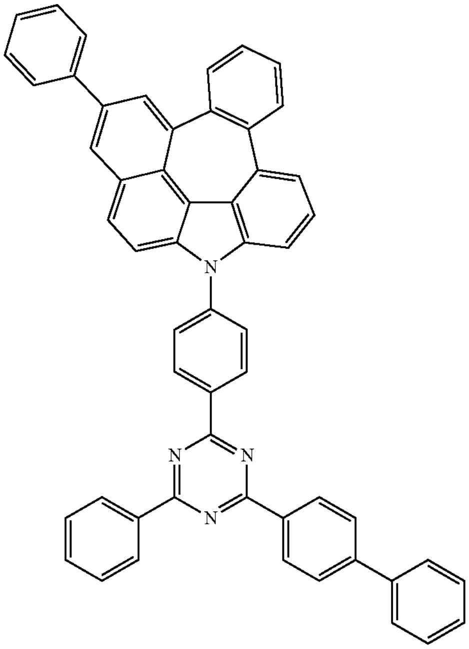

-continued
C-651
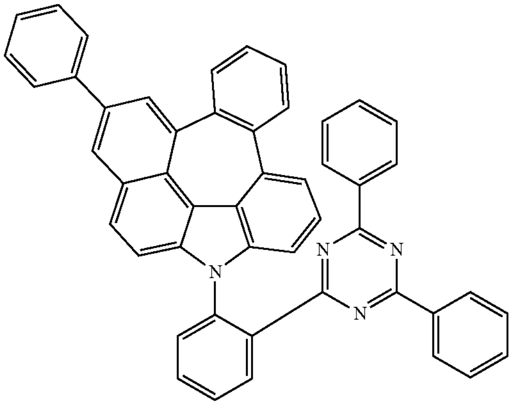
C-652
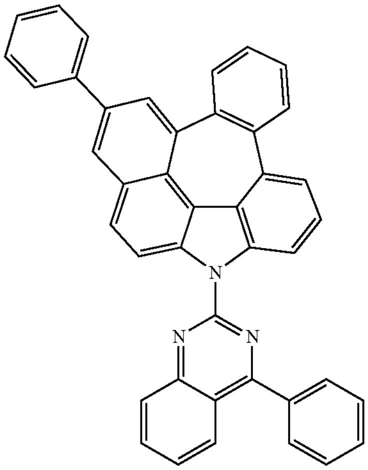
C-653
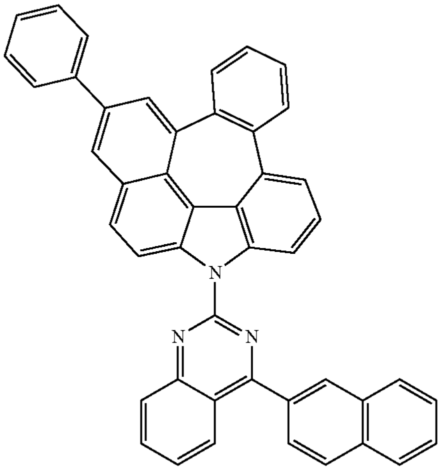
-continued
C-654
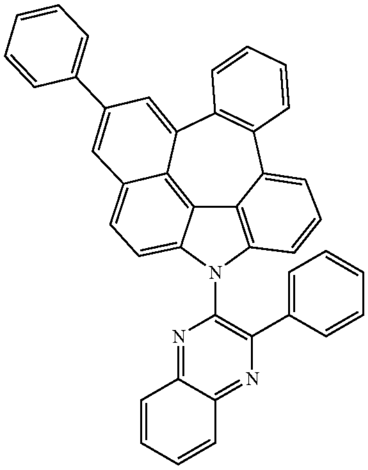
C-655
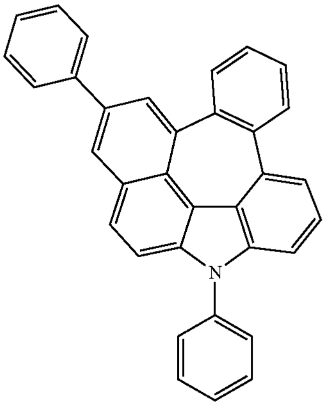
C-656
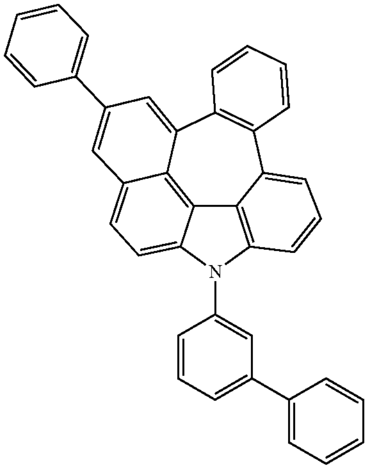

-continued
C-657
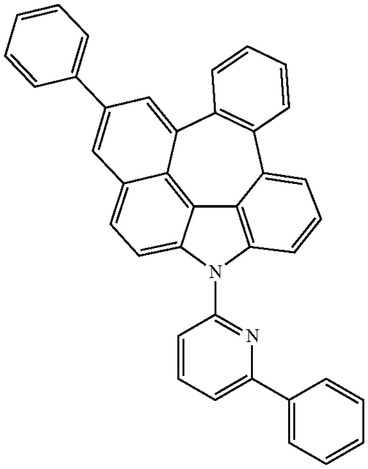
C-658
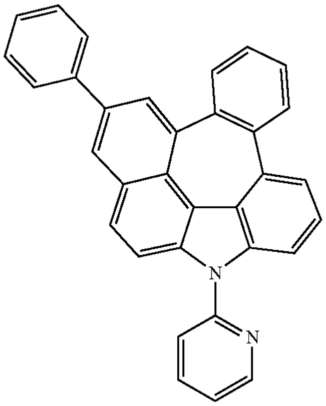
C-659
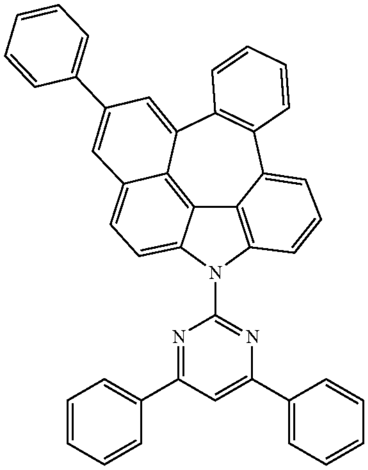
-continued
C-660
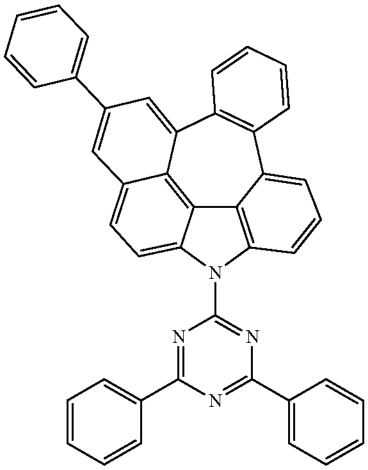
C-661
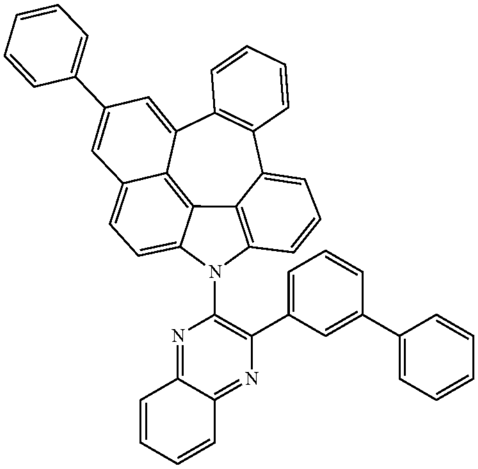
C-662
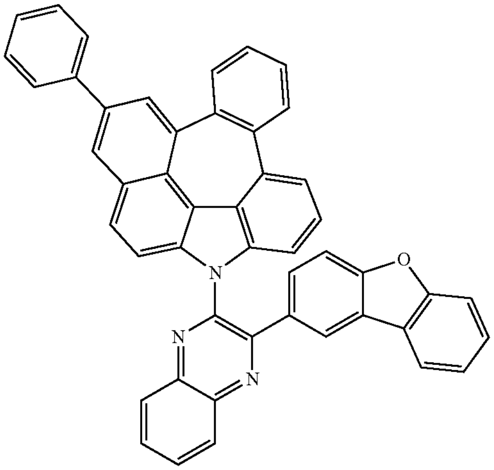
and -continued

C-663

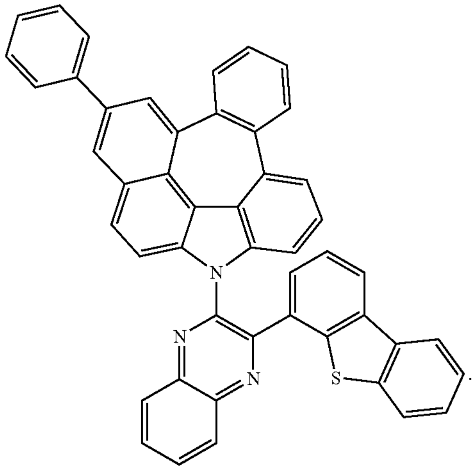

7. A plurality of host materials comprising a first host material comprising the compound represented by at least one of formulas 3 to 6 according to claim 3, and a second host material comprising the compound represented by formula 2 according to claim 1.

8. An organic electroluminescent device comprising the plurality of host materials according to claim 7.

9. An organic electroluminescent device comprising the composition material for an organic electroluminescent device according to claim 1.

* * * * *